US012577285B2

(12) United States Patent
Mujacic et al.

(10) Patent No.: US 12,577,285 B2
(45) Date of Patent: Mar. 17, 2026

(54) PROCESS FOR PRODUCING A COMPOSITION OF ENGINEERED T CELLS

(71) Applicant: Juno Therapeutics, Inc., Seattle, WA (US)

(72) Inventors: Mirna Mujacic, Seattle, WA (US); Ayu Rahardjo, Seattle, WA (US); Pascal Beauchesne, Seattle, WA (US); Kien Khuu-Duong, Seattle, WA (US); Ivie Aifuwa, Seattle, WA (US); Calvin Chan, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 254 days.

(21) Appl. No.: 16/769,971

(22) PCT Filed: Dec. 7, 2018

(86) PCT No.: PCT/US2018/064628
§ 371 (c)(1),
(2) Date: Jun. 4, 2020

(87) PCT Pub. No.: WO2019/113557
PCT Pub. Date: Jun. 13, 2019

(65) Prior Publication Data
US 2020/0384025 A1     Dec. 10, 2020

Related U.S. Application Data

(60) Provisional application No. 62/774,855, filed on Dec. 3, 2018, provisional application No. 62/774,165, filed
(Continued)

(51) Int. Cl.
*C07K 14/725* (2006.01)
*A61K 40/11* (2025.01)
(Continued)

(52) U.S. Cl.
CPC .......... *C07K 14/7051* (2013.01); *A61K 40/11* (2025.01); *A61K 40/31* (2025.01);
(Continued)

(58) Field of Classification Search
CPC ............ A61K 35/17; A61K 2039/5156; A61K 2039/5158; A61K 39/0011;
(Continued)

(56) References Cited

U.S. PATENT DOCUMENTS 1,631,788 A     6/1927  Bennett
4,452,773 A     6/1984  Molday
(Continued)

FOREIGN PATENT DOCUMENTS

CN     103 305 464     9/2013
CN     103 502 438     1/2014
(Continued)

OTHER PUBLICATIONS

Kahn, M.L., et al (1992) Optimization of Retroviral Vector-Mediated Gene Transfer into Endothelial Cells in Vitro Circulation Research 71(6); 1508-1517 (Year: 1992).*
(Continued)

*Primary Examiner* — Joanne Hama
*Assistant Examiner* — Audrey L Buttice
(74) *Attorney, Agent, or Firm* — Morrison & Foerster LLP

(57) ABSTRACT

The present disclosure provides methods for genetically engineering T cells, such as CD4+ T cells and/or CD8+ T cells, for use in cell therapy. In some aspects, the provided methods include one or more steps for pooling enriched CD4+ and CD8+ cells, such as at a 1:1 ratio, and then incubating the cells under stimulating conditions, introducing a recombinant polypeptide to the cells through transduction or transfection, and/or cultivating the cells under
(Continued)

conditions that promote proliferation and/or expansion. In some aspects, the provided methods are an efficient, reliable means to produce genetically engineered T cells with a high degree of success.

53 Claims, 11 Drawing Sheets

Specification includes a Sequence Listing.

Related U.S. Application Data on Nov. 30, 2018, provisional application No. 62/754,564, filed on Nov. 1, 2018, provisional application No. 62/740,903, filed on Oct. 3, 2018, provisional application No. 62/721,604, filed on Aug. 22, 2018, provisional application No. 62/716,971, filed on Aug. 9, 2018, provisional application No. 62/614,965, filed on Jan. 8, 2018, provisional application No. 62/596,774, filed on Dec. 8, 2017.

(51) Int. Cl.
| | |
|---|---|
| *A61K 40/31* | (2025.01) |
| *A61K 40/42* | (2025.01) |
| *C12N 5/0783* | (2010.01) |

(52) U.S. Cl.
CPC ........ *A61K 40/4215* (2025.01); *C12N 5/0636* (2013.01); *A61K 2239/31* (2023.05); *A61K 2239/38* (2023.05); *A61K 2239/48* (2023.05); *C12N 2510/00* (2013.01)

(58) Field of Classification Search
CPC ............ C07K 14/7051; C07K 2319/03; C12N 5/0636; C12N 2510/00; C12N 2500/90; C12N 2501/00; C12N 2501/50; C12N 2501/599; C12N 2501/998
See application file for complete search history.

(56) References Cited

U.S. PATENT DOCUMENTS

| | | | |
|---|---|---|---|
| 4,690,915 | A | 9/1987 | Rosenberg |
| 4,795,698 | A | 1/1989 | Owen |
| 5,087,616 | A | 2/1992 | Myers |
| 5,168,049 | A | 12/1992 | Meade et al. |
| 5,200,084 | A | 4/1993 | Liberti |
| 5,219,740 | A | 6/1993 | Miller |
| 5,506,121 | A | 4/1996 | Skerra et al. |
| 5,773,224 | A | 6/1998 | Grandics et al. |
| 6,022,951 | A | 2/2000 | Sano et al. |
| 6,040,177 | A | 3/2000 | Riddell et al. |
| 6,060,273 | A | 5/2000 | Dirks et al. |
| 6,103,493 | A | 8/2000 | Skerra et al. |
| 6,123,655 | A | 9/2000 | Fell |
| 6,156,493 | A | 12/2000 | Stayton |
| 6,165,750 | A | 12/2000 | Stayton et al. |
| 6,207,453 | B1 | 3/2001 | Maass |
| 6,368,813 | B1 | 4/2002 | Reznik et al. |
| 6,410,319 | B1 | 6/2002 | Raubitschek |
| 6,451,995 | B1 | 9/2002 | Cheung |
| 6,733,433 | B1 | 5/2004 | Fell |
| 7,070,995 | B2 | 7/2006 | Jensen |
| 7,265,209 | B2 | 9/2007 | Jensen |
| 7,354,762 | B2 | 4/2008 | Jensen |
| 7,362,449 | B2 | 4/2008 | Dubois et al. |
| 7,446,179 | B2 | 11/2008 | Jensen |
| 7,446,190 | B2 | 11/2008 | Sadelain |
| 7,446,191 | B2 | 11/2008 | Jensen |
| 7,776,562 | B2 | 8/2010 | Busch et al. |
| 7,981,632 | B2 | 7/2011 | Schmidt |
| 8,008,450 | B2 | 8/2011 | Williams et al. |

| | | | | |
|---|---|---|---|---|
| 8,153,765 | B2 | 4/2012 | Park et al. | |
| 8,298,782 | B2 | 10/2012 | Busch et al. | |
| 8,324,353 | B2 | 12/2012 | Jensen | |
| 8,339,645 | B2 | 12/2012 | Nakawaki | |
| 8,389,282 | B2 | 3/2013 | Sadelain et al. | |
| 8,479,118 | B2 | 7/2013 | Lyndersay et al. | |
| 8,603,477 | B2 | 12/2013 | Afar et al. | |
| 8,735,540 | B2 | 5/2014 | Schmidt et al. | |
| 8,802,374 | B2 | 8/2014 | Jensen | |
| 8,822,647 | B2 | 9/2014 | Jensen | |
| 8,911,993 | B2 | 12/2014 | June et al. | |
| 9,023,604 | B2 | 5/2015 | Schmidt et al. | |
| 9,684,281 | B2 | 6/2017 | Mathuis et al. | |
| 9,904,248 | B2 | 2/2018 | Mathuis et al. | |
| 10,131,882 | B2 | 11/2018 | Matthew et al. | |
| 11,066,475 | B2 | 7/2021 | Sather et al. | |
| 11,400,115 | B2 | 8/2022 | Ramsbourg et al. | |
| 11,458,167 | B2 | 10/2022 | Jensen | |
| 2002/0131960 | A1 | 9/2002 | Sadelain | |
| 2002/0150914 | A1 | 10/2002 | Anderse et al. | |
| 2003/0170238 | A1 | 9/2003 | Gruenberg et al. | |
| 2003/0223994 | A1 | 12/2003 | Hoogenboom et al. | |
| 2004/0191260 | A1 | 9/2004 | Reiter et al. | |
| 2006/0034850 | A1 | 2/2006 | Weidanz et al. | |
| 2007/0092530 | A1 | 4/2007 | Weidanz et al. | |
| 2007/0116690 | A1 | 5/2007 | Yang et al. | |
| 2008/0085532 | A1 | 4/2008 | Gorlach et al. | |
| 2008/0171951 | A1 | 7/2008 | Fell | |
| 2009/0226474 | A1 | 9/2009 | Weidanz et al. | |
| 2009/0304679 | A1 | 12/2009 | Weidanz | |
| 2010/0260748 | A1 | 10/2010 | Elkins et al. | |
| 2011/0003380 | A1 | 1/2011 | Miltenyi | |
| 2011/0070581 | A1 | 3/2011 | Gupta | |
| 2011/0293667 | A1 | 12/2011 | Baksh et al. | |
| 2012/0189622 | A1 | 7/2012 | Tesar et al. | |
| 2013/0029418 | A1 | 1/2013 | Angel et al. | |
| 2013/0149337 | A1 | 6/2013 | Cooper et al. | |
| 2013/0287748 | A1 | 10/2013 | June | |
| 2014/0234893 | A1 | 8/2014 | Enenkel | |
| 2014/0255993 | A1* | 9/2014 | Follstad | C07K 16/00 |
| | | | | 435/69.6 |
| 2014/0271635 | A1 | 9/2014 | Brogdon et al. | |
| 2014/0294841 | A1 | 10/2014 | Scheinberg et al. | |
| 2015/0051266 | A1 | 2/2015 | Kochenderfer | |
| 2015/0283178 | A1 | 10/2015 | June et al. | |
| 2016/0046724 | A1 | 2/2016 | Brogdon et al. | |
| 2016/0152723 | A1 | 6/2016 | Chen et al. | |
| 2016/0237139 | A1 | 8/2016 | Pulé et al. | |
| 2016/0297884 | A1 | 10/2016 | Kuo et al. | |
| 2016/0346326 | A1 | 12/2016 | Bot et al. | |
| 2016/0362472 | A1 | 12/2016 | Bitter et al. | |
| 2017/0037369 | A1 | 2/2017 | Ramsborg et al. | |
| 2017/0051035 | A1 | 2/2017 | Payne et al. | |
| 2017/0051252 | A1 | 2/2017 | Morgan et al. | |
| 2017/0209492 | A1 | 7/2017 | June et al. | |
| 2017/0226216 | A1 | 8/2017 | Morgan et al. | |
| 2017/0281766 | A1 | 10/2017 | Wiltzius | |
| 2017/0283504 | A1 | 10/2017 | Wiltzius | |
| 2018/0085444 | A1 | 3/2018 | Morgan et al. | |
| 2018/0296602 | A1 | 10/2018 | Riddell et al. | |
| 2018/0334653 | A1 | 11/2018 | O'Neill | |
| 2019/0161553 | A1 | 5/2019 | Blythe et al. | |
| 2020/0354677 | A1 | 11/2020 | Lee et al. | |
| 2021/0163893 | A1 | 6/2021 | Westoby et al. | |
| 2021/0207080 | A1 | 7/2021 | Beauchesne et al. | |
| 2021/0324100 | A1 | 10/2021 | Blythe et al. | |
| 2021/0393690 | A1 | 12/2021 | Sather et al. | |
| 2022/0096651 | A1 | 3/2022 | Costa et al. | |
| 2023/0087953 | A1 | 3/2023 | Westoby et al. | |
| 2023/0090176 | A1 | 3/2023 | Ramsborg et al. | |
| 2023/0149462 | A1 | 5/2023 | Stirner et al. | |
| 2023/0190814 | A1 | 6/2023 | Ramsborg et al. | |
| 2023/0346734 | A1 | 11/2023 | Hudecek et al. | |

FOREIGN PATENT DOCUMENTS

| | | |
|---|---|---|
| CN | 104450614 | 3/2015 |
| CN | 105777911 | 7/2016 |
| CN | 105837693 | 8/2016 |

(56)         References Cited

FOREIGN PATENT DOCUMENTS

| CN | 106635955 A | 5/2017 |
| CN | 106754670 | 5/2017 |
| CN | 106 834 218 | 6/2017 |
| CN | 106801032 | 6/2017 |
| CN | 107 827 989 | 3/2018 |
| EP | 0452342 | 10/1991 |
| EP | 2537416 | 12/2012 |
| EP | 3372670 | 9/2018 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1996/24606 | 8/1996 |
| WO | WO 1998/040396 | 9/1998 |
| WO | WO 1998/040510 | 9/1998 |
| WO | WO 1999/018129 | 4/1999 |
| WO | WO 1999/025817 | 5/1999 |
| WO | WO 1999/060120 | 11/1999 |
| WO | WO 2000/014257 | 3/2000 |
| WO | WO 2000/038762 | 7/2000 |
| WO | WO 2000/043551 | 7/2000 |
| WO | WO 2002/077018 | 10/2002 |
| WO | WO 2003/020763 | 3/2003 |
| WO | WO 2003/068201 | 8/2003 |
| WO | WO 2004/029221 | 4/2004 |
| WO | WO 2004/033685 | 4/2004 |
| WO | WO 2004/096975 | 11/2004 |
| WO | WO 2006/000830 | 1/2006 |
| WO | WO 2006/099875 | 9/2006 |
| WO | WO 2007/117602 | 10/2007 |
| WO | WO 2008/035631 | 3/2008 |
| WO | WO 2009/003493 | 1/2009 |
| WO | WO 2009/072003 | 6/2009 |
| WO | WO 2009/072006 | 6/2009 |
| WO | WO 2009/080829 | 7/2009 |
| WO | WO 2010/033140 | 3/2010 |
| WO | WO 2010/104949 | 9/2010 |
| WO | WO 2011/044186 | 4/2011 |
| WO | WO 2012/081650 | 6/2012 |
| WO | WO 2012/092612 | 7/2012 |
| WO | WO 2012/129514 | 9/2012 |
| WO | WO 2013/011011 | 1/2013 |
| WO | WO 2013/038272 | 3/2013 |
| WO | WO 2013/062365 | 5/2013 |
| WO | WO 2013/071154 | 5/2013 |
| WO | WO 2013/123061 | 8/2013 |
| WO | WO 2013/124474 | 8/2013 |
| WO | WO 2013/166321 | 11/2013 |
| WO | WO 2014/011996 | 1/2014 |
| WO | WO 2014/031687 | 2/2014 |
| WO | WO- 2014/055668 | 4/2014 |
| WO | WO 2014/076277 | 5/2014 |
| WO | WO 2014/100385 | 6/2014 |
| WO | WO 2014/144039 | 9/2014 |
| WO | WO 2014/210064 | 12/2014 |
| WO | WO 2015/095895 | 6/2015 |
| WO | WO 2015/157252 | 10/2015 |
| WO | WO 2015/157384 | 10/2015 |
| WO | WO 2015/157391 | 10/2015 |
| WO | WO 2015/158671 | 10/2015 |
| WO | WO 2015/158868 | 10/2015 |
| WO | WO 2015/164675 | 10/2015 |
| WO | WO-2015164745 A1 * | 10/2015 | ............ A61K 35/17 |
| WO | WO 2015/181253 | 12/2015 |
| WO | WO 2016/014565 | 1/2016 |
| WO | WO 2016/014789 | 1/2016 |
| WO | WO-2016019300 A1 * | 2/2016 | ........... A61K 31/436 |
| WO | WO 2016/073602 | 5/2016 |
| WO | WO 2016/090190 | 6/2016 |
| WO | WO 2016/090312 | 6/2016 |
| WO | WO 2016/090320 | 6/2016 |
| WO | WO 2016/090327 | 6/2016 |
| WO | WO 2016/090329 | 6/2016 |
| WO | WO 2016/090369 | 6/2016 |
| WO | WO 2016/094304 | 6/2016 |

| WO | WO 2016/109410 | 7/2016 |
| WO | WO 2016/130598 | 8/2016 |
| WO | WO 2016/154628 | 9/2016 |
| WO | WO 2016/164580 | 10/2016 |
| WO | WO 2017/015427 | 1/2017 |
| WO | WO 2017/015490 | 1/2017 |
| WO | WO 2017/023803 | 2/2017 |
| WO | WO 2017/027291 | 2/2017 |
| WO | WO 2017/041143 | 3/2017 |
| WO | WO 2017/064084 | 4/2017 |
| WO | WO 2017/068421 | 4/2017 |
| WO | WO 2017/087547 | 5/2017 |
| WO | WO 2015/164745 | 6/2017 |
| WO | WO 2017/096329 | 6/2017 |
| WO | WO 2017/130223 | 8/2017 |
| WO | WO 2017/156479 | 9/2017 |
| WO | WO 2017/157505 | 9/2017 |
| WO | WO 2017/161353 | 9/2017 |
| WO | WO 2017/173256 | 10/2017 |
| WO | WO 2017/177137 | 10/2017 |
| WO | WO 2017/180993 | 10/2017 |
| WO | WO 2018/085690 | 5/2018 |
| WO | WO 2018/106732 | 6/2018 |
| WO | WO 2018/162352 | 9/2018 |
| WO | WO 2018/170188 | 9/2018 |
| WO | WO 2018/175988 | 9/2018 |
| WO | WO 2018/191723 | 10/2018 |
| WO | WO 2018/197675 | 11/2018 |
| WO | WO 2018/197949 | 11/2018 |
| WO | WO 2018/204427 | 11/2018 |
| WO | WO 2019/089855 | 5/2019 |
| WO | WO 2019/090003 | 5/2019 |
| WO | WO 2019/113556 | 6/2019 |
| WO | WO 2019/113557 | 6/2019 |
| WO | WO 2020/033927 | 2/2020 |
| WO | WO 2020/092848 | 5/2020 |

OTHER PUBLICATIONS

Janas, M., et al (2015) Perfusion's Role in Maintenance of High-Density T-cell Cultures BioProcesses International pp. 1-12 (Year: 2015).*

Sun, J., et al (2015) Early transduction produces highly functional chimeric antigen receptor-modified virus-specific T-cells with central memory markers: a production assistant for Cell therapy (PACT) translational application Journal for Immuno Therapy of Cancer 3(5); 1-17 (Year: 2015).*

Klaver, Y., et al (2016) T cell Maturation Stage Prior to and During GMP Processing Informs on CAR T Cell Expansion in Patients Frontiers in Immunology 7(648); 1-7 (Year: 2016).*

Frayer, C.D., et al (2018) Mean Body Weight, Height, Waist circumference, and Body Mass Index Among Adults: United States 1999-2000 through 2015-2016 National Health Statistics Reports 122; 1-16 (Year: 2018).*

Applikon Biotechnology/BioPharma-Reporter (2016) How automation has changed the way we count cells BioPharma-Reporter.com; 1-4 (Year: 2016).*

Okern, G., et al (2015) CTS™ immune cell SR for serum free culture and expansion of human T cells Journal for Immuno Therapy of Cancer 3(suppl 2): P1 (Year: 2015).*

Life Technologies Corporation (2013) OpTmizer™CTS™MT-cell Expansion SFM Technical information; pp. 1-2 (Year: 2013).*

Berthois, Y., et al (1986) Phenol red in tissue culture media is a weak estrogen: Implications concerning the study of estrogen-responsive cells in culture Proc. Natl. Acad. Sci 83; 2496-2500 (Year: 1986).*

Navarro, F.C., and S.K. Watkins (2017) Estrogen Stimulation Differentially Impacts Human Male and Female Antigen-specific T cell Anti-Tumor Function and Polyfunctionality Gender and the Genome 1(4); 167-179 (Year: 2017).*

Hirakawa, M., et al (2015) IL-2, IL-7, IL-15, and IL-6 induce differential activation of naïve and memory T cell subsets Blood 126(23); 3425; pp. 1-4 (Year: 2015).*

U.S. Appl. No. 16/770,052, filed Jun. 4, 2020, by Pascal et al. (Copy not provided). (Copy not submitted herewith pursuant to the waiver of 37 C.F. R. § 1.98(a)(2)(iii) issued by the Office on Sep. 21, 2004).

(56)         References Cited

OTHER PUBLICATIONS

Abramson et al., "Transcend NHL 001: Ininunotherapy with the CD19-Directed CAR T-Cell Product JCARO17 Results in High Complete Response Rates in Relapsed or Refractory B-Cell Non-Hodgkin Lymphoma," Blood (2016) 128(22):4192.

Argarana et al., "Molecular cloning and nucleotide sequence of the streptavidin gene," Nucl Acids Res (1986) 14(4):1871-1882.

Aksoy et al., "Human primary T cells: a practical guide," dated Jun. 19, 2018. Retrieved from https://peerj.com/preprints/26993.html.

Al-Hujaily et al., "Development of novel immunotherapies for multiple myeloma," Int J Mol Sci. (2016) 17:1506.

Ali et al., "T cells expressing an anti-B-cell maturation antigen chimeric antigen receptor cause remissions of multiple myeloma," Blood (2016) 128 (13): 1688-1700.

Al-Lazikani et al., "Standard conformations for the canonical structures of immunoglobulins," J Mol Biol (1997) 273(4):927-948.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Anonymous, "Scientists helping scietists ™ | WWW Optimization of Human T Cell Expansion Protocol: Effects of Early Cell Dilution," (2018).

Barrett et al., "Chimeric Antigen Receptor Therapy for Cancer," Annu Rev Med (2014) 65:333-347.

Baum et al., "Retrovirus Vectors: Toward the plentivirus," Mol Ther (2006) 13:1050-1063.

Benson et al., "CS1-Directed monoclonal antibody therapy for multiple myeloma," J Clin Oncol (2012) 30(16):2012-2015.

Berdeja et al. First-in-human multicenter study of bb2121 anti-BCMA CAR T-cell therapy for relapsed/refractory multiple myeloma: Updated results. Journal of Clinical Oncology. 2017;35(15_suppl):3010-3010.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177):177ra38.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-1146.

Carrillo et al., "The multiple sequence alighment problem in biology," SIAM Journal of Applied Mathmathics (1988) 48(5):1073-1082.

Carpenter et al., "B-cell maturation antigen is a promising target for adoptive T-cell therapy of multiple myeloma," Clin Cancer Res. (2013) 19:2048-2060.

Cavaletti et al., "Chemotherapy-induced peripheral neurotoxicity," Nat Rev Neurol (2010) 6(12):657-666.

Cavalieri et al., "Human T lymphocytes transduced by lentiviral vectors in the absence of TCR activation maintain an intact immune competence," Blood (2003) 102(2): 497-505.

Chang et al., "Identification and selective expansion of functionally superior T cells expressing chimeric antigen receptors," J Transl Med (2015) 13(1):161.

Cheadle et al., "Chimeric antigen receptors for T-cell based therapy," Methods Mol Biol (2012) 907:645-666.

Chervin et al., "Engineering higher affinity T cell receptors using a T cell display system," J Immunol Methods. (2008) 339(2): 175-84.

Chicaybam et al., "An efficient low cost method for gene transfer to T lymphocytes," PLoS ONE (2013) 8(3): e60298.

Cho et al., "Human mammalian cell sorting using a highly integrated micro-fabricated fluorescence-activated cell sorfer (µFACS)," Lab on a Chip (2010) 10:1567-1573.

Chothia et al.,. "The outline structure of the T-cell alpha beta receptor," EMBO J. (1988) 7(12): 3745-55.

Chu et al., "CS1-specific chimeric antigen receptor (CAR)-engineered natural killer cells enhance in vitro and in vivo antitumor activity against human multiple myeloma," Leukemia (2014) 28(4):917-927.

Church et al., "Tumor-specific CD4+ T cells maintain effector and memory tumor-specific CD8+ T cells," Eur J Immunol (2014) 44: 69-79.

Clackson et al., "Making antibody fragments using phage display libraries," Nature (1991) 352(6336):624-628.

Cohen et al., "Recombinant antibodies with MHC-restricted, peptide-specific, T-cell receptor-like specificity: new tools to study antigen presentation and TCR-peptide-MHC interactions,"0 J Mol RecogN (2003) 16:324-332.

Cohen et al., "Recognition of Fresh Human Tumor by Human Peripheral Blood Lymphocytes Transduced with a Bicistronic Retroviral Vector Encoding a Murine Anti-p53 TCR," J Immunol (2005) 175(9):5799-5808.

Cooper et al., "T-cell clones can be rendered specific for CD19: toward the selective augmentation of the graft-versus-B-lineage leukemia effect," Blood. (2003) 101:1637-1644.

Cruz-Guilloty et al., "Runx3 and T-box proteins cooperate to establish the transcriptional program of effector CTLs," J Exp Med (2009) 206: 51-9.

Darling et al., "Kinetic exclusion assay technology: characterization of molecular interactions," Assay Drug Dev Technol. (2004) 2:647-657.

Davila et al., "CD19 CAR-targeted T cells induce long-term remission and B Cell Aplasia in an immunocompetent mouse model of B cell acute lymphoblastic leukemia," PLoS ONE (2013) 8(4): e61338.

Davila et al., "Efficacy and toxicity management of 19-28z CAR T cell therapy in B cell acute lymphoblastic leukemia," Science Translational Medicine (2014) 6(224):224ra25.

De Felipe et al., "Targeting of proteins derived from self-processing polyproteins containing multiple signal sequences," Trafic (2004) 5(8):616-626.

De Felipe, "Skipping the co-expression problem: the new 2A "Chysel" technology," Genetics Vaccines and Therapy (2004) 2:13.

Dimopoulos et al., "Current treatment landscape for relapsed and/or refractory multiple myeloma," Nat Rev Clin Oncol. (2015) 12:42-54.

Fairhead et al., "Plug-and-Play Pairing via Defined Divalent Streptavidins," J Mol Biol (2014) 426(1):199-214.

Fan et al., "Durable remissions with BCMA-specific chimeric antigen receptor (CAR)-modified T cells in patients with refractory/relapsed multiple myeloma," Journal of Clinical Oncology (2017) 35(18_suppl): LBA3001-LBA3001.

Fedorov et al., "PD-1- and CTLA-4-Based Inhibitory Chimeric Antigen Receptors (iCARs) Divert off-Target Immunotherapy Responses," Sci Transl Medicine (2013) 5(215):215ra172.

Fraietta et al., "Biomarkers of Response to Anti-CD19 Chimeric Antigen Receptor (CAR) T-Cell Therapy in Patients with Chronic Lymphocytic Leukemia," Blood (2016) 128(22):57.

Fraietta et al., "Determinants of response and resistance to CD19 chimeric antigen receptor (CAR) T cell therapy of chronic lymphocytic leukemia," Nat Med. (May 2018) 24(5):563-571. Epub Apr. 30, 2018.

Frecha et al., "Advances in the field of lentivector-based transduction of T and B lymphocytes for gene therapy," Mol Ther (2010) 18(10):1748-1757.

Garfall et al., "Immunotherapy with chimeric antigen receptors for multiple myeloma," Discov Med (2014) 17(91):37-46.

Gargett et al., "Different cytokine and stimulation conditions influence the expansion and immune phenotype of third-generation chimeric antigen receptor T cells specific for tumor antigen GD2," Cytotherapy (2015) 17(4):487-495.

Gattinoni et al., "T memory stem cells in health and disease," Nat Med (2017), 23: 18-27.

(56) References Cited

OTHER PUBLICATIONS

Gearing et al., "The international standard for human interleukin-2. Calibration by international collaborative study," J Immunological Methods (1988) 114(1-2):3-9.
Ghassemi et al., "Reducing Ex Vivo Culture Improves the Antileukemic Activity of Chimeric Antigen Receptor (CAR) T Cells", Cancer Immunol Res. (Sep. 2018) 6(9):1100-1109. Epub Jul. 20, 2018.
Godin et al., "Microfluidics and photonics for Bio-System-on-a-Chip: a review of advancements in technology towards a microfluidic flow cytometry chip," J Biophotonics (2008) 1(5):355-376.
Grupp et al., "Chimeric Antigen Receptor-Modified T Cells for Acute Lymphoid Leukemia," N Engl J Med (2013) 368:1509-1518.
Hackett et al., "A transposon and transposase system for human application," Molecular Therapy: The Journal of the American Society of Gene Therapy (2010) 18:674-683.
Hermans et al., "The VITAL assay: a versatile fluorometric technique for assessing CTL- and NKT-mediated cytotoxicity against multiple targets in vitro and in vivo," J Immunol Methods (2004) 285(1):25-40.
Holler et al., "In vitro evolution of a T cell receptor with high affinity for peptide/MHC," Proc Natl Acad Sci U S A. (2000) 97(10): 5387-5392.
Holler et al., "TCRs with high affinity for foreign pMHC show self-reactivity," Nat Immunol. Jan. 2003;4(1):55-62.
Honegger et al., "Yet another numbering scheme for immunoglobulin variable domains: an automatic modeling and analysis tool," J Mol Biol (2001) 309(3):657-670.
Howarth et al., "A monovalent streptavidin with a single femtomolar biotin binding site," Nature Methods (2006) 3:267-273
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res (2013) 19(12):3153-3164.
Hudecek et al., "The nonsignaling extracellular spacer domain of chimeric antigen receptors is decisive for in vivo antitumor activity," Cancer Immunol Res (2015) 3(2):125-135.
Hunziker et al., "Exhaustion of cytotoxic T cells during adoptive immunotherapy of virus carrier mice can be prevented by B cells or CD4+ T cells," Eur J Immunol (2002) 32(2):374-382.
Imadome, "The clinical condition and diagnosis of EBV-T/NK-LPD (CAEBV, EBV-HLH etc.)," [Rinsho Ketsueki] Japanese J Clin Hematol (2013) 54(10):1992-98. (Reference in Japanese).
Imamoto et al., "Advantages of AlaGln as an additive to cell culture medium: use with anti-CD20 chimeric antibody-producing POTELLIGENT™ CHO cell lines," Cytotechnology (2013) 65:135-143.
Irving et al., "Engineering Chimeric Antigen Receptor T-Cells for Racing in Solid Tumors: Don't Forget the Fuel," Front Immunol. (Apr. 3, 2017) 8:267.
Johnston, et al., "Biolistic transformation: microbes to mice," Nature (1990) 346: 776-777.
Jores et al., "Resolution of hypervariable regions in T-cell receptor beta chains by a modified Wu-Kabat index of amino acid diversity.," PNAS (1990) 87(23):9138-9142.
Kapustin et al., "Cryptic splice sites and split genes," Nucleic Acids Res. (2011) 39(14):5837-5844.
Klebanoff et al., "IL-15 enhances the in vivo antitumor activity of tumor-reactive CD8+ T cells," Proc Natl Acad Sci USA (2004) 101: 1969-74.
Klebanoff et al., "Sorting through subsets: which T-cell populations mediate highly effective adoptive immunotherapy?," J Immunother. (2012) 35(9): 651-660.
Kochenderfer et al., "B-cell depletion and remissions of malignancy along with cytokine-associated toxicity in a clinical trial of anti-CD19 chimeric-antigen-receptor-transduced T cells," Blood (2012) 119(12):2709-2720.
Kochenderfer et al., "Construction and preclinical evaluation of an anti-CD19 chimeric antigen receptor," J. Immunotherapy (2009) 32(7): 689-702.

Kochenderfer et al., "Treating B-cell cancer with T cells expressing anti-CD19 chimeric antigen receptors," Nature Reviews Clinical Oncology (2013) 10:267-276.
Koste et al., "T-cell receptor transfer into human T cells with ecotropic retroviral vectors," Gene Therapy (2014) 21: 533-538.
Kotb, "Bacterial pyrogenic exotoxins as superantigens," Clin Microbiol Rev. (1995) 8(3):411-426.
Kurucz et al., "A bacterially expressed single-chain Fv construct from the 2B4 T-cell receptor," Proc Natl Acad Sci U S A. (1993) 90(9): 3830-3834.
Lada et al., "Quantitation of integrated HIV provirus by pulsed-field gel electrophoresis and droplet digital PCR," J Clin Microbiol (2018) 56(12):e01158.
Lee et al., "Current concepts in the diagnosis and management of cytokine release syndrome," Blood (2014) 124(2):188-195.
Lefranc et al., "IMGT unique numbering for immunoglobulin and T cell receptor variable domains and Ig superfamily V-like domains," Dev Comp Immunol (2003) 27(1):55-77.
Li et al., "Multiparameter cell affinity chromatography: Separation and analysis in a single microfluidic channel," Anal Chem (2012) 84(19):8140-8148.
Li et al., "Directed evolution of human T-cell receptors with picomolar affinities by phage display," Nature Biotechnology (2005) 23:349-354.
Li et al., "Comparison of anti-CD3 and anti-CD28-coated beads with soluble anti-CD3 for expanding human T cells: Differing impact on CD8 T cell phenotype and responsiveness to restimulation," J Transl Med (2010) 8(1):104.
Ll et al., "Comparison of inlet geomery in microfluidic cell affinity chromatography," Analytical chemistry (2011) 83(3):774-781.
Li et al., "Negative enrichment of target cells by microfluidic affinity chromatography," Analytical Chemistry (2011) 83(20):7863-7869.
Llm et al., "Engineered streptavidin monomer and dimer with improved stability and function," Biochemistry (2010) 50:8682-8691.
Ling et al., "B-cell and plasma cell antigens: new and previously defined clusters," Leucocyte typing III. (1987) 302-355.
Liu et al., "Inclusion of Strep-tag II in design of antigen receptors for T-cell immunotherapy," Nature Biotechnology (2016) 34(4):430-434.
Lu et al., "A Rapid Cell Expansion Process for Production of Engineered Autologous CAR-T Cell Therapies," Human Gene Therapy Methods (2016) 27(6):209-218.
Lupton et al., "Dominant positive and negative selection using a hygromycin phosphotransferase-Thymidine kinase dusion gene," Molecular and cellular biology (1991) 11(6):3374-3378.
MacCallum et al., "Antibody-antigen interactions: contact analysis and binding site topography," J Mol Biol (1996) 262(5):732-745.
Manuri et al., "piggyBac transposon/transposase system to generate CD19-specific T cells for the treatment of B-lineage malignancies," Hum Gene Ther (2010) 21(4): 427-437.
Martin et al., "Modeling antibody hypervariable loops: a combined algorithm," PNAS (1989) 86(23):9268-9272.
Miller et al., "Improved retroviral vectors for gene transfer and expression," BioTechniques (1989) 7:980-990.
Miller et al., "Retrovirus packaging cells," Human Gene Therapy (1990) 1:5-14.
Naldini et al., "Lentiviruses as gene transfer agents for delivery to non-dividing cells", Curr Opin Biotechnol., Oct. 9, 1998; 5:457-63.
Neeson et al., "Ex vivo culture of chimeric antigen receptor T cells generates functional CD8+ T cells with effector and central memory-like phenotype," Gene Therapy (2010) 17(9):1105-1116.
Okamoto et al., "A promising vector for TCR gene therapy: differential effect of siRNA, 2A peptide, and disulfide bond on the introduced TCR expression," Mol Ther Nucl Acids (2012) 1(12):1-11.
Park et al., "Treating cancer with genetically engineered T cells," Trends Biotechnol. (2011) 29(11): 550-557.
Parkhurst et al., "Characterization of genetically modified T-cell receptors that recognize the CEA:691-699 peptide in the context of HLA-A2.1 on human colorectal cancer cells," Clin Cancer Res (2009) 15:169-180.

(56)          References Cited

OTHER PUBLICATIONS

Portolano et al., "Lack of promiscuity in autoantigen-specific H and L chain combinations as revealed by human H and L chain "roulette"," J Immunol (1993) 150(3):880-887.

Pullagurla et al., "Parallel affinity-based isolation of leukocyte subsets using microfluidics: application for stroke diagnosis," Analytical chemistry (2014) 86(8):4058-4065.

Riddell et al., "The Fred Hutchinson Cancer Research Center and the University of Washington School of Medicine, Department of Medicine, Division of Oncology Oct. 7, 1991," Human Gene Therapy (1992) 3:319-338.

Rosenberg, et al., "Cell transfer immunotherapy for metastatic solid cancer—what clinicians need to know," Nat Rev Clin Oncol. (2011) 8(10):577-85.

Sadelain et al., "The basic principles of chimeric antigen receptor design," Cancer Discov. (2013) 3(4): 388-398.

Scarpa et al., "Characterization of recombinant helper retroviruses from Moloney-based vectors in ecotropic and amphotropic packaging cell lines," Virology (1991) 180:849-852.

Schlueter et al., "Specificity and Binding Properties of a Single-chain T Cell Receptor," J Mol Biol (1996) 859-869.

Schuler et al., SYFPEITHI, Database for Searching and T-Cell Epitope Prediction. in Immunoinformatics Methods in Molecular Biology, (2007) 409(1): 75-93.

Sharma et al., "Efficient sleeping beauty DNA transposition from DNA minicircles," Molec Ther Nucl Acids (2013) 2, e74.

Singh et al., "ProPred: prediction of HLA-DR binding sites," Bioinformatics. (2001) 17(12): 1236-1237.

Smith et al., "Ex vivo expansion of human T cells for adoptive immunotherapy using the novel xeno-free CTS immune cell serum replacement," Clin Transl Immunol (2015) 4:e31.

Soman et al., "MTS dye based colorimetric CTLL-2 cell proliferation assay for product release and stability monitoring of interleukin-15: assay qualification, standardization and statistical analysis," J Immunol Methods (2009) 348(1-2):83-94.

Sommermeyer et al., "Chimeric antigen receptor-modified T cells derived from defined CD8+ and CD4+ subsets confer superior antitumor reactivity in vivo," Leukemia (2016) 30: 492-500.

Soo Hoo et al., "Characterization of a single-chain T-cell receptor expressed in Escherichia coli," Proc Natl Acad Sci U S A. (1992) 89(10): 4759-4763.

Stemberger et al., "Novel Serial Positive Enrichment Technology Enables Clinical Multiparameter Cell Sorting," PLoS One (2012) 7(4): e35798.

Sun et al., "Defective CD8 T cell memory following acute infection without CD4 T cell help," Science (2003) 300: 339-42.

Tai et al., "Targeting B-cell maturation antigen in multiple myeloma," Immunotherapy (2015) 7:1187-1199.

Terakura et al., "Generation of CD19-chimeric antigen receptor modified CD8+ T cells derived from virus-specific central memory T cells," Blood (2012) 1:72-82.

Themeli et al., "Generation of tumor-targeted human T lymphocytes from induced pluripotent stem cells for cancer therapy," Nat Biotechnol. (2013) 31(10): 928-933.

Tran et al., "Minimally cultured tumor-infiltrating lymphocytes display optimal characteristics for adoptive cell therapy," J Immunother (2008) 31: 742-51.

Tsukahara et al., "CD19 target-engineered T-cells accumulate at tumor lesions in human B-cell lymphoma xenograft mouse models," Biochem Biophys Res Commun (2013) 438(1): 84-89.

Turtle et al., "CD19 CAR-T cells of defined CD4+:CD8+ composition in adult B cell ALL patients," J. Clin. Invest. (2016) 126(6):2123-38.

Turtle et al., "Engineered T cells for anti-cancer therapy," Curr. Opin. Immunol. (2012) 24(5): 633-39.

Van Tendeloo et al., "High-level transgene expression in primary human T lymphocytes and adult bone marrow CD34+ cells via electroporation-mediated gene delivery," Gene Therapy (2000) 7(16): 1431-1437).

Varela-Rohena et al., "Control of HIV-1 immune escape by CD8 T cells expressing enhanced T-cell receptor," Nature Medicine (2008) 14(12):1390-1395.

Venkateshaiah et al., "GPRC5D Is a Cell Surface Plasma Cell Marker Whose Expression Is High in Myeloma Cells and Reduced Following Coculture With Osteoclasts," Blood (2013) 122 (21): 3099.

Verhoeyen et al., "Lentiviral vector gene transfer into human T cells," Methods Mol Biol. (2009) 506: 97-114.

Vormittag et al., "A guide to manufacturing CAR T cell therapies," Curr Opin in Biotechnology (2018) 53:164-181.

Wadhwa et al., "Receptor mediated glycotargeting," J. Drug Targeting (1995) 3: 111.

Wadhwa et al., "Strategies for detection, measurement and characterization of unwanted antibodies induced by therapeutic biologicals," J Immunol Methods (2003) 278(1-2):1-17.

Wang et al., "Clinical manufacturing of CAR T cells: foundation of a promising therapy," Molecular Therapy—Oncolytics (2016) 3:16015.

Wang et al., "Phenotypic and functional attributes of lentivirus-modified CD19-specific human CD8+ central memory T cells manufactured at clinical scale," J Immunother. (2012) 35(9):689-701.

Wang et al., "Open-tubular capillary cell affinity chromatography: single and tandem blood cell separation," Anal Chem (2008) 80(6):2118-2124.

Wu et al., "Adoptive T-cell therapy using autologous tumor-infiltrating lymphocytes for metastatic melanoma: current status and future outlook," Cancer (2012) 18(2): 160-175.

Wu et al., "Engineering soluble monomeric streptavidin with reversible biotin binding capability," J Biol Chem (2005) 280(24):23225-23231.

Wulflng et al., "Correctly folded T-cell receptor fragments in the periplasm of Escherichia coli. Influence of folding catalysts," J Mol Biol. (1994) 242(5): 655-669.

Xu et al., "Cytokine release syndrome in cancer immunotherapy with chimeric antigen receptor engineered T cells," Cancer Letters (2014) 343(2):172-178.

Xu et al., "Multiparameter comparative analysis reveals differential impacts of various cytokines on CART cell phenotype and function ex vivo and in vivo," Oncotarget (2016) 7(50):82354-82368.

Xu et al., "Closely related T-memory stem cells correlate with in vivo expansion of CAR.CD19-T cells and are preserved by IL-7 and IL-15," Blood (2014) 123(24):3750-3759.

Yarilin, "Immunology principles," M. Medicine (1999) 184-195, 339-347 (English Translation included).

Zhao et al., "Development of the First World Health Organization Lentiviral Vector Standard: Toward the production control and standardization of lentivirus-based gene therapy products," Human Gene Therapy Methods (2017) 28(4):205-214.

Zhang et al., "A novel approach to make homogeneous protease-stable monovalent streptavidin," Biochem Biophys Res Commun (2015) 463(4):1059-1063.

Brown et al., "Structure-Based Mutagenesis of the Human Immunodeficiency Virus Type 1 DNA Attachment Site: Effects on Integration and cDNA Synthesis," J Viral (1999) 73(11):9011-9020.

Cheson et al., "Recommendations for initial evaluation, staging, and response assessment of Hodgkin and non-Hodgkin lymphoma: the Lugano classification," J Clin Oncol (2014) 32(27):3059-3068.

Coustan-Smith et al., "Immunological detection of minimal residual disease in children with acute lymphoblastic leukaemia," Lancet (1998) 351(9102):P550-554.

Eaker et al., "Concise review: guidance in developing commercializable autologous/patient-specific cell therapy manufacturing," Stem Cells Transl Med. (2013) 2(11): 871-83.

Entschladen et al., "Differential requirement of protein tyrosine kinases and protein kinase C in the regulation of T cell locomotion in three-dimensional collagen matrices," J Immunol. (1997) 159(7): 3203-3210.

Fraietta et al., "Identification of functional determinants of response and resistance to CD19 chimeric antigen receptor (CAR) T-cell therapy if chronic lymphocytic leukemia," Blood (2017) 130:3181.

(56)                    References Cited

OTHER PUBLICATIONS

Gardner et al., "Intent to treat leukemia remission by CD19CAR T cells of defined formulation and dose in children and young adults," Blood (2017) 129(25):3322-3331.

Ghobadi et al., "Chimeric antigen receptor T cell therapy for non-Hodgkin lymphoma," Curr Res Transl Med (2018) 66(2):43-49.

Hallek et al., "Guidelines for the diagnosis and treatment of chronic lymphocytic leukemia: a report from the International Workshop on Chronic Lymphocytic Leukemia updating the National Cancer Institute-Working Group 1996 guidelines," Blood (2008) 111(12):5446-5456.

Harrington et al., "Development of JCARH125: Optimization of a Fully Human Anti-Bcma CAR for Use in the Treatment of Multiple Myeloma," Blood (2017) 130(Suppl_1):1813.

Johnson et al., "Imaging for Staging and Response Assessment in Lymphoma," Radiology (2015) 276(2):323-338.

Kisielow et al., "Ly antigens as markers for functionally distinct subpopulations of thymus-derived lymphocytes of the mouse," Nature (1975) 253: 219-20.

Kindt et al., "Antigens and Antibodies," in Chapter 4 of Kuby Immunology, 6th ed., W.H. Freeman and Co., N.Y, (2007) pp. 91, 14 pages.

Lee et al., "T cells expressing CD19 chimeric antigen receptors for acute lymphoblastic leukaemia in children and young adults: a phase 1 dose-escalation trial." The Lancet (2015) 385(9967) : 517-528.

Long et al., "4-1BB Costimulation Ameliorates T Cell Exhaustion Induced by Tonic Signaling of Chimeric Antigen Receptors," Nat Med (2015) 21(6):581-590.

Mailankody et al., "JCARH125, Anti-BCMA CAR T-cell Therapy for Relapsed/Refractory Multiple Myeloma: Initial Proof of Concept Results from a Phase ½ Multicenter Study (EVOLVE)," Oral Presentation 957 at 2018 American Society of Hematology Annual Meeting, Dec. 1-4, 2018.

Mailankody et al., "JCARH125, Anti-BCMA CAR T-cell Therapy for Relapsed/Refractory Multiple Myeloma: Initial Proof of Concept Results from a Phase ½ Multicenter Study (EVOLVE)," Blood (2018) 132(Supplement 1):957.

Maude et al., "Tisagenlecleucel in Children and Young Adults with B-Cell Lymphoblastic Leukemia," New Engl J Med (2018) 378(5):439-448.

McWilliams et al., "Mutations in the 5' end of the human immunodeficiency virus type 1 polypurine tract affect RNase H cleavage specificity and virus titer," J Viral (2003) 77(20):11150-11157.

Philpott et al., "Use of Nonintegrating Lentiviral Vectors for Gene Therapy," Human Gene Therapy (2007) 18:483.

Rajkumar et al., "International Myeloma Working Group updated criteria for the diagnosis of multiple myeloma," Lancet Oncol (2014) 15:e538-48.

Seckinger et al., "Target Expression, Generation, Preclinical Activity, and Pharmacokinetics of the BCMA-T Cell Bispecific Antibody EM801 for Multiple Myeloma Treatment," Cancer Cell (2017) 31:396-410.

Singh et al., "Early memory phenotypes drive T cell proliferation in patients with pediatric malignancies," Sci Transl Med (2016) 8(320):320ra3.

Smith et al., "Development and Evaluation of an Optimal Human Single-Chain Variable Fragment-Derived BCMA-Targeted Car T Cell Vector," Mol Ther (2018) 26(6):1447-1456.

Tai et al., "Antibody-Based Therapies in Multiple Myeloma," Bone Marrow Research (2010) vol. 2011. Article ID 924058.

U.S. Appl. No. 17/850,875, filed Jun. 27, 2022, by Ramsborg et al.

U.S. Appl. No. 17/353,648, filed Jun. 21, 2021, by Blythe et al.

Casati et al., "Clinical-scale selection and viral transduction of human naïve and central memory CD8+ T cells for adoptive cell therapy of cancer patients," Cancer Immunology (2013) 62(10):1563-1573.

Gacerez et al., "How Chimeric Antigen Receptor Design Affects Adoptive T Cell Therapy," J Cell Physiol. (2016) 231(12): 2590-2598.

Garfall et al., "Posterior Reversible Encephalopathy Syndrome (PRES) after infusion of anti-Bcma CAR T cells (CART-BCMA) for multiple myeloma: Successful Treatment with Cyclophophamide," Blood (2016) 128(22):5702.

Gunzer et al.,, "Two-step negative enrichment of CD4+ and CD8+ T cells from murine spleen via nylon wool adherence and an optimized antibody cocktail," J Immunol Methods. (2001) 258(1-2): 55-63.

Larson et al., "Defined cell composition and precise control over JCAR017 dose enables identification of relationships between chimeric antigen receptor T cell product attributes, pharmacokinetics, and clinical endpoints in NHL", Cancer Res (Jul. 1, 2018) 78(13 Supplement): 960.

Larson et al., "Defined cell composition and precise control over JCAR017 dose enables identification of relationships between chimeric antigen receptor T cell product attributes, pharmacokinetics, and clinical endpoints in NHL", Poster 960 Presentation at 2018 AACR Annual Meeting, Apr. 14-18, 2018.

Medvec et al., "Improved Expansion and In Vivo Function of Patient T Cells by a Serum-free Medium," Mol Ther Methods Clin Dev. (2017) 8:65-74.

Milone et al., "Chimeric Receptors Containing CD137 Signal Transduction Domains Mediate Enhanced Survival of T Cells and Increased Antileukemic Efficacy In Vivo," Mol Ther (2009) 17(8):1453-64.

Moeller et al., "Adoptive transfer of gene-engineered CD4+ helper T cells induces potent primary and secondary tumor rejection," Blood (2005) 106(9):2995-3003.

Nascimbeni et al., "Peripheral CD4+CD8+ T cells are differentiated effector memory cells with antiviral functions," Blood (2004) 104(2):478-86.

Ormhoj et al., "CARs in the lead against Multiple Myeloma," Curr Hematol Malig Rep. (2017) 12(2): 119-125.

Skea et al., "The selective expansion of functional T cell subsets," J Hematother Stem Cell Res. (1999) 8(5): 525-38.

Turtle et al., "Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes," Blood (2015) 126:184.

Turtle et al., "Immunotherapy of non-Hodgkin's lymphoma with a defined ratio of CD8+ and CD4+ CD19-specific chimeric antigen receptor-modified T cells," Sci Transl Med (2016) 8(355):355ra116.

Al-Shanti et al., "Human purified CD8+ T cells: Ex vivo expansion model to generate a maximum yield of functional cytotoxic cells," Immunol Invest. (2007);36(1):85-104.

Anson et al., "An improved β-galactosidase reporter gene," Journal of Biotechnology (2004) 108:17-30.

Bondanza et al., "IL-7 receptor expression identifies suicide gene-modified allospecific CD8+ T cells capable of self-renewal and differentiation into antileukemia effectors," Blood. (2011) 117(24):6469-78.

Chang et al., "Investigation of interfacial properties of pure and mixed poloxamers for surfactant-mediated shear protection of mammalian cells," Colloids Surf B Biointerfaces. (2017) 156:358-365.

Davis et al., "Assessment of a positive selection technique using an avidin column to isolate human peripheral blood T cell subsets," J Immunol Methods. (1994) 175(2):247-57.

Ex-Cell 302. Material Safety Data Sheet. SAFC Bioscience. p. 1-2. (Year: 2006).

Fernandes et al., "Kinetics of class II MHC expression on cytotoxic T cells generated by skin allograft," Tissue Antigens. (1990) 36(3):93-9.

Finney et al., "Activation of resting human primary T cells with chimeric receptors: costimulation from CD28, inducible costimulator, CD134, and CD137 in series with signals from the TCR zeta chain," J Immunol. (2004) 172(1):104-13.

GlutaMAX-1. Gibco. p. 1 (Year: 2010).

Harrington et al., "JCARH125: Development of an Optimized Fully Human Anti-BCMA CAR for the Treatment of Multiple Myeloma",

(56)  References Cited

OTHER PUBLICATIONS

Poster Presentation 1813 at 2017 American Society of Hematology Annual Meeting, Dec. 9-12, 2017.
Imadome, "The clinical condition and diagnosis of EBV-T/NK-LPD (CAEBV, EBV-HLH etc.)," [Rinsho Ketsueki] Japanese J Clin Hematol (2013) 54(10):1992-98. (Reference in Japanese) English Translation provided.
Jeon et al. Development of a serum-free medium for in vitro expansion of human cytotoxic T lymphocytes using a statistical design. BMC Biotechnology 2010, 10:70. p. 1-9 (Year: 2010).
Karnieli et al. A consensus introduction to serum replacements and serum-free media for cellular therapies. Cytotherapy, 2017; 19: 155-169 (Year: 2017).
Kemper et al., "Label-free quantitative cell division monitoring of endothelial cells by digital holographic microscopy," J Biomed Opt. (2010) 15(3):036009.
Levine et al., "Global manufacturing of CAR T cell therapy" Mol. Ther. Methods & Clin. Dev. (2016) 4: 92-101.
Mak et al., "Glutathione Primes T Cell Metabolism for Inflammation," Immunity. (2017) 46(4):675-689.
Marthandan et al., "An investigation of the effects of the antioxidants, ebselen or N-acetyl cysteine on human peripheral blood mononuclear cells and T cells," Immun Ageing. (2013) 10(1):7.
Pearce et al., "Control of effector CD8+ T cell function by the transcription factor Eomesodermin," Science (2003) 302: 1041-3.
Presnyak et al., "Codon optimality is a major determinant of mRNA stability," Cell (2015) 160(6):1111-1124.
Ramsborg et al., "JCAR017 Is a Defined Composition CAR T Cell Product with Product and Process Controls That Deliver Precise Doses of CD4 and CD8 CAR T Cell to Patients with NHL", Poster 4471 Presentation at 2017 American Society of Hematology, Dec. 9-12, 2017.
RPMI-1640 medium. Sigma-Aldrich. p. 1-2 (Year: 2007).
Technical Bulletin. Animal-Component Free Recombinant Human Insulin is Suitable for Use in Serum-Free Media. SAFC Bioscience. p. 1-4 (Year: 2006).
Yanagi, et al., "Transcripts from a single full-length cDNA clone of hepatitis C virus are infectious when directly transfected into the liver of a chimpanzee,"PNAS, vol. 94(16), Aug. 5, 1997, p. 8738-8743
Abou-El-Enein et al., "Scalable Manufacturing of CAR T cells for Cancer Immunotherapy," Blood Cancer Discov (2021) 2(5):408-422.
Akron Biotech "Exceptional purity, consistency and performance. Expand T-Cells and NK-Cells with Akron's cGMP IL-15," (2023):1-9.
Colonna et al., "Orvacabtagene Autoleucel (orva-cel; JCARH125): a Fully Human BCMA-Targeted Second-Generation CAR T Cell Product Characterized by a Predominant Central Memory Phenotype with High in Vitro and In Vivo Proliferative Potential and Sustained in Vivo Persistence," Blood (2020) 136 (Supplement 1): 11-12.
Dong, Modern Biology, Beijing Institute of Technology Press, 1st edition, p. 328, Jul. 31, 2016 (Article in Chinese; English translation provided).
Dupont et al., "Comparative dose-responses of recombinant human IL-2 and IL-7 on STAT5 phosphorylation in CD4+FOXP3- cells versus regulatory T cells: a whole blood perspective," Cytokine. (2014) 69(1):146-9.
Hinrichs et al., "Human effector CD8+ T cells derived from naive rather than memory subsets possess superior traits for adoptive immunotherapy," Blood. (2011) 117(3):808-14.
Huang et al., "Genetic Engineering Antibody,"South China University of Technology Press (Dec. 1997): p. 63. English translation provided.
Jethwa et al., "Use of gene-modified regulatory T-cells to control autoimmune and alloimmune pathology: is now the right time?" Clin Immunol. (2014) 150(1):51-63.

Jonnalagadda et al., "Chimeric antigen receptors with mutated IgG4 Fc spacer avoid fc receptor binding and improve T cell persistence and antitumor efficacy," Mol Ther. (2015) 23(4):757-68.
Kaartinen et al., "Low interleukin-2 concentration favors generation of early memory T cells over effector phenotypes during chimeric antigen receptor T-cell expansion," Cytotherapy (2017) 19(6):689-702.
Katz et al., "Therapeutic targeting of CD19 in hematological malignancies: past, present, future and beyond." Leuk Lymphoma. (2014) 55(5):999-1006.
Marenghi et al., "The role of perfusion in maintaining high density T-cell cultures," GE (2014):1-2.
Mei et al., "Rationale of anti-CD19 immunotherapy: an option to target autoreactive plasma cells in autoimmunity," Arthritis Res Ther. (2012) 14 Suppl 5(Suppl 5):S1.
NCBI Gene, "TNFRSF17 TNF receptorsuperfamily member 17 [*Homo sapiens* (human)]," Updated Sep. 7, 2023, 6 pages.
Poltorak et al., "Expamers: a new technology to control T cell activation," Sci Rep. (2020) 10(1):17832.
Qian et al., "Advances in the Development of Interleukin-2 and its Analogues," Chinese Journal of Pharmaceuticals. (2020) 947-955. (Article in Chinese; English abstract provided).
Qian et al., "Progress of Engineering Chimeric Antigen Receptor in Tumor Therapy," Letters in Biotechnology. (2017) 28:2; 188-195. (Article in Chinese; English abstract provided).
Qin et al., "Incorporation of a hinge domain improves the expansion of chimeric antigen receptor T cells," J Hematol Oncol. (2017) 10(1):68.
RPM 1640. catalog #32404, downloaded from https ://www.thermofisher.com/us/en/home/technical-resources/media-formulation.192.html. p. 1-2 (Year: 2023).
Thermo Fisher Scientific "Glutamax Supplement can keep your cells healthier for longer," Retrieved on Sep. 22, 2023, 3 pages.
Who unit chart. PeproTech. downloaded from https://www.peprotech .com/en/who-unit-chart. p. 1-2 (Year: 2023).
Amos et al., "The role of caspase 3 and BclxL in the action of interleukin 7 (IL-7): a survival factor in activated human T cells," Cytokine. (1998) 10(9):662-8.
Beckman et al., "Antibody constructs in cancer therapy: protein engineering strategies to improve exposure in solid tumors," Cancer (2007) 109(2):170-179.
Cespedes et al., "Mouse models in oncogenesis and cancer therapy," Clin Transl Oncol (2006) 8(5):318-329.
Dennis, "Off by a whisker," Nature (2006) 442:739-741.
Fujimori et al., "A Modeling Analysis of Monoclonal Antibody Percolation Through Tumors: a Binding-Site Barrier," J Nucl Med (1990) 31(7):1191-1198.
Hou et al., "Tutorial on Animal Cell Culture Techniques," Gansu Science and Technology Press (2009) 520, Chapter 9, p. 105. (Article in Chinese; English translation provided).
Huang et al., "Recombinant immunotherapeutics: current state and perspectives regarding the feasibility of the market," Appl. Microbiol. Biotechnol. (2010) 87:401-410.
Jiang Bo, Fundamentals and Clinics of Apoptosis, People's Military Medical Press, p. 141, Jul. 1999 (Reference in Chinese; English translation provided).
Rudnick et al., "Affinity and Avidity in Antibody-Based Tumor Targeting." Cancer Biother Radiopharm (2009) 24(2):155-161.
Saligrama et al., "IL-15 maintains T-cell survival via S-nitrosylation-mediated inhibition of caspase-3," Cell Death Differ. (2014) 21(6):904-14.
Talmadge et al., "Murine Models to Evaluate Novel and Conventional Therapeutic Strategies for Cancer," Am J Pathol (2007) 170(3):793-804.
Thurber et al., "Antibody tumor penetration: transport opposed by systemic and antigen-mediated clearance," Adv Drug Deliv Rev (2008) 60(12):1421-1434.
Voskoglou-Nomikos et al., "Clinical Predictive Value of the in Vitro Cell Line, Human Xenograft, and Mouse Allograft Preclinical Cancer Models," Clin Can Res (2003) 9:4227-4239.
Akbar et al., "A compact vocabulary of paratope-epitope interactions enables predictability of antibody-antigen binding," Cell Reports (Mar. 16, 2021) 34(11):108856, 21 pages.

(56) References Cited

OTHER PUBLICATIONS

Litvinova et al., "The influence of immunoregulatory cytokines IL-2, IL-7, and IL-15 upon activation, proliferation, and apoptosis of immune memory T-cells in vitro," Cell and Tissue Biology (2013) 7(6):539-544.

Lo et al., "Conformational epitope matching and prediction based on protein surface spiral features," BMC Genomics (May 31, 2021) 22:116, 16 pages.

Mackensen et al., "Anti-CD19 CAR T cell therapy for refractory systemic lupus erythematosus," Nat Med (2022) 28(10):2124-2132 and Supplementary Materials.

Marks et al., "How repertoire data are changing antibody science," J. Biol. Chem. (Jul. 2020) 295(29):9823-9837.

Mougiakakos et al., "CD19-Targeted CAR T Cells in Refractory Systemic Lupus Erythematosus," N Engl J Med (2021) 385(6):567-569 and Supplementary Appendix.

Salmon, "Arming T cells against B cells in systemic lupus erythematosus," Nat Med (2022) 28(10):2009-2010.

Smith et al., "Development and Evaluation of a Human Single Chain Variable Fragment (scFv) Derived BCMA Targeted CAR T Cell Vector Leads to a High Objective Response Rate in Patients with Advanced MM," Blood (2017) 130:742, 6 pages.

Vajda et al., "Progress toward improved understanding of antibody maturation," Current Opinion in Structural Biology (Apr. 2021) 67:226-231.

Weigmann, "Cell Isolation of Spleen Mononuclear Cells," Bio-Protocol (2013) 3(9):4 pages.

* cited by examiner

Average CD45RA/CCR7+ CD4/CD8 Ratio based on donor

Average %CD62L-/CCR7+ CD4/CD8 Ratio

Bivariate Fit of CAR+ CD4/CD8 Ratio by
Incoming %CD45RA+CCR7+ CD4/CD8 Ratio

Bivariate Fit of CAR+ CD4/CD8 Ratio by
Incoming %CD62L-CCR7+ CD4/CD8 Ratio

SEQUENCE LISTING

<160> NUMBER OF SEQ ID NOS: 94

<210> SEQ ID NO 1
<211> LENGTH: 12
<212> TYPE: PRT
<213> ORGANISM: Homo sapiens
<220> FEATURE:
<223> OTHER INFORMATION: Spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: Spacer (IgG4hinge)

<400> SEQUENCE: 2
gaatctaagt acggaccgcc ctgcccccct tgccct                                    36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
                20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
        50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
                100                 105                 110

Leu Ser Leu Ser Leu Gly Lys
            115

<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

-continued

```
Ser Gln Glu Asp Pro Glu Val Gln Phe Asn Trp Tyr Val Asp Gly Val
    50              55              60

Glu Val His Asn Ala Lys Thr Lys Pro Arg Glu Glu Gln Phe Asn Ser
65              70              75              80

Thr Tyr Arg Val Val Ser Val Leu Thr Val Leu His Gln Asp Trp Leu
                85              90              95

Asn Gly Lys Glu Tyr Lys Cys Lys Val Ser Asn Lys Gly Leu Pro Ser
            100             105             110

Ser Ile Glu Lys Thr Ile Ser Lys Ala Lys Gly Gln Pro Arg Glu Pro
            115             120             125

Gln Val Tyr Thr Leu Pro Pro Ser Gln Glu Glu Met Thr Lys Asn Gln
    130             135             140

Val Ser Leu Thr Cys Leu Val Lys Gly Phe Tyr Pro Ser Asp Ile Ala
145             150             155             160

Val Glu Trp Glu Ser Asn Gly Gln Pro Glu Asn Asn Tyr Lys Thr Thr
                165             170             175

Pro Pro Val Leu Asp Ser Asp Gly Ser Phe Phe Leu Tyr Ser Arg Leu
            180             185             190

Thr Val Asp Lys Ser Arg Trp Gln Glu Gly Asn Val Phe Ser Cys Ser
            195             200             205

Val Met His Glu Ala Leu His Asn His Tyr Thr Gln Lys Ser Leu Ser
    210             215             220

Leu Ser Leu Gly Lys
225

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5               10              15

Gln Pro Gln Ala Glu Gly Ser Leu Ala Lys Ala Thr Thr Ala Pro Ala
            20              25              30

Thr Thr Arg Asn Thr Gly Arg Gly Gly Glu Glu Lys Lys Lys Glu Lys
            35              40              45

Glu Lys Glu Glu Gln Glu Glu Arg Glu Thr Lys Thr Pro Glu Cys Pro
    50              55              60

Ser His Thr Gln Pro Leu Gly Val Tyr Leu Leu Thr Pro Ala Val Gln
65              70              75              80

Asp Leu Trp Leu Arg Asp Lys Ala Thr Phe Thr Cys Phe Val Val Gly
                85              90              95

Ser Asp Leu Lys Asp Ala His Leu Thr Trp Glu Val Ala Gly Lys Val
            100             105             110

Pro Thr Gly Gly Val Glu Glu Gly Leu Leu Glu Arg His Ser Asn Gly
            115             120             125

Ser Gln Ser Gln His Ser Arg Leu Thr Leu Pro Arg Ser Leu Trp Asn
    130             135             140

Ala Gly Thr Ser Val Thr Cys Thr Leu Asn His Pro Ser Leu Pro Pro
145             150             155             160

Gln Arg Leu Met Ala Leu Arg Glu Pro Ala Ala Gln Ala Pro Val Lys
                165             170             175
```

```
Leu Ser Leu Asn Leu Leu Ala Ser Ser Asp Pro Pro Glu Ala Ala Ser
        180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His
        275                 280
```

```
<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg
                20
```

```
<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
                100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160
```

```
Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
                180                 185                 190

Gln Val Cys His Ala Leu Cys Ser Pro Glu Gly Cys Trp Gly Pro Glu
                195                 200                 205

Pro Arg Asp Cys Val Ser Cys Arg Asn Val Ser Arg Gly Arg Glu Cys
        210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
                260                 265                 270

His Tyr Ile Asp Gly Pro His Cys Val Lys Thr Cys Pro Ala Gly Val
                275                 280                 285

Met Gly Glu Asn Asn Thr Leu Val Trp Lys Tyr Ala Asp Ala Gly His
        290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
                340                 345                 350

Ile Gly Leu Phe Met
        355

<210> SEQ ID NO 8
<211> LENGTH: 27
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
                20                  25

<210> SEQ ID NO 9
<211> LENGTH: 66
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30
```

```
Phe Pro Gly Pro Ser Lys Pro Phe Trp Val Leu Val Val Val Gly Gly
        35              40              45

Val Leu Ala Cys Tyr Ser Leu Leu Val Thr Val Ala Phe Ile Ile Phe
    50              55              60

Trp Val
65

<210> SEQ ID NO 10
<211> LENGTH: 41
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 10

Arg Ser Lys Arg Ser Arg Leu Leu His Ser Asp Tyr Met Asn Met Thr
1               5               10              15

Pro Arg Arg Pro Gly Pro Thr Arg Lys His Tyr Gln Pro Tyr Ala Pro
            20              25              30

Pro Arg Asp Phe Ala Ala Tyr Arg Ser
        35              40

<210> SEQ ID NO 11
<211> LENGTH: 41
<212> TYPE: PRT
<213> ORGANISM: Homo sapiens
<220> FEATURE:
<223> OTHER INFORMATION: CD28

<400> SEQUENCE: 11

Arg Ser Lys Arg Ser Arg Gly Gly His Ser Asp Tyr Met Asn Met Thr
1               5               10              15

Pro Arg Arg Pro Gly Pro Thr Arg Lys His Tyr Gln Pro Tyr Ala Pro
            20              25              30

Pro Arg Asp Phe Ala Ala Tyr Arg Ser
        35              40

<210> SEQ ID NO 12
<211> LENGTH: 42
<212> TYPE: PRT
<213> ORGANISM: Homo sapiens
<220> FEATURE:
<223> OTHER INFORMATION: 4-1BB
<300> PUBLICATION INFORMATION:
<308> DATABASE ACCESSION NUMBER: UniProt Q07011.1
<309> DATABASE ENTRY DATE: 1995-02-01

<400> SEQUENCE: 12

Lys Arg Gly Arg Lys Lys Leu Leu Tyr Ile Phe Lys Gln Pro Phe Met
1               5               10              15

Arg Pro Val Gln Thr Thr Gln Glu Glu Asp Gly Cys Ser Cys Arg Phe
            20              25              30

Pro Glu Glu Glu Glu Gly Gly Cys Glu Leu
        35              40

<210> SEQ ID NO 13
<211> LENGTH: 112
<212> TYPE: PRT
<213> ORGANISM: Homo sapiens
<220> FEATURE:
```

<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 112
<212> TYPE: PRT
<213> ORGANISM: Homo sapiens
<220> FEATURE:
<223> OTHER INFORMATION: CD3 zeta

<400> SEQUENCE: 14

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

-continued

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 16
<211> LENGTH: 335
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu
1                   5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
                35                  40                  45

Thr His Thr Pro Pro Leu Asp Pro Gln Glu Leu Asp Ile Leu Lys Thr
                50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
                100                 105                 110

Thr Ser Leu Gly Leu Arg Ser Leu Lys Glu Ile Ser Asp Gly Asp Val
                115                 120                 125

Ile Ile Ser Gly Asn Lys Asn Leu Cys Tyr Ala Asn Thr Ile Asn Trp
                130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
                180                 185                 190

Cys Arg Asn Val Ser Arg Gly Arg Glu Cys Val Asp Lys Cys Asn Leu
                195                 200                 205

Leu Glu Gly Glu Pro Arg Glu Phe Val Glu Asn Ser Glu Cys Ile Gln
                210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
                260                 265                 270

Leu Val Trp Lys Tyr Ala Asp Ala Gly His Val Cys His Leu Cys His
                275                 280                 285

Pro Asn Cys Thr Tyr Gly Cys Thr Gly Pro Gly Leu Glu Gly Cys Pro
                290                 295                 300

Thr Asn Gly Pro Lys Ile Pro Ser Ile Ala Thr Gly Met Val Gly Ala
305                 310                 315                 320

```
Leu Leu Leu Leu Leu Val Val Ala Leu Gly Ile Gly Leu Phe Met
                325                 330                 335

<210> SEQ ID NO 17
<211> LENGTH: 18
<212> TYPE: PRT
<213> ORGANISM: Artificial Sequence
<220> FEATURE:
<223> OTHER INFORMATION: T2A

<400> SEQUENCE: 17

Glu Gly Arg Gly Ser Leu Leu Thr Cys Gly Asp Val Glu Glu Asn Pro
1               5                   10                  15

Gly Pro

<210> SEQ ID NO 18
<211> LENGTH: 22
<212> TYPE: PRT
<213> ORGANISM: Artificial Sequence
<220> FEATURE:
<223> OTHER INFORMATION: P2A

<400> SEQUENCE: 18

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 19
<211> LENGTH: 19
<212> TYPE: PRT
<213> ORGANISM: Artificial Sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1               5                   10                  15

Pro Gly Pro

<210> SEQ ID NO 20
<211> LENGTH: 20
<212> TYPE: PRT
<213> ORGANISM: Artificial Sequence
<220> FEATURE:
<223> OTHER INFORMATION: E2A

<400> SEQUENCE: 20

Gln Cys Thr Asn Tyr Ala Leu Leu Lys Leu Ala Gly Asp Val Glu Ser
1               5                   10                  15

Asn Pro Gly Pro
            20

<210> SEQ ID NO 21
<211> LENGTH: 22
<212> TYPE: PRT
<213> ORGANISM: Artificial Sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1               5                   10                  15
```

Glu Ser Asn Pro Gly Pro
            20

<210> SEQ ID NO 22
<211> LENGTH: 9
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 22

Pro Gly Gly Gly Ser Gly Gly Gly Gly
1               5

<210> SEQ ID NO 23
<211> LENGTH: 17
<212> TYPE: PRT
<213> ORGANISM: Artificial Sequence
<220> FEATURE:
<223> OTHER INFORMATION: Linker

<400> SEQUENCE: 23

Gly Ser Ala Asp Asp Ala Lys Lys Asp Ala Ala Lys Lys Asp Gly Lys
1               5                   10                  15

Ser

<210> SEQ ID NO 24
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 24
atgcttctcc tggtgacaag ccttctgctc tgtgagttac cacacccagc attcctcctg      60
atccca                                                                  66

<210> SEQ ID NO 25
<211> LENGTH: 22
<212> TYPE: PRT
<213> ORGANISM: Artificial Sequence
<220> FEATURE:
<223> OTHER INFORMATION: GMCSFR alpha chain signal sequence

<400> SEQUENCE: 25

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 26
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 26

Met Ala Leu Pro Val Thr Ala Leu Leu Leu Pro Leu Ala Leu Leu Leu
1               5                   10                  15

His Ala

-continued

<210> SEQ ID NO 27
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 27

Glu Val Gln Leu Val Gln Ser Gly Ala Glu Met Lys Lys Pro Gly Ala
1               5                   10                  15

Ser Leu Lys Leu Ser Cys Lys Ala Ser Gly Tyr Thr Phe Ile Asp Tyr
            20                  25                  30

Tyr Val Tyr Trp Met Arg Gln Ala Pro Gly Gln Gly Leu Glu Ser Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Arg Ser Gln Arg Asp Gly Tyr Met Asp Tyr Trp Gly Gln Gly Thr
            100                 105                 110

Leu Val Thr Val Ser Ser
        115

<210> SEQ ID NO 28
<211> LENGTH: 105
<212> TYPE: PRT
<213> ORGANISM: Artificial Sequence
<220> FEATURE:
<223> OTHER INFORMATION: Variable light (VL) Anti-BCMA

<400> SEQUENCE: 28

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly
            100                 105

<210> SEQ ID NO 29
<211> LENGTH: 228
<212> TYPE: PRT
<213> ORGANISM: Homo sapiens
<220> FEATURE:
<221> NAME/KEY: PEPTIDE
<222> LOCATION: (0)...(0)
<223> OTHER INFORMATION: Hinge-CH2-CH3 spacer -continued

<400> SEQUENCE: 29

Glu Ser Lys Tyr Gly Pro Pro Cys Pro Pro Cys Pro Ala Pro Pro Val
1               5               10              15

Ala Gly Pro Ser Val Phe Leu Phe Pro Pro Lys Pro Lys Asp Thr Leu
            20              25              30

Met Ile Ser Arg Thr Pro Glu Val Thr Cys Val Val Val Asp Val Ser
        35              40              45

Gln Glu Asp Pro Glu Val Gln Phe Asn Trp Tyr Val Asp Gly Val Glu
    50              55              60

Val His Asn Ala Lys Thr Lys Pro Arg Glu Glu Gln Phe Gln Ser Thr
65              70              75              80

Tyr Arg Val Val Ser Val Leu Thr Val Leu His Gln Asp Trp Leu Asn
            85              90              95

Gly Lys Glu Tyr Lys Cys Lys Val Ser Asn Lys Gly Leu Pro Ser Ser
            100             105             110

Ile Glu Lys Thr Ile Ser Lys Ala Lys Gly Gln Pro Arg Glu Pro Gln
            115             120             125

Val Tyr Thr Leu Pro Pro Ser Gln Glu Glu Met Thr Lys Asn Gln Val
    130             135             140

Ser Leu Thr Cys Leu Val Lys Gly Phe Tyr Pro Ser Asp Ile Ala Val
145             150             155             160

Glu Trp Glu Ser Asn Gly Gln Pro Glu Asn Asn Tyr Lys Thr Thr Pro
            165             170             175

Pro Val Leu Asp Ser Asp Gly Ser Phe Phe Leu Tyr Ser Arg Leu Thr
            180             185             190

Val Asp Lys Ser Arg Trp Gln Glu Gly Asn Val Phe Ser Cys Ser Val
            195             200             205

Met His Glu Ala Leu His Asn His Tyr Thr Gln Lys Ser Leu Ser Leu
    210             215             220

Ser Leu Gly Lys
225

<210> SEQ ID NO 30
<211> LENGTH: 117
<212> TYPE: PRT
<213> ORGANISM: Artificial Sequence
<220> FEATURE:
<223> OTHER INFORMATION: Variable heavy (VH) Anti-BCMA

<400> SEQUENCE: 30

Gln Ile Gln Leu Val Gln Ser Gly Pro Glu Leu Lys Lys Pro Gly Glu
1               5               10              15

Thr Val Lys Ile Ser Cys Lys Ala Ser Gly Tyr Thr Phe Thr Asp Tyr
            20              25              30

Ser Ile Asn Trp Val Lys Arg Ala Pro Gly Lys Gly Leu Lys Trp Met
        35              40              45

Gly Trp Ile Asn Thr Glu Thr Arg Glu Pro Ala Tyr Ala Tyr Asp Phe
    50              55              60

Arg Gly Arg Phe Ala Phe Ser Leu Glu Thr Ser Ala Ser Thr Ala Tyr
65              70              75              80

Leu Gln Ile Asn Asn Leu Lys Tyr Glu Asp Thr Ala Thr Tyr Phe Cys
            85              90              95

Ala Leu Asp Tyr Ser Tyr Ala Met Asp Tyr Trp Gly Gln Gly Thr Ser
            100             105             110

Val Thr Val Ser Ser
        115

<210> SEQ ID NO 31
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 31

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 32
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 32

Gln Ile Gln Leu Val Gln Ser Gly Pro Asp Leu Lys Lys Pro Gly Glu
1               5                   10                  15

Thr Val Lys Leu Ser Cys Lys Ala Ser Gly Tyr Thr Phe Thr Asn Phe
            20                  25                  30

Gly Met Asn Trp Val Lys Gln Ala Pro Gly Lys Gly Phe Lys Trp Met
        35                  40                  45

Ala Trp Ile Asn Thr Tyr Thr Gly Glu Ser Tyr Phe Ala Asp Asp Phe
    50                  55                  60

Lys Gly Arg Phe Ala Phe Ser Val Glu Thr Ser Ala Thr Thr Ala Tyr
65                  70                  75                  80

Leu Gln Ile Asn Asn Leu Lys Thr Glu Asp Thr Ala Thr Tyr Phe Cys
                85                  90                  95

Ala Arg Gly Glu Ile Tyr Tyr Gly Tyr Asp Gly Gly Phe Ala Tyr Trp
            100                 105                 110

Gly Gln Gly Thr Leu Val Thr Val Ser Ala
        115                 120

<210> SEQ ID NO 33
<211> LENGTH: 107
<212> TYPE: PRT
<213> ORGANISM: Artificial Sequence
<220> FEATURE:
<223> OTHER INFORMATION: Variable light (VL) Anti-BCMA -continued

<400> SEQUENCE: 33

```
Asp Val Val Met Thr Gln Ser His Arg Phe Met Ser Thr Ser Val Gly
1               5                   10                  15

Asp Arg Val Ser Ile Thr Cys Arg Ala Ser Gln Asp Val Asn Thr Ala
            20                  25                  30

Val Ser Trp Tyr Gln Gln Lys Pro Gly Gln Ser Pro Lys Leu Leu Ile
        35                  40                  45

Phe Ser Ala Ser Tyr Arg Tyr Thr Gly Val Pro Asp Arg Phe Thr Gly
    50                  55                  60

Ser Gly Ser Gly Ala Asp Phe Thr Leu Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Asp Ile Lys
            100                 105
```

<210> SEQ ID NO 34
<211> LENGTH: 116
<212> TYPE: PRT
<213> ORGANISM: Artificial Sequence
<220> FEATURE:
<223> OTHER INFORMATION: Variable heavy (VH) Anti-BCMA

<400> SEQUENCE: 34

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Ser Gly Ser Phe Asp Asn Trp Gly Gln Gly Thr Leu Val
            100                 105                 110

Thr Val Ser Ser
        115
```

<210> SEQ ID NO 35
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 35

```
Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60
```

-continued

```
Gly Ser Lys Ser Gly Thr Ser Ala Ser Leu Ala Ile Ser Gly Leu Gln
65                  70              75                  80

Ser Glu Asp Glu Ala Asp Tyr Tyr Cys Ala Ala Trp Asp Gly Ser Leu
                85              90                  95

Asn Gly Leu Val Phe Gly Gly Gly Thr Lys Leu Thr Val Leu Gly
            100             105                 110

<210> SEQ ID NO 36
<211> LENGTH: 5
<212> TYPE: PRT
<213> ORGANISM: Artificial Sequence
<220> FEATURE:
<223> OTHER INFORMATION: Linker

<400> SEQUENCE: 36

Gly Gly Gly Gly Ser
1               5

<210> SEQ ID NO 37
<211> LENGTH: 4
<212> TYPE: PRT
<213> ORGANISM: Artificial Sequence
<220> FEATURE:
<223> OTHER INFORMATION: Linker

<400> SEQUENCE: 37

Gly Gly Gly Ser
1

<210> SEQ ID NO 38
<211> LENGTH: 15
<212> TYPE: PRT
<213> ORGANISM: Artificial Sequence
<220> FEATURE:
<223> OTHER INFORMATION: Linker

<400> SEQUENCE: 38

Gly Gly Gly Gly Ser Gly Gly Gly Gly Ser Gly Gly Gly Gly Ser
1               5                   10                  15

<210> SEQ ID NO 39
<211> LENGTH: 18
<212> TYPE: PRT
<213> ORGANISM: Artificial Sequence
<220> FEATURE:
<223> OTHER INFORMATION: Linker

<400> SEQUENCE: 39

Gly Ser Thr Ser Gly Ser Gly Lys Pro Gly Ser Gly Glu Gly Ser Thr
1               5                   10                  15

Lys Gly

<210> SEQ ID NO 40
<211> LENGTH: 21
<212> TYPE: PRT
<213> ORGANISM: Artificial Sequence
<220> FEATURE:
<223> OTHER INFORMATION: Linker

<400> SEQUENCE: 40

Ser Arg Gly Gly Gly Gly Ser Gly Gly Gly Gly Ser Gly Gly Gly Gly
1               5                   10                  15

Ser Leu Glu Met Ala
            20
```

<210> SEQ ID NO 41
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 41

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Ser Lys Ser Ile Val Ser Tyr Met Asp Tyr Trp
            100                 105                 110

Gly Gln Gly Thr Leu Val Thr Val Ser Ser
        115                 120

<210> SEQ ID NO 42
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 42

Leu Pro Val Leu Thr Gln Pro Pro Ser Thr Ser Gly Thr Pro Gly Gln
1               5                   10                  15

Arg Val Thr Val Ser Cys Ser Gly Ser Ser Ser Asn Ile Gly Ser Asn
            20                  25                  30

Val Val Phe Trp Tyr Gln Gln Leu Pro Gly Thr Ala Pro Lys Leu Val
        35                  40                  45

Ile Tyr Arg Asn Asn Gln Arg Pro Ser Gly Val Pro Asp Arg Phe Ser
    50                  55                  60

Val Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly
            100                 105                 110

<210> SEQ ID NO 43
<211> LENGTH: 120
<212> TYPE: PRT
<213> ORGANISM: Artificial Sequence
<220> FEATURE:
<223> OTHER INFORMATION: Variable heavy (VH) Anti-BCMA

<400> SEQUENCE: 43

Gln Val Gln Leu Val Gln Ser Gly Ala Glu Val Lys Lys Pro Gly Ser
1               5                   10                  15

-continued

```
Ser Val Lys Val Ser Cys Lys Ala Ser Gly Gly Thr Phe Ser Ser Tyr
        20                  25                  30

Ala Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Gly Ser Tyr Arg Trp Glu Asp Ser Trp Gly Gln
            100                 105                 110

Gly Thr Leu Val Thr Val Ser Ser
        115                 120
```

<210> SEQ ID NO 44
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 44

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Phe Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Ser Tyr Val Phe Gly Thr Gly Thr Lys Val Thr Val Leu Gly
            100                 105                 110
```

<210> SEQ ID NO 45
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 45

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
        20                  25                  30

Tyr Met His Trp Val Arg Gln Ala Pro Gly Gln Arg Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Ile Thr Val Thr Arg Asp Thr Ser Ser Asn Thr Gly Tyr
65                  70                  75                  80

Met Glu Leu Thr Arg Leu Arg Ser Asp Asp Thr Ala Val Tyr Tyr Cys
                85                  90                  95
```

```
Ala Arg Ser Pro Tyr Ser Gly Val Leu Asp Lys Trp Gly Gln Gly Thr
            100                 105                 110

Leu Val Thr Val Ser Ser
        115

<210> SEQ ID NO 46
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 46

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

<210> SEQ ID NO 47
<211> LENGTH: 11
<212> TYPE: PRT
<213> ORGANISM: Artificial Sequence
<220> FEATURE:
<223> OTHER INFORMATION: CDR L1

<400> SEQUENCE: 47

Arg Ala Ser Gln Asp Ile Ser Lys Tyr Leu Asn
1               5                   10

<210> SEQ ID NO 48
<211> LENGTH: 7
<212> TYPE: PRT
<213> ORGANISM: Artificial Sequence
<220> FEATURE:
<223> OTHER INFORMATION: CDR L2

<400> SEQUENCE: 48

Ser Arg Leu His Ser Gly Val
1               5

<210> SEQ ID NO 49
<211> LENGTH: 9
<212> TYPE: PRT
<213> ORGANISM: Artificial Sequence
<220> FEATURE:
<223> OTHER INFORMATION: CDR L3

<400> SEQUENCE: 49

Gly Asn Thr Leu Pro Tyr Thr Phe Gly
1               5

<210> SEQ ID NO 50
```

```
<211> LENGTH: 5
<212> TYPE: PRT
<213> ORGANISM: Artificial Sequence
<220> FEATURE:
<223> OTHER INFORMATION: CDR H1

<400> SEQUENCE: 50

Asp Tyr Gly Val Ser
1               5

<210> SEQ ID NO 51
<211> LENGTH: 16
<212> TYPE: PRT
<213> ORGANISM: Artificial Sequence
<220> FEATURE:
<223> OTHER INFORMATION: CDR H2

<400> SEQUENCE: 51

Val Ile Trp Gly Ser Glu Thr Thr Tyr Tyr Asn Ser Ala Leu Lys Ser
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: CDR H3

<400> SEQUENCE: 52

Tyr Ala Met Asp Tyr Trp Gly
1               5

<210> SEQ ID NO 53
<211> LENGTH: 120
<212> TYPE: PRT
<213> ORGANISM: Artificial Sequence
<220> FEATURE:
<223> OTHER INFORMATION: VH

<400> SEQUENCE: 53

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 54
<211> LENGTH: 107
<212> TYPE: PRT
<213> ORGANISM: Artificial Sequence
<220> FEATURE:
<223> OTHER INFORMATION: VL
```

<400> SEQUENCE: 54

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105
```

<210> SEQ ID NO 55
<211> LENGTH: 245
<212> TYPE: PRT
<213> ORGANISM: Artificial Sequence
<220> FEATURE:
<223> OTHER INFORMATION: scFv

<400> SEQUENCE: 55

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240
```

```
Val Thr Val Ser Ser
            245

<210> SEQ ID NO 56
<211> LENGTH: 11
<212> TYPE: PRT
<213> ORGANISM: Artificial Sequence
<220> FEATURE:
<223> OTHER INFORMATION: CDR L1

<400> SEQUENCE: 56

Lys Ala Ser Gln Asn Val Gly Thr Asn Val Ala
1               5                   10

<210> SEQ ID NO 57
<211> LENGTH: 7
<212> TYPE: PRT
<213> ORGANISM: Artificial Sequence
<220> FEATURE:
<223> OTHER INFORMATION: CDR L2

<400> SEQUENCE: 57

Ser Ala Thr Tyr Arg Asn Ser
1               5

<210> SEQ ID NO 58
<211> LENGTH: 9
<212> TYPE: PRT
<213> ORGANISM: Artificial Sequence
<220> FEATURE:
<223> OTHER INFORMATION: CDR L3

<400> SEQUENCE: 58

Gln Gln Tyr Asn Arg Tyr Pro Tyr Thr
1               5

<210> SEQ ID NO 59
<211> LENGTH: 5
<212> TYPE: PRT
<213> ORGANISM: Artificial Sequence
<220> FEATURE:
<223> OTHER INFORMATION: CDR H1

<400> SEQUENCE: 59

Ser Tyr Trp Met Asn
1               5

<210> SEQ ID NO 60
<211> LENGTH: 17
<212> TYPE: PRT
<213> ORGANISM: Artificial Sequence
<220> FEATURE:
<223> OTHER INFORMATION: CDR H2

<400> SEQUENCE: 60

Gln Ile Tyr Pro Gly Asp Gly Asp Thr Asn Tyr Asn Gly Lys Phe Lys
1               5                   10                  15

Gly

<210> SEQ ID NO 61
<211> LENGTH: 13
<212> TYPE: PRT
<213> ORGANISM: Artificial Sequence
<220> FEATURE:
<223> OTHER INFORMATION: CDR H3
```

-continued

<400> SEQUENCE: 61

Lys Thr Ile Ser Ser Val Val Asp Phe Tyr Phe Asp Tyr
1               5                   10

<210> SEQ ID NO 62
<211> LENGTH: 122
<212> TYPE: PRT
<213> ORGANISM: Artificial Sequence
<220> FEATURE:
<223> OTHER INFORMATION: VH

<400> SEQUENCE: 62

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
                100                 105                 110

Gly Gln Gly Thr Thr Val Thr Val Ser Ser
            115                 120

<210> SEQ ID NO 63
<211> LENGTH: 108
<212> TYPE: PRT
<213> ORGANISM: Artificial Sequence
<220> FEATURE:
<223> OTHER INFORMATION: VL

<400> SEQUENCE: 63

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Pro Leu Ile
            35                  40                  45

Tyr Ser Ala Thr Tyr Arg Asn Ser Gly Val Pro Asp Arg Phe Thr Gly
        50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
                100                 105

<210> SEQ ID NO 64
<211> LENGTH: 15
<212> TYPE: PRT
<213> ORGANISM: Artificial Sequence
<220> FEATURE:
<223> OTHER INFORMATION: Linker -continued

<400> SEQUENCE: 64

Gly Gly Gly Gly Ser Gly Gly Gly Gly Ser Gly Gly Gly Gly Ser
1               5                   10                  15

<210> SEQ ID NO 65
<211> LENGTH: 245
<212> TYPE: PRT
<213> ORGANISM: Artificial Sequence
<220> FEATURE:
<223> OTHER INFORMATION: scFv

<400> SEQUENCE: 65

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
                100                 105                 110

Gly Gln Gly Thr Thr Val Thr Val Ser Ser Gly Gly Gly Gly Ser Gly
            115                 120                 125

Gly Gly Gly Ser Gly Gly Gly Gly Ser Asp Ile Glu Leu Thr Gln Ser
        130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
                180                 185                 190

Ser Gly Val Pro Asp Arg Phe Thr Gly Ser Gly Ser Gly Thr Asp Phe
                195                 200                 205

Thr Leu Thr Ile Thr Asn Val Gln Ser Lys Asp Leu Ala Asp Tyr Phe
            210                 215                 220

Cys Gln Gln Tyr Asn Arg Tyr Pro Tyr Thr Ser Gly Gly Gly Thr Lys
225                 230                 235                 240

Leu Glu Ile Lys Arg
                245

<210> SEQ ID NO 66
<211> LENGTH: 12
<212> TYPE: PRT
<213> ORGANISM: Artificial Sequence
<220> FEATURE:
<223> OTHER INFORMATION: HC-CDR3

<400> SEQUENCE: 66

His Tyr Tyr Tyr Gly Gly Ser Tyr Ala Met Asp Tyr
1               5                   10

<210> SEQ ID NO 67

```
<211> LENGTH: 7
<212> TYPE: PRT
<213> ORGANISM: Artificial Sequence
<220> FEATURE:
<223> OTHER INFORMATION: LC-CDR2

<400> SEQUENCE: 67

His Thr Ser Arg Leu His Ser
1               5

<210> SEQ ID NO 68
<211> LENGTH: 9
<212> TYPE: PRT
<213> ORGANISM: Artificial Sequence
<220> FEATURE:
<223> OTHER INFORMATION: LC-CDR3

<400> SEQUENCE: 68

Gln Gln Gly Asn Thr Leu Pro Tyr Thr
1               5

<210> SEQ ID NO 69
<211> LENGTH: 735
<212> TYPE: DNA
<213> ORGANISM: Artificial Sequence
<220> FEATURE:
<223> OTHER INFORMATION: Sequence encoding scFv

<400> SEQUENCE: 69
gacatccaga tgacccagac cacctccagc ctgagcgcca gcctgggcga ccgggtgacc      60
atcagctgcc gggccagcca ggacatcagc aagtacctga actggtatca gcagaagccc     120
gacggcaccg tcaagctgct gatctaccac accagccggc tgcacagcgg cgtgcccagc     180
cggtttagcg gcagcggctc cggcaccgac tacagcctga ccatctccaa cctggaacag     240
gaagatatcg ccacctactt ttgccagcag ggcaacacac tgccctacac ctttggcggc     300
ggaacaaagc tggaaatcac cggcagcacc tccggcagcg gcaagcctgg cagcggcgag     360
ggcagcacca agggcgaggt gaagctgcag gaaagcggcc ctggcctggt ggcccccagc     420
cagagcctga gcgtgacctg caccgtgagc ggcgtgagcc tgcccgacta cggcgtgagc     480
tggatccggc agcccccag gaagggcctg gaatggctgg gcgtgatctg gggcagcgag     540
accacctact acaacagcgc cctgaagagc cggctgacca tcatcaagga caacagcaag     600
agccaggtgt tcctgaagat gaacagcctg cagaccgacg acaccgccat ctactactgc     660
gccaagcact actactacgg cggcagctac gccatggact actggggcca gggcaccagc     720
gtgaccgtga gcagc                                                       735

<210> SEQ ID NO 70
<211> LENGTH: 5
<212> TYPE: PRT
<213> ORGANISM: Artificial Sequence
<220> FEATURE:
<223> OTHER INFORMATION: Hinge
<220> FEATURE:
<221> NAME/KEY: VARIANT
<222> LOCATION: (1)...(1)
<223> OTHER INFORMATION: Xaa = Gly, Cys or Arg
<220> FEATURE:
<221> NAME/KEY: VARIANT
<222> LOCATION: (4)...(4)
<223> OTHER INFORMATION: Xaa = Cys or Thr
```

-continued

<400> SEQUENCE: 70

Xaa Pro Pro Xaa Pro
1               5

<210> SEQ ID NO 71
<211> LENGTH: 18
<212> TYPE: PRT
<213> ORGANISM: Artificial Sequence
<220> FEATURE:
<223> OTHER INFORMATION: Linker

<400> SEQUENCE: 71

Gly Ser Thr Ser Gly Ser Gly Lys Pro Gly Ser Gly Glu Gly Ser Thr
1               5                   10                  15

Lys Gly

<210> SEQ ID NO 72
<211> LENGTH: 159
<212> TYPE: PRT
<213> ORGANISM: Streptomyces avidinii
<220> FEATURE:
<223> OTHER INFORMATION: Streptavidin
<300> PUBLICATION INFORMATION:
<308> DATABASE ACCESSION NUMBER: UniProt No. P22629
<309> DATABASE ENTRY DATE: 1991-08-01

<400> SEQUENCE: 72

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
                20                  25                  30

Ala Gly Ala Asp Gly Ala Leu Thr Gly Thr Tyr Glu Ser Ala Val Gly
            35                  40                  45

Asn Ala Glu Ser Arg Tyr Val Leu Thr Gly Arg Tyr Asp Ser Ala Pro
        50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 73
<211> LENGTH: 126
<212> TYPE: PRT
<213> ORGANISM: Streptomyces avidinii
<220> FEATURE:
<223> OTHER INFORMATION: Minimal streptavidin

<400> SEQUENCE: 73

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
                20                  25                  30

```
Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
                100                 105                 110

Gly His Asp Thr Phe Thr Lys Val Lys Pro Ser Ala Ala Ser
                115                 120                 125
```

<210> SEQ ID NO 74
<211> LENGTH: 126
<212> TYPE: PRT
<213> ORGANISM: Artificial Sequence
<220> FEATURE:
<223> OTHER INFORMATION: Mutein Streptavidin Ile44-Gly45-Ala-46-Arg47

<400> SEQUENCE: 74

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ile Gly
                20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
                100                 105                 110

Gly His Asp Thr Phe Thr Lys Val Lys Pro Ser Ala Ala Ser
                115                 120                 125
```

<210> SEQ ID NO 75
<211> LENGTH: 8
<212> TYPE: PRT
<213> ORGANISM: Artificial Sequence
<220> FEATURE:
<223> OTHER INFORMATION: Strep-tag II

<400> SEQUENCE: 75

```
Trp Ser His Pro Gln Phe Glu Lys
1               5
```

<210> SEQ ID NO 76
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 76

```
Trp Ser His Pro Gln Phe Glu Lys Gly Gly Gly Ser Gly Gly Gly Ser
1               5                   10                  15
```

```
Gly Gly Gly Ser Trp Ser His Pro Gln Phe Glu Lys
        20                  25

<210> SEQ ID NO 77
<211> LENGTH: 24
<212> TYPE: PRT
<213> ORGANISM: Artificial Sequence
<220> FEATURE:
<223> OTHER INFORMATION: Twin-Strep-tag

<400> SEQUENCE: 77

Trp Ser His Pro Gln Phe Glu Lys Gly Gly Gly Ser Gly Gly Gly Ser
1               5                   10                  15

Trp Ser His Pro Gln Phe Glu Lys
        20

<210> SEQ ID NO 78
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 78

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
        20                  25

<210> SEQ ID NO 79
<211> LENGTH: 127
<212> TYPE: PRT
<213> ORGANISM: Artificial Sequence
<220> FEATURE:
<223> OTHER INFORMATION: Mutein Streptavidin Ile44-Gly45-Ala-46-Arg47

<400> SEQUENCE: 79

Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Ile
        20                  25                  30

Gly Ala Arg Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 80
<211> LENGTH: 8
<212> TYPE: PRT
<213> ORGANISM: Artificial Sequence
<220> FEATURE:
<223> OTHER INFORMATION: Streptavidin-binding peptide
<220> FEATURE:
<221> NAME/KEY: VARIANT
<222> LOCATION: (2)...(2)
```

-continued

```
<223> OTHER INFORMATION: Xaa = any amino acid
<220> FEATURE:
<221> NAME/KEY: VARIANT
<222> LOCATION: (7)...(7)
<223> OTHER INFORMATION: Xaa = Gly or Glu
<220> FEATURE:
<221> NAME/KEY: VARIANT
<222> LOCATION: (8)...(8)
<223> OTHER INFORMATION: Xaa = Gly, Lys or Arg

<400> SEQUENCE: 80

Trp Xaa His Pro Gln Phe Xaa Xaa
1               5

<210> SEQ ID NO 81
<211> LENGTH: 8
<212> TYPE: PRT
<213> ORGANISM: Artificial Sequence
<220> FEATURE:
<223> OTHER INFORMATION: Streptavidin binding peptide, Strep-tag

<400> SEQUENCE: 81

Trp Arg His Pro Gln Phe Gly Gly
1               5

<210> SEQ ID NO 82
<211> LENGTH: 17
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: VARIANT
<222> LOCATION: (9)...(9)
<223> OTHER INFORMATION: Xaa = any amino acid
<220> FEATURE:
<221> NAME/KEY: REPEAT
<222> LOCATION: (9)...(9)
<223> OTHER INFORMATION: Repeated 8 or 12 times

<400> SEQUENCE: 82

Trp Ser His Pro Gln Phe Glu Lys Xaa Trp Ser His Pro Gln Phe Glu
1               5                   10                  15

Lys

<210> SEQ ID NO 83
<211> LENGTH: 20
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: REPEAT
<222> LOCATION: (9)...(12)
<223> OTHER INFORMATION: Repeated 2 or 3 times

<400> SEQUENCE: 83

Trp Ser His Pro Gln Phe Glu Lys Gly Gly Gly Ser Trp Ser His Pro
1               5                   10                  15

Gln Phe Glu Lys
            20

<210> SEQ ID NO 84
<211> LENGTH: 30
<212> TYPE: PRT
<213> ORGANISM: Artificial Sequence
<220> FEATURE:
```

<223> OTHER INFORMATION: Twin-Strep-tag

<400> SEQUENCE: 84

Ser Ala Trp Ser His Pro Gln Phe Glu Lys Gly Gly Gly Ser Gly Gly
1               5                   10                  15

Gly Ser Gly Gly Gly Ser Trp Ser His Pro Gln Phe Glu Lys
            20                  25                  30

<210> SEQ ID NO 85
<211> LENGTH: 30
<212> TYPE: PRT
<213> ORGANISM: Artificial Sequence
<220> FEATURE:
<223> OTHER INFORMATION: Twin-Strep-tag

<400> SEQUENCE: 85

Ser Ala Trp Ser His Pro Gln Phe Glu Lys Gly Gly Gly Ser Gly Gly
1               5                   10                  15

Gly Ser Gly Gly Ser Ala Trp Ser His Pro Gln Phe Glu Lys
            20                  25                  30

<210> SEQ ID NO 86
<211> LENGTH: 159
<212> TYPE: PRT
<213> ORGANISM: Artificial Sequence
<220> FEATURE:
<223> OTHER INFORMATION: Mutein Streptavidin Val44-Thr45-Ala46-Arg47

<400> SEQUENCE: 86

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 87
<211> LENGTH: 126
<212> TYPE: PRT
<213> ORGANISM: Artificial Sequence
<220> FEATURE:
<223> OTHER INFORMATION: Mutein Streptavidin Val44-Thr45-Ala46-Arg47

<400> SEQUENCE: 87

Glu Ala Gly Ile Thr Gly Thr Trp Tyr Asn Gln Leu Gly Ser Thr Phe
1               5                   10                  15

-continued

```
Ile Val Thr Ala Gly Ala Asp Gly Ala Leu Thr Gly Thr Tyr Val Thr
        20              25              30

Ala Arg Gly Asn Ala Glu Ser Arg Tyr Val Leu Thr Gly Arg Tyr Asp
        35              40              45

Ser Ala Pro Ala Thr Asp Gly Ser Gly Thr Ala Leu Gly Trp Thr Val
    50              55              60

Ala Trp Lys Asn Asn Tyr Arg Asn Ala His Ser Ala Thr Thr Trp Ser
65              70              75              80

Gly Gln Tyr Val Gly Gly Ala Glu Ala Arg Ile Asn Thr Gln Trp Leu
                85              90              95

Leu Thr Ser Gly Thr Thr Glu Ala Asn Ala Trp Lys Ser Thr Leu Val
            100             105             110

Gly His Asp Thr Phe Thr Lys Val Lys Pro Ser Ala Ala Ser
        115             120             125
```

<210> SEQ ID NO 88
<211> LENGTH: 127
<212> TYPE: PRT
<213> ORGANISM: Artificial Sequence
<220> FEATURE:
<223> OTHER INFORMATION: Mutein Streptavidin Val44-Thr45-Ala46-Arg47

<400> SEQUENCE: 88

```
Met Glu Ala Gly Ile Thr Gly Thr Trp Tyr Asn Gln Leu Gly Ser Thr
1               5               10              15

Phe Ile Val Thr Ala Gly Ala Asp Gly Ala Leu Thr Gly Thr Tyr Val
        20              25              30

Thr Ala Arg Gly Asn Ala Glu Ser Arg Tyr Val Leu Thr Gly Arg Tyr
        35              40              45

Asp Ser Ala Pro Ala Thr Asp Gly Ser Gly Thr Ala Leu Gly Trp Thr
    50              55              60

Val Ala Trp Lys Asn Asn Tyr Arg Asn Ala His Ser Ala Thr Thr Trp
65              70              75              80

Ser Gly Gln Tyr Val Gly Gly Ala Glu Ala Arg Ile Asn Thr Gln Trp
                85              90              95

Leu Leu Thr Ser Gly Thr Thr Glu Ala Asn Ala Trp Lys Ser Thr Leu
            100             105             110

Val Gly His Asp Thr Phe Thr Lys Val Lys Pro Ser Ala Ala Ser
        115             120             125
```

<210> SEQ ID NO 89
<211> LENGTH: 4
<212> TYPE: PRT
<213> ORGANISM: Artificial Sequence
<220> FEATURE:
<223> OTHER INFORMATION: Streptavidin-binding peptide

<400> SEQUENCE: 89

```
His Pro Gln Phe
1
```

<210> SEQ ID NO 90
<211> LENGTH: 8
<212> TYPE: PRT
<213> ORGANISM: Artificial Sequence
<220> FEATURE:
<223> OTHER INFORMATION: Streptavidin-binding peptide
<220> FEATURE:
<221> NAME/KEY: VARIANT
<222> LOCATION: (1)...(1)
<223> OTHER INFORMATION: Xaa = Trp, Lys or Arg

```
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (7)...(7)
<223> OTHER INFORMATION: Xaa = Gly or Glu
<220> FEATURE:
<221> NAME/KEY: VARIANT
<222> LOCATION: (8)...(8)
<223> OTHER INFORMATION: Xaa = Gly, Lys or Arg

<400> SEQUENCE: 90

Xaa Xaa His Pro Gln Phe Xaa Xaa
1               5

<210> SEQ ID NO 91
<211> LENGTH: 159
<212> TYPE: PRT
<213> ORGANISM: Artificial Sequence
<220> FEATURE:
<223> OTHER INFORMATION: Mutein Streptavidin Ile44-Gly45-Ala-46-Arg47

<400> SEQUENCE: 91

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
                20                  25                  30

Ala Gly Ala Asp Gly Ala Leu Thr Gly Thr Tyr Ile Gly Ala Arg Gly
            35                  40                  45

Asn Ala Glu Ser Arg Tyr Val Leu Thr Gly Arg Tyr Asp Ser Ala Pro
        50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
                100                 105                 110

Gly Thr Thr Glu Ala Asn Ala Trp Lys Ser Thr Leu Val Gly His Asp
            115                 120                 125

Thr Phe Thr Lys Val Lys Pro Ser Ala Ala Ser Ile Asp Ala Ala Lys
        130                 135                 140

Lys Ala Gly Val Asn Asn Gly Asn Pro Leu Asp Ala Val Gln Gln
145                 150                 155

<210> SEQ ID NO 92
<211> LENGTH: 126
<212> TYPE: PRT
<213> ORGANISM: Artificial Sequence
<220> FEATURE:
<223> OTHER INFORMATION: Mutein Streptavidin Val44-Thr45-Ala46-Arg47 and
        Glu117, Gly120, Try121 (mutein m1-9)

<400> SEQUENCE: 92

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45
```

```
Ser Ala Pro Ala Thr Asp Gly Ser Gly Thr Ala Leu Gly Trp Thr Val
    50              55              60

Ala Trp Lys Asn Asn Tyr Arg Asn Ala His Ser Ala Thr Thr Trp Ser
65              70              75              80

Gly Gln Tyr Val Gly Gly Ala Glu Ala Arg Ile Asn Thr Gln Trp Leu
                85              90              95

Leu Thr Ser Gly Thr Thr Glu Glu Asn Ala Gly Tyr Ser Thr Leu Val
            100             105             110

Gly His Asp Thr Phe Thr Lys Val Lys Pro Ser Ala Ala Ser
        115             120             125
```

<210> SEQ ID NO 93
<211> LENGTH: 139
<212> TYPE: PRT
<213> ORGANISM: Artificial Sequence
<220> FEATURE:
<223> OTHER INFORMATION: Mutein Streptavidin Val44-Thr45-Ala46-Arg47 and
      Glu117, Gly120, Try121 (mutein m1-9)

<400> SEQUENCE: 93

```
Asp Pro Ser Lys Asp Ser Lys Ala Gln Val Ser Ala Ala Glu Ala Gly
1               5               10              15

Ile Thr Gly Thr Trp Tyr Asn Gln Leu Gly Ser Thr Phe Ile Val Thr
                20              25              30

Ala Gly Ala Asp Gly Ala Leu Thr Gly Thr Tyr Val Thr Ala Arg Gly
        35              40              45

Asn Ala Glu Ser Arg Tyr Val Leu Thr Gly Arg Tyr Asp Ser Ala Pro
    50              55              60

Ala Thr Asp Gly Ser Gly Thr Ala Leu Gly Trp Thr Val Ala Trp Lys
65              70              75              80

Asn Asn Tyr Arg Asn Ala His Ser Ala Thr Thr Trp Ser Gly Gln Tyr
                85              90              95

Val Gly Gly Ala Glu Ala Arg Ile Asn Thr Gln Trp Leu Leu Thr Ser
            100             105             110

Gly Thr Thr Glu Glu Asn Ala Gly Tyr Ser Thr Leu Val Gly His Asp
        115             120             125

Thr Phe Thr Lys Val Lys Pro Ser Ala Ala Ser
    130             135
```

<210> SEQ ID NO 94
<211> LENGTH: 127
<212> TYPE: PRT
<213> ORGANISM: Artificial Sequence
<220> FEATURE:
<223> OTHER INFORMATION: Minimal streptavidin

<400> SEQUENCE: 94

```
Met Glu Ala Gly Ile Thr Gly Thr Trp Tyr Asn Gln Leu Gly Ser Thr
1               5               10              15

Phe Ile Val Thr Ala Gly Ala Asp Gly Ala Leu Thr Gly Thr Tyr Glu
                20              25              30

Ser Ala Val Gly Asn Ala Glu Ser Arg Tyr Val Leu Thr Gly Arg Tyr
        35              40              45

Asp Ser Ala Pro Ala Thr Asp Gly Ser Gly Thr Ala Leu Gly Trp Thr
    50              55              60

Val Ala Trp Lys Asn Asn Tyr Arg Asn Ala His Ser Ala Thr Thr Trp
65              70              75              80
```

```
Ser Gly Gln Tyr Val Gly Gly Ala Glu Ala Arg Ile Asn Thr Gln Trp
             85                   90                95

Leu Leu Thr Ser Gly Thr Thr Glu Ala Asn Ala Trp Lys Ser Thr Leu
             100              105               110

Val Gly His Asp Thr Phe Thr Lys Val Lys Pro Ser Ala Ala Ser
         115              120               125
```

PROCESS FOR PRODUCING A COMPOSITION OF ENGINEERED T CELLS

CROSS-REFERENCE TO RELATED APPLICATIONS

This application is a National Stage application under 35 U.S.C. § 371 of International Application No. PCT/US2018/064628, filed on Dec. 7, 2018 which claims priority to U.S. provisional application 62/596,774, filed Dec. 8, 2017, entitled "PROCESS FOR PRODUCING A COMPOSITION OF ENGINEERED T CELLS"; U.S. provisional application No. 62/614,965, filed Jan. 8, 2018, entitled "PROCESS FOR PRODUCING A COMPOSITION OF ENGINEERED T CELLS"; U.S. provisional application No. 62/716,971, filed Aug. 9, 2018, entitled "PROCESS FOR PRODUCING A COMPOSITION OF ENGINEERED T CELLS"; U.S. provisional application No. 62/721,604, filed Aug. 22, 2018, entitled "PROCESS FOR PRODUCING A COMPOSITION OF ENGINEERED T CELLS"; U.S. provisional application No. 62/740,903, filed Oct. 3, 2018, entitled "PROCESS FOR PRODUCING A COMPOSITION OF ENGINEERED T CELLS"; U.S. provisional application No. 62/754,564, filed Nov. 1, 2018, entitled "PROCESS FOR PRODUCING A COMPOSITION OF ENGINEERED T CELLS"; U.S. provisional application No. 62/774,165, filed Nov. 30, 2018, entitled "PROCESS FOR PRODUCING A COMPOSITION OF ENGINEERED T CELLS"; and U.S. provisional application No. 62/774,855, filed Dec. 3, 2018, entitled "PROCESS FOR PRODUCING A COMPOSITION OF ENGINEERED T CELLS," the contents of which are incorporated by reference in their entirety for all purposes.

INCORPORATION BY REFERENCE OF SEQUENCE LISTING

The present application is being filed along with a Sequence Listing in electronic format. The Sequence Listing is provided as a file entitled 735042014300SeqList.txt, created Jun. 4, 2020 which is 69,466 bytes in size. The information in the electronic format of the Sequence Listing is incorporated by reference in its entirety.

FIELD

The present disclosure provides methods for genetically engineering T cells, such as CD4+ T cells and/or CD8+ T cells, for use in cell therapy. In some aspects, the provided methods include one or more steps for pooling enriched CD4+ and CD8+ cells, such as at a 1:1 ratio, and then incubating the cells under stimulating conditions, introducing a recombinant polypeptide to the cells through transduction or transfection, and/or cultivating the cells under conditions that promote proliferation and/or expansion. In some aspects, the provided methods are an efficient, reliable means to produce genetically engineered T cells with a high degree of success.

BACKGROUND

Various cell therapy methods are available for treating diseases and conditions. Among cell therapy methods are methods involving immune cells, such as T cells, genetically engineered with a recombinant receptor, such as a chimeric antigen receptors. Improved methods for manufacturing and/or engineering such cell therapies are needed, including to provide for a more efficient process and/or an improved cell composition product.

SUMMARY

In some embodiments, provided herein is a method for producing a composition of engineered cells, the method comprising: (a) combining a composition of CD4+ T cells and a composition of CD8+ T cells at a ratio of between 2:1 and 1:2 CD4+ to CD8+ T cells, thereby generating an input composition; (b) incubating the input composition under stimulating conditions, thereby generating a stimulated composition; wherein said stimulating conditions comprise the presence of a stimulatory reagent capable of activating one or more intracellular signaling domains of one or more components of a TCR complex and/or one or more intracellular signaling domains of one or more costimulatory molecules; and wherein the input composition comprises at least $100 \times 10^6$ total CD4+ and CD8+ T cells at a concentration of less than $5 \times 10^6$ cells/ml.

In some embodiments, provided herein is a method for producing a composition of engineered cells, the method comprising incubating an input composition under stimulating conditions, thereby generating a stimulated composition, wherein: the input composition comprises a ratio of between 2:1 and 1:2 CD4+ to CD8+ T cells, and wherein the input composition comprises at least $100 \times 10^6$ total CD4+ and CD8+ T cells at a concentration of less than $5 \times 10^6$ cells/ml; and the stimulating conditions comprise the presence of a stimulatory reagent capable of activating one or more intracellular signaling domains of one or more components of a TCR complex and/or one or more intracellular signaling domains of one or more costimulatory molecules.

In some embodiments, provided herein is a method for producing a composition of engineered cells, the method comprising introducing a recombinant receptor into cells of a T cell composition, said T cell composition comprising a concentration of at least or at least about $1 \times 10^6$ viable cells per mL, wherein at least 80%, at least 85%, at least 90%, or at least 95% of the cells of the T cell composition are CD4+ T cells or CD8+ T cells.

In certain embodiments, the incubation is performed in serum free media. In certain embodiments, the input composition comprises at least 80%, at least 85%, at least 90%, or at least 95% cells that are CD4+ T cells or CD8+ T cells. In certain embodiments, the input composition comprises between $100 \times 10^6$ and $500 \times 10^6$ total CD4+ and CD8+ T cells. In certain embodiments, the input composition comprises at or about $300 \times 10^6$ total CD4+ and CD8+ T cells. In certain embodiments, the total CD4+ and CD8+ T cells are viable cells. In certain embodiments, the input composition comprises a concentration of between $1 \times 10^6$ cells/mL and $5 \times 10^6$ cells/mL. In certain embodiments, the input composition comprises a concentration of or of about $3 \times 10^6$ cells/mL. In certain embodiments, the input composition comprises a ratio of between 1.5:1 and 1:1.5 CD4+ to CD8+ cells. In certain embodiments, the input composition comprises a ratio of between 1.2:1 and 0.8:1 CD4+ to CD8+ cells.

In certain embodiments, the input composition comprises a ratio of or of about 1:1 CD4+ to CD8+ cells. In certain embodiments, the input composition comprises CD4+ and CD8+ that are surface positive for CD45RA and CCR7.

In certain embodiments, the ratio of CD4+ cells surface positive for CD45RA and CCR7 to CD8+ cells surface positive for CD45RA and CCR7 is or is about 1.1:1.

In certain embodiments, the input composition comprises CD4+ and CD8+ cells that are surface positive for CD27 and CCR7.

In certain embodiments, the ratio of the CD4+ cells that are surface positive for CD27 and CCR7 to CD8+ cells surface positive for CD27 and CCR7 is or is about 1.69:1.

In certain embodiments, the input composition comprises CD4+ and CD8+ cells that are surface positive for CCR7 and surface negative for CD62L, optionally at a ratio of between 2.0:1 to 1.5:1.

Some embodiments further comprise: introducing a recombinant receptor into cells from the stimulated composition thereby generating an engineered cell composition, wherein the introducing comprises contacting the cells of the stimulated composition with an agent comprising a polynucleotide encoding the recombinant receptor. Some embodiments further comprise introducing a recombinant receptor into cells from the stimulated composition thereby generating an engineered cell composition, wherein the introducing comprises transducing the cells of the stimulated composition with a viral vector comprising a polynucleotide encoding the recombinant receptor. In some embodiments, the introducing is performed in serum free media.

In particular embodiments, provided herein is a method for producing a composition of engineered cells, the method comprising: (a) combining a composition of CD4+ T cells and a composition of CD8+ T cells at a ratio of between 2:1 and 1:2 CD4+ to CD8+ T cells, thereby generating an input composition; (b) incubating the input composition under stimulating conditions, thereby generating a stimulated composition; wherein said stimulating conditions comprise the presence of a stimulatory reagent capable of activating one or more intracellular signaling domains of one or more components of a TCR complex and/or one or more intracellular signaling domains of one or more costimulatory molecules; and wherein the input composition comprises at least $100 \times 10^6$ total CD4+ and CD8+ T cells at a concentration of less than $5 \times 10^6$ cells/mL.

In some embodiments of any of the provided methods, the CD4+ and CD8+ cells in the input composition are enriched or selected from a primary sample from a subject, optionally wherein the CD4+ and CD8+ cells in the input composition are separately enriched or selected from a primary sample from a subject. In certain embodiments of any of the provided methods, the composition of CD4+ T cells comprises at least 80%, at least 85%, at least 90%, or at least 95% CD4+ T cells. In particular embodiments of any of the provided methods, the composition of CD8+ T cells comprises at least 80%, at least 85%, at least 90%, or at least 95% CD8+ T cells.

In some embodiments, provided herein is a method for producing a composition of engineered cells, the method comprising incubating an input composition under stimulating conditions, thereby generating a stimulated composition, wherein: the input composition comprises a ratio of between 2:1 and 1:2 CD4+ to CD8+ T cells, and wherein the input composition comprises at least $100 \times 10^6$ total CD4+ and CD8+ T cells at a concentration of less than $5 \times 10^6$ cells/mL; and the stimulating conditions comprise the presence of a stimulatory reagent capable of activating one or more intracellular signaling domains of one or more components of a TCR complex and/or one or more intracellular signaling domains of one or more costimulatory molecules.

In certain embodiments of any of the provided methods, the incubation is performed in serum free media. In particular embodiments of any of the provided methods, the input composition comprises at least 80%, at least 85%, at least 90%, or at least 95% cells that are CD4+ T cells or CD8+ T cells. In particular embodiments of any of the provided methods, the input composition comprises between $100 \times 10^6$ and $500 \times 10^6$ total CD4+ and CD8+ T cells. In certain embodiments of any of the provided methods, the input composition comprises at or about $300 \times 10^6$ total CD4+ and CD8+ T cells.

In some embodiments of any of the provided methods, the total CD4+ and CD8+ T cells are viable cells. In particular embodiments of any of the provided methods, the input composition comprises a concentration of between $1 \times 10^6$ cells/mL and $5 \times 10^6$ cells/mL. In certain embodiments of any of the provided methods, the input composition comprises a concentration of or of about $3 \times 10^6$ cells/mL. In particular embodiments of any of the provided methods, the input composition comprises a ratio of between 1.5:1 and 1:1.5 CD4+ to CD8+ cells. In some embodiments of any of the provided methods, the input composition comprises a ratio of between 1.2:1 and 0.8:1 CD4+ to CD8+ cells.

In certain embodiments of any of the provided methods, the input composition comprises a ratio of or of about 1:1 CD4+ to CD8+ cells. In particular embodiments of any of the provided methods, the input composition comprises CD4+ and CD8+ that are surface positive for CD45RA and CCR7. In some embodiments of any of the provided methods, the ratio of CD4+ cells surface positive for CD45RA and CCR7 to CD8+ cells surface positive for CD45RA and CCR7 is or is about 1.1:1. In certain embodiments of any of the provided methods, the input composition comprises CD4+ and CD8+ cells that are surface positive for CD27 and CCR7. In particular embodiments of any of the provided methods, the ratio of the CD4+ cells that are surface positive for CD27 and CCR7 to CD8+ cells surface positive for CD27 and CCR7 is or is about 1.69:1. In some embodiments of any of the provided methods, the input composition comprises CD4+ and CD8+ cells that are surface positive for CCR7 and surface negative for CD62L, optionally at a ratio of between 2.0:1 to 1.5:1.

In certain embodiments of any of the provided methods, the methods further comprise: introducing a recombinant receptor into cells from the stimulated composition thereby generating an engineered cell composition, wherein the introducing comprises contacting the cells of the stimulated composition with an agent comprising a polynucleotide encoding the recombinant receptor.

In particular embodiments of any of the provided methods: the contacting is by transfection with a vector, wherein the vector is a transposon, optionally a Sleeping Beauty (SB) transposon or a Piggybac transposon; or the contacting is by transduction with a viral vector.

In some embodiments of any of the provided methods further comprise: introducing a recombinant receptor into cells from the stimulated composition thereby generating an engineered cell composition, wherein the introducing comprises transducing the cells of the stimulated composition with a viral vector comprising a polynucleotide encoding the recombinant receptor. In certain embodiments of any of the provided methods, the introducing is performed in serum free media.

In particular embodiments of any of the provided methods, the introducing the stimulated composition comprises less than $300 \times 10^6$ cells. In some embodiments of any of the provided methods, for the introducing, the stimulated composition comprises between $50 \times 10^6$ cells and $200 \times 10^6$ cells. In certain embodiments of any of the provided methods, for the introducing, the stimulated composition comprises at or about $100 \times 10^6$ cells. In particular embodiments of any of the provided methods, for the introducing, the stimulated composition comprises a concentration of less than $3\times10^6$ cells/mL. In some embodiments of any of the provided methods, for the introducing, the stimulated composition comprises a concentration of between $0.5\times10^6$ cells/mL and $2\times10^6$ cells/mL. In certain embodiments of any of the provided methods, for the introducing, the stimulated composition comprises a concentration of or about $1\times10^6$ cells/mL.

Particular embodiments of any of the provided methods comprise adjusting the composition of the stimulated composition after incubating under stimulating conditions prior to introducing the recombinant receptor into cells of the stimulated composition. In some embodiments of any of the provided methods, the cells of the stimulated composition are viable cells. In certain embodiments, provided herein is a method for producing a composition of engineered cells, the method comprising introducing a recombinant receptor into cells of a T cell composition, said T cell composition comprising a concentration of at least or at least about $1\times10^6$ viable cells per mL, wherein at least 80%, at least 85%, at least 90%, or at least 95% of the cells of the T cell composition are CD4+ T cells or CD8+ T cells.

In particular embodiments of any of the provided methods, the concentration of the T cell composition is less than $5\times10^6$ viable cells per mL. In some embodiments of any of the provided methods, the T cell composition comprises at least or at least about or about $100\times10^6$ viable cells. In certain embodiments of any of the provided methods, the T cell composition comprises less than $300\times10^6$ viable cells. In particular embodiments of any of the provided methods, the introducing comprises contacting the T cells by transduction a viral vector comprising a polynucleotide encoding the recombinant receptor.

In some embodiments of any of the provided methods, the introducing is performed in serum free media. In certain embodiments of any of the provided methods, one or more cells of the T cell composition are activated and/or comprise surface expression of the LDL receptor.

In particular embodiments of any of the provided methods, at least 10%, at least 20%, at least 30%, at least 40%, at least 50%, or at least 60% of the cells of the cell composition: (i) express a surface marker selected from the group consisting of HLA-DR, CD25, CD69, CD71, CD40L and 4-1BB; (ii) comprise intracellular expression of a cytokine selected from the group consisting of IL-2, IFN-gamma, TNF-alpha; (iii) are in the G1 or later phase of the cell cycle; and/or (iv) are capable of proliferating.

In some embodiments of any of the provided methods, prior to the introduction, the cells of the composition where generated by a process comprising incubating an input composition comprising CD4+ and CD8+ T cells under stimulating conditions, wherein said stimulating conditions comprise the presence of a stimulatory reagent capable of activating one or more intracellular signaling domains of one or more components of a TCR complex and/or one or more intracellular signaling domains of one or more costimulatory molecules. In certain embodiments of any of the provided methods, the incubating was performed in serum free media.

In particular embodiments, provided herein is a method for producing a composition of engineered cells, the method comprising: (a) incubating an input composition under stimulating conditions, thereby generating a stimulated composition, wherein: the input composition comprises a ratio of between 2:1 and 1:2 CD4+ to CD8+ T cells and comprises at least $100\times10^6$ CD4+ and CD8+ T cells at a concentration of less than $5\times10^6$ cells/mL; and the stimulating conditions comprise the presence of a stimulatory reagent capable of activating one or more intracellular signaling domains of one or more components of a TCR complex and/or one or more intracellular signaling domains of one or more costimulatory molecules; and (b) introducing a recombinant receptor into less than $300\times10^6$ cells of the stimulated composition thereby generating an engineered cell composition, wherein the introducing comprises contacting the cells of the stimulated composition with a viral vector comprising a polynucleotide encoding the recombinant receptor.

In some embodiments of any of the provided methods, the incubation and/or the introducing is performed in serum free media. In certain embodiments of any of the provided methods, the CD4+ and CD8+ T cells are viable cells. In particular embodiments of any of the provided methods, the cells from the stimulated composition are viable cells.

In some embodiments of any of the provided methods, the introducing is initiated within 2 days after the initiation of the of the incubation under stimulating conditions and/or within 2 days after the CD4+ T cells and the CD8+ T cells of the input composition are combined. In certain embodiments of any of the provided methods, the introducing is initiated within 36 hours after the initiation of the of the incubation under stimulating conditions and/or within 36 hours after the CD4+ T cells and the CD8+ T cells of the input composition are combined. In particular embodiments of any of the provided methods, the introducing is initiated within 30 hours after the initiation of the of the incubation under stimulating conditions and/or within 30 hours after the CD4+ T cells and the CD8+ T cells of the input composition are combined.

Some embodiments of any of the provided methods further comprise cultivating the engineered composition under conditions to promote proliferation and/or expansion of the engineered cells, thereby producing an output composition comprising the engineered T cells. In certain embodiments of any of the provided methods, the cultivating is performed in serum free media.

In particular embodiments, provided herein is a method for producing a composition of engineered cells, the method comprising: (a) incubating an input composition under stimulating conditions, thereby generating a stimulated composition; wherein the input composition comprises a ratio of between 2:1 and 1:2 CD4+ to CD8+ T cells, and wherein the input composition comprises at least $100\times10^6$ total CD4+ and CD8+ T cells at a concentration of less than $5\times10^6$ cells/mL; and wherein said stimulating conditions comprise the presence of a stimulatory reagent capable of activating one or more intracellular signaling domains of one or more components of a TCR complex and/or one or more intracellular signaling domains of one or more costimulatory molecules; (b) introducing a recombinant receptor into less than $300\times10^6$ cells from the stimulated composition thereby generating an engineered cell composition, wherein the introducing comprises transducing the cells of the stimulated composition with a viral vector comprising a polynucleotide encoding the recombinant receptor; and (c) cultivating the engineered composition under conditions to promote proliferation and/or expansion of the engineered cells, thereby producing an output composition comprising the engineered T cells.

In some embodiments of any of the provided methods, the incubating, introducing, and/or cultivating is performed in serum free media.

In certain embodiments of any of the provided methods, the input composition comprises a ratio of between 1.5:1 and 1:1.5 CD4+ to CD8+ cells, between 1.2:1 and 0.8:1 CD4+ to CD8+ cells, optionally at or about 1:1 CD4+ to CD8+ T cells. In particular embodiments of any of the provided methods, wherein the input composition comprises CD4+ and CD8+ that are surface positive for CD45RA and CCR7. In some embodiments of any of the provided methods, the ratio of CD4+ cells surface positive for CD45RA and CCR7 to CD8+ cells surface positive for CD45RA and CCR7 is or is about 1.1:1. In certain embodiments of any of the provided methods, the input composition comprises CD4+ and CD8+ cells that are surface positive for CD27 and CCR7. In particular embodiments of any of the provided methods, the ratio of the CD4+ cells that are surface positive for CD27 and CCR7 to CD8+ cells surface positive for CD27 and CCR7 is or is about 1.69:1. In some embodiments of any of the provided methods, the input composition comprises CD4+ and CD8+ cells that are surface positive for CCR7 and surface negative for CD62L.

In certain embodiments of any of the provided methods, for the introducing the stimulated composition comprises less than $300 \times 10^6$ cells. In particular embodiments of any of the provided methods, for the introducing, the stimulated composition comprises between $50 \times 10^6$ cells and $200 \times 10^6$ cells, optionally at or about $100 \times 10^6$ cells. In some embodiments of any of the provided methods, for the introducing, the stimulated composition comprises a concentration of less than $3 \times 10^6$ cells/mL. In certain embodiments of any of the provided methods, for the introducing, the stimulated composition comprises a concentration of between $0.5 \times 10^6$ cells/mL and $2 \times 10^6$ cells/mL, optionally at or about $1 \times 10^6$ cells/mL. In particular embodiments of any of the provided methods, comprising adjusting the composition of the stimulated composition after incubating under stimulating conditions prior to introducing the recombinant receptor into cells of the stimulated composition.

In particular embodiments of any of the provided methods, the incubation is performed in the presence of one or more cytokines, e.g., in a serum-free medium. In certain embodiments of any of the provided methods, the one or more cytokines are selected from recombinant IL-2, recombinant IL-7, and/or recombinant IL-15. In some embodiments of any of the provided methods, the one or more cytokines comprise: between 10 and 200 IU/mL recombinant IL-2; between 100 IU/mL and 1,000 IU/mL recombinant IL-7; and/or between 10 and 200 IU/mL recombinant IL-15. In particular embodiments of any of the provided methods, the one or more cytokines comprise: between 10 and 200 IU/mL recombinant IL-2; between 100 IU/mL and 1,000 IU/mL recombinant IL-7; and between 10 and 200 IU/mL recombinant IL-15.

In certain embodiments of any of the provided methods, at least 10%, at least 20%, at least 30%, at least 40%, at least 50%, or at least 60% of the cells of the stimulated composition: (i) express a surface marker selected from the group consisting of HLA-DR, CD25, CD69, CD71, CD40L and 4-1BB; (ii) comprise intracellular expression of a cytokine selected from the group consisting of IL-2, IFN-gamma, TNF-alpha; (iii) are in the G1 or later phase of the cell cycle; and/or (iv) are capable of proliferating.

In some embodiments of any of the provided methods, the stimulatory reagent comprises a primary agent that specifically binds to a member of a TCR complex, optionally that specifically binds to CD3. In particular embodiments of any of the provided methods, the stimulatory reagent further comprises a secondary agent that specifically binds to a T cell costimulatory molecule, optionally wherein the costimulatory molecule is selected from CD28, CD137

(4-1-BB), OX40, or ICOS. In certain embodiments of any of the provided methods, the primary and/or secondary agents comprise an antibody, optionally wherein the stimulatory reagent comprises incubation with an anti-CD3 antibody and an anti-CD28 antibody, or an antigen-binding fragment thereof.

In some embodiments of any of the provided methods, the primary agent and/or secondary agent are present on the surface of a solid support. In particular embodiments of any of the provided methods, the solid support is or comprises a bead. In certain embodiments of any of the provided methods, the bead comprises a diameter of greater than or greater than about 3.5 μm but no more than about 9 μm or no more than about 8 μm or no more than about 7 μm or no more than about 6 μm or no more than about 5 μm. In some embodiments of any of the provided methods, the bead comprises a diameter of or about 4.5 μm. In particular embodiments of any of the provided methods, the bead is inert. In certain embodiments of any of the provided methods, the bead is or comprises a polystyrene surface. In some embodiments of any of the provided methods, the bead is magnetic or superparamagnetic.

In particular embodiments of any of the provided methods, the ratio of beads to cells is less than 3:1. In certain embodiments of any of the provided methods, the ratio of beads to cells is from or from about 2:1 to 0.5:1. In some embodiments of any of the provided methods, the ratio of beads to cells is at or at about 1:1.

In particular embodiments of any of the provided methods, the input composition is incubated under stimulating conditions for less than 48 hours. In certain embodiments of any of the provided methods, the input composition is incubated under stimulating conditions for between 12 hours and 36 hours, inclusive. In some embodiments of any of the provided methods, the input composition is incubated under stimulating conditions for between 18 hours and 30 hours, inclusive. In particular embodiments of any of the provided methods, the input composition is incubated under stimulating conditions for or for about 24 hours.

In certain embodiments of any of the provided methods, the contacting, optionally transduction, is carried out for less than 48 hours. In some embodiments of any of the provided methods, the contacting, optionally transduction, is carried out between 12 hours and 36 hours, inclusive. In particular embodiments of any of the provided methods, the contacting, optionally transduction, is carried out for between 18 hours and 30 hours, inclusive. In certain embodiments of any of the provided methods, the contacting, optionally transduction, is performed for or for about 24 hours.

In some embodiments of any of the provided methods, the viral vector is a retroviral vector. In particular embodiments of any of the provided methods, the viral vector is a lentiviral vector or gammaretroviral vector. In certain embodiments of any of the provided methods, the contacting, optionally transduction, is carried out in the absence of a transduction adjuvant. In some embodiments of any of the provided methods, the introducing is performed in the presence of one or more cytokines, e.g., in a serum-free medium. In particular embodiments of any of the provided methods, the one or more cytokines are selected from recombinant IL-2, recombinant IL-7, and/or recombinant IL-15.

In certain embodiments of any of the provided methods, the one or more cytokines comprise: between 10 and 200 IU/mL recombinant IL-2; between 100 IU/mL and 1,000 IU/mL recombinant IL-7; and/or between 10 and 200 IU/mL recombinant IL-15. In some embodiments of any of the provided methods, the one or more cytokines comprise:

between 10 and 200 IU/mL recombinant IL-2; between 100 IU/mL and 1,000 IU/mL recombinant IL-7; and between 10 and 200 IU/mL recombinant IL-15.

In particular embodiments of any of the provided methods, at least a portion of the cultivating is performed with mixing and/or perfusion. In certain embodiments of any of the provided methods, at least a portion of the cultivating is performed with perfusion at a rate of, of about, or of least 500 mL/day, 600 mL/day, 700 mL/day, 750 mL/day, 800 mL/day, 900 mL/day, 1,000 mL/day, 1,200 mL/day, 1,400 mL/day, 1,500 mL/day, 1,600 mL/day, 1,800 mL/day, and/or 2,000 mL/day. In some embodiments of any of the provided methods, at least a first portion of the cultivating is performed with a perfusion rate of, of about, or of least 500 mL/day, 750 mL/day, or 1,000 mL/day, and wherein at least a second portion of the cultivating is performed with a perfusion rate of, of about, or of at least 1,200 mL/day, 1,400 mL/day, or 1,500 mL/day.

In particular embodiments of any of the provided methods, at the perfusion is initiated and/or increased when the cells reach a specific density. In certain embodiments of any of the provided methods, the specific density is, is about, or is at least $0.4\times10^6$ cells, $0.5\times10^6$ cells, $0.6\times10^6$ cells, $0.8\times10^6$ cells, $1.0\times10^6$ cells, $1.2\times10^6$ cells, $1.4\times10^6$ cells, $1.6\times10^6$ cells, $1.8\times10^6$ cells, $2.0\times10^6$ cells, $2.2\times10^6$ cells, or $2.4\times10^6$ cells. In some embodiments of any of the provided methods, the perfusion is initiated and/or increased to a rate of or of about 750 mL/day when the cells reach a density of or of about $0.6\times10^6$ cells/mL. In particular embodiments of any of the provided methods, the perfusion is initiated and/or increased to a rate of or of about 1500 mL/day when the cells reach a density of or of about $2.0\times10^6$ cells/mL.

In certain embodiments of any of the provided methods, the cultivating is performed in the presence of one or more cytokines, e.g., in a serum-free medium. In some embodiments of any of the provided methods, the one or more cytokines are selected from recombinant IL-2, recombinant IL-7, and/or recombinant IL-15. In particular embodiments of any of the provided methods, the one or more cytokines comprise: between 50 and 400 IU/mL recombinant IL-2; between 100 IU/mL and 2,000 IU/mL recombinant IL-7; and/or between 50 and 400 IU/mL recombinant IL-15. In particular embodiments of any of the provided methods, the cultivating is performed in the presence of between 50 and 400 IU/mL recombinant IL-2; between 100 IU/mL and 2,000 IU/mL recombinant IL-7; and between 50 and 400 IU/mL recombinant IL-15, e.g., in a serum-free medium. In certain embodiments of any of the provided methods, the one or more cytokines comprise: between 50 and 400 IU/mL recombinant IL-2; between 100 IU/mL and 1,000 IU/mL recombinant IL-7; and/or between 10 and 200 IU/mL recombinant IL-15.

In some embodiments of any of the provided methods, wherein the cultivating is initiated within 3 days after the initiation of the of the incubation under stimulating conditions and/or within 3 days after the CD4+ T cells and the CD8+ T cells of the input composition are combined. In particular embodiments of any of the provided methods, wherein the cultivating is initiated within 60 hours after the initiation of the of the incubation under stimulating conditions and/or within 60 hours after the CD4+ T cells and the CD8+ T cells of the input composition are combined. In certain embodiments of any of the provided methods, wherein the cultivating is initiated within 48 hours after the initiation of the of the incubation under stimulating conditions and/or within 48 hours after the CD4+ T cells and the CD8+ T cells of the input composition are combined.

In some embodiments of any of the provided methods, wherein the cultivating is performed at least until the composition comprises a threshold number of T cells. In particular embodiments of any of the provided methods, the threshold number of T cells is, is about, or is at least $2400\times10^6$ cells. In particular embodiments of any of the provided methods, the threshold number of T cells is, is about, or is at least $5500\times10^6$ cells.

In particular embodiments of any of the provided methods, the cultivating is continued for at least one day after the threshold number of T cells is reached. In certain embodiments of any of the provided methods, the threshold number of T cells is, is about, or is at least $900\times10^6$ cells. In certain embodiments of any of the provided methods, the threshold number of T cells is, is about, or is at least $1200\times10^6$ cells. In certain embodiments of any of the provided methods, the cultivation ends when the number of T cells is, is about, or is at least $2400\times10^6$ cells. In some embodiments of any of the provided methods, the threshold number of T cells is, is about, or is at least $3500\times10^6$ cells. In certain embodiments of any of the provided methods, the cultivation ends when the number of T cells is, is about, or is at least $5500\times10^6$ cells.

Certain embodiments of any of the provided methods, comprise collecting cells of the output composition subsequent to the cultivating. Some embodiments of any of the provided methods comprise collecting cells of the output composition subsequent to the cultivating, wherein the cells of the output composition are collected at least 9 days after the initiation of the incubation under stimulating conditions. Certain embodiments of any of the provided methods comprise collecting cells of the output composition subsequent to the cultivating, wherein the cells of the output composition are collected at least 10 days after the initiation of the incubation under stimulating conditions.

Particular embodiments of any of the provided methods comprise a 95% confidence interval of the amount of time between initiation of the incubating and the collecting cells of the output composition that is within 8 days to 25 days. Certain embodiments of any of the provided methods comprise a 95% confidence interval of the amount of time between initiation of the incubating and the collecting cells of the output composition that is within 9 days to 21 days. Some embodiments of any of the provided a 95% confidence interval of the amount of time between initiation of the incubating and the collecting cells of the output composition that is within 9 days to 16 days.

Particular embodiments of any of the provided methods further comprise formulating cells of the output composition for cryopreservation and/or administration to a subject, optionally in the presence of a pharmaceutically acceptable excipient. In certain embodiments of any of the provided methods, the cells of the output composition are formulated in the presence of a cryoprotectant. In some embodiments of any of the provided methods, the cryoprotectant comprises DMSO. In particular embodiments of any of the provided methods, the cells of the output composition are formulated in a container, optionally a vial or a bag.

Certain embodiments of any of the provided methods comprise isolating the CD4+ and/or the CD8+ T cells from a biological sample prior to the incubating. In some embodiments of any of the provided methods, the isolating comprises, selecting cells based on surface expression of CD4 and/or CD8, optionally by positive or negative selection. In particular embodiments of any of the provided methods, the isolating comprises carrying out immunoaffinity-based selection. In certain embodiments of any of the provided methods, the biological sample comprises primary T cells obtained from a subject. In some embodiments of any of the provided methods, the subject is a human subject.

In particular embodiments of any of the provided methods, the biological sample is or comprises a whole blood sample, a buffy coat sample, a peripheral blood mononuclear cell (PBMC) sample, an unfractionated T cell sample, a lymphocyte sample, a white blood cell sample, an apheresis product, or a leukapheresis product. In certain embodiments of any of the provided methods, the recombinant receptor is capable of binding to a target antigen that is associated with, specific to, and/or expressed on a cell or tissue of a disease, disorder or condition. In some embodiments of any of the provided methods, the disease, disorder or condition is an infectious disease or disorder, an autoimmune disease, an inflammatory disease, or a tumor or a cancer.

In particular embodiments of any of the provided methods, the target antigen is a tumor antigen. In certain embodiments of any of the provided methods, the target antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, VEGF receptors, VEGF-R2, Wilms Tumor 1 (WT-1), a pathogen-specific antigen and an antigen associated with a universal tag.

In some embodiments of any of the provided methods, the recombinant receptor is or comprises a functional non-TCR antigen receptor or a TCR or antigen-binding fragment thereof.

In particular embodiments of any of the provided methods, the recombinant receptor is a chimeric antigen receptor (CAR). In certain embodiments of any of the provided methods, the recombinant receptor is an anti-BCMA CAR. In some embodiments of any of the provided methods, the chimeric antigen receptor comprises an extracellular domain comprising an antigen-binding domain. In particular embodiments of any of the provided methods, the antigen-binding domain is or comprises an antibody or an antibody fragment thereof, which optionally is a single chain fragment. In certain embodiments of any of the provided methods, the fragment comprises antibody variable regions joined by a flexible linker. In some embodiments of any of the provided methods, the fragment comprises an scFv. In particular embodiments of any of the provided methods, the chimeric antigen receptor further comprises a spacer and/or a hinge region.

In certain embodiments of any of the provided methods, the chimeric antigen receptor comprises an intracellular signaling region. In some embodiments of any of the provided methods, the intracellular signaling region comprises an intracellular signaling domain. In particular embodiments of any of the provided methods, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In certain embodiments of any of the provided methods, the intracellular signaling domain is or comprises an intracellular signaling domain of a CD3 chain, optionally a CD3-zeta (CD3ζ) chain, or a signaling portion thereof.

In some embodiments of any of the provided methods, the chimeric antigen receptor further comprises a transmembrane domain disposed between the extracellular domain and the intracellular signaling region. In particular embodiments of any of the provided methods, the intracellular signaling region further comprises a costimulatory signaling region. In certain embodiments of any of the provided methods, the costimulatory signaling region comprises an intracellular signaling domain of a T cell costimulatory molecule or a signaling portion thereof.

In some embodiments of any of the provided methods, the costimulatory signaling region comprises an intracellular signaling domain of a CD28, a 4-1BB or an ICOS or a signaling portion thereof.

In particular embodiments of any of the provided methods, the costimulatory signaling region is between the transmembrane domain and the intracellular signaling region. In certain embodiments of any of the provided methods, the output composition comprising the threshold number or greater number of cells is produced among greater than or greater than about 85%, greater than or greater than about 90% or greater than or greater than about 95% of the iterations of the method.

In some embodiments of any of the provided methods, the serum-free media comprises: 0.5 mM to 5 mM of a dipeptide form of L-glutamine in a base media; 0.5 mM to 5 mM L-glutamine; and at least one protein, wherein the media is free of serum. In particular embodiments of any of the provided methods, the dipeptide form of L-glutamine is L-alanyl-L-glutamine.

In certain embodiments of any of the provided methods, the concentration of the dipeptide form of L-glutamine in the serum-free media is or is about 2 mM. In some embodiments of any of the provided methods, the concentration of L-glutamine in the serum-free media is or is about 2 mM. In particular embodiments of any of the provided methods, the at least one protein comprises one or more of albumin, insulin or transferrin, optionally one or more of a human or recombinant albumin, insulin or transferrin.

In some of any embodiments of the methods provided herein, during at least a portion of the cultivating, the cells are monitored for cell viability, concentration, density, number, or a combination thereof. In some of any such embodiments, the monitoring is carried out by an optical method, optionally microscopy. In some of any such embodiments, the monitoring is carried out by bright field microscopy, fluorescence microscopy, differential interference contrast microscopy, phase contrast microscopy, digital holography microscopy (DHM), differential digital holography microscopy (DDHM), or a combination thereof. In some of any such embodiments, the monitoring is carried out by differential digital holography microscopy (DDHM). In some of any such embodiments, the monitoring is carried out intermittently or continuously during the at least a portion of the cultivation, optionally is carried out at least every 1 hour, 6 hours, 12 hours, 18 hours, 24 hours, or 26 hours during the cultivation. In some of any such embodiments, the monitoring is carried out until the cells reach the threshold number of T cells, the threshold number of viable T cells, the threshold concentration of T cells or the threshold concentration of viable T cells. In some of any such embodiments, the monitoring and cultivation is carried out in a closed system.

In some of any embodiments of the methods provided herein, at least 30%, at least 40%, at least 50%, at least 60%, at least 70%, at least 75%, at least 80%, at least 85%, at least 90%, at least 95%, or greater than 95% of the cells in the output composition are of a memory phenotype; wherein at least 30%, at least 40%, at least 50%, at least 60%, at least 70%, at least 75%, at least 80%, at least 85%, at least 90%, at least 95%, or greater than 95% of the cells in the output composition are of a central memory phenotype; wherein at least 30%, at least 40%, at least 50%, at least 60%, at least 70%, at least 75%, at least 80%, at least 85%, at least 90%, at least 95%, or greater than 95% of the cells in the output composition are CD27+, CD28+, CCR7+, CD45RA−, CD45RO+, CD62L+, CD3+, CD95+, granzyme B−, and/or CD127+; and/or wherein at least 30%, at least 40%, at least 50%, at least 60%, at least 70%, at least 75%, at least 80%, at least 85%, at least 90%, at least 95%, or greater than 95% of the cells in the output composition are CCR7+/CD45RA− or are CCR7+/CD45RO+.

In some of any embodiments of the methods provided herein, iterations of the method produce a plurality of the output compositions, optionally from human biological samples in which the method is carried out among a plurality of different individual subjects, wherein: the mean percentage of cells of a memory phenotype in the plurality of the output compositions is between about 40% and about 65%, between about 40% and about 45%, between about 45% and about 50%, between about 50% and about 55%, between about 55% and about 60%, or between about 60% and about 65%; the mean percentage of cells of a central memory phenotype in the plurality of the output compositions is between about 40% and about 65%, between about 40% and about 45%, between about 45% and about 50%, between about 50% and about 55%, between about 55% and about 60%, or between about 60% and about 65%; the mean percentage of cells that are CD27+, CD28+, CCR7+, CD45RA−, CD45RO+, CD62L+, CD3+, CD95+, granzyme B−, and/or CD127+ in the plurality of the output compositions is between about 40% and about 65%, between about 40% and about 45%, between about 45% and about 50%, between about 50% and about 55%, between about 55% and about 60%, or between about 60% and about 65%; the mean percentage of cells that are CCR7+/CD45RA− or CCR7+/CD45RO+ in the plurality of the output compositions is between about 40% and about 65%, between about 40% and about 45%, between about 45% and about 50%, between about 50% and about 55%, between about 55% and about 60%, or between about 60% and about 65%; the mean percentage of central memory CD4+ T cells in the engineered CD4+ T cells, optionally CAR+CD4+ T cells, of the plurality of the output compositions is between about 40% and about 65%, between about 40% and about 45%, between about 45% and about 50%, between about 50% and about 55%, between about 55% and about 60%, or between about 60% and about 65%; the mean percentage of central memory CD8+ T cells in the engineered CD8+ T cells, optionally CAR+CD8+ T cells, of the plurality of the output compositions is between about 40% and about 65%, between about 40% and about 45%, between about 45% and about 50%, between about 50% and about 55%, between about 55% and about 60%, or between about 60% and about 65%; and/or the mean percentage of central memory T cells, optionally CD4+ central memory T cells and CD8+ central memory T cells, in the engineered T cells, optionally CAR+ T cells, of the plurality of the output compositions is between about 40% and about 65%, between about 40% and about 45%, between about 45% and about 50%, between about 50% and about 55%, between about 55% and about 60%, or between about 60% and about 65%.

In some of any embodiments of the methods provided herein, the methods produces output compositions exhibiting a predetermined feature, optionally a threshold number of cells expressing the CAR in the output composition, in at least about 80%, about 90%, about 95%, about 97%, about 99%, about 100%, or 100% of the human biological samples in which it is carried out among a plurality of different individual subjects. In some of any such embodiments, the plurality of different individual subject comprise subjects having a disease or condition. In some of any such embodiments, the disease or condition is a cancer. In some of any such embodiments, the cancer is a hematological cancer, optionally multiple myeloma. In some of any such embodiments, at least 30%, at least 40%, at least 50%, at least 60%, at least 70%, at least 75%, at least 80%, at least 85%, at least 90%, at least 95%, or greater than 95% of the cells in the composition are of a memory phenotype; wherein at least 30%, at least 40%, at least 50%, at least 60%, at least 70%, at least 75%, at least 80%, at least 85%, at least 90%, at least 95%, or greater than 95% of the cells in the composition are of a central memory phenotype; wherein at least 30%, at least 40%, at least 50%, at least 60%, at least 70%, at least 75%, at least 80%, at least 85%, at least 90%, at least 95%, or greater than 95% of the cells in the composition are CD27+, CD28+, CCR7+, CD45RA−, CD45RO+, CD62L+, CD3+, granzyme B−, and/or CD127+; and/or wherein at least 30%, at least 40%, at least 50%, at least 60%, at least 70%, at least 75%, at least 80%, at least 85%, at least 90%, at least 95%, or greater than 95% of the cells in the output composition are CCR7+/CD45RA− or are CCR7+/CD45RO+.

In certain embodiments, provided herein is a composition comprising engineered cells produced by any method provided herein. Some embodiments of any of the provided compositions comprise a pharmaceutically acceptable carrier. Particular embodiments of any of the provided compositions comprise a cryoprotectant, optionally DMSO.

In certain embodiments, provided herein is an article of manufacture, comprising any composition provided herein and instructions for administering the output composition to a subject. In certain embodiments of any of the provided articles of manufacture, the subject has a disease or condition, optionally wherein the recombinant receptor specifically recognizes or specifically bind to an antigen associated with, or expressed or present on cells of, the disease or condition.

BRIEF DESCRIPTION OF THE DRAWINGS

FIG. 2A shows a plot of bivariate fit analysis of the ratio of CD45RA+/CCR7+/CD4+ to CD45RA+/CCR7+/CD8+ cells in a starting mixture of selected CD4 and CD8 cells compared to the CAR+CD4+/CD8+ ratio in an engineered CAR+ T cell composition. FIG. 2B shows a plot of bivariate fit analysis of the ratio of the CD62L−/CCR7+/CD4+ T cells to CD62L−/CCR7+/CD8+ T cells in a starting mixture of selected CD4 and CD8 cells compared to the CAR+CD4+/ CD8+ ratio in an engineered CAR+ T cell composition. FIG. 2C shows a plot of bivariate fit analysis of the ratio of the CD27+/CCR7+/CD4+ T cells to CD27+/CCR7+/CD8+ T cells in a starting mixture of selected CD4 and CD8 cells compared to the CAR+CD4+/CD8+ ratio in an engineered CAR+ T cell composition. The curved lines represent the boundaries of the bivariate normal ellipse at p=0.950. Data points represent the mean ratios of multiple compositions from each subject, including healthy donors (circles) and a patient with multiple myeloma (plus signs).

FIG. 3A shows a plot of bivariate fit analysis of the ratio of CD27+/CCR7+/CD4+ to CD27+/CCR7+/CD8+ cells in a starting mixture of selected CD4 and CD8 cells compared to the CAR+CD4+/CD8+ ratio in an engineered CAR+ T cell composition. FIG. 3B shows a plot of bivariate fit analysis of the ratio of the CD27+/CCR7+/CD4+ T cells to CD27+/ CCR7+/CD8+ T cells in a starting mixture of selected CD4 and CD8 cells compared to the CAR+CD4+/CD8+ ratio in an engineered CAR+ T cell composition. FIG. 3C shows a plot of bivariate fit analysis of the ratio of the CD62L−/ CCR7+/CD4+ T cells to CD62L−/CCR7+/CD8+ T cells in a starting mixture of selected CD4 and CD8 cells compared to the CAR+CD4+/CD8+ ratio in an engineered CAR+ T cell composition. The curved lines represent the boundaries of the bivariate normal ellipse at p=0.950.

DETAILED DESCRIPTION

Figures 1A, 1B:
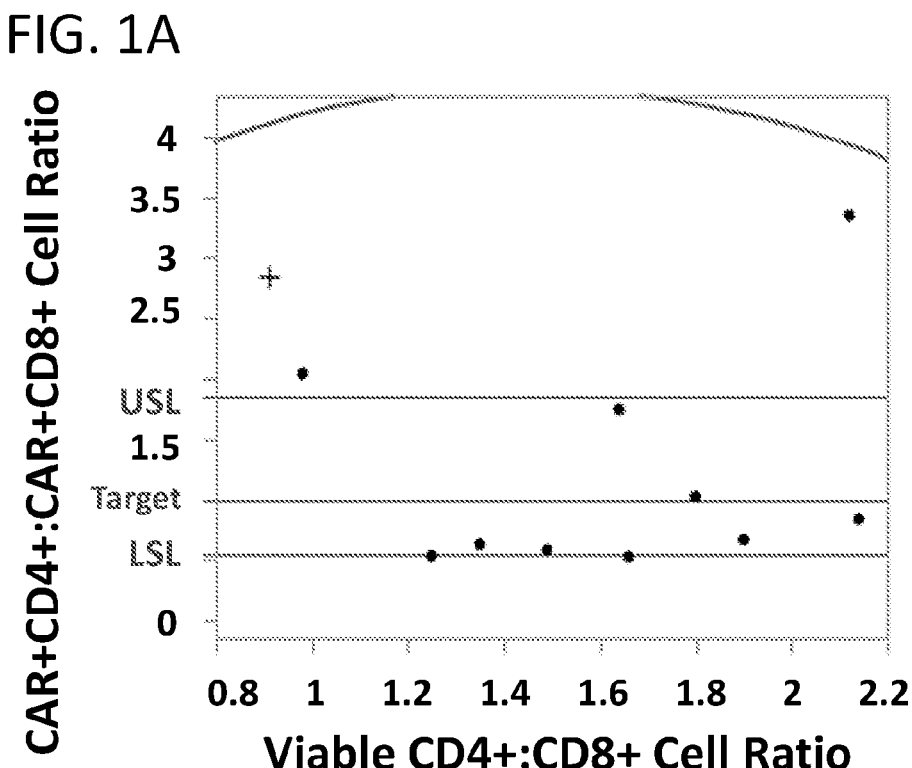
FIG. 1A shows a plot of bivariate fit analysis of the ratio of viable CD4+ cells to viable CD8+ cells (viable CD4+/CD8+ ratio) in an apheresis sample compared to the ratio of CAR+CD4+ T cells to CAR+CD8+ T cells (CAR+CD4+/CD8+ ratio) in a T cell composition after T cell activation, transduction with a chimeric antigen receptor (CAR) construct and expansion. The curved lines represent the boundaries of the bivariate normal ellipse at p=0.990. Data points represent the mean ratios of four samples from each subject, including healthy subjects (circles) and a subject with myeloma (plus sign).
FIG. 1B shows a plot of bivariate fit analysis of the CD45RA+/CCR7+CD4/CD8 ratio in a starting mixture of selected CD4 and CD8 cells compared to the CAR+CD4+/CD8+ ratio in a T cell composition after T cell activation, transduction with a chimeric antigen receptor (CAR) construct and expansion. The curved lines represent the boundaries of the bivariate normal ellipse at p=0.990. Data points represent the mean ratios of four samples from each subject, including healthy subjects (circles) and a subject with myeloma (plus sign).

Provided herein are methods for generating or producing compositions of engineered cells, such as engineered CD4+ and CD8+ T cells, that express a recombinant receptor. In particular embodiments, the methods are used in connection with a process that includes incubating cells, such as a composition of input cells, under stimulating conditions; genetically engineering cells, e.g., by transducing or transfecting a polynucleotide encoding a recombinant receptor, and/or cultivating the engineered cells under conditions that promote cell proliferation and/or expansion.

In some embodiments, provided herein is a method for producing a composition of engineered cells that includes combining CD4+ T cells and CD8+ T cells at a ratio of between 2:1 and 1:2 to generate an input composition, and incubating the input composition under stimulatory conditions. In certain embodiments, the method includes incubating an input composition containing a ratio of between 2:1 and 1:2 CD4+ T cells to CD8+ T cells. In certain embodiments, the input composition comprises at least 100×10^6 total CD4+ and CD8+ T cells at a concentration of less than 5×10^6 cells/mL.

In certain embodiments, provided herein is a method for producing a composition of engineered cells that includes introducing a recombinant receptor into a set fixed or amount of cells, e.g., at least or about 1×10^6, 10×10^6, 100×10^6, or 1,000×10^6 cells, of a cell composition. In some embodiments, the cells are stimulated cells. In certain embodiments, the cells are viable cells. In particular embodiments, the introducing comprises transducing the T cells of the stimulated composition with a viral vector comprising a polynucleotide encoding the recombinant receptor. In certain embodiments, the cell composition comprises at least 80%, at least 85%, at least 90%, or at least 95% cells that are CD4+ T cells or CD8+ T cells.

In some embodiments, provided herein is a method for producing a composition of engineered cells that includes (i) incubating an input composition under stimulating conditions, thereby generating a stimulated composition; wherein the input composition comprises a ratio of between 2:1 and 1:2 CD4+ to CD8+ T cells, and wherein the input composition comprises at least 100×10^6 total CD4+ and CD8+ T cells at a concentration of less than 5×10^6 cells/mL; (ii) introducing a recombinant receptor into less than 300×10^6 cells from the stimulated composition thereby generating an engineered cell composition, wherein the introducing comprises transducing the cells of the stimulated composition with a viral vector comprising a polynucleotide encoding the recombinant receptor; and (iii) cultivating the engineered composition under conditions to promote proliferation and/ or expansion of the engineered cells, thereby producing an output composition comprising the engineered T cells.

Different processes are available for generating genetically engineered T cell populations, including for generating engineered T cells that express a chimeric antigen receptor.

However, in some embodiments, some of these processes may require a long or a relatively long amount of time to generate the engineered cells. In certain embodiments, some of these processes may vary in their ability to successfully generate engineered cells suitable for therapy from across different subjects. In certain embodiments, some of these processes may produce genetically engineered T cell compositions with a high degree of variation for parameters such as cell health, viability, transduction efficiency, and/or cell activity.

The provided embodiments address one or more of these issues. In particular embodiments, the provided methods generate engineered T cells suitable for therapy, e.g., autologous cell therapy, in a short or relatively short amount of time as compared to some existing processes. Furthermore, in some embodiments, the provided methods result in a more consistent, and less variable, process in terms of the amount of time required for producing engineered cells from samples collected from among different subjects. In particular embodiments, the provided methods are able to successfully generate engineered T cells suitable for cell therapy from a high proportion of subjects. In certain embodiments, the resulting cell compositions contain high or relatively high portions of healthy cells, e.g., cells that are viable and/or do not express an apoptotic marker, high or relatively high portions of cells that express a recombinant receptor, and/or cells with a high or relatively high activity, e.g., cytotoxic, anti-tumor, and/or cytokine production, in response to antigen stimulation. In some embodiments, the provided methods provide a process for producing engineered cell products and in some aspects have particular success rates such as high success rates or rates of success greater than a threshold rate, such as those that are able to generate therapeutic cell compositions, such as able to generate such compositions having certain required or desired features, for a large number or percentage of samples, such as for all or a high percentage of samples each derived from a different individual subject or patient, such as a subject or patient to be treated with the therapeutic composition (e.g., in the context of autologous cell therapy). In some aspects, the subjects or patients have a disease or condition such as a cancer such as a blood or hematological cancer such as a multiple myeloma. In some aspects, the samples—from which, for a high percentage thereof, it is possible to generate therapeutic cell compositions—are patient samples including those that are variable for example in terms of cell phenotypes or other parameters of the samples or cells thereof.

In some embodiments, the provided methods generate engineered T cell compositions that have improved or high degrees of cell health such as compared to cell compositions generated via other processes. In some embodiments, the compositions include a high percentage of cells that are negative of an apoptotic marker. In some embodiments, the provided methods generate T cell compositions comprising polyfunctional cells with robust cytokine production. In some embodiments, the provided methods generate T cell compositions that are enriched for a memory phenotype, enriched for a central memory phenotype, and/or enriched for cells that are CD27+, CD28+, CCR7+, CD45RA−, CD45RO+, CD62L+, CD3+, CD95+, granzyme B−, and/or CD127+. In some embodiments, at least 20, 25, 30, 35, 40, 45, 50, 55, 60, 65, 70, 75, or 80% or more of the cells in the composition (or at least 20, 25, 30, 35, 40, 45, 50, 55, 60, 65, 70, 75, or 80% or more of the cells in the composition for at least half or a majority of samples produced using the methods or, on average, for samples produced using the methods), of the T cells in the composition, or of the engineered T cells in the composition, are T cells of a central memory phenotype; are CD27+, CD28+; are CCR7+, CD45RA−; and/or are CCR7+, CD45RO+. In some embodiments, at least 50, 55, 60, 65, 70, 75, or 80 or 85 or 90 or 95% or more of the cells in the composition (or at least 50, 55, 60, 65, 70, 75, or 80 or 85 or 90 or 95% or more of the cells in the composition for at least half or a majority of samples produced using the methods or, on average, for samples produced using the methods), of the T cells in the composition, or of the engineered T cells in the composition, are T cells of a memory phenotype; are CD45RA−; and/or are CD45RO+.

In particular embodiments, the provided methods are used in connection with a process for efficiently producing or generating engineered cells that are suitable for use in a cell therapy. In certain embodiments, the timing, conditions, and reagents used for each step of the process improve the efficiency of each subsequent step and/or the overall process. For example, in some embodiments, cells may be incubated, transduced, and/or cultivated at cell concentrations that are high enough to achieve a desired effect, e.g., stimulation of the cells or improved transduction efficiency, but at concentrations that are low enough to avoid slowed growth or reduced survival in subsequent processing steps. Further, in some embodiments, the steps of the process are timed to begin or end at specific time points to improve the efficiency of subsequent process steps and/or of whole process. For example, in some embodiments, steps for incubation and engineering (e.g., transducing or transfecting, the cells) are completed earlier in the process than in alternative methods, which, in certain embodiments, improves the survival and/or health, and/or the speed of the proliferation and expansion of the cells during subsequent the cultivation step. Thus, in one aspect, the specific timing, conditions, and reagents of each step influences the cells beyond the individual step and, in certain embodiments, influence the performance of the entire process.

In some embodiments, the methods are used in connection with a process that generates or produces genetically engineered cells that are suitable for cell therapy in a manner that may be faster and more efficient than the alternative processes. In certain embodiments, the methods provided herein have a high rate of success for generating or producing compositions of engineered cells from broader population of subjects than what may be possible from alternative processes. In certain embodiments, the engineered cells produced or generated by the provided methods may have greater health, viability, activation, and may have greater expression of the recombinant receptor than cells produced by alternative methods. Thus, in some aspects, the speed and efficiency of the provided methods for generating engineered cells for cell therapy allow for easier planning and coordination of cell therapy treatments, such as autologous therapy, to a broader population of subjects than what may be possible by some alternative methods.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. PROCESS FOR GENERATING ENGINEERING CELLS

Provided herein are methods for generating an output composition of engineered cells, such as engineered CD4+T and CD8+ T cells, that express a recombinant protein, e.g., a recombinant receptor such as a T cell receptor (TCR) or a chimeric antigen receptor (CAR). In certain embodiments, the methods provided herein are used in connection with manufacturing, generating, or producing a cell therapy, and may be used in connection with additional processing steps, such as steps for the isolation, separation, selection, activation or stimulation, transduction, washing, suspension, dilution, concentration, and/or formulation of the cells. In some embodiments, the methods of generating or producing engineered cells, e.g., engineered CD4+ and CD8+ T cells, include one or more of isolating cells from a subject, preparing, processing, incubating under stimulating conditions, and/or engineering (e.g. transducing) the cells. In some embodiments, the method includes processing steps carried out in an order in which: input cells, e.g. primary CD4+ and CD8+ cells, are first isolated, such as selected or separated, from a biological sample; input cells are incubated under stimulating conditions, engineered with vector particles, e.g., viral vector particles, to introduce a recombinant polynucleotide into the cells, e.g., by transduction or transfection; cultivating the engineered cells, e.g., transduced cells, such as to expand the cells; and collected, harvested, and/or filled into a container, e.g., a bag or vial, with all or a portion of the cells to formulated the cells in an output composition. In some embodiments, the cells of the generated output composition are re-introduced into the same subject, before or after cryopreservation. In some embodiments, the output compositions of engineered cells are suitable for use in a therapy, e.g., an autologous cell therapy.

In particular embodiments, the provided methods are used in connection with generating output compositions of cells expressing a recombinant receptor from an initial or input composition of cells. In certain embodiments, the input composition is produced, generated, and/or made by combining, mixing, and/or pooling cells including from composition of cells containing enriched T cells, enriched CD4+ T cells, and/or enriched CD8+ T cells (herein after also referred to as compositions of enriched T cells, compositions of enriched CD4+ T cells, and compositions of enriched CD8+ T cells, respectively). In some embodiments, the input composition of cells is a composition of combined, mixed, and/or pooled CD4+ and CD8+ T cells. In certain embodiments, the provided methods are used in connection with one or more of: activating and/or stimulating a cells, e.g., cells of an input composition; genetically engineering the activated and/or stimulated cells, e.g., to introduce a polynucleotide encoding a recombinant protein by transduction or transfection; and/or cultivating the engineered cells, e.g., under conditions that promote proliferation and/or expansion. In certain embodiments, the methods may also be used in connection with isolating or selecting cells from a biological sample to generate an input composition of enriched T cells, such as from a biological sample taken, collected, and/or obtained from a subject. In particular embodiments, the provided methods may be used in connection with harvesting, collecting, and/or formulating compositions of enriched T cells after the cells have been incubated, activated, stimulated, engineered, transduced, transfected, and/or cultivated.

In some embodiments, incubating cells under stimulating conditions is or includes incubating the cells with a stimulatory reagent, e.g., a stimulatory reagent described herein such as in Section I-B-1. In particular embodiments, a set or fixed amount of cells, such as an amount of cells greater than at least $100 \times 10^6$ cells are incubated under stimulating conditions at a set or fixed concentration, such as a concentration of less than $5 \times 10^6$ cells/mL. In certain embodiments, the incubation is performed for a set or fixed amount of time, such as an amount of time under 2 days or for an amount of time between 18 hours and 30 hours.

In certain embodiments, methods provided herein are performed in connection with engineering, e.g., transducing or transfecting the cells. In some embodiments, a set or fixed amount of cells, e.g., viable CD4+ and CD8+ cells, are subjected to engineering. In some embodiments, an amount of cells greater than at least $10 \times 10^6$ cells are incubated under stimulating conditions at a set or fixed concentration, such as a concentration of less than $3 \times 10^6$ cells/mL. In certain embodiments, the engineering is performed for a set or fixed amount of time, such as an amount of time under 2 days or for an amount of time between 18 hours and 30 hours.

In certain embodiments, at least a portion of the cultivation step is performed with constant mixing and/or perfusion, e.g., with a bioreactor in a closed system. In certain embodiments, the mixing and/or perfusion incorporates a steady and/or gradual replacement of used or old cell media or solution with fresh media or solution. In some embodiments, the cultivation is initiated within an amount of time, e.g., within 2, 3, 4, or 5 days from the start or initiation of the incubation under stimulatory conditions; within 2, 3, 4, or 5 days from the mixing, pooling, and/or combining cells, e.g., CD4+ and CD8+ cells, to generate an input composition; within 3, 4, 5, or 6 days from when the biological samples are collected; and/or within 3, 4, 5, or 6 days isolation, selection, and/or enrichment of compositions of enriched T cells, e.g., CD4+ and/or CD8+ T cells, from a biological sample.

In some embodiments, one or more process steps are carried out, at least in part, in serum free media. In some embodiments, the serum free media is a defined and/or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

In some embodiments, the provided methods are carried out such that one, more, or all steps in the preparation of cells for clinical use, e.g., in adoptive cell therapy, are carried out without exposing the cells to non-sterile conditions. In some embodiments of such a process, the cells are isolated, separated or selected, transduced, washed, optionally activated or stimulated and formulated, all within a closed system. In some embodiments, the one or more of the steps are carried out apart from the closed system or device. In some such embodiments, the compositions of enriched cells are transferred apart from the closed system or device under sterile conditions, such as by sterile transfer to a separate closed system.

In particular embodiments, the compositions of enriched T cells may be collected, formulated for cryoprotection, cryofrozen, and/or stored below 0° C., below −20° C., or at or below −70 C or −80° C. prior to, during, or after any stage or step of the process for generating output compositions of enriched T cells expressing recombinant receptors. In some embodiments, the cells may be stored for an amount of time under 1, 2, 3, 4, 5, 6, 7, 8, 9, or 10 days, or an amount of time under 1, 2, 3, 4, 5, 6, 7, 8 weeks, or for an amount of time at least 1, 2, 3, 4, 5, 6, 7, or 8 weeks, or for more than 8 weeks. After storage, the compositions of enriched T cells may be thawed and the processing may be resumed from the same point in the process. In some embodiments, input compositions of enriched T cells are cryofrozen and stored prior to further processing, e.g., incubation under stimulating conditions. In particular embodiments, cultivated and/or formulated compositions of enriched T cells are cryofrozen and stored prior to being administered to as subject, e.g., as an autologous cell therapy.

In certain embodiments, the methods provided herein are used in connection with a process whereby engineered cells are generated by a process that includes steps for incubating the cells under stimulating conditions, transducing the cells to express a recombinant receptor, e.g., a CAR, and cultivating the cells under conditions that promote proliferation or expansion. In particular embodiments, the incubation is performed for between 18 and 30 hours, such as for or for about 24 hours, and the transduction is subsequently performed for between 18 and 30 hours, such as for or for about 24 hours. In certain embodiments, the cells are cultivated under conditions that promote stimulation and/or expansion after the cells have been stimulated and transduced. In certain embodiments, the incubation is initiated, such as by contacting the cells with a stimulatory reagent, and the transduction is initiated with 48 hours, within 36 hours, or within 30 hours after the incubation has been initiated. In some embodiments, the cultivation is performed after the incubation and transduction, and the cultivation is initiated within 72 hours, within 66 hours, or within 60 hours after the incubation, has been initiated. In certain embodiments, the cultivation is performed until a threshold amount, density, and/or expansion of cells is achieved, until at least one day after the threshold amount, density, and/or expansion of cells is achieved, and/or until at least 8 days, 9 days, 10 days, 11 days, or 12 days after the initiation of the incubation.

In certain embodiments, at any stage or step in the process, a portion of the cells may be sampled or collected, e.g., cells may be taken from the composition of enriched T cells while the composition remains in the closed system, such as during the isolation, incubation, engineering, cultivation, and/or formulation. In certain embodiments, such cells may be analyzed for makers, features, or characteristics including but not limited to viability, apoptosis, activation, stimulation, growth, and/or exhaustion. In some embodiments, the cells are sampled or collected by an automated process while the composition of enriched T cells remains in the closed system. In some embodiments, the analysis of sampled or collected cells is automated. In particular embodiments, the analysis is performed in a closed system under sterile conditions.

In some embodiments, provided herein is a process whereby engineered cells are generated comprising the steps of incubating an input cell composition under a stimulating condition (e.g., to activate T cells in the composition), subjecting the cell composition to engineering (e.g. transduction) to express a recombinant receptor, e.g., a CAR, cultivating the cells under conditions that promote cell proliferation or expansion, and/or harvesting or collecting the cells to generate a cell composition comprising engineered cells, e.g., engineered T cells for a cell therapy. In some embodiments, the input cell composition is incubated under stimulating conditions that include: the ratio of a stimulatory reagent (e.g., a bead reagent as described in Section I-B-1) to cells is of or of about 1:1; the input composition comprises CD4+ T cells and CD8+ T cells at a ratio of or of about 1:1 (e.g., a composition enriched for CD4+ T cells and a composition enriched for CD8+ T cells can be pooled, mixed, and/or combined at a ratio of or of about 1:1 to generate the input composition); the total duration of the incubation under the stimulating conditions, e.g. with the stimulatory reagent, is between about 12 hours and about 36 hours, e.g., between about 18 hours and about 30 hours; the cells, e.g., cells of the input composition, are incubated under the stimulating conditions such as in the presence of a stimulatory reagent, at a density between about $5\times10^5$ cells/mL and about $5\times10^7$ cells/mL, e.g., at or at about $3\times10^6$ cells/mL; and/or the cells, e.g., cells of the input composition, are stimulated and/or activated in a serum-free media (e.g., a serum-free medium comprising one or more recombinant cytokines, such as IL-2, IL-7, and IL-15). In some embodiments, the cells are subjected to engineering under conditions that include: contacting the cells with a nucleic acid molecule encoding a recombinant protein, e.g. a recombinant receptor, under centrifugation, such as spin-oculation (e.g. centrifugal inoculation), e.g., at about 1600×g for about 60 minutes; the cells are subjected to engineering at a density between about $5\times10^5$ cells/mL and about $5\times10^7$ cells/mL, e.g., at or at about $1\times10^6$ cells/mL; about $100\times10^6$ cells from the composition cultured under stimulating conditions are subjected to engineering; the total duration of the engineering step, e.g. transduction, is between about 12 hours and about 36 hours, e.g., between about 18 hours and about 30 hours; and/or the cells are subjected to engineering in a serum-free media (e.g., a serum-free medium comprising one or more recombinant cytokines, such as IL-2, IL-7, and IL-15). In some embodiments, the cells are cultivated under conditions that promote cell proliferation or expansion that include: the cells are cultivated under rocking and/or perfusion conditions; and/or the cells are cultivated in a serum-free media (e.g., a serum-free medium comprising one or more recombinant cytokines, such as IL-2, IL-7, and IL-15, optionally with higher concentrations of the recombinant cytokines than the serum-free medium used for the stimulation/activation and/or the engineering). In some embodiments, the cultivation ends and the cells are harvested when cells achieve a threshold amount, concentration, and/or expansion, e.g., a threshold cell count (e.g., total nucleated cell count) of at least about $3500\times10^6$ cells or about $5500\times10^6$ cells. In some embodiments, when the cells have not achieved a target or threshold at a given time during the stimulation/activation, engineering, cultivation, and/or harvest processes, the cells may be stimulated/activated, subjected to engineering, and/or cultivated until a later time point when the target or threshold is reached.

In some embodiments, provided herein is a process whereby engineered cells are generated comprising the steps of incubating an input cell composition under a stimulating condition (e.g., to activate T cells in the composition), subjecting the cell composition to engineering (e.g. transduction) to express a recombinant receptor, e.g., a CAR, cultivating the cells under conditions that promote cell proliferation or expansion, and/or harvesting or collecting the cells to generate a cell composition comprising engineered cells, e.g., engineered T cells for a cell therapy. In some embodiments, the input cell composition is incubated under stimulating conditions that include: the ratio of a stimulatory reagent (e.g., a bead reagent as described in Section I-B-1) to cells is of or of about 1:1; the input composition comprises CD4+ T cells and CD8+ T cells at a ratio of or of about 1:1 (e.g., a composition enriched for CD4+ T cells and a composition enriched for CD8+ T cells can be pooled, mixed, and/or combined at a ratio of or of about 1:1 to generate the input composition); the total duration of the incubation under the stimulating conditions, e.g. with the stimulatory reagent, is between about 12 hours and about 36 hours, e.g., between about 18 hours and about 30 hours; the cells, e.g., cells of the input composition, are incubated under the stimulating conditions such as in the presence of a stimulatory reagent, at a density between about $5 \times 10^5$ cells/mL and about $5 \times 10^7$ cells/mL, e.g., at or at about $3 \times 10^6$ cells/mL; and/or the cells, e.g., cells of the input composition, are stimulated and/or activated in a serum-free media (e.g., a serum-free medium comprising one or more recombinant cytokines, such as IL-2, IL-7, and IL-15). In some embodiments, the cells are subjected to engineering under conditions that include: contacting the cells with a nucleic acid molecule encoding a recombinant protein, e.g. a recombinant receptor, under centrifugation, such as spin-oculation (e.g. centrifugal inoculation), e.g., at about 1600×g for about 60 minutes; the cells are subjected to engineering at a density between about $5 \times 10^5$ cells/mL and about $5 \times 10^7$ cells/mL, e.g., at or at about $1 \times 10^6$ cells/mL; at least about $100 \times 10^6$ cells and up to about $200 \times 10^6$ cells from the composition cultured under stimulating conditions are subjected to engineering; the total duration of the engineering step, e.g. transduction, is between about 12 hours and about 36 hours, e.g., between about 18 hours and about 30 hours; and/or the cells are subjected to engineering in a serum-free media (e.g., a serum-free medium comprising one or more recombinant cytokines, such as IL-2, IL-7, and IL-15). In some embodiments, the cells are cultivated under conditions that promote cell proliferation or expansion that include: the cells are cultivated under rocking and/or perfusion conditions; and/or the cells are cultivated in a serum-free media (e.g., a serum-free medium comprising one or more recombinant cytokines, such as IL-2, IL-7, and IL-15, optionally with higher concentrations of the recombinant cytokines than the serum-free medium used for the stimulation/activation and/or the engineering). In some embodiments, the cultivation ends and the cells are harvested when they achieve a threshold amount, concentration, and/or expansion, e.g., a threshold cell count (e.g., total nucleated cell count) of at least about $2400 \times 10^6$ cells, and when the cells achieve a threshold viability, e.g., at least about 75% or at least about 85% of the cells are viable. In some embodiments, when the cells have not achieved a target or threshold at a given time during the stimulation/activation, engineering, cultivation, and/or harvest processes, the cells may be stimulated/activated, subjected to engineering, and/or cultivated until a later time point when the target or threshold is reached.

In some embodiments, cells or compositions of cells that are produced and/or processed by the provided methods may be compared to cells or compositions of cells processed or produced by an exemplary and/or alternative process. In some embodiments, the alternative and/or exemplary process may differ in one or more specific aspects, but otherwise contains similar or the same features, aspects, steps, stages, reagents, and/or conditions of the embodiment or aspect of the provided methods that be compared. For example, when the provided methods are used in connection with incubating cells in the presence of a reagent, such cells may be compared to cells that are not incubated with the reagent in an exemplary and/or alternative process. In some embodiments, unless otherwise specified, the provided methods and the exemplary and/or alternative process would have been otherwise similar and/or identical, such as with similar or identical steps for isolating, selecting, enriching, activating, stimulating, engineering, transfecting, transducing, cultivating, and/or formulating. In some embodiments, unless otherwise specified, the provided methods and the alternative process isolate, select, and/or enrich cells from the same or similar types of biological samples, and/or process cells and/or input cells of the same cell type.

Also provided are cells and compositions prepared by the methods, including pharmaceutical compositions and formulations, and kits, systems, and devices for carrying out the methods. Also provided are methods for use of the cells and compositions prepared by the methods, including therapeutic methods, such as methods for adoptive cell therapy, and pharmaceutical compositions for administration to subjects.

A. Samples and Cell Preparation

In particular embodiments, the provided methods are used in connection with isolating, selecting, and/or enriching cells from a biological sample to generate one or more input compositions of enriched cells, e.g., T cells. In some embodiments, the provided methods include isolation of cells or compositions thereof from biological samples, such as those obtained from or derived from a subject, such as one having a particular disease or condition or in need of a cell therapy or to which cell therapy will be administered. In some aspects, the subject is a human, such as a subject who is a patient in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{2+}/Mg^{2+}$ free PBS. In certain embodiments, components of a blood cell sample are removed and the cells directly resuspended in culture media.

In some embodiments, the preparation methods include steps for freezing, e.g., cryopreserving, the cells, either before or after isolation, selection and/or enrichment and/or incubation for transduction and engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. In some embodiments, the cells are frozen, e.g., cryofrozen or cryopreserved, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between at or about 1% and at or about 15%, between at or about 6% and at or about 12%, between at or about 5% and at or about 10%, or between at or about 6% and at or about 8% DMSO. In particular embodiments, the cells are frozen, e.g., cryofrozen or cryopreserved, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and −5%, between 0.25% and 4%, between 0.5% and 2%, or between 1% and 2% HSA. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to or to about −80° C. at a rate of or of about 1° per minute and stored in the vapor phase of a liquid nitrogen storage tank.

In some embodiments, isolation of the cells or populations includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components. In some embodiments, the methods include density-based cell separation methods, such as the preparation of white blood cells from peripheral blood by lysing the red blood cells and centrifugation through a Percoll or Ficoll gradient.

In some embodiments, at least a portion of the selection step includes incubation of cells with a selection reagent. The incubation with a selection reagent or reagents, e.g., as part of selection methods which may be performed using one or more selection reagents for selection of one or more different cell types based on the expression or presence in or on the cell of one or more specific molecules, such as surface markers, e.g., surface proteins, intracellular markers, or nucleic acid. In some embodiments, any known method using a selection reagent or reagents for separation based on such markers may be used. In some embodiments, the selection reagent or reagents result in a separation that is affinity- or immunoaffinity-based separation. For example, the selection in some aspects includes incubation with a reagent or reagents for separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

In some aspects of such processes, a volume of cells is mixed with an amount of a desired affinity-based selection reagent. The immunoaffinity-based selection can be carried out using any system or method that results in a favorable energetic interaction between the cells being separated and the molecule specifically binding to the marker on the cell, e.g., the antibody or other binding partner on the solid surface, e.g., particle. In some embodiments, methods are carried out using particles such as beads, e.g. magnetic beads, that are coated with a selection agent (e.g. antibody) specific to the marker of the cells. The particles (e.g. beads) can be incubated or mixed with cells in a container, such as a tube or bag, while shaking or mixing, with a constant cell density-to-particle (e.g., bead) ratio to aid in promoting energetically favored interactions. In other cases, the methods include selection of cells in which all or a portion of the selection is carried out in the internal cavity of a centrifugal chamber, for example, under centrifugal rotation. In some embodiments, incubation of cells with selection reagents, such as immunoaffinity-based selection reagents, is performed in a centrifugal chamber. In certain embodiments, the isolation or separation is carried out using a system, device, or apparatus described in International Patent Application, Publication Number WO2009/072003, or US 20110003380 A1. In one example, the system is a system as described in International Publication Number WO2016/073602.

In some embodiments, by conducting such selection steps or portions thereof (e.g., incubation with antibody-coated particles, e.g., magnetic beads) in the cavity of a centrifugal chamber, the user is able to control certain parameters, such as volume of various solutions, addition of solution during processing and timing thereof, which can provide advantages compared to other available methods. For example, the ability to decrease the liquid volume in the cavity during the incubation can increase the concentration of the particles (e.g. bead reagent) used in the selection, and thus the chemical potential of the solution, without affecting the total number of cells in the cavity. This in turn can enhance the pairwise interactions between the cells being processed and the particles used for selection. In some embodiments, carrying out the incubation step in the chamber, e.g., when associated with the systems, circuitry, and control as described herein, permits the user to effect agitation of the solution at desired time(s) during the incubation, which also can improve the interaction.

In some embodiments, at least a portion of the selection step is performed in a centrifugal chamber, which includes incubation of cells with a selection reagent. In some aspects of such processes, a volume of cells is mixed with an amount of a desired affinity-based selection reagent that is far less than is normally employed when performing similar selections in a tube or container for selection of the same number of cells and/or volume of cells according to manufacturer's instructions. In some embodiments, an amount of selection reagent or reagents that is/are no more than at or about 5%, no more than at or about 10%, no more than at or about 15%, no more than at or about 20%, no more than at or about 25%, no more than at or about 50%, no more than at or about 60%, no more than at or about 70% or no more than at or about 80% of the amount of the same selection reagent(s) employed for selection of cells in a tube or container-based incubation for the same number of cells and/or the same volume of cells according to manufacturer's instructions is employed.

In some embodiments, for selection, e.g., immunoaffinity-based selection of the cells, the cells are incubated in the cavity of the chamber in a composition that also contains the selection buffer with a selection reagent, such as a molecule that specifically binds to a surface marker on a cell that it desired to enrich and/or deplete, but not on other cells in the composition, such as an antibody, which optionally is coupled to a scaffold such as a polymer or surface, e.g., bead, e.g., magnetic bead, such as magnetic beads coupled to monoclonal antibodies specific for CD4 and CD8. In some embodiments, as described, the selection reagent is added to cells in the cavity of the chamber in an amount that is substantially less than at or about (e.g. is no more than at or about 5%, 10%, 20%, 30%, 40%, 50%, 60%, 70% or 80% of the amount) as compared to the amount of the selection reagent that is typically used or would be necessary to achieve about the same or similar efficiency of selection of the same number of cells or the same volume of cells when selection is performed in a tube with shaking or rotation. In some embodiments, the incubation is performed with the addition of a selection buffer to the cells and selection reagent to achieve a target volume with incubation of the reagent of, for example, at or about 10 mL to at or about 200 mL, such as at least or at least about or about or 10 mL, 20 mL, 30 mL, 40 mL, 50 mL, 60 mL, 70 mL, 80 mL, 90 mL, 100 mL, 150 mL or 200 mL. In some embodiments, the selection buffer and selection reagent are pre-mixed before addition to the cells. In some embodiments, the selection buffer and selection reagent are separately added to the cells. In some embodiments, the selection incubation is carried out with periodic gentle mixing condition, which can aid in promoting energetically favored interactions and thereby permit the use of less overall selection reagent while achieving a high selection efficiency.

In some embodiments, the total duration of the incubation with the selection reagent is from or from about 5 minutes to or to about 6 hours, such as 30 minutes to 3 hours, for example, at least or at least about 30 minutes, 60 minutes, 120 minutes or 180 minutes.

In some embodiments, the incubation generally is carried out under mixing conditions, such as in the presence of spinning, generally at relatively low force or speed, such as speed lower than that used to pellet the cells, such as from or from about 600 rpm to or to about 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, such process is carried out within the entirely closed system to which the chamber is integral. In some embodiments, this process (and in some aspects also one or more additional step, such as a previous wash step washing a sample containing the cells, such as an apheresis sample) is carried out in an automated fashion, such that the cells, reagent, and other components are drawn into and pushed out of the chamber at appropriate times and centrifugation effected, so as to complete the wash and binding step in a single closed system using an automated program.

In some embodiments, after the incubation and/or mixing of the cells and selection reagent and/or reagents, the incubated cells are subjected to a separation to select for cells based on the presence or absence of the particular reagent or reagents. In some embodiments, the separation is performed in the same closed system in which the incubation of cells with the selection reagent was performed. In some embodiments, after incubation with the selection reagents, incubated cells, including cells in which the selection reagent has bound are transferred into a system for immunoaffinity-based separation of the cells. In some embodiments, the system for immunoaffinity-based separation is or contains a magnetic separation column.

Such separation steps can be based on positive selection, in which the cells having bound the reagents, e.g. antibody or binding partner, are retained for further use, and/or negative selection, in which the cells having not bound to the reagent, e.g., antibody or binding partner, are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

In some embodiments, the process steps further include negative and/or positive selection of the incubated and cells, such as using a system or apparatus that can perform an affinity-based selection. In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types. In certain embodiments, separation steps are repeated and or performed more than once, where the positively or negatively selected fraction from one step is subjected to the same separation step, such as a repeated positive or negative selection. In some examples, a single separation step is repeated and/or performed more than once, for example to increase the purity of the selected cells and/or to further remove and/or deplete the negatively selected cells from the negatively selected fraction. In certain embodiments, one or more separation steps are performed two times, three times, four times, five times, six times, seven times, eight times, nine times, ten times, or more than ten times. In certain embodiments, the one or more selection steps are performed and/or repeated between one and ten times, between one and five times, or between three and five times.

For example, in some aspects, specific subpopulations of T cells, such as cells positive or expressing high levels of one or more surface markers, e.g., CD28+, CD62L+, CCR7+, CD27+, CD95+, CD127+, CD4+, CD8+, CD45RA+, and/or CD45RO+ T cells, are isolated by positive or negative selection techniques. In some embodiments, such cells are selected by incubation with one or more antibody or binding partner that specifically binds to such markers. In some embodiments, the antibody or binding partner can be conjugated, such as directly or indirectly, to a solid support or matrix to effect selection, such as a magnetic bead or paramagnetic bead. For example, CD3+, CD28+ T cells can be positively selected using anti-CD3/anti-CD28 conjugated magnetic beads (e.g., DYNA-BEADS® M-450 CD3/CD28 T Cell Expander, and/or ExpACT® beads).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See, e.g., Terakura et al., (2012) Blood. 1:72-82; Wang et al. (2012) J Immunother. 35(9):689-701. In some embodiments, combining $T_{CM}$-enriched CD8+ T cells and CD4+ T cells further enhances efficacy.

In some embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD27, CD28, CD95, CD3, and/or CD127; in some aspects, it is based on negative selection for cells expressing or highly expressing CD45RA and/or granzyme B. In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or subpopulation, such that both the positive and negative fractions from the CD4-based separation are retained and used in subsequent steps of the methods, optionally following one or more further positive or negative selection steps. In some embodiments, the selection for the CD4+ cell population and the selection for the CD8+ cell population are carried out simultaneously. In some embodiments, the CD4+ cell population and the selection for the CD8+ cell population are carried out sequentially, in either order. In some embodiments, methods for selecting cells can include those as described in published U.S. App. No. US20170037369. In some embodiments, the selected CD4+ cell population and the selected CD8+ cell population may be combined subsequent to the selecting. In some aspects, the selected CD4+ cell population and the selected CD8+ cell population may be combined in a bioreactor bag as described herein.

In some embodiments, central memory CD8+ cells are CD27+, CD28+, CD62L+, CCR7+, CD45RA-, and/or CD45RO+. In some embodiments, central memory CD8+ cells are CD62L+ and CD45RO+. In some embodiments, central memory CD8+ cells are CCR7+ and CD45RO+. In some embodiments, central memory CD8+ cells are CCR7+ and CD45RA-. In some embodiments, central memory CD8+ cells are CD62L+ and CCR7+. In some embodiments, central memory CD8+ cells are CD62L+/CD45RA-, CCR7+/CD45RA-, CD62L+/CCR7+, or CD62L+/CCR7+/CD45RA-, and have intermediate to high expression of CD44. In some embodiments, central memory CD8+ cells are CD27+/CD28+/CD62L+/CD45RA-, CD27+/CD28+/CCR7+/CD45RA-, CD27+/CD28+/CD62L+/CCR7+, or CD27+/CD28+/CD62L+/CCR7+/CD45RA-.

In particular embodiments, a biological sample, e.g., a sample of PBMCs or other white blood cells, are subjected to selection of CD4+ T cells, where both the negative and positive fractions are retained. In certain embodiments, CD8+ T cells are selected from the negative fraction. In some embodiments, a biological sample is subjected to selection of CD8+ T cells, where both the negative and positive fractions are retained. In certain embodiments, CD4+ T cells are selected from the negative fraction.

In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

In some embodiments, CD4+T helper cells are sorted into naïve, central memory, and effector cells by identifying cell populations that have cell surface antigens. CD4+ lymphocytes can be obtained by standard methods. In some embodiments, naive CD4+T lymphocytes are CD45RO-, CD45RA+, CD62L+, or CD4+ T cells. In some embodiments, central memory CD4+ cells are CD62L+ and CD45RO+. In some embodiments, central memory CD4+ cells are CD27+, CD28+, CD62L+, CCR7+, CD45RA-, and/or CD45RO+. In some embodiments, central memory CD4+ cells are CD62L+ and CD45RO+. In some embodiments, central memory CD4+ cells are CCR7+ and CD45RO+. In some embodiments, central memory CD4+ cells are CCR7+ and CD45RA−. In some embodiments, central memory CD4+ cells are CD62L+ and CCR7+. In some embodiments, central memory CD4+ cells are CD62L+/CD45RA−, CCR7+/CD45RA−, CD62L+/CCR7+, or CD62L+/CCR7+/CD45RA−, and have intermediate to high expression of CD44. In some embodiments, central memory CD4+ cells are CD27+/CD28+/CD62L+/ CD45RA−, CD27+/CD28+/CCR7+/CD45RA−, CD27+/ CD28+/CD62L+/CCR7+, or CD27+/CD28+/CD62L+/ CCR7+/CD45RA−. In some embodiments, effector CD4+ cells are CD62L- and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ).

In some aspects, the incubated sample or composition of cells to be separated is incubated with a selection reagent containing small, magnetizable or magnetically responsive material, such as magnetically responsive particles or microparticles, such as paramagnetic beads (e.g., such as Dynalbeads or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some aspects, separation is achieved in a procedure in which the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In some embodiments, the affinity-based selection is via magnetic-activated cell sorting (MACS) (Miltenyi Biotech, Auburn, CA). Magnetic Activated Cell Sorting (MACS), e.g., CliniMACS systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the isolation and/or selection results in one or more compositions of enriched T cells, e.g., CD3+ T cells, CD4+ T cells, and/or CD8+ T cells. In some embodiments, two or more separate compositions of enriched T cells are isolated, selected, enriched, or obtained from a single biological sample. In some embodiments, separate compositions are isolated, selected, enriched, and/or obtained from separate biological samples collected, taken, and/or obtained from the same subject.

In certain embodiments, the isolation and/or selection results in one or more compositions of enriched T cells that includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD3+ T cells. In particular embodiment, the composition of enriched T cells consists essentially of CD3+ T cells.

In certain embodiments, the isolation and/or enrichment results in a compositions of enriched CD4+ T cells that includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD4+ T cells. In certain embodiments, the input composition of CD4+ T cells includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% CD8+ T cells, and/or contains no CD8+ T cells, and/or is free or substantially free of CD8+ T cells. In some embodiments, the composition of enriched T cells consists essentially of CD4+ T cells.

In certain embodiments, the isolation and/or enrichment results in a compositions of enriched CD8+ T cells that includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD8+ T cells. In certain embodiments, the composition of CD8+ T cells contains less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% CD4+ T cells, and/or contains no CD4+ T cells, and/or is free of or substantially free of CD4+ T cells. In some embodiments, the composition of enriched T cells consists essentially of CD8+ T cells.

In some embodiments, the one or more compositions enriched T cells are frozen, e.g., cryopreserved and/or cryofrozen, after isolation, selection and/or enrichment. In particular embodiments, a composition of enriched CD4+ T cells are frozen, e.g., cryopreserved and/or cryofrozen, after isolation, selection and/or enrichment. In certain embodiments, a composition of enriched CD8+ T cells are frozen, e.g., cryopreserved and/or cryofrozen, after isolation, selection and/or enrichment. In some embodiments, the one or more compositions of enriched T cells are frozen e.g., cryopreserved and/or cryofrozen, prior to any steps of incubating, activating, stimulating, engineering, transducing, transfecting, cultivating, expanding, harvesting, and/or formulating the composition of cells. In particular embodiments, a composition of enriched CD4+ T cells are frozen e.g., cryopreserved and/or cryofrozen, prior to any steps of incubating, activating, stimulating, engineering, transducing, transfecting, cultivating, expanding, harvesting, and/or formulating the composition of cells. In some embodiments, a composition of enriched CD8+ T cells are frozen e.g., cryopreserved and/or cryofrozen, prior to any steps of incubating, activating, stimulating, engineering, transducing, transfecting, cultivating, expanding, harvesting, and/or formulating the composition of cells. In particular embodiments, the one or more cryofrozen input compositions are stored, e.g., at or at about –80° C., for between 12 hours and 7 days, between 24 hours and 120 hours, or between 2 days and 5 days. In particular embodiments, the one or more cryofrozen input compositions are stored at or at about –80° C., for an amount of time of less than 10 days, 9 days, 8 days, 7 days, 6 days, or 5 days, 4 days, 3 days, 2 days, or 1 day. In some embodiments, the one or more cryofrozen input compositions are stored at or at about –80° C., for or for about 1 day, 2 days, 3 days, 4 days, 5 days, or 6 days.

In some embodiments, the sample containing cells (e.g., an apheresis product or a leukapheresis product) is washed in order to remove one or more anti-coagulants, such as heparin, added during apheresis or leukapheresis.

In some embodiments, the sample containing cells (e.g., a whole blood sample, a buffy coat sample, a peripheral blood mononuclear cells (PBMC) sample, an unfractionated T cell sample, a lymphocyte sample, a white blood cell sample, an apheresis product, or a leukapheresis product) is cryopreserved and/or cryoprotected (e.g., frozen) and then thawed prior to any steps for isolating, selecting, activating, stimulating, engineering, transducing, transfecting, incubating, culturing, harvesting, formulating a population of the cells, and/or administering the formulated cell population to a subject.

In particular embodiments, an apheresis product or a leukapheresis product is cryopreserved and/or cryoprotected (e.g., frozen) and then thawed before being subject to a cell selection or isolation step (e.g., a T cell selection or isolation step) as described infra. In some embodiments, after a cryopreserved and/or cryoprotected apheresis product or leukapheresis product is subject to a T cell selection or isolation step, no additional cryopreservation and/or cryoprotection step is performed during or between any of the subsequent steps, such as the steps of activating, stimulating, engineering, transducing, transfecting, incubating, culturing, harvesting, formulating a population of the cells, and/or administering the formulated cell population to a subject. For example, T cells selected from a thawed cryopreserved and/or cryoprotected apheresis product or leukapheresis product are not again cryopreserved and/or cryoprotected before being thawed for a downstream process, such as T cell activation/stimulation or transduction.

In particular embodiments, the cryopreserved and/or cryoprotected apheresis product or leukapheresis product is banked (e.g., without T cell selection before freezing the sample), which, in some aspects, can allow more flexibility for subsequent manufacturing steps. In one aspect, banking cells before selection increases cell yields for a downstream process, and banking cells earlier may mean they are healthier and may be easier to meet manufacturing success criteria. In another aspect, once thawed, the cryopreserved and/or cryoprotected apheresis product or leukapheresis product can be subject to one or more different selection methods. Advantages of this approach are, among other things, to enhance the availability, efficacy, and/or other aspects of cells of a cell therapy for treatment of a disease or condition of a subject, such as in the donor of the sample and/or another recipient.

In some embodiments, the sample (e.g. apheresis or leukapheresis sample) is collected and cryopreserved and/or cryoprotected prior to or without prior cell selection (e.g., without prior T cell selection, such as selection by chromatography), at a time after the donor is diagnosed with a disease or condition. In some aspects, the time of cryopreservation also is before the donor has received one or more of the following: any initial treatment for the disease or condition, any targeted treatment or any treatment labeled for treatment for the disease or condition, or any treatment other than radiation and/or chemotherapy. In some embodiments, the sample is collected after a first relapse of a disease following initial treatment for the disease, and before the donor or subject receives subsequent treatment for the disease. The initial and/or subsequent treatments may be a therapy other than a cell therapy. In some embodiments, the collected cells may be used in a cell therapy following initial and/or subsequent treatments. In one aspect, the cryopreserved and/or cryoprotected sample without prior cell selection may help reduce up-front costs, such as those associated with non-treatment patients in a randomized clinic trial who may crossover and require treatment later.

In some embodiments, the sample (e.g. apheresis or leukapheresis sample) is collected and cryopreserved and/or cryoprotected prior to or without prior cell selection (e.g., without prior T cell selection, such as selection by chromatography), at a time after a second relapse of a disease following a second line of treatment for the disease, and before the donor or subject receives subsequent treatment for the disease. In some embodiments, patients are identified as being likely to relapse after a second line of treatment, for example, by assessing certain risk factors. In some embodiments, the risk factors are based on disease type and/or genetics, such as double-hit lymphoma, primary refractory cancer, or activated B-cell lymphoma. In some embodiments, the risk factors are based on clinical presentation, such as early relapse after first-line treatment, or other poor prognostic indicators after treatment (e.g., IPI (International Prognostic Index)>2).

In some embodiments, the sample (e.g. apheresis or leukapheresis sample) is collected and cryopreserved and/or cryoprotected prior to or without prior cell selection (e.g., without prior T cell selection, such as selection by chromatography), at a time before the donor or subject is diagnosed with a disease. In some aspects, the donor or subject may be determined to be at risk for developing a disease. In some aspects, the donor or subject may be a healthy subject. In certain cases, the donor or subject may elect to bank or store cells without being deemed at risk for developing a disease or being diagnosed with a disease in the event that cell therapy is required at a later stage in life. In some embodiments, a donor or subject may be deemed at risk for developing a disease based on factors such as genetic mutations, genetic abnormalities, genetic disruptions, family history, protein abnormalities (such as deficiencies with protein production and/or processing), and lifestyle choices that may increase the risk of developing a disease. In some embodiments, the cells are collected as a prophylactic.

In some embodiments, the cryopreserved and/or cryoprotected sample of cells (e.g. apheresis or leukapheresis sample), such as a sample of cells that has not been subjected to a prior cell selection (e.g., without prior T cell selection, such as selection by chromatography) is stored, or banked, for a period of time greater than or equal to at or about 12 hours, 24 hours, 36 hours, or 48 hours. In some embodiments, the sample is stored or banked for a period of time greater than or equal to 1 week, 2 weeks, 3 weeks, or 4 weeks. In some embodiments, the sample is placed into long-term storage or long-term banking. In some aspects, the sample is stored for a period of time greater than or equal to at or about 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, or more.

In some embodiments, an apheresis or leukapheresis sample taken from a donor is shipped in a cooled environment to a storage or processing facility, and/or cryogenically stored at the storage facility or processed at the processing facility. In some embodiments, before shipping, the sample is processed, for example, by selecting T cells, such as CD4+ and/or CD8+ T cells. In some embodiments, such processing is performed after shipping and before cryogenically storing the sample. In some embodiments, the processing is performed after thawing the sample following cryogenically storage.

By allowing donors to store their cells at a stage when the donors, and thus their cells, have not undergone extensive treatment for a disease and/or prior to contracting of a disease or condition or diagnosis thereof, such cells may have certain advantages for use in cell therapy compared to cells harvested after one or after multiple rounds of treatment. For example, cells harvested before one or more rounds of treatment may be healthier, may exhibit higher levels of certain cellular activities, may grow more rapidly, and/or may be more receptive to genetic manipulation than cells that have undergone several rounds of treatment. Another example of an advantage according to embodiments described herein may include convenience. For example, by collecting, optionally processing, and storing a donor's cells before they are needed for cell therapy, the cells would be readily available if and when a recipient later needs them. This could increase apheresis lab capacity, providing technicians with greater flexibility for scheduling the apheresis collection process.

Exemplary methods and systems for cryogenic storage and processing of cells from a sample, such as an apheresis sample, can include those described in International published application no. WO2018170188. In some embodiments, the method and systems involve collecting apheresis before the patient needs cell therapy, and then subjecting the apheresis sample to cryopreservation for later use in a process for engineering the cells, e.g. T cells, with a recombinant receptor (e.g. CAR). In some cases, such processes can include those described herein. In some embodiments, an apheresis sample is collected from a subject and cryopreserved prior to subsequent T cell selection, activation, stimulation, engineering, transduction, transfection, incubation, culturing, harvest, formulation of a population of the cells, and/or administration of the formulated cell population to a subject. In such examples, the cryopreserved apheresis sample is thawed prior to subjecting the sample to one or more selection steps, such as any as described herein.

In some embodiments, the cryopreserved and/or cryoprotected sample of cells (e.g. apheresis or leukapheresis sample), such as a sample of cells that has not been subject to a prior cell selection (e.g., without prior T cell selection, such as selection by chromatography) is thawed prior to its use for downstream processes for manufacture of a cell population for cell therapy, for example, a T cell population containing CAR+ T cells. In some embodiments, such a cryopreserved and/or cryoprotected sample of cells (e.g. apheresis or leukapheresis sample) is used in connection with the process provided herein for engineered a T cell therapy, such as a CAR+ T cell therapy. In particular examples, no further step of cryopreservation is carried out prior to or during the harvest/formulation steps.

1. Input Compositions

In certain embodiments, the provided methods are used in connection with producing and/or preparing an input composition of cells. In certain embodiments, the input cell composition is a composition of cells for use in genetic engineering, e.g., cells that will be genetically engineered and/or that will undergo a process to produce genetically engineered cells. In certain embodiments, the cells will be treated with, contacted with, and/or incubated with a nucleic acid that encodes a recombinant receptor. In certain embodiments, the input cell composition contains CD4+ T cells and CD8+ T cells. In particular embodiments, the input cell composition contain CD4+ T cells and CD8+ T cells that are naïve and/or naïve-like T cells.

In some embodiments, the desired, fixed, and/or controlled ratio is the ratio or number of cells at which two types of cells or isolated cell populations are included in an input cell composition, designed to result in an output cell composition with a desired, defined, and/or controlled ratio of engineered CD4+ to CD8+ T cells, or within a tolerated error rate or difference thereof, at the completion of the incubation and/or engineering step or other processing steps and/or upon thaw and/or just prior to administration to a subject.

In particular embodiments, the input composition is a composition of enriched CD3+ T cells. In some embodiments, the input composition is or includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD3+ T cells. In some embodiments, the input composition consists essentially of CD3+ T cells. In certain embodiments, the input composition is a composition of cells enriched for enriched CD4+ T cells and CD8+ T cells. In particular embodiments, the input composition is or includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% cells that are CD4+ or CD8+ T cells. In some embodiments, the input composition consists essentially of CD4+ and CD8+ T cells.

In particular embodiments, the input composition contains between at or about 30% and at or about 70%, between at or about 35% and at or about 65%, between at or about 40% and at or about 60%, between at or about 45% and at or about 55%, or about 50% or 50% CD4+ T cells and between at or about 30% and at or about 70%, between at or about 35% and at or about 65%, between at or about 40% and at or about 60%, between at or about 45% and at or about 55%, or about 50% or 50% CD8+ T cells. In certain embodiments, the input composition contains between at or about 45% and at or about 55%, about 50%, or 50% CD4+ T cells and between at or about 45% and at or about 55%, about 50%, or 50% CD8+ T cells.

In some embodiments, at least one separate composition of enriched CD4+ T cells and at least one separate composition of enriched CD8+ T cells are isolated, selected, enriched, or obtained from a single biological sample, e.g., a sample of PBMCs or other white blood cells from the same donor such as a patient or healthy individual. In some embodiments, a separate composition of enriched CD4+ T cells and a separate composition of enriched CD8+ T cells originated, e.g., were initially isolated, selected, and/or enriched, from the same biological sample, such as a single biological sample obtained, collected, and/or taken from a single subject. In some embodiments, a biological sample is first subjected to selection of CD4+ T cells, where both the negative and positive fractions are retained, and the negative fraction is further subjected to selection of CD8+ T cells. In other embodiments, a biological sample is first subjected to selection of CD8+ T cells, where both the negative and positive fractions are retained, and the negative fraction is further subjected to selection of CD4+ T cells. In some embodiments, methods of selection are carried out as described in International PCT publication No. WO2015/164675. In some aspects, a biological sample is first positively selected for CD8+ T cells to generate at least one composition of enriched CD8+ T cells, and the negative fraction is then positively selected for CD4+ T cells to generate at least one composition of enriched CD4+ T cells, such that the at least one composition of enriched CD8+ T cells and the at least one composition of enriched CD4+ T cells are separate compositions from the same biological sample, e.g., from the same donor patient or healthy individual. In some aspects, two or more separate compositions of enriched T cells, e.g., at least one being a composition of enriched CD4+ T cells and at least one being a separate composition of enriched CD8+ T cells from the same donor, are separately frozen, e.g., cryofrozen or cryopreserved in a cryopreservation media. In some aspects, the separately cryopreserved cell compositions are stored and/or shipped in separate containers in one or more shipment. In some aspects, the separately cryopreserved cell compositions are thawed and optionally washed.

In some aspects, two or more separate compositions of enriched T cells, e.g., at least one being a composition of enriched CD4+ T cells and at least one being a separate composition of enriched CD8+ T cells from the same biological sample, are thawed and mixed, combined, and/or pooled, and the compositions may be optionally washed before or after the mixing, combining, and/or pooling. In some aspects, the mixed, combined, and/or pooled and optionally washed compositions of enriched T cells form an input composition. In some aspects, the input composition (e.g., comprising CD4+ T cells and CD8+ T cells at a ratio of or of about 1:1) is activated and/or stimulated by contacting with a stimulatory reagent (e.g., by incubation with CD3/CD28 conjugated magnetic beads for T cell activation), and the volume of a cell composition from the activation/stimulation is optionally adjusted, e.g., reduced, in order to achieve a target volume. In some aspects, the activated/stimulated cell composition is engineered, transduced, and/or transfected, e.g., using a retroviral vector encoding a recombinant protein (e.g. CAR), to express the same recombinant protein in the CD4+ T cells and CD8+ T cells of the cell composition. In some aspects, the volume of a cell composition from the engineering is optionally adjusted, e.g., reduced, in order to achieve a target volume. In some aspects, the method comprises removing the stimulatory reagent, e.g., magnetic beads, from the cell composition. In some aspects, a cell composition containing engineered CD4+ T cells and engineered CD8+ T cells is cultivated, e.g., for expansion of the CD4+ T cell and/or CD8+T cell populations therein. In certain embodiments, a cell composition from the cultivation is harvested and/or collected and/or formulated, e.g., by washing the cell composition in a formulation buffer. In certain embodiments, a formulated cell composition comprising CD4+ T cells and CD8+ T cells is frozen, e.g., cryofrozen or cryopreserved in a cryopreservation media. In some aspects, the cryopreserved formulation may be stored and/or shipped in one or more containers. In some aspects, engineered CD4+ T cells and CD8+ T cells in the formulation originate from the same donor or biological sample and express the same recombination protein (e.g., CAR), and the formulation is administered to a subject in need thereof such as the same donor.

In particular embodiments, the input composition contains a ratio of between 3:1 and 1:3, between 2:1 and 1:2, between 1.5 and 0.75, between 1.25 and 0.75, or between 1.2 and 0.8 CD4+ T cells to CD8+ T cells. In certain embodiments, the input composition contains a ratio of or of about 1:1 CD4+ T cells to CD8+ T cells.

In some embodiments, cells from a composition of enriched CD4+ T cells and cells from a composition of enriched CD8+ T cells are mixed, combined, and/or pooled to generate an input composition containing CD4+ T cells and CD8+ T cells. In certain embodiments, the compositions of enriched CD4+ T cells and CD8+ T cells are pooled, mixed, and/or combined prior to incubating the cells under stimulating conditions. In certain embodiments, the compositions of enriched CD4+ and CD8+ T cells are pooled, mixed, and/or combined subsequent to isolating, enriching, and/or selecting the CD4+ and CD8+ T cells from a biological sample. In particular embodiments, the compositions of enriched CD4+ and CD8+ T cells are pooled, mixed, and/or combined subsequent to freezing, e.g., cryofreezing, and thawing the compositions of enriched CD4+ and CD8+ T cells.

In certain embodiments, the input composition is produced, generated, or made by mixing, pooling, and/or combining cells from a composition of enriched CD4+ cells with cells from a composition of enriched CD8+ cells. In certain embodiments, the composition of enriched CD4+ T cells contains at least at or about 60%, 65%, 70%, 75%, 80%, 85%, 90%, 95%, 98%, 99%, or 99.9% CD4+ T cells. In particular embodiments, the composition of enriched CD4+ T cells contains 100% CD4+ T cells or contains about 100% CD4+ T cells. In certain embodiments, the composition of enriched T cells includes or contains less than at or about 20%, less than at or about 10%, less than at or about 5%, less than at or about 1%, less than at or about 0.1%, or less than at or about 0.01% CD8+ T cells, and/or contains no CD8+ T cells, and/or is free or substantially free of CD8+ T cells. In some embodiments, the populations of cells consist essentially of CD4+ T cells. In certain embodiments, the composition of enriched CD8+ T cells contains at least at or about 75%, 80%, 85%, 90%, 95%, 98%, 99%, or 99.9% CD8+ T cells, or contains or contains about 100% CD8+ T cells. In certain embodiments, the composition of enriched CD8+ T cells includes or contains less than at or about 20%, less than at or about 10%, less than at or about 5%, less than at or about 1%, less than at or about 0.1%, or less than at or about 0.01% CD4+ T cells, and/or contains no CD4+ T cells, and/or is free or substantially free of CD4+ T cells. In some embodiments, the populations of cells consist essentially of CD8+ T cells.

In certain embodiments, CD4+ T cells and CD8+ T cells are pooled, mixed, and/or combined at a ratio of between 1:10 and 10:1, between 1:5 and 5:1, between 4:1 and 1:4, between 3:1, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells. In particular embodiments, CD4+ T cells and CD8+ T cells are pooled, mixed, and/or combined at a ratio of between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells. In some embodiments, CD4+ T cells and CD8+ T cells are pooled, mixed, and/or combined at a ratio of or of about 1:1 CD4+ T cells to CD8+ T cells.

In some embodiments, cells from a compositions of enriched CD4+ T cells and a composition of enriched CD8+ T cells are pooled, mixed, and/or combined at a ratio of between 1:10 and 10:1, between 1:5 and 5:1, between 4:1 and 1:4, between 3:1, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells. In particular embodiments, cells from compositions of enriched CD4+ T cells and CD8+ T cells are pooled, mixed, and/or combined at a ratio of between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells. In some embodiments, cells from compositions of enriched CD4+ T cells and CD8+ T cells are pooled, mixed, and/or combined at a ratio of or of about 1:1 CD4+ T cells to CD8+ T cells.

In certain embodiments, the input composition contains a ratio, e.g., a defined, controlled, and/or fixed ratio, CD4+ naïve-like T cells to CD8+ naïve-like T cells. In particular embodiments, the ratio of CD4+ naïve-like T cells to CD8+ naïve-like T cells is between 10:1 to 0.05:1, between 8:1 to 0.1:1, between 5:1 to 0.2:1, between 2.5:1 to 0.25:1, between 2.2:1 to 0.8:1, between 2:1 to 0.5:1, or between 1.5:1 to 1:1, inclusive. In particular embodiments, the ratio of CD4+ naïve-like T cells to CD8+ naïve-like T cells is between 2:1 to 0.8:1, between 1.6:1 to 0.8:1, between 1.4:1 to 0.8:1, between 1.2:1 to 0.8:1, or between 1.2:1 to 0.8:1, inclusive. In some embodiments, the ratio is between 2.2:1 to 0.8:1, inclusive. In certain embodiments, the ratio of CD4+ naïve-like T cells to CD8+ naïve-like T cells is or is about 2.2:1, 2.1:1, 2.0:1, 1.9:1, 1.8:1, 1.7:1, 1.6:1, 1.5:1, 1.4:1, 1.3:1, 1.2:1, 1.1:1, 1.0:1, 0.9:1, or 0.8:1. In certain embodiments, the ratio is or is about 1.1:1.

In particular embodiments, the input composition has an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ total cells or total viable cells. In certain embodiments, the input composition has an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ cells that express CD4 or CD8. In some embodiments, the input composition has an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ naïve-like CD4+ and naïve-like CD8+ T cells.

In particular embodiments, the input composition has between at or about $1\times10^6$ and at or about $1\times10^{10}$, between at or about $1\times10^7$ and at or about $1\times10^9$, between at or about $5\times10^7$ and at or about $5\times10^8$, or between at or about $1\times10^8$ and at or about $3\times10^8$ total cells or total viable cells. In certain embodiments, the input composition has an amount of or about between at or about $1\times10^6$ and at or about $1\times10^{10}$, between at or about $1\times10^7$ and at or about $1\times10^9$, between at or about $5\times10^7$ and at or about $5\times10^8$, or between at or about $1\times10^8$ and at or about $3\times10^8$ cells that express CD4 or CD8. In some embodiments, the input composition has an amount of or about between at or about $1\times10^6$ and at or about $1\times10^{10}$, between at or about $1\times10^7$ and at or about $1\times10^9$, between at or about $5\times10^7$ and at or about $5\times10^8$, or between at or about $1\times10^8$ and at or about $3\times10^8$ naïve-like CD4+ and at or about naïve-like CD8+ T cells.

In some embodiments, the input composition has or contains at least at or about 1%, at least at or about 5%, at least at or about 10%, at least at or about 20%, at least at or about 30%, at least at or about 40%, at least at or about 50%, at least at or about 60%, at least at or about 70%, at least at or about 75%, at least at or about 80%, at least at or about 85%, at least at or about 90%, at least at or about 95%, at least at or about 96%, at least at or about 97%, at least at or about 98%, at least at or about 99%, at least at or about 99.5%, at least at or about 99.9%, or 100% or about 100% naïve-like cells. In particular embodiments, the input composition contains or includes no more than at or about 100%, no more than at or about 99%, no more than at or about 98%, no more than at or about 97%, no more than at or about 96%, no more than at or about 95%, no more than at or about 90%, or no more than at or about 85% naïve-like cells.

In particular embodiments, the methods provided herein include one or more steps of producing, generating, and/or making an input composition. In certain embodiments, the producing, generating, and/or making an input composition includes one or more steps of mixing or combining a cells of a composition of CD4+ T cells with cells of a composition of CD8+ T cells.

In some embodiments, the cells, e.g., the CD4+ T cells CD8+ T cells, of the input composition have been isolated and/or selected from a sample, e.g., a biological sample. In certain embodiments, the source of the cells of the input composition are compositions of cells, e.g., compositions of CD4+ and CD8+ T cells, that have been isolated and/or selected from the sample. In particular embodiments, the composition of CD4+ T cells and the composition of CD8+ T cells are isolated and/or selected from a sample, e.g., a biological sample. In certain embodiments, the composition of CD4+ T cells and the composition of CD8+ T cells are isolated and/or selected from the same sample. In certain embodiments, the composition of CD4+ T cells and the composition of CD8+ T cells are isolated and/or selected from samples taken or obtained from the same subject.

In particular embodiments, the composition of CD4+ T cells contains or includes at least at or about 60%, at least at or about 75%, at least at or about 80%, at least at or about 85%, at least at or about 90%, at least at or about 95%, at least at or about 96%, at least at or about 97%, at least at or about 98%, at least at or about 99%, at least at or about 99.5%, at least at or about 99.9%, or 100% or about 100% CD4+ T cells. In some embodiments, the composition of CD4+ T cells contains or includes no more than at or about 100%, no more than at or about 99%, no more than at or about 98%, no more than at or about 97%, no more than at or about 96%, no more than at or about 95%, no more than at or about 90%, or no more than at or about 85% CD4+ T cells.

In certain embodiments, the composition of CD8+ T cells contains or includes at least at or about 60%, at least at or about 75%, at least at or about 80%, at least at or about 85%, at least at or about 90%, at least at or about 95%, at least at or about 96%, at least at or about 97%, at least at or about 98%, at least at or about 99%, at least at or about 99.5%, at least at or about 99.9%, or 100% or about 100% CD8+ T cells. In particular embodiments, the composition of CD8+ T cells contains or includes no more than at or about 100%, no more than at or about 99%, no more than at or about 98%, no more than at or about 97%, no more than at or about 96%, no more than at or about 95%, no more than at or about 90%, or no more than at or about 85% CD8+ T cells.

In certain embodiments, the producing, generating, and/or making an input composition includes one or more steps of measuring, determining, and/or quantifying the amount, portion, number, number per volume, number per weight, and/or percentage of viable CD4+ T cells and/or viable CD8+ T cells that are present in the composition of CD4+ T cells and/or the composition of CD8+ T cells, e.g., prior to combining or mixing the cells of the cell compositions. In particular embodiments, the producing, generating, and/or making an input composition includes one or more steps of measuring, determining, and/or quantifying the amount, portion, number, number per volume, number per weight, and/or percentage of naïve-like CD4+ T cells and/or naïve-like CD8+ T cells that are present in the composition of CD4+ T cells and/or the composition of CD8+ T cells. In some embodiments, the naïve-like CD4+ and/or naïve-like CD8+ T cells are viable naïve-like cells.

In certain embodiments, the producing, generating, and/or making an input composition includes one or more steps of measuring, determining, and/or quantifying the amount, portion, number, number per volume, number per weight, and/or percentage of viable CD4+ T cells and/or viable CD8+ T cells that are present in the sample, e.g., the biological sample. In particular embodiments, the producing, generating, and/or making an input composition includes one or more steps of measuring, determining, and/or quantifying the amount, portion, number, number per volume, number per weight, and/or percentage of naïve-like CD4+ T cells and/or naïve-like CD8+ T cells that are present in the sample. In some embodiments, the naïve-like CD4+ and/or naïve-like CD8+ T cells are viable naïve-like cells.

In some embodiments, the cells of the input composition are isolated and/or selected from a sample, e.g., a biological sample. In particular embodiments, the portions of naïve-like cells in the sample, e.g., portion of naïve-like CD4+ and CD8+ T cells are known or have been determined, measured, or assessed. In some embodiments, cells from the sample are isolated and/or selected to directly produce a cell composition, e.g., an input composition, with a defined, fixed, or controlled ratio of naïve-like CD4+ T cells to naïve-like CD8+ T cells. In certain embodiments, the cells are isolated and/or selected with immunoaffinity bead selection. In some embodiments, the cells are isolated and/or selected with affinity columns. In particular embodiments, the cells from the sample are isolated or selected according to any of the methods described in WO 2015/164675 to produce a cell composition with a defined, controlled, and/or fixed ratio of naïve-like CD4+ cells to naïve-like CD8+ cells.

In certain embodiments, the input composition contains cells that were directly isolated and/or selected from a sample by a first and second isolation or selection. In certain embodiments, the input composition is produced by performing a first and second selection to isolate an amount, number, or concentration of CD4+ T cells and CD8+ T cells sufficient to produce the defined, fixed, and/or controlled ratio of naïve-like CD4+ to naïve-like CD8+ T cells.

In some embodiments, the cells from the sample are directly isolated, selected, and/or enriched to produce an input composition enriched for CD4+ cells and CD8+ cells. In some embodiments, the amount, number, percentage, number per volume, and/or number per weight of naïve-like CD4+ and naïve-like CD8+ cells have been measured, assessed, and/or determined in the sample, and the CD4+ and CD8+ cells are isolated, selected, and/or enriched in sufficient amounts to achieve an input composition with the defined, fixed, or controlled ratio of naïve-like CD4+ to naïve-like CD8+ T cells. In some embodiments, the cells that are directly isolated, selected, and/or enriched from the sample are the input composition and are used in subsequent processing steps, such as subsequent processing steps involving incubation, stimulation, activation, engineering and/or formulation of the enriched cells.

In some embodiments, the isolated, selected, and/or enriched cells from the sample, such as an input composition, contain a ratio of CD4+ cells to CD8+ cells at a defined, fixed, or controlled ratio of naïve-like CD4+ cells to naïve-like CD8+ cells. In embodiments of the methods provided herein, the first and/or second selections, or selections for sub-populations thereof, of the sample can be performed in a manner to result in an input composition with a desired ratio of naïve-like CD4+ T cells to naïve-like CD8+ cells.

In some embodiments, prior to performing the first and/or second selection from the sample, the ratio of CD4+ to CD8+ T cells in the sample, e.g., the biological sample, is determined. In certain embodiments, prior to performing the first and/or second selection, the ratio of naïve-like CD4+ to naïve-like CD8+ T cells in the sample is determined. Based on the particular ratio of the CD4+ to CD8+ T cells and/or naïve-like CD4+ to CD8+ T cells in the sample, which can vary among samples, the particular mode of selection can be individualized to the sample, for example by sizing of chromatography columns or selection of amount or concentration of immunoaffinity reagents, to achieve the desired, fixed, or controlled ratio. The relative level or frequency of various cell populations in a subject can be determined based on assessing surface expression of a marker or markers present on such populations or sub-populations. A number of well-known methods for assessing expression level of surface markers or proteins may be used, such as detection by affinity-based methods, e.g., immunoaffinity-based methods, e.g., in the context of cell surface proteins, such as by flow cytometry.

In some contexts, the appropriate ratio for naïve-like CD4+ and CD8+ T cells can vary depending on context, e.g., for example, for a particular disease, condition, or prior treatment of a subject from which cells are derived, and/or a particular antigen-specificity of the cells, relative representation among cells of a particular type (e.g., CD4+ cells) of various subpopulations, e.g., effector versus memory versus naïve cells, and/or one or more conditions under which cells will be incubated, such as medium, stimulating agents, time of culture, buffers, oxygen content carbon dioxide content, antigen, cytokine, antibodies, and other components. Thus, it may be that a cell type which typically or in general is known to proliferate or expand more rapidly than another will not always have such a property in every context. Thus, in some aspects, the ratio of naïve-like CD4+ T cells and naïve-like CD8+ T cells is determined based on known capacities of cell types in a normal or typical context, coupled with assessment of phenotypes or states of the cells or subject from which the cells are derived, and/or empirical evidence.

In some embodiments, the separation and/or steps is carried out using immunomagnetic beads. In some embodiments, a cell sample containing CD4+ and CD8+ cells is contacted with magnetic beads containing a first immunoaffinity reagent that binds to CD4 or CD8 and magnetic beads containing a second immunoaffinity reagent that binds to the other of the CD4 or CD8. The separation and/or steps can occur simultaneously and/or sequentially.

In some embodiments, the first and/or second immunoaffinity reagent are present in the incubation composition at a sub-optimal yield concentration, whereby the enriched composition contains less than all, e.g., 70%, of the total CD4+ cells in the incubation composition and/or less than all, e.g., 70%, of the CD8+ cells in the incubation composition, thereby producing a composition enriched for CD4+ and CD8+ T cells.

In some embodiments, the suboptimal yield concentration of the affinity reagent is a concentration below a concentration used or required to achieve an optimal or maximal yield of bound cells in a given selection or enrichment involving incubating cells with the reagent and recovering or separating cells having bound to the reagent ("yield," for example, being the number of the cells so-recovered or selected compared to the total number of cells in the incubation that are targeted by the reagent or to which the reagent is specific or that have a marker for which the reagent is specific and capable of binding). The suboptimal yield concentration generally is a concentration or amount of the reagent that in such process or step achieves less than all, e.g., no more than 70% yield of bound cells, e.g., CD4+ and/or CD8+ T cells, upon recovery of the cells having bound to the reagent. In some embodiments, no more than at or about 50%, 45%, 40%, 30%, or 25% yield is achieved by the suboptimal concentration of the affinity reagent. The concentration may be expressed in terms of number or mass of particles or surfaces per cell and/or number of mass or molecules of agent (e.g., antibody, such as antibody fragment) per cell. In particular embodiments, the suboptimal yield concentrations are sufficient to derive or achieve the fixed, controlled, and/or defined ratio of naïve-like CD4+ T cells to naïve-like CD8+ T cells.

In some embodiments, e.g., when operating in a suboptimal yield concentration for each or one or more of two or more selection reagents with affinity to CD4+ and/or CD8+ T cells, one or more of such reagents is used at a concentration that is higher than one or more of the other such reagent(s), in order to bias the ratio of the cell type recognized by that reagent as compared to the cell type(s) recognized by the other(s). For example, the reagent specifically binding to the marker for which it is desired to bias the ratio may be included at a concentration (e.g., agent or mass per cells) that is increased by half, 1-fold, 2-fold, 3-fold, 4-fold, 5-fold, 10-fold, or more, compared to other(s), depending on how much it is desired to increase the ratio.

In some embodiments, when operating in the suboptimal range and/or with enough cells to achieve saturation of reagents, the amount of immunoaffinity reagent is proportional to the approximate yield of enriched cells. In certain embodiments, an appropriate amount or concentration of immunoaffinity reagents that depend on the desired ratio of the generated composition containing the enriched or selected CD4+ and CD8+ T cells can be determined as a matter of routine.

In some embodiments, the separation and/or isolation steps are carried out using magnetic beads in which immunoaffinity reagents are reversibly bound, such as via a peptide ligand interaction with a streptavidin mutein as described in WO 2015/164675. Exemplary of such magnetic beads are Streptamers®. In some embodiments, the separation and/or steps is carried out using magnetic beads, such as those commercially available from Miltenyi Biotec.

In some embodiments, the first selection or enrichment of CD4+ and CD8+ cells from a sample are performed using immunoaffinity-based reagents that include at least a first and second affinity chromatography matrix, respectively, having immobilized thereon an antibody. In some embodiments, one or both of the first and/or second selection can employ a plurality of affinity chromatography matrices and/or antibodies, whereby the plurality of matrices and/or antibodies employed for the same selection, i.e. the first selection or the second selection, are serially connected. In some embodiments, the affinity chromatography matrix or matrices employed in a first and/or second selection adsorbs or is capable of selecting or enriching at least at or about $50 \times 10^6$ cells/mL, $100 \times 10^6$ cells/mL, $200 \times 10^6$ cells/mL or $400 \times 10^6$ cells/mL. In some embodiments, the adsorption capacity can be modulated based on the diameter and/or length of the column. In some embodiments, the culture-initiating ratio of the selected or enriched composition is achieved by choosing a sufficient amount of matrix and/or at a sufficient relative amount to achieve the culture-initiating ratio assuming based on, for example, the adsorption capacity of the column or columns for selecting cells.

In one exemplary embodiment, the CD4+ T cells and CD8+ T cells have an equal or similar portion of naïve-like cells, and the adsorption capacity of the matrix or matrices is the same between the first and second selection, e.g. is or is about $1 \times 10^8$ cells/mL for both, whereby enrichment or selection of cells in the first selection and second selection results in a composition containing a CD4+ cells to CD8+ cells with a naïve-like CD4+ to CD8+ T cell ratio of or of about 1:1. In particular embodiments, an appropriate volume, diameter or number of affinity matrix chromatography columns for the first and/or second selection depending on portions of naïve-like cells and on the desired ratio of the generated input composition can be chosen or determined as a matter of routine.

In some embodiments, the adsorption capacity of a column matrix or matrices is adjusted to account for differences in the frequency of a naïve-like cells, e.g., naïve like CD4+ or CD8+ cells, compared to the frequency of cells of the respective CD4+ or CD8+ parent population in the starting sample from the subject. The relative level or frequency of various cell populations in a subject can be determined based on assessing surface expression of a marker or markers present on such populations or sub-populations. A number of well-known methods for assessing expression level of surface markers or proteins may be used, such as detection by affinity-based methods, e.g., immunoaffinity-based methods, e.g., in the context of cell surface proteins, such as by flow cytometry.

In some embodiments, naïve-like cells, e.g., naïve-like CD4+ and/or CD8+ T cells, are assessed, measured, and/or detected in cell compositions, e.g., CD4+ and/or CD8+ T cell compositions, or in a sample, e.g., a biological sample. In some embodiments, a naïve-like T cell is a T cell that is positive for the expression of one or more markers that indicate that the cell is naïve and/or is a naïve-like cell. In certain embodiments, a naïve-like T cell is a cell that is positive for the expression of a marker that is associated with a naïve or naïve-like state in T cells. In particular embodiments, a naïve-like T cell is a T cell that is negative for the expression of one or more markers that indicates that the cell is not naïve and/or is a not a naïve-like cell. In certain embodiments, a naïve-like T cell is a cell that is negative for the expression of a marker that is associated with a non-naïve or non-naïve-like state in T cells. In certain embodiments, a non-naïve or non-naïve-like state in a T cells includes, for example but not limited to, effector T ($T_{EFF}$)

cells, memory T cells, central memory T cells ($T_{CM}$), effector memory T ($T_{EM}$) cells, and combinations thereof.

In some embodiments, a naïve-like T cell is positive for the expression of at least one, two, three, four, five, six, seven, eight, nine, ten, or more than ten markers that indicate that the cell is naïve and/or is a naïve-like cell, and/or is associated with a naïve or naïve-like state in T cells. In some embodiments, the markers are expressed on the cell surface. In certain embodiments, the naïve-like T cell is negative for the expression of at least one, two, three, four, five, six, seven, eight, nine, ten, or more than ten markers that indicate that the cell is non-naïve and/or is a non-naïve-like cell, and/or is associated with a non-naïve or non-naïve-like state in T cells.

Markers that indicate that the T cell is naïve and/or is a naïve-like T cell, and/or are associated with a naïve or naïve-like state in T cells include, but are not limited to, CD27, CD28, CD45RA, CD62L, and/or CCR7. In some embodiments, the naïve-like T cell, e.g., the naïve-like CD4+ and/or CD8+ T cell, is positive for expression of CD27, CD28, CD45RA, CD62L, and/or CCR7. In certain embodiments, the naïve-like T cell is positive for the surface expression of one or more of CD27, CD28, CD45RA, CD62L, and/or CCR7.

Markers that indicate that the cell is a non-naïve and/or is a non-naïve-like T cell, and/or are associated with a non-naïve or non-naïve-like state in T cells include, but are not limited to, CD25, CD45RO, CD56, KLRG1, and/or CD95. In some embodiments, the naïve-like T cell, e.g., a naïve-like CD4+ and/or CD8+ T cell, is negative for expression of CD25, CD45RO, CD56, and/or KLRG1. In particular embodiments, the naïve-like T cell, e.g., a naïve-like CD4+ and/or CD8+ T cell, has low expression of a marker associated with non-naïve or non-naïve-like cells. In particular embodiments, the naïve-like T cell has low expression of CD95. In certain embodiments, the naïve-like T cell is negative for the surface expression of one or more of CD25, CD45RO, CD56, and/or KLRG1.

In some embodiments, low expression of a marker associated with non-naïve or non-naïve-like cells is or includes at least 10%, at least 20%, at least 30%, at least 40%, at least 50%, at least 60%, at least 70%, at least 80%, at least 90%, at least 95%, or at least 99% less expression than the expression of the marker in a cell that is a non-naïve-like cells, and/or a cell that is positive for one or more markers that indicate that the cell is a non-naïve and/or is a non-naïve-like T cell, and/or are associated with a non-naïve or non-naïve-like state in T cells. In certain embodiments, low expression of a marker associated with non-naïve or non-naïve-like cells is or includes at least at or about 10%, at least at or about 20%, at least at or about 30%, at least at or about 40%, at least at or about 50%, at least at or about 60%, at least at or about 70%, at least at or about 80%, at least at or about 90%, at least at or about 95%, or at least at or about 99% less expression than the expression of the marker in an effector T ($T_{EFF}$) cell, a memory T cell, a central memory T cell ($T_{CM}$), and/or an effector memory T ($T_{EM}$) cell.

In some embodiments, markers that indicate that the cell is a non-naïve and/or is a non-naïve-like T cell, and/or are associated with a non-naïve or non-naïve-like state in T cells include, one or more cytokines. For example, in certain embodiments, a non-naïve or non-naïve-like T cells is negative for the expression and/or the production of one or more of IL-2, IFN-γ, IL-4, and IL-10. In some embodiments, the one or more cytokines are secreted. In particular embodiments, the one or more cytokines are expressed internally by the non-naïve-like T cells, for example, during or after treatment with an agent that prevents, inhibits, or reduces secretion.

In certain embodiments, a naïve-like T cell is positive for the expression, e.g., surface expression, of CD45RA and CCR7. In particular embodiments, a naïve-like CD4+ T cell is positive for the expression, e.g., surface expression, of CD45RA and CCR7. In some embodiments, a naïve-like CD8+ T cell is positive for the expression, e.g., surface expression, of CD45RA and CCR7. In particular embodiments, a naïve-like T cell is positive for the expression, e.g., surface expression, of CD45RA, CD27, and CCR7 and is negative for the expression, e.g., surface expression of CD45RO. In particular embodiments, a naïve-like CD4+ T cell is positive for the expression, e.g., surface expression, of CD45RA, CD27, and CCR7 and is negative for the expression, e.g., surface expression of CD45RO. In some embodiments, a naïve-like CD8+ T cell is positive for the expression, e.g., surface expression, of CD45RA, CD27, and CCR7 and is negative for the expression, e.g., surface expression of CD45RO.

In certain embodiments, the CD4+ and/or CD8+ T cells are viable cells. In certain embodiments, the CD4+ and/or CD8+ T cells are viable naïve-like cells. The viable cell is positive for the expression of a marker that indicates that the cell undergoes normal functional cellular processes and/or has not undergone or is not under the process of undergoing necrosis or programmed cell death. In some embodiments, viability can be assessed by the redox potential of the cell, the integrity of the cell membrane, or the activity or function of mitochondria. In some embodiments, viability is the absence of a specific molecule associated with cell death, or the absence of the indication of cell death in an assay.

In certain embodiments, cell viability is assessed with an assay that may include, but is not limited to, dye uptake assays (e.g., calcein AM assays), XTT cell viability assays, and dye exclusion assays (e.g., trypan blue, Eosin, or propidium dye exclusion assays). In particular embodiments, a viable cell has negative expression of one or more apoptotic markers, e.g., annexin V or active Caspase 3. In some embodiments, the viable cell is negative for the expression of one or more apoptosis marker that may include, but are not limited to, a caspase, e.g., caspase 2, caspase 3, caspase 6, caspase 7, caspase 8, caspase 9, and caspase 10, Bcl-2 family members, e.g., Bax, Bad, and Bid, Annexin V, and/or TUNEL staining.

In some embodiments, expression is or includes an amount, level, concentration, and/or presence of the marker. In particular embodiments, the marker is polypeptide. In some embodiments, the marker is an mRNA. In some embodiments, the expression is or includes an amount, level, concentration, and/or presence of a polypeptide, e.g., the marker polypeptide. In certain embodiments, an amount, level, concentration, and/or presence of a polynucleotide, e.g., an mRNA or a cDNA derived from the mRNA, that encodes the marker. In certain embodiments, expression is or includes an amount, level, concentration, and/or presence of the marker on or exposed on the cell surface or within the cell membrane. In certain embodiments, expression is or includes an amount, level, concentration, and/or presence of the marker on or exposed on the cell surface or within the cell membrane. In particular embodiments, the expression is or includes internal expression, e.g., an amount, level, concentration, and/or presence of the marker within the cell internally, such as within the cytosol, nucleus, endoplasmic reticulum, and/or the Golgi apparatus.

In some embodiments, the markers are measured, assessed, and/or quantified by performing an in vitro assay. In some examples, the in vitro assay is an immunoassay, an aptamer-based assay, a histological or cytological assay, or an mRNA expression level assay. In some cases, the in vitro assay used can be an enzyme-linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay or avidity assay. In some embodiments, the expression of the markers is measured, assessed, and/or quantified by RNA-seq. In particular embodiments, the expression of the markers is measured, assessed, and/or quantified by immunostaining techniques. In particular embodiments, the expression of the markers is measured, assessed, and/or quantified by flow cytometry analysis. In some embodiments, the expression of the markers is measured, assessed, and/or quantified by internal cytokine staining.

In some embodiments, the markers are measured, assessed, and/or quantified in cells of the CD4+ T cell composition. In particular embodiments, at least at or about 1%, at least at or about 5%, at least at or about 10%, at least at or about 15%, at least at or about 20%, at least at or about 25%, at least at or about 30%, at least at or about 35%, at least at or about 40%, at least at or about 45%, at least at or about 50%, at least at or about 55%, at least at or about 60%, at least at or about 65%, at least at or about 70%, at least at or about 75%, at least at or about 80%, at least at or about 85%, at least at or about 90%, at least at or about 95%, at least at or about 95%, at least at or about 97%, or at least at or about 99% of the CD4+ T cells are naïve-like CD4+ T cells. In certain embodiments, between at or about 10% and at or about 50%, between at or about 20% and at or about 60%, between at or about 25% and at or about 75%, between at or about 30% and at or about 80%, between at or about 40% and at or about 90%, between at or about 50% and at or about 100%, between at or about 30% and at or about 50%, between at or about 40% and at or about 60%, between at or about 50% and at or about 70%, between at or about 60% and at or about 80%, between at or about 70% and at or about 90%, between at or about 80% and at or about 100%, between at or about 5% and at or about 25%, between at or about 25% and at or about 50%, between at or about 50% and at or about 75%, or between at or about 75% and at or about 99% of the CD4+ T cells are naïve-like CD4+ T cells. In certain embodiments, the naïve-like CD4+ T cells are viable naïve-like CD4+ T cells.

In certain embodiments, the markers are measured, assessed, and/or quantified in cells of the CD8+ T cell composition. In particular embodiments, at least at or about 1%, at least at or about 5%, at least at or about 10%, at least at or about 15%, at least at or about 20%, at least at or about 25%, at least at or about 30%, at least at or about 35%, at least at or about 40%, at least at or about 45%, at least at or about 50%, at least at or about 55%, at least at or about 60%, at least at or about 65%, at least at or about 70%, at least at or about 75%, at least at or about 80%, at least at or about 85%, at least at or about 90%, at least at or about 95%, at least at or about 95%, at least at or about 97%, or at least at or about 99% of the CD8+ T cells are naïve-like CD8+ T cells. In certain embodiments, between at or about 10% and at or about 50%, between at or about 20% and at or about 60%, between at or about 25% and at or about 75%, between at or about 30% and at or about 80%, between at or about 40% and at or about 90%, between at or about 50% and at or about 100%, between at or about 30% and at or about 50%, between at or about 40% and at or about 60%, between at or about 50% and at or about 70%, between at or about 60% and at or about 80%, between at or about 70% and at or about 90%, between at or about 80% and at or about 100%, between at or about 5% and at or about 25%, between at or about 25% and at or about 50%, between at or about 50% and at or about 75%, or between at or about 75% and at or about 99% of the CD8+ T cells are naïve-like CD4+ T cells. In certain embodiments, the naïve-like CD8+ T cells are viable naïve-like CD8+ T cells.

In some embodiments, cells from a composition of CD4+ T cells are mixed or combined with cells from a composition of CD8+ T cells in amounts and/or proportions sufficient to produce an input composition with a ratio of CD4+ naïve-like T cells to CD8+ naïve-like T cells between 10:1 to 0.05:1, between 8:1 to 0.1:1, between 5:1 to 0.2:1, between 2.5:1 to 0.25:1, between 2.2:1 to 0.8:1, between 2:1 to 0.5:1, or between 1.5:1 to 1:1, inclusive. In some embodiments, the cells are mixed in amounts and/or proportions sufficient to a ratio of CD4+ naïve-like T cells to CD8+ naïve-like T cells of between 2.2:1 to 0.8:1, inclusive. In certain embodiments, the cells are mixed or combined to a ratio of CD4+ naïve-like T cells to CD8+ naïve-like T cells of or of about 2.2:1, 2.1:1, 2.0:1, 1.9:1, 1.8:1, 1.7:1, 1.6:1, 1.5:1, 1.4:1, 1.3:1, 1.2:1, 1.1:1, 1.0:1, 0.9:1, or 0.8:1. In certain embodiments, the cells are mixed or combined to a ratio of or of about 1.1:1.

In some embodiments, an amount of or about $1×10^6$, $5×10^6$, $1×10^7$, $5×10^7$, $1.0×10^8$, $1.1×10^8$, $1.2×10^8$, $1.3×10^8$, $1.4×10^8$, $1.5×10^8$, $1.6×10^8$, $1.7×10^8$, $1.8×10^8$, $1.9×10^8$, $2.0×10^8$, $2.1×10^8$, $2.2×10^8$, $2.3×10^8$, $2.4×10^8$, $2.5×10^8$, $2.6×10^8$, $2.7×10^8$, $2.8×10^8$, $2.9×10^8$, $3.0×10^8$, $3.5×10^8$, $4.0×10^8$, $4.5×10^8$, $5×10^8$, $5×10^8$, or $1×10^9$, total or total viable CD4+ T cells are mixed or combined with an amount of or about $1×10^6$, $5×10^6$, $1×10^7$, $5×10^7$, $1.0×10^8$, $1.1×10^8$, $1.2×10^8$, $1.3×10^8$, $1.4×10^8$, $1.5×10^8$, $1.6×10^8$, $1.7×10^8$, $1.8×10^8$, $1.9×10^8$, $2.0×10^8$, $2.1×10^8$, $2.2×10^8$, $2.3×10^8$, $2.4×10^8$, $2.5×10^8$, $2.6×10^8$, $2.7×10^8$, $2.8×10^8$, $2.9×10^8$, $3.0×10^8$, $3.5×10^8$, $4.0×10^8$, $4.5×10^8$, $5×10^8$, $5.5×10^8$, or $1×10^9$ total or total viable CD8+ T cells to produce an input composition with a defined ratio of CD4+ naïve-like T cells to CD8+ naïve-like T cells. In certain embodiments, between $1×10^6$ and $1×10^{10}$, between $1×10^7$ and $1×10^9$, between $5×10^7$ and $5×10^8$, or between $1×10^8$ and $3×10^8$ total or total viable CD4+ T cells are mixed or combined with an amount of or about between $1×10^6$ and $1×10^{10}$, between $1×10^7$ and $1×10^9$, between $5×10^7$ and $5×10^8$, or between $1×10^8$ and $3×10^8$ total or total viable CD8+ T cells to produce an input composition with a defined ratio of CD4+ naïve-like T cells to CD8+ naïve-like T cells.

In some embodiments, an amount of or about $1×10^6$, $5×10^6$, $1×10^7$, $5×10^7$, $1.0×10^8$, $1.1×10^8$, $1.2×10^8$, $1.3×10^8$, $1.4×10^8$, $1.5×10^8$, $1.6×10^8$, $1.7×10^8$, $1.8×10^8$, $1.9×10^8$, $2.0×10^8$, $2.1×10^8$, $2.2×10^8$, $2.3×10^8$, $2.4×10^8$, $2.5×10^8$, $2.6×10^8$, $2.7×10^8$, $2.8×10^8$, $2.9×10^8$, $3.0×10^8$, $3.5×10^8$, $4.0×10^8$, $4.5×10^8$, $5×10^8$, $5×10^8$, or $1×10^9$ naïve-like CD4+ T cells are mixed or combined with an amount of or about $1×10^6$, $5×10^6$, $1×10^7$, $5×10^7$, $1.0×10^8$, $1.1×10^8$, $1.2×10^8$, $1.3×10^8$, $1.4×10^8$, $1.5×10^8$, $1.6×10^8$, $1.7×10^8$, $1.8×10^8$, $1.9×10^8$, $2.0×10^8$, $2.1×10^8$, $2.2×10^8$, $2.3×10^8$, $2.4×10^8$, $2.5×10^8$, $2.6×10^8$, $2.7×10^8$, $2.8×10^8$, $2.9×10^8$, $3.0×10^8$, $3.5×10^8$, $4.0×10^8$, $4.5×10^8$, $5×10^8$, $5.5×10^8$, or $1×10^9$ naïve-like CD8+ T cells to produce an input composition with a defined ratio of CD4+ naïve-like T cells to CD8+ naïve-like T cells. In certain embodiments, between $1×10^6$ and $1×10^{10}$, between $1×10^7$ and $1×10^9$, between $5×10^7$ and $5×10^8$, or between $1×10^8$ and $3×10^8$ naïve-like CD4+ T cells are mixed or combined with an amount of or about between $1\times10^6$ and $1\times10^{10}$, between $1\times10^7$ and $1\times10^9$, between $5\times10^7$ and $5\times10^8$, or between $1\times10^8$ and $3\times10^8$ naïve-like CD8+ T cells to produce an input composition with a defined ratio of CD4+ naïve-like T cells to CD8+ naïve-like T cells.

In particular embodiments, the ratio of naïve-like CD4+ T cells to naïve-like CD8+ T cells of the input composition has been adjusted, changed, and/or altered compared to the ratio of the naïve-like CD4+ T cells to naïve-like CD8+ T cells of a sample, e.g., a biological sample. In particular embodiments, the ratio of naïve-like CD4+ T cells to naïve-like CD8+ T cells is or is about or is at least 5%, 10%, 20%, 30%, 40%, 50%, 60%, 70%, 80%, 90%, 95%, 100%, 1-fold, 1.5-fold, 2-fold, 2.5-fold, 3-fold, 4-fold, 5-fold, 10-fold, 20-fold, 50-fold, 100-fold adjusted, changed, or altered from the biological sample. In certain embodiments, the sample is the sample from where cells of the input composition were derived, isolated, selected, and/or obtained.

In some embodiments, producing, generating, and/or making an input composition includes one or more steps of mixing or combining cells of a CD4+ T cell composition with cells of a CD8+ T cell compositions to produce an input composition with a ratio of between 2.2:1 to 0.8:1 naïve-like CD4+ T cells to naïve-like CD8+ T cells. In particular embodiments, number, number per volume, number per weight, and/or the amount, level, or percentage of naïve-like cells are measured, assessed, and/or quantified in the CD4+ T cell composition and the CD8+ T cell composition prior to the mixing or combining. In some embodiments, the amount, level, number, number per volume, number per weight, and/or percentage of naïve-like cells are measured, assessed, and/or quantified by detecting CD45RA+; CCR7+ T cells. In particular embodiments, the input composition has a ratio of between 2.2:1 to 0.8:1 CD45RA+/CCR7+/CD4+ T cells to CD45RA+/CCR7+/CD8+ T cells. In some embodiments, the input composition has a ratio of or of about 1.1:1 CD45RA+/CCR7+/CD4+ T cells to CD45RA+/CCR7+/CD8+ T cells.

In certain embodiments, the input cell composition contains a ratio, e.g., a defined, controlled, and/or fixed ratio, of CD45RA+/CCR7+/CD4+ T cells to CD45RA+/CCR7+/CD8+ T cells. In particular embodiments, the ratio of CD45RA+/CCR7+/CD4+ T cells to CD45RA+/CCR7+/CD8+ T cells is between 10:1 to 0.05:1, between 8:1 to 0.1:1, between 5:1 to 0.2:1, between 2.5:1 to 0.25:1, between 2.2:1 to 0.8:1, between 2:1 to 0.5:1, or between 1.5:1 to 1:1, inclusive. In particular embodiments, the ratio of CD45RA+/CCR7+/CD4+ T cells to CD45RA+/CCR7+/CD8+ T cells is between 2:1 to 0.8:1, between 1.6:1 to 0.8:1, between 1.4:1 to 0.8:1, between 1.2:1 to 0.8:1, or between 1.2:1 to 0.8:1, inclusive. In some embodiments, the ratio is between 2.2:1 to 0.8:1, inclusive. In certain embodiments, the ratio of CD45RA+/CCR7+/CD4+ T cells to CD45RA+/CCR7+/CD8+ T cells is or is about 2.2:1, 2.1:1, 2.0:1, 1.9:1, 1.8:1, 1.7:1, 1.6:1, 1.5:1, 1.4:1, 1.3:1, 1.2:1, 1.1:1, 1.0:1, 0.9:1, or 0.8:1. In certain embodiments, the ratio is or is about 1.1:1.

In particular embodiments, the input cell composition has an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ total cells or total viable cells. In certain embodiments, the input cell composition has an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times$ $10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ cells that express CD4 or CD8. In some embodiments, the input cell composition has an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ CD45RA+/CCR7+/CD4+ and CD45RA+/CCR7+/CD8+ T cells.

In particular embodiments, the input cell composition has between $1\times10^6$ and $1\times10^{10}$, between $1\times10^7$ and $1\times10^9$, between $5\times10^7$ and $5\times10^8$, or between $1\times10^8$ and $3\times10^8$ total cells or total viable cells. In certain embodiments, the input cell composition has an amount of or about between $1\times10^6$ and $1\times10^{10}$, between $1\times10^7$ and $1\times10^9$, between $5\times10^7$ and $5\times10^8$, or between $1\times10^8$ and $3\times10^8$ cells that express CD4 or CD8. In some embodiments, the input cell composition has an amount of or about between $1\times10^6$ and $1\times10^{10}$, between $1\times10^7$ and $1\times10^9$, between $5\times10^7$ and $5\times10^8$, or between $1\times10^8$ and $3\times10^8$ CD45RA+/CCR7+/CD4+ and CD45RA+/CCR7+/CD8+ T cells.

In some embodiments, the input cell composition has or contains at least 1%, at least 5%, at least 10%, at least 20%, at least 30%, at least 40%, at least 50%, at least 60%, at least 70%, at least 75%, at least 80%, at least 85%, at least 90%, at least 95%, at least 96%, at least 97%, at least 98%, at least 99%, at least 99.5%, at least 99.9%, or 100% or about 100% CD45RA+/CCR7+ cells. In particular embodiments, the input cell composition contains or includes no more than 100%, no more than 99%, no more than 98%, no more than 97%, no more than 96%, no more than 95%, no more than 90%, or no more than 85% CD45RA+/CCR7+ cells.

In some embodiments, an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$, total or total viable CD4+ T cells are mixed or combined with an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5.5\times10^8$, or $1\times10^9$ total or total viable CD8+ T cells to produce an input cell composition with a defined ratio of CD45RA+/CCR7+/CD4+ T cells to CD45RA+/CCR7+/CD8+ T cells. In certain embodiments, between $1\times10^6$ and $1\times10^{10}$, between $1\times10^7$ and $1\times10^9$, between $5\times10^7$ and $5\times10^8$, or between $1\times10^8$ and $3\times10^8$ total or total viable CD4+ T cells are mixed or combined with an amount of or about between $1\times10^6$ and $1\times10^{10}$, between $1\times10^7$ and $1\times10^9$, between $5\times10^7$ and $5\times10^8$, or between $1\times10^8$ and $3\times10^8$ total or total viable CD8+ T cells to produce an input cell composition with a defined ratio of CD45RA+/CCR7+/CD4+ T cells to CD45RA+/CCR7+/CD8+ T cells.

In particular embodiments, the ratio of CD45RA+/CCR7+/CD4+ T cells to CD45RA+/CCR7+/CD8+ T cells of the input cell composition has been adjusted, changed, and/or altered compared to the ratio of the CD45RA+/CCR7+/CD4+ T cells to CD45RA+/CCR7+/CD8+ T cells of a sample, e.g., a biological sample. In particular embodiments, the ratio of CD45RA+/CCR7+/CD4+ T cells to CD45RA+/CCR7+/CD8+ T cells is or is about or is at least 5%, 10%, 20%, 30%, 40%, 50%, 60%, 70%, 80%, 90%, 95%, 100%, 1-fold, 1.5-fold, 2-fold, 2.5-fold, 3-fold, 4-fold, 5-fold, 10-fold, 20-fold, 50-fold, 100-fold adjusted, changed, or altered from the biological sample. In certain embodiments, the sample is the sample from where cells of the input cell composition were derived, isolated, selected, and/or obtained.

In certain embodiments, the input cell composition contains a ratio, e.g., a defined, controlled, and/or fixed ratio, of CD27+/CCR7+/CD4+ T cells to CD27+/CCR7+/CD8+ T cells. In particular embodiments, the ratio of CD27+/CCR7+/CD4+ T cells to CD27+/CCR7+/CD8+ T cells is between 10:1 to 0.05:1, between 8:1 to 0.1:1, between 5:1 to 0.2:1, between 2.5:1 to 0.25:1, between 2.2:1 to 0.8:1, between 2:1 to 0.5:1, or between 2:1 to 1:1, inclusive. In particular embodiments, the ratio of CD27+/CCR7+/CD4+ T cells to CD27+/CCR7+/CD8+ T cells is between 2:1 to 0.8:1, between 1.8:1 to 1:1, between 1.8:1 to 1.2:1, between 1.2:1 to 1.4:1, or between 1.8:1 to 1.6:1, inclusive. In some embodiments, the ratio is between 1.8:1 to 1.6:1, inclusive. In certain embodiments, the ratio of CD27+/CCR7+/CD4+ T cells to CD27+/CCR7+/CD8+ T cells is or is about 2.2:1, 2.1:1, 2.0:1, 1.9:1, 1.8:1, 1.7:1, 1.69:1, 1.6:1, 1.5:1, 1.4:1, or 1.3:1. In certain embodiments, the ratio is or is about 1.69:1.

In particular embodiments, the input cell composition has an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ total cells or total viable cells. In certain embodiments, the input cell composition has an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ cells that express CD4 or CD8. In some embodiments, the input cell composition has an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ CD27+/CCR7+/CD4+ and CD27+/CCR7+/CD8+ T cells.

In particular embodiments, the input cell composition has between $1\times10^6$ and $1\times10^{10}$, between $1\times10^7$ and $1\times10^9$, between $5\times10^7$ and $5\times10^8$, or between $1\times10^8$ and $3\times10^8$ total cells or total viable cells. In certain embodiments, the input cell composition has an amount of or about between $1\times10^6$ and $1\times10^{10}$, between $1\times10^7$ and $1\times10^9$, between $5\times10^7$ and $5\times10^8$, or between $1\times10^8$ and $3\times10^8$ cells that express CD4 or CD8. In some embodiments, the input cell composition has an amount of or about between $1\times10^6$ and $1\times10^{10}$, between $1\times10^7$ and $1\times10^9$, between $5\times10^7$ and $5\times10^8$, or between $1\times10^8$ and $3\times10^8$ $^{CD}27+/CCR7+/CD4+$ and CD27+/CCR7+/CD8+ T cells.

In some embodiments, the input cell composition has or contains at least at or about 1%, at least at or about 5%, at least at or about 10%, at least at or about 20%, at least at or about 30%, at least at or about 40%, at least at or about 50%, at least at or about 60%, at least at or about 70%, at least at or about 75%, at least at or about 80%, at least at or about 85%, at least at or about 90%, at least at or about 95%, at least at or about 96%, at least at or about 97%, at least at or about 98%, at least at or about 99%, at least at or about 99.5%, at least at or about 99.9%, or 100% or about 100% CD27+/CCR7+ cells. In particular embodiments, the input cell composition contains or includes no more than at or about 100%, no more than at or about 99%, no more than at or about 98%, no more than at or about 97%, no more than at or about 96%, no more than at or about 95%, no more than at or about 90%, or no more than at or about 85% CD27+/CCR7+ cells.

In some embodiments, an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$, total or total viable CD4+ T cells are mixed or combined with an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5.5\times10^8$, or $1\times10^9$ total or total viable CD8+ T cells to produce an input cell composition with a defined ratio of CD27+/CCR7+/CD4+ T cells to CD27+/CCR7+/CD8+ T cells. In certain embodiments, between $1\times10^6$ and $1\times10^{10}$, between $1\times10^7$ and $1\times10^9$, between $5\times10^7$ and $5\times10^8$, or between $1\times10^8$ and $3\times10^8$ total or total viable CD4+ T cells are mixed or combined with an amount of or about between $1\times10^6$ and $1\times10^{10}$, between $1\times10^7$ and $1\times10^9$, between $5\times10^7$ and $5\times10^8$, or between $1\times10^8$ and $3\times10^8$ total or total viable CD8+ T cells to produce an input cell composition with a defined ratio of CD27+/CCR7+/CD4+ T cells to CD27+/CCR7+/CD8+ T cells.

In particular embodiments, the ratio of CD27+/CCR7+/CD4+ T cells to CD27+/CCR7+/CD8+ T cells of the input cell composition has been adjusted, changed, and/or altered compared to the ratio of the CD27+/CCR7+/CD4+ T cells to CD27+/CCR7+/CD8+ T cells of a sample, e.g., a biological sample. In particular embodiments, the ratio of CD27+/CCR7+/CD4+ T cells to CD27+/CCR7+/CD8+ T cells is or is about or is at least 5%, 10%, 20%, 30%, 40%, 50%, 60%, 70%, 80%, 90%, 95%, 100%, 1-fold, 1.5-fold, 2-fold, 2.5-fold, 3-fold, 4-fold, 5-fold, 10-fold, 20-fold, 50-fold, 100-fold adjusted, changed, or altered from the biological sample. In certain embodiments, the sample is the sample from where cells of the input cell composition were derived, isolated, selected, and/or obtained.

In certain embodiments, the input cell composition contains a ratio, e.g., a defined, controlled, and/or fixed ratio, of CD62L−/CCR7+/CD4+ T cells to CD62L−/CCR7+/CD8+ T cells. In particular embodiments, the ratio of CD62L−/CCR7+/CD4+ T cells to CD62L−/CCR7+/CD8+ T cells is between 10:1 to 0.05:1, between 8:1 to 0.1:1, between 5:1 to 0.2:1, between 2.5:1 to 0.25:1, between 2.2:1 to 0.8:1, between 2:1 to 0.5:1, or between 1.5:1 to 1:1, inclusive. In particular embodiments, the ratio of CD62L−/CCR7+/CD4+ T cells to CD62L−/CCR7+/CD8+ T cells is between 2:1 to 0.8:1, between 1.6:1 to 0.8:1, between 1.4:1 to 0.8:1, between 1.2:1 to 0.8:1, or between 1.2:1 to 0.8:1, inclusive. In some embodiments, the ratio is between 2.2:1 to 0.8:1, inclusive. In certain embodiments, the ratio of CD62L−/CCR7+/CD4+ T cells to CD62L−/CCR7+/CD8+ T cells is or is about 2.2:1, 2.1:1, 2.0:1, 1.9:1, 1.8:1, 1.7:1, 1.6:1, 1.5:1, 1.4:1, 1.3:1, 1.2:1, 1.1:1, 1.0:1, 0.9:1, or 0.8:1. In certain embodiments, the ratio is or is about 1.1:1.

In particular embodiments, the input cell composition has between $1\times10^6$ and $1\times10^{10}$, between $1\times10^7$ and $1\times10^9$, between $5\times10^7$ and $5\times10^8$, or between $1\times10^8$ and $3\times10^8$ total cells or total viable cells. In certain embodiments, the input cell composition has an amount of or about between $1\times10^6$ and $1\times10^{10}$, between $1\times10^7$ and $1\times10^9$, between $5\times10^7$ and $5\times10^8$, or between $1\times10^8$ and $3\times10^8$ cells that express CD4 or CD8. In some embodiments, the input cell composition has an amount of or about between $1\times10^6$ and $1\times10^{10}$, between $1\times10^7$ and $1\times10^9$, between $5\times10^7$ and $5\times10^8$, or between $1\times10^8$ and $3\times10^8$ $^{CD}$62L−/CCR7+/CD4+ and CD62L−/CCR7+/CD8+ T cells.

In some embodiments, the input cell composition has or contains at least at or about 1%, at least at or about 5%, at least at or about 10%, at least at or about 20%, at least at or about 30%, at least at or about 40%, at least at or about 50%, at least at or about 60%, at least at or about 70%, at least at or about 75%, at least at or about 80%, at least at or about 85%, at least at or about 90%, at least at or about 95%, at least at or about 96%, at least at or about 97%, at least at or about 98%, at least at or about 99%, at least at or about 99.5%, at least at or about 99.9%, or 100% or about 100% CD62L−/CCR7+ cells. In particular embodiments, the input cell composition contains or includes no more than at or about 100%, no more than at or about 99%, no more than at or about 98%, no more than at or about 97%, no more than at or about 96%, no more than at or about 95%, no more than at or about 90%, or no more than at or about 85% CD62L−/CCR7+ cells.

In some embodiments, an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$, total or total viable CD4+ T cells are mixed or combined with an amount of or about $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5.5\times10^8$, or $1\times10^9$ total or total viable CD8+ T cells to produce an input cell composition with a defined ratio of CD62L−/CCR7+/CD4+ T cells to CD62L−/CCR7+/CD8+ T cells. In certain embodiments, between $1\times10^6$ and $1\times10^{10}$, between $1\times10^7$ and $1\times10^9$, between $5\times10^7$ and $5\times10^8$, or between $1\times10^8$ and $3\times10^8$ total or total viable CD4+ T cells are mixed or combined with an amount of or about between $1\times10^6$ and $1\times10^{10}$, between $1\times10^7$ and $1\times10^9$, between $5\times10^7$ and $5\times10^8$, or between $1\times10^8$ and $3\times10^8$ total or total viable CD8+ T cells to produce an input cell composition with a defined ratio of CD62L−/CCR7+/CD4+ T cells to CD62L−/CCR7+/CD8+ T cells.

In particular embodiments, the ratio of CD62L−/CCR7+/CD4+ T cells to CD62L−/CCR7+/CD8+ T cells of the input cell composition has been adjusted, changed, and/or altered compared to the ratio of the CD62L−/CCR7+/CD4+ T cells to CD62L−/CCR7+/CD8+ T cells of a sample, e.g., a biological sample. In particular embodiments, the ratio of CD62L−/CCR7+/CD4+ T cells to CD62L−/CCR7+/CD8+ T cells is or is about or is at least 5%, 10%, 20%, 30%, 40%, 50%, 60%, 70%, 80%, 90%, 95%, 100%, 1-fold, 1.5-fold, 2-fold, 2.5-fold, 3-fold, 4-fold, 5-fold, 10-fold, 20-fold, 50-fold, 100-fold adjusted, changed, or altered from the biological sample. In certain embodiments, the sample is the sample from where cells of the input cell composition were derived, isolated, selected, and/or obtained.

In some embodiments, producing, generating, and/or making an input cell composition includes one or more steps of mixing or combining cells of a CD4+ T cell composition with cells of a CD8+ T cell compositions to produce an input cell composition with a ratio of between 2.2:1 to 0.8:1 CD45RA+/CCR7+/CD4+ T cells to CD45RA+/CCR7+/CD8+ T cells. In particular embodiments, number, number per volume, number per weight, and/or the amount, level, or percentage of CD45RA+/CCR7+ cells are measured, assessed, and/or quantified in the CD4+ T cell composition and the CD8+ T cell composition prior to the mixing or combining. In some embodiments, the amount, level, number, number per volume, number per weight, and/or percentage of CD45RA+/CCR7+ cells are measured, assessed, and/or quantified by detecting CD45RA+; CCR7+ T cells. In particular embodiments, the input cell composition has a ratio of between 2.2:1 to 0.8:1 CD45RA+/CCR7+/CD4+ T cells to CD45RA+/CCR7+/CD8+ T cells. In some embodiments, the input cell composition has a ratio of or of about 1.1:1 CD45RA+/CCR7+/CD4+ T cells to CD45RA+/CCR7+/CD8+ T cells.

In some embodiments, producing, generating, and/or making an input cell composition includes one or more steps of mixing or combining cells of a CD4+ T cell composition with cells of a CD8+ T cell compositions to produce an input cell composition with a ratio of between 2.4:1 to 1:1 CD27+/CCR7+/CD4+ T cells to CD27+/CCR7+/CD8+ T cells. In particular embodiments, number, number per volume, number per weight, and/or the amount, level, or percentage of CD27+/CCR7+ cells are measured, assessed, and/or quantified in the CD4+ T cell composition and the CD8+ T cell composition prior to the mixing or combining. In some embodiments, the amount, level, number, number per volume, number per weight, and/or percentage of CD27+/CCR7+ cells are measured, assessed, and/or quantified by detecting CD45RA+; CCR7+ T cells. In particular embodiments, the input cell composition has a ratio of between 2.4:1 to 1:1 CD27+/CCR7+/CD4+ T cells to CD27+/CCR7+/CD8+ T cells. In some embodiments, the input cell composition has a ratio of or of about 1.69:1 CD27+/CCR7+/CD4+ T cells to CD27+/CCR7+/CD8+ T cells.

In some embodiments, producing, generating, and/or making an input cell composition includes one or more steps of mixing or combining cells of a CD4+ T cell composition with cells of a CD8+ T cell compositions to produce an input cell composition with a ratio of between 2.2:1 to 0.8:1 CD62L−/CCR7+/CD4+ T cells to CD62L−/CCR7+/CD8+ T cells. In particular embodiments, number, number per volume, number per weight, and/or the amount, level, or percentage of CD62L−/CCR7+ cells are measured, assessed, and/or quantified in the CD4+ T cell composition and the CD8+ T cell composition prior to the mixing or combining. In some embodiments, the amount, level, number, number per volume, number per weight, and/or percentage of CD62L−/CCR7+ cells are measured, assessed, and/or quantified by detecting CD62L−/CCR7+ T cells. In particular embodiments, the input cell composition has a ratio of between 2.2:1 to 0.8:1 CD62L−/CCR7+/CD4+ T cells to CD62L−/CCR7+/CD8+ T cells. In some embodiments, the input cell composition has a ratio of or of about 1.1:1 CD62L−/CCR7/CD4+ T cells to CD62L−/CCR7/CD8+ T cells.

B. Activation and Stimulation

In some embodiments, the provided methods are used in connection with incubating cells under stimulating conditions. In some embodiments, the stimulating conditions include conditions that activate or stimulate, and/or are capable of activating or stimulating a signal in the cell, e.g., a CD4+ T cell, such as a signal generated from a TCR and/or a coreceptor. In some embodiments, the stimulating conditions include one or more steps of culturing, cultivating, incubating, activating, propagating the cells with and/or in the presence of a stimulatory reagent, e.g., a reagent that activates or stimulates, and/or is capable of activating or stimulating a signal in the cell. In some embodiments, the stimulatory reagent stimulates and/or activates a TCR and/or a coreceptor. In particular embodiments, the stimulatory reagent is a reagent provided herein, e.g., as described in Section I-B-1.

In certain embodiments, one or more compositions of enriched T cells are incubated under stimulating conditions prior to genetically engineering the cells, e.g., transfecting and/or transducing the cells, such as by a method or technique provided herein, e.g., a method or technique described in Section I-C. In particular embodiments, the composition of enriched T cells that is incubated under stimulating conditions is an input composition. In certain embodiments, the cells of the input compositions have previously been isolated, selected, enriched, or obtained from a biological sample. In particular embodiments, the cells from the input composition have been previously cryofrozen and stored, and are thawed prior to the incubation.

In some embodiments, the provided methods are used in connection with the one or more processing steps that include a step of stimulating cells, such as cells from the input compositions. In certain embodiments, the incubation may be prior to or in connection with genetic engineering, such as genetic engineering resulting from embodiments of transduction described herein, e.g., methods described in Section I-C. In some embodiments, the stimulation results in activation and/or proliferation of the cells, for example, prior to engineering, e.g., transduction.

In some embodiments, the processing steps include incubations of cells, such as input cells and/or cells of the input composition, in which the incubation steps can include culture, cultivation, stimulation, activation, and/or propagation of cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

In certain embodiments, the cells, e.g., cells of the input composition, are incubated e.g., under stimulating conditions such as in the presence of a stimulatory reagent, at a density of less than at or about $5\times10^7$ cells/mL, $4\times10^7$ cells/mL, $3\times10^7$ cells/mL, $2\times10^7$ cells/mL, $1\times10^7$ cells/mL, $9\times10^6$ cells/mL, $8\times10^6$ cells/mL, $7\times10^6$ cells/mL, $6\times10^6$ cells/mL, $5\times10^6$ cells/mL, $4\times10^6$ cells/mL, or $3\times10^6$ cells/mL. In particular embodiments, the cells are incubated at a density of less than $5\times10^6$ cells/mL. In some embodiments, the cells are incubated at a density of between $1\times10^3$ cells/mL and $1\times10^9$ cells/mL, $1\times10^4$ cells/mL and $1\times10^8$ cells/mL, $1\times10^5$ cells/mL and $1\times10^7$ cells/mL, $5\times10^5$ cells/mL and $1\times10^7$ cells/mL, $1\times10^6$ cells/mL and $5\times10^6$ cells/mL, or $3\times10^6$ cells/mL and $5\times10^6$ cells/mL. In particular embodiments, the cells are incubated at a density of or of about $1\times10^6$ cells/mL, $1.5\times10^6$ cells/mL, $2\times10^6$ cells/mL, $2.5\times10^6$ cells/mL, $3\times10^6$ cells/mL, $3.5\times10^6$ cells/mL, $4\times10^6$ cells/mL, $4.5\times10^6$ cells/mL, or $5\times10^6$ cells/mL. In particular embodiments, the cells are incubated at a density of or of about $3\times10^6$ cells/mL. In some embodiments, the cells are viable cells. In certain embodiments, the cells are negative for an apoptotic marker, e.g., Annexin V or active caspase 3. In particular embodiments, the cells are or include CD4+ T cells and CD8+ T cells.

In particular embodiments, indicators of viability include but are not limited to, indicators of cellular replication, mitochondrial function, energy balance, membrane integrity and cell mortality. In certain embodiments, the indicators of viability further include indicators of oxidative stress, metabolic activation, metabolic stability, enzyme induction, enzyme inhibition, and interaction with cell membrane transporters. In some embodiments, the viable cells include cells undergoing normal functional cellular processes and/or cell that have not undergone or are not under the process of undergoing necrosis or programmed cell death. In some embodiments, viability can be assessed by the redox potential of the cell, the integrity of the cell membrane, or the activity or function of mitochondria. In some embodiments, viability is the absence of a specific molecule associated with cell death, or the absence of the indication of cell death in an assay. In certain embodiments, the viability of cells can be detected, measured, and/or assessed by a number of routine means. Non-limiting examples of such viability assays include, but are not limited to, dye uptake assays (e.g., calcein AM assays), XTT cell viability assays, and dye exclusion assays (e.g., trypan blue, Eosin, or propidium dye exclusion assays). Viability assays are useful for determining the number or percentage (e.g., frequency) of viable cells in a cell dose, a cell composition, and/or a cell sample.

In particular embodiments, the apoptotic marker may include any known marker associated with apoptosis, and may include expression of genes, proteins, or active forms of proteins, or the appearance of features associated with apoptosis, such as blebbing and/or nuclear breakdown. In certain embodiments, the apoptotic marker is a marker associated with apoptosis that may include, but is not limited to, pro-apoptotic factors known to initiate apoptosis, members of the death receptor pathway, activated members of the mitochondrial (intrinsic) pathway, Bcl-2 family members such as Bax, Bad, and Bid, Fas, FADD, presence of nuclear shrinkage (e.g., monitored by microscope), presence of chromosomal DNA fragmentation (e.g., presence of chromosomal DNA ladder), or markers associated with apoptosis assays, e.g., TUNEL staining, and Annexin V staining. In some embodiments, the marker of apoptosis is caspase expression, e.g., expression of the active forms of caspase-1, caspase-2, caspase-3, caspase-7, caspase-8, caspase-9, caspase-10 and/or caspase-13. In some embodiments, the apoptotic marker is Annexin V. In certain embodiments, the apoptotic marker is active caspase-3.

In some embodiments, between at or about $1\times10^5$ and at or about $500,000\times10^6$ cells, between at or about $1\times10^6$ and at or about $50,000\times10^6$ cells, between at or about $10\times10^6$ and at or about $5,000\times10^6$ cells, between at or about $1\times10^6$ and at or about $1,000\times10^6$ cells, between at or about $50\times10^6$ and at or about $5,000\times10^6$ cells, between at or about $10\times10^6$ and at or about $1,000\times10^6$ cells, between at or about $100\times10^6$ and at or about $2,500\times10^6$ cells, e.g., cells of the input composition, are incubated e.g., under stimulating conditions such as in the presence of a stimulatory reagent. In particular embodiments, at least, at, or at about $50\times10^6$ cells, $100\times10^6$ cells, $150\times10^6$ cells, $200\times10^6$ cells, $250\times10^6$ cells, $300\times10^6$ cells, $350\times10^6$ cells, $400\times10^6$ cells, $450\times10^6$ cells, or $500\times10^6$ cells are incubated, e.g., under stimulating conditions. In some embodiments, the cells are viable cells. In certain embodiments, the cells are negative for a marker of apoptosis, e.g., Annexin V or active caspase 3. In particular embodiments, the cells are or include CD4+ T cells and CD8+ T cells.

In some embodiments, between at or about $1\times10^5$ and at or about $25,000\times10^6$, between at or about $1\times10^6$ and at or about $25,000\times10^6$, between at or about $10\times10^6$ and at or about $2,500\times10^6$, between at or about $1\times10^6$ and at or about $500\times10^6$, between at or about $50\times10^6$ and at or about $2,500 \times 10^6$, between at or about $10 \times 10^6$ and at or about $500 \times 10^6$, between at or about $50 \times 10^6$ and at or about $300 \times 10^6$ CD4+ T cells, e.g., CD4+ T cells of the input composition, are incubated e.g., under stimulating conditions such as in the presence of a stimulatory reagent. In particular embodiments, at least, at, or at about $25 \times 10^6$, $50 \times 10^6$, $75 \times 10^6$, $100 \times 10^6$, $125 \times 10^6$, $150 \times 10^6$, $175 \times 10^6$, $200 \times 10^6$, $225 \times 10^6$, or $250 \times 10^6$ CD4+ T cells are incubated, e.g., under stimulating conditions. In some embodiments, the CD4+ T cells are viable CD4+ T cells. In certain embodiments, the CD4+ T cells are negative for a marker of apoptosis, e.g., Annexin V or active caspase 3.

In certain embodiments, between at or about $1 \times 10^5$ and at or about $25,000 \times 10^6$, between at or about $1 \times 10^6$ and at or about $25,000 \times 10^6$, between at or about $10 \times 10^6$ and at or about $2,500 \times 10^6$, between at or about $1 \times 10^6$ and at or about $500 \times 10^6$, between at or about $50 \times 10^6$ and at or about $2,500 \times 10^6$, between at or about $10 \times 10^6$ and at or about $500 \times 10^6$, between at or about $50 \times 10^6$ and at or about $300 \times 10^6$ CD8+ T cells, e.g., CD8+ T cells of the input composition, are incubated e.g., under stimulating conditions such as in the presence of a stimulatory reagent. In some embodiments, at least, at, or at about $25 \times 10^6$, $50 \times 10^6$, $75 \times 10^6$, $100 \times 10^6$, $125 \times 10^6$, $150 \times 10^6$, $175 \times 10^6$, $200 \times 10^6$, $225 \times 10^6$, or $250 \times 10^6$ CD8+ T cells are incubated, e.g., under stimulating conditions. In some embodiments, the CD8+ T cells are viable CD8+ T cells. In certain embodiments, the CD8+ T cells are negative for a marker of apoptosis, e.g., Annexin V or active caspase 3.

In some embodiments, the conditions for stimulation and/or activation can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or stimulatory reagents include one or more reagent, e.g., ligand, which is capable of stimulating or activating an intracellular signaling domain of a TCR complex. In some aspects, the agent turns on or initiates TCR/CD3 intracellular signaling cascade in a T cell, such as agents suitable to deliver a primary signal, e.g., to initiate activation of an ITAM-induced signal, such as those specific for a TCR component, e.g., anti-CD3, and/or an agent that promotes a costimulatory signal, such as one specific for a T cell costimulatory receptor, e.g., anti-CD28, or anti-4-1BB, for example, bound to solid support such as a bead, and/or one or more cytokines. Among the stimulatory reagents are anti-CD3/anti-CD28 beads (e.g., DYNABEADS® M-450 CD3/CD28 T Cell Expander, and/or ExpACT® beads). Optionally, the expansion method may further comprise the step of adding anti-CD3 and/or anti CD28 antibody to the culture medium. In some embodiments, the stimulating agents include cytokines.

In particular embodiments, the stimulating conditions include incubating, culturing, and/or cultivating the cells with a stimulatory reagent. In particular embodiments, the stimulatory reagent is a reagent provided herein, e.g., a reagent described in Section I-B-1. In certain embodiments, the stimulatory reagent contains or includes a bead. In certain embodiments, the start and or initiation of the incubation, culturing, and/or cultivating cells under stimulating conditions occurs when the cells are come into contact with and/or are incubated with the stimulatory reagent. In particular embodiments, the cells are incubated prior to, during, and/or subsequent to genetically engineering the cells, e.g., introducing a recombinant polynucleotide into the cell such as by transduction or transfection.

In some embodiments, the composition of enriched T cells is incubated at a ratio of stimulatory reagent and/or beads to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of stimulatory reagent and/or beads to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of stimulatory reagent to cells is about 1:1 or is 1:1.

In particular embodiments, the stimulating conditions include incubating, culturing, and/or cultivating the cells, e.g., cells from an input composition, with and/or in the presence of one or more cytokines. In particular embodiments, the one or more cytokines are recombinant cytokines. In some embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes IL-2.

In certain embodiments, the amount or concentration of the one or more cytokines are measured and/or quantified with International Units (IU). International units may be used to quantify vitamins, hormones, cytokines, vaccines, blood products, and similar biologically active substances. In some embodiments, IU are or include units of measure of the potency of biological preparations by comparison to an international reference standard of a specific weight and strength e.g., WHO 1st International Standard for Human IL-2, 86/504. International Units are the only recognized and standardized method to report biological activity units that are published and are derived from an international collaborative research effort. In particular embodiments, the IU for composition, sample, or source of a cytokine may be obtained through product comparison testing with an analogous WHO standard product. For example, in some embodiments, the IU/mg of a composition, sample, or source of human recombinant IL-2, IL-7, or IL-15 is compared to the WHO standard IL-2 product (NIB SC code: 86/500), the WHO standard IL-17 product (NIBSC code: 90/530) and the WHO standard IL-15 product (NIB SC code: 95/554), respectively.

In some embodiments, the biological activity in IU/mg is equivalent to $(ED_{50}$ in ng/mL$)^{-1} \times 10^6$. In particular embodiments, the $ED_{50}$ of recombinant human IL-2 or IL-15 is equivalent to the concentration required for the half-maximal stimulation of cell proliferation (XTT cleavage) with CTLL-2 cells. In certain embodiments, the $ED_{50}$ of recombinant human IL-7 is equivalent to the concentration required for the half-maximal stimulation for proliferation of PHA-activated human peripheral blood lymphocytes. Details relating to assays and calculations of IU for IL-2 are discussed in Wadhwa et al., Journal of Immunological Methods (2013), 379 (1-2): 1-7; and Gearing and Thorpe, Journal of Immunological Methods (1988), 114 (1-2): 3-9; details relating to assays and calculations of IU for IL-15 are discussed in Soman et al. Journal of Immunological Methods (2009) 348 (1-2): 83-94.

In some embodiments, the cells, e.g., the input cells, are incubated with a cytokine, e.g., a recombinant human cytokine, at a concentration of between at or about 1 IU/mL and at or about 1,000 IU/mL, between at or about 10 IU/mL and at or about 50 IU/mL, between at or about 50 IU/mL and at or about 100 IU/mL, between at or about 100 IU/mL and at or about 200 IU/mL, between at or about 100 IU/mL and at or about 500 IU/mL, between at or about 250 IU/mL and at or about 500 IU/mL, or between at or about 500 IU/mL and at or about 1,000 IU/mL.

In some embodiments, the cells, e.g., the input cells, are incubated with IL-2, e.g., human recombinant IL-2, at a concentration between at or about 1 IU/mL and at or about 500 IU/mL, between at or about 10 IU/mL and at or about 250 IU/mL, between at or about 50 IU/mL and at or about 200 IU/mL, between at or about 50 IU/mL and at or about 150 IU/mL, between at or about 75 IU/mL and at or about 125 IU/mL, between at or about 100 IU/mL and at or about 200 IU/mL, or between at or about 10 IU/mL and at or about 100 IU/mL, e.g., in a serum-free medium. In particular embodiments, cells, e.g., cells of the input composition, are incubated with recombinant IL-2 at a concentration at or at about 50 IU/mL, 60 IU/mL, 70 IU/mL, 80 IU/mL, 90 IU/mL, 100 IU/mL, 110 IU/mL, 120 IU/mL, 130 IU/mL, 140 IU/mL, 150 IU/mL, 160 IU/mL, 170 IU/mL, 180 IU/mL, 190 IU/mL, or 100 IU/mL. In some embodiments, the cells, e.g., the input cells, are incubated in the presence of or of about 100 IU/mL of recombinant IL-2, e.g., human recombinant IL-2.

In some embodiments, the cells, e.g., the input cells, are incubated with recombinant IL-7, e.g., human recombinant IL-7, at a concentration between at or about 100 IU/mL and at or about 2,000 IU/mL, between at or about 500 IU/mL and at or about 1,000 IU/mL, between at or about 100 IU/mL and at or about 500 IU/mL, between at or about 500 IU/mL and at or about 750 IU/mL, between at or about 750 IU/mL and at or about 1,000 IU/mL, or between at or about 550 IU/mL and at or about 650 IU/mL, e.g., in a serum-free medium. In particular embodiments, the cells, e.g., the input cells, are incubated with IL-7 at a concentration at or at about 50 IU/mL, 100 IU/mL, 150 IU/mL, 200 IU/mL, 250 IU/mL, 300 IU/mL, 350 IU/mL, 400 IU/mL, 450 IU/mL, 500 IU/mL, 550 IU/mL, 600 IU/mL, 650 IU/mL, 700 IU/mL, 750 IU/mL, 800 IU/mL, 750 IU/mL, 750 IU/mL, 750 IU/mL, or 1,000 IU/mL. In particular embodiments, the cells, e.g., the input cells, are incubated in the presence of or of about 600 IU/mL of IL-7, e.g., human recombinant IL-7.

In some embodiments, the cells, e.g., the input cells, are incubated with recombinant IL-15, e.g., human recombinant IL-15, at a concentration between at or about 1 IU/mL and at or about 500 IU/mL, between at or about 10 IU/mL and at or about 250 IU/mL, between at or about 50 IU/mL and at or about 200 IU/mL, between at or about 50 IU/mL and at or about 150 IU/mL, between at or about 75 IU/mL and at or about 125 IU/mL, between at or about 100 IU/mL and at or about 200 IU/mL, or between at or about 10 IU/mL and at or about 100 IU/mL, e.g., in a serum-free medium. In particular embodiments, cells, e.g., a cell of the input composition, are incubated with recombinant IL-15 at a concentration at or at about 50 IU/mL, 60 IU/mL, 70 IU/mL, 80 IU/mL, 90 IU/mL, 100 IU/mL, 110 IU/mL, 120 IU/mL, 130 IU/mL, 140 IU/mL, 150 IU/mL, 160 IU/mL, 170 IU/mL, 180 IU/mL, 190 IU/mL, or 200 IU/mL. In some embodiments, the cells, e.g., the input cells, are incubated in the presence of or of about 100 IU/mL of recombinant IL-15, e.g., human recombinant IL-15.

In particular embodiments, the cells, e.g., cells from the input composition, are incubated under stimulating conditions in the presence of IL-2, IL-7, and/or IL-15, e.g., in a serum-free medium. In some embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15. In certain embodiments, the cells are incubated under stimulating conditions in the presence of recombinant IL-2, IL-7, and IL-15, e.g., in a serum-free medium.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the incubation is performed in serum free media. In some embodiments, the serum free media is a defined and/or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

In some embodiments, at least a portion of the incubation in the presence of one or more stimulating conditions or a stimulatory reagent is carried out in the internal cavity of a centrifugal chamber, for example, under centrifugal rotation, such as described in International Publication Number WO2016/073602. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g. is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a centrifugal chamber, e.g. in a tube or bag with periodic shaking or rotation. In some embodiments, the incubation is performed with the addition of an incubation buffer to the cells and stimulating agent to achieve a target volume with incubation of the reagent of, for example, 10 mL to 200 mL, such as at least or at least about or about or 10 mL, 20 mL, 30 mL, 40 mL, 50 mL, 60 mL, 70 mL, 80 mL, 90 mL, 100 mL, 150 mL or 200 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from or from about 600 rpm to or to about 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, the total duration of the incubation under stimulating conditions, e.g. with the stimulatory reagent, is between or between about 1 hour and 96 hours, 1 hour and 72 hours, 1 hour and 48 hours, 4 hours and 36 hours, 8 hours and 30 hours, 12 hours and 24 hours, 18 hours and 30 hours, such as at least or at least about 6 hours, 12 hours, 18 hours, 24 hours, 36 hours or 72 hours. In some embodiments, the total duration of the incubation, e.g., with the stimulatory reagent, is between or between about 18 hours and about 30 hours.

In some embodiments, the cells are cultured, cultivated, and/or incubated under stimulating conditions prior to and/ or during a step for introducing a polynucleotide, e.g., a polynucleotide encoding a recombinant receptor, to the cells, e.g., by transduction and/or transfection, such as described by Section I-C. In certain embodiments the cells are cultured, cultivated, and/or incubated under stimulating conditions for an amount of time between 30 minutes and 2 hours, between 1 hour and 8 hours, between 6 hours and 12 hours, between 12 hours and 18 hours, between 16 hours and 24 hours, between 18 hours and 30 hours, between 24 hours and 48 hours, between 24 hours and 72 hours, between 42 hours and 54 hours, between 60 hours and 120 hours between 96 hours and 120 hours, between 90 hours and between 1 days and 7 days, between 3 days and 8 days, between 1 day and 3 days, between 4 days and 6 days, or between 4 days and 5 days prior to the genetic engineering. In some embodiments, the cells are incubated under stimulating conditions for or for about between 18 hours and 30 hours. In particular embodiments, the cells are incubated under stimulating conditions for or for about 24 hours.

In some embodiments, incubating the cells under stimulating conditions includes incubating the cells with a stimulatory reagent that is described in Section I-B-1. In some embodiments, the stimulatory reagent contains or includes a bead, such as a paramagnetic bead, and the cells are incubated with the stimulatory reagent at a ratio of less than 3:1 (beads:cells), such as a ratio of 1:1. In particular embodiments, the cells are incubated with the stimulatory reagent in the presence of one or more cytokines. In some embodiments, the cells are incubated with the stimulatory reagent at a ratio of 1:1 (beads:cells) in the presence of recombinant IL-2, IL-7, and IL-15.

In particular embodiments, an input composition of cells containing CD4+ and CD8+ T cells are incubated under stimulating conditions. In certain embodiments, the cells are incubated in serum free media. In particular embodiments, the input composition contains a ratio of CD4+ T cells to CD8+ T cells of or of about 1:1. In certain embodiments at least at or about $100\times10^6$ cells, e.g., cells from the input composition, are incubated, such as at a density of less than at or about $5\times10^6$ cells/mL, under stimulating conditions. In particular embodiments, at least at or about $50\times10^6$ CD4+ T cells and at least at or about $50\times10^6$ CD8+ T cells are incubated under stimulating conditions. In some embodiments, the cells are incubated for between 18 hours and 30 hours. In particular embodiments, incubating the cells under stimulating conditions includes incubating the cells with a stimulatory reagent in the presence of IL-2, IL-7, and/or IL-15. In certain embodiments, the cells are incubated with the stimulatory reagent at a ratio of less than 3:1 stimulatory reagent to cells. In some embodiments, the cells are incubated with between at or about 50 IU/mL and at or about 200 IU/mL IL-2, between at or about 400 and at or about 1,000 IU/mL IL-7, and/or between at or about 50 IU/mL and at or about 200 IU/mL IL-15.

In certain embodiments, the between $100\times10^6$ and $500\times10^6$ cells of an input composition containing CD4+ and CD8+T at a ratio of or of about 1:1, are incubated under stimulating conditions. In certain embodiments, the cells are viable cells and/or are negative for an apoptotic marker. In some embodiments, at or about $300\times10^6$ cells of the input composition are incubated. In particular embodiments, the cells are incubated in serum free media. In particular embodiments the cells are incubated at a density of or of about $3\times10^6$ cells/mL. In some embodiments, at or about $150\times10^6$ CD4+ T cells and at or about $150\times10^6$ CD8+ T cells are incubated. In particular embodiments, the cells are incubated with a stimulatory reagent at a ratio of or of about 1:1 stimulatory reagent to cells. In certain embodiments, the cells are incubated in the presence of or of about 100 IU/mL IL-2, of or of about 600 IU/mL IL-7, and between 50 IU/mL and/or or of about 200 IU/mL IL-15.

1. Stimulatory Reagents

In some embodiments, incubating a composition of enriched cells under stimulating conditions is or includes incubating and/or contacting the composition of enriched cells with a stimulatory reagent that is capable of activating and/or expanding T cells. In some embodiments, the stimulatory reagent is capable of stimulating and/or activating one or more signals in the cells. In some embodiments, the one or more signals are mediated by a receptor. In particular embodiments, the one or more signals are or are associated with a change in signal transduction and/or a level or amount of secondary messengers, e.g., cAMP and/or intracellular calcium, a change in the amount, cellular localization, confirmation, phosphorylation, ubiquitination, and/or truncation of one or more cellular proteins, and/or a change in a cellular activity, e.g., transcription, translation, protein degradation, cellular morphology, activation state, and/or cell division. In particular embodiments, the stimulating conditions include incubating, culturing, and/or cultivating the cells with a stimulatory reagent. In certain embodiments, the stimulatory reagent contains or includes a bead. In certain embodiments, the initiation of the stimulation occurs when the cells are incubated or contacted with the stimulatory reagent. In particular embodiments, the stimulatory reagent contains or includes an oligomeric reagent, e.g., a streptavidin mutein oligomer. In particular embodiments, the stimulatory reagent activates and/or is capable of activating one or more intracellular signaling domains of one or more components of a TCR complex and/or one or more intracellular signaling domains of one or more costimulatory molecules.

In some embodiments, the stimulating conditions or stimulatory reagents include one or more agent, e.g., ligand, which is capable of activating an intracellular signaling domain of a TCR complex. In some embodiments, an agent as contemplated herein can include, but is not limited to, RNA, DNA, proteins (e.g., enzymes), antigens, polyclonal antibodies, monoclonal antibodies, antibody fragments, carbohydrates, lipids lectins, or any other biomolecule with an affinity for a desired target. In some embodiments, the desired target is a T cell receptor and/or a component of a T cell receptor. In certain embodiments, the desired target is CD3. In certain embodiment, the desired target is a T cell costimulatory molecule, e.g., CD28, CD137 (4-1-BB), OX40, or ICOS. The one or more agents may be attached directly or indirectly to the bead by a variety of methods known and available in the art. The attachment may be covalent, noncovalent, electrostatic, or hydrophobic and may be accomplished by a variety of attachment means, including for example, a chemical means, a mechanical means, or an enzymatic means. In some embodiments, the agent is an antibody or antigen binding fragment thereof, such as a Fab. In some embodiments, a biomolecule (e.g., a biotinylated anti-CD3 antibody) may be attached indirectly to the bead via another biomolecule (e.g., anti-biotin antibody) that is directly attached to the bead.

In some embodiments, the stimulatory reagent contains one or more agent (e.g. antibody or antigen binding fragment thereof, such as a Fab) that specifically binds to one or more of the following macromolecules on a cell (e.g., a T cell): CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD11a (LFA-1), CD62L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3 or fragment thereof including the corresponding ligands to these macromolecules or fragments thereof. In some embodiments, the stimulatory reagent contains one or more agent (e.g. antibody or antigen binding fragment thereof, such as a Fab) that specifically binds to one or more of the following macromolecules on a cell (e.g. a T cell): CD28, CD62L, CCR7, CD27, CD127, CD3, CD4, CD8, CD45RA, and/or CD45RO. In some embodiments, the one or more agent is or is capable of being attached to a bead (e.g., a paramagnetic bead). In some embodiments, the one or more agent is or is capable of being attached (e.g., reversibly attached) to an oligomeric reagent, e.g., a streptavidin mutein oligomer.

In some embodiments, the one or more agent comprises an antibody or antigen binding fragment thereof, such as a Fab. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). In some embodiments, the stimulatory reagent is or comprises an antibody fragment (including antigen-binding fragment), e.g., a Fab, Fab'-SH, Fv, scFv, or (Fab')2 fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species). In some embodiments, the agent is or comprises an antibody that binds to and/or recognizes one or more components of a T cell receptor. In particular embodiments, the agent is or comprises an anti-CD3 antibody. In certain embodiments, the agent is or comprises an antibody that binds to and/or recognizes a co-receptor. In some embodiments, the stimulatory reagent is or comprises an anti-CD28 antibody.

In some embodiments, the cells, e.g., cells of the input population, are stimulated in the presence of a ratio of stimulatory reagent to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of stimulatory reagent to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of stimulatory reagent to cells is about 1:1 or is 1:1.

In some embodiments, the cells are stimulated in the presence of, of about, or of at least 0.01 μg, 0.02 μg, 0.03 μg, 0.04 μg, 0.05 μg, 0.1 μg, 0.2 μg, 0.3 μg, 0.4 μg, 0.5 μg, 0.75 μg, 1 μg, 2 μg, 3 μg, 4 μg, 5 μg, 6 μg, 7 μg, 8 μg, 9 μg, or 10 μg of the stimulatory reagent per $10^6$ cells. In some embodiments, the cells are stimulated in the presence of or of about 4 μg per $10^6$ cells. In particular embodiments, the cells are stimulated in the presence of or of about 0.8 μg per $10^6$ cells. In various embodiments, the cells are stimulated in the presence of or of about 0.8 μg per $10^6$ cells.

a. Bead Reagents

In certain embodiments, the stimulatory reagent contains a particle, e.g., a bead, that is conjugated or linked to one or more agents, e.g., biomolecules, that are capable of activating and/or expanding cells, e.g., T cells. In some embodiments, the one or more agents are bound to a bead. In some embodiments, the bead is biocompatible, i.e., composed of a material that is suitable for biological use. In some embodiments, the beads are non-toxic to cultured cells, e.g., cultured T cells. In some embodiments, the beads may be any particles which are capable of attaching agents in a manner that permits an interaction between the agent and a cell.

In some embodiments, a stimulatory reagent contains one or more agents that are capable of activating and/or expanding cells, e.g., T cells, that are bound to or otherwise attached to a bead, for example to the surface of the bead. In certain embodiments, the bead is a non-cell particle. In particular embodiments, the bead may include a colloidal particle, a microsphere, nanoparticle, a magnetic bead, or the like. In some embodiments the beads are agarose beads. In certain embodiments, the beads are sepharose beads.

In particular embodiments, the stimulatory reagent contains beads that are monodisperse. In certain embodiments, beads that are monodisperse comprise size dispersions having a diameter standard deviation of less than 5% from each other.

In some embodiments, the bead contains one or more agents, such as an agent that is coupled, conjugated, or linked (directly or indirectly) to the surface of the bead. In some embodiments, an agent as contemplated herein can include, but is not limited to, RNA, DNA, proteins (e.g., enzymes), antigens, polyclonal antibodies, monoclonal antibodies, antibody fragments, carbohydrates, lipids lectins, or any other biomolecule with an affinity for a desired target. In some embodiments, the desired target is a T cell receptor and/or a component of a T cell receptor. In certain embodiments, the desired target is CD3. In certain embodiment, the desired target is a T cell costimulatory molecule, e.g., CD28, CD137 (4-1-BB), OX40, or ICOS. The one or more agents may be attached directly or indirectly to the bead by a variety of methods known and available in the art. The attachment may be covalent, noncovalent, electrostatic, or hydrophobic and may be accomplished by a variety of attachment means, including for example, a chemical means, a mechanical means, or an enzymatic means. In some embodiments, a biomolecule (e.g., a biotinylated anti-CD3 antibody) may be attached indirectly to the bead via another biomolecule (e.g., anti-biotin antibody) that is directly attached to the bead.

In some embodiments, the stimulatory reagent contains a bead and one or more agents that directly interact with a macromolecule on the surface of a cell. In certain embodiments, the bead (e.g., a paramagnetic bead) interacts with a cell via one or more agents (e.g., an antibody) specific for one or more macromolecules on the cell (e.g., one or more cell surface proteins). In certain embodiments, the bead (e.g., a paramagnetic bead) is labeled with a first agent described herein, such as a primary antibody (e.g., an anti-biotin antibody) or other biomolecule, and then a second agent, such as a secondary antibody (e.g., a biotinylated anti-CD3 antibody) or other second biomolecule (e.g., streptavidin), is added, whereby the secondary antibody or other second biomolecule specifically binds to such primary antibodies or other biomolecule on the particle.

In some embodiments, the stimulatory reagent contains one or more agents (e.g. antibody) that is attached to a bead (e.g., a paramagnetic bead) and specifically binds to one or more of the following macromolecules on a cell (e.g., a T cell): CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD11a (LFA-1, 112), CD62L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3 or fragment thereof including the corresponding ligands to these macromolecules or fragments thereof. In some embodiments, an agent (e.g. antibody) attached to the bead specifically binds to one or more of the following macromolecules on a cell (e.g. a T cell): CD28, CD62L, CCR7, CD27, CD127, CD3, CD4, CD8, CD45RA, and/or CD45RO.

In some embodiments, one or more of the agents attached to the bead is an antibody. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). In some embodiments, the stimulatory reagent is an antibody fragment (including antigen-binding fragment), e.g., a Fab, Fab'-SH, Fv, scFv, or (Fab')2 fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species). In some embodiments, the agent is an antibody that binds to and/or recognizes one or more components of a T cell receptor. In particular embodiments, the agent is an anti-CD3 antibody. In certain embodiments, the agent is an antibody that binds to and/or recognizes a co-receptor. In some embodiments, the stimulatory reagent comprises an anti-CD28 antibody. In some embodiments, the bead has a diameter of greater than at or about 0.001 $\mu$m, greater than at or about 0.01 $\mu$m, greater than at or about 0.1 $\mu$m, greater than at or about 1.0 $\mu$m, greater than at or about 10 $\mu$m, greater than at or about 50 $\mu$m, greater than at or about 100 $\mu$m or greater than at or about 1000 $\mu$m and no more than at or about 1500 $\mu$m. In some embodiments, the bead has a diameter of at or about 1.0 $\mu$m to at or about 500 $\mu$m, at or about 1.0 $\mu$m to at or about 150 $\mu$m, at or about 1.0 $\mu$m to at or about 30 $\mu$m, at or about 1.0 $\mu$m to at or about 10 $\mu$m, at or about 1.0 $\mu$m to at or about 5.0 $\mu$m, at or about 2.0 $\mu$m to at or about 5.0 $\mu$m, or at or about 3.0 $\mu$m to at or about 5.0 $\mu$m. In some embodiments, the bead has a diameter of at or about 3 $\mu$m to at or about 5 $\mu$m. In some embodiments, the bead has a diameter of at least or at least about or about 0.001 $\mu$m, 0.01 $\mu$m, 0.1 $\mu$m, 0.5 $\mu$m, 1.0 $\mu$m, 1.5 $\mu$m, 2.0 $\mu$m, 2.5 $\mu$m, 3.0 $\mu$m, 3.5 $\mu$m, 4.0 $\mu$m, 4.5 $\mu$m, 5.0 $\mu$m, 5.5 $\mu$m, 6.0 $\mu$m, 6.5 $\mu$m, 7.0 $\mu$m, 7.5 $\mu$m, 8.0 $\mu$m, 8.5 $\mu$m, 9.0 $\mu$m, 9.5 $\mu$m, 10 $\mu$m, 12 $\mu$m, 14 $\mu$m, 16 $\mu$m, 18 $\mu$m or 20 $\mu$m. In certain embodiments, the bead has a diameter of or about 4.5 $\mu$m. In certain embodiments, the bead has a diameter of or about 2.8 $\mu$m.

In some embodiments, the beads have a density of greater than at or about 0.001 g/cm$^3$, greater than at or about 0.01 g/cm$^3$, greater than at or about 0.05 g/cm$^3$, greater than at or about 0.1 g/cm$^3$, greater than at or about 0.5 g/cm$^3$, greater than at or about 0.6 g/cm$^3$, greater than at or about 0.7 g/cm$^3$, greater than at or about 0.8 g/cm$^3$, greater than at or about 0.9 g/cm$^3$, greater than at or about 1 g/cm$^3$, greater than at or about 1.1 g/cm$^3$, greater than at or about 1.2 g/cm$^3$, greater than at or about 1.3 g/cm$^3$, greater than at or about 1.4 g/cm$^3$, greater than at or about 1.5 g/cm$^3$, greater than at or about 2 g/cm$^3$, greater than at or about 3 g/cm$^3$, greater than at or about 4 g/cm$^3$, or greater than at or about 5 g/cm$^3$. In some embodiments, the beads have a density of between at or about 0.001 g/cm$^3$ and at or about 100 g/cm$^3$, at or about 0.01 g/cm$^3$ and at or about 50 g/cm$^3$, at or about 0.1 g/cm$^3$ and at or about 10 g/cm$^3$, at or about 0.1 g/cm$^3$ and at or about. 5 g/cm$^3$, at or about 0.5 g/cm$^3$ and at or about 1 g/cm$^3$, at or about 0.5 g/cm$^3$ and at or about 1.5 g/cm$^3$, at or about 1 g/cm$^3$ and at or about 1.5 g/cm$^3$, at or about 1 g/cm$^3$ and at or about 2 g/cm$^3$, or at or about 1 g/cm$^3$ and at or about 5 g/cm$^3$. In some embodiments, the beads have a density of at or about 0.5 g/cm$^3$, at or about 0.5 g/cm$^3$, at or about 0.6 g/cm$^3$, at or about 0.7 g/cm$^3$, at or about 0.8 g/cm$^3$, at or about 0.9 g/cm$^3$, at or about 1.0 g/cm$^3$, at or about 1.1 g/cm$^3$, at or about 1.2 g/cm$^3$, at or about 1.3 g/cm$^3$, at or about 1.4 g/cm$^3$, at or about 1.5 g/cm$^3$, at or about 1.6 g/cm$^3$, at or about 1.7 g/cm$^3$, at or about 1.8 g/cm$^3$, at or about 1.9 g/cm$^3$, or at or about 2.0 g/cm$^3$. In certain embodiments, the beads have a density of at or about 1.6 g/cm$^3$. In particular embodiments, the beads or particles have a density of at or about 1.5 g/cm$^3$. In certain embodiments, the particles have a density of at or about 1.3 g/cm$^3$.

In certain embodiments, a plurality of the beads has a uniform density. In certain embodiments, a uniform density comprises a density standard deviation of less than at or about 10%, less than at or about 5%, or less than at or about 1% of the mean bead density.

In some embodiments, the beads have a surface area of between at or about 0.001 m$^2$ per each gram of particles (m$^2$/g) to at or about 1,000 m$^2$/g, at or about. 010 m$^2$/g to at or about 100 m$^2$/g, at or about 0.1 m$^2$/g to at or about 10

$m^2/g$, at or about 0.1 $m^2/g$ to at or about 1 $m^2/g$, at or about 1 $m^2/g$ to at or about 10 $m^2/g$, at or about 10 $m^2/g$ to at or about 100 $m^2/g$, at or about 0.5 $m^2/g$ to at or about 20 $m^2/g$, at or about 0.5 $m^2/g$ to at or about 5 $m^2/g$, or at or about 1 $m^2/g$ to at or about 4 $m^2/g$. In some embodiments, the particles or beads have a surface area of at or about 1 $m^2/g$ to at or about 4 $m^2/g$.

In some embodiments, the bead contains at least one material at or near the bead surface that can be coupled, linked, or conjugated to an agent. In some embodiments, the bead is surface functionalized, i.e. comprises functional groups that are capable of forming a covalent bond with a binding molecule, e.g., a polynucleotide or a polypeptide. In particular embodiments, the bead comprises surface-exposed carboxyl, amino, hydroxyl, tosyl, epoxy, and/or chloromethyl groups. In particular embodiments, the beads comprise surface exposed agarose and/or sepharose. In certain embodiments, the bead surface comprises attached stimulatory reagents that can bind or attach binding molecules. In particular embodiments, the biomolecules are polypeptides. In some embodiments, the beads comprise surface exposed protein A, protein G, or biotin.

In some embodiments, the bead reacts in a magnetic field. In some embodiments, the bead is a magnetic bead. In some embodiments, the magnetic bead is paramagnetic. In particular embodiments, the magnetic bead is superparamagnetic. In certain embodiments, the beads do not display any magnetic properties unless they are exposed to a magnetic field.

In particular embodiments, the bead comprises a magnetic core, a paramagnetic core, or a superparamagnetic core. In some embodiments, the magnetic core contains a metal. In some embodiments, the metal can be, but is not limited to, iron, nickel, copper, cobalt, gadolinium, manganese, tantalum, zinc, zirconium or any combinations thereof. In certain embodiments, the magnetic core comprises metal oxides (e.g., iron oxides), ferrites (e.g., manganese ferrites, cobalt ferrites, nickel ferrites, etc.), hematite and metal alloys (e.g., CoTaZn). In some embodiments, the magnetic core comprises one or more of a ferrite, a metal, a metal alloy, an iron oxide, or chromium dioxide. In some embodiments, the magnetic core comprises elemental iron or a compound thereof. In some embodiments, the magnetic core comprises one or more of magnetite ($Fe_3O_4$), maghemite ($\gamma Fe_2O_3$), or greigite ($Fe_3S_4$). In some embodiments, the inner core comprises an iron oxide (e.g., $Fe_3O_4$).

In certain embodiments, the bead contains a magnetic, paramagnetic, and/or superparamagnetic core that is covered by a surface functionalized coat or coating. In some embodiments, the coat can contain a material that can include, but is not limited to, a polymer, a polysaccharide, a silica, a fatty acid, a protein, a carbon, agarose, sepharose, or a combination thereof. In some embodiments, the polymer can be a polyethylene glycol, poly (lactic-co-glycolic acid), polyglutaraldehyde, polyurethane, polystyrene, or a polyvinyl alcohol. In certain embodiments, the outer coat or coating comprises polystyrene. In particular embodiments, the outer coating is surface functionalized.

In some embodiments, the stimulatory reagent comprises a bead that contains a metal oxide core (e.g., an iron oxide core) and a coat, wherein the metal oxide core comprises at least one polysaccharide (e.g., dextran), and wherein the coat comprises at least one polysaccharide (e.g., amino dextran), at least one polymer (e.g., polyurethane) and silica. In some embodiments the metal oxide core is a colloidal iron oxide core. In certain embodiments, the one or more agents include an antibody or antigen-binding fragment thereof. In particular embodiments, the one or more agents include an anti-CD3 antibody and an anti-CD28 antibody. In some embodiments, the stimulatory reagent comprises an anti-CD3 antibody, anti-CD28 antibody, and an anti-biotin antibody. In some embodiments, the stimulatory reagent comprises an anti-biotin antibody. In some embodiments, the bead has a diameter of about 3 μm to about 10 μm. In some embodiments, the bead has a diameter of about 3 μm to about 5 μm. In certain embodiments, the bead has a diameter of about 3.5 μm.

In some embodiments, the stimulatory reagent comprises one or more agents that are attached to a bead comprising a metal oxide core (e.g., an iron oxide inner core) and a coat (e.g., a protective coat), wherein the coat comprises polystyrene. In certain embodiments, the beads are monodisperse, paramagnetic (e.g., superparamagnetic) beads comprising a paramagnetic (e.g., superparamagnetic) iron core, e.g., a core comprising magnetite ($Fe_3O_4$) and/or maghemite ($\gamma Fe_2O_3$) c and a polystyrene coat or coating. In some embodiments, the bead is non-porous. In some embodiments, the beads contain a functionalized surface to which the one or more agents are attached. In certain embodiments, the one or more agents are covalently bound to the beads at the surface. In some embodiments, the one or more agents include an antibody or antigen-binding fragment thereof. In some embodiments, the one or more agents include an anti-CD3 antibody and an anti-CD28 antibody. In some embodiments, the one or more agents include an anti-CD3 antibody and/or an anti-CD28 antibody, and an antibody or antigen fragment thereof capable of binding to a labeled antibody (e.g., biotinylated antibody), such as a labeled anti-CD3 or anti-CD28 antibody. In certain embodiments, the beads have a density of about 1.5 $g/cm^3$ and a surface area of about 1 $m^2/g$ to about 4 $m^2/g$. In particular embodiments; the beads are monodisperse superparamagnetic beads that have a diameter of about 4.5 μm and a density of about 1.5 $g/cm^3$. In some embodiments, the beads the beads are monodisperse superparamagnetic beads that have a mean diameter of about 2.8 μm and a density of about 1.3 $g/cm^3$.

In some embodiments, the composition of enriched T cells is incubated with stimulatory reagent a ratio of beads to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of beads to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of beads to cells is about 1:1 or is 1:1.

b. Oligomeric Reagents

In particular embodiments, the stimulatory reagent contains an oligomeric reagent, e.g., a streptavidin mutein reagent, that is conjugated, linked, or attached to one or more agent, e.g., ligand, which is capable of activating an intracellular signaling domain of a TCR complex. In some embodiments, the one or more agents have an attached binding domain or binding partner (e.g., a binding partner C) that is capable of binding to oligomeric reagent at a particular binding sites (e.g., binding site Z). In some embodiments, a plurality of the agent is reversibly bound to the oligomeric reagent. In various embodiments, the oligomeric reagent has a plurality of the particular binding sites which, in certain embodiments, are reversibly bound to a plurality of agents at the binding domain (e.g., binding partner C). In some embodiments, the amount of bound agents are reduced or decreased in the presence of a competition reagent, e.g., a reagent that is also capable of binding to the particular binding sites (e.g., binding site Z). Among oligomeric stimulatory reagents, including anti-CD3/anti-CD28 oligomeric streptavidin mutein reagent, are described in International PCT publication NO. WO2018/197949.

In some embodiments, the stimulatory reagent is or includes a reversible systems in which at least one agent (e.g., an agent that is capable of producing a signal in a cell such as a T cell) is associated, e.g., reversibly associated, with the oligomeric reagent. In some embodiments, the reagent contains a plurality of binding sites capable of binding, e.g., reversibly binding, to the agent. In some cases, the reagent is a oligomeric particle reagent having at least one attached agent capable of producing a signal in a cell such as a T cell. In some embodiments, the agent contains at least one binding site, e.g., a binding site B, that can specifically bind an epitope or region of the molecule and also contains a binding partner, also referred to herein as a binding partner C, that specifically binds to at least one binding site of the reagent, e.g., binding site Z of the reagent. In some embodiments, the binding interaction between the binding partner C and the at least one binding site Z is a non-covalent interaction. In some cases, the binding interaction between the binding partner C and the at least one binding site Z is a covalent interaction. In some embodiments, the binding interaction, such as non-covalent interaction, between the binding partner C and the at least one binding site Z is reversible.

Substances that may be used as oligomeric reagents in such reversible systems are known, see e.g., U.S. Pat. Nos. 5,168,049; 5,506,121; 6,103,493; 7,776,562; 7,981,632; 8,298,782; 8,735,540; 9,023,604; and International published PCT Appl. Nos. WO2013/124474 and WO2014/076277. Non-limiting examples of reagents and binding partners capable of forming a reversible interaction, as well as substances (e.g. competition reagents) capable of reversing such binding, are described below.

In some embodiments, the oligomeric reagent is an oligomer of streptavidin, streptavidin mutein or analog, avidin, an avidin mutein or analog (such as neutravidin) or a mixture thereof, in which such oligomeric reagent contains one or more binding sites for reversible association with the binding domain of the agent (e.g., a binding partner C). In some embodiments, the binding domain of the agent can be a biotin, a biotin derivative or analog, or a streptavidin-binding peptide or other molecule that is able to specifically bind to streptavidin, a streptavidin mutein or analog, avidin or an avidin mutein or analog.

In certain embodiments, one or more agents (e.g., agents that are capable of producing a signal in a cell such as a T cell) associate with, such as are reversibly bound to, the oligomeric reagent, such as via the plurality of the particular binding sites (e.g., binding sites Z) present on the oligomeric reagent. In some cases, this results in the agents being closely arranged to each other such that an avidity effect can take place if a target cell having (at least two copies of) a cell surface molecule that is bound by or recognized by the agent is brought into contact with the agent.

In some embodiments, the oligomeric reagent is a streptavidin oligomer, a streptavidin mutein oligomer, a streptavidin analog oligomer, an avidin oligomer, an oligomer composed of avidin mutein or avidin analog (such as neutravidin) or a mixture thereof. In particular embodiments, the oligomeric reagents contain particular binding sites that are capable of binding to a binding domain (e.g., the binding partner C) of an agent. In some embodiments, the binding domain can be a biotin, a biotin derivative or analog, or a streptavidin-binding peptide or other molecule that is able to specifically bind to streptavidin, a streptavidin mutein or analog, avidin or an avidin mutein or analog.

In some embodiments, the streptavidin can be wild-type streptavidin, streptavidin muteins or analogs, such as streptavidin-like polypeptides. Likewise, avidin, in some aspects, includes wild-type avidin or muteins or analogs of avidin such as neutravidin, a deglycosylated avidin with modified arginines that typically exhibits a more neutral pi and is available as an alternative to native avidin. Generally, deglycosylated, neutral forms of avidin include those commercially available forms such as "Extravidin" available through Sigma Aldrich, or "NeutrAvidin" available from Thermo Scientific or Invitrogen, for example.

In some embodiments, the reagent is a streptavidin or a streptavidin mutein or analog. In some embodiments, wild-type streptavidin (wt-streptavidin) has the amino acid sequence disclosed by Argarana et al, Nucleic Acids Res. 14 (1986) 1871-1882 (SEQ ID NO: 72). In general, streptavidin naturally occurs as a tetramer of four identical subunits, i.e. it is a homo-tetramer, where each subunit contains a single binding site for biotin, a biotin derivative or analog or a biotin mimic. An exemplary sequence of a streptavidin subunit is the sequence of amino acids set forth in SEQ ID NO: 72, but such a sequence also can include a sequence present in homologs thereof from other Streptomyces species. In particular, each subunit of streptavidin may exhibit a strong binding affinity for biotin with an equilibrium dissociation constant ($K_D$) on the order of at or about $10^{-14}$ M. In some cases, streptavidin can exist as a monovalent tetramer in which only one of the four binding sites is functional (Howarth et al. (2006) Nat. Methods, 3:267-73; Zhang et al. (2015) Biochem. Biophys. Res. Commun., 463:1059-63)), a divalent tetramer in which two of the four binding sites are functional (Fairhead et al. (2013) J. Mol. Biol., 426:199-214), or can be present in monomeric or dimeric form (Wu et al. (2005) J. Biol. Chem., 280:23225-31; Lim et al. (2010) Biochemistry, 50:8682-91).

In some embodiments, streptavidin may be in any form, such as wild-type or unmodified streptavidin, such as a streptavidin from a Streptomyces species or a functionally active fragment thereof that includes at least one functional subunit containing a binding site for biotin, a biotin derivative or analog or a biotin mimic, such as generally contains at least one functional subunit of a wild-type streptavidin from Streptomyces avidinii set forth in SEQ ID NO: 72 or a functionally active fragment thereof. For example, in some embodiments, streptavidin can include a fragment of wild-type streptavidin, which is shortened at the N- and/or C-terminus. Such minimal streptavidins include any that begin N-terminally in the region of amino acid positions 10 to 16 of SEQ ID NO: 72 and terminate C-terminally in the region of amino acid positions 133 to 142 of SEQ ID NO: 72. In some embodiments, a functionally active fragment of streptavidin contains the sequence of amino acids set forth in SEQ ID NO: 73. In some embodiments, streptavidin, such as set forth in SEQ ID NO: 73, can further contain an N-terminal methionine at a position corresponding to Ala13 with numbering set forth in SEQ ID NO: 72. Reference to the position of residues in streptavidin or streptavidin muteins is with reference to numbering of residues in SEQ ID NO: 72.

Examples of streptavidins or streptavidin muteins are mentioned, for example, in WO 86/02077, DE 19641876 A1, U.S. Pat. No. 6,022,951, WO 98/40396 or WO 96/24606. Examples of streptavidin muteins are known in the art, see e.g., U.S. Pat. Nos. 5,168,049; 5,506,121;

6,022,951; 6,156,493; 6,165,750; 6,103,493; or 6,368,813; or International published PCT App. No. WO2014/076277.

In some embodiments, a streptavidin mutein can contain amino acids that are not part of an unmodified or wild-type streptavidin or can include only a part of a wild-type or unmodified streptavidin. In some embodiments, a streptavidin mutein contains at least one subunit that can have one more amino acid substitutions (replacements) compared to a subunit of an unmodified or wild-type streptavidin, such as compared to the wild-type streptavidin subunit set forth in SEQ ID NO: 72 or a functionally active fragment thereof, e.g. set forth in SEQ ID NO: 73 or SEQ ID NO: 94.

In some embodiments, the binding affinity, such as dissociation constant ($K_d$), of streptavidin or a streptavidin mutein for a binding domain is less than at or about $1\times10^4$M, $5\times10^4$ M, $1\times10^{-5}$ M, $5\times10^{-5}$M, $1\times10^{-6}$ M, $5\times10^{-6}$ M or $1\times10^{-7}$ M, but generally greater than $1\times10^{-13}$ M, $1\times10^{-12}$ M or $1\times10^{-11}$ M. For example, peptide sequences (Strep-tags), such as disclosed in U.S. Pat. No. 5,506,121, can act as biotin mimics and demonstrate a binding affinity for streptavidin, e.g., with a $K_D$ of approximately between $10^4$ and $10^{-5}$ M. In some cases, the binding affinity can be further improved by making a mutation within the streptavidin molecule, see e.g. U.S. Pat. No. 6,103,493 or International published PCT App. No. WO2014/076277. In some embodiments, binding affinity can be determined by methods known in the art, such as any described herein.

In some embodiments, the reagent, such as a streptavidin or streptavidin mutein, exhibits binding affinity for a peptide ligand binding partner, which peptide ligand binding partner can be the binding partner C present in the agent (e.g., receptor-binding agent or selection agent). In some embodiments, the peptide sequence contains a sequence with the general formula His-Pro-Xaa, where Xaa is glutamine, asparagine, or methionine, such as contains the sequence set forth in SEQ ID NO: 89. In some embodiments, the peptide sequence has the general formula set forth in SEQ ID NO: 90, such as set forth in SEQ ID NO: 80. In one example, the peptide sequence is Trp-Arg-His-Pro-Gln-Phe-Gly-Gly (also called Strep-Tag®, set forth in SEQ ID NO: 81). In one example, the peptide sequence is Trp-Ser-His-Pro-Gln-Phe-Glu-Lys (also called Strep-Tag® II, set forth in SEQ ID NO: 75). In some embodiments, the peptide ligand contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa, where Xaa is glutamine, asparagine, or methionine, and wherein the other binding module has the same or different streptavidin peptide ligand, such as set forth in SEQ ID NO: 90 (see e.g. International Published PCT Appl. No. WO02/077018; U.S. Pat. No. 7,981,632). In some embodiments, the peptide ligand contains a sequence having the formula set forth in any of SEQ ID NO: 82 or 83. In some embodiments, the peptide ligand has the sequence of amino acids set forth in any of SEQ ID NOS: 76-78 and 84-85. In most cases, all these streptavidin binding peptides bind to the same binding site, namely the biotin binding site of streptavidin. If one or more of such streptavidin binding peptides is used as binding partners C, e.g. C1 and C2, the multimerization reagent and/or oligomeric particle reagents bound to the one or more agents via the binding partner C is typically composed of one or more streptavidin muteins.

In some embodiments, the streptavidin mutein is a mutant as described in U.S. Pat. No. 6,103,493. In some embodiments, the streptavidin mutein contains at least one mutation within the region of amino acid positions 44 to 53, based on the amino acid sequence of wild-type streptavidin, such as set forth in SEQ ID NO: 72. In some embodiments, the streptavidin mutein contains a mutation at one or more residues 44, 45, 46, and/or 47. In some embodiments, the streptavidin mutein contains a replacement of Glu at position 44 of wild-type streptavidin with a hydrophobic aliphatic amino acid, e.g. Val, Ala, Be or Leu, any amino acid at position 45, an aliphatic amino acid, such as a hydrophobic aliphatic amino acid at position 46 and/or a replacement of Val at position 47 with a basic amino acid, e.g. Arg or Lys, such as generally Arg. In some embodiments, Ala is at position 46 and/or Arg is at position 47 and/or Val or Ile is at position 44. In some embodiments, the streptavidin mutant contains residues Val44-Thr45-Ala46-Arg47, such as set forth in exemplary streptavidin muteins containing the sequence of amino acids set forth in SEQ ID NO: 86 or SEQ ID NO: 87 or 88 (also known as streptavidin mutant 1, SAM1). In some embodiments, the streptavidin mutein contains residues Ile44-Gly45-Ala46-Arg47, such as set forth in exemplary streptavidin muteins containing the sequence of amino acids set forth in SEQ ID NO: 91, 74, or 79 (also known as SAM2). In some cases, such streptavidin mutein are described, for example, in U.S. Pat. No. 6,103, 493, and are commercially available under the trademark Strep-Tactin®. In some embodiments, the mutein streptavidin contains the sequence of amino acids set forth in SEQ ID NO: 92 or SEQ ID NO: 93. In particular embodiments, the molecule is a tetramer of streptavidin or a streptavidin mutein comprising a sequence set forth in any of SEQ ID NOS: 73, 87, 74, 92, 94, 88, or 79, which, as a tetramer, is a molecule that contains 20 primary amines, including 1 N-terminal amine and 4 lysines per monomer.

In some embodiments, streptavidin mutein exhibits a binding affinity characterized by an equilibrium dissociation constant ($K_D$) that is or is less than at or about $3.7\times10^{-5}$ M for the peptide ligand (Trp-Arg-His-Pro-Gln-Phe-Gly-Gly; also called Strep-Tag®, set forth in SEQ ID NO: 81) and/or that is or is less than at or about $7.1\times10^{-5}$ M for the peptide ligand (Trp-Ser-His-Pro-Gln-Phe-Glu-Lys; also called Strep-Tag® II, set forth in SEQ ID NO: 75) and/or that is or is less than at or about $7.0\times10^{-5}$ M, $5.0\times10^{-5}$ M, $1.0\times10^{-5}$ M, $5.0\times10^{-6}$ M, $1.0\times10^{-6}$ M, $5.0\times10^{-7}$ M, or $1.0\times10^{-7}$ M, but generally greater than at or about $1\times10^{-13}$ M, $1\times10^{-12}$ M or $1\times10^{-11}$ M for any of the peptide ligands set forth in any of SEQ ID NOS: 75, 82-85, 76-78, 80, 81, 89, and 90.

In some embodiments, the resulting streptavidin mutein exhibits a binding affinity characterized by an equilibrium association constant ($K_A$) that is or is greater than at or about $2.7\times10^4$ M$^{-1}$ for the peptide ligand (Trp-Arg-His-Pro-Gln-Phe-Gly-Gly; also called Strep-Tag®, set forth in SEQ ID NO: 81) and/or that is or is greater than at or about $1.4\times10^4$ M$^{-1}$ for the peptide ligand (Trp-Ser-His-Pro-Gln-Phe-Glu-Lys; also called Strep-Tag® II, set forth in SEQ ID NO: 75) and/or that is or is greater than at or about $1.43\times10^4$M$^{-1}$, $1.67\times10^4$M$^{-1}$, $2\times10^4$M$^{-1}$, $3.33\times10^4$M$^{-1}$, $5\times10^4$ M$^{-1}$, $1\times10^5$ M$^{-1}$, $1.11\times10^5$M$^{-1}$, $1.25\times10^5$M$^{-1}$, $1.43\times10^5$M$^{-1}$, $1.67\times10^5$M$^{-1}$, $2\times10^5$M$^{-1}$, $3.33\times10^5$M$^{-1}$, $5\times10^5$M$^{-1}$, $1\times10^6$ M$^{-1}$, $1.11\times10^6$M$^{-1}$, $1.25\times10^6$M$^{-1}$, $1.43\times10^6$M$^{-1}$, $1.67\times10^6$M$^{-1}$, $2\times10^6$M$^{-1}$, $3.33\times10^6$M$^{-1}$, $5\times10^6$ M$^{-1}$, $1\times10^7$ M$^{-1}$, but generally less than $1\times10^{13}$ M$^{-1}$, $1\times10^{12}$ M$^{-1}$ or $1\times10^{11}$ M$^{-1}$ for any of the peptide ligands set forth in any of SEQ ID NOS: 75, 82-85, 76-78, 80, 81, 89, and 90.

In particular embodiments, provided herein is an oligomeric particle reagent that is composed of and/or contains a plurality of streptavidin or streptavidin mutein tetramers. In certain embodiments, the oligomeric particle reagent provided herein contains a plurality of binding sites that reversibly bind or are capable of reversibly binding to one or more agents, e.g., a stimulatory agent and/or a selection agent. In some embodiments, the oligomeric particle has a radius, e.g., an average or mean radius, of between at or about 70 nm and at or about 125 nm, inclusive; a molecular weight of between at or about $1\times10^7$ g/mol and at or about $1\times10^9$ g/mol, inclusive; and/or between at or about 1,000 and at or about 5,000 streptavidin or streptavidin mutein tetramers, inclusive. In some embodiments, the oligomeric particle reagent is bound, e.g., reversibly bound, to one or more agents such as an agent that binds to a molecule, e.g. receptor, on the surface of a cell. In certain embodiments, the one or more agents are or comprise an antibody or antigen binding fragment thereof, such as a Fab. In some embodiments, the one or more agents specifically bind to one or more of the following macromolecules on a cell (e.g., a T cell): CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD11a (LFA-1), CD62L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3 or fragment thereof including the corresponding ligands to these macromolecules or fragments thereof. In some embodiments, the one or more agents specifically bind to one or more of the following macromolecules on a cell (e.g. a T cell): CD28, CD62L, CCR7, CD27, CD127, CD3, CD4, CD8, CD45RA, and/or CD45RO. In some embodiments, the one or more agent comprises an antibody or antigen binding fragment thereof, such as a Fab, and the antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). In some embodiments, the one or more reagent is or comprises an antibody fragment (including antigen-binding fragment), e.g., a Fab, Fab'-SH, Fv, scFv, or (Fab')2 fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species). In some embodiments, the one or more reagent is or comprises an antibody that binds to and/or recognizes one or more components of a T cell receptor. In particular embodiments, the one or more reagent is or comprises an anti-CD3 antibody. In certain embodiments, the one or more reagent is or comprises an antibody that binds to and/or recognizes a co-receptor. In some embodiments, the one or more reagent is or comprises an anti-CD28 antibody. In some embodiments, the one or more reagent is or comprises an anti-CD3 and/or an anti-CD28 antibody or antigen binding fragment thereof, such as an antibody or antigen fragment thereof that contains a binding partner, e.g., a streptavidin binding peptide, e.g. Strep-Tag® II. In particular embodiments, the one or more agent is or comprises an anti-CD3 and/or an anti-CD28 Fab containing a binding partner, e.g., a streptavidin binding peptide, e.g. Strep-Tag® II.

In some embodiments, provided herein is an oligomeric particle reagent that is composed of and/or contains a plurality of streptavidin or streptavidin mutein tetramers. In certain embodiments, the oligomeric particle reagent provided herein contains a plurality of binding sites that reversibly bind or are capable of reversibly binding to one or more agents, e.g., a stimulatory agent and/or a selection agent. In some embodiments, the oligomeric particle has a radius, e.g., an average radius, of between at or about 80 nm and at or about 120 nm, inclusive; a molecular weight, e.g., an average molecular weight of between at or about $7.5\times10^6$ g/mol and at or about $2\times10^8$ g/mol, inclusive; and/or an amount, e.g., an average amount, of between at or about 500 and at or about 10,000 streptavidin or streptavidin mutein tetramers, inclusive. In some embodiments, the oligomeric particle reagent is bound, e.g., reversibly bound, to one or more agents, such as an agent that binds to a molecule, e.g. receptor, on the surface of a cell. In some embodiments, the agent is an anti-CD3 and/or an anti-CD28 Fab, such as a Fab that contains a binding partner, e.g., a streptavidin binding peptide, e.g. Strep-Tag® II. In particular embodiments, the one or more agents is an anti-CD3 and/or an anti CD28 Fab containing a binding partner, e.g., a streptavidin binding peptide, e.g. Strep-Tag® II.

In some embodiments, the cells are stimulated in the presence of, of about, or of at least at or about 0.01 µg, 0.02 µg, 0.03 µg, 0.04 µg, 0.05 µg, 0.1 µg, 0.2 µg, 0.3 µg, 0.4 µg, 0.5 µg, 0.75 µg, 1 µg, 2 µg, 3 µg, 4 µg, 5 µg, 6 µg, 7 µg, 8 µg, 9 µg, or 10 µg of the oligomeric stimulatory reagent per $10^6$ cells. In some embodiments, the cells are stimulated in the presence of or of about 4 µg per $10^6$ cells. In particular embodiments, the cells are stimulated in the presence of or of about 0.8 µg per $10^6$ cells. In certain aspects, 4 µg of the oligomeric stimulatory reagent is or includes at or about 3 µg of oligomeric particles and at or about 1 µg of attached agents, e.g., at or about 0.5 µg of anti-CD3 Fabs and at or about 0.5 µg of anti-CD28 Fabs.

2 Removal of the Stimulatory Reagent from Cells

In some embodiments, the stimulatory reagent is removed or separated from the cells or cell populations prior to collecting, harvesting, or formulating the cells. In some embodiments, the stimulatory reagents are removed or separated from the cells or cell populations after or during the incubation, e.g., an incubation described herein such as in Section I-D. In certain embodiments, the cells or cell population undergoes a process, procedure, step, or technique to remove the stimulatory reagent after the incubation but prior to steps for collecting, harvesting, or formulating the cells. In particular embodiments, the cells or cell population undergoes a process, procedure, step, or technique to remove the stimulatory reagent after the incubation. In some aspects, when stimulatory reagent is separated or removed from the cells during the incubation, the cells are returned to the same incubation conditions as prior to the separation or removal for the remaining duration of the incubation.

In certain embodiments, the stimulatory reagent is removed and/or separated from the cells. In particular embodiments, the binding and/or association between a stimulatory reagent and cells may, in some circumstances, be reduced over time during the incubation. In certain embodiments, one or more agents may be added to reduce the binding and/or association between the stimulatory reagent and the cells. In particular embodiments, a change in cell culture conditions, e.g., the addition of an agent and/or a change in media temperature and/or pH, may reduce the binding and/or association between the stimulatory reagent and the cells. Thus, in some embodiments, the stimulatory reagent may be removed from an incubation, cell culture system, and/or a solution separately from the cells, e.g., without removing the cells from the incubation, cell culture system, and/or a solution as well.

In certain embodiments, the stimulatory reagent is separated and/or removed from the cells after an amount of time. In particular embodiments, the amount of time is an amount of time from the initiation of the stimulation. In particular embodiments the start of the incubation is considered at or at about the time the cells are contacted with the stimulatory reagent and/or a media or solution containing the stimulatory reagent. In particular embodiments, the stimulatory reagent is removed or separated from the cells within or within about 120 hours, 108 hours, 96 hours, 84 hours, 72 hours, 60 hours, 48 hours, 36 hours, 24 hours, or 12 hours, inclusive, of the initiation of the stimulation. In particular embodiments, the stimulatory reagent is removed or separated from the cells at or at about 48 hours after the stimulation is initiated. In certain embodiments, the stimulatory reagent is removed or separated from the cells at or at about 72 hours after the stimulation is initiated. In some embodiments, the stimulatory reagent is removed or separated from the cells at or at about 96 hours after the stimulation is initiated.

Methods for removing stimulatory reagents (e.g. stimulatory reagents that are or contain particles such as bead particles or magnetizable particles) from cells are known. In certain embodiments, a bead stimulatory reagent, e.g., an anti-CD3/anti-CD28 antibody conjugated paramagnetic bead, is separated or removed from the cells or the cell population. In some embodiments, the use of competing antibodies, such as non-labeled antibodies, can be used, which, for example, bind to a primary antibody of the stimulatory reagent and alter its affinity for its antigen on the cell, thereby permitting for gentle detachment. In some cases, after detachment, the competing antibodies may remain associated with the particle (e.g. bead particle) while the unreacted antibody is or may be washed away and the cell is free of isolating, selecting, enriching and/or activating antibody. Exemplary of such a reagent is DETACaBEAD (Friedl et al. 1995; Entschladen et al. 1997). In some embodiments, particles (e.g. bead particles) can be removed in the presence of a cleavable linker (e.g. DNA linker), whereby the particle-bound antibodies are conjugated to the linker (e.g. CELLection, Dynal). In some cases, the linker region provides a cleavable site to remove the particles (e.g. bead particles) from the cells after isolation, for example, by the addition of DNase or other releasing buffer. In some embodiments, other enzymatic methods can also be employed for release of a particle (e.g. bead particle) from cells. In some embodiments, the particles (e.g. bead particles or magnetizable particles) are biodegradable.

In some embodiments, the stimulatory reagent is magnetic, paramagnetic, and/or superparamagnetic, and/or contains a bead that is magnetic, paramagnetic, and/or superparamagnetic, and the stimulatory reagent may be removed from the cells by exposing the cells to a magnetic field. Examples of suitable equipment containing magnets for generating the magnetic field include DynaMag CTS (Thermo Fisher), Magnetic Separator (Takara) and EasySep Magnet (Stem Cell Technologies).

In particular embodiments, the stimulatory reagent is removed or separated from the cells prior to the completion of the provided methods, e.g., prior to harvesting, collecting, and/or formulating engineered cells produced by the methods provided herein. In some embodiments, the stimulatory reagent is removed and/or separated from the cells after engineering, e.g., transducing or transfecting, the cells. In certain embodiments, the stimulatory reagent is removed after the cultivation of the cells, e.g., prior to the cultivation of the engineered, e.g., transfected or transduced, cells under conditions to promote proliferation and/or expansion. In particular embodiments, the stimulatory reagent is removed after the cells achieve a threshold number, density, and/or expansion during the cultivation of the cells. In some embodiments, the stimulatory reagent is removed prior to formulating the cells, e.g., prior to forming the cultivated cells, such as cultivated cells that had achieved the threshold number, concentration, or expansion.

In some embodiments, the stimulatory bead reagent, e.g., the stimulatory magnetic bead reagent, is removed or separated from the cells or cell populations prior to collecting, harvesting, or formulating the cells. In some embodiments, the stimulatory bead reagent, e.g., the stimulatory magnetic bead reagent, are removed or separated from the cells or cell populations by exposure to a magnetic field during or after the incubation, e.g., an incubation described herein such as in Section I-D. In certain embodiments, the cells or cell population are exposed to the magnetic field to remove the stimulatory bead reagent, e.g., the stimulatory magnetic bead reagent, after the incubation but prior to steps for collecting, harvesting, or formulating the cells. In particular embodiments, the cells or cell population undergoes is exposed to the magnetic field to remove the stimulatory bead reagent, e.g., the stimulatory magnetic bead reagent, after the incubation. In some aspects, when the stimulatory bead reagent is separated or removed from the cells or cell population during the incubation, the cells or cell population are returned to the same incubation conditions as prior to the exposure to the magnetic field for the remaining duration of the incubation.

In particular embodiments, the stimulatory bead reagent, e.g., the stimulatory magnetic bead reagent, is removed or separated from the cells, e.g., by exposure to a magnetic field, within or within about 120 hours, 108 hours, 96 hours, 84 hours, 72 hours, 60 hours, 48 hours, 36 hours, 24 hours, or 12 hours, inclusive, of the initiation of the stimulation. In certain embodiments, the stimulatory bead reagent, e.g., the stimulatory magnetic bead reagent, is removed or separated from the cells, e.g., by exposure to a magnetic field, at or at about 72 hours after the stimulation is initiated. In some embodiments, the stimulatory bead reagent, e.g., the stimulatory magnetic bead reagent, is removed or separated from the cells, e.g., by exposure to a magnetic field, at or at about 96 hours after the stimulation is initiated.

In certain embodiments, the stimulatory reagent is separated and/or removed from the cells after an amount of time. In particular embodiments, the amount of time is an amount of time from the start and/or initiation of the incubation under stimulating conditions. In particular embodiments the start of the incubation is considered at or at about the time the cells are contacted with the stimulatory reagent and/or a media or solution containing the stimulatory reagent. In particular embodiments, the stimulatory reagent is removed or separated from the cells within or within about 28 days, 21 days, 20 days, 19 days, 18 days, 17 days, 16 days, 15 days, 14 days, 13 days, 12 days, 11 days, 10 days, and 9 days after the start or initiation of the incubation. In some embodiments, the stimulatory reagent is removed or separated from the cells within or within about 28 days, 21 days, 20 days, 19 days, 18 days, 17 days, 16 days, 15 days, 14 days, 13 days, 12 days, 11 days, 10 days, 9 days after the CD4+ T cells and CD8+ T cells are pooled, combined, and/or mixed into the input composition. In certain embodiments, the stimulatory reagent is removed or separated from the cells within or within about 28 days, 21 days, 20 days, 19 days, 18 days, 17 days, 16 days, 15 days, 14 days, 13 days, 12 days, 11 days, 10 days, 9 days after the CD4+ T cells and CD8+ T cells are obtained, isolated, enriched, and/or selected from a biological sample.

In some embodiments, removal of a stimulatory agent, such as an oligomeric stimulatory reagent as described, included adding to the population of incubated T cells a substance, such as a competition agent, was added to T cells to disrupt, such as to lessen and/or terminate, the signaling of the stimulatory agent or agents. In some embodiments, the population of the incubated T cells contains the presence of a substance, such as a competition agent, e.g. biotin or a biotin analog, e.g. D-Biotin. In some embodiments, the substance, such as a competition agent, e.g. biotin or a biotin analog, e.g. D-Biotin, is present in an amount that is at least 1.5-fold greater, at least 2-fold, at least 3-fold, at least 4-fold, at least 5-fold, at least 10-fold, at least 100-fold, at least 1000-fold or more greater than the amount of the substance in a reference population or preparation of cultured T cells in which the substance was not added exogenously during the incubation. In some embodiments, the amount of the substance, such as a competition agent, e.g. biotin or a biotin analog, e.g. D-Biotin, in the population of cultured T cells is from at or about 10 µM to at or about 100 µM, at or about 100 µM to at or about 1 mM, at or about 100 µM to at or about 500 µM or at or about 10 µM to at or about 100 µM. In some embodiments, 10 µM or about 10 µM of biotin or a biotin analog, e.g., D-biotin, is added to the cells or the cell population to separate or remove the oligomeric stimulatory reagent from the cells or cell population.

In certain embodiments, the one or more agents (e.g., agents that stimulate or activate a TCR and/or a coreceptor) associate with, such as are reversibly bound to, the oligomeric reagent, such as via the plurality of the particular binding sites (e.g., binding sites Z) present on the oligomeric reagent. In some cases, this results in the agents being closely arranged to each other such that an avidity effect can take place if a target cell having (at least two copies of) a cell surface molecule that is bound by or recognized by the agent is brought into contact with the agent. In some aspects, the receptor binding reagent has a low affinity towards the receptor molecule of the cell at binding site B, such that the receptor binding reagent dissociates from the cell in the presence of the competition reagent. Thus, in some embodiments, the agents are removed from the cells in the presence of the competition reagent.

In some embodiments, the oligomeric stimulatory reagent is a streptavidin mutein oligomer with reversibly attached anti-CD3 and anti-CD28 Fabs. In some embodiments, the Fabs are attached contain streptavidin binding domains, e.g., that allow for the reversible attachment to the streptavidin mutein oligomer. In some cases, anti-CD3 and anti-CD28 Fabs are closely arranged to each other such that an avidity effect can take place if a T cell expressing CD3 and/or CD28 is brought into contact with the oligomeric stimulatory reagent with the reversibly attached Fabs. In some aspects, the Fabs have a low affinity towards CD3 and CD28, such that the Fabs dissociate from the cell in the presence of the competition reagent, e.g., biotin or a biotin variant or analogue. Thus, in some embodiments, the Fabs are removed or dissociated from the cells in the presence of the competition reagent, e.g., D-biotin.

In some embodiments, the stimulatory oligomeric reagent, e.g., the stimulatory oligomeric streptavidin mutein reagent, is removed or separated from the cells or cell populations prior to collecting, harvesting, or formulating the cells. In some embodiments, stimulatory oligomeric reagent, e.g., the stimulatory oligomeric streptavidin mutein reagent, is removed or separated from the cells or cell populations by contact or exposure to a competition reagent, e.g., biotin or a biotin analog such as D-biotin, after or during the incubation, e.g., an incubation described herein such as in Section I-D. In certain embodiments, the cells or cell population are contacted or exposed to a competition reagent, e.g., biotin or a biotin analog such as D-biotin, to remove stimulatory oligomeric reagent, e.g., the stimulatory oligomeric streptavidin mutein reagent, after the incubation but prior to steps for collecting, harvesting, or formulating the cells. In particular embodiments, the cells or cell population are contacted or exposed to a competition reagent, e.g., biotin or a biotin analog such as D-biotin, to remove the stimulatory oligomeric reagent, e.g., the stimulatory oligomeric streptavidin mutein reagent, after the incubation. In some aspects, when stimulatory oligomeric reagent, e.g., the stimulatory oligomeric streptavidin mutein reagent, is separated or removed from the cells during the incubation, e.g., by contact or exposure to a competition reagent, e.g., biotin or a biotin analog such as D-biotin, the cells are returned to the same incubation conditions as prior to the separation or removal for the remaining duration of the incubation.

In some embodiments, the cells are contacted with, with about, or with at least at or about 0.01 µM, 0.05 µM, 0.1 µM, 0.5 µM, 1 µM, 2 µM, 3 µM, 4 µM, 5 µM, 10 µM, 100 µM, 500 µM, 0.01 µM, 1 mM, or 10 mM of the competition reagent to remove or separate the oligomeric stimulatory reagent from the cells. In various embodiments, the cells are contacted with, with about, or with at least at or about 0.01 µM, 0.05 µM, 0.1 µM, 0.5 µM, 1 µM, 2 µM, 3 µM, 4 µM, 5 µM, 10 µM, 100 µM, 500 µM, 0.01 µM, 1 mM, or 10 mM of biotin or a biotin analog such as D-biotin, to remove or separate the stimulatory streptavidin mutein oligomers with reversibly attached anti-CD3 and anti-CD28 Fabs from the cells.

In particular embodiments, the stimulatory oligomeric reagent, e.g., the stimulatory oligomeric streptavidin mutein reagent, is removed or separated from the cells within or within about 120 hours, 108 hours, 96 hours, 84 hours, 72 hours, 60 hours, 48 hours, 36 hours, 24 hours, or 12 hours, inclusive, of the initiation of the stimulation. In particular embodiments, the stimulatory oligomeric reagent, e.g., the stimulatory oligomeric streptavidin mutein reagent, is removed or separated from the cells at or at about 48 hours after the stimulation is initiated. In certain embodiments, the stimulatory oligomeric reagent, e.g., the stimulatory oligomeric streptavidin mutein reagent, is removed or separated from the cells at or at about 72 hours after the stimulation is initiated. In some embodiments, the stimulatory oligomeric reagent, e.g., the stimulatory oligomeric streptavidin mutein reagent is removed or separated from the cells at or at about 96 hours after the stimulation is initiated.

C. Engineering Cells

In some embodiments, the processing steps include subjecting cells, e.g. stimulated cells, to engineering, such as under conditions for introduction of a nucleic acid molecule encoding a recombinant protein into one or more cells. Exemplary of such recombinant proteins are recombinant receptors, such as any described in Section II. Methods for engineering cells, such as for introduction of the nucleic acid molecules encoding the recombinant protein, such as recombinant receptor, in cells may be carried out using any of a number of known methods, such as using vectors or other agents that contain a polynucleotide that encodes the recombinant protein. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation.

In certain embodiments, cells and/or compositions of enriched T cells are subjected to engineering, e.g., by a process that involves transduction or transfection of cells, prior to cultivating the cells. In some cases, the cultivating is carried out under conditions that promote proliferation and/or expansion, such as by a method provided herein, e.g., in Section I-D. In particular embodiments, the cells are subjected to engineering after the cells have been stimulated, activated, and/or incubated under stimulating conditions, such as by any of the methods provided herein, e.g., in Section I-B. In particular embodiments, the cells are stimulated cells and/or the composition of cells is a stimulated compositions of cells, such as by previous incubation under stimulating conditions, e.g., as described in Section I-B. In particular embodiments, the one or more stimulated compositions have been previously cryofrozen and stored, and are thawed prior to engineering.

In some embodiments, a set and/or fixed number of cells, e.g., stimulated cells, are subjected to engineering, such as by contacting such cells with an agent (e.g. lentiviral vector) containing a polynucleotide encoding a recombinant protein (e.g. CAR) for engineering cells, e.g., such as by transduction or transfection. In particular embodiments, between at or about $1 \times 10^5$ and at or about $50,000 \times 10^6$ cells, between at or about $1 \times 10^6$ and at or about $50,000 \times 10^6$ cells, between at or about $10 \times 10^6$ and at or about $5,000 \times 10^6$ cells, between at or about $1 \times 10^6$ and at or about $1,000 \times 10^6$ cells, between at or about $50 \times 10^6$ and at or about $5,000 \times 10^6$ cells, between at or about $10 \times 10^6$ and at or about $1,000 \times 10^6$ cells, between at or about $50 \times 10^6$ and at or about $500 \times 10^6$ cells, e.g., stimulated cells, are subjected to engineering, e.g., such as by transduction or transfection. In particular embodiments, at least, at, or at about $50 \times 10^6$ cells, $100 \times 10^6$ cells, $150 \times 10^6$ cells, $200 \times 10^6$ cells, or $250 \times 10^6$ cells are subjecting to engineering. In particular embodiments, at least about $100 \times 10^6$ cells are subjected to engineering. In particular embodiments, up to $200 \times 10^6$ cells are subjected to engineering. In particular embodiments, between about $100 \times 10^6$ and about $200 \times 10^6$ cells are subjected to engineering. In some embodiments, the cells are stimulated cells. In particular embodiments, the cells are viable cells. In certain embodiments, the cells are negative for a marker of apoptosis, e.g., Annexin V or active caspase 3. In certain embodiments, the cells are viable cells that have been stimulated, such as by an incubation under stimulating conditions.

In some embodiments, the number of cells (e.g., stimulated cells) to be subjected to engineering, such as by contacting such cells with an agent (e.g. lentiviral vector) containing a polynucleotide encoding a recombinant protein (e.g. CAR), e.g., such as by transduction or transfection, is the total number of cells after the activation or stimulation, and up to a maximum of $200 \times 10^6$ total cells. In some embodiments, for input compositions that are originated from different donors, different numbers of cells after the activation or stimulation may be subject to engineering, e.g., transduction or transfection. In some embodiments, in cases where the total number of cells after the activation or stimulation is or exceeds $200 \times 10^6$, a maximum of up to $200 \times 10^6$ cells are subjected to engineering, while in cases where the total number of cells after the activation or stimulation is below $200 \times 10^6$, all of the post-activation or post-stimulation cells are subjected to engineering. In some embodiments, the cells are stimulated cells. In particular embodiments, the cells are viable cells. In certain embodiments, the cells are negative for a marker of apoptosis, e.g., Annexin V or active caspase 3. In certain embodiments, the cells are viable cells that have been stimulated, such as by an incubation under stimulating conditions.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications. In certain embodiments, the gene transfer is accomplished by first incubating the cells under stimulating conditions, such as by any of the methods described herein, e.g., in Section I-B.

In certain embodiments, methods for genetic engineering are carried out by contacting one or more cells of a composition with a nucleic acid molecule encoding the recombinant protein, e.g. recombinant receptor. In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the engineering, e.g., transduction or transfection, is performed in serum free media. In some embodiments, the serum free media is a defined and/or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

In some embodiments, the cells, e.g., stimulated cells, are subjected to engineering, e.g., transduced or transfected, in the presence of a transduction adjuvant. Exemplary transduction adjuvants include, but are not limited to, polycations, fibronectin or fibronectin-derived fragments or variants, and RetroNectin. In certain embodiments, the cells are subjected to engineering in the presence of polycations, fibronectin or fibronectin-derived fragments or variants, and/or RetroNectin. In particular embodiments, the cells are subjected to engineering in the presence of a polycation that is polybrene, DEAE-dextran, protamine sulfate, poly-L-lysine, or a cationic liposome. In particular embodiments, the cells are subjected to engineering in the presence of protamine sulfate.

In some embodiments, the cells, e.g., stimulated cells, are subjected to engineering, e.g., transduced or transfected, in the absence of a transduction adjuvant. Thus, in particular embodiments, the cells are subjected to engineering in the absence of polycations, fibronectin or fibronectin-derived fragments or variants, and RetroNectin. In particular embodiments, the cells are subjected to engineering in the absence of a polycation that is polybrene, DEAE-dextran, protamine sulfate, poly-L-lysine, or a cationic liposome. In particular embodiments, the cells are subjected to engineering in the absence of protamine sulfate.

In some embodiments, the cells, e.g., T cells, may be transduced either during or after activation, stimulation, and/or expansion e.g. with a T cell receptor (TCR) or a chimeric antigen receptor (CAR). This transduction for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some aspects, the cells further are subjected to engineering to promote expression of cytokines or other factors.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some embodiments, the introducing is carried out by contacting one or more cells of a composition with a nucleic acid molecule encoding the recombinant protein, e.g. recombinant receptor. In some embodiments, the contacting can be effected with centrifugation, such as spinoculation (e.g. centrifugal inoculation). Such methods include any of those as described in International Publication Number WO2016/073602. Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Exemplary kits for use with such systems include, but are not limited to, single-use kits sold by BioSafe SA under product names CS-430.1, CS-490.1, CS-600.1 or CS-900.2.

In some embodiments, the system is included with and/or placed into association with other instrumentation, including instrumentation to operate, automate, control and/or monitor aspects of the transduction step and one or more various other processing steps performed in the system, e.g. one or more processing steps that can be carried out with or in connection with the centrifugal chamber system as described herein or in International Publication Number WO2016/073602. This instrumentation in some embodiments is contained within a cabinet. In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced and the viral vector particles, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or compositions during the methods. The containers can be connected at one or more positions in the system, such as at a position corresponding to an input line, diluent line, wash line, waste line and/or output line.

In some embodiments, the chamber is associated with a centrifuge, which is capable of effecting rotation of the chamber, such as around its axis of rotation. Rotation may occur before, during, and/or after the incubation in connection with transduction of the cells and/or in one or more of the other processing steps. Thus, in some embodiments, one or more of the various processing steps is carried out under rotation, e.g., at a particular force. The chamber is typically capable of vertical or generally vertical rotation, such that the chamber sits vertically during centrifugation and the side wall and axis are vertical or generally vertical, with the end wall(s) horizontal or generally horizontal.

In some embodiments, the composition containing cells and composition containing viral vector particles, and optionally air, can be combined or mixed prior to providing the compositions to the cavity. In some embodiments, the composition containing cells and composition containing viral vector particles, and optionally air, are provided separately and combined and mixed in the cavity. In some embodiments, a composition containing cells, a composition containing viral vector particles, and optionally air, can be provided to the internal cavity in any order. In any of such some embodiments, a composition containing cells and viral vector particles is the input composition once combined or mixed together, whether such is combined or mixed inside or outside the centrifugal chamber and/or whether cells and viral vector particles are provided to the centrifugal chamber together or separately, such as simultaneously or sequentially.

In some embodiments, intake of the volume of gas, such as air, occurs prior to the incubating the cells and viral vector particles, such as rotation, in the transduction method. In some embodiments, intake of the volume of gas, such as air, occurs during the incubation of the cells and viral vector particles, such as rotation, in the transduction method.

In some embodiments, the liquid volume of the cells or viral vector particles that make up the transduction composition, and optionally the volume of air, can be a predetermined volume. The volume can be a volume that is programmed into and/or controlled by circuitry associated with the system.

In some embodiments, intake of the transduction composition, and optionally gas, such as air, is controlled manually, semi-automatically and/or automatically until a desired or predetermined volume has been taken into the internal cavity of the chamber. In some embodiments, a sensor associated with the system can detect liquid and/or gas flowing to and from the centrifuge chamber, such as via its color, flow rate and/or density, and can communicate with associated circuitry to stop or continue the intake as necessary until intake of such desired or predetermined volume has been achieved. In some aspects, a sensor that is programmed or able only to detect liquid in the system, but not gas (e.g. air), can be made able to permit passage of gas, such as air, into the system without stopping intake. In some such embodiments, a non-clear piece of tubing can be placed in the line near the sensor while intake of gas, such as air, is desired. In some embodiments, intake of gas, such as air, can be controlled manually.

In aspects of the provided methods, the internal cavity of the centrifuge chamber is subjected to high speed rotation. In some embodiments, rotation is effected prior to, simultaneously, subsequently or intermittently with intake of the liquid input composition, and optionally air. In some embodiments, rotation is effected subsequent to intake of the liquid input composition, and optionally air. In some embodiments, rotation is by centrifugation of the centrifugal chamber at a relative centrifugal force at the inner surface of side wall of the internal cavity and/or at a surface layer of the cells of at or about or at least at or about 800 g, 1000 g, 1100 g, 1500, 1600 g, 1800 g, 2000 g, 2200 g, 2500 g, 3000 g, 3500 g or 4000 g. In some embodiments, rotation is by centrifugation at a force that is greater than or about 1100 g, such as by greater than or about 1200 g, greater than or about 1400 g, greater than or about 1600 g, greater than or about 1800 g, greater than or about 2000 g, greater than or about 2400 g, greater than or about 2800 g, greater than or about 3000 g or greater than or about 3200 g. In some embodiments, rotation is by centrifugation at a force that is or is about 1600 g.

In some embodiments, the method of transduction includes rotation or centrifugation of the transduction composition, and optionally air, in the centrifugal chamber for greater than or about 5 minutes, such as greater than or about 10 minutes, greater than or about 15 minutes, greater than or about 20 minutes, greater than or about 30 minutes, greater than or about 45 minutes, greater than or about 60 minutes, greater than or about 90 minutes or greater than or about 120 minutes. In some embodiments, the transduction composition, and optionally air, is rotated or centrifuged in the centrifugal chamber for greater than 5 minutes, but for no more than 60 minutes, no more than 45 minutes, no more than 30 minutes or no more than 15 minutes. In particular embodiments, the transduction includes rotation or centrifugation for or for about 60 minutes.

In some embodiments, the method of transduction includes rotation or centrifugation of the transduction composition, and optionally air, in the centrifugal chamber for between at or about 10 minutes and at or about 60 minutes, at or about 15 minutes and at or about 60 minutes, at or about 15 minutes and at or about 45 minutes, at or about 30 minutes and at or about 60 minutes or at or about 45 minutes and at or about 60 minutes, each inclusive, and at a force at the internal surface of the side wall of the internal cavity and/or at a surface layer of the cells of at least or greater than at or about 1000 g, 1100 g, 1200 g, 1400 g, 1500 g, 1600 g, 1800 g, 2000 g, 2200 g, 2400 g, 2800 g, 3200 g or 3600 g. In particular embodiments, the method of transduction includes rotation or centrifugation of the transduction composition, e.g., the cells and the viral vector particles, at or at about 1600 g for or for about 60 minutes.

In some embodiments, the gas, such as air, in the cavity of the chamber is expelled from the chamber. In some embodiments, the gas, such as air, is expelled to a container that is operably linked as part of the closed system with the centrifugal chamber. In some embodiments, the container is a free or empty container. In some embodiments, the air, such as gas, in the cavity of the chamber is expelled through a filter that is operably connected to the internal cavity of the chamber via a sterile tubing line. In some embodiments, the air is expelled using manual, semi-automatic or automatic processes. In some embodiments, air is expelled from the chamber prior to, simultaneously, intermittently or subsequently with expressing the output composition containing incubated cells and viral vector particles, such as cells in which transduction has been initiated or cells have been transduced with a viral vector, from the cavity of the chamber.

In some embodiments, the transduction and/or other incubation is performed as or as part of a continuous or semi-continuous process. In some embodiments, a continuous process involves the continuous intake of the cells and viral vector particles, e.g., the transduction composition (either as a single pre-existing composition or by continuously pulling into the same vessel, e.g., cavity, and thereby mixing, its parts), and/or the continuous expression or expulsion of liquid, and optionally expelling of gas (e.g. air), from the vessel, during at least a portion of the incubation, e.g., while centrifuging. In some embodiments, the continuous intake and continuous expression are carried out at least in part simultaneously. In some embodiments, the continuous intake occurs during part of the incubation, e.g., during part of the centrifugation, and the continuous expression occurs during a separate part of the incubation. The two may alternate. Thus, the continuous intake and expression, while carrying out the incubation, can allow for a greater overall volume of sample to be processed, e.g., transduced.

In some embodiments, the incubation is part of a continuous process, the method including, during at least a portion of the incubation, effecting continuous intake of said transduction composition into the cavity during rotation of the chamber and during a portion of the incubation, effecting continuous expression of liquid and, optionally expelling of gas (e.g. air), from the cavity through the at least one opening during rotation of the chamber.

In some embodiments, the semi-continuous incubation is carried out by alternating between effecting intake of the composition into the cavity, incubation, expression of liquid from the cavity and, optionally expelling of gas (e.g. air) from the cavity, such as to an output container, and then intake of a subsequent (e.g., second, third, etc.) composition containing more cells and other reagents for processing, e.g., viral vector particles, and repeating the process. For example, in some embodiments, the incubation is part of a semi-continuous process, the method including, prior to the incubation, effecting intake of the transduction composition into the cavity through said at least one opening, and subsequent to the incubation, effecting expression of fluid from the cavity; effecting intake of another transduction composition comprising cells and the viral vector particles into said internal cavity; and incubating the another transduction composition in said internal cavity under conditions whereby said cells in said another transduction composition are transduced with said vector. The process may be continued in an iterative fashion for a number of additional rounds. In this respect, the semi-continuous or continuous methods may permit production of even greater volume and/or number of cells.

In some embodiments, a portion of the transduction incubation is performed in the centrifugal chamber, which is performed under conditions that include rotation or centrifugation.

In some embodiments, the method includes an incubation in which a further portion of the incubation of the cells and viral vector particles is carried out without rotation or centrifugation, which generally is carried out subsequent to the at least portion of the incubation that includes rotation or centrifugation of the chamber. In some such embodiments, the further incubation is effected under conditions to result in integration of the viral vector into a host genome of one or more of the cells. It is within the level of a skilled artisan to assess or determine if the incubation has resulted in integration of viral vector particles into a host genome, and hence to empirically determine the conditions for a further incubation. In some embodiments, integration of a viral vector into a host genome can be assessed by measuring the level of expression of a recombinant protein, such as a heterologous protein, encoded by a nucleic acid contained in the genome of the viral vector particle following incubation. A number of well-known methods for assessing expression level of recombinant molecules may be used, such as detection by affinity-based methods, e.g., immunoaffinity-based methods, e.g., in the context of cell surface proteins, such as by flow cytometry. In some examples, the expression is measured by detection of a transduction marker and/or reporter construct. In some embodiments, nucleic acid encoding a truncated surface protein is included within the vector and used as a marker of expression and/or enhancement thereof.

In some embodiments, the composition containing cells and viral particles can be rotated, generally at relatively low force or speed, such as speed lower than that used to pellet the cells, such as from or from about 600 rpm to or to about 1700 rpm (e.g. at or about or at least 600 rpm, 1000 rpm, or 1500 rpm or 1700 rpm). In some embodiments, the rotation is carried at a force, e.g., a relative centrifugal force, of from or from about 100 g to 3200 g (e.g. at or about or at least at or about 100 g, 200 g, 300 g, 400 g, 500 g, 1000 g, 1500 g, 2000 g, 2500 g, 3000 g or 3200 g), as measured for example at an internal or external wall of the chamber or cavity. The term "relative centrifugal force" or RCF is generally understood to be the effective force imparted on an object or substance (such as a cell, sample, or pellet and/or a point in the chamber or other container being rotated), relative to the earth's gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

In certain embodiments, the composition containing cells and viral particles is rotated for greater than or about 5 minutes, such as greater than or about 10 minutes, greater than or about 15 minutes, greater than or about 20 minutes, greater than or about 30 minutes, greater than or about 45 minutes, greater than or about 60 minutes, greater than or about 90 minutes or greater than or about 120 minutes; or between or between about 5 minutes and 120 minutes, 30 minutes and 90 minutes, 15 minutes and 60 minutes, 15 minutes and 45 minutes, 30 minutes and 60 minutes or 45 minutes and 60 minutes, each inclusive. In some embodiments, the composition is rotated for or for about 60 minutes.

In certain embodiments, cells, e.g., stimulated cells, are cultured during the engineering, e.g., transduction or transfection, at a density of less than at or about $1 \times 10^7$ cells/mL, $9 \times 10^6$ cells/mL, $8 \times 10^6$ cells/mL, $7 \times 10^6$ cells/mL, $6 \times 10^6$ cells/mL, $5 \times 10^6$ cells/mL, $4 \times 10^6$ cells/mL, or $3 \times 10^6$ cells/mL. In some embodiments, the cells are subjected to engineering at a density of between at or about $1 \times 10^3$ cells/mL and at or about $1 \times 10^9$ cells/mL, at or about $1 \times 10^4$ cells/mL and at or about $1 \times 10^8$ cells/mL, at or about $1 \times 10^5$ cells/mL and at or about $1 \times 10^7$ cells/mL, or at or about $5 \times 10^5$ cells/mL and at or about $1 \times 10^7$ cells/mL. In particular embodiments, the cells are subjected to engineering at a density of or of about $5 \times 10^5$ cells/mL, $1 \times 10^6$ cells/mL, $2 \times 10^6$ cells/mL, $3 \times 10^6$ cells/mL, $4 \times 10^6$ cells/mL, or $5 \times 10^6$ cells/mL. In particular embodiments, the cells are subjected to engineering at a density of or of about $1 \times 10^6$ cells/mL. In certain embodiments, the cells are cultured after the rotation, e.g., rotation of the composition containing the cells and the viral particles. In certain embodiments, the cells have been rotated with the viral particles.

In some embodiments, engineering the cells includes a culturing, contacting, or incubation with the vector, e.g., the viral vector of the non-viral vector. In certain embodiments, culturing, contacting, and/or incubating the cells with the vector is performed for, for about, or for at least 4 hours, 6 hours, 8 hours, 12 hours, 16 hours, 18 hours, 24 hours, 30 hours, 36 hours, 40 hours, 48 hours, 54 hours, 60 hours, 72 hours, 1 day, 2 days, 3 days, 4 days, 5 days, 6 days, or 7 days, or more than 7 days. In some embodiments, culturing, contacting, and/or incubating the cells with the vector is performed for an amount of time between 30 minutes and 2 hours, between 1 hour and 8 hours, between 6 hours and 12 hours, between 12 hours and 18 hours, between 16 hours and 24 hours, between 18 hours and 30 hours, between 24 hours and 48 hours, between 24 hours and 72 hours, between 42 hours and 54 hours, between 60 hours and 120 hours between 96 hours and 120 hours, between 90 hours and between 1 days and 7 days, between 3 days and 8 days, between 1 day and 3 days, between 4 days and 6 days, or between 4 days and 5 days prior to the genetic engineering. In some embodiments, the cells are cultured, contacted, and/or incubated with the vector for or for about between 18 hours and 30 hours. In particular embodiments, the cells are cultured, contacted, and/or incubated with the vector for or for about 24 hours.

In some embodiments, during at least a part of the genetic engineering, e.g. transduction, and/or subsequent to the genetic engineering the cells are transferred to the bioreactor bag assembly for culture of the genetically engineered cells, such as for cultivation or expansion of the cells, as described above.

In particular embodiments, the cells are subjected to engineering in the presence of one or more cytokines. In certain embodiments, the one or more cytokines are recombinant cytokines. In particular embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes recombinant IL-2.

In some embodiments, the cells, e.g., the stimulated cells, are subjected to engineering, e.g., transduced or transfected, in the presence of one or more cytokines, e.g., a recombinant human cytokine, at a concentration of between at or about 1 IU/mL and at or about 1,000 IU/mL, between at or about 10 IU/mL and at or about 50 IU/mL, between at or about 50 IU/mL and at or about 100 IU/mL, between at or about 100 IU/mL and at or about 200 IU/mL, between at or about 100 IU/mL and at or about 500 IU/mL, between at or about 250 IU/mL and at or about 500 IU/mL, or between at or about 500 IU/mL and at or about 1,000 IU/mL.

In some embodiments, the cells, e.g., stimulated cells, are subjected to engineering, e.g., transfected or transduced, in the presence of IL-2, e.g., human recombinant IL-2, at a concentration between at or about 1 IU/mL and at or about 500 IU/mL, between at or about 10 IU/mL and at or about 250 IU/mL, between at or about 50 IU/mL and at or about 200 IU/mL, between at or about 50 IU/mL and at or about 150 IU/mL, between at or about 75 IU/mL and at or about 125 IU/mL, between at or about 100 IU/mL and at or about 200 IU/mL, or between at or about 10 IU/mL and at or about 100 IU/mL. In particular embodiments, cells, e.g., stimulated cells and/or cells of the stimulated cell composition, are incubated with recombinant IL-2 at a concentration at or at about 50 IU/mL, 60 IU/mL, 70 IU/mL, 80 IU/mL, 90 IU/mL, 100 IU/mL, 110 IU/mL, 120 IU/mL, 130 IU/mL, 140 IU/mL, 150 IU/mL, 160 IU/mL, 170 IU/mL, 180 IU/mL, 190 IU/mL, or 100 IU/mL. In some embodiments, the cells, e.g., the stimulated cells, are incubated in the presence of or of about 100 IU/mL of recombinant IL-2, e.g., human recombinant IL-2.

In some embodiments, the cells, e.g., stimulated cells, are subjected to engineering, e.g., transfected or transduced, in the presence of IL-7, e.g., human recombinant IL-7, at a concentration between at or about 100 IU/mL and at or about 2,000 IU/mL, between at or about 500 IU/mL and at or about 1,000 IU/mL, between at or about 100 IU/mL and at or about 500 IU/mL, between at or about 500 IU/mL and at or about 750 IU/mL, between at or about 750 IU/mL and at or about 1,000 IU/mL, or between at or about 500 IU/mL and at or about 700 IU/mL. In particular embodiments, the cells, e.g., stimulated cells, are engineered, e.g., transduced or transfected, with IL-7 at a concentration at or at about 50 IU/mL, 100 IU/mL, 150 IU/mL, 200 IU/mL, 250 IU/mL, 300 IU/mL, 350 IU/mL, 400 IU/mL, 450 IU/mL, 500 IU/mL, 550 IU/mL, 600 IU/mL, 650 IU/mL, 700 IU/mL, 750 IU/mL, 800 IU/mL, 750 IU/mL, 750 IU/mL, 750 IU/mL, or 1,000 IU/mL. In particular embodiments, the cells, e.g., stimulated cells, incubated in the presence of or of about 600 IU/mL of IL-7.

In certain embodiments, the cells, e.g., stimulated cells, are subjected to engineering, e.g., transfected or transduced, in the presence of IL-15, e.g., human recombinant IL-15, at a concentration between at or about 1 IU/mL and at or about 500 IU/mL, between at or about 10 IU/mL and at or about 250 IU/mL, between at or about 50 IU/mL and at or about 200 IU/mL, between at or about 50 IU/mL and at or about 150 IU/mL, between at or about 75 IU/mL and at or about 125 IU/mL, between at or about 100 IU/mL and at or about 200 IU/mL, or between at or about 10 IU/mL and at or about 100 IU/mL. In some embodiments, cells, e.g., stimulated cells and/or cells of the stimulated cell composition, are incubated with recombinant IL-15 at a concentration at or at about 50 IU/mL, 60 IU/mL, 70 IU/mL, 80 IU/mL, 90 IU/mL, 100 IU/mL, 110 IU/mL, 120 IU/mL, 130 IU/mL, 140 IU/mL, 150 IU/mL, 160 IU/mL, 170 IU/mL, 180 IU/mL, 190 IU/mL, or 100 IU/mL. In particular embodiments, the cells, e.g., the stimulated cells, are incubated in the presence of or of about 100 IU/mL of recombinant IL-15, e.g., human recombinant IL-15.

In particular embodiments, cells, e.g., stimulated cells are subjected to engineering under stimulating conditions in the presence of IL-2, IL-7, and/or IL-15. In certain embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15. In certain embodiments, the cells are subjected to engineering, e.g., transduced or transfected, under stimulating conditions in the presence of recombinant IL-2, IL-7, and IL-15.

In some embodiments, the provided methods are used in connection with transducing a viral vector containing a polynucleotide encoding a recombinant receptor into less than $300 \times 10^6$ cells, e.g., cells of a stimulated cell composition. In certain embodiments, at or about $100 \times 10^6$ cells, e.g., cells of a stimulated cell composition are transduced. In certain embodiments, the cells are viable cells. In some embodiments, the transduction is performed in serum free media. In some embodiments, the transduction is performed in the presence of IL-2, IL-7, and IL-15. In particular embodiments, the cells, e.g., the cells of the stimulated cell composition contain at least at or about 80%, at least at or about 85%, at least at or about 90%, or at least at or about 95% cells that are CD4+ T cells or CD8+ T cells. In some embodiments, the transduction is performed for between 24 and 48 hours, between 36 and 12 hours, between 18 and 30 hours, or for or for about 24 hours. In certain embodiments, the transduction step is initiated within two days, within 36 hours, or within 30 hours of the start or initiation of the incubation, e.g., the incubation under stimulating conditions.

1. Preparation of Viral Vector Particles for Transduction

The viral vector genome is typically constructed in a plasmid form that can be transfected into a packaging or producer cell line. In any of such examples, the nucleic acid encoding a recombinant protein, such as a recombinant receptor, is inserted or located in a region of the viral vector, such as generally in a non-essential region of the viral genome. In some embodiments, the nucleic acid is inserted into the viral genome in the place of certain viral sequences to produce a virus that is replication defective.

Any of a variety of known methods can be used to produce retroviral particles whose genome contains an RNA copy of the viral vector genome. In some embodiments, at least two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components.

In some embodiments, the packaging plasmid can contain all retroviral, such as HIV-1, proteins other than envelope proteins (Naldini et al., 1998). In other embodiments, viral vectors can lack additional viral genes, such as those that are associated with virulence, e.g. vpr, vif, vpu and nef, and/or Tat, a primary transactivator of HIV. In some embodiments, lentiviral vectors, such as HIV-based lentiviral vectors, comprise only three genes of the parental virus: gag, pol and rev, which reduces or eliminates the possibility of reconstitution of a wild-type virus through recombination.

In some embodiments, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences, e.g., recombinant nucleic acids, of interest. In some aspects, in order to prevent replication of the genome in the target cell, however, endogenous viral genes required for replication are removed and provided separately in the packaging cell line.

In some embodiments, a packaging cell line is transfected with one or more plasmid vectors containing the components necessary to generate the particles. In some embodiments, a packaging cell line is transfected with a plasmid containing the viral vector genome, including the LTRs, the cis-acting packaging sequence and the sequence of interest, i.e. a nucleic acid encoding an antigen receptor, such as a CAR; and one or more helper plasmids encoding the virus enzymatic and/or structural components, such as Gag, pol and/or rev. In some embodiments, multiple vectors are utilized to separate the various genetic components that generate the retroviral vector particles. In some such embodiments, providing separate vectors to the packaging cell reduces the chance of recombination events that might otherwise generate replication competent viruses. In some embodiments, a single plasmid vector having all of the retroviral components can be used.

In some embodiments, the retroviral vector particle, such as lentiviral vector particle, is pseudotyped to increase the transduction efficiency of host cells. For example, a retroviral vector particle, such as a lentiviral vector particle, in some embodiments is pseudotyped with a VSV-G glycoprotein, which provides a broad cell host range extending the cell types that can be transduced. In some embodiments, a packaging cell line is transfected with a plasmid or polynucleotide encoding a non-native envelope glycoprotein, such as to include xenotropic, polytropic or amphotropic envelopes, such as Sindbis virus envelope, GALV or VSV-G.

In some embodiments, the packaging cell line provides the components, including viral regulatory and structural proteins, that are required in trans for the packaging of the viral genomic RNA into lentiviral vector particles. In some embodiments, the packaging cell line may be any cell line that is capable of expressing lentiviral proteins and producing functional lentiviral vector particles. In some aspects, suitable packaging cell lines include 293 (ATCC CCL X), 293T, HeLa (ATCC CCL 2), D17 (ATCC CCL 183), MDCK (ATCC CCL 34), BHK (ATCC CCL-10) and Cf2Th (ATCC CRL 1430) cells.

In some embodiments, the packaging cell line stably expresses the viral protein(s). For example, in some aspects, a packaging cell line containing the gag, pol, rev and/or other structural genes but without the LTR and packaging components can be constructed. In some embodiments, a packaging cell line can be transiently transfected with nucleic acid molecules encoding one or more viral proteins along with the viral vector genome containing a nucleic acid molecule encoding a heterologous protein, and/or a nucleic acid encoding an envelope glycoprotein.

In some embodiments, the viral vectors and the packaging and/or helper plasmids are introduced via transfection or infection into the packaging cell line. The packaging cell line produces viral vector particles that contain the viral vector genome. Methods for transfection or infection are well known. Non-limiting examples include calcium phosphate, DEAE-dextran and lipofection methods, electroporation and microinjection.

When a recombinant plasmid and the retroviral LTR and packaging sequences are introduced into a special cell line (e.g., by calcium phosphate precipitation for example), the packaging sequences may permit the RNA transcript of the recombinant plasmid to be packaged into viral particles, which then may be secreted into the culture media. The media containing the recombinant retroviruses in some embodiments is then collected, optionally concentrated, and used for gene transfer. For example, in some aspects, after cotransfection of the packaging plasmids and the transfer vector to the packaging cell line, the viral vector particles are recovered from the culture media and titered by standard methods used by those of skill in the art.

In some embodiments, a retroviral vector, such as a lentiviral vector, can be produced in a packaging cell line, such as an exemplary HEK 293T cell line, by introduction of plasmids to allow generation of lentiviral particles. In some embodiments, a packaging cell is transfected and/or contains a polynucleotide encoding gag and pol, and a polynucleotide encoding a recombinant receptor, such as an antigen receptor, for example, a CAR. In some embodiments, the packaging cell line is optionally and/or additionally transfected with and/or contains a polynucleotide encoding a rev protein. In some embodiments, the packaging cell line is optionally and/or additionally transfected with and/or contains a polynucleotide encoding a non-native envelope glycoprotein, such as VSV-G. In some such embodiments, approximately two days after transfection of cells, e.g. HEK 293T cells, the cell supernatant contains recombinant lentiviral vectors, which can be recovered and titered.

Recovered and/or produced retroviral vector particles can be used to transduce target cells using the methods as described. Once in the target cells, the viral RNA is reverse-transcribed, imported into the nucleus and stably integrated into the host genome. One or two days after the integration of the viral RNA, the expression of the recombinant protein, e.g. antigen receptor, such as CAR, can be detected.

2. Non-Viral Vectors

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl* Acids 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated micropar-ticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, recombinant nucleic acids are transferred into T cells via transposons. Transposons (trans-posable elements), are mobile segments of DNA that can move from one locus to another within genomes. These elements move via a conservative, "cut-and-paste" mechanism: the transposase catalyzes the excision of the transpo-son from its original location and promotes its reintegration elsewhere in the genome. Transposase-deficient elements can be mobilized if the transposase is provided by another transposase gene. Thus, transposons can be utilized to incor-porate a foreign DNA into a host genome without the use of a viral transduction system. Examples of transposons suit-able for use with mammalian cells, e.g., human primary leukocytes, include but are not limited to Sleeping Beauty and Piggybac.

Transposon-based transfection is a two-component sys-tem consisting of a transposase and a transposon. In some embodiments, the system comprises a transposon is engi-neered to comprise a foreign DNA (also referred herein as cargo DNA), e.g., a gene encoding a recombinant receptor, that is flanked by inverted repeat/direct repeat (IR/DR) sequences that are recognized by an accompanying trans-poses. In some embodiments, a non-viral plasmid encodes a transposase under the control of a promoter. Transfection of the plasmid into a host cell results in a transitory expression of the transposase, thus for an initial period following transfection, the transposase is expressed at sufficiently levels to integrate the transposon into the genomic DNA. In some embodiments, the transposase itself is not integrated into the genomic DNA, and therefor expression of the transposase decreases over time. In some embodiments, the transposase expression is expressed by the host cell at levels sufficient to integrate a corresponding transposon for less than about 4 hours, less than about 8 hours, less than about 12 hours, less than about 24 hours, less than about 2 days, less than about 3 days, less than about 4 days, less than about 5 days, less than about 6 days, less than about 7 days, less than about 2 weeks, less than about 3 weeks, less than about 4 weeks, less than about weeks, or less than about 8 weeks. In some embodiments, the cargo DNA that is introduced into the host's genome is not subsequently removed from the host's genome, at least because the host dose not express an endogenous transposase capable of excising the cargo DNA.

Sleeping Beauty (SB) is a synthetic member of the Tc/1-mariner superfamily of transposons, reconstructed from dormant elements harbored in the salmonid fish genome. SB transposon-based transfection is a two-compo-nent system consisting of a transposase and a transposon containing inverted repeat/direct repeat (IR/DR) sequences that result in precise integration into a TA dinucleotide. The transposon is designed with an expression cassette of inter-est flanked by IR/DRs. The SB transposase binds specific binding sites that are located on the IR of the Sleeping beauty transposon. The SB transposase mediates integration of the transposon, a mobile element encoding a cargo sequence flanked on both sides by inverted terminal repeats that harbor binding sites for the catalytic enzyme (SB). Stable expression results when SB inserts gene sequences into vertebrate chromosomes at a TA target dinucleotide through a cut-and-paste mechanism. This system has been used to engineer a variety of vertebrate cell types, including primary human peripheral blood leukocytes. In some embodiments, the cells are contacted, incubated, and/or treated with an SB transposon comprising a cargo gene, e.g., a gene encoding a recombinant receptor or a CAR, flanked by SB IR sequences. In particular embodiments, the cells to be transfected are contacted, incubated, and/or treated with a plasmid comprising an SB transposon comprising a cargo gene, e.g., a gene encoding a CAR, flanked by SB IR sequences. In certain embodiments, the plasmid further comprises a gene encoding an SB transposase that is not flanked by SB IR sequences.

PiggyBac (PB) is another transposon system that can be used to integrate cargo DNA into a host's, e.g., a human's, genomic DNA. The PB transposase recognizes PB transpo-son-specific inverted terminal repeat sequences (ITRs) located on both ends of the transposon and efficiently moves the contents from the original sites and efficiently integrates them into TTAA chromosomal sites. The PB transposon system enables genes of interest between the two ITRs in the PB vector to be mobilized into target genomes. The PB system has been used to engineer a variety of vertebrate cell types, including primary human cells. In some embodi-ments, the cells to be transfected are contacted, incubated, and/or treated with an PB transposon comprising a cargo gene, e.g., a gene encoding a CAR, flanked by PB IR sequences. In particular embodiments, the cells to be trans-fected are contacted, incubated, and/or treated with a plas-mid comprising a PB transposon comprising a cargo gene, e.g., a gene encoding a CAR, flanked by PB IR sequences. In certain embodiments, the plasmid further comprises a gene encoding an SB transposase that is not flanked by PB IR sequences.

In some embodiments, the various elements of the trans-poson/transposase the employed in the subject methods, e.g., SB or PB vector(s), may be produced by standard methods of restriction enzyme cleavage, ligation and molecular cloning. One protocol for constructing the subject vectors includes the following steps. First, purified nucleic acid fragments containing desired component nucleotide sequences as well as extraneous sequences are cleaved with restriction endonucleases from initial sources, e.g., a vector comprising the transposase gene. Fragments containing the desired nucleotide sequences are then separated from unwanted fragments of different size using conventional separation methods, e.g., by agarose gel electrophoresis. The desired fragments are excised from the gel and ligated together in the appropriate configuration so that a circular nucleic acid or plasmid containing the desired sequences, e.g., sequences corresponding to the various elements of the subject vectors, as described above is produced. Where desired, the circular molecules so constructed are then amplified in a prokaryotic host, e.g., E. coli. The procedures of cleavage, plasmid construction, cell transformation and plasmid production involved in these steps are well known to one skilled in the art and the enzymes required for restriction and ligation are available commercially. (See, for example, R. Wu, Ed., Methods in Enzymology, Vol. 68, Academic Press, N.Y. (1979); T. Maniatis, E. F. Fritsch and J. Sambrook, Molecular Cloning: A Laboratory Manual, Cold Spring Harbor Laboratory Press, Cold Spring Harbor, N.Y. (1982); Catalog 1982-83, New England Biolabs, Inc.; Catalog 1982-83, Bethesda Research Laboratories, Inc. An example of how to construct the vectors employed in the subject methods is provided in the Experimental section, infra. The preparation of a representative Sleeping Beauty transposon system is also disclosed in WO 98/40510 and WO 99/25817).

In some embodiments, transduction with transposons is performed with a plasmid that comprises a transposase gene and a plasmid that comprises a transposon that contains a cargo DNA sequence that is flanked by inverted repeat/direct repeat (IR/DR) sequences that are recognized by the transposase. In certain embodiments, the cargo DNA sequence encodes a heterologous protein, e.g., a recombinant T cell receptor or a CAR. In some embodiments, the plasmid comprises transposase and the transposon. In some embodiments, the transposase is under control of a ubiquitous promoter, or any promoter suitable to drive expression of the transposase in the target cell. Ubiquitous promoters include, but are not limited to, EF1a, CMB, SV40, PGK1, Ubc, human β-actin, CAG, TRE, UAS, Ac5, CaMKIIa, and U6. In some embodiments, the cargo DNA comprises a selection cassette allowing for the selection of cells with stable integration of the cargo DNA into the genomic DNA. Suitable selection cassettes include, but are not limited to, selection cassettes encoding a kanamycin resistance gene, spectinomycin resistance gene, streptomycin resistance gene, ampicillin resistance gene, carbenicillin resistance gene, hygromycin resistance gene, bleomycin resistance gene, erythromycin resistance gene, and polymyxin B resistance gene.

In some embodiments, the components for transduction with a transposon, e.g., plasmids comprising an SB transposase and SB transposon, are introduced into the target cell. Any convenient protocol may be employed, where the protocol may provide for in vitro or in vivo introduction of the system components into the target cell, depending on the location of the target cell. For example, where the target cell is an isolated cell, the system may be introduced directly into the cell under cell culture conditions permissive of viability of the target cell, e.g., by using standard transformation techniques. Such techniques include, but are not necessarily limited to: viral infection, transformation, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

In some embodiments, the SB transposon and the SB transposase source are introduced into a target cell of a multicellular organism, e.g., a mammal or a human, under conditions sufficient for excision of the inverted repeat flanked nucleic acid from the vector carrying the transposon and subsequent integration of the excised nucleic acid into the genome of the target cell. Some embodiments further comprise a step of ensuring that the requisite transposase activity is present in the target cell along with the introduced transposon. Depending on the structure of the transposon vector itself, i.e. whether or not the vector includes a region encoding a product having transposase activity, the method may further include introducing a second vector into the target cell which encodes the requisite transposase activity.

In some embodiments, the amount of vector nucleic acid comprising the transposon and the amount of vector nucleic acid encoding the transposase that is introduced into the cell is sufficient to provide for the desired excision and insertion of the transposon nucleic acid into the target cell genome. As such, the amount of vector nucleic acid introduced should provide for a sufficient amount of transposase activity and a sufficient copy number of the nucleic acid that is desired to be inserted into the target cell. The amount of vector nucleic acid that is introduced into the target cell varies depending on the efficiency of the particular introduction protocol that is employed, e.g., the particular ex vivo administration protocol that is employed.

Once the vector DNA has entered the target cell in combination with the requisite transposase, the nucleic acid region of the vector that is flanked by inverted repeats, i.e. the vector nucleic acid positioned between the Sleeping Beauty transposase recognized inverted repeats, is excised from the vector via the provided transposase and inserted into the genome of the targeted cell. As such, introduction of the vector DNA into the target cell is followed by subsequent transposase mediated excision and insertion of the exogenous nucleic acid carried by the vector into the genome of the targeted cell. In particular embodiments, the vector is integrated into the genomes of at least at or about 1%, at least at or about 2%, at least at or about 3%, at least at or about 4%, at least at or about 5%, at least at or about 6% at least at or about 7% at least at or about 8%, at least at or about 9%, at least at or about 10%, at least at or about 15%, or at least at or about 20% of the cells that are transfected with the SB transposon and/or SB transposase. In some embodiments, integration of the nucleic acid into the target cell genome is stable, i.e., the vector nucleic acid remains present in the target cell genome for more than a transient period of time and is passed on a part of the chromosomal genetic material to the progeny of the target cell.

In certain embodiments, the transposons are used to integrate nucleic acids, i.e. polynucleotides, of various sizes into the target cell genome. In some embodiments, the size of DNA that is inserted into a target cell genome using the subject methods ranges from at or about 0.1 kb to at or about 200 kb, from at or about 0.5 kb to at or about 100 kb, from at or about 1.0 kb to at or about 8.0 kb, from at or about 1.0 to at or about 200 kb, from at or about 1.0 to at or about 10 kb, from at or about 10 kb to at or about 50 kb, from at or about 50 kb to at or about 100 kb, or from at or about 100 kb to at or about 200 kb. In some embodiments, the size of DNA that is inserted into a target cell genome using the subject methods ranges from at or about 1.0 kb to at or about 8.0 kb. In some embodiments, the size of DNA that is inserted into a target cell genome using the subject methods ranges from at or about 1.0 to at or about 200 kb. In particular embodiments, the size of DNA that is inserted into a target cell genome using the subject methods ranges from at or about 1.0 kb to at or about 8.0 kb.

D. Cultivating and/or Expanding the Cells

In some embodiments, the provided methods include one or more steps for cultivating cells, such as by cultivating the cells under conditions that promote proliferation and/or expansion. In some embodiments, cells, e.g., engineered CD4+ and CD8+ T cells, are cultivated under conditions that promote proliferation and/or expansion subsequent to genetically engineering the cells, e.g., introducing a recombinant polypeptide into the cells by transduction or transfection. In particular embodiments, the cells are cultivated after the cells have been incubated under stimulating conditions and/or after the cells have been transduced or transfected with a recombinant polynucleotide, e.g., a polynucleotide encoding the recombinant receptor. In some embodiments, the cultivation produces cultivated cells. In certain embodiments, the cultivation produces a cultivated composition, e.g., a composition of cultivated cells. In some embodiments, the one or more processing steps include a step of stimulating the isolated cells, such as selected cell populations. The incubation may be prior to or in connection with genetic engineering, such as genetic engineering resulting from embodiments of the transduction method described herein, e.g., in Section I-C. In some embodiments, the stimulation results in activation and/or proliferation of the cells, for example, prior to transduction.

In certain embodiments, cells and/or compositions of engineered T cells are cultivated, e.g., under conditions that promote expansion and/or proliferation, prior to collecting and formulating the cells, such as by a method provided herein, e.g., Section I-E. In particular embodiments, the cells are cultivated after the cells have been engineered, transduced, and/or transfected, such as by any of the methods provided herein, e.g., in Section I-C. In particular embodiments, the engineered compositions have been previously cryofrozen and stored, and are thawed prior to the cultivation.

In certain embodiments, a composition of cells is cultivated. In particular embodiments, about or at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% of the cells of the composition are T CD3+ cells. In certain embodiments, about or at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% of the cells of the composition are cells that are CD4+ or CD8+ T cells.

In some embodiments, at least at or about 50%, at least at or about 60%, at least at or about 70%, at least at or about 80%, at least at or about 90%, or at least at or about 95% of the cells that undergo or that have undergone engineering, transfection, and/or transduction are cultivated. In particular embodiments, all or about all of the cells that undergo or that have undergone engineering, transfection, and/or transduction are cultivated.

In some embodiments, the cells, e.g., the engineered cells are cultivated in a volume of media that is, is about, or is at least 100 mL, 200 mL, 300 mL, 400 mL, 500 mL, 600 mL, 700 mL, 800 mL, 900 mL, 1,000 mL, 1,200 mL, 1,400 mL, 1,600 mL, 1,800 mL, 2,000 mL, 2,200 mL, or 2,400 mL. In some embodiments, the cells are cultivated at an initial volume that is later adjusted to a different volume. In particular embodiments, the volume is later adjusted during the cultivation. In particular embodiments, the volume is increased from the initial volume during the cultivation. In certain embodiments, the volume is increased when the cells achieve a density during the cultivation. In certain embodiment, the initial volume is or is about 500 mL.

In particular embodiments, the volume is increased from the initial volume when the cells achieve a density or concentration during the cultivation. In particular embodiments, the volume is increased when the cells achieve a density and/or concentration of, of about, or of at least at or about $0.1 \times 10^6$ cells/mL, $0.2 \times 10^6$ cells/mL, $0.4 \times 10^6$ cells/mL, $0.6 \times 10^6$ cells/mL, $0.8 \times 10^6$ cells/mL, $1 \times 10^6$ cells/mL, $1.2 \times 10^6$ cells/mL, $1.4 \times 10^6$ cells/mL, $1.6 \times 10^6$ cells/mL, $1.8 \times 10^6$ cells/mL, $2.0 \times 10^6$ cells/mL, $2.5 \times 10^6$ cells/mL, $3.0 \times 10^6$ cells/mL, $3.5 \times 10^6$ cells/mL, $4.0 \times 10^6$ cells/mL, $4.5 \times 10^6$ cells/mL, $5.0 \times 10^6$ cells/mL, $6 \times 10^6$ cells/mL, $8 \times 10^6$ cells/mL, or $10 \times 10^6$ cells/mL. In some embodiments, the density and/or concentration is of viable cells in the culture. In some embodiments, the volume is increased from the initial volume when the cells achieve a density and/or concentration of, of at least, or of about $0.6 \times 10^6$ cells/mL.

In some embodiments, the cells achieve a density and/or concentration, and the volume is increased by, by about, or by at least at or about 100 mL, 200 mL, 300 mL, 400 mL, 500 mL, 600 mL, 700 mL, 800 mL, 900 mL, 1,000 mL, 1,200 mL, 1,400 mL, 1,600 mL, 1,800 mL, 2,000 mL, 2,200 mL or 2,400 mL. In some embodiments, the volume is increased by 500 mL. In particular embodiments, the volume is increased to a volume of, of about, or of at least at or about 500 mL, 600 mL, 700 mL, 800 mL, 900 mL, 1,000 mL, 1,200 mL, 1,400 mL, 1,600 mL, 1,800 mL, 2,000 mL, 2,200 mL or 2,400 mL. In certain embodiments, the volume is increased to a volume of 1,000 mL. In certain embodiments, the volume is increase at a rate of, of at least at or about, or of about 5 mL, 10 mL, 20 mL, 25 mL, 30 mL, 40 mL, 50 mL, 60 mL, 70 mL, 75 mL, 80 mL, 90 mL, or 100 mL, every 1, 2, 3, 4, 5, 6, 7, 8, 9, or 10 minutes. In certain embodiments, the rate is or is about 50 mL every 8 minutes.

In some embodiments, the cells, e.g., the engineered cells, are initially cultivated at a volume of 500 mL. In particular embodiments, the volume is increased to 1,000 mL when the cells reach a density or concentration of $0.6 \times 10^6$ cells/mL during the cultivation.

In some embodiments, the cultivation is performed in serum free media. In some embodiments, the serum free media is a defined and/or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

In some embodiments, the provided methods are used in connection with a step for cultivating the cells under conditions that promote expansion and/or proliferation. Such conditions include those designed to induce proliferation, expansion, activation, and/or survival of cells in the population, to mimic antigen exposure, and/or to prime the cells for genetic engineering, such as for the introduction of a recombinant antigen receptor.

In some embodiments, the conditions for cultivation can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulatory reagent is removed and/or separated from the cells subsequent to and/or after the cultivation. In certain embodiments, the stimulatory agent is removed and/or separated from the cells after and/or subsequent to the cultivation and prior to formulating the cells, e.g., formulating an output composition of cultivated output cells. In some embodiments, the stimulatory reagent is a stimulatory reagent that is described herein, e.g., in Section I-B-1. In particular embodiments, the stimulatory reagent is removed and/or separated from the cells as described herein, e.g., in Section I-B-2.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, at least a portion of the cultivation is carried out in the internal cavity of a centrifugal chamber, for example, under centrifugal rotation, such as described in International Publication Number WO2016/073602. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g. is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a centrifugal chamber, e.g. in a tube or bag with periodic shaking or rotation. In some embodiments, the cultivation is performed with the addition of an cultivation buffer to the cells and stimulating agent to achieve a target volume of, for example, 10 mL to 2,000 mL, such as at least or at least about or about or 10 mL, 20 mL, 30 mL, 40 mL, 50 mL, 60 mL, 70 mL, 80 mL, 90 mL, 100 mL, 150 mL, 200 mL, 300 mL, 400 mL, 500 mL, 600 mL, 700 mL, 800 mL, 900 mL, 1,000 mL, 1,200 mL, 1,400 mL, 1,600 mL, 1,800 mL, 2,000 mL, 2,200 mL or 2,400 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from or from about 600 rpm to or to about 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, the total duration of the incubation, e.g. with the stimulating agent, is between or between about 1 hour and 96 hours, 1 hour and 72 hours, 1 hour and 48 hours, 4 hours and 36 hours, 8 hours and 30 hours or 12 hours and 24 hours, such as at least or at least about 6 hours, 12 hours, 18 hours, 24 hours, 36 hours or 72 hours. In some embodiments, the further incubation is for a time between or about between 1 hour and 48 hours, 4 hours and 36 hours, 8 hours and 30 hours or 12 hours and 24 hours, inclusive.

In particular embodiments, a composition of enriched T cells is cultivated in the presence of one or more cytokines. In certain embodiments, the one or more cytokines are recombinant cytokines. In particular embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes recombinant IL-2.

In some embodiments, the cells, e.g., engineered cells, are cultivated in the presence of a cytokine, e.g., a recombinant human cytokine, at a concentration of between at or about 1 IU/mL and at or about 2,000 IU/mL, between at or about 10 IU/mL and at or about 100 IU/mL, between at or about 50 IU/mL and at or about 200 IU/mL, between at or about 100 IU/mL and at or about 500 IU/mL, between at or about 100 IU/mL and at or about 1,000 IU/mL, between at or about 500 IU/mL and at or about 2,000 IU/mL, or between at or about 100 IU/mL and at or about 1,500 IU/mL.

In some embodiments, the cells, e.g., the engineered cells, are cultivated with IL-2, e.g., human recombinant IL-2, at a concentration between at or about 1 IU/mL and at or about 500 IU/mL, between at or about 10 IU/mL and at or about 400 IU/mL, between at or about 100 IU/mL and at or about 300 IU/mL, between at or about 100 IU/mL and at or about 250 IU/mL, between at or about 150 IU/mL and at or about 300 IU/mL, between at or about 200 IU/mL and at or about 400 IU/mL, or between at or about 150 IU/mL and at or about 300 IU/mL, e.g., in a serum-free medium. In particular embodiments, cells, e.g., cells of the input composition, are incubated with recombinant IL-2 at a concentration at, at about, or at least at or about 100 IU/mL, 120 IU/mL, 140 IU/mL, 160 IU/mL, 180 IU/mL, 200 IU/mL, 220 IU/mL, 240 IU/mL, 260 IU/mL, 280 IU/mL, 300 IU/mL, 320 IU/mL, 340 IU/mL, 360 IU/mL, 380 IU/mL, or 400 IU/mL. In some embodiments, the cells, e.g., the input cells, are cultivated in the presence of or of about 200 IU/mL of recombinant IL-2, e.g., human recombinant IL-2.

In some embodiments, the cells, e.g., the engineered cells, are cultivated with recombinant IL-7, e.g., human recombinant IL-7, at a concentration between at or about 100 IU/mL and at or about 2,000 IU/mL, between at or about 500 IU/mL and at or about 1,500 IU/mL, between at or about 600 IU/mL and at or about 1200 IU/mL, between at or about 800 IU/mL and at or about 1600 IU/mL, between at or about 900 IU/mL and at or about 1,800 IU/mL, or between at or about 1,000 IU/mL and at or about 1,500 IU/mL, e.g., in a serum-free medium. In particular embodiments, the cells, e.g., the engineered cells, are incubated with IL-7 at a concentration at, at least at or about, or at about 200 IU/mL, 300 IU/mL, 400 IU/mL, 500 IU/mL, 600 IU/mL, 700 IU/mL, 800 IU/mL, 900 IU/mL, 1,000 IU/mL, 1,200 IU/mL, 1,400 IU/mL, 1,600 IU/mL, 1,800 IU/mL, 2,000 IU/mL, 2,200 IU/mL, or 2,400 IU/mL. In particular embodiments, the cells, e.g., the engineered cells, are cultivated in the presence of or of about 1,200 IU/mL of IL-7.

In some embodiments, the cells, e.g., the engineered cells, are cultivated with IL-15, e.g., human recombinant IL-15, at a concentration between at or about 1 IU/mL and at or about 500 IU/mL, between at or about 10 IU/mL and at or about 400 IU/mL, between at or about 100 IU/mL and at or about 300 IU/mL, between at or about 100 IU/mL and at or about 250 IU/mL, between at or about 150 IU/mL and at or about 300 IU/mL, between at or about 200 IU/mL and at or about 400 IU/mL, or between at or about 150 IU/mL and at or about 150 IU/mL, e.g., in a serum-free medium. In particular embodiments, cells, e.g., cells of the engineered composition, are incubated with recombinant IL-15 at a concentration at, at about, or at least at or about 100 IU/mL, 120 IU/mL, 140 IU/mL, 160 IU/mL, 180 IU/mL, 200 IU/mL, 220 IU/mL, 240 IU/mL, 260 IU/mL, 280 IU/mL, 300 IU/mL, 320 IU/mL, 340 IU/mL, 360 IU/mL, 380 IU/mL, or 400 IU/mL. In some embodiments, the cells, e.g., the engineered T cells, are cultivated in the presence of or of about 200 IU/mL of recombinant IL-15, e.g., human recombinant IL-15.

In particular embodiments, the cells, e.g., engineered cells and/or cells from the engineered composition, are cultivated in the presence of IL-2, IL-7, and/or IL-15, e.g., in a serum-free medium. In some embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15. In certain embodiments, the cells are cultivated in the presence of recombinant IL-2, IL-7, and IL-15.

In particular embodiments, the cultivation is performed in a closed system. In certain embodiments, the cultivation is performed in a closed system under sterile conditions. In particular embodiments, the cultivation is performed in the same closed system as one or more steps of the provided systems. In some embodiments the composition of enriched T cells is removed from a closed system and placed in and/or connected to a bioreactor for the cultivation. Examples of suitable bioreactors for the cultivation include, but are not limited to, GE Xuri W25, GE Xuri W5, Sartorius BioSTAT RM 20|50, Finesse SmartRocker Bioreactor Systems, and Pall XRS Bioreactor Systems. In some embodiments, the bioreactor is used to perfuse and/or mix the cells during at least a portion of the cultivation step.

In some embodiments, cells cultivated while enclosed, connected, and/or under control of a bioreactor undergo expansion during the cultivation more rapidly than cells that are cultivated without a bioreactor, e.g., cells that are cultivated under static conditions such as without mixing, rocking, motion, and/or perfusion. In some embodiments, cells cultivated while enclosed, connected, and/or under control of a bioreactor reach or achieve a threshold expansion, cell count, concentration and/or density within 21 days, 14 days, 10 days, 8 days, 7 days, 6 days, 5 days, 4 days, 3 days, 2 days, 60 hours, 48 hours, 36 hours, 24 hours, or 12 hours. In some embodiments, cells cultivated while enclosed, connected, and/or under control of a bioreactor reach or achieve a threshold expansion, concentration, cell count, and/or density at least at or about 50%, at least at or about 60%, at least at or about 70%, at least at or about 80%, at least at or about 90%, at least at or about 95%, at least at or about 100%, at least at or about 150%, at least at or about 1-fold, at least at or about 2-fold, at least at or about 3-fold, at least at or about 4-fold, at least at or about 5-fold than cells cultivated in an exemplary and/or alternative process where cells are not cultivated while enclosed, connected, and/or under control of a bioreactor.

In some embodiments, the mixing is or includes rocking and/or motioning. In some cases, the bioreactor can be subject to motioning or rocking, which, in some aspects, can increase oxygen transfer. Motioning the bioreactor may include, but is not limited to rotating along a horizontal axis, rotating along a vertical axis, a rocking motion along a tilted or inclined horizontal axis of the bioreactor or any combination thereof. In some embodiments, at least a portion of the incubation is carried out with rocking. The rocking speed and rocking angle may be adjusted to achieve a desired agitation. In some embodiments the rock angle is 20°, 19°, 18°, 17°, 16°, 15°, 14°, 13°, 12°, 11°, 10°, 9°, 8°, 7°, 6°, 5°, 4°, 3°, 2° or 1°. In certain embodiments, the rock angle is between 6-16°. In other embodiments, the rock angle is between 7-16°. In other embodiments, the rock angle is between 8-12°. In some embodiments, the rock rate is 1, 2, 3, 4, 5, 6, 7, 8, 9, 10, 11, 1 12, 13, 14 15, 16, 17, 18, 19, 20, 21, 22, 23, 24, 25, 26, 27, 28, 29, 30, 31, 32, 33, 34, 35, 36, 37, 38, 39, 40 rpm. In some embodiments, the rock rate is between 4 and 12 rpm, such as between 4 and 6 rpm, inclusive.

In some embodiments, the bioreactor maintains the temperature at or near 37° C. and CO2 levels at or near 5% with a steady air flow at, at about, or at least at or about 0.01 L/min, 0.05 L/min, 0.1 L/min, 0.2 L/min, 0.3 L/min, 0.4 L/min, 0.5 L/min, 1.0 L/min, 1.5 L/min, or 2.0 L/min or greater than 2.0 L/min. In certain embodiments, at least a portion of the cultivation is performed with perfusion, such as with a rate of 750 mL/day and/or 1500 mL/day, e.g., depending on the timing in relation to the start of the cultivation and/or density of the cultivated cells. In some embodiments, At least a portion of the cell culture expansion is performed with a rocking motion, such as at an angle of between 5° and 10°, such as 6°, at a constant rocking speed, such as a speed of between 5 and 15 RPM, such as 6 RMP or 10 RPM.

In some embodiments, the at least a portion of the cultivation step is performed under constant perfusion, e.g., a perfusion at a slow steady rate. In some embodiments, the perfusion is or include an outflow of liquid e.g., used media, and an inflow of fresh media. In certain embodiments, the perfusion replaces used media with fresh media. In some embodiments, at least a portion of the cultivation is performed under perfusion at a steady rate of or of about or of at least at or about 100 mL/day, 200 mL/day, 250 mL/day, 275 mL/day, 290 mL/day, 300 mL/day, 350 mL/day, 400 mL/day, 450 mL/day, 500 mL/day, 550 mL/day, 575 mL/day, 580 mL/day, 600 mL/day, 650 mL/day, 700 mL/day, 750 mL/day, 800 mL/day, 850 mL/day, 900 mL/day, 950 mL/day, 1000 mL/day, 1100 mL/day, 1160 mL/day, 1200 mL/day, 1400 mL/day, 1500 mL day, 1600 mL/day, 1800 mL/day, 2000 mL/day, 2200 mL/day, or 2400 mL/day.

In particular embodiments, cultivation is started under conditions with no perfusion, and perfusion started after a set and/or predetermined amount of time, such as or as about or at least 12 hours, 24 hours, 36 hours, 48 hours, 60 hours, 72 hours, or more than 72 hours after the start or initiation of the cultivation. In particular embodiments, perfusion is started when the density or concentration of the cells reaches a set or predetermined density or concentration. In some embodiments, the perfusion is started when the cultivated cells reach a density or concentration of, of about, or at least at or about $0.1 \times 10^6$ cells/mL, $0.2 \times 10^6$ cells/mL, $0.4 \times 10^6$ cells/mL, $0.6 \times 10^6$ cells/mL, $0.8 \times 10^6$ cells/mL, $1 \times 10^6$ cells/mL, $1.2 \times 10^6$ cells/mL, $1.4 \times 10^6$ cells/mL, $1.6 \times 10^6$ cells/mL, $1.8 \times 10^6$ cells/mL, $2.0 \times 10^6$ cells/mL, $2.5 \times 10^6$ cells/mL, $3.0 \times 10^6$ cells/mL, $3.5 \times 10^6$ cells/mL, $4.0 \times 10^6$ cells/mL, $4.5 \times 10^6$ cells/mL, $5.0 \times 10^6$ cells/mL, $6 \times 10^6$ cells/mL, $8 \times 10^6$ cells/mL, or $10 \times 10^6$ cells/mL, or viable cells thereof.

In particular embodiments, the perfusion is performed at different speeds during the cultivation. For example, in some embodiments, when the rate of the perfusion depends on the density and/or concentration of the cultivated cells. In certain embodiments, the rate of perfusion is increased when the cells reach a set or predetermined density or concentration. The perfusion rate may change, e.g., change from one steady perfusion rate to an increased steady perfusion rate, once, twice, three times, four times, five times, more than five times, more than ten times, more than 15 times, more than 20 times, more than 25 times, more than 50 times, or more than 100 times during the cultivation. In some embodiments, the steady perfusion rate increases when the cells reach a set or predetermined cell density or concentration of, of about, or at least at or about $0.6 \times 10^6$ cells/mL, $0.8 \times 10^6$ cells/mL, $1 \times 10^6$ cells/mL, $1.2 \times 10^6$ cells/mL, $1.4 \times 10^6$ cells/mL, $1.6 \times 10^6$ cells/mL, $1.8 \times 10^6$ cells/mL, $2.0 \times 10^6$ cells/mL, $2.5 \times 10^6$ cells/mL, $3.0 \times 10^6$ cells/mL, $3.5 \times 10^6$ cells/mL, $4.0 \times 10^6$ cells/mL, $4.5 \times 10^6$ cells/mL, $5.0 \times 10^6$ cells/mL, $6 \times 10^6$ cells/mL, $8 \times 10^6$ cells/mL, or $10 \times 10^6$ cells/mL, or viable cells thereof.

In some embodiments, cultivation is started under conditions with no perfusion, and, perfusion is started when the density or concentration of the cells reaches a set or predetermined density or concentration. In some embodiments, the perfusion is started at a rate of, of about, or of at least at or about 100 mL/day, 200 mL/day, 250 mL/day, 275 mL/day, 290 mL/day, 300 mL/day, 350 mL/day, 400 mL/day, 450 mL/day, 500 mL/day, 550 mL/day, 575 mL/day, 580 mL/day, 600 mL/day, 650 mL/day, 700 mL/day, 750 mL/day, 800 mL/day, 850 mL/day, 900 mL/day, 950 mL/day, 1000 mL/day, 1100 mL/day, 1160 mL/day, 1200 mL/day, 1400 mL/day, 1600 mL/day, 1800 mL/day, 2000 mL/day, 2200 mL/day, or 2400 mL/day when the density or concentration of the cells reaches a set or predetermined density or concentration. In some embodiments, the perfusion is started when the cultivated cells reach a density or concentration of, of about, or at least at or about $0.1 \times 10^6$ cells/mL, $0.2 \times 10^6$ cells/mL, $0.4 \times 10^6$ cells/mL, $0.6 \times 10^6$ cells/mL, $0.8 \times 10^6$ cells/mL, $1 \times 10^6$ cells/mL, $1.2 \times 10^6$ cells/mL, $1.4 \times 10^6$ cells/mL, $1.6 \times 10^6$ cells/mL, $1.8 \times 10^6$ cells/mL, $2.0 \times 10^6$ cells/mL, $2.5 \times 10^6$ cells/mL, $3.0 \times 10^6$ cells/mL, $3.5 \times 10^6$ cells/mL, $4.0 \times 10^6$ cells/mL, $4.5 \times 10^6$ cells/mL, $5.0 \times 10^6$ cells/mL, $6 \times 10^6$ cells/mL, $8 \times 10^6$ cells/mL, or $10 \times 10^6$ cells/mL, or viable cells thereof. In some embodiments, the perfusion is performed when the cells are cultivated in a volume of, of about, or at least at or about 300 mL, 400 mL, 500 mL, 600 mL, 700 mL, 800 mL, 900 mL, or 1000 mL. In some embodiments, the volume is 1000 mL.

In certain embodiments, at least part of the cultivation is performed with perfusion at a certain rate, and the perfusion rate is increased to, to about, or to at least at or about 100 ml/day, 200 mL/day, 250 mL/day, 275 mL/day, 290 mL/day, 300 mL/day, 350 mL/day, 400 mL/day, 450 mL/day, 500 mL/day, 550 mL/day, 575 mL/day, 580 mL/day, 600 mL/day, 650 mL/day, 700 mL/day, 750 mL/day, 800 mL/day, 850 mL/day, 900 mL/day, 950 mL/day, 1000 mL/day, 1100 mL/day, 1160 mL/day, 1200 mL/day, 1400 mL/day, 1600 mL/day, 1800 mL/day, 2000 mL/day, 2200 mL/day, or 2400 mL/day when the density or concentration of the cells reaches a set or predetermined density or concentration. In some embodiments, the perfusion is started when the cultivated cells reach a density or concentration of, of about, or at least at or about $0.1 \times 10^6$ cells/mL, $0.2 \times 10^6$ cells/mL, $0.4 \times 10^6$ cells/mL, $0.6 \times 10^6$ cells/mL, $0.8 \times 10^6$ cells/mL, $1 \times 10^6$ cells/mL, $1.2 \times 10^6$ cells/mL, $1.4 \times 10^6$ cells/mL, $1.6 \times 10^6$ cells/mL, $1.8 \times 10^6$ cells/mL, $2.0 \times 10^6$ cells/mL, $2.5 \times 10^6$ cells/mL, $3.0 \times 10^6$ cells/mL, $3.5 \times 10^6$ cells/mL, $4.0 \times 10^6$ cells/mL, $4.5 \times 10^6$ cells/mL, $5.0 \times 10^6$ cells/mL, $6 \times 10^6$ cells/mL, $8 \times 10^6$ cells/mL, or $10 \times 10^6$ cells/mL, or viable cells thereof.

In some embodiments, In certain embodiments, cultivation is started under conditions with either no perfusion or perfusion at a certain rate, and the perfusion rate is increased to, to about, or to at 750 mL/day when the density or concentration of the cells reaches a concentration of, of about, or of at least $0.61 \times 10^6$ cells/mL. In certain embodiments, the cells are perfused at a rate of, of about, or at least 750 mL/day when the density or concentration of the cells reaches a concentration of, of about, or of at least $0.61 \times 10^6$ cells/mL when the cells are cultivated at a volume of, of about, or at least 1000 mL. In some embodiments, the perfusion rate is increased to, to about, or to at 1500 mL/day when the density or concentration of the cells reaches a concentration of, of about, or of at least $2 \times 10^6$ cells/mL.

In some aspects, cultivation with perfusion, such as at a high rate of perfusion, e.g., at, at about, or at least at or about 500 mL/day, 600 mL/day, 700 mL/day, 750 mL/day, 800 mL/day, 900 mL/day, 1000 mL/day, 1100 mL/day, 1200 mL/day, 1300 mL/day, 1400 mL/day, 1500 mL/day, 1600 mL/day, 1700 mL/day, 1800 mL/day, 1900 mL/day, or 2000 mL/day improves cell health, viability, survival, proliferation, expansion, and/or function, such as by increasing and/or optimizing nutrient availability to the cells, maintaining pH, and/or minimizing the presence of cellular waste.

In some aspects, cultivation with perfusion may improve the removal and/or reduction of residual process reagents. In certain embodiments, residual process reagents might interfere with and/or complicate the interpretation of assays, measurements, and/or tests that are performed during or after the process. Such assays may include, but are not limited to, measurements for sterility, endotoxins, residual beads, viral DNA, e.g., replication competent viral DNA, cell counts, viability assays, cell health assays, and cell activity assays. In some embodiments, higher rates of perfusion clear more residual process reagents than lower rates of perfusion.

In some embodiments, a composition of enriched cells is cultivated in the presence of a surfactant. In particular embodiments, cultivating the cells of the composition reduces the amount of shear stress that may occur during the cultivation, e.g., due to mixing, rocking, motion, and/or perfusion. In some embodiments, a surfactant is or includes an agent that reduces the surface tension of liquids and/or solids. For example, a surfactant includes a fatty alcohol (e.g., steryl alcohol), a polyoxyethylene glycol octylphenol ether (e.g., Triton X-100), or a polyoxyethylene glycol sorbitan alkyl ester (e.g., polysorbate 20, 40, 60). In some embodiments, the surfactant is or includes an anionic surfactant, a cationic surfactant, a zwitterionic surfactant, or a nonionic surfactant added thereto. In certain embodiments the surfactant is selected from the group consisting of Polysorbate 80 (PS80), polysorbate 20 (PS20), poloxamer 188 (P188). In certain embodiments, the surfactant is poloxamer, e.g., poloxamer 188.

In certain embodiments, the cultivation is performed in the absence of a surfactant.

In particular embodiments, the cultivation ends when cells achieve a threshold amount, concentration, and/or expansion. In some embodiments, the cultivation ends when the cells achieve a threshold total amount of cells, e.g., threshold cell count. In some embodiments, the threshold cell count is or is about or is at least at or about $50\times10^6$ cells, $100\times10^6$ cells, $200\times10^6$ cells, $300\times10^6$ cells, $400\times10^6$ cells, $600\times10^6$ cells, $800\times10^6$ cells, $1000\times10^6$ cells, $1200\times10^6$ cells, $1400\times10^6$ cells, $1600\times10^6$ cells, $1800\times10^6$ cells, $2000\times10^6$ cells, $2500\times10^6$ cells, $3000\times10^6$ cells, $3500\times10^6$ cells, $5000\times10^6$ cells, $3500\times10^6$ cells, $10,000\times10^6$ cells, $12,000\times10^6$ cells, $15,000\times10^6$ cells or $20,000\times10^6$ cells, or viable cells thereof. In some embodiments, the threshold cell count is or is about or is at least of $3500\times10^6$ cells or $5500\times10^6$ cells. In some embodiments, the threshold cell count is or is about or is less than about $5500\times10^6$ cells. In some embodiments, the threshold cell count is or is about or is less than about $3500\times10^6$ cells. In some embodiments, the threshold cell count is or is about or is less than about $3000\times10^6$ cells. In some embodiments, the threshold cell count is or is about or is at least of $2500\times10^6$ cells. In some embodiments, the threshold cell count is or is about or is at least of $2000\times10^6$ cells. In some embodiments, the threshold cell count is or is about or is at least of $3000\times10^6$ cells. In some embodiments, the threshold cell count is between at or about $3000\times10^6$ cells and about at or $2000\times10^6$ cells. In particular embodiments, the cultivation ends when the cells achieve a threshold cell count. In some embodiments, the cultivation ends at, at about, or within at or about 6 hours, 12 hours, 24 hours, 36 hours, 1 day, 2 days, 3 days, 4 days, 5 days, 6 days, or 7 or more days, after the threshold cell count is achieved. In particular embodiments, the cultivation ends at or at about 1 day after the threshold cell count is achieved. In certain embodiments, the cultivation ends between 18 and 30 hours after the threshold cell count is active.

In particular embodiments, the cultivation ends when cells achieve a threshold cell density or concentration. In some embodiments, the threshold cell density or concentration for an output composition is or is about or is at least at or about $1\times10^6$ cells/mL, $5\times10^6$ cells/mL, $10\times10^6$ cells/mL, $15\times10^6$ cells/mL, $20\times10^6$ cells/mL, $25\times10^6$ cells/mL, $30\times10^6$ cells/mL, $35\times10^6$ cells/mL, $40\times10^6$ cells/mL, $45\times10^6$ cells/mL, $50\times10^6$ cells/mL, $55\times10^6$ cells/mL, $60\times10^6$ cells/mL, $65\times10^6$ cells/mL, $70\times10^6$ cells/mL, $75\times10^6$ cells/mL, $80\times10^6$ cells/mL, $85\times10^6$ cells/mL, $90\times10^6$ cells/mL, $95\times10^6$ cells/mL, $100\times10^6$ cells/mL, or viable cells thereof. In some embodiments, the mean or median threshold cell density or concentration for a plurality of output compositions is or is about or is at least at or about $1\times10^6$ cells/mL, $5\times10^6$ cells/mL, $10\times10^6$ cells/mL, $15\times10^6$ cells/mL, $20\times10^6$ cells/mL, $25\times10^6$ cells/mL, $30\times10^6$ cells/mL, $35\times10^6$ cells/mL, $40\times10^6$ cells/mL, $45\times10^6$ cells/mL, $50\times10^6$ cells/mL, $55\times10^6$ cells/mL, $60\times10^6$ cells/mL, $65\times10^6$ cells/mL, $70\times10^6$ cells/mL, $75\times10^6$ cells/mL, $80\times10^6$ cells/mL, $85\times10^6$ cells/mL, $90\times10^6$ cells/mL, $95\times10^6$ cells/mL, $100\times10^6$ cells/mL, or viable cells thereof.

In particular embodiments, about a day or about 24 hours before the cells achieve the threshold amount, concentration, and/or expansion (e.g., before the cells achieve a threshold total amount of cells, e.g., threshold cell count), the total amount of cells is or is about or is at least at or about $50\times10^6$ cells, $100\times10^6$ cells, $200\times10^6$ cells, $300\times10^6$ cells, $400\times10^6$ cells, $600\times10^6$ cells, $800\times10^6$ cells, $1000\times10^6$ cells, $1200\times10^6$ cells, $1400\times10^6$ cells, $1600\times10^6$ cells, $1800\times10^6$ cells, $2000\times10^6$ cells, $2500\times10^6$ cells, $3000\times10^6$ cells, $3500\times10^6$ cells, $5000\times10^6$ cells, $3500\times10^6$ cells, $10,000\times10^6$ cells, $12,000\times10^6$ cells, $15,000\times10^6$ cells or $20,000\times10^6$ cells, or viable cells thereof. In some embodiments, about a day or about 24 hours before the cells achieve the threshold cell count, the total amount of cells is between at or about $100\times10^6$ cells and at or about $4000\times10^6$ cells. In some embodiments, at or about a day or at or about 24 hours before the cells achieve the threshold cell count, the total amount of cells is less than at or about $3000\times10^6$ cells. In some embodiments, at or about a day or at or about 24 hours before the cells achieve the threshold cell count, the total amount of cells is between at or about $500\times10^6$ cells and at or about $1500\times10^6$ cells. In some embodiments, at or about a day or at or about 24 hours before the cells achieve the threshold cell count, the total amount of cells is between at or about $500\times10^6$ cells and at or about $1000\times10^6$ cells. In some embodiments, at or about a day or at or about 24 hours before the cells achieve the threshold cell count, the total amount of cells is at or about or is at least of $900\times10^6$ cells.

In particular embodiments, the threshold cell count is or is about or is at least at or about $1000\times10^6$ cells, $1200\times10^6$ cells, $1400\times10^6$ cells, $1600\times10^6$ cells, $1800\times10^6$ cells, $2000\times10^6$ cells, $2500\times10^6$ cells, $3000\times10^6$ cells, $3500\times10^6$ cells, or viable cells thereof, while about a day or about 24 hours before the cells achieve the threshold cell count, the total amount of cells is or is about or is at least of $100\times10^6$ cells, $200\times10^6$ cells, $300\times10^6$ cells, $400\times10^6$ cells, $600\times10^6$ cells, $800\times10^6$ cells, $1000\times10^6$ cells, $1200\times10^6$ cells, $1400\times10^6$ cells, or $1600\times10^6$ cells, or viable cells thereof. In some embodiments, the threshold cell count is between at or about $2000\times10^6$ cells and at or about $3000\times10^6$ cells, or viable cells thereof, while at or about a day or at or about 24 hours before the cells achieve the threshold cell count, the total amount of cells is between at or about $500\times10^6$ cells and at or about $1500\times10^6$ cells, or viable cells thereof. In some embodiments, the threshold cell count is of or about $2500\times10^6$ cells, or viable cells thereof, while about a day or about 24 hours before the cells achieve the threshold cell count, the total amount of cells is of or about 900×10⁶ cells, or viable cells thereof.

In some embodiments, the cultivation is step is performed for the amount of time required for the cells to achieve a threshold amount, density, and/or expansion. In some embodiments, the cultivation is performed for or for about, or for less than at or about, 6 hours, 12 hours, 18 hours, 24 hours, 36 hours, 48 hours, 60 hours, 72 hours, 2 days, 3 days 4 days, 5 days, 5.5 days, 6 days, 7 days, 7.5 days, 8 days, 9 days, 10 days, 1 week, 2 weeks, 3 weeks, or 4 weeks. In particular embodiments, the mean amount of time required for the cells of a plurality of separate compositions of enriched T cells that were isolated, enriched, and/or selected from different biological samples to achieve the threshold density is, is about, or is less than at or about 6 hours, 12 hours, 18 hours, 24 hours, 36 hours, 48 hours, 60 hours, 72 hours, 2 days, 3 days 4 days, 5 days, 6 days, 7 days, 7 days, 8 days, 9 days, 10 days, 1 week, 2 weeks, 3 weeks, or 4 weeks. In certain embodiments, the mean amount of time required for the cells of a plurality of separate compositions of enriched T cells that were isolated, enriched, and/or selected from different biological samples to achieve the threshold density is, is about, or is less than at or about 6 hours, 12 hours, 18 hours, 24 hours, 36 hours, 48 hours, 60 hours, 72 hours, 2 days, 3 days 4 days, 5 days, 6 days, 7 days, 7 days, 8 days, 9 days, 10 days, 1 week, 2 weeks, 3 weeks, or 4 weeks.

In some embodiments, the cultivation ends when the cells achieve a threshold total amount of cells, e.g., threshold cell count, of about 5500×10⁶ cells, and the amount of time required for the cells to achieve the threshold amount from the start of the cultivation is between about 6 days and about 7 days or between 6 days and 7 days.

In some embodiments, the cultivation ends (e.g., when the cells are ready for harvest) when the cells achieve a threshold total amount of cells, e.g., threshold cell count, of at or about 5500×10⁶ cells. In some embodiments, at or about a day or at or about 24 hours before the cells achieve the threshold amount of cells, e.g., threshold cell count, the total amount of cells is at or about 3000×10⁶ cells. In some embodiments, the total amount of cells is at or about 3000×10⁶ cells the day before the cells achieve the threshold cell count of at or about 5500×10⁶ cells. In some embodiments, the amount of time required for the cells to achieve the threshold amount from the start of the cultivation is between at or about 6 days and at or about 10 days or between 6 days and 10 days, such as between at or about 7 days and at or about 10 days or between 7 days and 10 days. In some embodiments, the median of the amount of time required for the cells to achieve the threshold amount from the start of the cultivation is at or about 8 days or is 8 days.

In some embodiments, the cultivation ends when the cells achieve a threshold total amount of cells, e.g., threshold cell count, of at or about 2000×10⁶ cells, at or about 2500×10⁶ cells, or at or about 3000×10⁶ cells, and the amount of time required for the cells to achieve the threshold amount from the start of the cultivation is between at or about 4 days and at or about 5 days, at or about 5 days, or 5 days. In some embodiments, the threshold cell count is between at or about 3000×10⁶ cells and at or about 2000×10⁶ cells and the amount of time required for the cells to achieve the threshold amount from the start of the cultivation is between at or about 4 days and at or about 5 days, at or about 5 days, or 5 days.

In some embodiments, the cultivation ends (e.g., when the cells are ready for harvest) when the cells achieve a threshold total amount of cells, e.g., threshold cell count, of at or about 2500×10⁶ cells. In some embodiments, at or about a day or at or about 24 hours before the cells achieve the threshold amount of cells, e.g., threshold cell count, the total amount of cells is at or about 900×10⁶ cells. In some embodiments, the total amount of cells is at or about 900×10⁶ cells the day before the cells achieve the threshold cell count of at or about 2500×10⁶ cells. In some embodiments, the amount of time required for the cells to achieve the threshold amount from the start of the cultivation is between at or about 6 days and at or about 9 days or between 6 days and 9 days. In some embodiments, the amount of time required for the cells to achieve the threshold amount from the start of the cultivation is between at or about 5 days and at or about 9 days or between 5 days and 9 days. In some embodiments, the median of the amount of time required for the cells to achieve the threshold amount from the start of the cultivation is at or about 7 days or is 7 days.

In some embodiments, the cultivation is performed for at least a minimum amount of time. In some embodiments, the cultivation is performed for at least 14 days, at least 12 days, at least 10 days, at least 7 days, at least 6 days, at least 5 days, at least 4 days, at least 3 days, at least 2 days, at least 36 hours, at least 24 hours, at least 12 hours, or at least 6 hours, even if the threshold is achieved prior to the minimum amount of time. In some embodiments, the minimum amount of time is, is about, or is at least 7 days, 8 days, 9 days, or 10 days. In certain embodiments, the minimum amount of time is 8 days.

In certain embodiments, the cultivation is performed for at least a minimum amount of time. In certain embodiments, the cultivation is performed until, until about, or until at least 8 days, 9 days, 10 days, 11 days, 12 days, or 13 days have passed from the start or initiation of the incubation under stimulatory reagents, e.g., from when the cells are contacted with the stimulatory reagent; from when the cells and/or compositions of cells, e.g., CD4+ and CD8+ cells, are mixed to generate the input composition.

In certain embodiments, the cultivated cells are output cells. In some embodiments, a composition of enriched T cells that has been cultivated is an output composition of enriched T cells. In particular embodiments, CD4+ T cells and/or CD8+ T cells that have been cultivated are output CD4+ and/or CD8+ T cells.

In certain embodiments, the cells are harvested prior to, prior to about, or prior to at least one, two, three, four, five, six, eight, ten, twenty, or more cell doublings of the cell population, e.g., doublings that occur during the cultivation or expansion. In particular embodiments, the amount of cell doublings may be calculated by measuring the number of viable cells in a population at different time points, such as at different times or stages of the cultivation or expansion process. In particular embodiment, the cell doubling can be calculated by comparing the total amount of viable cells at one time point to the total number of viable cells present at an earlier time point. In certain embodiments, the cultivation or expansion is completed prior to, to about, or to at least one, two, three, four, five, six, eight, ten, twenty, or more cell doublings of the cell population, e.g., doublings that occur during the cultivation or expansion. In certain aspects, the cell doubling is calculated by determining the total nucleated cell number (TNC) when the cultivation or expansion is initiated and when the cultivation or expansion completed, and then determining the natural log of the product of the TNC at the completion divided by the TNC at the initiation, and then dividing said natural log of the product by the natural log of 2.

In various embodiments, the cells are collected or harvested at a time before the cells of the input population have doubled more than three, two, or one time(s). In some aspects, reducing the doubling that may occur during a cultivation or expansion process will, in some embodiments, increase the portion of engineered T cells that are naïve-like and/or of a memory phenotype, such as a central memory phenotype. In some embodiments, increasing the doubling during a cultivation or expansion process increases T cell differentiation that may occur during the cultivation or expansion process. In some aspects, it is contemplated that, for a process for generating or producing engineered cell compositions, reducing the expansion or cell doublings that occur during the process, e.g., during the cultivation or expansion, increase the amount or portion of naïve-like T cells and/or T cells of a memory phenotype, such as a central memory phenotype, of the resulting engineered cell composition. In particular aspects, increasing the expansion or cell doublings that occur during the process increase the amount or portion of differentiated T cells of the resulting engineered cell composition. In some aspects, it is contemplated that process, such as the processes provided herein, that increase or enlarge the portion of naïve-like cells and/or T cells of a memory phenotype, such as a central memory phenotype, in the resulting engineered cell composition may increase the potency, efficacy, and persistence, e.g., in vivo after administration, of the engineered cell composition.

In some aspects, the number of doublings of that occurs in a population is determined using the following formula:

$$\text{Cell doublings} = \frac{\ln\left(\frac{TNC \text{ at harvest}}{TNC \text{ 3 days post-activation}}\right)}{\ln 2}. \tag{1}$$

In certain embodiments, the population doubling of a cell composition determined using the formula is or is about, or is greater than or than about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is or is about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is between about 3.0 and about 9.0, or between about 5 and about 7.5.

In some aspects, the number of doublings of that occurs in a population is determined using the following formula:

$$\text{Cell doublings} = \frac{\ln\left(\frac{TNC \text{ at harvest}}{\begin{array}{c} TNC \text{ at initiation of} \\ \text{the stimulating} \end{array}}\right)}{\ln 2}. \tag{2}$$

In certain embodiments, the population doubling of a cell composition determined using the formula is or is about, or is greater than or than about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is or is about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is between about 3.0 and about 9.0, or between about 5 and about 7.5.

In certain embodiments, the number of doublings that occurs in a population is determined suing the following formula:

$$\text{Cell doublings} = \frac{\ln\left(\frac{TNC \text{ at harvest}}{TNC \text{ following stimulation}}\right)}{\ln 2}. \tag{3}$$

In certain embodiments, the population doubling of a cell composition determined using the formula is or is about, or is greater than or than about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is or is about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is between about 3.0 and about 9.0, or between about 5 and about 7.5.

In various embodiments, the number of doublings that occurs in a population is determined suing the following formula:

$$\text{Cell doublings} = \frac{\ln\left(\frac{TNC \text{ at harvest}}{TNC \text{ at transduction}}\right)}{\ln 2}. \tag{4}$$

In certain embodiments, the population doubling of a cell composition determined using the formula is or is about, or is greater than or than about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is or is about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is between about 3.0 and about 9.0, or between about 5 and about 7.5.

In particular embodiments, the number of doublings that occurs in a population is determined suing the following formula:

$$\text{Cell doublings} = \frac{\ln\left(\frac{TNC \text{ at harvest}}{\begin{array}{c} TNC \text{ at the begining} \\ \text{of the cultivation or expansion} \end{array}}\right)}{\ln 2}. \tag{5}$$

In certain embodiments, the population doubling of a cell composition determined using the formula is or is about, or is greater than or than about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is or is about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is between about 3.0 and about 9.0, or between about 5 and about 7.5.

In certain embodiments, the cultivation or expansion is completed before the total number cells, e.g., total number of cultivated cells or cells undergoing the expansion, is greater than or than about one, two, three, four, five, six, eight, ten, twenty, or more than twenty times the number of cells of the input population, e.g., the total number of cells that were contacted with the stimulatory reagent. In certain embodiments, the cultivation or expansion is completed before the total number cells, e.g., total number of cultivated cells or cells undergoing the expansion, is or is about, or is greater than or than about 2.0, 2.5, 3.0, 3.5, 4.0, 4.5, 5.0, 5.5, 6.0, 6.5, 7.0, 7.5, 8.0, 8.5, 9.0, 9.5, or 10.0 times the number of cells of the input population, e.g., the total number of cells that were contacted with the stimulatory reagent. In various embodiments, the cultivation or expansion is completed before the total number of cultivated cells is greater than or than about one, two, three, four, five, six, eight, ten, twenty, or more than twenty times the total number of cells that were transformed, transduced, or spinoculated, e.g., the total number of cells that were contacted with a viral vector. In certain embodiments, the cultivation or expansion is completed before the total number cells, e.g., total number of cultivated cells or cells undergoing the expansion, is or is about, or is greater than or than about 2.0, 2.5, 3.0, 3.5, 4.0, 4.5, 5.0, 5.5, 6.0, 6.5, 7.0, 7.5, 8.0, 8.5, 9.0, 9.5, or 10.0 times the total number of cells that were transformed, transduced, or spinoculated, e.g., the total number of cells that were contacted with a viral vector. In certain embodiments, the population doubling of a cell composition is or is about, or is greater than or than about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is or is about 2.0, 2.5, 3.0, 3.5, 4.0, 4.5, 5.0, 5.5, 6.0, 6.5, 7.0, 7.5, 8.0, 8.5, 9.0, 9.5, or 10.0. In certain embodiments, the mean population doubling of a plurality of cell compositions is between about 3.0 and about 9.0, or between about 5 and about 7.5. In certain embodiments, the cells are T cells, viable T cells, CD3+ T cells, CD4+ T cells, CD8+ T cells, CAR expressing T cells, or a combination of any of the foregoing.

In particular embodiments, when the cultivation ends, cells in an output composition achieve a cell density or concentration of or of about, or cells in a plurality of output compositions achieve a mean or median cell density or concentration of or of about, $1\times10^6$ cells/mL, $5\times10^6$ cells/mL, $10\times10^6$ cells/mL, $15\times10^6$ cells/mL, $20\times10^6$ cells/mL, $25\times10^6$ cells/mL, $30\times10^6$ cells/mL, $35\times10^6$ cells/mL, $40\times10^6$ cells/mL, $45\times10^6$ cells/mL, $50\times10^6$ cells/mL, $55\times10^6$ cells/mL, $60\times10^6$ cells/mL, $65\times10^6$ cells/mL, $70\times10^6$ cells/mL, $75\times10^6$ cells/mL, $80\times10^6$ cells/mL, $85\times10^6$ cells/mL, $90\times10^6$ cells/mL, $95\times10^6$ cells/mL, $100\times10^6$ cells/mL, or viable cells thereof. In particular embodiments, when the cultivation ends, cells in an output composition achieve a cell density or concentration, or cells in a plurality of output compositions achieve a mean or median cell density or concentration, between or between about $15\times10^6$ cells/mL and about $45\times10^6$ cells/mL, between or between about $20\times10^6$ cells/mL and about $40\times10^6$ cells/mL, such as about $21\times10^6$ cells/mL, $22\times10^6$ cells/mL, $23\times10^6$ cells/mL, $24\times10^6$ cells/mL, $25\times10^6$ cells/mL, $26\times10^6$ cells/mL, $27\times10^6$ cells/mL, $28\times10^6$ cells/mL, $29\times10^6$ cells/mL, $30\times10^6$ cells/mL, $31\times10^6$ cells/mL, $32\times10^6$ cells/mL, $33\times10^6$ cells/mL, $34\times10^6$ cells/mL, $35\times10^6$ cells/mL, $36\times10^6$ cells/mL, $37\times10^6$ cells/mL, $38\times10^6$ cells/mL, or $39\times10^6$ cells/mL. In some embodiments, the mean or median cell density or concentration is between about $30\times10^6$ cells/mL and about $40\times10^6$ cells/mL, between about $15\times10^6$ cells/mL and about $25\times10^6$ cells/mL, between about $35\times10^6$ cells/mL and about $40\times10^6$ cells/mL, or between about $20\times10^6$ cells/mL and about $25\times10^6$ cells/mL.

Monitoring Cells During Cultivation

In some embodiments, the cells are monitored during the cultivation step. Monitoring may be performed, for example, to ascertain (e.g., measure, quantify) cell morphology, cell viability, cell death, and/or cell concentration (e.g., viable cell concentration, viable cell count). In some embodiments, the monitoring is performed manually, such as by a human operator. In some embodiments, the monitoring is performed by an automated system. The automated system may require minimal or no manual input to monitor the cultivated cells. In some embodiments, the monitoring is performed both manually and by an automated system.

In certain embodiments, the cells are monitored by an automated system requiring no manual input. In some embodiments, the automated system is compatible with a bioreactor, for example a bioreactor as described herein, such that cells undergoing cultivation can be removed from the bioreactor, monitored, and subsequently returned to the bioreactor. In some embodiments, the monitoring and cultivation occur in a closed loop configuration. In some aspects, in a closed loop configuration, the automated system and bioreactor remain sterile. In embodiments, the automated system is sterile. In some embodiments, the automated system is an in-line system.

In some embodiments, the automated system includes the use of optical techniques (e.g., microscopy) for detecting cell morphology, cell viability, cell death, and/or cell concentration (e.g., viable cell concentration, viable cell count). Any optical technique suitable for determining, for example, cell features, viability, and concentration and count are contemplated herein. Non-limiting examples of useful optical techniques include bright field microscopy, fluorescence microscopy, differential interference contrast microscopy, phase contrast microscopy, digital holography microscopy (DHM), differential digital holography microscopy (DDHM), or a combination thereof. Differential digital holography microscopy, DDHM, and differential DHM may be used herein interchangeably. In certain embodiments, the automated system includes a differential digital holography microscope. In certain embodiments, the automated system includes a differential digital holography microscope including illumination means (e.g., laser, led). Descriptions of DDHM methodology and use may be found, for example, in U.S. Pat. No. 7,362,449; EP 1,631,788; U.S. Pat. Nos. 9,904,248; and 9,684,281, which are incorporated herein by reference in their entirety.

DDHM permits label-free, non-destructive imaging of cells, resulting in high-contrast holographic images. The images may undergo object segmentation and further analysis to obtain a plurality of morphological features that quantitatively describe the imaged objects (e.g., cultivated cells, cellular debris). As such, various features (e.g., cell morphology, cell viability, cell concentration, cell count) may be directly assessed or calculated from DDHM using, for example, the steps of image acquisition, image processing, image segmentation, and feature extraction. In some embodiments, the automated system includes a digital recording device to record holographic images. In some embodiments, the automated system includes a computer including algorithms for analyzing holographic images. In some embodiments, the automated system includes a monitor and/or computer for displaying the results of the holographic image analysis. In some embodiments, the analysis is automated (i.e., capable of being performed in the absence of user input). An example of a suitable automated system for monitoring cells during the cultivating step includes, but is not limited to, Ovizio iLine F (Ovizio Imaging Systems NV/SA, Brussels, Belgium).

In certain embodiments, the monitoring is performed continuously during the cultivation step. In some embodiments, the monitoring is performed in real-time during the cultivation step. In some embodiments, the monitoring is performed at discrete time points during the cultivation step. In some embodiments, the monitoring is performed at least every 15 minutes for the duration of the cultivating step. In some embodiments, the monitoring is performed at least every 30 minutes for the duration of the cultivating step. In some embodiments, the monitoring is performed at least every 45 minutes for the duration of the cultivating step. In some embodiments, the monitoring is performed at least every hour for the duration of the cultivating step. In some embodiments, the monitoring is performed at least every 2 hours for the duration of the cultivating step. In some embodiments, the monitoring is performed at least every 4 hours for the duration of the cultivating step. In some embodiments, the monitoring is performed at least every 6 hours for the duration of the cultivating step. In some embodiments, the monitoring is performed at least every 8 hours for the duration of the cultivating step. In some embodiments, the monitoring is performed at least every 10 hours for the duration of the cultivating step. In some embodiments, the monitoring is performed at least every 12 hours for the duration of the cultivating step. In some embodiments, the monitoring is performed at least every 14 hours for the duration of the cultivating step. In some embodiments, the monitoring is performed at least every 16 hours for the duration of the cultivating step. In some embodiments, the monitoring is performed at least every 18 hours for the duration of the cultivating step. In some embodiments, the monitoring is performed at least every 20 hours for the duration of the cultivating step. In some embodiments, the monitoring is performed at least every 22 hours for the duration of the cultivating step. In some embodiments, the monitoring is performed at least once a day for the duration of the cultivating step. In some embodiments, the monitoring is performed at least once every second day for the duration of the cultivating step. In some embodiments, the monitoring is performed at least once every third day for the duration of the cultivating step. In some embodiments, the monitoring is performed at least once every fourth day for the duration of the cultivating step. In some embodiments, the monitoring is performed at least once every fifth day for the duration of the cultivating step. In some embodiments, the monitoring is performed at least once every sixth day for the duration of the cultivating step. In some embodiments, the monitoring is performed at least once every seventh day for the duration of the cultivating step. In some embodiments, the monitoring is performed at least once every eighth day for the duration of the cultivating step. In some embodiments, the monitoring is performed at least once every ninth day for the duration of the cultivating step. In some embodiments, the monitoring is performed at least once every tenth day for the duration of the cultivating step. In some embodiments, the monitoring is performed at least once during the cultivating step.

In some embodiments, features of the cells that can be determined by the monitoring, including using optical techniques such as DHM or DDHM, include cell viability, cell concentration, cell number and/or cell density. In some embodiments, cell viability is characterized or determined. In some embodiments, cell concentration, density and/or number is characterized or determined. In some embodiments, viable cell concentration, viable cell number and/or viable cell density is characterized or determined. In some embodiments, the cultivated cells are monitored by the automated system until a threshold of expansion is reached, such as described above. In some embodiments, once a threshold of expansion is reached, the cultivated cells are harvested, such as by automatic or manual methods, for example, by a human operator. The threshold of expansion may depend on the total concentration, density and/or number of cultured cells determined by the automated system. Alternatively, the threshold of expansion may depend on the viable cell concentration, density and/or number. Number and count may be used herein interchangeably.

In some embodiments, the harvested cells are formulated as described, such as in the presence of a pharmaceutically acceptable carrier. In some embodiments, the harvested cells are formulated in the presence of a cryoprotectant.

E. Formulating the Cells

In some embodiments, one or more process steps (e.g. carried out in the centrifugal chamber and/or closed system) for manufacturing, generating or producing a cell therapy and/or engineered cells may include formulation of cells, such as formulation of genetically engineered cells resulting from the provided transduction processing steps prior to or after the culturing, e.g. cultivation and expansion, and/or one or more other processing steps as described. In some embodiments, the provided methods associated with formulation of cells include processing transduced cells, such as cells transduced and/or expanded using the processing steps described above, in a closed system.

In some embodiments, the stimulatory reagent is removed and/or separated from the cells prior to the formulating. In particular embodiments, the stimulatory reagent is removed and/or separated from the cells after the cultivation. In certain embodiments, the stimulatory agent is removed and/or separated from the cells subsequent to the cultivation and prior to formulating the cultivated cells, e.g., under conditions that promote proliferation and/or expansion. In certain embodiments, the stimulatory reagent is a stimulatory reagent that is described in herein, e.g., in Section I-B-1. In particular embodiments, the stimulatory reagent is removed and/or separated from the cells as described herein, e.g., in Section I-B-2.

In some embodiments, the cells are formulated between 0 days and 10 days, between 0 and 5 days, between 2 days and 7 days, between 0.5 days, and 4 days, or between 1 day and 3 days after the cells after the threshold cell count, density, and/or expansion has been achieved during the cultivation. In certain embodiments, the cells are formulated at or at or about or within 12 hours, 18 hours, 24 hours, 1 day, 2 days, or 3 days after the threshold cell count, density, and/or expansion has been achieved during the cultivation. In some embodiments, the cells are formulated within or within about 1 day after the threshold cell count, density, and/or expansion has been achieved during the cultivation.

In some embodiments, the provided methods for manufacturing, generating or producing a cell therapy and/or engineered cells may include formulation of cells, such as formulation of genetically engineered cells resulting from the provided processing steps prior to or after the incubating, engineering, and cultivating, and/or one or more other processing steps as described. In some embodiments, the provided methods associated with formulation of cells include processing transduced cells, such as cells transduced and/or expanded using the processing steps described above, in a closed system. In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods, such as in the prevention or treatment of diseases, conditions, and disorders, or in detection, diagnostic, and prognostic methods.

In some cases, the cells are processed in one or more steps (e.g. carried out in the centrifugal chamber and/or closed system) for manufacturing, generating or producing a cell therapy and/or engineered cells may include formulation of cells, such as formulation of genetically engineered cells resulting from the provided transduction processing steps prior to or after the culturing, e.g. cultivation and expansion, and/or one or more other processing steps as described. In some cases, the cells can be formulated in an amount for dosage administration, such as for a single unit dosage administration or multiple dosage administration. In some embodiments, the provided methods associated with formulation of cells include processing transduced cells, such as cells transduced and/or expanded using the processing steps described above, in a closed system.

In certain embodiments, one or more compositions of enriched T cells are formulated. In particular embodiments, one or more compositions of enriched T cells are formulated after the one or more compositions have been engineered and/or cultivated. In particular embodiments, the one or more compositions are input compositions. In some embodiments, the one or more input compositions have been previously cryofrozen and stored, and are thawed prior to the incubation.

In certain embodiments, the formulated cells are output cells. In some embodiments, a formulated composition of enriched T cells is an output composition of enriched T cells. In particular embodiments, the formulated CD4+ T cells and formulated CD8+ T cells are the output CD4+ and CD8+ T cells. In particular embodiments, a formulated cell composition, e.g., a formulated composition of enriched CD4+ and CD8+ cells, is an output cell composition, e.g., an output composition of enriched CD4+ and CD8+ cells.

In some embodiments, cells can be formulated into a container, such as a bag or vial. In some embodiments, the cells are formulated between 0 days and 10 days, between 0 and 5 days, between 2 days and 7 days, between 0.5 days, and 4 days, or between 1 day and 3 days after the cells after the threshold cell count, density, and/or expansion has been achieved during the cultivation. In certain embodiments, the cells are formulated at or at or about or within 12 hours, 18 hours, 24 hours, 1 day, 2 days, or 3 days after the threshold cell count, density, and/or expansion has been achieved during the cultivation. In some embodiments, the cells are formulated within or within about 1 day after the threshold cell count, density, and/or expansion has been achieved during the cultivation.

In certain embodiments, the cells are cultivated for a minimum duration or amount of time, for example, so that cells are harvested in a less activated state than if they were formulated at an earlier time point during the cultivation, regardless of when the threshold is achieved. In some embodiments, the cells are cultivated between 0 day and 3 days, e.g., between 0 and 3 days, between 1 and 2 days, at or at about 1 day, at or at about 2 days, or at or at about 3 days, after the threshold cell count, density, and/or expansion has been achieved during the cultivation. In certain embodiments, the cells active the threshold cell count, density, and/or expansion and remain cultivated for a minimum time or duration prior to the formulation. In some embodiments, cells that have achieved the threshold are not formulated until they have been cultivated for a minimum duration and/or amount of time, such as a minimum time or duration of between 1 day and 14 days, 2 days and 7 days, or 3 days and 6 days, or a minimum time or duration of the cultivation of or of about 2 days, 3 days, 4 days, 5 days, 6 days, 7 days, or more than 7 days. In some embodiments, the minimum time or duration of the cultivation is between 3 days and 6 days.

In some embodiments, the cells are formulated in a pharmaceutically acceptable buffer, which may, in some aspects, include a pharmaceutically acceptable carrier or excipient. In some embodiments, the processing includes exchange of a medium into a medium or formulation buffer that is pharmaceutically acceptable or desired for administration to a subject. In some embodiments, the processing steps can involve washing the transduced and/or expanded cells to replace the cells in a pharmaceutically acceptable buffer that can include one or more optional pharmaceutically acceptable carriers or excipients. Exemplary of such pharmaceutical forms, including pharmaceutically acceptable carriers or excipients, can be any described below in conjunction with forms acceptable for administering the cells and compositions to a subject. The pharmaceutical composition in some embodiments contains the cells in amounts effective to treat or prevent the disease or condition, such as a therapeutically effective or prophylactically effective amount.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

Compositions in some embodiments are provided as sterile liquid preparations, e.g., isotonic aqueous solutions, suspensions, emulsions, dispersions, or viscous compositions, which may in some aspects be buffered to a selected pH. Liquid compositions can comprise carriers, which can be a solvent or dispersing medium containing, for example, water, saline, phosphate buffered saline, polyol (for example, glycerol, propylene glycol, liquid polyethylene glycol) and suitable mixtures thereof. Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

In some embodiments, the formulation buffer contains a cryopreservative. In some embodiments, the cell are formulated with a cyropreservative solution that contains 1.0% to 30% DMSO solution, such as a 5% to 20% DMSO solution or a 5% to 10% DMSO solution. In some embodiments, the cryopreservation solution is or contains, for example, PBS containing 20% DMSO and 8% human serum albumin (HSA), or other suitable cell freezing media. In some embodiments, the cryopreservative solution is or contains, for example, at least or about 7.5% DMSO. In some embodiments, the processing steps can involve washing the transduced and/or expanded cells to replace the cells in a cryopreservative solution. In some embodiments, the cells are frozen, e.g., cryofrozen or cryopreserved, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryofrozen or cryopreserved, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and −5%, between 0.25% and 4%, between 0.5% and 2%, or between 1% and 2% HSA.

In particular embodiments, the composition of enriched T cells, e.g., T cells that have been stimulated, engineered, and/or cultivated, are formulated, cryofrozen, and then stored for an amount of time. In certain embodiments, the formulated, cryofrozen cells are stored until the cells are released for infusion. In particular embodiments, the formulated cryofrozen cells are stored for between 1 day and 6 months, between 1 month and 3 months, between 1 day and 14 days, between 1 day and 7 days, between 3 days and 6 days, between 6 months and 12 months, or longer than 12 months. In some embodiments, the cells are cryofrozen and stored for, for about, or for less than 1 days, 2 days, 3 days, 4 days, 5 days, 6 days, or 7 days. In certain embodiments, the cells are thawed and administered to a subject after the storage. In certain embodiments, the cells are stored for or for about 5 days.

In some embodiments, the formulation is carried out using one or more processing step including washing, diluting or concentrating the cells, such as the cultured or expanded cells. In some embodiments, the processing can include dilution or concentration of the cells to a desired concentration or number, such as unit dose form compositions including the number of cells for administration in a given dose or fraction thereof. In some embodiments, the processing steps can include a volume-reduction to thereby increase the concentration of cells as desired. In some embodiments, the processing steps can include a volume-addition to thereby decrease the concentration of cells as desired. In some embodiments, the processing includes adding a volume of a formulation buffer to transduced and/or expanded cells. In some embodiments, the volume of formulation buffer is from or from about 10 mL to 1000 mL, such as at least or at least about or about 50 mL, 100 mL, 200 mL, 300 mL, 400 mL, 500 mL, 600 mL, 700 mL, 800 mL, 900 mL or 1000 mL.

In some embodiments, such processing steps for formulating a cell composition is carried out in a closed system. Exemplary of such processing steps can be performed using a centrifugal chamber in conjunction with one or more systems or kits associated with a cell processing system, such as a centrifugal chamber produced and sold by Biosafe SA, including those for use with the Sepax® or Sepax 2® cell processing systems. An exemplary system and process is described in International Publication Number WO2016/073602. In some embodiments, the method includes effecting expression from the internal cavity of the centrifugal chamber a formulated composition, which is the resulting composition of cells formulated in a formulation buffer, such as pharmaceutically acceptable buffer, in any of the above embodiments as described. In some embodiments, the expression of the formulated composition is to a container, such as a bag that is operably linked as part of a closed system with the centrifugal chamber. In some embodiments, the container, such as bag, is connected to a system at an output line or output position.

In some embodiments, the closed system, such as associated with a centrifugal chamber or cell processing system, includes a multi-port output kit containing a multi-way tubing manifold associated at each end of a tubing line with a port to which one or a plurality of containers can be connected for expression of the formulated composition. In some aspects, a desired number or plurality of output containers, e.g., bags, can be sterilely connected to one or more, generally two or more, such as at least 3, 4, 5, 6, 7, 8 or more of the ports of the multi-port output. For example, in some embodiments, one or more containers, e.g., bags can be attached to the ports, or to fewer than all of the ports. Thus, in some embodiments, the system can effect expression of the output composition into a plurality of output bags.

In some aspects, cells can be expressed to the one or more of the plurality of output bags in an amount for dosage administration, such as for a single unit dosage administration or multiple dosage administration. For example, in some embodiments, the output bags may each contain the number of cells for administration in a given dose or fraction thereof. Thus, each bag, in some aspects, may contain a single unit dose for administration or may contain a fraction of a desired dose such that more than one of the plurality of output bags, such as two of the output bags, or 3 of the output bags, together constitute a dose for administration.

Thus, the containers, e.g., output bags, generally contain the cells to be administered, e.g., one or more unit doses thereof. The unit dose may be an amount or number of the cells to be administered to the subject or twice the number (or more) of the cells to be administered. It may be the lowest dose or lowest possible dose of the cells that would be administered to the subject.

In some embodiments, each of the containers, e.g., bags, individually comprises a unit dose of the cells. Thus in some embodiments, each of the containers comprises the same or approximately or substantially the same number of cells. In some embodiments, each unit dose contains at least or at least about $1\times10^6$, $2\times10^6$, $5\times10^6$, $1\times10^7$, $5\times10^7$, or $1\times10^8$ engineered cells, total cells, T cells, or PBMCs. In some embodiments, the volume of the formulated cell composition in each bag is 10 mL to 100 mL, such as at least or at least about 20 mL, 30 mL, 40 mL, 50 mL, 60 mL, 70 mL, 80 mL, 90 mL or 100 mL.

In some embodiments, such cells produced by the method, or a composition comprising such cells, are administered to a subject for treating a disease or condition.

F. Exemplary Features of the Process

In particular embodiments, the provided methods are used in connection with a process that produces or generates an output composition of enriched T cells from one or more input compositions and/or from a single biological sample. In certain embodiments, the output composition contains cells that express a recombinant receptor, e.g., a TCR or a CAR. In particular embodiments, the cells of the output compositions are suitable for administration to a subject as a therapy, e.g., an autologous cell therapy. In some embodiments, the output composition is a composition of enriched CD4+ and CD8+ T cells.

In some embodiments, the provided methods are used in connection with an entire process for generating or producing output cells and/or an output compositions of enriched T cells, such as a process including some or all of the steps of: collecting or obtaining a biological sample; isolating, selecting, or enriching input cells from the biological sample; cryofreezing and storing the input cells; thawing and/or incubating the input cells under stimulating conditions; engineering the stimulated cells to express or contain a recombinant polynucleotide, e.g., a polynucleotide encoding a recombinant receptor such as a CAR; cultivating the engineered cells to a threshold amount, density, or expansion; formulating the cultivated cells in an output composition; and/or cryofreezing and storing the formulated output cells until the cells are released for infusion and/or are suitable to be administered to a subject. In some embodiments, the entire process is performed with a single composition of enriched T cells, e.g., CD4+ and CD8+ T cells. In certain embodiments, the process is performed with two or more input compositions of enriched T cells that are combined prior to and/or during the process to generate or produce a single output composition of enriched T cells. In some embodiments, the enriched T cells are or include engineered T cells, e.g., T cells transduced to express a recombinant receptor.

In some embodiments, the process associated with the provided methods is compared to an alternative process. In particular embodiments, the alternative process may differ in one or more specific aspects, but otherwise contains similar or the same features, aspects, steps, stages, reagents, and/or conditions of the process associated with the provided methods. In some embodiments, the alternative process is similar as the process associated with the provided methods, but differs in a manner that includes, but is not limited to, one or more of; different reagents and/or media formulations; presence of serum during the incubation, transduction, transfection, and/or cultivation; different cellular makeup of the input composition, e.g., ratio of CD4+ to CD8+ T cells; different amount and/or concentration of input cells incubated under stimulating conditions; different stimulating conditions and/or a different stimulatory reagent; different ratio of stimulatory reagent to cells; different vector and/or method of transduction; different timing or order for incubating, transducing, and/or transfecting the cells; absence or difference of one or more recombinant cytokines present during the incubation, transduction, transfection, and/or cultivation; different amount and/or concentration of cells that are transduced; different rocking and/or perfusion conditions during cultivation; and/or a different threshold amount, density, or expansion achieved during the cultivation.

In certain embodiments, the process is completed within a duration and/or amount of time of or of about 35 days, 34 days, 33 days, 32 days, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, or less than 9 days. In some embodiments, the process is completed within 25 days. In certain embodiments, the process is completed within 21 days. In particular embodiments, the process is completed within a duration and/or amount of time between 14 days and 18 days. In some embodiments, the process is deemed completed when: the composition is harvested and/or formulated; the composition is ready to be harvested and/or formulated; the composition has reached a target threshold value for harvest; the composition is released and/or ready for post-formulation testing; the composition is ready to be administered to the subject, and/or the composition is administered to the subject; including the storage times for cryofrozen compositions. In particular embodiments, when the process is performed on more than one composition of enriched T cells obtained from the same biological sample, the process is complete when at least one representative sample of each and every composition from the same biological sample has completed the process.

In some embodiments, the process is completed within 21 days as measured from the start or collection of the biological sample and/or the isolation, selection, stimulation, and/or enrichment of input cells from the biological sample to when the output cells are released for infusion. In particular embodiments, the process is completed between 14 days and 18 days as measured from the start or collection of the biological sample and/or the isolation, selection, stimulation, and/or enrichment of input cells from the biological sample to when the output cells are ready for post-formulation testing, released for infusion, and/or ready to be administered to the subject.

In certain embodiments, the duration and/or amount of time during the process that occurs from the start or initiation of the incubation under stimulating conditions to the time at which a the output cells are collected, formulated, and/or cryofrozen is 5 days or about 5 days, between 5 days and 25 days, between 7 days and 18 days, between 8 and 15 days, between 14 and 18 days, between 8 and 14 days, between 8 and 15 days, such as between 8 and 13 days or between 9 days and 13 days. In particular embodiments, the duration and/or amount of time during the process that occurs from the start or initiation of the incubation under stimulating conditions to the time at which a the output cells are collected, formulated, and/or cryofrozen is between 7 days and 10 days, between 6 days and 9 days or between 5 days and 8 days.

In certain embodiments, the median amount of time and/or duration of the process that occurs from the start or initiation of the incubation to the time at which the threshold is achieved is about or less than about 5 days, between 5 days and 25 days, between 7 days and 18 days, between 9 days and 13 days, between 14 days to 18 days, or is, is less than, or is about 5 days, 5.5 days, 6 days, 6.5 days, 7 days, 7.5 days, 8 days, 9 days, 10 days, 11 days, 12 days, or 13 days. In particular embodiments, the mean amount of time and/or duration of the process that occurs from the start or initiation of the incubation to the time at which the threshold is achieved is about or less than about 5 days, between 5 days and 25 days, between 7 days and 18 days, between 14 and 18 days, between 8 days and 13 days, or between 9 days and 13 days, or is, is less than, or is about 5 days, 5.5 days, 6 days, 6.5 days, 7 days, 7.5 days, 8 days, 9 days, 10 days, 11 days, 12 days, or 13 days. In particular embodiments, the duration and/or amount of time during the process that occurs from the start or initiation of the incubation under stimulating conditions to the time at which the threshold is achieved is 5 days or about 5 days, between 5 days and 7 days, between 7 days and 10 days, between 6 days and 9 days or between 5 days and 8 days.

In some embodiments, the success rate at which engineered cells (e.g. CAR T-cells) can be successfully manufactured by the provided process is at least at or about 85%, 90%, 95%, 96%, 97%, 98%, 99%, or 100%. In some aspects, the success rate is determined as the percentage of subjects whose samples have been collected, e.g. by apheresis, for engineering by the provided process, in which such cells meet process criteria for harvesting of output cells, including collection, formulation and/or cryopreservation of output cells, at a time that is about or less than about 5 days, between 5 days and 10 days, such as between 7 days and 10 days, between 6 days and 9 days or between 5 days and 8 days, such as 5 days, 5.5 days, 6 days, 6.5 days, 7 days, or 7.5 days, after the initiation of the stimulation with a stimulatory reagent. In some aspects, the success rate is determined as the percentage of subjects whose samples have been collected, e.g. by apheresis, for engineering by the provided process, in which such cells meet process criteria for re-infusion of the engineered cells to the subject, including post-formulation testing, release for infusion, and/or ready to be administered to the subject, at a time that is within 21 days after the initiation of the stimulation with the stimulatory reagent.

In some embodiments, the duration and/or amount of time during the process that occurs from the start or initiation of the incubation under stimulating conditions to the time at which a the output cells are collected, formulated, and/or cryofrozen is between 9 days and 15 days for, for about, or for at least at or about 85%, 90%, 95%, 96%, 97%, 98%, 99%, or 100% of subjects among a plurality of subjects subjected to the provided process for manufacturing cells. In certain embodiments, the duration and/or amount of time during the process that occurs from the start or initiation of the incubation under stimulating conditions to the time at which a the output cells are collected, formulated, and/or cryofrozen is between 14 days and 18 days for, for about, or for at least at or about 85%, 90%, 95%, 96%, 97%, 98%, 99%, or 100% of subjects among a plurality of subjects subjected to the provided process for manufacturing cells. In particular embodiments, the duration and/or amount of time during the process that occurs from the start or initiation of the incubation under stimulating conditions to the time at which a the output cells are collected, formulated, and/or cryofrozen is between 7 and 10 days for, for about, or for at least at or about 85%, 90%, 95%, 96%, 97%, 98%, 99%, or 100% of subjects among a plurality of subjects subjected to the provided process for manufacturing cells. In particular embodiments, the duration and/or amount of time during the process that occurs from the start or initiation of the incubation under stimulating conditions to the time at which a the output cells are collected, formulated, and/or cryofrozen is between 6 and 9 days for, for about, or for at least at or about 85%, 90%, 95%, 96%, 97%, 98%, 99%, or 100% of subjects among a plurality of subjects subjected to the provided process for manufacturing cells. In particular embodiments, the duration and/or amount of time during the process that occurs from the start or initiation of the incubation under stimulating conditions to the time at which a the output cells are collected, formulated, and/or cryofrozen is between 5 and 8 days for, for about, or for at least at or about 85%, 90%, 95%, 96%, 97%, 98%, 99%, or 100% of subjects among a plurality of subjects subjected to the provided process for manufacturing cells. In some embodiments, such subjects are patients that have a disease or condition, such as a cancer, such as multiple myeloma.

In some embodiments, the duration and/or amount of time during the process that occurs from the isolation, enrichment, and/or selection of the compositions of enriched CD4+ and CD8+ cells from a biological sample, e.g., apheresis and/or leukapheresis, to the time at which the output cells are collected, formulated, and/or cryofrozen is between 5 days and 25 days, between 7 days and 18 days, between 14 and 18 days, between 8 and 19 days, between 8 and 14 days, or between 10 and 16 days. In certain embodiments, the output cells are collected, formulated, and/or harvested between 10 and 16 days after the isolation, enrichment, and/or selection for at least 85%, at least 90%, at least 95%, at least 96%, at least 97%, at least 98%, at least 99% or 100% of the subjects among a plurality of subjects subjected to the provided process for manufacturing cells. In particular embodiments, the output cells are collected, formulated, and/or harvested between 14 and 18 days after the isolation, enrichment, and/or selection for at least 85%, at least 90%, at least 95%, at least 96%, at least 97%, at least 98%, at least 99% or 100% of the subjects among a plurality of subjects subjected to the provided process for manufacturing cells.

In some embodiments, the process is completed within a duration and/or amount of time of or of about 35 days, 34 days, 33 days, 32 days, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, or less than 9 days, as measured from the start or collection of the biological sample, e.g., an apheresis or leukapheresis sample, to when the output composition is administered or ready to be administered to the subject, the output cells are harvested and/or formulated; the output cells are ready to be harvested and/or formulated; the output cells have reached a target threshold value for harvest; and/or the output composition is released for testing, including the storage times for cryofrozen compositions. In some embodiments, the process is completed within 21 days as measured from the start or collection of the biological sample to when the output cells are ready to be and/or are released for infusion e.g., into to a subject.

In some embodiments, the process is completed, within a confidence interval of or of at least at or about 75%, 80%, 85%, 90%, 95%, 97%, 98%, 99% or 99.9%, within a duration and/or amount of time of or of about 35 days, 34 days, 33 days, 32 days, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, or less than 9 days, as measured from the start or collection of the biological sample and/or the isolation, selection, stimulation, and/or enrichment of input cells from the biological sample to when the output cells are released for infusion, including the storage times for cryofrozen compositions. In certain embodiments, the process is completed, within a confidence interval of or of at least at or about 75%, 80%, 85%, 90%, 95%, 97%, 98%, 99% or 99.9%, within 14 days to 18 days as measured from the start or collection of the biological sample and/or the isolation, selection, stimulation, and/or enrichment of input cells from the biological sample to when the output cells are released for infusion, including the storage times for cryofrozen compositions.

In certain embodiments, the process is completed, within a confidence interval of or of at least at or about 75%, 80%, 85%, 90%, 95%, 97%, 98%, 99% or 99.9%, within a duration and/or amount of time of or of about 35 days, 34 days, 33 days, 32 days, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, or less than 9 days, as measured from the collection of the biological sample and/or the isolation, selection, stimulation, and/or enrichment of T cells, e.g., input T cells, from the biological sample to when the output cells are administered to the subject and/or are ready to be administered to the subject, including the storage times for cryofrozen cell compositions. In certain embodiments, the process is completed, within a confidence interval of or of at least at or about 75%, 80%, 85%, 90%, 95%, 97%, 98%, 99% or 99.9%, within a duration and/or amount of time of between 14 days and 18 days, as measured from the collection of the biological sample and/or the isolation, selection, stimulation, and/or enrichment of T cells, e.g., input T cells, from the biological sample to when the output cells are administered to the subject and/or are ready to be administered to the subject, including the storage times for cryofrozen cell compositions.

In certain embodiments, the process is completed, within a confidence interval of or of at least at or about 75%, 80%, 85%, 90%, 95%, 97%, 98%, 99% or 99.9%, within a duration and/or amount of time of or of about 35 days, 34 days, 33 days, 32 days, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, or less than 9 days, as measured from the collection of the biological sample and/or the isolation, selection, stimulation, and/or enrichment of T cells, e.g., input T cells, from the biological sample to when the output cells are ready for post-formulation testing, including the storage times for cryofrozen cell compositions. In certain embodiments, the process is completed, within a confidence interval of or of at least at or about 75%, 80%, 85%, 90%, 95%, 97%, 98%, 99% or 99.9%, within a duration and/or amount of time of between 14 days and 18 days, as measured from the collection of the biological sample and/or the isolation, selection, stimulation, and/or enrichment of T cells, e.g., input T cells, from the biological sample to when the output cells are ready for post-formulation testing, including the storage times for cryofrozen cell compositions.

In certain embodiments, the duration and/or amount of time to complete the process is between 10 days and 35 days, between 12 days and 33 days, between 17 days and 25 days, between 14 days and 18 days, or between 19 days and 23 days, e.g., when storage time is included, for samples from a plurality of subjects, and/or for at least a certain percentage of subjects, such as those having a particular indication or disease, for example for at least at or about 85%, 86%, 87%, 88%, 89%, 90%, 91%, 92%, 93%, 94%, 95% or greater than 95% of such subjects. In certain embodiments, the median amount of time and/or duration to complete the process (such as when measured from taking of the sample from the subject to when the product is ready or released for infusion to the subject) on a plurality of starting compositions from different biological samples is between 15 days and 27 days, between 17 days and 25 days, between 14 and 18 days, or between 19 days and 23 days or is, is about or is less than 14 days, 15 days, 16 days, 17 days, 18 days, 19 days, 20 days, 21 days, 22 days, or 23 days, e.g., when storage time is included. In particular embodiments, the mean amount of time and/or duration to complete the process on a plurality of compositions from different biological samples is between 15 days and 27 days, between 17 days and 25 days, between 14 days and 18 days, or between 19 days and 23 days or is, is less than, or is about 14 days, 15 days, 16 days, 17 days, 18 days, 19 days, 20 days, 21 days, 22 days, or 23 days, e.g., when transport and/or storage time is included. In particular embodiments, the duration to complete the process on a plurality of compositions from different biological samples is between 15 days and 27 days, between 17 days and 25 days, between 14 to 18 days, or between 19 days and 23 days or is, is less than, or is about 14 days, 15 days, 16 days, 17 days, 18 days, 19 days, 20 days, 21 days, 22 days, or 23 days, e.g., when storage time is included.

In certain embodiments, the duration of the process, such as across a range of starting compositions, such as from different biological samples and/or subjects with different diseases, is less than or no more than 21 days; in some aspects, such result is achieved with a greater than at or about 85%, 90%, 91%, 92%, 93%, 94%, or 95% rate of success in manufacturing product across such samples or patients. In particular embodiments, the duration of the process, such as across a range of starting compositions, e.g., from different biological samples and/or subjects with different diseases, is between 14 days and 18 days; in some aspects, such result is achieved with a greater than 85%, 90%, 91%, 92%, 93%, 94%, or 95% rate of success in manufacturing product across such samples or patients.

In some embodiments, the duration and/or amount of time to complete the process is between 7 days and 27 days, between 9 days and 25 days, between 11 days and 18 days, between 14 days and 18 days, or between 11 days and 15 days when the storage time of cryofrozen cells is not included or factor in. In certain embodiments, the median amount of time and/or duration required to complete the process on a plurality of compositions from different biological samples is between 7 days and 27 days, between 9 days and 25 days, between 11 days and 18 days, between 14 days and 18 days, or between 11 days and 15 days, or is, is less than, or is about 11 days, 12 days, 13 days, 14 days, 15 days, 16 days, 17 days, or 18 days when the storage time of cryofrozen cells is not included or factor in. In particular embodiments, the mean amount of time and/or duration required to complete the process on a plurality of compositions from different biological samples is between 7 days and 27 days, between 9 days and 25 days, between 11 days and 18 days, between 14 days and 18 days, or between 11 days and 15 days, or is, is less than, or is about 11 days, 12 days, 13 days, 14 days, 15 days, 16 days, 17 days, or 18 days when the storage time of cryofrozen cells is not included or factor in. In some embodiments, the mean amount of time and/or duration required to complete the process on a plurality of compositions from different biological samples is less than 21 days when the storage time of cryofrozen cells is not included.

In particular embodiments, the amount of time to complete the process on at least 10% of a plurality of compositions obtained from different sources, e.g., different biological samples and/or different input compositions of enriched T cells isolated, enriched, and/or selected from different biological samples, is between 7 days and 18 days, between 14 days and 18 days, between 10 days and 17 days, or between 11 days and 15 days or is or is about 11 days, 12 days, or 13 days when the storage time of cryofrozen cells is not included or factor in. In particular embodiments, the amount of time required to complete the process on at least 50% of a plurality of compositions from different biological sources is between 7 days and 27 days, between 9 days and 25 days, between 11 days and 18 days, between 14 days and 18 days, or between 11 days and 15 days, or is, is less than, or is about 11 days, 12 days, 13 days, 14 days, 15 days, 16 days, 17 days, or 18 days when the storage time of cryofrozen cells is not included or factor in. In certain embodiments, the amount of time required to complete the process on at least 90% of a plurality of compositions from different sources is between 7 days and 27 days, between 9 days and 25 days, between 11 days and 18 days, between 14 days and 18 days, or between 11 days and 15 days, or is, is less than, or is about 11 days, 12 days, 13 days, 14 days, 15 days, 16 days, 17 days, or 18 days when the storage time of cryofrozen cells is not included or factor in. In certain embodiments, the amount of time required to complete the process on at least 90% of a plurality of compositions from different sources is less than 21 days when the storage time of cryofrozen cells is not included.

In some embodiments, the duration and/or amount of time during the process that occurs from the start or initiation of the incubation under stimulating conditions to the time at which a threshold amount, density, and/or degree of expansion (such as a particular fold expansion such as four-fold or a particular dose) is achieved during cultivation is between 5 days and 25 days, between 7 days and 18 days, between 14 days and 18 days, or between 8 and 15 days, such as between 8 and 13 days or between 9 days and 13 days. In certain embodiments, the median amount of time and/or duration of the process that occurs from the start or initiation of the incubation to the time at which the threshold is achieved is between 5 days and 25 days, between 7 days and 18 days, between 14 and 18 days, or between 9 days and 13 days, or is, is less than, or is about 8 days, 9 days, 10 days, 11 days, 12 days, or 13 days. In particular embodiments, the mean amount of time and/or duration of the process that occurs from the start or initiation of the incubation to the time at which the threshold is achieved is between 5 days and 25 days, between 7 days and 18 days, between 14 days and 18 days, or between 9 days and 13 days, or is or is about 9 days, 10 days, 11 days, 12 days, or 13 days.

In some embodiments, the duration and/or amount of time of the process from the start or initiation of the incubation under stimulating conditions to the time at which the threshold amount, density, and/or expansion is achieved during cultivation is at least at or about 5%, at least at or about 10%, at least at or about 15%, at least at or about 20%, at least at or about 25%, at least at or about 30%, at least at or about 35%, at least at or about 40%, at least at or about 45%, at least at or about 50%, at least at or about 55%, at least at or about 60%, at least at or about 65%, at least at or about 70%, at least at or about 75%, at least at or about 80%, at least at or about 85%, or at least at or about 90% less time than that of an alternative process. In particular embodiments, the duration and/or amount of time during the process from the start or initiation of the incubation under stimulating conditions to the time at which the threshold amount, density, and/or expansion is achieved during cultivation is shorter than the duration and/or amount of time of an alternative process by, by about, or by at least 0.5 days, 1 day, 1.5 days, 2 days, 3 days, 4 days, 5 days, 6 days, 7 days, 8 days, 9 days, 10 days, 11 days, 12 days, 13 days, 14 days, or more than 14 days.

In certain embodiments, the amount of time required for at least 10% of a plurality of compositions from different biological samples to reach the threshold amount, density, and/or expansion from the start or initiation of the incubation under stimulating conditions to the time that the threshold amount, density, and/or expansion is achieved during the cultivation is between 5 days and 20 days, between 7 days and 15 days, or between 9 days and 11 days, or is, is less than, or is about 7 days, 8 days, 9 days, or 10 days. In particular embodiments, the amount of time required for at least 50% of a plurality of compositions from different biological samples to reach the threshold amount, density, and/or expansion from the start or initiation of the incubation under stimulating conditions is between 5 days and 25 days, between 7 days and 18 days, or between 9 days and 13 days, or is, is less than, or is about 7 days, 8 days, 9 days, 10 days, 11 days, 12 days, of 13 days. In some embodiments, the amount of time required for at least 90% of a plurality of compositions from different biological samples to reach the threshold amount, density, and/or expansion from the start or initiation of the incubation under stimulating conditions is s between 5 days and 25 days, between 7 days and 18 days, or between 9 days and 13 days, or is or is about 7 days, 8 days, 9 days, 10 days, 11 days, 12 days, of 13 days.

In some embodiments, the provided methods are used in connection with successfully generating or producing output compositions of engineered T cells that are suitable for use in cell therapy. In some embodiments, an output composition is successfully generated if the cells of the composition achieve the threshold cell count, density, and/or expansion during cultivation. In particular embodiments, an output composition is successfully generated if the cells of at least at or about 40%, 50%, 60%, 70%, 80%, 85%, 90%, or 95% of the cells express the recombinant receptor. In particular embodiments, an output composition is successfully produced or generated if the output composition is suitable for therapeutic use, e.g., as an autologous cell therapy. In particular embodiments, an output composition is suitable for therapeutic use if the cells of the output compositions meet one or more criteria. In some embodiments, the cells and/or cell compositions that are suitable for use in cell therapy are sterile (e.g., lack detectable microbial contamination), free of endotoxin, free of replication competent virus, viable, active (e.g., possess cytolytic activity and/or release cytokine in response to a target antigen), and/or contain a high portion of cells that express the recombinant receptor.

In some embodiments, a portion, sample, and/or fraction of the output cells are collected, e.g., prior to cryofreezing, and are tested with one or more assays. In some embodiments, the one or more assays include assays to evaluate the output cells, e.g., assess, evaluate, and/or quantify features, phenotypes, and/or characteristics of the output cells, e.g., to determine or verify the safety and/or biological characteristics of the output cells. In some embodiments, the one or more assays may include assays to verify that the portion, sample, and/or fraction of the output cells are sterile. In particular embodiments the assays include tests for the presence of microbial contamination, bacterial endotoxins, residual reagents, and/or replication competent virus. In some embodiments, the one or more assays measure, detect, and/or quantify one or more biological characteristics. In certain embodiments, the one or more assays measure, detect, and/or quantify cell count, cell density, cell phenotype, e.g., surface expression of CD3, CD4, and/or CD8, viability, and/or activity, e.g., cytokine release and/or cytolytic activity.

In particular embodiments, the one or more assays are performed before the output cells are released for infusion, ready for administration to a subject, and/or administered to a subject. In particular embodiments, output cells are released for infusion, ready for administration to a subject, and/or administered to a subject after one or more assays have been performed, e.g., on a portion, fraction, and/or sample of output cells. In particular embodiments, output cells are released for infusion, ready for administration to a subject, and/or administered to a subject after the output cells are determined to be safe, e.g., sterile and/or free, and/or have desired biological characteristics following the completion of the one or more assays.

In particular embodiments, the provided methods have an at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% probability or likelihood of successfully generating or producing an output composition of enriched T cells from a composition of input cells and/or a biological sample. In certain embodiments, the probability or likelihood is between 85% and 100%, between 90% and 95%, or between 92% and 94%. In certain embodiments, the provided methods successfully generate or produce an output composition of enriched T cells from at least at or about 70%, at least at or about 75%, at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, or at least at or about 99% of compositions and/or samples from a plurality of compositions of input cells and/or of a plurality of biological samples. In some embodiments, the provided methods successfully generate or produce an output composition of enriched T cells from between at or about 85% and at or about 100%, between at or about 90% and at or about 95%, or between at or about 92% and at or about 94% of compositions and/or samples from a plurality of compositions of input cells and/or of a plurality of biological samples.

In some embodiments, the process is completed within 21 days for cells obtained, selected, or enriched from at least at or about 75%, 80%, 85%, 90%, 95%, 97%, 98%, 99%, or at least 99.9% of samples from different subjects and has a success rate of at least 80%, 85%, 90%, 95%, 99%, or greater. In some embodiments, the process is completed within 21 days for cells obtained, selected, or enriched from at or at least at or about 90%, at or at least at or about 91%, at or at least at or about 92%, at or at least at or about 93%, at or at least at or about 94%, at or at least at or about 95%, at or at least at or about 96%, at or at least at or about 97%, at or at least at or about 98% or at or at least at or about 99%, or 100% of samples from different subjects. In some embodiments, the process has a success rate of at or at least at or about 90%, 91%, 92%, 93%, 94%, 95%, 96%, 97%, 98%, 99%, or 100% for producing engineered cells ready for infusion to a subject within 21 days from obtaining, selecting or enriching the cells from the subject. In certain embodiments, the process is completed within 21 days for cells obtained, selected, or enriched from at least at or about 75%, 80%, 85%, 90%, 95%, 97%, 98%, 99%, or at least 99.9% of samples from different subjects and has a success rate of at least 80%, 85%, 90%, 95%, 99%, or greater.

In particular embodiments, the process is completed between 14 days and 18 days for cells obtained, selected, or enriched from at least at or about 75%, 80%, 85%, 90%, 95%, 97%, 98%, 99%, or at least 99.9% of samples from different subjects and has a success rate of at least 80%, 85%, 90%, 95%, 99%, or greater. In certain embodiments, the process is completed between 14 days and 18 days for cells obtained, selected, or enriched from at least at or about 75%, 80%, 85%, 90%, 95%, 97%, 98%, 99%, or at least 99.9% of samples from different subjects and has a success rate of at least 80%, 85%, 90%, 95%, 99%, or greater.

In particular embodiments, the process associated with the provided methods has a probability or likelihood of successfully generating or producing an output composition that is greater than the probability or likelihood for an alternative and/or exemplary process of successfully generating or producing an output composition by at least at or about 0.5%, at least at or about 1%, at least at or about 1.5%, at least at or about 2%, at least at or about 2.5%, at least at or about 3%, at least at or about 3.5%, at least at or about 4.0%, at least at or about 4.5%, at least at or about 5%, at least at or about 5.5%, at least at or about 6%, at least at or about 6.5%, at least at or about 7%, at least at or about 7.5%, at least at or about 8%, at least at or about 8.5%, at least at or about 9%, at least at or about 9.5%, or at least at or about 10%, or by more than 10%.

G. Exemplary Features of the Output Compositions

In certain embodiments, the provided methods are used in connection with a process for generating or producing output cells and/or output compositions of enriched T cells.

In particular embodiments, the output cells and/or output compositions of enriched T cells are or include cells that were collected, obtained, isolated, selected, and/or enriched from the biological sample, such as a blood sample or leukapheresis sample; incubated under stimulating conditions; engineered, e.g., transduced, to express or contain a recombinant polynucleotide, e.g., a polynucleotide encoding a recombinant receptor such as a CAR; cultivated to a threshold amount, density, or expansion; and/or formulated. In some embodiments, the of the output composition have been previously cryofrozen and thawed, e.g., during, prior to, and/or after one or more steps of the process. In some embodiments, the output composition contains T cells, e.g., CD4+ T cells and CD8+ T cells, that express a recombinant receptor, e.g., a CAR.

In particular embodiments, the output composition is a composition of cells enriched for enriched CD3+ T cells. In some embodiments, the output composition is or includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD3+ T cells. In some embodiments, the output composition consists essentially of CD3+ T cells. In certain embodiments, the output composition is a composition of cells enriched for enriched CD4+ T cells and CD8+ T cells. In particular embodiments, the output composition is or includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% cells that are CD4+ or CD8+ T cells. In some embodiments, the output composition consists essentially of CD4+ and CD8+ T cells.

In particular embodiments, the output composition contains between at or about 10% and at or about 90%, between at or about 20% and at or about 80%, between at or about 25% and at or about 75%, between at or about 30% and at or about 70%, between at or about 35% and at or about 65%, between at or about 40% and at or about 60%, between at or about 55% and at or about 45%, or about 50% or 50% CD4+ T cells and at or about between at or about 10% and at or about 90%, between at or about 20% and at or about 80%, between at or about 25% and at or about 75%, between at or about 30% and at or about 70%, between at or about 35% and at or about 65%, between at or about 40% and at or about 60%, between at or about 55% and at or about 45%, or about 50% or 50% CD8+ T cells. In certain embodiments, the output composition contains between at or about 35% and at or about 65%, between at or about 40% and at or about 60%, between at or about 55% and at or about 45%, or about 50% or 50% CD4+ T cells and at or about between at or about 35% and at or about 65%, between at or about 40% and at or about 60%, between at or about 55% and at or about 45%, or about 50% or 50% CD8+ T cells. In particular embodiments, the output contains between at or about 35% and at or about 65% CD4+ T cells and at or about between at or about 35% and at or about 65% CD8+ T cells. In particular embodiments, the output composition contains a ratio of between 3:1 and 1:3, between 2.5:1 and 1:2.5, between 2:1 and 1:2, between 1.5:1 and 1:1.5, between 1.4:1 and 1:1.4, between 1.3:1 and 1:1.3, between 1.2:1 and 1:1.2, or between 1.1:1 and 1:1.1 CD4+ T cells to CD8+ T cells. In some embodiments, the composition of cells has a ratio of or of about 3:1, 2.8:1, 2.5:1, 2.25:1, 2:1, 1.8:1, 1.6:1, 1.5:1, 1.4:1, 1.3:1, 1.2:1, 1.1:1, 1.2:1, 1.1:1, 1:1, 1:1.1, 1:1.2, 1:1.3, 1:1.4, 1:1.5, 1:1.6, 1:1.8, 1:2, 1:2.25, 1:2.5, 1:2.8, 1:3.

In some embodiments, at least at or about 75%, at least at or about 80%, at least at or about 85%, at least at or about 90%, at least at or about 95%, at least at or about 97%, at least at or about 98%, or at least at or about 99% of the output compositions produced by the methods provided herein have a ratio of CD4+ T cells to CD8+ T cells of between 10:90 and 90:10, between 20:80 and 80:20, between 75:25 and 25:75, between 70:30 and 30:70, between 35:65 and 65:35, between 40:60 and 60:40, between 45:55 and 55:45, or about 50:50 or 50:50. In particular embodiments, at least 80%, at least 85%, or at least 90% of the output compositions produced by the methods provided herein have a ratio of between 3:1 and 1:3, between 2.5:1 and 1:2.5, between 2:1 and 1:2, between 1.5:1 and 1:1.5, between 1.4:1 and 1:1.4, between 1.3:1 and 1:1.3, between 1.2:1 and 1:1.2, or between 1.1:1 and 1:1.1 CD4+ T cells to CD8+ T cells. In certain embodiments, at least 90% of the output compositions produced by the methods provided herein have a ratio of CD4+ T cells to CD8+ T cells of between 1:2 and 2:1. In particular embodiments, at least 90% of the output compositions produced by the methods provided herein have a ratio of CD4+ T cells to CD8+ T cells of between 1.5:1 and 1:1.5, between 1.25:1 and 1:1.25, between 1.1:1 and 1:1.1.

In some embodiments, the output composition contains a ratio of between 3:1 and 1:3, between 2.5:1 and 1:2.5, between 2:1 and 1:2, between 1.5:1 and 1:1.5, between 1.4:1 and 1:1.4, between 1.3:1 and 1:1.3, between 1.2:1 and 1:1.2, or between 1.1:1 and 1:1.1 CD4+ T cells that express the recombinant receptor, e.g., the CAR, to CD8+ T cells that express the recombinant receptor, e.g., the CAR. In some embodiments, the composition of cells has a ratio of or of about 3:1, 2.8:1, 2.5:1, 2.25:1, 2:1, 1.8:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.8, 1:2, 1:2.25, 1:2.5, 1:2.8, 1:3.

In particular embodiments, at least 80%, at least 85%, or at least 90% of the output compositions produced by the methods provided herein have a ratio of between 3:1 and 1:3, between 2.5:1 and 1:2.5, between 2:1 and 1:2, between 1.5:1 and 1:1.5, between 1.4:1 and 1:1.4, between 1.3:1 and 1:1.3, between 1.2:1 and 1:1.2, or between 1.1:1 and 1:1.1 CD4+ T cells that express the recombinant receptor, e.g., the CAR, to CD8+ T cells that express the recombinant receptor, e.g., the CAR. In certain embodiments, at least 90% of the output compositions produced by the methods provided herein have a ratio of CD4+ T cells to CD8+ T cells of between 1:2 and 2:1. In particular embodiments, at least 90% of the output compositions produced by the methods provided herein have a ratio of CD4+ T cells to CD8+ T cells of between 1.5:1 and 1:1.5, between 1.25:1 and 1:1.25, between 1.1:1 and 1:1.1.

In some embodiments, an output composition generated or produced in connection with the provided methods contains cells expressing a recombinant receptor, e.g., a TCR or a CAR. In some embodiments, expressing a recombinant receptor may include, but is not limited to, having one or more recombinant receptor proteins localized at the cell membrane and/or cell surface, having a detectable amount of recombinant receptor protein, having a detectable amount of mRNA encoding the recombinant receptor, having or containing a recombinant polynucleotide that encodes the recombinant receptor, and/or having or containing an mRNA or protein that is a surrogate marker for recombinant receptor expression.

In some embodiments, at least at or about 30%, at least at or about 40%, at least at or about 45%, at least at or about 50%, at least at or about 55%, at least at or about 60%, at least at or about 65%, at least at or about 70%, at least at or about 75%, at least at or about 80%, at least at or about 85%, at least at or about 90%, at least at or about 95%, at least at or about 97%, at least at or about 99%, or more than 99% of the cells of the output composition express the recombinant receptor. In certain embodiments, at least at or about 50% of the cells of the output composition express the recombinant receptor. In certain embodiments, at least at or about 30%, at least at or about 40%, at least at or about 45%, at least at or about 50%, at least at or about 55%, at least at or about 60%, at least at or about 65%, at least at or about 70%, at least at or about 75%, at least at or about 80%, at least at or about 85%, at least at or about 90%, at least at or about 95%, at least at or about 97%, at least at or about 99%, or more than 99% of the CD3+ T cells of the output composition express the recombinant receptor. In some embodiments, at least at or about 50% of the CD3+ T cells of the output composition express the recombinant receptor. In particular embodiments, at least at or about at least at or about 30%, at least at or about 40%, at least at or about 45%, at least at or about 50%, at least at or about 55%, at least at or about 60%, at least at or about 65%, at least at or about 70%, at least at or about 75%, at least at or about 80%, at least at or about 85%, at least at or about 90%, at least at or about 95%, at least at or about 97%, at least at or about 99%, or more than 99% of the CD4+ T cells of the output composition express the recombinant receptor. In particular embodiments, at least at or about 50% of the CD4+ T cells of the output composition express the recombinant receptor. In some embodiments, at least at or about at least at or about 30%, at least at or about 40%, at least at or about 45%, at least at or about 50%, at least at or about 55%, at least at or about 60%, at least at or about 65%, at least at or about 70%, at least at or about 75%, at least at or about 80%, at least at or about 85%, at least at or about 90%, at least at or about 95%, at least at or about 97%, at least at or about 99%, or more than 99% of the CD8+ T cells of the output composition express the recombinant receptor. In certain embodiments, at least at or about 50% of the CD8+ T cells of the output composition express the recombinant receptor.

In particular embodiments, the output composition contains at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% viable cells. In some embodiments, the output composition contains at least at or about 75% viable cells. In certain embodiments, the output composition contains at least at or about 85%, at least at or about 90%, or at least at or about 95% viable cells. In some embodiments, the output composition contains at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% viable CD3+ T cells. In particular embodiments, the output composition contains at least at or about 75% viable CD3+ T cells. In certain embodiments, the output composition contains at least at or about 85%, at least at or about 90%, or at least at or about 95% viable CD3+ T cells. In some embodiments, the output composition contains at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% viable CD4+ T cells. In certain embodiments, the output composition contains at least at or about 75% viable CD4+ T cells. In particular embodiments, the output composition contains at least at or about 85%, at least at or about 90%, or at least at or about 95% viable CD4+ T cells. In particular embodiments, the output composition contains at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% viable CD8+ T cells. In some embodiments, the output composition contains at least at or about 75% viable CD8+ T cells. In certain embodiments, the output composition contains at least at or about 85%, at least at or about 90%, or at least at or about 95% viable CD8+ T cells.

In particular embodiments, the output cells have a low portion and/or frequency of cells that are undergoing and/or are prepared, primed, and/or entering apoptosis. In particular embodiments, the output cells have a low portion and/or frequency of cells that are positive for an apoptotic marker. In some embodiments, less than at or about 40%, less than at or about 35%, less than at or about 30%, less than at or about 25%, less than at or about 20%, less than at or about 15%, less than at or about 10%, less than at or about 5%, or less than at or about 1% of the cells of the output composition express, contain, and/or are positive for an apoptotic marker. In certain embodiments, less than at or about 25% of the cells of the output composition express, contain, and/or are positive for a marker of apoptosis. In certain embodiments, less than at or about less than at or about 10% cells of the output composition express, contain, and/or are positive for an apoptotic marker.

In particular embodiments, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of recombinant receptor-expressing (e.g., CAR+) cells of the output composition are viable cells, e.g., cells negative for an apoptotic marker, such as a caspase (e.g., an activated caspase-3). In certain embodiments, at least at or about 85%, at least at or about 90%, or at least at or about 95% of recombinant receptor-expressing (e.g., CAR+) cells of the output composition are viable cells, e.g., cells negative for an apoptotic marker, such as a caspase (e.g., an activated caspase-3). In some embodiments, at least at or about 90% of recombinant receptor-expressing (e.g., CAR+) cells of the output composition are viable cells, e.g., cells negative for an apoptotic marker, such as a caspase (e.g., an activated caspase-3). In some embodiments, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of CD3+ T cells of the output composition are viable cells, e.g., cells negative for an apoptotic marker, such as a caspase (e.g., an activated caspase-3). In certain embodiments, at least at or about 85%, at least at or about 90%, or at least at or about 95% of CD3+ T cells of the output composition are viable cells, e.g., cells negative for an apoptotic marker, such as a caspase (e.g., an activated caspase-3). In particular embodiments, at least at or about 90% of CD3+ T cells of the output composition are viable cells, e.g., cells negative for an apoptotic marker, such as a caspase (e.g., an activated caspase-3). In some embodiments, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of recombinant receptor-expressing (e.g., CAR+) CD3+ T cells of the output composition are viable cells, e.g., cells negative for an apoptotic marker, such as a caspase (e.g., an activated caspase-3). In particular embodiments, at least at or about 85%, at least at or about 90%, or at least at or about 95% of recombinant receptor-expressing (e.g., CAR+) CD3+ T cells of the output composition are viable cells, e.g., cells negative for an apoptotic marker, such as a caspase (e.g., an activated caspase-3). In certain embodiments, at least at or about 90% of recombinant receptor-expressing (e.g., CAR+) CD3+ T cells of the output composition are viable cells, e.g., cells negative for an apoptotic marker, such as a caspase (e.g., an activated caspase-3).

In particular embodiments, on average, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of recombinant receptor-expressing (e.g., CAR+) cells of a plurality of output compositions produced by the method disclosed herein are viable cells, e.g., cells negative for an apoptotic marker, such as a caspase (e.g., an activated caspase-3). In certain embodiments, on average, at least at or about 85%, at least at or about 90%, or at least at or about 95% of recombinant receptor-expressing (e.g., CAR+) cells of a plurality of output compositions produced by the method disclosed herein are viable cells, e.g., cells negative for an apoptotic marker, such as a caspase (e.g., an activated caspase-3). In some embodiments, on average, at least at or about 90% of recombinant receptor-expressing (e.g., CAR+) cells of a plurality of output compositions produced by the method disclosed herein are viable cells, e.g., cells negative for an apoptotic marker, such as a caspase (e.g., an activated caspase-3). In some embodiments, on average, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of CD3+ T cells of a plurality of output compositions produced by the method disclosed herein are viable cells, e.g., cells negative for an apoptotic marker, such as a caspase (e.g., an activated caspase-3). In certain embodiments, on average, at least at or about 85%, at least at or about 90%, or at least at or about 95% of CD3+ T cells of a plurality of output compositions produced by the method disclosed herein are viable cells, e.g., cells negative for an apoptotic marker, such as a caspase (e.g., an activated caspase-3). In particular embodiments, on average, at least at or about 90% of CD3+ T cells of a plurality of output compositions produced by the method disclosed herein are viable cells, e.g., cells negative for an apoptotic marker, such as a caspase (e.g., an activated caspase-3). In some embodiments, on average, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of recombinant receptor-expressing (e.g., CAR+) CD3+ T cells of a plurality of output compositions produced by the method disclosed herein are viable cells, e.g., cells negative for an apoptotic marker, such as a caspase (e.g., an activated caspase-3). In particular embodiments, on average, at least 85%, at least 90%, or at least 95% of recombinant receptor-expressing (e.g., CAR+) CD3+ T cells of a plurality of output compositions produced by the method disclosed herein are viable cells, e.g., cells negative for an apoptotic marker, such as a caspase (e.g., an activated caspase-3). In certain embodiments, on average, at least 90% of recombinant receptor-expressing (e.g., CAR+) CD3+ T cells of a plurality of output compositions produced by the method disclosed herein are viable cells, e.g., cells negative for an apoptotic marker, such as a caspase (e.g., an activated caspase-3). In any of the proceeding embodiments, the plurality of output compositions produced by the method disclosed herein may be originated from the same or different donors. In some aspects, at least two of the plurality of output compositions are originated from different donors. In some aspects, each of the plurality of output compositions is originated from one of a number of different donors, e.g., from about 2, about 5, about 10, about 15, about 20, about 25, about 30, about 35, about 40, about 45, about 50, about 55, about 60, or more than about 60 different donors, e.g., patients in need of a cell therapy such as a CAR-T cell therapy.

In particular embodiments, a majority of the cells of the output composition are naïve, central memory, and/or effector memory cells. In particular embodiments, a majority of the cells of the output composition are naïve or central memory cells. In some embodiments, a majority of the cells of the output composition are central memory cells. In some aspects, less differentiated cells, e.g., central memory cells, are longer lived and exhaust less rapidly, thereby increasing persistence and durability. In some aspects, a responder to a cell therapy, such as a CAR-T cell therapy, has increased expression of central memory genes. See, e.g., Fraietta et al. (2018) Nat Med. 24(5):563-571.

In certain embodiments, the cells of the output composition have a high portion and/or frequency of central memory cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the cells of the output composition are of a memory phenotype, are of a central memory phenotype, or are central memory T cells. In certain embodiments, at least or at or about 50%, at least or at or about 55%, at least or at or about 60%, or at least or at or about 65% of the cells of the output composition are central memory T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the cells of the output composition are of a memory phenotype, are of a central memory phenotype, or are central memory T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the T cells of the output composition are of a memory phenotype, are of a central memory phenotype, or are central memory T cells. In certain embodiments, at least or at or about 50%, at least or at or about 55%, at least or at or about 60%, or at least or at or about 65% of the T cells of the output composition are of a memory phenotype, are of a central memory phenotype, or are central memory T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the T cells of the output composition are of a memory phenotype, are of a central memory phenotype, or are central memory T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD4+ T cells of the output composition are central memory CD4+ T cells. In certain embodiments, at least or at or about 50%, at least or at or about 55%, at least or at or about 60%, or at least or at or about 65% of the CD4+ T cells of the output composition are central memory CD4+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD4+ T cells of the output composition are central memory CD4+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD4+ CAR+ T cells of the output composition are central memory CD4+ CAR+ T cells. In certain embodiments, at least or at or about 50%, at least or at or about 55%, at least or at or about 60%, or at least or at or about 65% of the CD4+ CAR+ T cells of the output composition are central memory CD4+ CAR+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD4+ CAR+ T cells of the output composition are central memory CD4+ CAR+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, or greater than 95% of the CD8+ T cells of the output composition are central memory CD8+ T cells. In certain embodiments, at least or at or about 50%, at least or at or about 55%, at least or at or about 60%, or at least or at or about 65% of the CD8+ T cells of the output composition are central memory CD8+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD8+ T cells of the output composition are central memory CD8+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, or greater than 95% of the CD8+ CAR+ T cells of the output composition are central memory CD8+ CAR+ T cells. In certain embodiments, at least or at or about 50%, at least or at or about 55%, at least or at or about 60%, or at least or at or about 65% of the CD8+ CAR+ T cells of the output composition are central memory CD8+ CAR+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD8+ CAR+ T cells of the output composition are central memory CD8+ CAR+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of CAR+ T cells (e.g., the CD4+ T cells and CD8+ T cells) of the output composition are central memory CD4+ or CD8+ T cells. In certain embodiments, at least or at or about 50%, at least or at or about 55%, at least or at or about 60%, or at least or at or about 65% of the CAR+ T cells (e.g., CD4+ T cells and CD8+ T cells) of the output composition are central memory CD4+ or CD8+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the cells in the composition are CD27+, CD28+, CCR7+, CD45RA−, CD45RO+, CD62L+, CD3+, CD95+, granzyme B−, and/or CD127+. In some embodiments, at least or at or about 50%, at least or at or about 55%, at least or at or about 60%, or at least or at or about 65% of the CAR+ T cells in the composition are CD27+, CD28+, CCR7+, CD45RA−, CD45RO+, CD62L+, CD3+, CD95+, granzyme B−, and/or CD127+.

In some embodiments, iterations of the method produce a plurality of the output compositions, optionally from human biological samples in which the method is carried out among a plurality of different individual subjects. In some embodiments, the average (i.e., mean) or median percentage of cells of a memory phenotype in the plurality of the output compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of cells of a central memory phenotype in the plurality of the output compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of cells that are CD27+, CD28+, CCR7+, CD45RA−, CD45RO+, CD62L+, CD3+, CD95+, granzyme B−, and/or CD127+ in the plurality of the output compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of cells that are CCR7+/CD45RA− or CCR7+/CD45RO+ in the plurality of the output compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of central memory CD4+ T cells in the engineered CD4+ T cells (e.g., CAR+CD4+ T cells) of the plurality of the output compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of central memory CD8+ T cells in the engineered CD8+ T cells (e.g., CAR+CD8+ T cells) of the plurality of the output compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of central memory T cells (e.g., CD4+ central memory T cells and CD8+ central memory T cells) in the engineered T cells (e.g., CAR+ T cells) of the plurality of the output compositions is between at or about 40% and at or about 65%, between at or about 40% and at or about 45%, between at or about 45% and at or about 50%, between at or about 55% and at or about 60%, or between at or about 60% and at or about 65%.

In some embodiments, on average, at least at or about 30%, at least at or about 40%, at least at or about 50%, at least at or about 60%, at least at or about 70%, at least at or about 75%, at least at or about 80%, at least at or about 85%, at least at or about 90%, at least at or about 95%, or greater than at or about 95% of the cells of a plurality of output compositions produced by the method disclosed herein are of a memory phenotype, are of a central memory phenotype, or are central memory T cells. In certain embodiments, on average, at least at or about 50%, at least at or about 55%, at least at or about 60%, or at least at or about 65% of the cells of a plurality of output compositions produced by the method disclosed herein are of a memory phenotype, are of a central memory phenotype, or are central memory T cells. In some embodiments, on average, at least at or about 30%, at least at or about 40%, at least at or about 50%, at least at or about 60%, at least at or about 70%, at least at or about 75%, at least at or about 80%, at least at or about 85%, at least at or about 90%, at least at or about 95%, or greater than at or about 95% of the cells of a plurality of output compositions produced by the method disclosed herein are CD27+, CD28+, CCR7+, CD45RA−, CD45RO+, CD62L+, CD3+, CD95+, granzyme B−, and/or CD127+. In some embodiments, at least at or about 50%, at least at or about 55%, at least at or about 60%, or at least at or about 65% of the cells of a plurality of output compositions produced by the method disclosed herein are CD27+, CD28+, CCR7+, CD45RA−, CD45RO+, CD62L+, CD3+, CD95+, granzyme B−, and/or CD127+. In some embodiments, on average, at least at or about 30%, at least at or about 40%, at least at or about 50%, at least at or about 60%, at least at or about 70%, at least at or about 75%, at least at or about 80%, at least at or about 85%, at least at or about 90%, at least at or about 95%, or greater than at or about 95% of the T cells of a plurality of output compositions produced by the method disclosed herein are of a memory phenotype, are of a central memory phenotype, or are central memory T cells. In certain embodiments, on average, at least at or about 50%, at least at or about 55%, at least at or about 60%, or at least at or about 65% of the T cells of a plurality of output compositions produced by the method disclosed herein are of a memory phenotype, are of a central memory phenotype, or are central memory T cells. In some embodiments, on average, at least at or about 30%, at least at or about 40%, at least at or about 50%, at least at or about 60%, at least at or about 70%, at least at or about 75%, at least at or about 80%, at least at or about 85%, at least at or about 90%, at least at or about 95%, or greater than at or about 95% of the CD4+ T cells of a plurality of output compositions produced by the method disclosed herein are central memory CD4+ T cells. In certain embodiments, on average, at least at or about 50%, at least at or about 55%, at least at or about 60%, or at least at or about 65% of the CD4+ T cells of a plurality of output compositions produced by the method disclosed herein are central memory CD4+ T cells. In some embodiments, on average, at least at or about 30%, at least at or about 40%, at least at or about 50%, at least at or about 60%, at least at or about 70%, at least at or about 75%, at least at or about 80%, at least at or about 85%, at least at or about 90%, at least at or about 95%, or greater than at or about 95% of the CD8+ T cells of a plurality of output compositions produced by the method disclosed herein are central memory CD8+ T cells. In certain embodiments, on average, at least at or about 50%, at least at or about 55%, at least at or about 60%, or at least at or about 65% of the CD8+ T cells of a plurality of output compositions produced by the method disclosed herein are central memory CD8+ T cells. In some embodiments, on average, at least at or about 30%, at least at or about 40%, at least at or about 50%, at least at or about 60%, at least at or about 70%, at least at or about 75%, at least at or about 80%, at least at or about 85%, at least at or about 90%, at least at or about 95%, or greater than at or about 95% of the CD4+ T cells and CD8+ T cells of a plurality of output compositions produced by the method disclosed herein are central memory CD4+ or CD8+ T cells. In certain embodiments, on average, at least at or about 50%, at least at or about 55%, at least at or about 60%, or at least at or about 65% of the CD4+ T cells and CD8+ T cells of a plurality of output compositions produced by the method disclosed herein are central memory CD4+ or CD8+ T cells. In any of the proceeding embodiments, the plurality of output compositions produced by the method disclosed herein may be originated from the same or different donors. In some aspects, at least two of the plurality of output compositions are originated from different donors. In some aspects, each of the plurality of output compositions is originated from one of a number of different donors, e.g., from about 2, about 5, about 10, about 15, about 20, about 25, about 30, about 35, about 40, about 45, about 50, about 55, about 60, or more than about 60 different donors, e.g., patients in need of a cell therapy such as a CAR-T cell therapy.

In certain embodiments, the cells of the output composition have a low portion and/or frequency of cells that are exhausted and/or senescent. In particular embodiments, the cells of the output composition have a low portion and/or frequency of cells that are exhausted and/or senescent. In some embodiments, less than at or about 40%, less than at or about 35%, less than at or about 30%, less than at or about 25%, less than at or about 20%, less than at or about 15%, less than at or about 10%, less than at or about 5%, or less than at or about 1% of the cells of the output composition are exhausted and/or senescent. In certain embodiments, less than at or about 25% of the cells of the output composition are exhausted and/or senescent. In certain embodiments, less than at or about less than at or about 10% of the cells of the output composition are exhausted and/or senescent.

In some embodiments, the cells of the output composition have a low portion and/or frequency of cells that are negative for CD27 and CD28 expression, e.g., surface expression. In particular embodiments, the cells of the output composition have a low portion and/or frequency of CD27–CD28– cells. In some embodiments, less than at or about 40%, less than at or about 35%, less than at or about 30%, less than at or about 25%, less than at or about 20%, less than at or about 15%, less than at or about 10%, less than at or about 5%, or less than at or about 1% of the cells of the output composition are CD27–CD28– cells. In certain embodiments, less than at or about 25% of the cells of the output composition are CD27–CD28– cells. In certain embodiments, less than at or about less than at or about 10% of the cells of the output composition are CD27–CD28– cells. In embodiments, less than at or about 5% of the cells of the output composition are CD27–CD28– cells.

In certain embodiments, the cells of the output composition have a high portion and/or frequency of cells that are positive for CD27 and CD28 expression, e.g., surface expression. In some embodiments, the cells of the output composition have a high portion and/or frequency of CD27+CD28+ cells. In some embodiments, at least at or about 50%, at least at or about 60%, at least at or about 70%, at least at or about 75%, at least at or about 80%, at least at or about 85%, at least at or about 90%, at least at or about 95%, or greater than at or about 95% of the cells of the output composition are CD27+CD28+ cells. In certain embodiments, less than at or about 25% of the cells of the output composition are CD27–CD28– cells. In certain embodiments, at least at or about 50% of the cells of the output composition are CD27+CD28+ cells. In embodiments, at least at or about 75% of the cells of the output composition are CD27+CD28+ cells.

In particular embodiments, the cells of the output composition have a low portion and/or frequency of cells that are $T_{EMRA}$ cells. In particular embodiments, the cells of the output composition have a low portion and/or frequency of $T_{EMRA}$ cells. In some embodiments, less than at or about 40%, less than at or about 35%, less than at or about 30%, less than at or about 25%, less than at or about 20%, less than at or about 15%, less than at or about 10%, less than at or about 5%, or less than at or about 1% of the cells of the output composition are $T_{EMRA}$ cells. In some embodiments, less than at or about 25% of the cells of the output composition are $T_{EMRA}$ cells. In some embodiments, less than at or about 10% of the cells of the output composition are $T_{EMRA}$ cells. In some embodiments, less than at or about 5% of the cells of the output composition are $T_{EMRA}$ cells.

In certain embodiments, the cells of the output composition have a low portion and/or frequency of cells that are negative for CCR7 and positive for CD45RA expression, e.g., surface expression. In some embodiments, the cells of the output composition have a low portion and/or frequency of CCR7-CD45RA+ cells. In particular embodiments, less than at or about 40%, less than at or about 35%, less than at or about 30%, less than at or about 25%, less than at or about 20%, less than at or about 15%, less than at or about 10%, less than at or about 5%, or less than at or about 1% of the cells of the output composition are CCR7-CD45RA+ cells. In some embodiments, less than at or about 25% of the cells of the output composition are CCR7-CD45RA+ cells. In particular embodiments, less than at or about less than at or about 10% of the cells of the output composition are CCR7-CD45RA+ cells. In certain embodiments, less than at or about 5% of the cells of the output composition are CCR7-CD45RA+ cells.

In certain embodiments, the cells of the output composition have a similar cytokine production in response to antigen-stimulation as output cells produced by an alternative process. In some embodiments, the cells of the output composition have a similar production of a cytokine, e.g., TNF-alpha, IFN-gamma, and/or IL-2, in response to antigen-stimulation as output cells produced by the exemplary, alternative process. In some embodiments, the cells of the output composition have, have about, or have at least a 50%, 60%, 70%, 75%, 80%, 90%, 100%, 125%, 150%, 1-fold, 2-fold, 3-fold, 4-fold, or 5-fold increase in the production of one or more cytokines in response to stimulation by an antigen compared to an alternative process. In some embodiments, the production of a cytokine may be measured or assessed by standard known techniques, including but not limited to ELISA and/or antibody based detection methods.

In particular embodiments, the cells of the output composition have a similar portion, percentage, and/or amount of cells that produce one or more cytokines in response to antigen-stimulation as the portion, percentage, and/or amount of the output cells produced by an alternative process. In certain embodiments, about or at least 10%, 20%, 25%, 30%, 40%, 50%, 60%, 70%, 75%, 80%, 90%, 95%, or 100% of the cells of the output composition produce the one or more cytokines, e.g., TNF-alpha, IFN-gamma, and/or IL-2, in response to antigen-stimulation. In particular embodiments, the portion, percentage, and/or amount of cells of the output composition that produce the one or more cytokines is about or at least 5%, 10%, 15%, 20%, 25%, 30%, 35%, 40%, 45%, 50%, 75%, 100%, 125%, 150%, or 1-fold, 2-fold, 3-fold, greater than the portion, percentage, and/or amount of output cells produced by the alternative process that produce the one or more cytokines. In certain embodiments, the portion, percentage, and/or amount of the cells that produce a cytokine may be measured or assessed by any known or standard technique, including intracellular cytokine staining (ICS) assays.

In particular embodiments, the output composition contains functional cells that express a recombinant receptor, e.g., a CAR. In some embodiments, at least a portion of the cells that express a recombinant receptor produce one or more cytokines in response to antigen stimulation. In some embodiments, the one or more cytokines include, but are not limited to, IL-2, TNF-alpha, and/or IFN-gamma. In some embodiments, cells of the output composition, e.g., a sample and/or a portion of the output cells, are tested, assessed, and/or measured for antigen stimulated function and/or activity. In certain embodiments, the cells are tested for cytokine production following or during antigen stimulation by any known assay capable of measuring cytokine production, expression, and/or secretion. In some embodiments, the cells are tested with internal cytokine staining (ICS) assay. In particular embodiments, at least 25% CD4+ cells and at least 15% of CD8+ cells that express a recombinant receptor are positive for IL-2 following antigen stimulation as measured by ICS. In some embodiments, at least 5% CD4+ cells and at least 5% of CD8+ cells that express a recombinant receptor are positive for IFN-gamma following antigen stimulation as measured by ICS. In certain embodiments, at least 40% CD4+ cells and at least 20% of CD8+ cells that express a recombinant receptor are positive for TNF-alpha following antigen stimulation as measured by ICS. In certain embodiments, at least 2.5% of the CD4+ cells and at least 2% of the CD8+ cells that express a recombinant receptor are positive for all of IL-2, IFN-gamma, and TNF-alpha following antigen stimulation as measured by ICS.

In certain embodiments, at least a portion of the cells that express a recombinant receptor produce one or more cytokines in response to activation or stimulation, e.g., general activation or stimulation, T cell activation or stimulation and/or activation or stimulation by PMA and ionomycin. In some embodiments, the one or more cytokines include, but are not limited to, IL-2, TNF-alpha, and/or IFN-gamma. In certain embodiments, cells of the output composition, e.g., a sample and/or a portion of the output cells, are tested, assessed, and/or measured for function and/or activity by activation or stimulation, e.g., with PMA and ionomycin. In certain embodiments, the cells are tested for cytokine production following or during activation or stimulation by any known assay capable of measuring cytokine production, expression, and/or secretion, such as with an ICS assay. In some embodiments, the cells are stimulated with PMA and ionomycin and are assessed with an ICS assay. In some embodiments, at least 50% CD4+ cells and at least 25% of CD8+ cells that express a recombinant receptor are positive for IL-2 following stimulation or activation with PMA and ionomycin as measured by ICS. In some embodiments, at least 30% CD4+ cells and at least 10% of CD8+ cells that express a recombinant receptor are positive for IFN-gamma following stimulation or activation with PMA and ionomycin as measured by ICS. In certain embodiments, at least 50% CD4+ cells and at least 15% of CD8+ cells that express a recombinant receptor are positive for TNF-alpha following stimulation or activation with PMA and ionomycin as measured by ICS. In certain embodiments, at least 10% of the CD4+ cells and at least 5% of the CD8+ cells that express a recombinant receptor are positive for all of IL-2, IFN-gamma, and TNF-alpha following stimulation or activation with PMA and ionomycin as measured by ICS.

In some embodiments, administering the cells of the output composition to a subject, e.g., a subject with a disease or condition such as a cancer, improves the probability and/or likelihood of survival. For example, in some embodiments, the cells of the output composition are administered to a subject with disease or condition, the probability and/or likelihood of survival over, over about, or over at least 2, 3, 4, 5, 6, 7, 8, 9, 10, 11, or 12 months, or over 1, 2, 3, 4, 5, 10, or more than 10 years is at least 30%, 40%, 50%, 60%, 70%, 80%, 90%, or 100%. In certain embodiments, the administration with the cells of the output composition provides at least a 10%, 20%, 25%, 30%, 40%, 50%, 60%, 70%, 80%, 90%, 100%, 125%, 150%, or at least a 1-fold, 2-fold, 3-fold, 4-fold, or 5-fold greater probability and/or likelihood of survival than administration with output cells of an alternative process.

In certain embodiments, the cells of the output composition are administered to a subject. In some embodiments, the cells of the output composition are administered to treat a disease or condition. In some embodiments, the disease or condition is cancer. In some embodiments, the cells the output compositions are administered to the subject, and the subject experiences a reduction in cancer cells and/or tumor volume. In some embodiments, the subject has, has about, or has at least a 25%, 50%, 60%, 70%, 75%, 80%, 85%, 90%, 95%, 97%, 98%, 99%, 100% reduction of the amount of cancer cells and/or tumor reduction following administration of the cells of the output composition, e.g., as compared to the amount of cancer cells and/or the tumor volume in the subject prior to the administration. In some embodiments, administration of cells of the output composition results in an increased reduction of tumor volume and/or the amount of cancer cells in the subject as compared to the reduction of tumor volume and/or the amount of cancer cells in the subject following administration of output cells produced by an exemplary alternative process In particular embodiments, administration of cells of the output composition results in an increase in the reduction of tumor volume and/or the amount of cancer cells in the subject of, of about, or of at least 5%, 10%, 20%, 30%, 40%, 50%, 60%, 70%, 80%, 90%, 100%, 125%, 150%, 1-fold, 2-fold, 3-fold, 4-fold, of 5-fold, as compared to the reduction of tumor volume and/or the amount of cancer cells in the subject following administration of output cells produced by the exemplary alternative process.

In particular embodiments, cells of the output composition, e.g., a portion and/or a dose of cells of the output composition, are administered to a subject. In some embodiments, the subject that is administered cells of the output composition has a probability and/or a likelihood of achieving and/or experiencing a complete response (CR). In certain embodiments, the likelihood and/or probability of achieving and/or experiencing CR is at least at or about 10%, at least at or about 15%, at least at or about 20%, at least at or about 25%, at least at or about 30%, at least at or about 35%, at least at or about 40%, at least at or about 45%, at least at or about 50%, at least at or about 55%, at least at or about 60%, at least at or about 70%, at least at or about 80%, at least at or about 90%, or at least at or about 95%. In certain embodiments, the probability and/or likelihood of achieving and/or experiencing CR is at least at or about 25%. In particular embodiments, the probability and/or likelihood of achieving CR is at least at or about 50%.

In certain embodiments, the subject that is administered cells of the output composition has a probability and/or a likelihood of achieving and/or experiencing ORR. In certain embodiments, the likelihood and/or probability of achieving and/or experiencing ORR is at least at or about at least at or about 40%, at least at or about 45%, at least at or about 50%, at least at or about 55%, at least at or about 60%, at least at or about 70%, at least at or about 80%, at least at or about 90%, or at least at or about 95%. In certain embodiments, the probability and/or likelihood of achieving and/or experiencing ORR is at least at or about 80%. In particular embodiments, the probability and/or likelihood of achieving ORR is at least at or about 90%. In certain embodiments, the probability and/or likelihood of achieving ORR is or is about 100%.

In some embodiments, the efficacy of the output cells, e.g., the probability that a subject will achieve and/or experience CR or ORR following administration of cells of the output composition, is greater than that of a therapeutic cell composition containing cells expressing a recombinant receptor that are produced by an alternative process. In certain embodiments, there is an at least at or about 5%, 10%, 15%, 20%, 25%, 30%, 40%, 50%, 60%, 70%, 80%, 90%, 100%, 125%, 150%, 1-fold, 2-fold, 5-fold, 10-fold, 50-fold, or 100-fold greater probability of achieving CR or ORR following administration of the output cells as compared to administration of the cells of the therapeutic cell composition that are produced by the alternative process.

In particular embodiments, the cells of the output composition have a similar cytolytic activity towards cells expressing an antigen bound by and/or recognized by the recombinant receptor (e.g., target cells) as output cells produced by an exemplary, alternative process. In some embodiments, when the cells of the output composition are exposed to the cells that express the antigen, e.g., the target cells, the cells of the output composition kill, kill about, or kill at least at or about 25%, 30%, 35%, 40%, 45%, 50%, 55%, 60%, 70%, 75%, 80%, 85%, 90%, 95%, or 100% of cells that express the antigen. In certain embodiments, the cells of the output composition kill at least at or about 25%, 50%, 75%, 100%, 150%, or 1-fold, 2-fold, 3-fold, 4-fold, or 5-fold greater amount of cells that express the antigen, e.g., target cells, than output cells produced by an exemplary alternative process under similar or the same conditions.

In some embodiments, the output cells produced by the methods provided herein have a high and/or a relatively high degree of safety. In some embodiments, cells of the output composition, e.g., a portion and/or a dose of cells of the output composition, are administered to a subject. In some embodiments, the subject that is administered cells of the output composition has a risk, probability, and/or a likelihood of experiencing a toxicity, e.g., CRS or neurotoxicity, that is less than at or about 80%, 75%, 70%, 60%, 50%, 40%, 30%, 25%, 20%, 15%, 10%, or 5%. In some embodiments, the toxicity is any grade of neurotoxicity or CRS. In certain embodiments, the subject administered cells of the output composition has a risk, probability, and/or likelihood of less than 80% for experiencing any grade of CRS or neurotoxicity. In particular embodiments, the subject administered cells of the output composition has a risk, probability, and/or likelihood of less than 80% for experiencing any grade of CRS or neurotoxicity.

In some embodiments, the subject that is administered cells of the output composition has a risk, probability, and/or a likelihood of experiencing a grade 3 or higher CRS that is less than at or about 50%, 40%, 30%, 25%, 20%, 15%, 10%, or 5%. In some embodiments, the subject administered cells of the output composition has a risk, probability, and/or likelihood of less than 10% for experiencing a grade 3 or higher CRS. In some embodiments, the subject administered cells of the output composition has a risk, probability, and/or likelihood of less than 5% for experiencing a grade 3 or higher CRS.

In certain embodiments, the subject that is administered cells of the output composition has a risk, probability, and/or a likelihood of experiencing a grade 3 or higher neurotoxicity that is less than at or about 50%, 40%, 30%, 25%, 20%, 15%, 10%, or 5%, or that is or is about 0%, and/or is negligible. In some embodiments, the subject administered cells of the output composition has a risk, probability, and/or likelihood of less than 5% for experiencing a grade 3 or higher neurotoxicity. In some embodiments, the subject administered cells of the output composition has a risk, probability, and/or likelihood of about 0% and/or a negligible risk for experiencing a grade 3 or higher neurotoxicity.

II. SERUM-FREE MEDIA FORMULATIONS AND RELATED COMPONENTS

The present application provides a serum-free media containing a synthetic amino acid (e.g., a dipeptide form of L-glutamine, e.g., L-alanyl-L-glutamine), a free form of glutamine (i.e., L-glutamine), and at least one protein. The present application also provides a liquid basal medium comprising at least one synthetic amino acid (e.g., a dipeptide form of L-glutamine, e.g., L-alanyl-L-glutamine), wherein the basal medium is free of a free form of glutamine (i.e., L-glutamine) and a protein. The present application also provides a frozen supplement comprising a free form of glutamine (i.e., L-glutamine), and, in some cases, at least one protein, such as a serum-substituting protein. One or more further supplements can be added, including one or more supplements containing at least one protein, such as a serum-substituting protein, or one or more other components supporting growth and expansion of cells. In some embodiments, the concentration of the synthetic amino acid (e.g., a dipeptide form of L-glutamine, e.g., L-alanyl-L-glutamine) is at or about 0.5 mM to at or about 5 mM (such as 2 mM). In some embodiments, the concentration of L-glutamine is at or about 0.5 mM to at or about 5 mM (such as 2 mM). In some embodiments, the at least one protein is a human protein or a recombinant protein, such as a serum-substituting protein, e.g. albumin. In some embodiments, the serum free media further comprises one or more cytokine (such as IL-2, IL-7, or IL-15). In some embodiments, the serum-free media does not comprise phenol red.

In some embodiments, the provided serum-free media is produced or prepared from a liquid basal medium and one or more supplements.

In some embodiments, there is provided a liquid basal medium containing a synthetic amino acid that is capable of being converted into L-glutamine in a cell culture, such as a synthetic amino acid that is a dipeptide form of L-glutamine, e.g., L-alanyl-L-glutamine. In some cases, the basal medium is free of L-glutamine and a protein. In some embodiments, the concentration of the synthetic amino acid (e.g., a dipeptide form of L-glutamine, e.g., L-alanyl-L-glutamine) is at or about 0.5 mM to at or about 5 mM (such as 2 mM). In some embodiments, the at least one protein is a human-derived protein, a recombinant protein, or both. In some embodiments, the basal medium does not comprise phenol red.

In some embodiments, there is provided a supplement comprising at least one protein and a free form of glutamine, e.g. L-glutamine, wherein the supplement is frozen or has been frozen after L-glutamine becomes a component thereof. In some embodiments, the concentration of L-glutamine in the supplement is less than 200 mM, such as less than 150 mM, 100 mM or less, such as 20 mM to 120 mM, or 40 mM to 100 mM, such as or about 80 mM. In some embodiments, the concentration of L-glutamine after the supplement has been combined with basal medium is about 0.5 mM to about 5 mM (such as 2 mM). In some embodiments, the at least one protein is not of a non-mammalian origin. In some embodiments, the at least one protein is a human protein or a human-derived protein or is recombinant. In some embodiments, the at least one protein includes albumin, e.g. human or recombinant human albumin.

A. Basal Medium

In some embodiments, the basal medium comprises an amino acid. In some embodiments, the amino acid comprises aspartic acid, glutamic acid, asparagine, serine, glutamine, histidine, glycine, threonine, arginine, alanine, tyrosine, cysteine, valine, methionine, norvaline, tryptophan, phenylalanine, isoleucine, leucine, lysine, hydroxyproline, sarcosine, and/or proline.

In some embodiments, the basal medium comprises at least one synthetic amino acid. In some embodiments, the synthetic amino acid is capable of being converted into a free form of glutamine (i.e., L-glutamine) in a cell culture comprising a cell. In some embodiments, the cell comprises a human cell. In some embodiments, the cell comprises an immune cell. In some embodiments, the cell is a genetically engineered cell. In some embodiments, the cell is a T cell. In some embodiments, the cell is a genetically engineered T cell. In some embodiments, the cell is genetically engineered to express a recombinant receptor (e.g., a chimeric antigen receptor). In some embodiments, the cell is a chimeric antigen receptor (CAR) expressing T cells.

In some embodiments, the synthetic amino acid is a stabilized form of glutamine (i.e., L-glutamine). In some embodiments, the synthetic amino acid is more stable than glutamine (i.e., L-glutamine) in an aqueous solution (e.g., a basal medium). In some embodiments, the synthetic amino acid does not produce a significant amount of glutamine in the basal medium. In some embodiments, the synthetic amino acid does not produce a significant amount of pyrrolidone carboxylic acid or ammonia. In some embodiments, the synthetic amino acid does not produce a significant amount of glutamine (i.e., L-glutamine) for at least about 1, 3, 5, 7, 9, 11 13, or 14 days in the basal medium. In some embodiments, the synthetic amino acid does not produce a significant amount of glutamine (i.e., L-glutamine) for at least about 1, 2, 3, 4, 5, 6, 7, or 8 weeks in the basal medium. In some embodiments, the synthetic amino acid does not produce a significant amount of glutamine (i.e., L-glutamine) for at least about 1, 2, 3, 4, 5, 6, 7, 8, 9, 10, 11, or 12 months in the basal medium. In some embodiments, the synthetic amino acid does not produce a significant amount of glutamine (i.e., L-glutamine) for at least 1, 2, 3, 4, or 5 years in the basal medium. In some embodiments, the synthetic amino acid does not produce a significant amount of pyrrolidone carboxylic acid or ammonia for at least about 1, 3, 5, 7, 9, 11 13, or 14 days in the basal medium. In some embodiments, the synthetic amino acid does not produce a significant amount of pyrrolidone carboxylic acid or ammonia for at least about 1, 2, 3, 4, 5, 6, 7, or 8 weeks in the basal medium. In some embodiments, the synthetic amino acid does not produce a significant amount of pyrrolidone carboxylic acid or ammonia for at least about 1, 2, 3, 4, 5, 6, 7, 8, 9, 10, 11, or 12 months in the basal medium. In some embodiments, the synthetic amino acid does not produce a significant amount of pyrrolidone carboxylic acid or ammonia for at least 1, 2, 3, 4, or 5 years in the basal medium.

In some embodiments, the synthetic amino acid is soluble in an aqueous solution (e.g., a basal medium). In some embodiments, the solubility of the synthetic amino acid in the aqueous solution is higher than a free form of glutamine (i.e., L-glutamine).

In some embodiments, the synthetic amino acid is capable of being transported into a cell, wherein it can be converted into a free form of glutamine (i.e., L-glutamine). In some embodiments, the cell comprises an immune cell. In some embodiments, the cell is a genetically engineered cell. In some embodiments, the cell is a T cell. In some embodiments, the cell is a genetically engineered T cell. In some embodiments, the cell is genetically engineered to express a recombinant receptor (e.g., a chimeric antigen receptor). In some embodiments, the cell is a chimeric antigen receptor (CAR) expressing T cells.

In some embodiments, the synthetic amino acid is a dipeptide. In some embodiments, the synthetic amino acid is a tripeptide. In some embodiments, the synthetic amino acid is a dipeptide form of L-glutamine (e.g., L-alanyl-L-glutamine).

In some embodiments, the concentration of the dipeptide form of L-glutamine (e.g., L-alanyl-L-glutamine) in the basal medium is about 0.5 mM-5 mM. In some embodiments, the concentration of the dipeptide form of L-glutamine (e.g., L-alanyl-L-glutamine) in the basal medium is at or about 2 mM. In some embodiments, the concentration of the dipeptide form of L-glutamine (e.g., L-alanyl-L-glutamine) is at or about 0.5 mM-1 mM, 0.5 mM-1.5 mM, 0.5 mM-2 mM, 0.5 mM-2.5 mM, 0.5 mM-3 mM, 0.5 mM-3.5 mM, 0.5 mM-4 mM, 0.5 mM-4.5 mM, 0.5 mM-5 mM, 1 mM-1.5 mM, 1 mM-2 mM, 1 mM-2.5 mM, 1 mM-3 mM, 1 mM-3.5 mM, 1 mM-4 mM, 1 mM-4.5 mM, 1 mM-5 mM, 1.5 mM-2 mM, 1.5 mM-2.5 mM, 1.5 mM-3 mM, 1.5 mM-3.5 mM, 1.5 mM-4 mM, 1.5 mM-4.5 mM, 1.5 mM-5 mM, 2 mM-2.5 mM, 2 mM-3 mM, 2 mM-3.5 mM, 2 mM-4 mM, 2 mM-4.5 mM, 2 mM-5 mM, 2.5 mM-3 mM, 2.5 mM-3.5 mM, 2.5 mM-4 mM, 2.5 mM-4.5 mM, 2.5 mM-5 mM, 3 mM-3.5 mM, 3 mM-4 mM, 3 mM-4.5 mM, 3 mM-5 mM, 3.5 mM-4 mM, 3.5 mM-4.5 mM, 3.5 mM-5 mM, 4 mM-4.5 mM, 4 mM-5 mM, or 4.5 mM-5 mM, each inclusive. In some embodiments, the concentration of the dipeptide form of L-glutamine (e.g., L-alanyl-L-glutamine) in the basal medium is at or about 5 mM-7.5 mM, 5 mM-10 mM, 5 mM-12.5 mM, 5 mM-15 mM, 5 mM-17.5 mM, 5 mM-20 mM, 7.5 mM-10 mM, 7.5 mM-12.5 mM, 7.5 mM-15 mM, 7.5 mM-17.5 mM, 7.5 mM-20 mM, 10 mM-12.5 mM, 10 mM-15 mM, 10 mM-17.5 mM, 10 mM-20 mM, 12.5 mM-15 mM, 12.5 mM-17.5 mM, 12.5 mM-20 mM, 15 mM-17.5 mM, 15 mM-20 mM, or 17.5 mM-20 mM, each inclusive. In some embodiments, the concentration of dipeptide form of L-glutamine (e.g., L-alanyl-L-glutamine) in the basal medium is at least about at or 0.5 mM, 1 mM, 1.5 mM, 2 mM, 2.5 mM, 3 mM, 3.5 mM, 4 mM, 4.5 mM, or 5 mM. In some embodiments, the concentration of the dipeptide form of L-glutamine (e.g., L-alanyl-L-glutamine) in the basal medium is or is about 2 mM. In some embodiments, the concentration of the dipeptide form of L-glutamine (e.g., L-alanyl-L-glutamine) in the basal medium is at most at or about 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, 10 mM, 12.5 mM, 15 mM, 17.5 mM, or 20 mM.

In some embodiments, the basal medium does not comprise L-glutamine or does not comprise a significant amount of L-glutamine. In some embodiments, the basal medium comprises L-glutamine. In some embodiments, the concentration of the L-glutamine in the basal medium is at or about or less than at or about 0.1 mM, 0.2 mM, 0.3 mM, 0.4 mM, or 0.5 mM. In some embodiments, the concentration of the L-glutamine in the basal medium is at or about or less than at or about 1 mM, 2 mM, 3 mM, 4 mM, or 5 mM.

In some embodiments, the one or more amino acids, including at least one synthetic amino acid that is capable of being converted into a free form of glutamine (i.e., L-glutamine), e.g. dipeptide form of L-glutamine, such as L-alanyl-L-glutamine, is provided in a base media. In some embodiments, the base media is an artificial or synthetic medium. In some embodiments, the base media is a balanced salt solution (e.g., PBS, DPBS, HBSS, EBSS). In some embodiments, the basal media is selected from Dulbecco's Modified Eagle's Medium (DMEM), Minimal Essential Medium (MEM), Basal Medium Eagle (BME), F-10, F-12, RPMI 1640, Glasgow's Minimal Essential Medium (GMEM), alpha Minimal Essential Medium (alpha MEM), Iscove's Modified Dulbecco's Medium, and M199. In some embodiments, the base media is a complex medium (e.g., RPMI-1640, IMDM). In some embodiments, the base medium is OpTmizer™ CTS™ T-Cell Expansion Basal Medium (ThermoFisher).

In some embodiments, the basal media comprises a nutrient mixture of inorganic salts, sugars, amino acids, optionally also containing vitamins, organic acids, antioxidants, and/or buffers.

In some embodiments, the basal medium comprises $CO_3$ and $HCO_3$. In some embodiments, the content of $CO_3/HCO_3$ content of the basal medium is balanced with gaseous CO2 (e.g., 5-10%), thereby maintaining an optimal pH in the medium. In some embodiments, the basal medium comprises a zwitterion, HEPES. In some embodiments, the basal medium comprises phenol red. In some embodiments, the basal medium does not comprise phenol red.

In some embodiments, the basal medium comprises an inorganic salt. In some embodiments, the inorganic salt promotes the osmotic balance. In some embodiments, the inorganic salt regulates membrane potential by providing sodium, potassium, and calcium ions.

In some embodiments, the basal medium comprises one or more carbohydrates. In some embodiments, the carbohydrate comprises glucose. In some embodiments, the carbohydrate comprises galactose. In some embodiments, the carbohydrate comprises maltose. In some embodiments, the carbohydrate comprises fructose.

In some embodiments, the basal medium comprises fatty acid. In some embodiments, the basal medium comprises lipid. In some embodiments, the basal medium comprises vitamin (e.g., Vitamin A, Vitamin B7, Vitamin B9, Vitamin B12, Vitamin C, Vitamin E). In some embodiments, the basal medium comprises a trace element. In some embodiments, the trace element comprises copper. In some embodiments, the trace element comprises zinc. In some embodiments, the trace element comprises selenium. In some embodiments, the trace element comprises tricarboxylic acid intermediate.

In some embodiments, the basal medium contains a mixture of inorganic salts, sugars, amino acids, and, optionally, vitamins, organic acids and/or buffers or other well known cell culture nutrients. In addition to nutrients, the medium also helps maintain pH and osmolality. In some aspects, the reagents of the basal media support cell growth, proliferation and/or expansion. A wide variety of commercially available basal media are well known to those skilled in the art, and include Dulbeccos' Modified Eagles Medium (DMEM), Roswell Park Memorial Institute Medium (RPMI), Iscove modified Dulbeccos' medium and Hams medium. In some embodiments, the basal medium is Iscove's Modified Dulbecco's Medium, RPMI-1640, or α-MEM.

In some embodiments, the basal medium is free of a protein. In some embodiments, the basal medium is free of a human protein (e.g., a human serum protein). In some embodiments, the basal medium is serum-free. In some embodiments, the basal medium is free of serum derived from human. In some embodiments, the basal medium is free of a recombinant protein. In some embodiments, the basal medium is free of a human protein and a recombinant protein.

In some embodiments, the basal medium comprises a protein or a peptide. In some embodiments, the protein is an albumin or albumin substitute. In some embodiments, the albumin is a human derived albumin. In some embodiments, the albumin is a recombinant albumin. In some embodiments, the albumin is a natural human serum albumin. In some embodiments, the albumin is a recombinant human serum albumin. In some embodiments, the albumin is a recombinant albumin from a non-human source. Albumin substitutes may be any protein or polypeptide source. Examples of such protein or polypeptide samples include but are not limited to bovine pituitary extract, plant hydrolysate (e.g., rice hydrolysate), fetal calf albumin (fetuin), egg albumin, human serum albumin (HSA), or another animal-derived albumins, chick extract, bovine embryo extract, AlbuMAX® I, and AlbuMAX® II. In some embodiments, the protein or peptide comprises a transferrin. In some embodiments, the protein or peptide comprises a fibronectin. In some embodiments, the protein or peptide comprises aprotinin. In some embodiments, the protein comprises fetuin.

In some embodiments, the basal medium (e.g. a basal medium) is a liquid formulation. In some embodiments, the basal medium (e.g. a basal medium) has not been frozen or is instructed not to be frozen (e.g., according to its protocol) prior to an intended use. In some embodiments, the basal medium is stored at or about 2° C. to 8° C. In some embodiments, the basal medium is stored at room temperature. In some embodiments, the basal medium is stable for at least at or about 1, 2, 3, 4, 5, or 6 weeks when stored at 2° C. to 8° C. In some embodiments, the basal medium is stable for at least at or about 1, 2, 3, 4, 5, or 6 months when stored at 2° C. to 8° C.

B. Supplement

In some embodiments, provided herein is a supplement, such as a first supplement, comprising a free form of glutamine (i.e., L-glutamine). In some embodiments, such a supplement is frozen prior to use and/or incorporation into a base media. In some embodiments, the supplement such as these described herein is intended to be used as a media supplement (e.g., a media supplement for a basal medium). In some embodiments, the first supplement is intended to be used as a supplement for the maintenance, expansion, and/or activation of a cell. In some embodiments, the first supplement is intended to be used as a supplement for the expansion of a cell. In some embodiments, the first supplement comprises a frozen supplement comprising at least one protein and a free form of glutamine (i.e., L-glutamine), wherein a basal cell culture medium supplemented with the first supplement is capable of supporting the expansion of a cell. In some embodiments, the cell is a primary cell. In some embodiments, the cell is an immune cell. In some embodiments, the cell is a T cell. In some embodiments, the cell is a CD4 T cell or CD8 T cell. In some embodiments, the cell is a cell from human. In some embodiments, the cell is an immune cell from human. In some embodiments, the cell is a T cell from human. In some embodiments, the cell is a primary immune cell from human. In some embodiments, the cell is a genetically engineered cell. In some embodiments, the cell is a genetically engineered cell derived from human. In some embodiments, the cell is a genetically engineered T cell (e.g., a chimeric antigen receptor (CAR) expressing T cell) from human.

In some embodiments, the first supplement is stored or is recommended to be stored at or about −20° C. to at or about 0° C. before its intended use. In some embodiments, the supplement is stored or is recommended to be stored at less than about 0° C. In some embodiments, the supplement is frozen immediately or quickly after the free form of glutamine (i.e., L-glutamine) becomes a component thereof until the time when the supplement is used for its intended use. In some embodiments, the supplement is frozen for the majority of the time after the free form of glutamine (i.e., L-glutamine) becomes a component thereof until the time when the supplement is used for its intended use. In some embodiments, the supplement is not kept as a liquid for more than 1, 2, 3, 4, 5, 6, or 7 days after the free form of glutamine (i.e., L-glutamine) becomes a component thereof until the time when the supplement is used for its intended use. In some embodiments, the supplement is not kept as a liquid for more than or more than about 4, 8, 12, 16, 20, or 24 hours after the free form of glutamine (i.e., L-glutamine) becomes a component thereof until the time when the supplement is used for its intended use. In some embodiments, the supplement is frozen for the majority of the time both before and after the free form of glutamine (i.e., L-glutamine) becomes a component thereof until the time when the supplement is used for its intended use. In some embodiments, the supplement is at or below room temperature (e.g., the temperature of the supplement is under or under about 20° C., 15° C., 10° C., 5° C., or 0° C.) when the free form of glutamine (i.e., L-glutamine) becomes a component of the supplement.

In some embodiments, the L-glutamine in the supplement does not precipitate when the supplement is thawed. In some embodiments, the L-glutamine in the supplement does not precipitate when the supplement is a liquid. In some embodiments, the L-glutamine in the supplement does not precipitate when the supplement is thawed under room temperature. In some embodiments, the concentration of L-glutamine in the supplement is at or about or less than or less than about 200 mM, 180 mM, 160 mM, 140 mM, 120 mM, 100 mM or 80 mM. In some embodiments, the concentration of L-glutamine in the supplement is at or about 10 mM to at or about 30 mM, at or about 10 mM to at or about 50 mM, at or about 10 mM to at or about 70 mM, at or about 10 mM to at or about 90 mM, at or about 10 mM to at or about 110 mM, at or about 10 mM to at or about 130 mM, at or about 10 mM to at or about 150 mM, at or about 10 mM to at or about 170 mM, at or about 30 mM to at or about 50 mM, at or about 30 mM to at or about 70 mM, at or about 30 mM to at or about 90 mM, at or about 30 mM to at or about 110 mM, at or about 30 mM to at or about 130 mM, at or about 30 mM to at or about 150 mM, at or about 30 mM to at or about 170 mM, at or about 50 mM to at or about 70 mM, at or about 50 mM to at or about 90 mM, at or about 50 mM to at or about 110 mM, at or about 50 mM to at or about 130 mM, at or about 50 mM to at or about 150 mM, at or about 50 mM to at or about 170 mM, at or about 70 mM to at or about 90 mM, at or about 70 mM to at or about 110 mM, at or about 70 mM to at or about 130 mM, at or about 70 mM to at or about 150 mM, at or about 70 mM to at or about 170 mM, at or about 90 mM to at or about 110 mM, at or about 90 mM to at or about 130 mM, at or about 90 mM to at or about 150 mM, at or about 90 mM to at or about 170 mM, at or about 110 mM to at or about 130 mM, at or about 110 mM to at or about 150 mM, at or about 110 mM to at or about 170 mM, at or about 130 mM to at or about 150 mM, at or about 130 mM to at or about 170 mM, or at or about 150 mM to at or about 170 mM. In some embodiments, the concentration of L-glutamine in the supplement is about 80 mM.

In some embodiments, the concentration of the free form of glutamine (i.e., L-glutamine) in the supplement is such that after the supplement is combined with a basal medium (such as these described herein), the concentration of the free form of glutamine (i.e., L-glutamine) in the media is at or about 0.5 mM-5 mM. In some embodiments, the concentration of the free form of glutamine (i.e., L-glutamine) in the basal medium is at or about 2 mM. In some embodiments, the concentration of the free form of glutamine (i.e., L-glutamine) is at or about 0.5 mM-1 mM, 0.5 mM-1.5 mM, 0.5 mM-2 mM, 0.5 mM-2.5 mM, 0.5 mM-3 mM, 0.5 mM-3.5 mM, 0.5 mM-4 mM, 0.5 mM-4.5 mM, 0.5 mM-5 mM, 1 mM-1.5 mM, 1 mM-2 mM, 1 mM-2.5 mM, 1 mM-3 mM, 1 mM-3.5 mM, 1 mM-4 mM, 1 mM-4.5 mM, 1 mM-5 mM, 1.5 mM-2 mM, 1.5 mM-2.5 mM, 1.5 mM-3 mM, 1.5 mM-3.5 mM, 1.5 mM-4 mM, 1.5 mM-4.5 mM, 1.5 mM-5 mM, 2 mM-2.5 mM, 2 mM-3 mM, 2 mM-3.5 mM, 2 mM-4 mM, 2 mM-4.5 mM, 2 mM-5 mM, 2.5 mM-3 mM, 2.5 mM-3.5 mM, 2.5 mM-4 mM, 2.5 mM-4.5 mM, 2.5 mM-5 mM, 3 mM-3.5 mM, 3 mM-4 mM, 3 mM-4.5 mM, 3 mM-5 mM, 3.5 mM-4 mM, 3.5 mM-4.5 mM, 3.5 mM-5 mM, 4 mM-4.5 mM, 4 mM-5 mM, or 4.5 mM-5 mM, each inclusive. In some embodiments, the concentration of the free form of glutamine (i.e., L-glutamine) in the basal medium is at or about 5 mM-7.5 mM, 5 mM-10 mM, 5 mM-12.5 mM, 5 mM-15 mM, 5 mM-17.5 mM, 5 mM-20 mM, 7.5 mM-10 mM, 7.5 mM-12.5 mM, 7.5 mM-15 mM, 7.5 mM-17.5 mM, 7.5 mM-20 mM, 10 mM-12.5 mM, 10 mM-15 mM, 10 mM-17.5 mM, 10 mM-20 mM, 12.5 mM-15 mM, 12.5 mM-17.5 mM, 12.5 mM-20 mM, 15 mM-17.5 mM, 15 mM-20 mM, or 17.5 mM-20 mM, each inclusive. In some embodiments, the concentration of the free form of glutamine (i.e., L-glutamine) in the basal medium is at least at or about 0.5 mM, 1 mM, 1.5 mM, 2 mM, 2.5 mM, 3 mM, 3.5 mM, 4 mM, 4.5 mM, or 5 mM. In some embodiments, the concentration of the free form of glutamine (i.e., L-glutamine) in the basal medium is at most at or about 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, 10 mM, 12.5 mM, 15 mM, 17.5 mM, or 20 mM.

In some embodiments, the first supplement contains one or more additional components. In some embodiments, a further supplement, such as a second supplement, is provided to provide one or more additional components. In some embodiments, the supplements, the first supplement and optionally one or more further supplements, e.g. second supplement, are combined with the basal media to provide the one or more additional components to the basal media.

In some embodiments, the one or more additional components include at least one protein. In some embodiments, the at least one protein is not of non-mammalian origin. In some embodiments, the at least one protein is human or derived from human. In some embodiments, the at least one protein is recombinant. In some embodiments, the at least one protein includes albumin, transferrin, insulin, fibronectin, aprotinin or fetuin. In some embodiments, the protein comprises one or more of albumin, insulin or transferrin, optionally one or more of a human or recombinant albumin, insulin or transferrin.

In some embodiments, the protein is an albumin or albumin substitute. In some embodiments, the albumin is a human derived albumin. In some embodiments, the albumin is a recombinant albumin. In some embodiments, the albumin is a natural human serum albumin. In some embodiments, the albumin is a recombinant human serum albumin. In some embodiments, the albumin is a recombinant albumin from a non-human source. Albumin substitutes may be any protein or polypeptide source. Examples of such protein or polypeptide samples include but are not limited to bovine pituitary extract, plant hydrolysate (e.g., rice hydrolysate), fetal calf albumin (fetuin), egg albumin, human serum albumin (HSA), or another animal-derived albumins, chick extract, bovine embryo extract, AlbuMAX® I, and AlbuMAX® II.

In some embodiments, the one or more additional components include an albumin. In some embodiments, the albumin is human albumin or derived from human albumin. In some embodiments, the albumin is derived from human serum or human plasma. In some embodiments, the albumin is a recombinant albumin. In some embodiments, the recombinant albumin is derived from human. In some embodiments, the recombinant albumin is not derived from human. In some embodiments, the supplement comprises a natural albumin. In some embodiments, the natural albumin is derived from human. In some embodiments, the natural albumin is not derived from human. In some embodiments, the concentration of the albumin in the supplement is such that after the supplement is combined with a basal medium (such as these described herein), at or about the concentration of the albumin in the media is at or about 0 mg/mL to at or about 2 mg/mL, at or about 0 mg/mL to at or about 4 mg/mL, at or about 0 mg/mL to at or about 6 mg/mL, at or about 0 mg/mL to at or about 8 mg/mL, at or about 0 mg/mL to at or about 10 mg/mL, at or about 0 mg/mL to at or about 12 mg/mL, at or about 2 mg/mL to at or about 4 mg/mL, at or about 2 mg/mL to at or about 6 mg/mL, at or about 2 mg/mL to at or about 8 mg/mL, at or about 2 mg/mL to at or about 10 mg/mL, at or about 2 mg/mL to at or about 12 mg/mL, at or about 4 mg/mL to at or about 6 mg/mL, at or about 4 mg/mL to at or about 8 mg/mL, at or about 4 mg/mL to at or about 10 mg/mL, at or about 4 mg/mL to at or about 12 mg/mL, at or about 6 mg/mL to at or about 8 mg/mL, at or about 6 mg/mL to at or about 10 mg/mL, at or about 6 mg/mL to at or about 12 mg/mL, at or about 8 mg/mL to at or about 10 mg/mL, at or about 8 mg/mL to at or about 12 mg/mL, at or about 10 mg/mL to at or about 12 mg/mL, or at or about 10 mg/mL to at or about 15 mg/mL each inclusive. In some embodiments, at or about the albumin in the media is at or about 5 mg/mL.

In some embodiments, the one or more additional components include a transferrin or transferrin substitute. In some embodiments, a transferrin substitute is a compound which may replace transferrin in the supplement to give substantially similar results as transferrin. Examples of transferrin substitutes include but are not limited to any iron chelate compound. Iron chelate compounds which may be used include but are not limited to iron chelates of ethylenediaminetetraacetic acid (EDTA), ethylene glycol-bis(β-aminoethyl ether)-N,N,N',N'-tetraacetic acid (EGTA), deferoxamine mesylate, dimercaptopropanol, diethylenetriamine-pentaacetic acid (DPT A), and trans-1,2-diaminocyclohexane-N,N,N',N'-tetraacetic acid (CDTA), as well as a ferric citrate chelate and a ferrous sulfate chelate. In some embodiments, the transferrin is iron saturated transferrin. In some embodiments, the transferrin is iron saturated human transferrin.

In some embodiments, the transferrin or transferrin substitute is human transferrin or is derived from human transferrin. In some embodiments, the transferrin or transferrin substitute is derived from human serum or plasma. In some embodiments, the transferrin or transferrin substitute is recombinant transferrin. In some embodiments, the concentration of the transferrin is such that after the supplement is combined with a basal medium (such as these described herein), the concentration of the transferrin in the media is at or about 10 mg/L to at or about 50 mg/L, at or about 10 mg/L to at or about 100 mg/L, at or about 10 mg/L to at or about 150 mg/L, at or about 10 mg/L to at or about 200 mg/L, at or about 10 mg/L to at or about 250 mg/L, at or about 10 mg/L to at or about 300 mg/L, at or about 10 mg/L to at or about 350 mg/L, at or about 10 mg/L to at or about 400 mg/L, at or about 10 mg/L to at or about 450 mg/L, at or about 10 mg/L to at or about 500 mg/L, at or about 10 mg/L to at or about 550 mg/L, at or about 10 mg/L to at or about 600 mg/L, at or about 10 mg/L to at or about 650 mg/L, at or about 10 mg/L to at or about 750 mg/L, at or about 50 mg/L to at or about 100 mg/L, at or about 50 mg/L to at or about 150 mg/L, at or about 50 mg/L to at or about 200 mg/L, at or about 50 mg/L to at or about 250 mg/L, at or about 50 mg/L to at or about 300 mg/L, at or about 50 mg/L to at or about 350 mg/L, at or about 50 mg/L to at or about 400 mg/L, at or about 50 mg/L to at or about 450 mg/L, at or about 50 mg/L to at or about 500 mg/L, at or about 50 mg/L to at or about 550 mg/L, at or about 50 mg/L to at or about 600 mg/L, at or about 50 mg/L to at or about 650 mg/L, at or about 50 mg/L to at or about 750 mg/L, at or about 100 mg/L to at or about 150 mg/L, at or about 100 mg/L to at or about 200 mg/L, at or about 100 mg/L to at or about 250 mg/L, at or about 100 mg/L to at or about 300 mg/L, at or about 100 mg/L to at or about 350 mg/L, at or about 100 mg/L to at or about 400 mg/L, at or about 100 mg/L to at or about 450 mg/L, at or about 100 mg/L to at or about 500 mg/L, at or about 100 mg/L to at or about 550 mg/L, at or about 100 mg/L to at or about 600 mg/L, at or about 100 mg/L to at or about 650 mg/L, at or about 100 mg/L to at or about 750 mg/L, at or about 150 mg/L to at or about 200 mg/L, at or about 150 mg/L to at or about 250 mg/L, at or about 150 mg/L to at or about 300 mg/L, at or about 150 mg/L to at or about 350 mg/L, at or about 150 mg/L to at or about 400 mg/L, at or about 150 mg/L to at or about 450 mg/L, at or about 150 mg/L to at or about 500 mg/L, at or about 150 mg/L to at or about 550 mg/L, at or about 150 mg/L to at or about 600 mg/L, at or about 150 mg/L to at or about 650 mg/L, at or about 150 mg/L to at or about 750 mg/L, at or about 200 mg/L to at or about 250 mg/L, at or about 200 mg/L to at or about 300 mg/L, at or about 200 mg/L to at or about 350 mg/L, at or about 200 mg/L to at or about 400 mg/L, at or about 200 mg/L to at or about 450 mg/L, at or about 200 mg/L to at or about 500 mg/L, at or about 200 mg/L to at or about 550 mg/L, at or about 200 mg/L to at or about 600 mg/L, at or about 200 mg/L to at or about 650 mg/L, at or about 200 mg/L to at or about 750 mg/L, at or about 250 mg/L to at or about 300 mg/L, at or about 250 mg/L to at or about 350 mg/L, at or about 250 mg/L to at or about 400 mg/L, at or about 250 mg/L to at or about 450 mg/L, at or about 250 mg/L to at or about 500 mg/L, at or about 250 mg/L to at or about 550 mg/L, at or about 250 mg/L to at or about 600 mg/L, at or about 250 mg/L to at or about 650 mg/L, at or about 250 mg/L to at or about 750 mg/L, at or about 300 mg/L to at or about 350 mg/L, at or about 300 mg/L to at or about 400 mg/L, at or about 300 mg/L to at or about 450 mg/L, at or about 300 mg/L to at or about 500 mg/L, at or about 300 mg/L to at or about 550 mg/L, at or about 300 mg/L to at or about 600 mg/L, at or about 300 mg/L to at or about 650 mg/L, at or about 300 mg/L to at or about 750 mg/L, at or about 350 mg/L to at or about 400 mg/L, at or about 350 mg/L to at or about 450 mg/L, at or about 350 mg/L to at or about 500 mg/L, at or about 350 mg/L to at or about 550 mg/L, at or about 350 mg/L to at or about 600 mg/L, at or about 350 mg/L to at or about 650 mg/L, at or about 350 mg/L to at or about 750 mg/L, at or about 400 mg/L to at or about 450 mg/L, at or about 400 mg/L to at or about 500 mg/L, at or about 400 mg/L to at or about 550 mg/L, at or about 400 mg/L to at or about 600 mg/L, at or about 400 mg/L to at or about 650 mg/L, at or about 400 mg/L to at or about 750 mg/L, at or about 450 mg/L to at or about 500 mg/L, at or about 450 mg/L to at or about 550 mg/L, at or about 450 mg/L to at or about 600 mg/L, at or about 450 mg/L to at or about 650 mg/L, at or about 450 mg/L to at or about 750 mg/L, at or about 500 mg/L to at or about 550 mg/L, at or about 500 mg/L to at or about 600 mg/L, at or about 500 mg/L to at or about 650 mg/L, at or about 500 mg/L to at or about 750 mg/L, at or about 550 mg/L to at or about 600 mg/L, at or about 500 mg/L to at or about 650 mg/L, at or about 500 mg/L to at or about 750 mg/L, at or about 550 mg/L to at or about 600 mg/L, at or about 550 mg/L to at or about 650 mg/L, at or about 550 mg/L to at or about 750 mg/L, at or about 600 mg/L to at or about 650 mg/L, at or about 600 mg/L to at or about 750 mg/L, or at or about 650 mg/L to at or about 750 mg/L. In some embodiments, the concentration of the transferrin is such that after the supplement is combined with a basal medium (such as these described herein), the concentration of the transferrin in the media is at or about 100 mg/L. In some embodiments, the concentration of the transferrin is such that after the supplement is combined with a basal medium (such as these described herein), the concentration of the transferrin in the media is at or about 50 mg/L to at or about 150 mg/L.

In some embodiments, the one or more additional components include insulin or insulin substitute. In some embodiments, an insulin substitute is a zinc containing compound which may be used in place of insulin to give substantially similar results as insulin. Examples of insulin substitutes include but are not limited to zinc chloride, zinc nitrate, zinc bromide, and zinc sulfate. A number of insulins are known to those of ordinary skill in the art. See Gilman, A. G. et al, Eds., The Pharmacological Basis of Therapeutics, Pergamon Press, New York, 1990, pp. 1463-1495. In some embodiments, insulin, rather than an insulin substitute, is used in the supplement and the medium. In some embodiments, the insulin is zinc insulin. In some embodiments, the insulin is human zinc insulin.

In some embodiments, the insulin is a human insulin or derived from human insulin. In some embodiments, the insulin is a recombinant insulin. In some embodiment, the insulin is a recombinant human insulin. In some embodiment, the concentration of the insulin (or insulin substitute) is such that after the supplement is combined with a basal medium (such as these described herein), at or about the concentration of the insulin (or insulin substitute) in the media is about 1 mg/L to at or about 2.5 mg/L, at or about 1 mg/L to at or about 5 mg/L, at or about 1 mg/L to at or about 7.5 mg/L, at or about 1 mg/L to at or about 10 mg/L, at or about 1 mg/L to at or about 12.5 mg/L, at or about 1 mg/L to at or about 15 mg/L, at or about 1 mg/L to at or about 17.5 mg/L, at or about 1 mg/L to at or about 20 mg/L, at or about 1 mg/L to at or about 22.5 mg/L, at or about 1 mg/L to at or about 25 mg/L, at or about 1 mg/L to at or about 27.5 mg/L, at or about 1 mg/L to at or about 30 mg/L, at or about 2.5 mg/L to at or about 5 mg/L, at or about 2.5 mg/L to at or about 7.5 mg/L, at or about 2.5 mg/L to at or about 10 mg/L, at or about 2.5 mg/L to at or about 12.5 mg/L, at or about 2.5 mg/L to at or about 15 mg/L, at or about 2.5 mg/L to at or about 17.5 mg/L, at or about 2.5 mg/L to at or about 20 mg/L, at or about 2.5 mg/L to at or about 22.5 mg/L, at or about 2.5 mg/L to at or about 25 mg/L, at or about 2.5 mg/L to at or about 27.5 mg/L, at or about 2.5 mg/L to at or about 30 mg/L, at or about 5 mg/L to at or about 7.5 mg/L, at or about 5 mg/L to at or about 10 mg/L, at or about 5 mg/L to at or about 12.5 mg/L, at or about 5 mg/L to at or about 15 mg/L, at or about 5 mg/L to at or about 17.5 mg/L, at or about 5 mg/L to at or about 20 mg/L, at or about 5 mg/L to at or about 22.5 mg/L, at or about 5 mg/L to at or about 25 mg/L, at or about 5 mg/L to at or about 27.5 mg/L, at or about 5 mg/L to at or about 30 mg/L, at or about 7.5 mg/L to at or about 10 mg/L, at or about 7.5 mg/L to at or about 12.5 mg/L, at or about 7.5 mg/L to at or about 15 mg/L, at or about 7.5 mg/L to at or about 17.5 mg/L, at or about 7.5 mg/L to at or about 20 mg/L, at or about 7.5 mg/L to at or about 22.5 mg/L, at or about 7.5 mg/L to at or about 25 mg/L, at or about 7.5 mg/L to at or about 27.5 mg/L, at or about 7.5 mg/L to at or about 30 mg/L, at or about 10 mg/L to at or about 12.5 mg/L, at or about 10 mg/L to at or about 15 mg/L, at or about 10 mg/L to at or about 17.5 mg/L, at or about 10 mg/L to at or about 20 mg/L, at or about 10 mg/L to at or about 22.5 mg/L, at or about 10 mg/L to at or about 25 mg/L, at or about 10 mg/L to at or about 27.5 mg/L, at or about 10 mg/L to at or about 30 mg/L, at or about 12.5 mg/L to at or about 15 mg/L, at or about 12.5 mg/L to at or about 17.5 mg/L, at or about 12.5 mg/L to at or about 20 mg/L, at or about 12.5 mg/L to at or about 22.5 mg/L, at or about 12.5 mg/L to at or about 25 mg/L, at or about 12.5 mg/L to at or about 27.5 mg/L, at or about 12.5 mg/L to at or about 30 mg/L, at or about 15 mg/L to at or about 17.5 mg/L, at or about 15 mg/L to at or about 20 mg/L, at or about 15 mg/L to at or about 22.5 mg/L, at or about 15 mg/L to at or about 25 mg/L, at or about 15 mg/L to at or about 27.5 mg/L, at or about 15 mg/L to at or about 30 mg/L, at or about 17.5 mg/L to at or about 20 mg/L, at or about 17.5 mg/L to at or about 22.5 mg/L, at or about 17.5 mg/L to at or about 25 mg/L, at or about 17.5 mg/L to at or about 27.5 mg/L, at or about 17.5 mg/L to at or about 30 mg/L, at or about 20 mg/L to at or about 22.5 mg/L, at or about 20 mg/L to at or about 25 mg/L, at or about 20 mg/L to at or about 27.5 mg/L, at or about 20 mg/L to at or about 30 mg/L, at or about 22.5 mg/L to at or about 25 mg/L, at or about 22.5 mg/L to at or about 27.5 mg/L, at or about 22.5 mg/L to at or about 30 mg/L, at or about 25 mg/L to at or about 27.5 mg/L, or at or about 27.5 mg/L to at or about 30 mg/L. In some embodiments, the concentration of insulin or insulin substitute in the media is at or about 10 mg/L. In some embodiments, the concentration of insulin or insulin substitute in the media is at or about 7.5 mg/L to at or about 12.5 mg/L.

In some embodiments, the supplement, e.g. first supplement, is prepared by adding or mixing L-glutamine with existing supplements containing one or more desired components. In some embodiments, L-glutamine is added or mixed with a serum replacement supplement, for example, Immune Cell Serum Replacement (ThermoFisher, #A2598101). In some embodiments, the L-glutamine is added to or mixed with a supplement that includes an immune cell serum replacement described in Smith et al. *Clin Transl Immunology.* 2015 January; 4(1): e31. In some embodiments, the concentration of L-glutamine in the supplement is at or about 10 mM to at or about 30 mM, at or about 10 mM to at or about 50 mM, at or about 10 mM to at or about 70 mM, at or about 10 mM to at or about 90 mM, at or about 10 mM to at or about 110 mM, at or about 10 mM to at or about 130 mM, at or about 10 mM to at or about 150 mM, at or about 10 mM to at or about 170 mM, at or about 30 mM to at or about 50 mM, at or about 30 mM to at or about 70 mM, at or about 30 mM to at or about 90 mM, at or about 30 mM to at or about 110 mM, at or about 30 mM to at or about 130 mM, at or about 30 mM to at or about 150 mM, at or about 30 mM to at or about 170 mM, at or about 50 mM to at or about 70 mM, at or about 50 mM to at or about 90 mM, at or about 50 mM to at or about 110 mM, at or about 50 mM to at or about 130 mM, at or about 50 mM to at or about 150 mM, at or about 50 mM to at or about 170 mM, at or about 70 mM to at or about 90 mM, at or about 70 mM to at or about 110 mM, at or about 70 mM to at or about 130 mM, at or about 70 mM to at or about 150 mM, at or about 70 mM to at or about 170 mM, at or about 90 mM to at or about 110 mM, at or about 90 mM to at or about 130 mM, at or about 90 mM to at or about 150 mM, at or about 90 mM to at or about 170 mM, at or about 110 mM to at or about 130 mM, at or about 110 mM to at or about 150 mM, at or about 110 mM to at or about 170 mM, at or about 130 mM to at or about 150 mM, at or about 130 mM to at or about 170 mM, or at or about 150 mM to at or about 170 mM. In some embodiments, the concentration of L-glutamine in the supplement is at or about 80 mM.

In some embodiments, the one or more additional components include a growth factor. In some embodiments, the growth factor comprises epidermal growth factor (EGF). In some embodiments, the growth factor comprises fibroblast growth factor (FGF). In some embodiments, the growth factor comprises insulin-like growth factor (IGF). In some embodiments, the growth factor comprises nerve growth factor (NGF). In some embodiments, the growth factor comprises platelet-derived growth factor (PDGF). In some embodiments, the growth factor comprises transforming growth factor (TGF).

In some embodiments, the one or more additional components include a hormone (e.g., growth hormone, insulin, hydrocortisone, triiodothyronine, estrogen, androgen, progesterone, prolactin, follicle-stimulating hormone, gastrin-releasing peptide). In some embodiment, the one or more additional components include alpha-globulin or beta-globulin. In some embodiment, the one or more additional components include a peptide or peptide fraction (e.g., protein hydrolysate derived from animal, microorganism or plant).

In some embodiments, the one or more additional components include a lipid. In some embodiments, the lipid comprises cholesterol. In some embodiments, the lipid comprises steroid. In some embodiments, the lipid comprises fatty acid (e.g., palmitate, stearate, oleate, linoleate). In some embodiments, the lipid comprises ethanolamine. In some embodiments, the lipid comprises choline. In some embodiments, the lipid comprises inositol.

In some embodiments, the one or more additional components comprises a transition metal. In some embodiments, the transition metal comprises iron. In some embodiments, the transition metal comprises zinc. In some embodiments, the transition metal comprises copper. In some embodiments, the transition metal comprises chromium. In some embodiments, the transition metal comprises iodine. In some embodiments, the transition metal comprises cobalt. In some embodiments, the transition metal comprises selenium. In some embodiments, the transition metal comprises magnesium. In some embodiments, the transition metal comprises molybdenum.

In some embodiments, the one or more additional components include a vitamin. In some embodiments, the vitamin comprises a fat-soluble vitamin (e.g., Vitamin A, Vitamin D, Vitamin E, Vitamin K). In some embodiments, the vitamin comprises a water-soluble vitamin (e.g., B1, B2, B6, $B_{12}$, C, folate).

In some embodiments, the one or more additional components include a polyamine. In some embodiments, the polyamine comprises putrescine. In some embodiments the polyamine comprises spermidine. In some embodiments, the polyamine comprises spermine.

In some embodiments, the one or more additional components include a reductant. In some embodiments, the reductant comprises a 2-mercaptoethanol. In some embodiments, the reductant includes an alpha-thioglycerol. In some embodiments, the reductant comprises reduced glutathione.

In some embodiments, the one or more additional components include a protective additive. In some embodiments, the protective additive comprises carboxymethyl cellulose. In some embodiments, the protective additive comprises polyvinyl pyrrolidone. In some embodiments, the protective additive comprises pluronic F-68. In some embodiments, the protective additive comprises Tween 80.

In some embodiments, the one or more additional components include an adhesion factor. In some embodiments the adhesion factor comprises fibronectin. In some embodiments, the adhesion factor comprises laminin.

In some embodiments, the one or more additional components is one or more of one or more antioxidants, one or more albumins or albumin substitutes, one or more lipid agents, one or more insulins or insulin substitutes, one or more transferrins or transferrin substitutes, one or more trace elements, and one or more glucocorticoids. In some embodiments, the antioxidants include N-acetyl-L-cysteine, 2-mercaptoethanol, or D,L-tocopherol acetate, or derivatives or mixtures thereof. In some embodiments, the albumin is human serum albumin. In some embodiments, the lipid agents include Human Ex-Cite® or ethanolamine or derivatives and mixtures thereof. In some embodiments, the insulin is human zinc insulin. In some embodiments, transferrin is human iron-saturated transferrin. In some embodiments, the trace element is Se4+. In some embodiments, glucocorticoid is hydrocortisone. In some embodiments, the supplement is concentrated.

In some embodiments, the one or more additional components comprises one or more antioxidants, and one or more ingredients selected from the group consisting of one or more albumins or albumin substitutes, one or more lipid agents, one or more insulins or insulin substitutes, one or more transferrins or transferrin substitutes, one or more trace elements, and one or more glucocorticoids In some embodiments, the one or more additional components comprises one or more of N-acetyl-L cysteine, human serum albumin, Human Ex-Cyte®, ethanolamine, human zinc insulin, human iron saturated transferrin, Se4+, hydrocortisone, D,L-tocopherol acetate, and/or 2-mercapto-ethanol.

In some embodiments, the one or more additional components include N-acetyl-L-cysteine (NAC). In some embodiments, the concentration of NAC is such that after the supplement is combined with a basal medium (such as these described herein), the concentration of NAC of in the basal medium is at or about 10 mg/L to at or about 50 mg/L, at or about 10 mg/L to at or about 100 mg/L, at or about 10 mg/L to at or about 150 mg/L, at or about 10 mg/L to at or about 200 mg/L, at or about 10 mg/L to at or about 250 mg/L, at or about 10 mg/L to at or about 300 mg/L, at or about 10 mg/L to at or about 350 mg/L, at or about 10 mg/L to at or about 400 mg/L, at or about 10 mg/L to at or about 450 mg/L, at or about 10 mg/L to at or about 500 mg/L, at or about 10 mg/L to at or about 550 mg/L, at or about 10 mg/L to at or about 600 mg/L, at or about 10 mg/L to at or about 650 mg/L, at or about 10 mg/L to at or about 700 mg/L, at or about 50 mg/L to at or about 100 mg/L, at or about 50 mg/L to at or about 150 mg/L, at or about 50 mg/L to at or about 200 mg/L, at or about 50 mg/L to at or about 250 mg/L, at or about 50 mg/L to at or about 300 mg/L, at or about 50 mg/L to at or about 350 mg/L, at or about 50 mg/L to at or about 400 mg/L, at or about 50 mg/L to at or about 450 mg/L, at or about 50 mg/L to at or about 500 mg/L, at or about 50 mg/L to at or about 550 mg/L, at or about 50 mg/L to at or about 600 mg/L, at or about 50 mg/L to at or about 650 mg/L, at or about 50 mg/L to at or about 700 mg/L, at or about 100 mg/L to at or about 150 mg/L, at or about 100 mg/L to at or about 200 mg/L, at or about 100 mg/L to at or about 250 mg/L, at or about 100 mg/L to at or about 300 mg/L, at or about 100 mg/L to at or about 350 mg/L, at or about 100 mg/L to at or about 400 mg/L, at or about 100 mg/L to at or about 450 mg/L, at or about 100 mg/L to at or about 500 mg/L, at or about 100 mg/L to at or about 550 mg/L, at or about 100 mg/L to at or about 600 mg/L, at or about 100 mg/L to at or about 650 mg/L, at or about 100 mg/L to at or about 700 mg/L, at or about 150 mg/L to at or about 200 mg/L, at or about 150 mg/L to at or about 250 mg/L, at or about 150 mg/L to at or about 300 mg/L, at or about 150 mg/L to at or about 350 mg/L, at or about 150 mg/L to at or about 400 mg/L, at or about 150 mg/L to at or about 450 mg/L, at or about 150 mg/L to at or about 500 mg/L, at or about 150 mg/L to at or about 550 mg/L, at or about 150 mg/L to at or about 600 mg/L, at or about 150 mg/L to at or about 650 mg/L, at or about 150 mg/L to at or about 700 mg/L, at or about 200 mg/L to at or about 250 mg/L, at or about 200 mg/L to at or about 300 mg/L, at or about 200 mg/L to at or about 350 mg/L, at or about 200 mg/L to at or about 400 mg/L, at or about 200 mg/L to at or about 450 mg/L, at or about 200 mg/L to at or about 500 mg/L, at or about 200 mg/L to at or about 550 mg/L, at or about 200 mg/L to at or about 600 mg/L, at or about 200 mg/L to at or about 650 mg/L, at or about 200 mg/L to at or about 700 mg/L, at or about 250 mg/L to at or about 300 mg/L, at or about 250 mg/L to at or about 350 mg/L, at or about 250 mg/L to at or about 400 mg/L, at or about 250 mg/L to at or about 450 mg/L, at or about 250 mg/L to at or about 500 mg/L, at or about 250 mg/L to at or about 550 mg/L, at or about 250 mg/L to at or about 600 mg/L, at or about 250 mg/L to at or about 650 mg/L, at or about 250 mg/L to at or about 700 mg/L, at or about 300 mg/L to at or about 350 mg/L, at or about 300 mg/L to at or about 400 mg/L, at or about 300 mg/L to at or about 450 mg/L, at or about 300 mg/L to at or about 500 mg/L, at or about 300 mg/L to at or about 550 mg/L, at or about 300 mg/L to at or about 600 mg/L, at or about 300 mg/L to at or about 650 mg/L, at or about 300 mg/L to at or about 700 mg/L, at or about 350 mg/L to at or about 400 mg/L, at or about 350 mg/L to at or about 450 mg/L, at or about 350 mg/L to at or about 500 mg/L, at or about 350 mg/L to at or about 550 mg/L, at or about 350 mg/L to at or about 600 mg/L, at or about 350 mg/L to at or about 650 mg/L, at or about 350 mg/L to at or about 700 mg/L, at or about 400 mg/L to at or about 450 mg/L, at or about 400 mg/L to at or about 500 mg/L, at or about 400 mg/L to at or about 550 mg/L, at or about 400 mg/L to at or about 600 mg/L, at or about 400 mg/L to at or about 650 mg/L, at or about 400 mg/L to at or about 700 mg/L, at or about 450 mg/L to at or about 500 mg/L, at or about 450 mg/L to at or about 550 mg/L, at or about 450 mg/L to at or about 600 mg/L, at or about 450 mg/L to at or about 650 mg/L, at or about 450 mg/L to at or about 700 mg/L, at or about 500 mg/L to at or about 550 mg/L, at or about 500 mg/L to at or about 600 mg/L, at or about 500 mg/L to at or about 650 mg/L, at or about 500 mg/L to at or about 700 mg/L, at or about 550 mg/L to at or about 600 mg/L, at or about 550 mg/L to at or about 650 mg/L, at or about 550 mg/L to at or about 700 mg/L, at or about 600 mg/L to at or about 650 mg/L, at or about 60 mg/L to at or about 700 mg/L, or at or about 650 mg/L to at or about 700 mg/L.

In some embodiments, the concentration of NAC in the basal medium is at or about 0 mM to at or about 1 mM, at or about 0 mM to at or about 2 mM, at or about 0 mM to at or about 3 mM, at or about 0 mM to at or about 4 mM, at or about 0 mM to at or about 5 mM, at or about 0 mM to at or about 6 mM, at or about 0 mM to at or about 7 mM, at or about 0 mM to at or about 8 mM, at or about 0 mM to at or about 9 mM, at or about 0 mM to at or about 10 mM, at or about 0 mM to at or about 12 mM, at or about 0 mM to at or about 14 mM, at or about 0 mM to at or about 16 mM, at or about 0 mM to at or about 18 mM, at or about 0 mM to at or about 20 mM, at or about 1 mM to at or about 2 mM, at or about 1 mM to at or about 3 mM, at or about 1 mM to at or about 4 mM, at or about 1 mM to at or about 5 mM, at or about 1 mM to at or about 6 mM, at or about 1 mM to at or about 7 mM, at or about 1 mM to at or about 8 mM, at or about 1 mM to at or about 9 mM, at or about 1 mM to at or about 10 mM, at or about 1 mM to at or about 12 mM, at or about 1 mM to at or about 14 mM, at or about 1 mM to at or about 16 mM, at or about 1 mM to at or about 18 mM, at or about 1 mM to at or about 20 mM, at or about 2 mM to at or about 3 mM, at or about 2 mM to at or about 4 mM, at or about 2 mM to at or about 5 mM, at or about 2 mM to at or about 6 mM, at or about 2 mM to at or about 7 mM, at or about 2 mM to at or about 8 mM, at or about 2 mM to at or about 9 mM, at or about 2 mM to at or about 10 mM, at or about 2 mM to at or about 12 mM, at or about 2 mM to at or about 14 mM, at or about 2 mM to at or about 16 mM, at or about 2 mM to at or about 18 mM, at or about 2 mM to at or about 20 mM, at or about 3 mM, at or about to at or about 4 mM, at or about 3 mM to at or about 5 mM, at or about 3 mM to at or about 6 mM, at or about 3 mM to at or about 7 mM, at or about 3 mM to at or about 8 mM, at or about 3 mM to at or about 9 mM, at or about 3 mM to at or about 10 mM, at or about 3 mM to at or about 12 mM, at or about 3 mM to at or about 14 mM, at or about 3 mM to at or about 16 mM, at or about 3 mM to at or about 18 mM, at or about 3 mM to at or about 20 mM, at or about 4 mM to at or about 5 mM, at or about 4 mM to at or about 6 mM, at or about 4 mM to at or about 7 mM, at or about 4 mM to at or about 8 mM, at or about 4 mM to at or about 9 mM, at or about 4 mM to at or about 10 mM, at or about 4 mM to at or about 12 mM, at or about 4 mM to at or about 14 mM, at or about 4 mM to at or about 16 mM, at or about 4 mM to at or about 18 mM, at or about 4 mM to at or about 20 mM, at or about 5 mM to at or about 6 mM, at or about 5 mM to at or about 7 mM, at or about 5 mM to at or about 8 mM, at or about 5 mM to at or about 9 mM, at or about 5 mM to at or about 10 mM, at or about 5 mM to at or about 12 mM, at or about 5 mM to at or about 14 mM, at or about 5 mM to at or about 16 mM, at or about 5 mM to at or about 18 mM, at or about 5 mM to at or about 20 mM, at or about 6 mM to at or about 7 mM, at or about 6 mM to at or about 8 mM, at or about 6 mM to at or about 9 mM, at or about 6 mM to at or about 10 mM, at or about 6 mM to at or about 12 mM, at or about 6 mM to at or about 14 mM, at or about 6 mM to at or about 16 mM, at or about 6 mM to at or about 18 mM, at or about 6 mM to at or about 20 mM, at or about 7 mM to at or about 8 mM, at or about 7 mM to at or about 9 mM, at or about 7 mM to at or about 10 mM, at or about 7 mM to at or about 12 mM, at or about 7 mM to at or about 14 mM, at or about 7 mM to at or about 16 mM, at or about 7 mM to at or about 18 mM, at or about 7 mM to at or about 20 mM, at or about 8 mM to at or about 9 mM, at or about 8 mM to at or about 10 mM, at or about 8 mM to at or about 12 mM, at or about 8 mM to at or about 14 mM, at or about 8 mM to at or about 16 mM, at or about 8 mM to at or about 18 mM, at or about 8 mM to at or about 20 mM, at or about 9 mM to at or about 10 mM, at or about 9 mM to at or about 12 mM, at or about 9 mM to at or about 14 mM, at or about 9 mM to at or about 16 mM, at or about 9 mM to at or about 18 mM, at or about 9 mM to at or about 20 mM, at or about 10 mM to at or about 12 mM, at or about 10 mM to at or about 14 mM, at or about 10 mM to at or about 16 mM, at or about 10 mM to at or about 18 mM, at or about 10 mM to at or about 20 mM, at or about 12 mM to at or about 14 mM, at or about 12 mM to at or about 16 mM, at or about 12 mM to at or about 18 mM, at or about 12 mM to at or about 20 mM, at or about 14 mM to at or about 16 mM, at or about 14 mM to at or about 18 mM, at or about 14 mM to at or about 20 mM, at or about 16 mM to at or about 18 mM, at or about 16 mM to at or about 20 mM, at or about 18 mM to at or about 20 mM.

In some embodiments, the one or more additional components include ethanolamine. In some embodiments, the concentration of ethanolamine is such that after the supplement is combined with a basal medium (such as these described herein), the concentration of ethanolamine in the basal medium is at or about 0 mg/L to at or about 2 mg/L, at or about 0 mg/L to at or about 4 mg/L, at or about 0 mg/L to at or about 6 mg/L, at or about 0 mg/L to at or about 8 mg/L, at or about 0 mg/L to at or about 10 mg/L, at or about 0 mg/L to at or about 12 mg/L, at or about 0 mg/L to at or about 14 mg/L, at or about 0 mg/L to at or about 16 mg/L, at or about 0 mg/L to at or about 18 mg/L, at or about 0 mg/L to at or about 20 mg/L, at or about 0 mg/L to at or about 22 mg/L, at or about 0 mg/L to at or about 24 mg/L, at or about 0 mg/L to at or about 26 mg/L, at or about 0 mg/L to at or about 28 mg/L, at or about 0 mg/L to at or about 30 mg/L, at or about 2 mg/L to at or about 4 mg/L, at or about 2 mg/L to at or about 6 mg/L, at or about 2 mg/L to at or about 8 mg/L, at or about 2 mg/L to at or about 10 mg/L, at or about 2 mg/L to at or about 12 mg/L, at or about 2 mg/L to at or about 14 mg/L, at or about 2 mg/L to at or about 16 mg/L, at or about 2 mg/L to at or about 18 mg/L, at or about 2 mg/L to at or about 20 mg/L, at or about 2 mg/L to at or about 22 mg/L, at or about 2 mg/L to at or about 24 mg/L, at or about 2 mg/L to at or about 26 mg/L, at or about 2 mg/L to at or about 28 mg/L, at or about 2 mg/L to at or about 30 mg/L, at or about 4 mg/L to at or about 6 mg/L, at or about 4 mg/L to at or about 8 mg/L, at or about 4 mg/L to at or about 10 mg/L, at or about 4 mg/L to at or about 12 mg/L, at or about 4 mg/L to at or about 14 mg/L, at or about 4 mg/L to at or about 16 mg/L, at or about 4 mg/L to at or about 18 mg/L, at or about 4 mg/L to at or about 20 mg/L, at or about 4 mg/L to at or about 22 mg/L, at or about 4 mg/L to at or about 24 mg/L, at or about 4 mg/L to at or about 26 mg/L, at or about 4 mg/L to at or about 28 mg/L, at or about 4 mg/L to at or about 30 mg/L, at or about 6 mg/L to at or about 8 mg/L, at or about 6 mg/L to at or about 10 mg/L, at or about 6 mg/L to at or about 12 mg/L, at or about 6 mg/L to at or about 14 mg/L, at or about 6 mg/L to at or about 16 mg/L, at or about 6 mg/L to at or about 18 mg/L, at or about 6 mg/L to at or about 20 mg/L, at or about 6 mg/L to at or about 22 mg/L, at or about 6 mg/L to at or about 24 mg/L, at or about 6 mg/L to at or about 26 mg/L, at or about 6 mg/L to at or about 28 mg/L, at or about 6 mg/L to at or about 30 mg/L, at or about 8 mg/L to at or about 10 mg/L, at or about 8 mg/L to at or about 12 mg/L, at or about 8 mg/L to at or about 14 mg/L, at or about 8 mg/L to at or about 16 mg/L, at or about 8 mg/L to at or about 18 mg/L, at or about 8 mg/L to at or about 20 mg/L, at or about 8 mg/L to at or about 22 mg/L, at or about 8 mg/L to at or about 24 mg/L, at or about 8 mg/L to at or about 26 mg/L, at or about 8 mg/L to at or about 28 mg/L, at or about 8 mg/L to at or about 30 mg/L, at or about 10 mg/L to at or about 12 mg/L, at or about 8 mg/L to at or about 14 mg/L, at or about 8 mg/L to at or about 16 mg/L, at or about 8 mg/L to at or about 18 mg/L, at or about 8 mg/L to at or about 20 mg/L, at or about 8 mg/L to at or about 22 mg/L, at or about 8 mg/L to at or about 24 mg/L, at or about 8 mg/L to at or about 26 mg/L, at or about 8 mg/L to at or about 28 mg/L, at or about 8 mg/L to at or about 30 mg/L, at or about 10 mg/L to at or about 12 mg/L, at or about 10 mg/L to at or about 14 mg/L, at or about 10 mg/L to at or about 16 mg/L, at or about 10 mg/L to at or about 18 mg/L, at or about 10 mg/L to at or about 20 mg/L, at or about 10 mg/L to at or about 22 mg/L, at or about 10 mg/L to at or about 24 mg/L, at or about 10 mg/L to at or about 26 mg/L, at or about 10 mg/L to at or about 28 mg/L, at or about 10 mg/L to at or about 30 mg/L, at or about 12 mg/L to at or about 14 mg/L, at or about 12 mg/L to at or about 16 mg/L, at or about 12 mg/L to at or about 18 mg/L, at or about 12 mg/L to at or about 20 mg/L, at or about 12 mg/L to at or about 22 mg/L, at or about 12 mg/L to at or about 24 mg/L, at or about 12 mg/L to at or about 26 mg/L, at or about 12 mg/L to at or about 28 mg/L, at or about 12 mg/L to at or about 30 mg/L, at or about 14 mg/L to at or about 16 mg/L, at or about 14 mg/L to at or about 18 mg/L, at or about 14 mg/L to at or about 20 mg/L, at or about 14 mg/L to at or about 22 mg/L, at or about 14 mg/L to at or about 24 mg/L, at or about 14 mg/L to at or about 26 mg/L, at or about 14 mg/L to at or about 28 mg/L, at or about 14 mg/L to at or about 30 mg/L, at or about 16 mg/L to at or about 18 mg/L, at or about 16 mg/L to at or about 20 mg/L, at or about 16 mg/L to at or about 22 mg/L, at or about 16 mg/L to at or about 24 mg/L, at or about 16 mg/L to at or about 26 mg/L, at or about 16 mg/L to at or about 28 mg/L, at or about 16 mg/L to at or about 30 mg/L, at or about 18 mg/L to at or about 20 mg/L, at or about 18 mg/L to at or about 22 mg/L, at or about 18 mg/L to at or about 24 mg/L, at or about 18 mg/L to at or about 26 mg/L, at or about 18 mg/L to at or about 28 mg/L, at or about 18 mg/L to at or about 30 mg/L, at or about 20 mg/L to at or about 22 mg/L, at or about 20 mg/L to at or about 24 mg/L, at or about 20 mg/L to at or about 26 mg/L, at or about 20 mg/L to at or about 28 mg/L, at or about 20 mg/L to at or about 30 mg/L, at or about 22 mg/L to at or about 24 mg/L, at or about 22 mg/L to at or about 26 mg/L, at or about 22 mg/L to at or about 28 mg/L, at or about 22 mg/L to at or about 30 mg/L, at or about 24 mg/L to at or about 26 mg/L, at or about 24 mg/L to at or about 28 mg/L, at or about 24 mg/L to at or about 30 mg/L, at or about 26 mg/L to at or about 28 mg/L, at or about 26 mg/L to at or about 30 mg/L, or at or about 28 mg/L to at or about 30 mg/L.

In some embodiments, the supplement is liquid. In some embodiments, the supplement is not frozen, or not recommended to be frozen for the storage. In some embodiments, the supplement comprises an albumin, N-acetyle-L-cysteine (NAC) and ethanolamine. In some embodiments, the supplement comprises an albumin, N-acetyle-L-cysteine (NAC) and ethanolamine, wherein the concentration of albumin, NAC and/or ethanolamine is such that after the supplement is combined with a basal medium (such as these described herein), the concentration of albumin, NAC and/or ethanolamine is substantially the same as described herein. In some embodiments, the albumin is a human derived albumin. In some embodiments, the albumin is a human derived albumin from human plasma or serum. In some embodiments, the supplement is a liquid and does not include, or does not include a significant amount of a free form of glutamine (i.e., L-glutamine).

In some embodiments, a further supplement, e.g. second supplement, is combined with the basal media to provide the one or more additional components. In some embodiments, the further supplement, e.g. second supplement, is a cell expansion supplement. In some embodiments, the further supplement, e.g. second supplement is or comprises OpTmizer® supplement (Thermofisher, part of A1048503).

In some embodiments, the supplement is concentrated at or about 2 to at or about 100 fold. In some embodiments, the supplement is at or about a 40× formulation. In some embodiments, a liter of the basal medium is supplemented with at or about 20 to 30 milliliters, such as 25±2 milliliter, of at least one supplement, including the first supplement and, in some cases, one or more further supplement.

C. Serum-Free Media

In some embodiments, the serum-free media comprises a synthetic amino acid (e.g., a dipeptide form of L-glutamine, e.g., L-alanyl-L-glutamine), a free form of glutamine (i.e., L-glutamine). In some embodiments, the synthetic amino acid (e.g., a dipeptide form of L-glutamine, e.g., L-alanyl-L-glutamine) is capable of being converted into a free form of glutamine (i.e., L-glutamine) in a cell culture comprising a cell, wherein the media is serum-free. In some embodiments, the cell comprises a human cell. In some embodiments, the cell comprises an immune cell. In some embodiments, the cell is a genetically engineered cell. In some embodiments, the cell is a T cell. In some embodiments, the cell is a genetically engineered T cell. In some embodiments, the cell is genetically engineered to express a recombinant receptor (e.g., a chimeric antigen receptor). In some embodiments, the cell is a chimeric antigen receptor (CAR) expressing T cells.

In some embodiments, the serum-free media further comprises at least one protein. In some embodiments, the serum-free media comprises a synthetic amino acid, wherein the synthetic amino acid (e.g., a dipeptide form of L-glutamine, e.g., L-alanyl-L-glutamine) is capable of being converted into a free form of glutamine (i.e., L-glutamine) in a cell culture comprising a cell, a free form of glutamine (i.e., L-glutamine), and at least one protein, wherein the media is serum free.

In some embodiments, the synthetic amino acid is a stabilized form of glutamine (i.e., L-glutamine). In some embodiments, the synthetic amino acid is more stable than glutamine (i.e., L-glutamine) in an aqueous solution (e.g., a serum-free media). In some embodiments, the synthetic amino acid does not produce a significant amount of glutamine in the serum-free media. In some embodiments, the synthetic amino acid does not produce a significant amount of pyrrolidone carboxylic acid or ammonia. In some embodiments, the synthetic amino acid does not produce a significant amount of glutamine (i.e., L-glutamine) for at least at or about 1, 3, 5, 7, 9, 11 13, or 14 days in the serum-free media. In some embodiments, the synthetic amino acid does not produce a significant amount of glutamine (i.e., L-glutamine) for at least at or about 1, 2, 3, 4, 5, 6, 7, or 8 weeks in the serum-free media. In some embodiments, the synthetic amino acid does not produce a significant amount of glutamine (i.e., L-glutamine) for at least at or about 1, 2, 3, 4, 5, 6, 7, 8, 9, 10, 11, or 12 months in the serum-free media. In some embodiments, the synthetic amino acid does not produce a significant amount of glutamine (i.e., L-glutamine) for at least at or about 1, 2, 3, 4, or 5 years in the serum-free media. In some embodiments, the synthetic amino acid does not produce a significant amount of pyrrolidone carboxylic acid or ammonia for at least at or about 1, 3, 5, 7, 9, 11 13, or 14 days in the serum-free media. In some embodiments, the synthetic amino acid does not produce a significant amount of pyrrolidone carboxylic acid or ammonia for at least at or about 1, 2, 3, 4, 5, 6, 7, or 8 weeks in the serum-free media. In some embodiments, the synthetic amino acid does not produce a significant amount of pyrrolidone carboxylic acid or ammonia for at least at or about 1, 2, 3, 4, 5, 6, 7, 8, 9, 10, 11, or 12 months in the serum-free media. In some embodiments, the synthetic amino acid does not produce a significant amount of pyrrolidone carboxylic acid or ammonia for at least at or about 1, 2, 3, 4, or 5 years in the serum-free media.

In some embodiments, the synthetic amino acid is soluble in an aqueous solution (e.g., a serum-free media). In some embodiments, the solubility of the synthetic amino acid in the aqueous solution is higher than a free form of glutamine (i.e., L-glutamine).

In some embodiments, the synthetic amino acid is capable of being transported into a cell, wherein it can be converted into a free form of glutamine (i.e., L-glutamine). In some embodiments, the cell comprises an immune cell. In some embodiments, the cell is a genetically engineered cell. In some embodiments, the cell is a T cell. In some embodiments, the cell is a genetically engineered T cell. In some embodiments, the cell is genetically engineered to express a recombinant receptor (e.g., a chimeric antigen receptor). In some embodiments, the cell is a chimeric antigen receptor (CAR) expressing T cells.

In some embodiments, the synthetic amino acid is a dipeptide. In some embodiments, the synthetic amino acid is a tripeptide. In some embodiments, the synthetic amino acid is a dipeptide form of L-glutamine (e.g., L-alanyl-L-glutamine).

In some embodiments, the concentration of the dipeptide form of L-glutamine (e.g., L-alanyl-L-glutamine) in the serum-free media is at or about 0.5 mM-5 mM. In some embodiments, the concentration of the dipeptide form of L-glutamine (e.g., L-alanyl-L-glutamine) in the serum-free media is at or about 2 mM. In some embodiments, the concentration of the dipeptide form of L-glutamine (e.g., L-alanyl-L-glutamine) is at or about 0.5 mM-1 mM, 0.5 mM-1.5 mM, 0.5 mM-2 mM, 0.5 mM-2.5 mM, 0.5 mM-3 mM, 0.5 mM-3.5 mM, 0.5 mM-4 mM, 0.5 mM-4.5 mM, 0.5 mM-5 mM, 1 mM-1.5 mM, 1 mM-2 mM, 1 mM-2.5 mM, 1 mM-3 mM, 1 mM-3.5 mM, 1 mM-4 mM, 1 mM-4.5 mM, 1 mM-5 mM, 1.5 mM-2 mM, 1.5 mM-2.5 mM, 1.5 mM-3 mM, 1.5 mM-3.5 mM, 1.5 mM-4 mM, 1.5 mM-4.5 mM, 1.5 mM-5 mM, 2 mM-2.5 mM, 2 mM-3 mM, 2 mM-3.5 mM, 2 mM-4 mM, 2 mM-4.5 mM, 2 mM-5 mM, 2.5 mM-3 mM, 2.5 mM-3.5 mM, 2.5 mM-4 mM, 2.5 mM-4.5 mM, 2.5 mM-5 mM, 3 mM-3.5 mM, 3 mM-4 mM, 3 mM-4.5 mM, 3 mM-5 mM, 3.5 mM-4 mM, 3.5 mM-4.5 mM, 3.5 mM-5 mM, 4 mM-4.5 mM, 4 mM-5 mM, or 4.5 mM-5 mM, each inclusive. In some embodiments, the concentration of the dipeptide form of L-glutamine (e.g., L-alanyl-L-glutamine) in the serum-free media is at or about 5 mM-7.5 mM, 5 mM-10 mM, 5 mM-12.5 mM, 5 mM-15 mM, 5 mM-17.5 mM, 5 mM-20 mM, 7.5 mM-10 mM, 7.5 mM-12.5 mM, 7.5 mM-15 mM, 7.5 mM-17.5 mM, 7.5 mM-20 mM, 10 mM-12.5 mM, 10 mM-15 mM, 10 mM-17.5 mM, 10 mM-20 mM, 12.5 mM-15 mM, 12.5 mM-17.5 mM, 12.5 mM-20 mM, 15 mM-17.5 mM, 15 mM-20 mM, or 17.5 mM-20 mM, each inclusive. In some embodiments, the concentration of dipeptide form of L-glutamine (e.g., L-alanyl-L-glutamine) in the serum-free media is at least at or about 0.5 mM, 1 mM, 1.5 mM, 2 mM, 2.5 mM, 3 mM, 3.5 mM, 4 mM, 4.5 mM, or 5 mM. In some embodiments, the concentration of the dipeptide form of L-glutamine (e.g., L-alanyl-L-glutamine) in the serum-free media is or is at or about 2 mM. In some embodiments, the concentration of the dipeptide form of L-glutamine (e.g., L-alanyl-L-glutamine) in the serum-free media is at most at or about 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, 10 mM, 12.5 mM, 15 mM, 17.5 mM, or 20 mM.

In some embodiments, the concentration of the free form of glutamine (i.e., L-glutamine) in the serum-free media is about 0.5 mM-5 mM. In some embodiments, the concentration of the free form of glutamine (i.e., L-glutamine) in the serum-free media is at or about 2 mM. In some embodiments, the concentration of the free form of glutamine (i.e., L-glutamine) in the serum-free media is at or about 0.5 mM-1 mM, 0.5 mM-1.5 mM, 0.5 mM-2 mM, 0.5 mM-2.5 mM, 0.5 mM-3 mM, 0.5 mM-3.5 mM, 0.5 mM-4 mM, 0.5 mM-4.5 mM, 0.5 mM-5 mM, 1 mM-1.5 mM, 1 mM-2 mM, 1 mM-2.5 mM, 1 mM-3 mM, 1 mM-3.5 mM, 1 mM-4 mM, 1 mM-4.5 mM, 1 mM-5 mM, 1.5 mM-2 mM, 1.5 mM-2.5 mM, 1.5 mM-3 mM, 1.5 mM-3.5 mM, 1.5 mM-4 mM, 1.5 mM-4.5 mM, 1.5 mM-5 mM, 2 mM-2.5 mM, 2 mM-3 mM, 2 mM-3.5 mM, 2 mM-4 mM, 2 mM-4.5 mM, 2 mM-5 mM, 2.5 mM-3 mM, 2.5 mM-3.5 mM, 2.5 mM-4 mM, 2.5 mM-4.5 mM, 2.5 mM-5 mM, 3 mM-3.5 mM, 3 mM-4 mM, 3 mM-4.5 mM, 3 mM-5 mM, 3.5 mM-4 mM, 3.5 mM-4.5 mM, 3.5 mM-5 mM, 4 mM-4.5 mM, 4 mM-5 mM, or 4.5 mM-5 mM, each inclusive. In some embodiments, the concentration of the free form of glutamine (i.e., L-glutamine) in the serum-free media is at or about 5 mM-7.5 mM, 5 mM-10 mM, 5 mM-12.5 mM, 5 mM-15 mM, 5 mM-17.5 mM, 5 mM-20 mM, 7.5 mM-10 mM, 7.5 mM-12.5 mM, 7.5 mM-15 mM, 7.5 mM-17.5 mM, 7.5 mM-20 mM, 10 mM-12.5 mM, 10 mM-15 mM, 10 mM-17.5 mM, 10 mM-20 mM, 12.5 mM-15 mM, 12.5 mM-17.5 mM, 12.5 mM-20 mM, 15 mM-17.5 mM, 15 mM-20 mM, or 17.5 mM-20 mM, each inclusive. In some embodiments, the concentration of the free form of glutamine (i.e., L-glutamine) in the media is at least at or about 0.5 mM, 1 mM, 1.5 mM, 2 mM, 2.5 mM, 3 mM, 3.5 mM, 4 mM, 4.5 mM, or 5 mM. In some embodiments, the concentration of the free form of glutamine (i.e., L-glutamine) in the serum-free media is at most at or about 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, 10 mM, 12.5 mM, 15 mM, 17.5 mM, or 20 mM.

In some embodiments, the concentration of the dipeptide form of L-glutamine, such as L-alanyl-L-glutamine in the serum-free media is at or about 0.5 mM to at or about 5 mM. In some embodiments, the concentration of the dipeptide form of L-glutamine, such as L-alanyl-L-glutamine in the serum-free media is at or about 2 mM. In some embodiments, the concentration of L-glutamine in the serum-free media is at or about 0.5 mM to at or about 5 mM. In some embodiments, the concentration of the L-glutamine in the serum-free media is at or about 2 mM.

In some embodiments, the serum-free media comprises at least one protein. In some embodiments, the at least one protein is not of non-mammalian origin. In some embodiments, the at least one protein is human or derived from human. In some embodiments, the at least one protein is recombinant. In some embodiments, the one or more additional components include at least one protein. In some embodiments, the at least one protein is not of non-mammalian origin. In some embodiments, the at least one protein is human or derived from human. In some embodiments, the at least one protein is recombinant. In some embodiments, the at least one protein includes albumin, transferrin, insulin, fibronectin, aprotinin or fetuin. In some embodiments, the protein comprises one or more of albumin, insulin or transferrin, optionally one or more of a human or recombinant albumin, insulin or transferrin.

In some embodiments, the serum-free media comprises an albumin. In some embodiments, the albumin is derived from human. In some embodiments, the albumin is derived from human serum or human plasma. In some embodiments, the albumin is a recombinant albumin. In some embodiments, the recombinant albumin is derived from human. In some embodiment, the recombinant albumin is not derived from human. In some embodiments, the supplement comprises a natural albumin. In some embodiments, the natural albumin is derived from human. In some embodiments, the natural albumin is not derived from human. In some embodiments, the concentration of the albumin in the serum-free media is at or about 0 mg/mL to at or about 2 mg/mL, at or about 0 mg/mL to at or about 4 mg/mL, at or about 0 mg/mL to at or about 6 mg/mL, at or about 0 mg/mL to at or about 8 mg/mL, at or about 0 mg/mL to at or about 10 mg/mL, at or about 0 mg/mL to at or about 12 mg/mL, at or about 2 mg/mL to at or about 4 mg/mL, at or about 2 mg/mL to at or about 6 mg/mL, at or about 2 mg/mL to at or about 8 mg/mL, at or about 2 mg/mL to at or about 10 mg/mL, at or about 2 mg/mL to at or about 12 mg/mL, at or about 4 mg/mL to at or about 6 mg/mL, at or about 4 mg/mL to at or about 8 mg/mL, at or about 4 mg/mL to at or about 10 mg/mL, at or about 4 mg/mL to at or about 12 mg/mL, at or about 6 mg/mL to at or about 8 mg/mL, at or about 6 mg/mL to at or about 10 mg/mL, at or about 6 mg/mL to at or about 12 mg/mL, at or about 8 mg/mL to at or about 10 mg/mL, at or about 8 mg/mL to at or about 12 mg/mL, at or about 10 mg/mL to at or about 12 mg/mL, or at or about 10 mg/mL to at or about 15 mg/mL each inclusive. In some embodiments, the albumin in the media is at or about 5 mg/mL.

In some embodiments, the serum-free media comprises a transferrin or transferrin substitute (such as these described herein). In some embodiments, the transferrin or transferrin substitute is derived from human. In some embodiments, the transferrin or transferrin substitute is derived from human serum or plasma. In some embodiments, the concentration of the transferrin in the serum-free media is at or about 10 mg/L to at or about 50 mg/L, at or about 10 mg/L to at or about 100 mg/L, at or about 10 mg/L to at or about 150 mg/L, at or about 10 mg/L to at or about 200 mg/L, at or about 10 mg/L to at or about 250 mg/L, at or about 10 mg/L to at or about 300 mg/L, at or about 10 mg/L to at or about 350 mg/L, at or about 10 mg/L to at or about 400 mg/L, at or about 10 mg/L to at or about 450 mg/L, at or about 10 mg/L to at or about 500 mg/L, at or about 10 mg/L to at or about 550 mg/L, at or about 10 mg/L to at or about 600 mg/L, at or about 10 mg/L to at or about 650 mg/L, at or about 10 mg/L to at or about 750 mg/L, at or about 50 mg/L to at or about 100 mg/L, at or about 50 mg/L to at or about 150 mg/L, at or about 50 mg/L to at or about 200 mg/L, at or about 50 mg/L to at or about 250 mg/L, at or about 50 mg/L to at or about 300 mg/L, at or about 50 mg/L to at or about 350 mg/L, at or about 50 mg/L to at or about 400 mg/L, at or about 50 mg/L to at or about 450 mg/L, at or about 50 mg/L to at or about 500 mg/L, at or about 50 mg/L to at or about 550 mg/L, at or about 50 mg/L to at or about 600 mg/L, at or about 50 mg/L to at or about 650 mg/L, at or about 50 mg/L to at or about 750 mg/L, at or about 100 mg/L to at or about 150 mg/L, at or about 100 mg/L to at or about 200 mg/L, at or about 100 mg/L to at or about 250 mg/L, at or about 100 mg/L to at or about 300 mg/L, at or about 100 mg/L to at or about 350 mg/L, at or about 100 mg/L to at or about 400 mg/L, at or about 100 mg/L to at or about 450 mg/L, at or about 100 mg/L to at or about 500 mg/L, at or about 100 mg/L to at or about 550 mg/L, at or about 100 mg/L to at or about 600 mg/L, at or about 100 mg/L to at or about 650 mg/L, at or about 100 mg/L to at or about 750 mg/L, at or about 150 mg/L to at or about 200 mg/L, at or about 150 mg/L to at or about 250 mg/L, at or about 150 mg/L to at or about 300 mg/L, at or about 150 mg/L to at or about 350 mg/L, at or about 150 mg/L to at or about 400 mg/L, at or about 150 mg/L to at or about 450 mg/L, at or about 150 mg/L to at or about 500 mg/L, at or about 150 mg/L to at or about 550 mg/L, at or about 150 mg/L to at or about 600 mg/L, at or about 150 mg/L to at or about 650 mg/L, at or about 150 mg/L to at or about 750 mg/L, at or about 200 mg/L to at or about 250 mg/L, at or about 200 mg/L to at or about 300 mg/L, at or about 200 mg/L to at or about 350 mg/L, at or about 200 mg/L to at or about 400 mg/L, at or about 200 mg/L to at or about 450 mg/L, at or about 200 mg/L to at or about 500 mg/L, at or about 200 mg/L to at or about 550 mg/L, at or about 200 mg/L to at or about 600 mg/L, at or about 200 mg/L to at or about 650 mg/L, at or about 200 mg/L to at or about 750 mg/L, at or about 250 mg/L to at or about 300 mg/L, at or about 250 mg/L to at or about 350 mg/L, at or about 250 mg/L to at or about 400 mg/L, at or about 250 mg/L to at or about 450 mg/L, at or about 250 mg/L to at or about 500 mg/L, at or about 250 mg/L to at or about 550 mg/L, at or about 250 mg/L to at or about 600 mg/L, at or about 250 mg/L to at or about 650 mg/L, at or about 250 mg/L to at or about 750 mg/L, at or about 300 mg/L to at or about 350 mg/L, at or about 300 mg/L to at or about 400 mg/L, at or about 300 mg/L to at or about 450 mg/L, at or about 300 mg/L to at or about 500 mg/L, at or about 300 mg/L to at or about 550 mg/L, at or about 300 mg/L to at or about 600 mg/L, at or about 300 mg/L to at or about 650 mg/L, at or about 300 mg/L to at or about 750 mg/L, at or about 350 mg/L to at or about 400 mg/L, at or about 350 mg/L to at or about 450 mg/L, at or about 350 mg/L to at or about 500 mg/L, at or about 350 mg/L to at or about 550 mg/L, at or about 350 mg/L to at or about 600 mg/L, at or about 350 mg/L to at or about 650 mg/L, at or about 350 mg/L to at or about 750 mg/L, at or about 400 mg/L to at or about 450 mg/L, at or about 400 mg/L to at or about 500 mg/L, at or about 400 mg/L to at or about 550 mg/L, at or about 400 mg/L to at or about 600 mg/L, at or about 400 mg/L to at or about 650 mg/L, at or about 400 mg/L to at or about 750 mg/L, at or about 450 mg/L to at or about 500 mg/L, at or about 450 mg/L to at or about 550 mg/L, at or about 450 mg/L to at or about 600 mg/L, at or about 450 mg/L to at or about 650 mg/L, at or about 450 mg/L to at or about 750 mg/L, at or about 500 mg/L to at or about 550 mg/L, at or about 500 mg/L to at or about 600 mg/L, at or about 500 mg/L to at or about 650 mg/L, at or about 500 mg/L to at or about 750 mg/L, at or about 550 mg/L to at or about 600 mg/L, at or about 500 mg/L to at or about 650 mg/L, at or about 500 mg/L to at or about 750 mg/L, at or about 550 mg/L to at or about 600 mg/L, at or about 550 mg/L to at or about 650 mg/L, at or about 550 mg/L to at or about 750 mg/L, at or about 600 mg/L to at or about 650 mg/L, at or about 600 mg/L to at or about 750 mg/L, or at or about 650 mg/L to at or about 750 mg/L. In some embodiments, the concentration of the transferrin in the serum-free media is at or about 100 mg/L. In some embodiments, the concentration of the transferrin in the serum-free media is at or about 50 mg/L to 150 mg/L.

In some embodiments, the supplement comprises insulin or insulin substitute (such as these described herein). In some embodiments, the insulin is derived from human. In some embodiments, the insulin is a recombinant insulin. In some embodiment, the insulin is a recombinant human insulin. In some embodiment, the concentration of the insulin (or insulin substitute) in the serum-free media is at or about 1 mg/L to at or about 2.5 mg/L, at or about 1 mg/L to at or about 5 mg/L, at or about 1 mg/L to at or about 7.5 mg/L, at or about 1 mg/L to at or about 10 mg/L, at or about 1 mg/L to at or about 12.5 mg/L, at or about 1 mg/L to at or about 15 mg/L, at or about 1 mg/L to at or about 17.5 mg/L, at or about 1 mg/L to at or about 20 mg/L, at or about 1 mg/L to at or about 22.5 mg/L, at or about 1 mg/L to at or about 25 mg/L, at or about 1 mg/L to at or about 27.5 mg/L, at or about 1 mg/L to at or about 30 mg/L, at or about 2.5 mg/L to at or about 5 mg/L, at or about 2.5 mg/L to at or about 7.5 mg/L, at or about 2.5 mg/L to at or about 10 mg/L, at or about 2.5 mg/L to at or about 12.5 mg/L, at or about 2.5 mg/L to at or about 15 mg/L, at or about 2.5 mg/L to at or about 17.5 mg/L, at or about 2.5 mg/L to at or about 20 mg/L, at or about 2.5 mg/L to at or about 22.5 mg/L, at or about 2.5 mg/L to at or about 25 mg/L, at or about 2.5 mg/L to at or about 27.5 mg/L, at or about 2.5 mg/L to at or about 30 mg/L, at or about 5 mg/L to at or about 7.5 mg/L, at or about 5 mg/L to at or about 10 mg/L, at or about 5 mg/L to at or about 12.5 mg/L, at or about 5 mg/L to at or about 15 mg/L, at or about 5 mg/L to at or about 17.5 mg/L, at or about 5 mg/L to at or about 20 mg/L, at or about 5 mg/L to at or about 22.5 mg/L, at or about 5 mg/L to at or about 25 mg/L, at or about 5 mg/L to at or about 27.5 mg/L, at or about 5 mg/L to at or about 30 mg/L, at or about 7.5 mg/L to at or about 10 mg/L, at or about 7.5 mg/L to at or about 12.5 mg/L, at or about 7.5 mg/L to at or about 15 mg/L, at or about 7.5 mg/L to at or about 17.5 mg/L, at or about 7.5 mg/L to at or about 20 mg/L, at or about 7.5 mg/L to at or about 22.5 mg/L, at or about 7.5 mg/L to at or about 25 mg/L, at or about 7.5 mg/L to at or about 27.5 mg/L, at or about 7.5 mg/L to at or about 30 mg/L, at or about 10 mg/L to at or about 12.5 mg/L, at or about 10 mg/L to at or about 15 mg/L, at or about 10 mg/L to at or about 17.5 mg/L, at or about 10 mg/L to at or about 20 mg/L, at or about 10 mg/L to at or about 22.5 mg/L, at or about 10 mg/L to at or about 25 mg/L, at or about 10 mg/L to at or about 27.5 mg/L, at or about 10 mg/L to at or about 30 mg/L, at or about 12.5 mg/L to at or about 15 mg/L, at or about 12.5 mg/L to at or about 17.5 mg/L, at or about 12.5 mg/L to at or about 20 mg/L, at or about 12.5 mg/L to at or about 22.5 mg/L, at or about 12.5 mg/L to at or about 25 mg/L, at or about 12.5 mg/L to at or about 27.5 mg/L, at or about 12.5 mg/L to at or about 30 mg/L, at or about 15 mg/L to at or about 17.5 mg/L, at or about 15 mg/L to at or about 20 mg/L, at or about 15 mg/L to at or about 22.5 mg/L, at or about 15 mg/L to at or about 25 mg/L, at or about 15 mg/L to at or about 27.5 mg/L, at or about 15 mg/L to at or about 30 mg/L, at or about 17.5 mg/L to at or about 20 mg/L, at or about 17.5 mg/L to at or about 22.5 mg/L, at or about 17.5 mg/L to at or about 25 mg/L, at or about 17.5 mg/L to at or about 27.5 mg/L, at or about 17.5 mg/L to at or about 30 mg/L, at or about 20 mg/L to at or about 22.5 mg/L, at or about 20 mg/L to at or about 25 mg/L, at or about 20 mg/L to at or about 27.5 mg/L, at or about 20 mg/L to at or about 30 mg/L, at or about 22.5 mg/L to at or about 25 mg/L, at or about 22.5 mg/L to at or about 27.5 mg/L, at or about 22.5 mg/L to at or about 30 mg/L, at or about 25 mg/L to at or about 27.5 mg/L, at or about 25 mg/L to at or about 30 mg/L, or at or about 27.5 mg/L to at or about 30 mg/L. In some embodiments, the concentration of insulin or insulin substitute in the serum-free media is at or about 10 mg/L. In some embodiments, the concentration of insulin or insulin substitute in the serum-free media is at or about 7.5 mg/L to at or about 12.5 mg/L.

In some embodiments, the serum-free media does not comprise phenol red. In some embodiments, the serum-free media comprises phenol red.

In some embodiments, the serum-free media comprises a nutrient mixture of inorganic salts, sugars, amino acids, optionally also containing vitamins, organic acids, antioxidants, lipids, growth factors, N-acetylcysteine, ethanolamine and/or buffers. Examples include those described herein, such as in the section above, including inorganic salts, sugars, amino acids, vitamins, organic acids, antioxidants, lipids, growth factors, N-acetylcysteine, ethanolamine and/or buffers.

In some embodiments, the serum free media comprises one or more ingredients selected from one or more of one or more antioxidants, one or more albumins or albumin substitutes, one or more lipid agents, one or more insulins or insulin substitutes, one or more transferrins or transferrin substitutes, one or more trace elements, one or more gluco-corticoids, one or more inorganic salts, one or more energy sources, one or more buffering agents, one or more pyruvate salts, one or more pH indicators, one or more amino acids, and one or more vitamins. In some embodiments, the antioxidants are selecting from the group consisting of N-acetyl-L-cysteine, 2-mercaptoethanol, and D,L-tocoph-erol acetate, or derivatives or mixtures thereof. In some embodiments, the albumin is human serum albumin. In some embodiments, the lipid agents are Human Ex-Cyte® and ethanolamine. In some embodiments, the insulin is human zinc insulin. In some embodiments, the transferrin is human iron-saturated transferrin. In some embodiments, the glucocorticoid is hydrocortisone. In some embodiments, inorganic salt ingredient comprises one or more inorganic salts selected from the group consisting of one or more calcium salts, one or more potassium salts, one or more magnesium salts, one or more sodium salts, one or more carbonate salts, and one or more phosphate salts. In some embodiments, the energy source is D-glucose. In some embodiments, the buffering agent is HEPES. In some embodiments, the pyruvate salt is sodium pyruvate. In some embodiments, the pH indicator is phenol red. In some embodiments, amino acid ingredient comprises one or more amino acids selected from the group consisting of glycine, L-alanine, L-asparagine, L-cysteine, L-aspartic acid, L-glu-tamic acid, L-phenylalanine, L-histidine, L-isoleucine, L-ly-sine, L-leucine, L-glutamine, L-arginine HCL, L-methio-nine, L-proline, L-hydroxyproline, L-serine, L-threonine, L-tryptophan, L-tyrosine, and L-valine, and salts and deriva-tives thereof. In some embodiments, the vitamin ingredient comprises one or more vitamins selected from the group consisting of biotin, D-calcium pantothenate, choline chlo-ride, folic acid, i-inositol, niacinamide, pyridoxal HCl, ribo-flavin, thiamine HCl, and vitamin B12 and derivatives thereof. In some embodiments, ingredients comprise N-acetyl-L-cysteine, 2-mercaptoethanol, human serum albumin, D,L-tocopherol acetate, Human Ex-Cyte®, etha-nolamine, human zinc insulin, iron-saturated transferrin, $Se^{4+}$, hydrocortisone, $Ca^{2+}$, $K^+$, $Mg^{2+}$, $Na^+$, $CO_3^{2-}$, $PO_4^{3-}$, D-glucose, HEPES, sodium pyruvate, phenol red, glycine, L-alanine, L-asparagine, L-cysteine, L-aspartic acid, L-glu-tamic acid, L-phenylalanine, L-histidine, L-isoleucine, L-ly-sine, L-leucine, L-glutamine, L-arginine HCL, L-methio-nine, L-proline, L-hydroxyproline, L-serine, L-threonine, L-tryptophan, L-tyrosine, and L-valine, biotin, D-calcium pantothenate, choline chloride, folic acid, i-inositol, niaci-namide, pyridoxal HCl, riboflavin, thiamine HCl, and vita-min B12.

In some embodiments, there is provided a serum-free media comprising a basal medium and at least one supple-ment. Various examples of basal medium and supplements are described herein, such as in the section above.

In some embodiments, the serum-free medium formula-tion comprises at or about 90% to at or about 97.5% (v/v) of the basal medium, at or about 2.5% to at or about 10% (v/v) of a supplement, e.g. a first supplement and/or a second supplement. In some embodiments, the serum-free medium formulation comprises at or about 90% to at or about 97.5% (v/v) of the basal medium, at or about 1.25% to at or about 5% (v/v) of a first supplement, and at or about 1.25% to at or about 5% (v/v) of a second supplement.

In some embodiments, there is provided a serum-free media comprising a basal medium, a first supplement and a second supplement. In some embodiments, the basal medium comprises a liquid comprising a synthetic amino acid (e.g., a dipeptide form of L-glutamine, e.g., L-alanyl-L-glutamine), and wherein the basal medium is free, or substantially free of a free form of glutamine (i.e., L-gluta-mine) and/or a protein. In some embodiments, the first supplement comprises a free form of glutamine (i.e., L-glu-tamine), wherein the first supplements is frozen or stored at a temperature under room temperature (e.g., under 20, 10, 15, 5, 0, −5, −10, −15, or −20° C.) for the majority of the time after glutamine becomes a component thereof and before the intended use (e.g., used as a supplement for a basal medium). In some embodiments, the first supplement comprises a free form of glutamine (i.e., L-glutamine), wherein the first supplements is frozen or stored at a temperature under room temperature (e.g., under 20, 10, 15, 5, 0, −5, −10, −15, or −20° C.) prior immediately to the combining with a medium (e.g., a basal medium). In some embodiments, the second supplement comprises an albumin, N-acetyle-L-cysteine (NAC) and/or ethanolamine. In some embodiments, the second supplement comprises one or more ingredients selected from the group consisting of one or more antioxidants, one or more albumins or albumin substitutes, one or more lipid agents, one or more insulins or insulin substitutes, one or more transferrins or transferrin substitutes, one or more trace elements, and one or more glucocorticoids.

In some embodiments, the serum-free media comprises one or more cytokine. In certain embodiments, the one or more cytokines are recombinant cytokines. In particular embodiments, the one or more cytokines are human recom-binant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), inter-leukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes recombinant IL-2. In some embodiments, the cytokine com-prises IL-2. In some embodiments, the one or more cytokine is selected from IL-2, IL-7 or IL-15.

In some embodiments, the concentration of a cytokine is about between at or about 1 IU/ml and at or about 2,000 IU/ml, between at or about 10 IU/ml and at or about 100 IU/ml, between at or about 50 IU/ml and at or about 500 IU/ml, between at or about 100 IU/ml and at or about 200 IU/ml, between at or about 500 IU/ml and at or about 1400 IU/ml, between at or about 250 IU/ml and at or about 500 IU/ml, or between at or about 500 IU/ml and at or about 2,500 IU/ml.

In some embodiments, the serum-free media comprises IL-2. In some embodiments, the concentration of IL-2 (e.g., human recombinant IL-2) is between at or about 2 IU/ml and at or about 500 IU/ml, between at or about 10 IU/ml and at or about 250 IU/ml, between at or about 100 IU/ml and at or about 500 IU/ml, or between at or about 100 IU/ml and at or about 400 IU/ml. In particular embodiments, the concentration of IL-2 is at or at about 50 IU/ml, 75 IU/ml, 100 IU/ml, 125 IU/ml, 150 IU/ml, 175 IU/ml, 200 IU/ml, 225 IU/ml, 250 IU/ml, 300 IU/ml, or 400 IU/ml. In some embodiments, the concentration of IL-2 is at or about 100 IU/ml. In some embodiments, the concentration of IL-2 is at or about 200 IU/ml.

In some embodiments, the serum-free media comprises IL-7. In some embodiments, the concentration of IL-7, e.g., human recombinant IL-7, is about between at or about 10 IU/ml and at or about 5,000 IU/ml, between at or about 500 IU/ml and at or about 2,000 IU/ml, between at or about 600 IU/ml and at or about 1,500 IU/ml, between at or about 500 IU/ml and at or about 2,500 IU/ml, between at or about 750 IU/ml and at or about 1,500 IU/ml, or between at or about 1,000 IU/ml and at or about 2,000 IU/ml. In particular embodiments, the concentration of IL-7 at or at about 100 IU/ml, 200 IU/ml, 300 IU/ml, 400 IU/ml, 500 IU/ml, 600 IU/ml, 700 IU/ml, 800 IU/ml, 900 IU/ml, 1,000 IU/ml, 1,200 IU/ml, 1,400 IU/ml, or 1,600 IU/ml. In some embodiments, the concentration of IL-7 is about at 600 IU/ml. In some embodiments, the concentration of IL-7 is about at 1,200 IU/ml.

In some embodiments, the serum-free media comprises IL-15. In some embodiments, the concentration of IL-15, e.g., human recombinant IL-15, is between at or about 2 IU/ml and at or about 500 IU/ml, between at or about 0.1 IU/ml and at or about 200 IU/ml, between at or about 1 IU/ml and at or about 50 IU/ml, between at or about 5 IU/ml and at or about 25 IU/ml, between at or about 25 IU/ml and at or about 501 U/ml, between at or about 5 IU/ml and at or about 15 IU/ml, or between at or about 10 IU/ml and at or about 50 IU/ml. In particular embodiments, the concentration of IL-15 is at or at about 1 IU/ml, 2 IU/ml, 3 IU/ml, 4 IU/ml, 5 IU/ml, 6 IU/ml, 7 IU/ml, 8 IU/ml, 9 IU/ml, 10 IU/ml, 11 IU/ml, 12 IU/ml, 13 IU/ml, 14 IU/ml, 15 IU/ml, 20 IU/ml, 25 IU/ml, 30 IU/ml, 40 IU/ml, 50 IU/ml, 100 IU/ml, or 200 IU/ml. In particular embodiments, the concentration of IL-15 is about 20 IU/ml. In some embodiments, the concentration of IL-15 is at or about 100 IU/ml. In some embodiments, the concentration of IL-15 is at or about 200 IU/ml.

In some embodiments, the serum-free media comprises a basal medium supplemented with a recombinant IL-2, a recombinant IL-7, and/or a recombinant IL-15, e.g., human recombinant IL-2, human recombinant IL-7, and/or human recombinant IL-15. In some embodiments, the serum-free media comprises a recombinant IL-2 between at or about 2 IU/ml and at or about 500 IU/ml, a recombinant IL-7 between at or about 10 IU/ml and at or about 5,000 IU/ml, and a recombinant IL-15 between at or about 2 IU/ml and at or about 500 IU/ml. In some embodiments, the serum-free media comprises a recombinant IL-2 between at or about 50 IU/ml and at or about 500 IU/ml, a recombinant IL-7 between at or about 100 IU/ml and at or about 2,000 IU/ml, and a recombinant IL-15 between at or about 50 IU/ml and at or about 500 IU/ml. In some embodiments, the serum-free media comprises a recombinant IL-2 between at or about 50 IU/ml and at or about 150 IU/ml, a recombinant IL-7 between at or about 500 IU/ml and at or about 1,000 IU/ml, and a recombinant IL-15 between at or about 50 IU/ml and at or about 150 IU/ml, e.g., for use in the stimulation/ activation and/or engineering of a cell composition. In some embodiments, the serum-free media comprises a recombinant IL-2 between at or about 150 IU/ml and at or about 250 IU/ml, a recombinant IL-7 between at or about 1000 IU/ml and at or about 1,500 IU/ml, and a recombinant IL-15 between at or about 150 IU/ml and at or about 250 IU/ml, e.g., for use in the cultivation or expansion of a cell composition. In some embodiments, the serum-free media used in the cultivation or expansion of a cell composition contains higher concentrations of one or more cytokines than the serum-free media used in the stimulation/activation and/or engineering of the cell composition. In some embodiments, the serum-free media used in the cultivation or expansion of a cell composition contains about or at least about 1.1, 1.2. 1.3, 1.4, 1.5, 1.6, 1.7, 1.8, 1.9, 2.0, 2.1, 2.2. 2.3, 2.4, 2.5, 2.6, 2.7, 2.8, 2.9, or 3.0 times the concentrations of one or more cytokines than the serum-free media used in the stimulation/activation and/or engineering of the cell composition.

In some embodiments, the serum-free media is a concentrated media formulation. In some embodiments, the serum-free media is not a concentrated media formulation. In some embodiments, the serum-free media is from at or about 2× to at or about 100× concentrated. In some embodiments, the serum-free media is at or about 10× formulation. In some embodiments, the serum-free media can be stored at or about 2° C. to 8° C.

In some embodiments, the media is capable of cultivating cells for at least 2 days, 3 days, 4 days, 5 days, 6 days, 7 days, 8 days, 9 days, 10 days, 11 days, 12 days or more without an additional supplement of a L-glutamine, a dipeptide form of glutamine or other form of glutamine.

In some embodiments, the serum-free media is capable of promoting cell expansion for at least 2 days, 3 days, 4 days, 5 days, 6 days, 7 days, 8 days, 9 days, 10 days, 11 days, 12 days or more without an additional supplement of a L-glutamine, a dipeptide form of glutamine or other form of glutamine.

In some embodiments, the serum-free media supports or promotes the expansion of a cell. In some embodiments, the media supports or promotes the viability of a cell. In some embodiments, the media supports or promotes the activation of a cell.

In some embodiments, the cell comprises an immune cell. In some embodiments, the cell comprises a primary immune cell. In some embodiments, the primary immune cell comprises a genetically engineered cell. In some embodiments, the primary immune cell comprises a T cell. In some embodiments, the primary immune cell comprises CD4 and/or CD8 T cell. In some embodiments, the CD4 and/or CD8 T cell is a genetically engineered T cell. In some embodiments, the T cell is genetically engineered to express a recombinant receptor (e.g., a chimeric antigen receptor). In some embodiments, the T cell comprises a chimeric antigen receptor (CAR) expressing T cells.

In some embodiments, the serum-free media supports or promotes the viability, expansion, and/or activation of cells, wherein the cells cultured with the serum-free media achieve comparable functional property (e.g., viability, expansion and production of cytokine or cytokines) as cells cultured with serum-containing media, such as media containing about 5-10% (v/v) human serum.

D. Methods of Preparation of Serum-Free Media

In some embodiments, there is provided a method for preparing a serum-free medium formulation, the method comprising combining: (a) a basal medium comprising a synthetic amino acid capable of being converted into a free form of glutamine (e.g., L-glutamine) in a cell culture; (b) a first supplement comprising a free form of glutamine (i.e., L-glutamine), wherein the first supplement was frozen for at least a portion of time after L-glutamine becomes a component thereof and prior to combining. In some embodiments, the synthetic amino acid is dipeptide form of L-glutamine (e.g., L-alanyl-L-glutamine). In some embodiments, the basal medium is serum-free. In some embodiments, the basal medium is a liquid formulation and/or has not been frozen prior to the combining and/or not recommended in a commercial protocol to be frozen when kept in storage. In some embodiments, the first supplement was frozen for the majority of time after L-glutamine became a component thereof and before combining with the basal medium. In some embodiments, the first supplement was frozen and thawed prior to the combining.

In some embodiments, the first supplement is thawed as a liquid formulation no more than at or about one week, such as no more than at or about 6, 5, 4, 3, 2, or 1 day, generally no more than at or about 12 hours, 6 hours, 2 hours, 1 hour or 30 minutes prior to being combined with the basal medium. In some embodiments, the first supplement containing L-glutamine is kept frozen shortly (such as within 6, 12, 16, 24, 36, 48 hours) or immediately before the combining. In some embodiments, the first supplement containing the L-glutamine was a liquid formulation for less than at or about 48, 24, 16, 12, 8, 4, or 2 hours before being combined with basal medium. In some embodiments, the synthetic amino acid is a dipeptide of L-glutamine. In some embodiments, the synthetic amino acid is L-alanyl-L-glutamine.

In some embodiments, the serum-free medium formulation comprises at or about 90% to 98.75% (v/v) of the basal medium and at or about 1.25% to 10% (v/v) of the first supplement. In some embodiments, the serum-free medium formulation comprises at or about 90% to 97.5% (v/v) of the basal medium and at or about 1.25% to 5% (v/v) of the first supplement. In some embodiments, the serum-free medium formulation comprises at or about 95% (v/v) of the basal medium and at or about 2.5%±0.2% (v/v) of the first supplement, such as at or about 2.5% (v/v). In some embodiments, a liter of the basal medium is supplemented with at or about 25 milliliter of the first supplement.

In some embodiments, the method further comprises combining a second supplement. In some embodiments, the second supplement comprises one or more additional components, such as any described above, including one or more antioxidants, one or more albumins or albumin substitutes, one or more lipid agents, one or more insulins or insulin substitutes, one or more transferrins or transferrin substitutes, one or more trace elements, and one or more glucocorticoids. Exemplary components of a second supplement are described above.

In some embodiments, the second supplement comprises an albumin, N-acetylcysteine (NAC) and ethanolamine. In some embodiments, the second supplement comprises an albumin, N-acetylcysteine (NAC) and ethanolamine, wherein the concentration of albumin, NAC and/or ethanolamine is such that after the second supplement is combined with a basal medium (such as these described herein), the concentration of albumin, NAC and/or ethanolamine is substantially the same as described herein. In some embodiments, the albumin is a human derived albumin. In some embodiments, the albumin is a human derived albumin from human plasma or serum. In some embodiments, the second supplement is a liquid and does not include, or does not include a significant amount of a free form of glutamine (i.e., L-glutamine).

In some embodiments, the second supplement comprises OpTmizer® supplement (Thermofisher, part of A1048503).

In some embodiments, the second supplement is liquid. In some embodiments, the second supplement is not frozen, or not recommended to be frozen for the storage. In some embodiments, the serum-free medium formulation comprises about 1.25% to 5% (v/v) of the second supplement, such as or about 2.5%±0.2%, such as or about 2.5% or 2.6%.

In some embodiments, a liter of the basal medium is supplemented with about 26 milliliter of the second supplement.

In some embodiments, the serum-free medium formulation comprises about 90% to 97.5% (v/v) of the basal medium, about 1.25% to 5% (v/v) of the first supplement, and about 1.25% to 5% (v/v) of the second supplement. In some embodiments, the serum-free medium formulation comprises about 95% (v/v) of the basal medium, about 2.5%±0.2% (v/v) of the first supplement, and about 2.5%±0.2% (v/v) of the second supplement.

III. RECOMBINANT RECEPTORS

In some embodiments, the cells that are treated, processed, engineered, and/or produced by the methods provided herein, e.g., the methods described in Section I, contain or express, or are engineered to contain or express, a recombinant protein, such as a recombinant receptor, e.g., a chimeric antigen receptor (CAR), or a T cell receptor (TCR). In certain embodiments, the methods provided herein produce and/or are capable of producing cells, or populations or compositions containing and/or enriched for cells, that are engineered to express or contain a recombinant protein. In some embodiments, T cells, or populations or compositions of T cells, are treated, processed, engineered, and/or produced.

In some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

Among the receptors are antigen receptors and receptors containing one or more component thereof. The recombinant receptors may include chimeric receptors, such as those containing ligand-binding domains or binding fragments thereof and intracellular signaling domains or regions, functional non-TCR antigen receptors, chimeric antigen receptors (CARs), and T cell receptors (TCRs), such as recombinant or transgenic TCRs, chimeric autoantibody receptor (CAAR) and components of any of the foregoing. The recombinant receptor, such as a CAR, generally includes the extracellular antigen (or ligand) binding domain linked to one or more intracellular signaling components, in some aspects via linkers and/or transmembrane domain(s).

1. Chimeric Antigen Receptors (CARs)

In some embodiments, engineered cells, such as T cells, are provided that express a CAR with specificity for a particular antigen (or marker or ligand), such as an antigen expressed on the surface of a particular cell type. In some embodiments, the antigen is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In particular embodiments, the recombinant receptor, such as chimeric receptor, contains an intracellular signaling region, which includes a cytoplasmic signaling domain or region (also interchangeably called an intracellular signaling domain or region), such as a cytoplasmic (intracellular) region capable of inducing a primary activation signal in a T cell, for example, a cytoplasmic signaling domain or region of a T cell receptor (TCR) component (e.g. a cytoplasmic signaling domain or region of a zeta chain of a CD3-zeta (CD3ζ) chain or a functional variant or signaling portion thereof) and/or that comprises an immunoreceptor tyrosine-based activation motif (ITAM).

In some embodiments, the chimeric receptor further contains an extracellular ligand-binding domain that specifically binds to a ligand (e.g. antigen) antigen. In some embodiments, the chimeric receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061, U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some embodiments, the antibody or antigen-binding portion thereof is expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR. In some embodiments, the extracellular antigen binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, the recombinant receptor, such as a chimeric receptor (e.g. CAR), includes a ligand-binding domain that binds, such as specifically binds, to an antigen (or a ligand). Among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the CAR contains an antibody or an antigen-binding fragment (e.g. scFv) that specifically recognizes an antigen, such as an intact antigen, expressed on the surface of a cell.

In some embodiments, the antigen (or a ligand) is a tumor antigen or cancer marker. In some embodiments, the antigen (or a ligand) the antigen is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen$_{1B}$ (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G protein-coupled receptor class C group 5 member D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the CAR is an anti-BCMA CAR that is specific for BCMA, e.g. human BCMA. Chimeric antigen receptors containing anti-BCMA antibodies, including mouse anti-human BCMA antibodies and human anti-human antibodies, and cells expressing such chimeric receptors have been previously described. See Carpenter et al., Clin Cancer Res., 2013, 19(8):2048-2060, WO 2016/090320, WO2016090327, WO2010104949A2 and WO2017173256. In some embodiments, the antigen or antigen binding domain is BCMA. In some embodiments, the scFv contains a $V_H$ and a $V_L$ derived from an antibody or an antibody fragment specific to BCMA. In some embodiments, the antibody or antibody fragment that binds BCMA is or contains a $V_H$ and a $V_L$ from an antibody or antibody fragment set forth in International Patent Applications, Publication Number WO 2016/090327 and WO 2016/090320.

In some embodiments, the anti-BCMA CAR contains an antigen-binding domain, such as an scFv, containing a variable heavy ($V_H$) and/or a variable light ($V_L$) region derived from an antibody described in WO 2016/090320 or WO2016090327. In some embodiments, the antigen-binding domain, such as an scFv, contains a $V_H$ set forth in SEQ ID NO: 30 and a $V_L$ set forth in SEQ ID NO:31. In some embodiments, the antigen-binding domain, such as an scFv, contains a $V_H$ set forth in SEQ ID NO: 32 and a $V_L$ set forth in SEQ ID NO:33. In some embodiments, the antigen-binding domain, such as an scFv, contains a VH set forth in SEQ ID NO: 34 and a $V_L$ set forth in SEQ ID NO: 35. In some embodiments, the antigen-binding domain, such as an scFv, contains a $V_H$ set forth in SEQ ID NO: 27 and a $V_L$ set forth in SEQ ID NO:28. In some embodiment the antigen-binding domain, such as an scFv, contains a $V_H$ set forth in SEQ ID NO: 41 and a $V_L$ set forth in SEQ ID NO: 42. In some embodiments, the antigen-binding domain, such as an scFv, contains a $V_H$ set forth in SEQ ID NO: 43 and a $V_L$ set forth in SEQ ID NO: 44. In some embodiments, the antigen-binding domain, such as an scFv, contains a $V_H$ set forth in SEQ ID NO: 45 and a $V_L$ set forth in SEQ ID NO: 46. In some embodiments, the $V_H$ or $V_L$ has a sequence of amino acids that exhibits at least 85%, 86%, 87%, 88%, 89%, 90%, 91%, 92%, 93%, 94%, 95%, 96%, 97%, 98%, 99% or more sequence identity to any of the foregoing $V_H$ or $V_L$ sequences, and retains binding to BCMA. In some embodiments, the $V_H$ region is amino-terminal to the $V_L$ region. In some embodiments, the $V_H$ region is carboxy-terminal to the $V_L$ region.

In some embodiments, the antigen or antigen binding domain is CD19. In some embodiments, the scFv contains a $V_H$ and a $V_L$ derived from an antibody or an antibody fragment specific to CD19. In some embodiments, the antibody or antibody fragment that binds CD19 is a mouse derived antibody such as FMC63 and SJ25C1. In some embodiments, the antibody or antibody fragment is a human antibody, e.g., as described in U.S. Patent Publication No. US 2016/0152723.

In some embodiments, the CAR is an anti-CD19 CAR that is specific for CD19, e.g. human CD19. In some embodiments the scFv and/or $V_H$ domains is derived from FMC63. FMC63 generally refers to a mouse monoclonal IgG1 antibody raised against Nalm-1 and -16 cells expressing CD19 of human origin (Ling, N. R., et al. (1987). *Leucocyte typing III*. 302). In some embodiments, the FMC63 antibody comprises CDR-H1 and CDR-H2 set forth in SEQ ID NOS: 50 and 51 respectively, and CDR-H3 set forth in SEQ ID NO: 52 or 66 and CDR-L1 set forth in SEQ ID NO: 47 and CDR-L2 set forth in SEQ ID NO: 48 or 67 and CDR-L3 set forth in SEQ ID NO: 49 or 68. In some embodiments, the FMC63 antibody comprises the heavy chain variable region ($V_H$) comprising the amino acid sequence of SEQ ID NO: 53 and the light chain variable region ($V_L$) comprising the amino acid sequence of SEQ ID NO: 54.

In some embodiments, the scFv comprises a variable light chain containing the CDR-L1 sequence of SEQ ID NO:47, a CDR-L2 sequence of SEQ ID NO:48, and a CDR-L3 sequence of SEQ ID NO:49 and/or a variable heavy chain containing a CDR-H1 sequence of SEQ ID NO:50, a CDR-H2 sequence of SEQ ID NO:51, and a CDR-H3 sequence of SEQ ID NO:52. In some embodiments, the scFv comprises a variable heavy chain region set forth in SEQ ID NO:53 and a variable light chain region set forth in SEQ ID NO:54. In some embodiments, the variable heavy and variable light chains are connected by a linker. In some embodiments, the linker is set forth in SEQ ID NO:70. In some embodiments, the scFv comprises, in order, a $V_H$, a linker, and a $V_L$. In some embodiments, the scFv comprises, in order, a $V_L$, a linker, and a $V_H$. In some embodiments, the scFv is encoded by a sequence of nucleotides set forth in SEQ ID NO:69 or a sequence that exhibits at least 85%, 86%, 87%, 88%, 89%, 90%, 91%, 92%, 93%, 94%, 95%, 96%, 97%, 98%, or 99% sequence identity to SEQ ID NO:69. In some embodiments, the scFv comprises the sequence of amino acids set forth in SEQ ID NO:55 or a sequence that exhibits at least 85%, 86%, 87%, 88%, 89%, 90%, 91%, 92%, 93%, 94%, 95%, 96%, 97%, 98%, or 99% sequence identity to SEQ ID NO:55.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). *Leucocyte typing III*. 302). In some embodiments, the SJ25C1 antibody comprises CDR-H1, CDR-H2 and CDR-H3 set forth in SEQ ID NOS: 59-61, respectively, and CDR-L1, CDR-L2 and CDR-L3 sequences set forth in SEQ ID NOS: 56-58, respectively. In some embodiments, the SJ25C1 antibody comprises the heavy chain variable region ($V_H$) comprising the amino acid sequence of SEQ ID NO: 62 and the light chain variable region ($V_L$) comprising the amino acid sequence of SEQ ID NO: 63.

In some embodiments, the scFv comprises a variable light chain containing a CDR-L1 sequence SEQ ID NO:56, a CDR-L2 sequence of SEQ ID NO: 57, and a CDR-L3 sequence of SEQ ID NO:58 and/or a variable heavy chain containing a CDR-H1 sequence of SEQ ID NO:59, a CDR-H2 sequence of SEQ ID NO:60, and a CDR-H3 sequence of SEQ ID NO:61. In some embodiments, the scFv comprises a variable heavy chain region set forth in SEQ ID NO:62 and a variable light chain region set forth in SEQ ID NO:63. In some embodiments, the variable heavy and variable light chain are connected by a linker. In some embodiments, the linker is set forth in SEQ ID NO:64. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:65 or a sequence that exhibits at least 85%, 86%, 87%, 88%, 89%, 90%, 91%, 92%, 93%, 94%, 95%, 96%, 97%, 98%, or 99% sequence identity to SEQ ID NO:65.

In some embodiments, the antigen is CD20. In some embodiments, the scFv contains a $V_H$ and a $V_L$ derived from an antibody or an antibody fragment specific to CD20. In some embodiments, the antibody or antibody fragment that binds CD20 is an antibody that is or is derived from Rituximab, such as is Rituximab scFv.

In some embodiments, the antigen is CD22. In some embodiments, the scFv contains a $V_H$ and a $V_L$ derived from an antibody or an antibody fragment specific to CD22. In some embodiments, the antibody or antibody fragment that binds CD22 is an antibody that is or is derived from m971, such as is m971 scFv.

In some embodiments, the antigen or antigen binding domain is GPRC5D. In some embodiments, the scFv contains a VH and a VL derived from an antibody or an antibody fragment specific to GPRC5D. In some embodiments, the antibody or antibody fragment that binds GPRC5D is or contains a VH and a VL from an antibody or antibody fragment set forth in International Patent Applications, Publication Number WO 2016/090329 and WO 2016/090312.

In some embodiments, the antibody is an antigen-binding fragment, such as a scFv, that includes one or more linkers joining two antibody domains or regions, such as a heavy chain variable ($V_H$) region and a light chain variable ($V_L$) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline. In some aspects, the linkers rich in glycine and serine (and/or threonine) include at least 80%, 85%, 90%, 91%, 92%, 93%, 94%, 95%, 96%, 97%, 98%, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS; SEQ ID NO:36) or GGGS (3GS; SEQ ID NO:37), such as between 2, 3, 4, and 5 repeats of such a sequence. Exemplary linkers include those having or consisting of an sequence set forth in SEQ ID NO:38 (GGGGSGGGGSGGGGS), SEQ ID NO:39 (GSTSGSGKPGSGEGSTKG) or SEQ ID NO: 40 (SRGGGGSGGGGSGGGGSLEMA).

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens. In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning a chain, in some cases with three a domains, and a non-covalently associated (32 microglobulin. Generally, MHC class II molecules are composed of two transmembrane glycoproteins, a and (3, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally $CD8^+$ T cells, but in some cases CD4+ T cells. In some embodiments, MHC class II molecules deliver peptides originating in the vesicular system to the cell surface, where they are typically recognized by $CD4^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by known methods (see e.g. US Published Application Nos. US 2002/0150914; US 2003/0223994; US 2004/0191260; US 2006/0034850; US 2007/00992530; US20090226474; US20090304679; and International PCT Publication No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US published application No. US20020150914, US2014/0294841; and Cohen C J. et al. (2003) *J Mol. Recogn.* 16:324-332.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, variable heavy chain (V$_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme); Al-Lazikani et al., (1997) JMB 273,927-948 ("Chothia" numbering scheme); MacCallum et al., J. Mol. Biol. 262: 732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

Table 1, below, lists exemplary position boundaries of CDR-L1, CDR-L2, CDR-L3 and CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-L1 located before CDR-L1, FR-L2 located between CDR-L1 and CDR-L2, FR-L3 located between CDR-L2 and CDR-L3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

Boundaries of CDRs according to various numbering schemes.

| CDR | Kabat | Chothia | AbM | Contact |
|---|---|---|---|---|
| CDR-L1 | L24--L34 | L24--L34 | L24--L34 | L30--L36 |
| CDR-L2 | L50--L56 | L50--L56 | L50--L56 | L46--L55 |
| CDR-L3 | L89--L97 | L89--L97 | L89--L97 | L89--L96 |
| CDR-H1 (Kabat Numbering[1]) | H31--H35B | H26--H32 . . . 34 | H26--H35B | H30--H35B |
| CDR-H1 (Chothia Numbering[2]) | H31--H35 | H26--H32 | H26--H35 | H30--H35 |
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273,927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes, or other known schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes, or other known schemes. In some embodiments, specific CDR sequences are specified. Exemplary CDR sequences of antibodies are described using various numbering schemes, although it is understood that an antibody can include CDRs as described according to any of the other aforementioned numbering schemes or other numbering schemes known to a skilled artisan.

Likewise, unless otherwise specified, a FR or individual specified FR(s) (e.g., FR-H1, FR-H2, FR-H3, FR-H4), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, AbM or Contact method, or other known schemes. In other cases, the particular amino acid sequence of a CDR or FR is given.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the chimeric antigen receptor, including TCR-like CARs, includes an extracellular portion containing an antibody or antibody fragment. In some embodiments, the antibody or fragment includes an scFv. In some aspects, the chimeric antigen receptor includes an extracellular portion containing the antibody or fragment and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

In some embodiments, the recombinant receptor such as the CAR, such as the antibody portion thereof, further includes a spacer, which may be or include at least a portion of an immunoglobulin constant region or variant or modified version thereof, such as a hinge region, e.g., an IgG4 hinge region, and/or a $C_H1/C_L$ and/or Fc region. In some embodiments, the recombinant receptor further comprises a spacer and/or a hinge region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer.

In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to $C_H2$ and $C_H3$ domains, or IgG4 hinge linked to the $C_H3$ domain. Exemplary spacers include, but are not limited to, those described in Hudecek et al. (2013) *Clin. Cancer Res.,* 19:3153, Hudecek et al. (2015) Cancer Immunol Res. 3(2): 125-135 or international patent application publication number WO2014031687, U.S. Pat. No. 8,822,647 or published app. No. US2014/0271635. In some embodiments, the spacer includes a sequence of an immunoglobulin hinge region, a $C_H2$ and $C_H3$ region. In some embodiments, one of more of the hinge, $C_H2$ and $C_H3$ is derived all or in part from IgG4 or IgG2. In some cases, the hinge, $C_H2$ and $C_H3$ is derived from IgG4. In some aspects, one or more of the hinge, $C_H2$ and $C_H3$ is chimeric and contains sequence derived from IgG4 and IgG2. In some examples, the spacer contains an IgG4/2 chimeric hinge, an IgG2/4 $C_H2$, and an IgG4 $C_H3$ region.

In some embodiments, the spacer can be derived all or in part from IgG4 and/or IgG2 and can contain mutations, such as one or more single amino acid mutations in one or more domains. In some examples, the amino acid modification is a substitution of a proline (P) for a serine (S) in the hinge region of an IgG4. In some embodiments, the amino acid modification is a substitution of a glutamine (Q) for an asparagine (N) to reduce glycosylation heterogeneity, such as an N177Q mutation at position 177, in the CH2 region, of the full-length IgG4 Fc sequence or an N176Q. at position 176, in the CH2 region, of the full-length IgG4 Fc sequence.

In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the encoded spacer is or contains the sequence set forth in SEQ ID NO: 29. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4, 5 or 29.

In some embodiments, the constant region or portion is of IgD. In some embodiments, the spacer has the sequence set forth in SEQ ID NO: 5. In some embodiments, the spacer has a sequence of amino acids that exhibits at least or at least about 85%, 86%, 87%, 88%, 89%, 90%, 91%, 92%, 93%, 94%, 95%, 96%, 97%, 98%, 99% or more sequence identity to any of SEQ ID NOS: 1, 3, 4 and 5.

The antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen binding component (e.g., antibody) is linked to one or more transmembrane and intracellular signaling regions. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling region are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the ROR1-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-0 or Fc receptor γ and CD8, CD4, CD25 or CD16.

In some embodiments, upon ligation of the CAR, the cytoplasmic domain or intracellular signaling region of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling region of an antigen receptor component or costimulatory molecule is used in place of an intact immunostimulatory chain, for example, if it transduces the effector function signal. In some embodiments, the intracellular signaling regions, e.g., comprising intracellular domain or domains, include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma or FcR beta. In some embodiments, cytoplasmic signaling molecule(s) in the CAR contain(s) a cytoplasmic signaling domain, portion thereof, or sequence derived from CD3 zeta.

In some embodiments, the CAR includes a signaling region and/or transmembrane portion of a costimulatory receptor, such as CD28, 4-1BB, OX40, DAP10, and ICOS. In some aspects, the same CAR includes both the signaling region and costimulatory components.

In some embodiments, the signaling region is included within one CAR, whereas the costimulatory component is provided by another CAR recognizing another antigen. In some embodiments, the CARs include activating or stimulatory CARs, and costimulatory CARs, both expressed on the same cell (see WO2014/055668).

In certain embodiments, the intracellular signaling region comprises a CD28 transmembrane and signaling domain linked to a CD3 (e.g., CD3-zeta) intracellular domain. In some embodiments, the intracellular signaling region comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain disposed between the extracellular domain and the intracellular signaling region.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 4-1BB.

In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 8 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO:8; in some embodiments, the transmembrane-domain containing portion of the recombinant receptor comprises the sequence of amino acids set forth in SEQ ID NO: 9 or a sequence of amino acids having at least or at least about 85%, 86%, 87%, 88%, 89%, 90%, 91%, 92%, 93%, 94%, 95%, 96%, 97%, 98%, 99% or more sequence identity thereto.

In some embodiments, the chimeric antigen receptor contains an intracellular domain of a T cell costimulatory molecule. In some aspects, the T cell costimulatory molecule is CD28 or 4-1BB.

In some embodiments, the intracellular signaling region comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 10 or 11 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular region comprises an intracellular costimulatory signaling domain of 4-1BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 12 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling region comprises a human CD3 chain, optionally a CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No. 7,446,190 or 8,911,993. In some embodiments, the intracellular signaling region comprises the sequence of amino acids set forth in SEQ ID NO: 13, 14 or 15 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO:1. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO:3. In some embodiments, the spacer is an Ig hinge, e.g., an IgG4 hinge, linked to a $C_H3$ domain only, such as set forth in SEQ ID NO:4. In some embodiments, the spacer is or comprises a glycine-serine rich sequence or other flexible linker such as known flexible linkers.

2. T Cell Receptors (TCRs)

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or C$_\beta$, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the genetically engineered antigen receptors include recombinant T cell receptors (TCRs) and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified by a skilled artisan. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPredl (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MHC class I binding sites, such models include, but are not limited to, ProPredl (described in more detail in Singh and Raghava, ProPred: prediction of HLA-DR binding sites. BIOINFORMATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007).

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known, See e.g., Soo Hoo, W. F. et al. PNAS (USA) 89, 4759 (1992); Wülfing, C. and Plückthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)$_5$-P- wherein P is proline, G is glycine and S is serine (SEQ ID NO:22). In some embodiments, the linker has the sequence GSADDAKKDAAKKDGKS (SEQ ID NO:23)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine.

Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can be a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; and Hackett et al. (2010) Molecular Therapy: The Journal of the American Society of Gene Therapy. 18:674-683.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

3. Chimeric Auto-Antibody Receptor (CAAR)

In some embodiments, the recombinant receptor is a chimeric autoantibody receptor (CAAR). In some embodiments, the CAAR is specific for an autoantibody. In some embodiments, a cell expressing the CAAR, such as a T cell engineered to express a CAAR, can be used to specifically bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/ 0051035.

In some embodiments, the CAAR comprises an autoantibody binding domain, a transmembrane domain, and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling region comprises a secondary or costimulatory signaling region (secondary intracellular signaling regions).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

4. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in International Patent Application Publication No: WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating or stimulating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating or stimulating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating or stimulating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the cells expressing the recombinant receptor further include inhibitory CARs (iCARs, see Fedorov et al., *Sci. Transl. Medicine,* 5(215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the two receptors induce, respectively, an activating and an inhibitory signal to the cell, such that ligation of one of the receptor to its antigen activates the cell or induces a response, but ligation of the second inhibitory receptor to its antigen induces a signal that suppresses or dampens that response. Examples are combinations of activating CARs and inhibitory CARs (iCARs). Such a strategy may be used, for example, to reduce the likelihood of off-target effects in the context in which the activating CAR binds an antigen expressed in a disease or condition but which is also expressed on normal cells, and the inhibitory receptor binds to a separate antigen which is expressed on the normal cells but not cells of the disease or condition.

In some aspects, the chimeric receptor is or includes an inhibitory CAR (e.g. iCAR) and includes intracellular components that dampen or suppress an immune response, such as an ITAM- and/or co stimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

B. Nucleic Acids, Vectors and Methods for Genetic Engineering

In some embodiments, the cells, e.g., T cells, are genetically engineered to express a recombinant receptor. In some embodiments, the engineering is carried out by introducing polynucleotides that encode the recombinant receptor. Also provided are polynucleotides encoding a recombinant receptor, and vectors or constructs containing such nucleic acids and/or polynucleotides.

In some cases, the nucleic acid sequence encoding the recombinant receptor contains a signal sequence that encodes a signal peptide. In some aspects, the signal sequence may encode a signal peptide derived from a native polypeptide. In other aspects, the signal sequence may encode a heterologous or non-native signal peptide, such as the exemplary signal peptide of the GMCSFR alpha chain set forth in SEQ ID NO:25 and encoded by the nucleotide sequence set forth in SEQ ID NO:24. In some cases, the nucleic acid sequence encoding the recombinant receptor, e.g., chimeric antigen receptor (CAR) contains a signal sequence that encodes a signal peptide. Non-limiting exemplary examples of signal peptides include, for example, the GMCSFR alpha chain signal peptide set forth in SEQ ID NO: 25 and encoded by the nucleotide sequence set forth in SEQ ID NO:24, or the CD8 alpha signal peptide set forth in SEQ ID NO:26.

In some embodiments, the polynucleotide encoding the recombinant receptor contains at least one promoter that is operatively linked to control expression of the recombinant receptor. In some examples, the polynucleotide contains two, three, or more promoters operatively linked to control expression of the recombinant receptor.

In certain cases where nucleic acid molecules encode two or more different polypeptide chains, e.g., a recombinant receptor and a marker, each of the polypeptide chains can be encoded by a separate nucleic acid molecule. For example, two separate nucleic acids are provided, and each can be individually transferred or introduced into the cell for expression in the cell. In some embodiments, the nucleic acid encoding the recombinant receptor and the nucleic acid encoding the marker are operably linked to the same promoter and are optionally separated by an internal ribosome entry site (IRES), or a nucleic acid encoding a self-cleaving peptide or a peptide that causes ribosome skipping, which optionally is a T2A, a P2A, a E2A or a F2A. In some embodiments, the nucleic acids encoding the marker and the nucleic acid encoding the recombinant receptor are operably linked to two different promoters. In some embodiments, the nucleic acid encoding the marker and the nucleic acid encoding the recombinant receptor are present or inserted at different locations within the genome of the cell. In some embodiments, the polynucleotide encoding the recombinant receptor is introduced into a composition containing cultured cells, such as by retroviral transduction, transfection, or transformation.

In some embodiments, such as those where the polynucleotide contains a first and second nucleic acid sequence, the coding sequences encoding each of the different polypeptide chains can be operatively linked to a promoter, which can be the same or different. In some embodiments, the nucleic acid molecule can contain a promoter that drives the expression of two or more different polypeptide chains. In some embodiments, such nucleic acid molecules can be multicistronic (bicistronic or tricistronic, see e.g., U.S. Pat. No. 6,060,273). In some embodiments, transcription units can be engineered as a bicistronic unit containing an IRES (internal ribosome entry site), which allows coexpression of gene products ((e.g. encoding the marker and encoding the recombinant receptor) by a message from a single promoter. Alternatively, in some cases, a single promoter may direct expression of an RNA that contains, in a single open reading frame (ORF), two or three genes (e.g. encoding the marker and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as a T2A, can cause the ribosome to skip (ribosome skipping) synthesis of a peptide bond at the C-terminus of a 2A element, leading to separation between the end of the 2A sequence and the next peptide downstream (see, for example, de Felipe, Genetic Vaccines and Ther. 2:13 (2004) and de Felipe et al. Traffic 5:616-626 (2004)). Various 2A elements are known. Examples of 2A sequences that can be used in the methods and system disclosed herein, without limitation, 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Publication No. 20070116690.

Any of the recombinant receptors described herein can be encoded by polynucleotides containing one or more nucleic acid sequences encoding recombinant receptors, in any combinations or arrangements. For example, one, two, three or more polynucleotides can encode one, two, three or more different polypeptides, e.g., recombinant receptors. In some embodiments, one vector or construct contains a nucleic acid sequence encoding marker, and a separate vector or construct contains a nucleic acid sequence encoding a recombinant receptor, e.g., CAR. In some embodiments, the nucleic acid encoding the marker and the nucleic acid encoding the recombinant receptor are operably linked to two different promoters. In some embodiments, the nucleic acid encoding the recombinant receptor is present downstream of the nucleic acid encoding the marker.

In some embodiments, the vector backbone contains a nucleic acid sequence encoding one or more marker(s). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, a E2A or a F2A. Extrinsic marker genes may in some cases be utilized in connection with engineered cell to permit detection or selection of cells and, in some cases, also to promote cell suicide.

Exemplary surrogate markers can include truncated forms of cell surface polypeptides such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors, such as a truncated human epidermal growth factor receptor 2 (tHER2), a truncated epidermal growth factor receptor (EGFRt, exemplary EGFRt sequence set forth in SEQ ID NO:7 or 16) or a prostate-specific membrane antigen (PSMA) or modified form thereof. EGFRt may contain an epitope recognized by the antibody cetuximab (Erbitux®) or other therapeutic anti-EGFR antibody or binding molecule, which can be used to identify or select cells that have been engineered with the EGFRt construct and a recombinant receptor, such as a chimeric antigen receptor (CAR), and/or to eliminate or separate cells expressing the receptor. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16.

In some embodiments, the marker is or comprises a fluorescent protein, such as green fluorescent protein (GFP), enhanced green fluorescent protein (EGFP), such as superfold GFP, red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from E. coli, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), or spleen focus forming virus (SFFV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population tion can then be liberated from the initial stimulus (the anti-CD3/anti-CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

IV. METHODS OF TREATMENT

In some embodiments, output compositions of enriched T cells produced by the methods provided herein, such as described in Section I, are administered as a cell therapy, e.g., an adoptive cell therapy. The engineered cells are useful in a variety of therapeutic, diagnostic and prophylactic indications. For example, the engineered cells or compositions comprising the engineered cells are useful in treating a variety of diseases and disorders in a subject. Such methods and uses include therapeutic methods and uses, for example, involving administration of the engineered cells, or compositions containing the same, to a subject having a disease, condition, or disorder, such as a tumor or cancer. In some embodiments, the engineered cells or compositions comprising the same are administered in an effective amount to effect treatment of the disease or disorder. Uses include uses of the engineered cells or compositions in such methods and treatments, and in the preparation of a medicament in order to carry out such therapeutic methods. In some embodiments, the methods are carried out by administering the engineered cells, or compositions comprising the same, to the subject having or suspected of having the disease or condition. In some embodiments, the methods thereby treat the disease or condition or disorder in the subject.

In particular embodiments, one or more cell compositions, e.g., output cell compositions described herein are administered as a cell therapy. In certain embodiments, the methods provided herein produce a single output composition of enriched T cells from input cells isolated, selected and/or enriched from a single biological sample that is administered as a cell therapy. In certain embodiments, the single output composition is a composition of enriched CD4+ and CD8+ T cells. Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10): 577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., acute myeloid (or myelogenous) leukemia (AML), chronic myeloid (or myelogenous) leukemia (CML), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM). In some embodiments, disease or condition is a B cell malignancy selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FL3B).

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G protein-coupled receptor class C group 5 member D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the disease or condition is a B cell malignancy. In some embodiments, the B cell malignancy is a leukemia or a lymphoma. In some aspects, the disease or condition is acute lymphoblastic leukemia (ALL), adult ALL, chronic lymphoblastic leukemia (CLL), non-Hodgkin lymphoma (NHL), or Diffuse Large B-Cell Lymphoma (DLBCL). In some cases, the disease or condition is an NHL, such as or including an NHL that is an aggressive NHL, diffuse large B cell lymphoma (DLBCL), NOS (de novo and transformed from indolent), primary mediastinal large B cell lymphoma (PMBCL), T cell/histiocyte-rich large B cell lymphoma (TCHRBCL), Burkitt's lymphoma, mantle cell lymphoma (MCL), and/or follicular lymphoma (FL), optionally, follicular lymphoma Grade 3B (FL3B). In some aspects, the recombinant receptor, such as a CAR, specifically binds to an antigen associated with the disease or condition or expressed in cells of the environment of a lesion associated with the B cell malignancy. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30, or combinations thereof.

In some embodiments, the disease or condition is a myeloma, such as a multiple myeloma. In some aspects, the recombinant receptor, such as a CAR, specifically binds to an antigen associated with the disease or condition or expressed in cells of the environment of a lesion associated with the multiple myeloma. Antigens targeted by the receptors in some embodiments include antigens associated with multiple myeloma. In some aspects, the antigen, e.g., the second or additional antigen, such as the disease-specific antigen and/or related antigen, is expressed on multiple myeloma, such as B cell maturation antigen (BCMA), G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI and/or FcRH5. Other exemplary multiple myeloma antigens include CD56, TIM-3, CD33, CD123, CD44, CD20, CD40, CD74, CD200, EGFR, J32-Microglobulin, HM1.24, IGF-1R, IL-6R, TRAIL-R1, and the activin receptor type IIA (ActRIIA). See Benson and Byrd, J. Clin. Oncol. (2012) 30(16): 2013-15; Tao and Anderson, Bone Marrow Research (2011):924058; Chu et al., Leukemia (2013) 28(4):917-27; Garfall et al., Discov Med. (2014) 17(91):37-46. In some embodiments, the antigens include those present on lymphoid tumors, myeloma, AIDS-associated lymphoma, and/or post-transplant lymphoproliferations, such as CD38. Antibodies or antigen-binding fragments directed against such antigens are known and include, for example, those described in U.S. Pat. Nos. 8,153,765; 8,603,477, 8,008,450; U.S. Pub. No. US20120189622 or US20100260748; and/or International PCT Publication Nos. WO2006099875, WO2009080829 or WO2012092612 or WO2014210064. In some embodiments, such antibodies or antigen-binding fragments thereof (e.g. scFv) are contained in multispecific antibodies, multispecific chimeric receptors, such as multispecific CARs, and/or multispecific cells.

In some embodiments, the disease or disorder is associated with expression of G protein-coupled receptor class C group 5 member D (GPRC5D) and/or expression of B cell maturation antigen (BCMA).

In some embodiments, the disease or disorder is a B cell-related disorder. In some of any of the provided embodiments of the provided methods, the disease or disorder associated with BCMA is an autoimmune disease or disorder. In some of any of the provided embodiments of the provided methods, the autoimmune disease or disorder is systemic lupus erythematosus (SLE), lupus nephritis, inflammatory bowel disease, rheumatoid arthritis, ANCA associated vasculitis, idiopathic thrombocytopenia purpura (ITP), thrombotic thrombocytopenia purpura (TTP), autoimmune thrombocytopenia, Chagas' disease, Grave's disease, Wegener's granulomatosis, poly-arteritis nodosa, Sjogren's syndrome, pemphigus vulgaris, scleroderma, multiple sclerosis, psoriasis, IgA nephropathy, IgM polyneuropathies, vasculitis, diabetes mellitus, Reynaud's syndrome, anti-phospholipid syndrome, Goodpasture's disease, Kawasaki disease, autoimmune hemolytic anemia, myasthenia gravis, or progressive glomerulonephritis.

In some embodiments, the disease or disorder is a cancer. In some embodiments, the cancer is a GPRC5D-expressing cancer. In some embodiments, the cancer is a plasma cell malignancy and the plasma cell malignancy is multiple myeloma (MM) or plasmacytoma. In some embodiments, the cancer is multiple myeloma (MM). In some embodiments, the cancer is a relapsed/refractory multiple myeloma.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells. In some embodiments, administration of the cell dose or any additional therapies, e.g., the lymphodepleting therapy, intervention therapy and/or combination therapy, is carried out via outpatient delivery.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 mg/m$^2$ and 500 mg/m$^2$, such as between or between about 200 mg/m$^2$ and 400 mg/m$^2$, or 250 mg/m$^2$ and 350 mg/m$^2$, inclusive. In some instances, the subject is administered about 300 mg/m$^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 mg/m$^2$ of cyclophosphamide, daily for 3 days, prior to initiation of the cell therapy.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m$^2$, 15 mg/m$^2$ and 50 mg/m$^2$, 20 mg/m$^2$ and 40 mg/m$^2$, or 24 mg/m$^2$ and 35 mg/m$^2$, inclusive. In some instances, the subject is administered about 30 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 mg/m$^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the first or subsequent dose.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable known methods, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known. See, for instance, Wadwa et al., J. Drug Targeting 3: 1 1 1 (1995), and U.S. Pat. No. 5,087,616.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agent includes a cytokine, such as IL-2, for example, to enhance persistence.

A. Dosing

In some embodiments, a dose of cells, e.g., the output cells as described herein, such as in Section I-G, is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the dose of cells comprises between at or about $2\times10^5$ of the cells/kg and at or about $2\times10^6$ of the cells/kg, such as between at or about $4\times10^5$ of the cells/kg and at or about $1\times10^6$ of the cells/kg or between at or about $6\times10^5$ of the cells/kg and at or about $8\times10^5$ of the cells/kg. In some embodiments, the dose of cells comprises no more than $2\times10^5$ of the cells (e.g. antigen-expressing, such as CAR-expressing cells) per kilogram body weight of the subject (cells/kg), such as no more than at or about $3\times10^5$ cells/kg, no more than at or about $4\times10^5$ cells/kg, no more than at or about $5\times10^5$ cells/kg, no more than at or about $6\times10^5$ cells/kg, no more than at or about $7\times10^5$ cells/kg, no more than at or about $8\times10^5$ cells/kg, no more than at or about $9\times10^5$ cells/kg, no more than at or about $1\times10^6$ cells/kg, or no more than at or about $2\times10^6$ cells/kg. In some embodiments, the dose of cells comprises at least or at least about or at or about $2\times10^5$ of the cells (e.g. antigen-expressing, such as CAR-expressing cells) per kilogram body weight of the subject (cells/kg), such as at least or at least about or at or about $3\times10^5$ cells/kg, at least or at least about or at or about $4\times10^5$ cells/kg, at least or at least about or at or about $5\times10^5$ cells/kg, at least or at least about or at or about $6\times10^5$ cells/kg, at least or at least about or at or about $7\times10^5$ cells/kg, at least or at least about or at or about $8\times10^5$ cells/kg, at least or at least about or at or about $9\times10^5$ cells/kg, at least or at least about or at or about $1\times10^6$ cells/kg, or at least or at least about or at or about $2\times10^6$ cells/kg.

In certain embodiments, the cells, or individual populations of sub-types of cells, are administered to the subject at a range of at or about 0.1 million to at or about 100 billion cells and/or that amount of cells per kilogram of body weight of the subject, such as, e.g., at or about 0.1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), at or about 1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), such as at or about 10 million to at or about 100 billion cells (e.g., at or about 20 million cells, at or about 30 million cells, at or about 40 million cells, at or about 60 million cells, at or about 70 million cells, at or about 80 million cells, at or about 90 million cells, at or about 10 billion cells, at or about 25 billion cells, at or about 50 billion cells, at or about 75 billion cells, at or about 90 billion cells, or a range defined by any two of the foregoing values), and in some cases at or about 100 million cells to at or about 50 billion cells (e.g., at or about 120 million cells, at or about 250 million cells, at or about 350 million cells, at or about 650 million cells, at or about 800 million cells, at or about 900 million cells, at or about 3 billion cells, at or about 30 billion cells, at or about 45 billion cells) or any value in between these ranges and/or per kilogram of body weight of the subject. Dosages may vary depending on attributes particular to the disease or disorder and/or patient and/or other treatments. In some embodiments, the dose of cells is a flat dose of cells or fixed dose of cells such that the dose of cells is not tied to or based on the body surface area or weight of a subject.

In some embodiments, for example, where the subject is a human, the dose includes fewer than about $5\times10^8$ total recombinant receptor (e.g., CAR)-expressing cells, T cells, or peripheral blood mononuclear cells (PBMCs), e.g., in the range of at or about $1\times10^6$ to at or about $5\times10^8$ such cells, such as at or about $2\times10^6$, $5\times10^6$, $1\times10^7$, $5\times10^7$, $1\times10^8$, $1.5\times10^8$, or $5\times10^8$ total such cells, or the range between any two of the foregoing values. In some embodiments, for example, where the subject is a human, the dose includes more than at or about $1\times10^6$ total recombinant receptor (e.g., CAR)-expressing cells, T cells, or peripheral blood mononuclear cells (PBMCs) and fewer than at or about $2\times10^9$ total recombinant receptor (e.g., CAR)-expressing cells, T cells, or peripheral blood mononuclear cells (PBMCs), e.g., in the range of at or about $2.5\times10^7$ to at or about $1.2\times10^9$ such cells, such as at or about $2.5\times10^7$, $5\times10^7$, $1\times10^8$, $1.5\times10^8$, $8\times10^8$, or $1.2\times10^9$ total such cells, or the range between any two of the foregoing values.

In some embodiments, the dose of genetically engineered cells comprises from at or about $1\times10^5$ to at or about $5\times10^8$ total CAR-expressing (CAR-expressing) T cells, from at or about $1\times10^5$ to at or about $2.5\times10^8$ total CAR-expressing T cells, from at or about $1\times10^5$ to at or about $1\times10^8$ total CAR-expressing T cells, from at or about $1\times10^5$ to at or about $5\times10^7$ total CAR-expressing T cells, from at or about $1\times10^5$ to at or about $2.5\times10^7$ total CAR-expressing T cells, from at or about $1\times10^5$ to at or about $1\times10^7$ total CAR-expressing T cells, from at or about $1\times10^5$ to at or about $5\times10^6$ total CAR-expressing T cells, from at or about $1\times10^5$ to at or about $2.5\times10^6$ total CAR-expressing T cells, from at or about $1\times10^5$ to at or about $1\times10^6$ total CAR-expressing T cells, from at or about $1\times10^6$ to at or about $5\times10^8$ total CAR-expressing T cells, from at or about $1\times10^6$ to at or about $2.5\times10^8$ total CAR-expressing T cells, from at or about $1\times10^6$ to at or about $1\times10^8$ total CAR-expressing T cells, from at or about $1\times10^6$ to at or about $5\times10^7$ total CAR-expressing T cells, from at or about $1\times10^6$ to at or about $2.5\times10^7$ total CAR-expressing T cells, from at or about $1\times10^6$ to at or about $1\times10^7$ total CAR-expressing T cells, from at or about $1\times10^6$ to at or about $5\times10^6$ total CAR-expressing T cells, from at or about $1\times10^6$ to at or about $2.5\times10^6$ total CAR-expressing T cells, from at or about $2.5\times10^6$ to at or about $5\times10^8$ total CAR-expressing T cells, from at or about $2.5\times10^6$ to at or about $2.5\times10^8$ total CAR-expressing T cells, from at or about $2.5 \times 10^6$ to at or about $1 \times 10^8$ total CAR-expressing T cells, from at or about $2.5 \times 10^6$ to at or about $5 \times 10^7$ total CAR-expressing T cells, from at or about $2.5 \times 10^6$ to at or about $2.5 \times 10^7$ total CAR-expressing T cells, from at or about $2.5 \times 10^6$ to at or about $1 \times 10^7$ total CAR-expressing T cells, from at or about $2.5 \times 10^6$ to at or about $5 \times 10^6$ total CAR-expressing T cells, from at or about $5 \times 10^6$ to at or about $5 \times 10^8$ total CAR-expressing T cells, from at or about $5 \times 10^6$ to at or about $2.5 \times 10^8$ total CAR-expressing T cells, from at or about $5 \times 10^6$ to at or about $1 \times 10^8$ total CAR-expressing T cells, from at or about $5 \times 10^6$ to at or about $5 \times 10^7$ total CAR-expressing T cells, from at or about $5 \times 10^6$ to at or about $2.5 \times 10^7$ total CAR-expressing T cells, from at or about $5 \times 10^6$ to at or about $1 \times 10^7$ total CAR-expressing T cells, from at or about $1 \times 10^7$ to at or about $5 \times 10^8$ total CAR-expressing T cells, from at or about $1 \times 10^7$ to at or about $2.5 \times 10^8$ total CAR-expressing T cells, from at or about $1 \times 10^7$ to at or about $1 \times 10^8$ total CAR-expressing T cells, from at or about $1 \times 10^7$ to at or about $5 \times 10^7$ total CAR-expressing T cells, from at or about $1 \times 10^7$ to at or about $2.5 \times 10^7$ total CAR-expressing T cells, from at or about $2.5 \times 10^7$ to at or about $5 \times 10^8$ total CAR-expressing T cells, from at or about $2.5 \times 10^7$ to at or about $2.5 \times 10^8$ total CAR-expressing T cells, from at or about $2.5 \times 10^7$ to at or about $1 \times 10^8$ total CAR-expressing T cells, from at or about $2.5 \times 10^7$ to at or about $5 \times 10^7$ total CAR-expressing T cells, from at or about $5 \times 10^7$ to at or about $5 \times 10^8$ total CAR-expressing T cells, from at or about $5 \times 10^7$ to at or about $2.5 \times 10^8$ total CAR-expressing T cells, from at or about $5 \times 10^7$ to at or about $1 \times 10^8$ total CAR-expressing T cells, from at or about $1 \times 10^8$ to at or about $5 \times 10^8$ total CAR-expressing T cells, from at or about $1 \times 10^8$ to at or about $2.5 \times 10^8$ total CAR-expressing T cells, from at or about or $2.5 \times 10^8$ to at or about $5 \times 10^8$ total CAR-expressing T cells. In some embodiments, the dose of genetically engineered cells comprises from or from about $2.5 \times 10^7$ to at or about $1.5 \times 10^8$ total CAR-expressing T cells, such as from or from about $5 \times 10^7$ to or to about $1 \times 10^8$ total CAR-expressing T cells.

In some embodiments, the dose of genetically engineered cells comprises at least at or about $1 \times 10^5$ CAR-expressing cells, at least at or about $2.5 \times 10^5$ CAR-expressing cells, at least at or about $5 \times 10^5$ CAR-expressing cells, at least at or about $1 \times 10^6$ CAR-expressing cells, at least at or about $2.5 \times 10^6$ CAR-expressing cells, at least at or about $5 \times 10^6$ CAR-expressing cells, at least at or about $1 \times 10^7$ CAR-expressing cells, at least at or about $2.5 \times 10^7$ CAR-expressing cells, at least at or about $5 \times 10^7$ CAR-expressing cells, at least at or about $1 \times 10^8$ CAR-expressing cells, at least at or about $1.5 \times 10^8$ CAR-expressing cells, at least about $5 \times 10^6$ CAR-expressing cells, at least or at least about $1 \times 10^7$ CAR-expressing cells, at least or at least about $2.5 \times 10^7$ CAR-expressing cells, at least or at least about $5 \times 10^7$ CAR-expressing cells, at least or at least about $1 \times 10^8$ CAR-expressing cells, at least or at or about $2.5 \times 10^8$ CAR-expressing cells, or at least at or about $5 \times 10^8$ CAR-expressing cells.

In some embodiments, the cell therapy comprises administration of a dose comprising a number of cell from or from about $1 \times 10^5$ to or to about $5 \times 10^8$ total recombinant receptor-expressing cells, total T cells, or total peripheral blood mononuclear cells (PBMCs), from or from about $5 \times 10^5$ to or to about $1 \times 10^7$ total recombinant receptor-expressing cells, total T cells, or total peripheral blood mononuclear cells (PBMCs) or from or from about $1 \times 10^6$ to or to about $1 \times 10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1 \times 10^5$ total recombinant receptor-expressing cells, total T cells, or total peripheral blood mononuclear cells (PBMCs), such at least or at least $1 \times 10^6$, at least or at least about $1 \times 10^7$, at least or at least about $1 \times 10^8$ of such cells. In some embodiments, the number is with reference to the total number of CD3-expressing or CD8-expressing, in some cases also recombinant receptor-expressing (e.g. CAR-expressing) cells. In some embodiments, the cell therapy comprises administration of a dose comprising a number of cell from or from about $1 \times 10^5$ to or to about $5 \times 10^8$ CD3-expressing or CD8-expressing total T cells or CD3-expressing or CD8-expressing recombinant receptor-expressing cells, from or from about $5 \times 10^5$ to or to about $1 \times 10^7$ CD3-expressing or CD8-expressing total T cells or CD3-expressing or CD8-expressing recombinant receptor-expressing cells, or from or from about $1 \times 10^6$ to or to about $1 \times 10^7$ CD3-expressing or CD8-expressing total T cells or CD3-expressing or CD8-expressing recombinant receptor-expressing cells, each inclusive. In some embodiments, the cell therapy comprises administration of a dose comprising a number of cell from or from about $1 \times 10^5$ to or to about $5 \times 10^8$ total CD3-expressing/CAR-expressing or CD8-expressing/CAR-expressing cells, from or from about $5 \times 10^5$ to or to about $1 \times 10^7$ total CD3-expressing/CAR-expressing or CD8-expressing/CAR-expressing cells, or from or from about $1 \times 10^6$ to or to about $1 \times 10^7$ total CD3-expressing/CAR-expressing or CD8-expressing/CAR-expressing cells, each inclusive.

In some embodiments, the T cells of the dose include CD4-expressing T cells, CD8-expressing T cells or CD4-expressing and CD8-expressing T cells.

In some embodiments, for example, where the subject is human, the CD8-expressing T cells of the dose, including in a dose including CD4-expressing and CD8-expressing T cells, includes between at or about $1 \times 10^6$ and at or about $5 \times 10^8$ total recombinant receptor (e.g., CAR)-expressing CD8-expressing cells, e.g., in the range of from at or about $5 \times 10^6$ to at or about $1 \times 10^8$ such cells, such as $1 \times 10^7$, $2.5 \times 10^7$, $5 \times 10^7$, $7.5 \times 10^7$, $1 \times 10^8$, $1.5 \times 10^8$, or $5 \times 10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1 \times 10^7$ to or to about $0.75 \times 10^8$ total recombinant receptor-expressing CD8-expressing T cells, from or from about $1 \times 10^7$ to or to about $5 \times 10^7$ total recombinant receptor-expressing CD8-expressing T cells, from or from about $1 \times 10^7$ to or to about $0.25 \times 10^8$ total recombinant receptor-expressing CD8-expressing T cells, each inclusive. In some embodiments, the dose of cells comprises the administration of at or about $1 \times 10^7$, $2.5 \times 10^7$, $5 \times 10^7$, $7.5 \times 10^7$, $1 \times 10^8$, $1.5 \times 10^8$, $2.5 \times 10^8$, or $5 \times 10^8$ total recombinant receptor-expressing CD8-expressing T cells.

In some embodiments, the dose of cells, e.g., recombinant receptor-expressing T cells, is administered to the subject as a single dose or is administered only one time within a period of two weeks, one month, three months, six months, 1 year or more.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose or as a plurality of compositions, provided in multiple individual compositions or infusions, over a specified period of time, such as over no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, the term "split dose" refers to a dose that is split so that it is administered over more than one day. This type of dosing is encompassed by the present methods and is considered to be a single dose.

Thus, the dose of cells may be administered as a split dose, e.g., a split dose administered over time. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include CD8+ and CD4+ T cells, respectively, and/or CD8+- and CD4+-enriched populations, respectively, e.g., CD4+ and/or CD8+ T cells each individually including cells genetically engineered to express the recombinant receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some composition, the first composition, e.g., first composition of the dose, comprises CD4+ T cells. In some composition, the first composition, e.g., first composition of the dose, comprises CD8+ T cells. In some embodiments, the first composition is administered prior to the second composition.

In some embodiments, the dose or composition of cells includes a defined or target ratio of CD4+ cells expressing a recombinant receptor to CD8+ cells expressing a recombinant receptor and/or of CD4+ cells to CD8+ cells, which ratio optionally is approximately 1:1 or is between approximately 1:3 and approximately 3:1, such as approximately 1:1. In some aspects, the administration of a composition or dose with the target or desired ratio of different cell populations (such as CD4+:CD8+ ratio or CAR+CD4+:CAR+ CD8+ ratio, e.g., 1:1) involves the administration of a cell composition containing one of the populations and then administration of a separate cell composition comprising the other of the populations, where the administration is at or approximately at the target or desired ratio. In some aspects, administration of a dose or composition of cells at a defined ratio leads to improved expansion, persistence and/or anti-tumor activity of the T cell therapy.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., recombinant receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8$^+$ and CD4$^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4$^+$ to CD8$^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4$^+$ to CD8$^+$ cells, and/or is based on a desired fixed or minimum dose of CD4$^+$ and/or CD8$^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of CD4$^+$ to CD8$^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, the methods also include administering one or more additional doses of cells expressing a chimeric antigen receptor (CAR) and/or lymphodepleting therapy, and/or one or more steps of the methods are repeated. In some embodiments, the one or more additional dose is the same as the initial dose. In some embodiments, the one or more additional dose is different from the initial dose, e.g., higher, such as 2-fold, 3-fold, 4-fold, 5-fold, 6-fold, 7-fold, 8-fold, 9-fold or 10-fold or more higher than the initial dose, or lower, such as e.g., higher, such as 2-fold, 3-fold, 4-fold, 5-fold, 6-fold, 7-fold, 8-fold, 9-fold or 10-fold or more lower than the initial dose. In some embodiments, administration of one or more additional doses is determined based on response of the subject to the initial treatment or any prior treatment, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

B. Response, Efficacy, and Survival

In some embodiments, cells, e.g., output cells, produced by the methods provided herein, e.g., such as described in Section-I, are administered to a subject, and the subject is monitored for response, survival, and/or signs or symptoms of toxicity.

In some embodiments, at least 35%, at least 40% or at least 50% of subjects treated with compositions of cells, e.g., therapeutic cell compositions containing CAR+CD4+ and CD8+ T cells, produce remission (CR); and/or at least 50%, at least 60% or at least 70% of the subjects treated according to the method achieve objective response rate (ORR). In some embodiments, at least or at least about 50% of subjects, at least or at least about 60% of the subjects, at least or at least about 70% of the subjects, at least or at least about 80% of the subjects or at least or at least about 90% of the subjects treated according to the method achieve CR and/or achieve an objective response (OR). In some embodiments, criteria assessed for effective treatment includes overall response rate (ORR), complete response (CR), duration of response (DOR) progression-free survival (PFS), and/or overall survival (OS).

In some embodiments, at least 40% or at least 50% of subjects treated according to the methods provided herein achieve complete remission (CR), exhibit progression-free survival (PFS) and/or overall survival (OS) of greater than at or about 3 months, 6 months or 12 months; on average, subjects treated according to the method exhibit a median PFS or OS of greater than at or about 6 months, 12 months, or 18 months; and/or the subject exhibits PFS or OS following therapy for at least at or about 6, 12, 18 or more months.

In some respects, progression-free survival (PFS) is described as the length of time during and after the treatment of a disease, such as cancer, that a subject lives with the disease but it does not get worse. In some aspects, objective response (OR) is described as a measurable response. In some aspects, objective response rate (ORR) is described as the proportion of patients who achieved CR or PR. In some aspects, overall survival (OS) is described as the length of time from either the date of diagnosis or the start of treatment for a disease, such as cancer, that subjects diagnosed with the disease are still alive. In some aspects, event-free survival (EFS) is described as the length of time after treatment for a cancer ends that the subject remains free of certain complications or events that the treatment was intended to prevent or delay. These events may include the return of the cancer or the onset of certain symptoms, such as bone pain from cancer that has spread to the bone, or death.

In some embodiments, the measure of duration of response (DOR) includes the time from documentation of tumor response to disease progression. In some embodiments, the parameter for assessing response can include durable response, e.g., response that persists after a period of time from initiation of therapy. In some embodiments, durable response is indicated by the response rate at approximately 1, 2, 3, 4, 5, 6, 7, 8, 9, 10, 11, 12, 18 or 24 months after initiation of therapy. In some embodiments, the response is durable for greater than 3 months or greater than 6 months.

In some embodiments, administering a dose or composition of cells produced by the methods provided herein reduces the burden of the disease or condition, e.g., number of tumor cells, size of tumor, duration of patient survival or event-free survival, to a greater degree and/or for a greater period of time as compared to the reduction that would be observed with a comparable method using cells generated by an alternative process. In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified.

In some embodiments, the event-free survival rate or overall survival rate of the subject is improved by administering cells produced from the provided methods, e.g., the methods described in Section-I, as compared with cell generated by alternative methods. For example, in some embodiments, event-free survival rate or probability for subjects treated by the methods at 6 months following the dose is greater than at or about 40%, greater than at or about 50%, greater than at or about 60%, greater than at or about 70%, greater than at or about 80%, greater than at or about 90%, or greater than at or about 95%. In some aspects, overall survival rate is greater than at or about 40%, greater than at or about 50%, greater than at or about 60%, greater than at or about 70%, greater than at or about 80%, greater than at or about 90%, or greater than at or about 95%. In some embodiments, the subject treated with the cells produced by the provided methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or at or about 6 months, or at least 1, 2, 3, 4, 5, 6, 7, 8, 9, or 10 years.

In some embodiments, following treatment by the method, the probability of relapse is reduced as compared to other methods, for example, methods in which the subject receives a cell therapy containing cells produced by alternative methods. For example, in some embodiments, the probability of relapse at 6 months following the first dose is less than at or about 80%, less than at or about 70%, less than at or about 60%, less than at or about 50%, less than at or about 40%, less than at or about 30%, less than at or about 20%, or less than at or about 10%.

C. Toxicity

In certain embodiments, cells, e.g., output cells, produced by the methods provided herein, e.g., such as described in Section-I, are administered to a subject, and the subject is monitored for signs or symptoms of toxicity.

In certain embodiments, the a dose or composition of cells, e.g., output cells produced by the provided methods result in a lower rate and/or lower degree of toxicity, toxic outcome or symptom, toxicity-promoting profile, factor, or property, such as a symptom or outcome associated with or indicative of cytokine release syndrome (CRS) or neurotoxicity, for example, compared to administration of an alternative cell therapy, such as an CAR+ T cell composition produced by an alternative process.

In some embodiments, administering cells produced by the provided methods do not result in a high rate or likelihood of toxicity or toxic outcomes, or reduces the rate or likelihood of toxicity or toxic outcomes, such as neurotoxicity (NT), cytokine release syndrome (CRS), such as compared to certain other cell therapies and/or cells produced by alternative methods. In some embodiments, the administering the cells, e.g., output cells, produced by the provided methods result in, or do not increase the risk of, severe NT (sNT), severe CRS (sCRS), macrophage activation syndrome, tumor lysis syndrome, fever of at least at or about 38 degrees Celsius for three or more days and a plasma level of CRP of at least at or about 20 mg/dL. In some embodiments, greater than or greater than about 30%, 35%, 40%, 50%, 55%, 60% or more of the subjects treated according to the provided methods do not exhibit any grade of CRS or any grade of neurotoxcity. In some embodiments, no more than 50% of subjects treated (e.g. at least 60%, at least 70%, at least 80%, at least 90% or more of the subjects treated) exhibit a cytokine release syndrome (CRS) higher than grade 2 and/or a neurotoxicity higher than grade 2. In some embodiments, at least 50% of subjects treated according to the method (e.g. at least 60%, at least 70%, at least 80%, at least 90% or more of the subjects treated) do not exhibit a severe toxic outcome (e.g. severe CRS or severe neurotoxicity), such as do notexhibit grade 3 or higher neurotoxicity and/or does not exhibit severe CRS, or does not do so within a certain period of time following the treatment, such as within a week, two weeks, or one month of the administration of the cells. In some embodiments, parameters assessed to determine certain toxicities include adverse events (AEs), dose-limiting toxicities (DLTs), CRS and NT.

Administration of adoptive T cell therapy, such as treatment with T cells expressing chimeric antigen receptors, can induce toxic effects or outcomes such as cytokine release syndrome and neurotoxicity. In some examples, such effects or outcomes parallel high levels of circulating cytokines, which may underlie the observed toxicity.

In some aspects, the toxic outcome is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure.

CRS may be treated using anti-inflammatory therapy such as an anti-IL-6 therapy, e.g., anti-IL-6 antibody, e.g., tocilizumab, or antibiotics or other agents as described. Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

In the context of administering CAR-expressing cells, CRS typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-1β, IL-6, IL-8, and IL-10.

Exemplary outcomes associated with CRS include fever, rigors, chills, hypotension, dyspnea, acute respiratory distress syndrome (ARDS), encephalopathy, ALT/AST elevation, renal failure, cardiac disorders, hypoxia, neurologic disturbances, and death. Neurological complications include delirium, seizure-like activity, confusion, word-finding difficulty, aphasia, and/or becoming obtunded. Other CRS-related outcomes include fatigue, nausea, headache, seizure, tachycardia, myalgias, rash, acute vascular leak syndrome, liver function impairment, and renal failure. In some aspects, CRS is associated with an increase in one or more factors such as serum-ferritin, d-dimer, aminotransferases, lactate dehydrogenase and triglycerides, or with hypofibrinogenemia or hepatosplenomegaly.

CRS criteria that appear to correlate with the onset of CRS to predict which patients are more likely to be at risk for developing sCRS have been developed (see Davila et al. Science translational medicine. 2014; 6(224):224ra25). Factors include fevers, hypoxia, hypotension, neurologic changes, elevated serum levels of inflammatory cytokines, such as a set of seven cytokines (IFNγ, IL-5, IL-6, IL-10, Flt-3L, fractalkine, and GM-CSF) whose treatment-induced elevation can correlate well with both pretreatment tumor burden and sCRS symptoms. Other guidelines on the diagnosis and management of CRS are known (see e.g., Lee et al, Blood. 2014; 124(2):188-95). In some embodiments, the criteria reflective of CRS grade are those detailed in Table 2 below.

TABLE 2

| Exemplary Grading Criteria for CRS | |
|---|---|
| Grade | Description of Symptoms |
| 1 Mild | Not life-threatening, require only symptomatic treatment such as antipyretics and anti-emetics (e.g., fever, nausea, fatigue, headache, myalgias, malaise) |
| 2 Moderate | Require and respond to moderate intervention: Oxygen requirement <40%, or Hypotension responsive to fluids or low dose of a single vasopressor, or Grade 2 organ toxicity (by CTCAE v4.0) |
| 3 Severe | Require and respond to aggressive intervention: Oxygen requirement ≥40%, or Hypotension requiring high dose of a single vasopressor (e.g., norepinephrine ≥20 μg/kg/min, dopamine ≥10 μg/kg/min, phenylephrine ≥200 μg/kg/min, or epinephrine ≥10 μg/kg/min), or Hypotension requiring multiple vasopressors (e.g., vasopressin + one of the above agents, or combination vasopressors equivalent to ≥20 μg/kg/min norepinephrine), or Grade 3 organ toxicity or Grade 4 transaminitis (by CTCAE v4.0) |
| 4 Life-threatening | Life-threatening: Requirement for ventilator support, or Grade 4 organ toxicity (excluding transaminitis) |
| 5 Fatal | Death |

In some embodiments, a criteria reflective of CRS grade are those detailed in Table 3 below.

TABLE 3

| Exemplary Grading Criteria for CRS | | | | |
|---|---|---|---|---|
| Symptoms/Signs | Grade 1 (mild) | Grade 2 (moderate) | Grade 3 (severe) | Grade 4 (life-threatening) |
| | | CRS grade is defined by the most severe symptom (excluding fever) | | |
| Temperature ≥38.5° C./ 101.3° F. | Any | Any | Any | Any |

TABLE 3-continued

Exemplary Grading Criteria for CRS

| Symptoms/Signs | Grade 1 (mild) | Grade 2 (moderate) | Grade 3 (severe) | Grade 4 (life-threatening) |
|---|---|---|---|---|
| | | CRS grade is defined by the most severe symptom (excluding fever) | | |
| Systolic blood pressure ≤90 mm Hg | N/A | Responds to fluid or single low-dose vasopressor | Needs high-dose or multiple vasopressors | Life-threatening |
| Need for oxygen to reach SaO₂ >90% | N/A | FiO2 <40% | FiO₂ ≥40% | Needs ventilator support |
| Organ toxicity | N/A | Grade 2 | Grade 3 or transaminitis | Grade 4 (excluding transaminitis) |

In some embodiments, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-10, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-10, Flt-3L, fracktalkine, and IL-5; and (c) at least one clinical sign of toxicity such as hypotension (requiring at least one intravenous vasoactive pressor) or hypoxia (PO₂<90%) or one or more neurologic disorder(s) (including mental status changes, obtundation, and/or seizures). In some embodiments, severe CRS includes CRS with a grade of 3 or greater, such as set forth in Table 2 or Table 3.

In some embodiments, outcomes associated with severe CRS or grade 3 CRS or greater, such as grade 4 or greater, include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen (PO₂) levels of less than at or about 90%); and/or one or more neurologic disorders (including mental status changes, obtundation, and seizures). In some embodiments, severe CRS includes CRS that requires management or care in the intensive care unit (ICU).

In some embodiments, the CRS, such as severe CRS, encompasses a combination of (1) persistent fever (fever of at least 38 degrees Celsius for at least three days) and (2) a serum level of CRP of at least at or about 20 mg/dL. In some embodiments, the CRS encompasses hypotension requiring the use of two or more vasopressors or respiratory failure requiring mechanical ventilation. In some embodiments, the dosage of vasopressors is increased in a second or subsequent administration.

In some embodiments, severe CRS or grade 3 CRS encompasses an increase in alanine aminotransferase, an increase in aspartate aminotransferase, chills, febrile neutropenia, headache, left ventricular dysfunction, encephalopathy, hydrocephalus, and/or tremor.

The method of measuring or detecting the various outcomes may be specified.

In some aspects, the toxic outcome is or is associated with neurotoxicity. In some embodiments, symptoms associated with a clinical risk of neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli *Nature Reviews Neurology* 6, 657-666 (December 2010); National Cancer Institute—Common Toxicity Criteria version 4.03 (NCI-CTCAE v4.03).

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

In some embodiments, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 4.

223

TABLE 4

| Exemplary Grading Criteria for neurotoxicity | |
| --- | --- |
| Grade | Description of Symptoms |
| 1<br>Asymptomatic<br>or Mild | Mild or asymptomatic symptoms |
| 2<br>Moderate | Presence of symptoms that limit instrumental activities of daily living (ADL), such as preparing meals, shopping for groceries or clothes, using the telephone, managing money |
| 3<br>Severe | Presence of symptoms that limit self-care ADL, such as bathing, dressing and undressing, feeding self, using the toilet, taking medications |
| 4<br>Life-threatening | Symptoms that are life-threatening, requiring urgent intervention |
| 5<br>Fatal | Death |

In some embodiments, the methods reduce symptoms associated with CRS or neurotoxicity compared to other methods. In some aspects, the provided methods reduce symptoms, outcomes or factors associated with CRS, including symptoms, outcomes or factors associated with severe CRS or grade 3 or higher CRS, compared to other methods. For example, subjects treated according to the present methods may lack detectable and/or have reduced symptoms, outcomes or factors of CRS, e.g. severe CRS or grade 3 or higher CRS, such as any described, e.g. set forth in Table 2 or Table 3. In some embodiments, subjects treated according to the present methods may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods. In some embodiments, subjects treated according to the present methods may have reduced symptoms associated with peripheral motor neuropathy, peripheral sensory neuropathy, dysethesia, neuralgia or paresthesia.

In some embodiments, the administering cells produced by the provided methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals.

In some embodiments, one or more interventions or agents for treating the toxicity, such as a toxicity-targeting therapies, is administered at a time at which or immediately after which the subject is determined to or confirmed to (such as is first determined or confirmed to) exhibit sustained fever, for example, as measured according to any of the aforementioned embodiments. In some embodiments, the one or more toxicity-targeting therapies is administered within a certain period of time of such confirmation or determination, such as within 30 minutes, 1 hour, 2 hours, 3 hours, 4 hours, 6 hours, or 8 hours thereof.

V. COMPOSITIONS AND FORMULATIONS

Also provided are compositions and formulations containing engineered cells expressing a recombinant receptor produced by the methods provided herein. In some embodiments, the compositions and formulations contain cells, such as a composition or dose of cells, produced by methods described herein, such as in Section I. In some embodiments, the compositions and formulations are or contain output compositions of cells, and optionally instructions for use, for example, instructions for administering the engineered cells to a subject, such as by methods described herein, such as in Section III.

In some embodiments, the dose of cells comprising cells engineered with a recombinant antigen receptor, e.g. CAR or TCR, is provided as a composition or formulation, such as a pharmaceutical composition or formulation. In certain embodiments, the dose contains cells of an output composition described herein, such as in Section I-G. In particular embodiments, the dose contains cells that were produced by a method described herein, e.g., in Section I. Such compositions can be used in accord with the provided methods, and/or with the provided articles of manufacture or compositions, such as in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

VI. ARTICLES OF MANUFACTURE AND KITS

Also provided are articles of manufacture and kits containing engineered cells expressing a recombinant receptor produced by the methods provided herein. In some embodiments, the articles of manufacture contain cells, such as a composition or dose of cells, produced by methods described herein, such as in Section I. In some embodiments, the kits and/or articles of manufacture are or contain output compositions of cells, and optionally instructions for use, for example, instructions for administering the engineered cells to a subject, such as by methods described herein, such as in Section III.

In some embodiments, provided herein are articles of manufacture and/or kits that include a composition comprising a therapeutically effective amount of any of the engineered cells described herein, and instructions for administering, to a subject for treating a disease or condition. In some embodiments, the instructions can specify some or all of the elements of the methods for administrating the cells that are provided herein. In some embodiments, the instructions specify particular instructions for administration of the cells for cell therapy, e.g., doses, timing, selection and/or identification of subjects for administration and conditions for administration. In some embodiments, the articles of manufacture and/or kits further comprise an agent for lymphodepleting therapy, and optionally further includes instructions for administering the lymphodepleting therapy. In some embodiments, the instructions can be included as a label or package insert accompanying the compositions for administration.

In some embodiments, the article of manufacture may have a container, optionally a vial, containing a composition containing CD4+ and CD8+ T cells expressing a recombinant receptor. In some embodiments, the article of manufacture or kit contains a composition of cells with a ratio of between 3:1 and 1:3, between 2.5:1 and 1:2.5, between 2:1 and 1:2, between 1.5:1 and 1:1.5, between 1.4:1 and 1:1.4, between 1.3:1 and 1:1.3, between 1.2:1 and 1:1.2, or between 1.1:1 and 1:1.1 CD4+ T cells to CD8+ T cells. In some embodiments, the composition of cells has a ratio of or of about 3:1, 2.8:1, 2.5:1, 2.25:1, 2:1, 1.8:1, 1.6:1, 1.5:1, 1.4:1, 1.3:1, 1.2:1, 1.1:1, 1:1,1:1.1, 1:1.2, 1:1.3, 1:1.4, 1:1.5, 1:1.6, 1:1.8, 1:2, 1:2.25, 1:2.5, 1:2.8, 1:3 CD4+ T cells to CD8+ T cells. In particular embodiments, the article of manufacture or kit contains a composition of cells with a ratio of between 3:1 and 1:3, between 2.5:1 and 1:2.5, between 2:1 and 1:2, between 1.5:1 and 1:1.5, between 1.4:1 and 1:1.4, between 1.3:1 and 1:1.3, between 1.2:1 and 1:1.2, or between 1.1:1 and 1:1.1 CD4+ T cells that express the recombinant receptor, e.g., the CAR, to CD8+ T cells that express the recombinant receptor, e.g., the CAR. In some embodiments, the composition of cells has a ratio of or of about 3:1, 2.8:1, 2.5:1, 2.25:1, 2:1, 1.8:1, 1.6:1, 1.5:1, 1.4:1, 1.3:1, 1.2:1, 1.1:1, 1:1,1:1.1, 1:1.2, 1:1.3, 1:1.4, 1:1.5, 1:1.6, 1:1.8, 1:2, 1:2.25, 1:2.5, 1:2.8, 1:3 CD4+ T cells that express the recombinant receptor, e.g., the CAR, to CD8+ T cells that express the recombinant receptor, e.g., the CAR.

In some embodiments, the instructions specify the dose of cells to be administered. For example, in some embodiments, the dose specified in the instructions include a total recombinant receptor (e.g., CAR)-expressing cells between at or about $1\times10^6$ and at or about $3\times10^8$, e.g., in the range of at or about $1\times10^7$ to at or about $2\times10^8$ such cells, such as at or about $1\times10^7$, $5\times10^7$, $1\times10^8$ or $1.5\times10^8$ total such cells, or the range between any two of the foregoing values. In some embodiments, the patient is administered multiple doses, and each of the doses or the total dose can be within any of the foregoing values.

In some embodiments, the container such as the vial comprises greater than or greater than at or about $10\times10^6$ T cells or recombinant receptor-expressing T cells, greater than or greater than at or about $15\times10^6$ T cells or recombinant receptor-expressing T cells, greater than or greater than at or about $25\times10^6$ T cells or recombinant receptor-expressing T cell. In some aspects, the vial comprises between at or about 10 million cells per mL and at or about 70 million cells per mL, between at or about 10 million cells per mL and at or about 50 million cells per mL, between at or about 10 million cells per mL and at or about 25 million cells per mL, between at or about 10 million cells per mL and at or about 15 million cells per mL, 15 million cells per mL and at or about 70 million cells per mL, between at or about 15 million cells per mL and at or about 50 million cells per mL, between at or about 15 million cells per mL and at or about 25 million cells per mL, between at or about 25 million cells per mL and at or about 70 million cells per mL, between at or about 25 million cells per mL and at or about 50 million cells per mL, and between at or about 50 million cells per mL and at or about 70 million cells per mL.

In some embodiments, the plurality of vials or plurality of cells or unit dose of cells specified for administration, collectively, comprises a dose of cells comprising from or from about $1\times10^5$ to or to about $5\times10^8$ total recombinant receptor-expressing T cells or total T cells, $1\times10^5$ to or to about $1\times10^9$ total recombinant receptor-expressing T cells or total T cells, from or from about $5\times10^5$ to or to about $1\times10^9$ total recombinant receptor-expressing T cells or total T cells, or from or from about $1\times10^6$ to or to about $1\times10^{10}$ total recombinant receptor-expressing T cells or total T cells, each inclusive. In some aspects, the article comprises one or more unit dose of the CD4+ and CD8+ T cells or of the CD4+ receptor+ T cells and CD8+ receptor+ T cells, wherein the unit dose comprises between at or about $1\times10^7$ and at or about $2\times10^8$ recombinant receptor-expressing T cells, between at or about $5\times10^7$ and at or about $1.5\times10^8$ recombinant receptor-expressing T cells, at or about $5\times10^7$ recombinant receptor-expressing T cells, at or about $1\times10^8$ recombinant receptor-expressing T cells, or at or about $1.5\times10^8$ recombinant receptor-expressing T cells, optionally wherein the information in the article specifies administration of one or of a plurality of unit doses and/or a volume corresponding to such one or plurality of unit doses.

In some embodiments, the instructions can specify dosage regimen and timing of the administration. For example, in some embodiments, the instructions can specify administering to the subject multiple doses, e.g., two or more doses, of the cells. In some embodiments, the instructions specify the timing of the multiple doses, e.g., the second dose being administered approximately 4, 5, 6, 7, 8, 9, 10, 11, 12, 13, 14, 15, 16, 17, 18, 19, 20 or 21 days after the first dose; and/or the dosage amount in each dose.

In some embodiments, the instructions specify the dose or number of cells or cell type(s) and/or a ratio of cell types, e.g., individual populations or sub-types, such as the CD4+ to CD8+ ratio. In some embodiments, the populations or sub-types of cells, such as CD8$^+$ and CD4$^+$ T cells. For example, in some embodiments, the instructions specify that the cells are administered at or within a tolerated range of an output ratio of multiple cell populations or sub-types, such as CD4+ and CD8+ T cells or sub-types, of between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In certain embodiments, the instructions specify that the compositions of enriched CD4+ T cells and enriched CD8+ T cells are combined at the desired ratio and administered to the subject as a single cell composition. In particular embodiments, the instructions specify the compositions of enriched CD4+ T cells and enriched CD8+ T cells are administered as separate compositions at the desired ratio. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

VII. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

As used herein, a composition refers to any mixture of two or more products, substances, or compounds, including cells. It may be a solution, a suspension, liquid, powder, a paste, aqueous, non-aqueous or any combination thereof.

As used herein, a "subject" is a mammal, such as a human or other animal, and typically is human.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

VIII. EXEMPLARY EMBODIMENTS

Among the provided embodiments are:

1. A method for producing a composition of engineered cells, the method comprising:

(a) combining a composition of CD4+ T cells and a composition of CD8+ T cells at a ratio of between 2:1 and 1:2 CD4+ to CD8+ T cells, thereby generating an input composition;

(b) incubating the input composition under stimulating conditions, thereby generating a stimulated composition; wherein said stimulating conditions comprise the presence of a stimulatory reagent capable of activating one or more intracellular signaling domains of one or more components of a TCR complex and/or one or more intracellular signaling domains of one or more costimulatory molecules;

and wherein the input composition comprises at least $100 \times 10^6$ total CD4+ and CD8+ T cells at a concentration of less than $5 \times 10^6$ cells/mL.

2. The method of embodiment 1, wherein the CD4+ and CD8+ cells in the input composition are enriched or selected from a primary sample from a subject, optionally wherein the CD4+ and CD8+ cells in the input composition are separately enriched or selected from a primary sample from a subject.

3. The method of embodiment 1 or embodiment 2, wherein the composition of CD4+ T cells comprises at least 80%, at least 85%, at least 90%, or at least 95% CD4+ T cells.

4. The method of embodiment 1 or 2, wherein the composition of CD8+ T cells comprises at least 80%, at least 85%, at least 90%, or at least 95% CD8+ T cells.

5. A method for producing a composition of engineered cells, the method comprising incubating an input composition under stimulating conditions, thereby generating a stimulated composition, wherein:

the input composition comprises a ratio of between 2:1 and 1:2 CD4+ to CD8+ T cells, and wherein the input composition comprises at least $100 \times 10^6$ total CD4+ and CD8+ T cells at a concentration of less than $5 \times 10^6$ cells/mL; and the stimulating conditions comprise the presence of a stimulatory reagent capable of activating one or more intracellular signaling domains of one or more components of a TCR complex and/or one or more intracellular signaling domains of one or more costimulatory molecules.

6. The method of any of embodiments 1-5, wherein the incubation is performed in serum free media.

7. The methods of any of embodiments 1-6, wherein the input composition comprises at least 80%, at least 85%, at least 90%, or at least 95% cells that are CD4+ T cells or CD8+ T cells.

8. The method of any of embodiments 1-7, wherein the input composition comprises between $100 \times 10^6$ and $500 \times 10^6$ total CD4+ and CD8+ T cells.

9. The method of any of embodiments 1-8, wherein the input composition comprises at or about $300 \times 10^6$ total CD4+ and CD8+ T cells.

10. The method of embodiment 9, wherein the total CD4+ and CD8+ T cells are viable cells.

11. The method of any of embodiments 1-10, wherein the input composition comprises a concentration of between $1 \times 10^6$ cells/mL and $5 \times 10^6$ cells/mL.

12. The method of any of embodiments 1-11, wherein the input composition comprises a concentration of or of about $3 \times 10^6$ cells/mL.

13. The method of any of embodiments 1-12, wherein the input composition comprises a ratio of between 1.5:1 and 1:1.5 CD4+ to CD8+ cells.

14. The method of any of embodiments 1-13, wherein the input composition comprises a ratio of between 1.2:1 and 0.8:1 CD4+ to CD8+ cells.

15. The method of any of embodiments 1-14, wherein the input composition comprises a ratio of or of about 1:1 CD4+ to CD8+ cells.

16. The method of any of embodiments 1-15, wherein the input composition comprises CD4+ and CD8+ that are surface positive for CD45RA and CCR7.

17. The method of embodiment 16, wherein the ratio of CD4+ cells surface positive for CD45RA and CCR7 to CD8+ cells surface positive for CD45RA and CCR7 is or is about 1.1:1.

18. The method of any of embodiments 1-17, wherein the input composition comprises CD4+ and CD8+ cells that are surface positive for CD27 and CCR7.

19. The method of embodiment 18, wherein the ratio of the CD4+ cells that are surface positive for CD27 and CCR7 to CD8+ cells surface positive for CD27 and CCR7 is or is about 1.69:1.

20. The method of any of embodiments 1-19, wherein the input composition comprises CD4+ and CD8+ cells that are surface positive for CCR7 and surface negative for CD62L, optionally at a ratio of between 2.0:1 to 1.5:1.

21. The method of any of embodiments 1-20, further comprising:

introducing a recombinant receptor into cells from the stimulated composition thereby generating an engineered cell composition, wherein the introducing comprises contacting the cells of the stimulated composition with an agent comprising a polynucleotide encoding the recombinant receptor.

22. The method of embodiment 21, wherein:

the contacting is by transfection with a vector, wherein the vector is a transposon, optionally a Sleeping Beauty (SB) transposon or a Piggybac transposon; or the contacting is by transduction with a viral vector.

23. The method of any of embodiments 1-22, further comprising:

introducing a recombinant receptor into cells from the stimulated composition thereby generating an engineered cell composition, wherein the introducing comprises transducing the cells of the stimulated composition with a viral vector comprising a polynucleotide encoding the recombinant receptor.

24. The method of any of embodiments 21-23, wherein the introducing is performed in serum free media.

25. The method of any of embodiments 21-24, wherein, for the introducing the stimulated composition comprises less than $300 \times 10^6$ cells.

26. The method of any of embodiments 21-25, wherein, for the introducing, the stimulated composition comprises between $50 \times 10^6$ cells and $200 \times 10^6$ cells.

27. The method of any of embodiments 21-26, wherein, for the introducing, the stimulated composition comprises at or about $100 \times 10^6$ cells.

28. The method of any of embodiments 21-27, wherein, for the introducing, the stimulated composition comprises a concentration of less than $3 \times 10^6$ cells/mL.

29. The method of any of embodiments 21-28, wherein, for the introducing, the stimulated composition comprises a concentration of between $0.5 \times 10^6$ cells/mL and $2 \times 10^6$ cells/mL.

30. The method of any of embodiments 21-29, wherein, for the introducing, the stimulated composition comprises a concentration of or about $1 \times 10^6$ cells/mL.

31. The method of any of embodiments 21-30, comprising adjusting the composition of the stimulated composition after incubating under stimulating conditions prior to introducing the recombinant receptor into cells of the stimulated composition.

32. The method of any of embodiments 21-32, wherein the cells of the stimulated composition are viable cells.

33. A method for producing a composition of engineered cells, the method comprising introducing a recombinant receptor into cells of a T cell composition, said T cell composition comprising a concentration of at least or about at least $1 \times 10^6$ viable cells per mL, wherein at least 80%, at least 85%, at least 90%, or at least 95% of the cells of the T cell composition are CD4+ T cells or CD8+ T cells.

34. The method of embodiment 33, wherein the concentration of the T cell composition is less than $5 \times 10^6$ viable cells per mL.

35. The method of any of embodiments 33 or 34, wherein the T cell composition comprises at least or about at least or about $100 \times 10^6$ viable cells.

36. The method of any of embodiments 33-35, wherein the T cell composition comprises less than $300 \times 10^6$ viable cells.

37. The method of any of embodiments 33-36, wherein the introducing comprises contacting the T cells by transduction a viral vector comprising a polynucleotide encoding the recombinant receptor.

38. The method of any of embodiments 33-37, wherein the introducing is performed in serum free media.

39. The method of any of embodiments 33-38, wherein one or more cells of the T cell composition are activated and/or comprise surface expression of the LDL receptor.

40. The method of any of embodiments 33-39, wherein at least 10%, at least 20%, at least 30%, at least 40%, at least 50%, or at least 60% of the cells of the cell composition:

(i) express a surface marker selected from the group consisting of HLA-DR, CD25, CD69, CD71, CD40L and 4-1BB;

(ii) comprise intracellular expression of a cytokine selected from the group consisting of IL-2, IFN-gamma, TNF-alpha;

(iii) are in the G1 or later phase of the cell cycle; and/or (iv) are capable of proliferating.

41. The method of any of embodiments 33-40, wherein prior to the introduction, the cells of the composition where generated by a process comprising incubating an input composition comprising CD4+ and CD8+ T cells under stimulating conditions, wherein said stimulating conditions comprise the presence of a stimulatory reagent capable of activating one or more intracellular signaling domains of one or more components of a TCR complex and/or one or more intracellular signaling domains of one or more costimulatory molecules.

42. The method of embodiment 41, wherein the incubating was performed in serum free media.

43. A method for producing a composition of engineered cells, the method comprising:

(a) incubating an input composition under stimulating conditions, thereby generating a stimulated composition, wherein:

the input composition comprises a ratio of between 2:1 and 1:2 CD4+ to CD8+ T cells and comprises at least $100 \times 10^6$ CD4+ and CD8+ T cells at a concentration of less than $5 \times 10^6$ cells/mL; and the stimulating conditions comprise the presence of a stimulatory reagent capable of activating one or more intracellular signaling domains of one or more components of a TCR complex and/or one or more intracellular signaling domains of one or more costimulatory molecules; and (b) introducing a recombinant receptor into less than $300 \times 10^6$ cells of the stimulated composition thereby generating an engineered cell composition, wherein the introducing comprises contacting the cells of the stimulated composition with a viral vector comprising a polynucleotide encoding the recombinant receptor.

44. The method of any of embodiments 43, wherein the incubation and/or the introducing is performed in serum free media.

45. The method of any of embodiments 43 or 44, wherein the CD4+ and CD8+ T cells are viable cells.

46. The method of any of embodiments 44, wherein the cells from the stimulated composition are viable cells.

47. The method of any of embodiments 33-46, wherein the introducing is initiated within 2 days after the initiation of the of the incubation under stimulating conditions and/or within 2 days after the CD4+ T cells and the CD8+ T cells of the input composition are combined.

48. The method of any of embodiments 33-47, wherein the introducing is initiated within 36 hours after the initiation of the of the incubation under stimulating conditions and/or within 36 hours after the CD4+ T cells and the CD8+ T cells of the input composition are combined.

49. The method of any of embodiments 33-48, wherein the introducing is initiated within 30 hours after the initiation of the of the incubation under stimulating conditions and/or within 30 hours after the CD4+ T cells and the CD8+ T cells of the input composition are combined.

50. The method of any of embodiments 33-49, further comprising cultivating the engineered composition under conditions to promote proliferation and/or expansion of the engineered cells, thereby producing an output composition comprising the engineered T cells.

51. The method of embodiment 50, wherein the cultivating is performed in serum free media.

52. A method for producing a composition of engineered cells, the method comprising:

(a) incubating an input composition under stimulating conditions, thereby generating a stimulated composition; wherein the input composition comprises a ratio of between 2:1 and 1:2 CD4+ to CD8+ T cells, and wherein the input composition comprises at least $100 \times 10^6$ total CD4+ and CD8+ T cells at a concentration of less than $5 \times 10^6$ cells/mL; and wherein said stimulating conditions comprise the presence of a stimulatory reagent capable of activating one or more intracellular signaling domains of one or more components of a TCR complex and/or one or more intracellular signaling domains of one or more costimulatory molecules;

(b) introducing a recombinant receptor into less than $300 \times 10^6$ cells from the stimulated composition thereby generating an engineered cell composition, wherein the introducing comprises transducing the cells of the stimulated composition with a viral vector comprising a polynucleotide encoding the recombinant receptor; and (c) cultivating the engineered composition under conditions to promote proliferation and/or expansion of the engineered cells, thereby producing an output composition comprising the engineered T cells.

53. The method of embodiment 52, wherein the incubating, introducing, and/or cultivating is performed in serum free media.

54. The method of embodiment 41-53, wherein the input composition comprises a ratio of between 1.5:1 and 1:1.5 CD4+ to CD8+ cells, between 1.2:1 and 0.8:1 CD4+ to CD8+ cells, optionally at or about 1:1 CD4+ to CD8+ T cells.

55. The method of any of embodiments 41-54, wherein the input composition comprises CD4+ and CD8+ that are surface positive for CD45RA and CCR7.

56. The method of embodiment 55, wherein the ratio of CD4+ cells surface positive for CD45RA and CCR7 to CD8+ cells surface positive for CD45RA and CCR7 is or is about 1.1:1.

57. The method of any of embodiments 41-56, wherein the input composition comprises CD4+ and CD8+ cells that are surface positive for CD27 and CCR7.

58. The method of embodiment 57, wherein the ratio of the CD4+ cells that are surface positive for CD27 and CCR7 to CD8+ cells surface positive for CD27 and CCR7 is or is about 1.69:1.

59. The method of any of embodiments 41-58, wherein the input composition comprises CD4+ and CD8+ cells that are surface positive for CCR7 and surface negative for CD62L.

60. The method of any of embodiments 43-59, wherein, for the introducing the stimulated composition comprises less than $300 \times 10^6$ cells.

61. The method of any of embodiments 43-60, wherein, for the introducing, the stimulated composition comprises between $50 \times 10^6$ cells and $200 \times 10^6$ cells, optionally at or about $100 \times 10^6$ cells.

62. The method of any of embodiments 43-61, wherein, for the introducing, the stimulated composition comprises a concentration of less than $3 \times 10^6$ cells/mL.

63. The method of any of embodiments 43-62, wherein, for the introducing, the stimulated composition comprises a concentration of between $0.5 \times 10^6$ cells/mL and $2 \times 10^6$ cells/mL, optionally at or about $1 \times 10^6$ cells/mL.

64. The method of any of embodiments 43-63, adjusting the composition of the stimulated composition after incubating under stimulating conditions prior to introducing the recombinant receptor into cells of the stimulated composition.

65. The methods of any of embodiments 1-64, wherein the incubation is performed in the presence of one or more cytokines.

66. The methods of embodiment 65, wherein the one or more cytokines are selected from recombinant IL-2, recombinant IL-7, and/or recombinant IL-15.

67. The method of embodiment 66, wherein the one or more cytokines comprise: between 10 and 200 IU/mL recombinant IL-2; between 100 IU/mL and 1,000 IU/mL recombinant IL-7; and/or between 10 and 200 IU/mL recombinant IL-15.

68. The method of embodiment 66 or 67, wherein the one or more cytokines comprise: between 10 and 200 IU/mL recombinant IL-2; between 100 IU/mL and 1,000 IU/mL recombinant IL-7; and between 10 and 200 IU/mL recombinant IL-15.

69. The method of any of embodiments 1-68, wherein at least 10%, at least 20%, at least 30%, at least 40%, at least 50%, or at least 60% of the cells of the stimulated composition:

(i) express a surface marker selected from the group consisting of HLA-DR, CD25, CD69, CD71, CD40L and 4-1BB;

(ii) comprise intracellular expression of a cytokine selected from the group consisting of IL-2, IFN-gamma, TNF-alpha;

(iii) are in the G1 or later phase of the cell cycle; and/or (iv) are capable of proliferating.

70. The method of any of embodiments 1-69, wherein the stimulatory reagent comprises a primary agent that specifically binds to a member of a TCR complex, optionally that specifically binds to CD3.

71. The method of embodiment 70, wherein the stimulatory reagent further comprises a secondary agent that specifically binds to a T cell costimulatory molecule, optionally wherein the costimulatory molecule is selected from CD28, CD137 (4-1-BB), OX40, or ICOS.

72. The method of embodiment 70 or embodiment 71, wherein the primary and/or secondary agents comprise an antibody, optionally wherein the stimulatory reagent comprises incubation with an anti-CD3 antibody and an anti-CD28 antibody, or an antigen-binding fragment thereof.

73. The method of any of embodiments 71-72, wherein the primary agent and/or secondary agent are present on the surface of a solid support.

74. The method of embodiment 73, wherein the solid support is or comprises a bead.

75. The method of embodiment 74, wherein the bead comprises a diameter of greater than or greater than about 3.5 µm but no more than about 9 µm or no more than about 8 µm or no more than about 7 µm or no more than about 6 µm or no more than about 5 µm.

76. The method of embodiment 74 or embodiment 75, wherein the bead comprises a diameter of or about 4.5 µm.

77. The method of any of embodiments 74-76, wherein the bead is inert.

78. The method of any of embodiments 74-77, wherein the bead is or comprises a polystyrene surface.

79. The method of any of embodiments 74-78, wherein the bead is magnetic or superparamagnetic.

80. The method of any of embodiments 74-79, wherein the ratio of beads to cells is less than 3:1.

81. The method of any of embodiments 74-80, wherein the ratio of beads to cells is from or from about 2:1 to 0.5:1.

82. The method of any of embodiments 74-81, wherein the ratio of beads to cells is at or at about 1:1.

83. The methods of any of embodiments 1-82, wherein the input composition is incubated under stimulating conditions for less than 48 hours.

84. The methods of any of embodiments 1-83, wherein the input composition is incubated under stimulating conditions for between 12 hours and 36 hours, inclusive.

85. The methods of any of embodiments 1-84, wherein the input composition is incubated under stimulating conditions for between 18 hours and 30 hours, inclusive.

86. The methods of any of embodiments 1-85, wherein the input composition is incubated under stimulating conditions for or for about 24 hours.

87. The methods of any of embodiments 23-86 wherein the contacting, optionally transduction, is carried out for less than 48 hours.

88. The methods of any of embodiments 23-87, wherein the contacting, optionally transduction, is carried out between 12 hours and 36 hours, inclusive.

89. The methods of any of embodiments 23-88, wherein the contacting, optionally transduction, is carried out for between 18 hours and 30 hours, inclusive.

90. The method of any of embodiments 23-89, wherein the contacting, optionally transduction, is performed for or for about 24 hours.

91. The method of any of embodiments 23-90, wherein the viral vector is a retroviral vector.

92. The method of any of embodiments 23-91, wherein the viral vector is a lentiviral vector or gammaretroviral vector.

93. The method of any of embodiments 23-92, wherein the contacting, optionally transduction, is carried out in the absence of a transduction adjuvant.

94. The methods of any of embodiments 23-93, wherein the introducing is performed in the presence of one or more cytokines.

95. The method of embodiment 94, wherein the one or more cytokines are selected from recombinant IL-2, recombinant IL-7, and/or recombinant IL-15.

96. The method of embodiment 94 or 95, wherein the one or more cytokines comprise: between 10 and 200 IU/mL recombinant IL-2; between 100 IU/mL and 1,000 IU/mL recombinant IL-7; and/or between 10 and 200 IU/mL recombinant IL-15.

97. The method of any of embodiments 94-96, wherein the one or more cytokines comprise: between 10 and 200 IU/mL recombinant IL-2; between 100 IU/mL and 1,000 IU/mL recombinant IL-7; and between 10 and 200 IU/mL recombinant IL-15.

98. The method of any of embodiments 50-97, wherein at least a portion of the cultivating is performed with mixing and/or perfusion.

99. The method of embodiment 98, wherein at least a portion of the cultivating is performed with perfusion at a rate of, of about, or of least 500 mL/day, 600 mL/day, 700 mL/day, 750 mL/day, 800 mL/day, 900 mL/day, 1,000 mL/day, 1,200 mL/day, 1,400 mL/day, 1,500 mL/day, 1,600 mL/day, 1,800 mL/day, and/or 2,000 mL/day.

100. The method of embodiment 98 or 99, wherein at least a first portion of the cultivating is performed with a perfusion rate of, of about, or of least 500 mL/day, 750 mL/day, or 1,000 mL/day, and wherein at least a second portion of the cultivating is performed with a perfusion rate of, of about, or of at least 1,200 mL/day, 1,400 mL/day, or 1,500 mL/day.

101. The method of any of embodiments 98-100, wherein at the perfusion is initiated and/or increased when the cells reach a specific density.

102. The method of embodiment 101, wherein the specific density is, is about, or is at least $0.4\times10^6$ cells, $0.5\times10^6$ cells, $0.6\times10^6$ cells, $0.8\times10^6$ cells, $1.0\times10^6$ cells, $1.2\times10^6$ cells, $1.4\times10^6$ cells, $1.6\times10^6$ cells, $1.8\times10^6$ cells, $2.0\times10^6$ cells, $2.2\times10^6$ cells, or $2.4\times10^6$ cells.

103. The method of any of embodiments 98-102, wherein at the perfusion is initiated and/or increased to a rate of or of about 750 mL/day when the cells reach a density of or of about $0.6\times10^6$ cells/ml.

104. The method of embodiment 98, wherein at the perfusion is initiated and/or increased to a rate of or of about 1500 mL/day when the cells reach a density of or of about $2.0\times10^6$ cells/mL.

105. The method of any of embodiments 50-104, wherein the cultivating is performed in the presence of one or more cytokines.

106. The method of embodiment 105, wherein the one or more cytokines are selected from recombinant IL-2, recombinant IL-7, and/or recombinant IL-15.

107. The method of embodiment 105 or 106, wherein the one or more cytokines comprise: between 50 and 400 IU/mL recombinant IL-2; between 100 IU/mL and 1,000 IU/mL recombinant IL-7; and/or between 10 and 200 IU/mL recombinant IL-15.

108. The method of any of embodiments 105-107, wherein the one or more cytokines comprise: between 50 and 400 IU/mL recombinant IL-2; between 100 IU/mL and 1,000 IU/mL recombinant IL-7; and between 10 and 200 IU/mL recombinant IL-15.

109. The method of any of embodiments 50-108, wherein the cultivating is initiated within 3 days after the initiation of the of the incubation under stimulating conditions and/or within 3 days after the CD4+ T cells and the CD8+ T cells of the input composition are combined.

110. The method of any of embodiments 50-109, wherein the cultivating is initiated within 60 hours after the initiation of the of the incubation under stimulating conditions and/or within 60 hours after the CD4+ T cells and the CD8+ T cells of the input composition are combined.

111. The method of any of embodiments 50-110, wherein the cultivating is initiated within 48 hours after the initiation of the of the incubation under stimulating conditions and/or within 48 hours after the CD4+ T cells and the CD8+ T cells of the input composition are combined.

112. The method of any of embodiments 50-111, wherein the cultivating is performed at least until the composition comprises a threshold number of T cells.

113. The method of embodiment 112, wherein the cultivating is continued for at least one day after the threshold number of T cells is reached.

114. The method of embodiment 113, wherein the threshold number of T cells is, is about, or is at least $1200 \times 10^6$ cells.

115. The method of any of embodiments 50-114, wherein the threshold number of T cells is, is about, or is at least $3500 \times 10^6$ cells.

116. The method of any of embodiments 50-115, wherein the threshold number of T cells is, is about, or is at least $5500 \times 10^6$ cells.

117. The method of any of embodiments 50-116, comprising collecting cells of the output composition subsequent to the cultivating.

118. The method of embodiment 50-117, comprising collecting cells of the output composition subsequent to the cultivating, wherein the cells of the output composition are collected at least 9 days after the initiation of the incubation under stimulating conditions.

119. The method of embodiment 50-118, comprising collecting cells of the output composition subsequent to the cultivating, wherein the cells of the output composition are collected at least 10 days after the initiation of the incubation under stimulating conditions.

120. The method of embodiment 118 or 119, comprising a 95% confidence interval of the amount of time between initiation of the incubating and the collecting cells of the output composition that is within 8 days to 25 days.

121. The method of embodiment 118 or 119, comprising a 95% confidence interval of the amount of time between initiation of the incubating and the collecting cells of the output composition that is within 9 days to 21 days.

122. The method of embodiment 118 or 119, comprising a 95% confidence interval of the amount of time between initiation of the incubating and the collecting cells of the output composition that is within 9 days to 16 days.

123. The method of any of embodiments 52-122, further comprising formulating cells of the output composition for cryopreservation and/or administration to a subject, optionally in the presence of a pharmaceutically acceptable excipient.

124. The method of embodiment 123, wherein the cells of the output composition are formulated in the presence of a cryoprotectant.

125. The method of embodiment 124, wherein the cryoprotectant comprises DMSO. 126. The method of any of embodiments 122-124, wherein the cells of the output composition are formulated in a container, optionally a vial or a bag.

127. The method of any of embodiments 1-126, further comprising isolating the CD4+ and/or the CD8+ T cells from a biological sample prior to the incubating.

128. The method of embodiment 127, wherein the isolating comprises, selecting cells based on surface expression of CD4 and/or CD8, optionally by positive or negative selection.

129. The method of embodiment 127 or embodiment 128, wherein the isolating comprises carrying out immunoaffinity-based selection.

130. The method of any of embodiments 127-129, wherein the biological sample comprises primary T cells obtained from a subject.

131. The method of embodiment 130, wherein the subject is a human subject.

132. The method of any of embodiments 127-131, wherein the biological sample is or comprises a whole blood sample, a buffy coat sample, a peripheral blood mononuclear cell (PBMC) sample, an unfractionated T cell sample, a lymphocyte sample, a white blood cell sample, an apheresis product, or a leukapheresis product.

133. The method of any of embodiments 1-132, wherein the recombinant receptor is capable of binding to a target antigen that is associated with, specific to, and/or expressed on a cell or tissue of a disease, disorder or condition.

134. The method of embodiment 133, wherein the disease, disorder or condition is an infectious disease or disorder, an autoimmune disease, an inflammatory disease, or a tumor or a cancer.

135. The method of embodiment 133 or 134, wherein the target antigen is a tumor antigen.

136. The method of any of embodiments 133-135, wherein the target antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, VEGF receptors, VEGF-R2, Wilms Tumor 1 (WT-1), a pathogen-specific antigen and an antigen associated with a universal tag.

137. The method of any of embodiments 1-136, wherein the recombinant receptor is or comprises a functional non-TCR antigen receptor or a TCR or antigen-binding fragment thereof.

138. The method of any of embodiments 1-137, wherein the recombinant receptor is a chimeric antigen receptor (CAR).

139. The method of any of embodiments 1-138, wherein the recombinant receptor is an anti-BCMA CAR.

140. The method of embodiment 138 or 139, wherein the chimeric antigen receptor comprises an extracellular domain comprising an antigen-binding domain.

141. The method of embodiment 140, wherein the antigen-binding domain is or comprises an antibody or an antibody fragment thereof, which optionally is a single chain fragment.

142. The method of embodiment 141, wherein the fragment comprises antibody variable regions joined by a flexible linker.

143. The method of embodiment 141 or embodiment 142, wherein the fragment comprises an scFv.

144. The method of any of embodiments 138-143, wherein the chimeric antigen receptor further comprises a spacer and/or a hinge region.

145. The method of any of embodiments 138-144, wherein the chimeric antigen receptor comprises an intracellular signaling region.

146. The method of embodiment 145, wherein the intracellular signaling region comprises an intracellular signaling domain.

147. The method of embodiment 146, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

148. The method of embodiment 146 or 147, wherein the intracellular signaling domain is or comprises an intracellular signaling domain of a CD3 chain, optionally a CD3-zeta (CD3ζ) chain, or a signaling portion thereof.

149. The method of any of embodiments 145-148, wherein the chimeric antigen receptor further comprises a transmembrane domain disposed between the extracellular domain and the intracellular signaling region.

150. The method of any of embodiments 145-149, wherein the intracellular signaling region further comprises a costimulatory signaling region.

151. The method of embodiment 150, wherein the costimulatory signaling region comprises an intracellular signaling domain of a T cell costimulatory molecule or a signaling portion thereof.

152. The method of embodiment 150 or embodiment 152, wherein the costimulatory signaling region comprises an intracellular signaling domain of a CD28, a 4-1BB or an ICOS or a signaling portion thereof.

153. The method of any of embodiments 150-152, wherein the costimulatory signaling region is between the transmembrane domain and the intracellular signaling region.

154. The method of any of embodiments 113-153, wherein the output composition comprising the threshold number or greater number of cells is produced among greater than or greater than about 85%, greater than or greater than about 90% or greater than or greater than about 95% of the iterations of the method.

155. The method of any of embodiments 1-154, wherein the serum-free media comprises:
0.5 mM to 5 mM of a dipeptide form of L-glutamine in a base media;
0.5 mM to 5 mM L-glutamine; and
at least one protein, wherein the media is free of serum.

156. The serum-free media of embodiment 155, wherein the dipeptide form of L-glutamine is L-alanyl-L-glutamine.

157. The serum-free media of embodiment 155 or embodiment 156, wherein the concentration of the dipeptide form of L-glutamine in the serum-free media is or is about 2 mM.

158. The serum-free media of any of embodiments 155-157, wherein the concentration of L-glutamine in the serum-free media is or is about 2 mM.

159. The serum-free media of any of embodiments 155-158, wherein the at least one protein comprises one or more of albumin, insulin or transferrin, optionally one or more of a human or recombinant albumin, insulin or transferrin.

160. A composition comprising engineered cells produced by a method of any of embodiments 1-159.

161. The composition of embodiment 160, further comprising a pharmaceutically acceptable carrier.

162. The composition of embodiment 160 or embodiment 161, comprising a cryoprotectant, optionally DMSO.

163. An article of manufacture, comprising the composition of any of embodiments 160-162, and instructions for administering the output composition to a subject.

164. The article of manufacture of embodiment 163, wherein the subject has a disease or condition, optionally wherein the recombinant receptor specifically recognizes or specifically bind to an antigen associated with, or expressed or present on cells of, the disease or condition.

165. The method of any of embodiments 55-159, wherein during at least a portion of the cultivating, the cells are monitored for cell viability, concentration, density, number, or a combination thereof.

166. The method of embodiment 165, wherein the monitoring is carried out by an optical method, optionally microscopy.

167. The method of embodiment 165 or embodiment 166, wherein the monitoring is carried out by bright field microscopy, fluorescence microscopy, differential interference contrast microscopy, phase contrast microscopy, digital holography microscopy (DHM), differential digital holography microscopy (DDHM), or a combination thereof.

168. The method of any of embodiments 165-167, wherein the monitoring is carried out by differential digital holography microscopy (DDHM).

169. The method of any of embodiments 165-168, wherein the monitoring is carried out intermittently or continuously during the at least a portion of the cultivation, optionally is carried out at least every 1 hour, 6 hours, 12 hours, 18 hours, 24 hours, or 26 hours during the cultivation.

170. The method of any of embodiments 165-169, wherein the monitoring is carried out until the cells reach the threshold number of T cells, the threshold number of viable T cells, the threshold concentration of T cells or the threshold concentration of viable T cells.

171. The method of any of embodiments 165-170, wherein the monitoring and cultivation is carried out in a closed system.

172. The method of any one of embodiments 50-159 and 165-171, wherein at least 30%, at least 40%, at least 50%, at least 60%, at least 70%, at least 75%, at least 80%, at least 85%, at least 90%, at least 95%, or greater than 95% of the cells in the output composition are of a memory phenotype; wherein at least 30%, at least 40%, at least 50%, at least 60%, at least 70%, at least 75%, at least 80%, at least 85%, at least 90%, at least 95%, or greater than 95% of the cells in the output composition are of a central memory phenotype; and/or wherein at least 30%, at least 40%, at least 50%, at least 60%, at least 70%, at least 75%, at least 80%, at least 85%, at least 90%, at least 95%, or greater than 95% of the cells in the output composition are CD27+, CD28+, CCR7+, CD45RA−, CD45RO+, CD62L+, CD3+, CD95+, granzyme B−, and/or CD127+.

173. The method of any one of embodiments 50-159 and 165-172, wherein iterations of the method produce a plurality of the output compositions, optionally from human biological samples in which the method is carried out among a plurality of different individual subjects, wherein:
the mean percentage of cells of a memory phenotype in the plurality of the output compositions is between about 40% and about 65%, between about 40% and about 45%, between about 45% and about 50%, between about 50% and about 55%, between about 55% and about 60%, or between about 60% and about 65%;

the mean percentage of cells of a central memory phenotype in the plurality of the output compositions is between about 40% and about 65%, between about 40% and about 45%, between about 45% and about 50%, between about 50% and about 55%, between about 55% and about 60%, or between about 60% and about 65%;

the mean percentage of cells that are CD27+, CD28+, CCR7+, CD45RA−, CD45RO+, CD62L+, CD3+, CD95+, granzyme B−, and/or CD127+ in the plurality of the output compositions is between about 40% and about 65%, between about 40% and about 45%, between about 45% and about 50%, between about 50% and about 55%, between about 55% and about 60%, or between about 60% and about 65%;

the mean percentage of cells that are CCR7+/CD45RA− or CCR7+/CD45RO+ in the plurality of the output compositions is between about 40% and about 65%, between about 40% and about 45%, between about 45% and about 50%, between about 50% and about 55%, between about 55% and about 60%, or between about 60% and about 65%;

the mean percentage of central memory CD4+ T cells in the engineered CD4+ T cells, optionally CAR+CD4+ T cells, of the plurality of the output compositions is between about 40% and about 65%, between about 40% and about 45%, between about 45% and about 50%, between about 50% and about 55%, between about 55% and about 60%, or between about 60% and about 65%;

the mean percentage of central memory CD8+ T cells in the engineered CD8+ T cells, optionally CAR+CD8+ T cells, of the plurality of the output compositions is between about 40% and about 65%, between about 40% and about 45%, between about 45% and about 50%, between about 50% and about 55%, between about 55% and about 60%, or between about 60% and about 65%; and/or the mean percentage of central memory T cells, optionally CD4+ central memory T cells and CD8+ central memory T cells, in the engineered T cells, optionally CAR+ T cells, of the plurality of the output compositions is between about 40% and about 65%, between about 40% and about 45%, between about 45% and about 50%, between about 50% and about 55%, between about 55% and about 60%, or between about 60% and about 65%.

174. The method of any of embodiments 1-159 and 165-173, wherein the methods produces output compositions exhibiting a predetermined feature, optionally a threshold number of cells expressing the CAR in the output composition, in at least about 80%, about 90%, about 95%, about 97%, about 99%, about 100%, or 100% of the human biological samples in which it is carried out among a plurality of different individual subjects.

175. The method of embodiment 174, wherein the plurality of different individual subject comprise subjects having a disease or condition.

176. The method of embodiment 175, wherein the disease or condition is a cancer.

177. The method of embodiment 176, wherein the cancer is a hematological cancer, optionally multiple myeloma.

178. The composition of embodiment 160, wherein:

at least 30%, at least 40%, at least 50%, at least 60%, at least 70%, at least 75%, at least 80%, at least 85%, at least 90%, at least 95%, or greater than 95% of the cells in the composition are of a memory phenotype;

wherein at least 30%, at least 40%, at least 50%, at least 60%, at least 70%, at least 75%, at least 80%, at least 85%, at least 90%, at least 95%, or greater than 95% of the cells in the composition are of a central memory phenotype;

wherein at least 30%, at least 40%, at least 50%, at least 60%, at least 70%, at least 75%, at least 80%, at least 85%, at least 90%, at least 95%, or greater than 95% of the cells in the composition are CD27+, CD28+, CCR7+, CD45RA−, CD45RO+, CD62L+, CD3+, granzyme B−, and/or CD127+; and/or wherein at least 30%, at least 40%, at least 50%, at least 60%, at least 70%, at least 75%, at least 80%, at least 85%, at least 90%, at least 95%, or greater than 95% of the cells in the output composition are CCR7+/CD45RA− or are CCR7+/CD45RO+.

IX. EXAMPLES

The following examples are included for illustrative purposes only and are not intended to limit the scope of the invention.

Example 1: Process for Generating Therapeutic Compositions of Engineered T Cells Expressing an Anti-BCMA CAR An engineered composition of primary T cells containing CD4+ and CD8+ T cells expressing an anti-BCMA chimeric antigen receptor (CAR) was produced by an exemplary process that included separately selecting CD4+ and CD8+ T cells from a sample prior to combining the selected cells at a defined ratio for subsequent processing steps. Separate compositions of CD4+ and CD8+ cells were selected from isolated PBMCs from a human leukapheresis sample, including from subjects having multiple myeloma (MM), and the selected cell compositions were cryofrozen. The selected CD4+ and CD8+ T cell compositions were subsequently thawed and mixed at a ratio of 1:1 of viable CD4+ T cells to viable CD8+ T cells prior to carrying out steps for stimulation, transduction and expansion.

Approximately $300 \times 10^6$ T cells ($150 \times 10^6$ CD4+ and $150 \times 10^6$ CD8+ T cells) from the mixed cell composition, at a density of about $3 \times 10^6$ cells/mL, were stimulated in the presence of paramagnetic polystyrene-coated beads with attached anti-CD3 and anti-CD28 antibodies at a 1:1 bead to cell ratio in an exemplary serum-free media (see, e.g., Example 3). The media also contained recombinant IL-2, IL-7, and IL-15. The stimulation was carried out by incubation for between 18 to 30 hours.

Following the incubation, approximately $100 \times 10^6$ viable cells from the stimulated cell composition were washed and resuspended in the exemplary serum free media containing recombinant IL-2, IL-7, and IL-15. No transduction adjuvant was added. The cells were transduced with a lentiviral vector encoding the anti-BCMA CAR by spinoculation for 60 minutes followed by incubation for about 18 to 30 hours at about 37° C. The density of the cells post-spinoculation was about $1 \times 10^6$ cells/mL. The CAR contained an scFv antigen-binding domain specific for BCMA, a CD28 transmembrane region, a 4-1BB costimulatory signaling region, and a CD3-zeta derived intracellular signaling domain.

The transduced cells were then cultivated for expansion by transfer to a bioreactor (e.g. a rocking motion bioreactor) in about 500 mL of the exemplary serum free media containing twice the concentration of IL-2, IL-7, and IL-15 as used during the incubation and transduction steps. In this exemplary process, the media did not contain poloxamer.

After a threshold cell density of greater than or about $0.6\times10^6$ cells/mL was achieved, media was added step-wise with shots of fresh media being added periodically, such as between about 2 and about 15 minutes to a volume of 1000 mL and the cells were cultivated under steady rocking conditions (non-perfusion) until a threshold viable cell density of greater than or about $0.6\times10^6$ cells/mL was achieved. If the viable cell density was greater than $0.8\times10^6$ cells/mL, a combination fill/perfusion step was initiated wherein first media was added in a step-wise manner as indicated above, until a target volume of 1000 mL, then perfusion was initiated as explained below. Media was then replaced by semi-continuous perfusion with continual mixing. The perfusion rate and/or rocking speed were increased at least one time during the expansion phase as cell density increased. The perfusion rate was increased at least one time during the expansion phase as cell density increased. Media was added to the culture in a step-wise manner with total volume per day determined by viable cell density (with higher rates once certain densities were reached), up to a rate, e.g., resulting in approximately 750 mL or 1500 mL of total fresh media added to the culture per day (with higher rates when higher cell concentrations were reached), with shots of fresh media added throughout the day periodically, such as between about every 0.5 and about every 1.5 or 2 hours. The cells were harvested at a time one day after the total number of nucleated cells (TNC) had reached at least or at least approximately $3500\times10^6$ and at a point at which the TNC number had reached at least or at least approximately $5500\times10^6$ total nucleated cells. Following harvest, the anti-CD3 and anti-CD28 antibody conjugated beads were removed from the cell composition by exposure to a magnetic field.

The cells were then formulated and aliquots of the composition transferred into containers, e.g., for downstream storage or use. In some embodiments, formulated compositions or portions thereof were transferred freezing bags appropriate for cryopreservation and storage of cell compositions, e.g., for potential administration to subjects (such as CryoStore Freezing Bags) and/or compositions or portions thereof were transferred to vials or other containers, such as for further analysis of the cells. Cells were cryofrozen, such as under conditions appropriate for downstream thawing and use for administration. In some cases, 30 mL volumes of formulated cells were used in individual bags. In some instances, cells were cryopreserved at a variable total cell concentration, for example, to permit a consistent number or concentration of CAR+ T cells in each dose in the context of cells for administration. In some embodiments, the target CAR+CD3+ cell number is at or approximately a desired number (such as at or about $37.5\times10^6$) CAR+CD3+ cells per 30 mL or per bag, which in some embodiments involves varying total cell concentrations among compositions generated from different donors or patients.

Figure 6A:
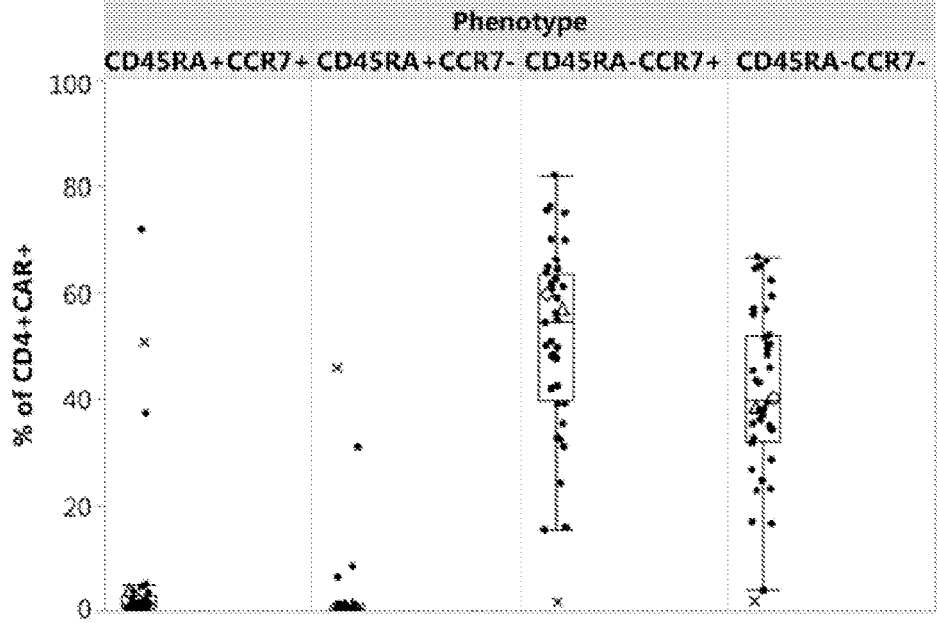
FIGS. 6A-6D depict exemplary phenotypical profiles of 40 engineered CAR+ T cell compositions, each from a multiple myeloma patient. CD45RA×CCR7 expression profiles among the CAR+ T cell compositions are shown for the CD4+ populations (FIG. 6A) and the CD8+ populations (FIG. 6B). CD27×CD28 expression profiles among the CAR+ T cell compositions are shown for the CD4+ populations (FIG. 6C) and the CD8+ populations (FIG. 6D). Each CAR+ T cell composition is shown by a dot (•), a cross (x), a diamond (◇), or a triangle (Δ).
Figure 6B:
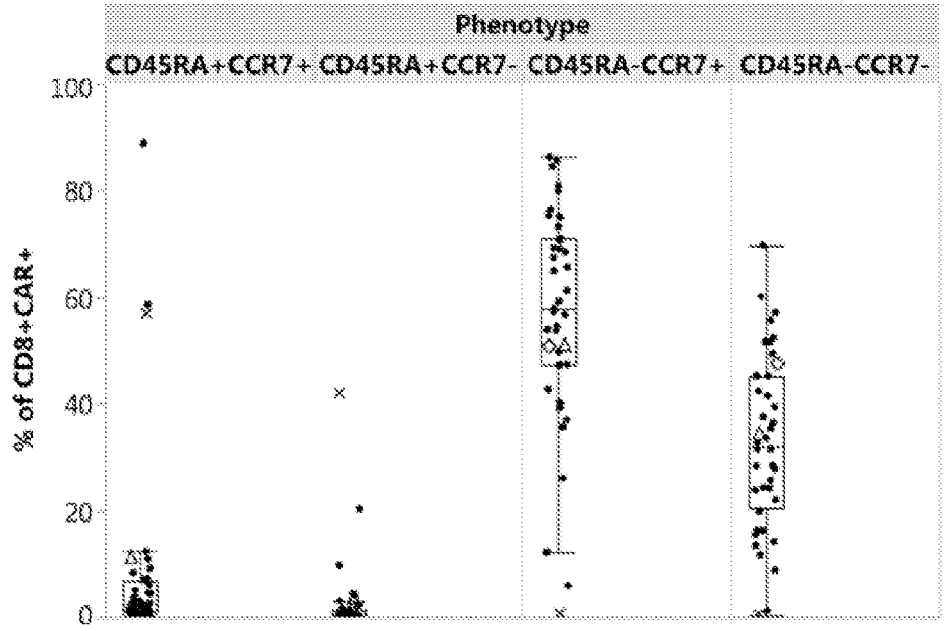
Figure 6C:
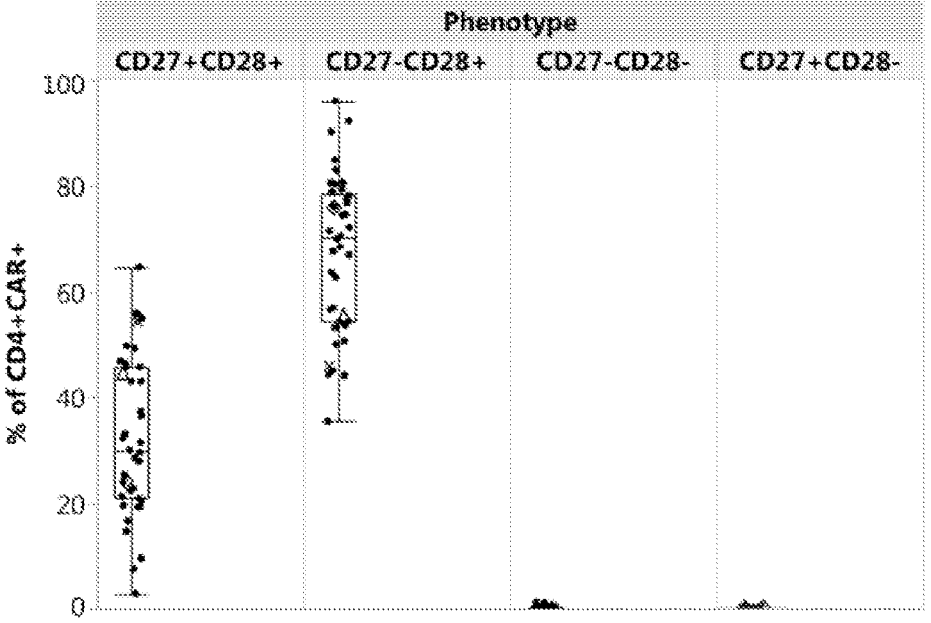
Figure 6D:
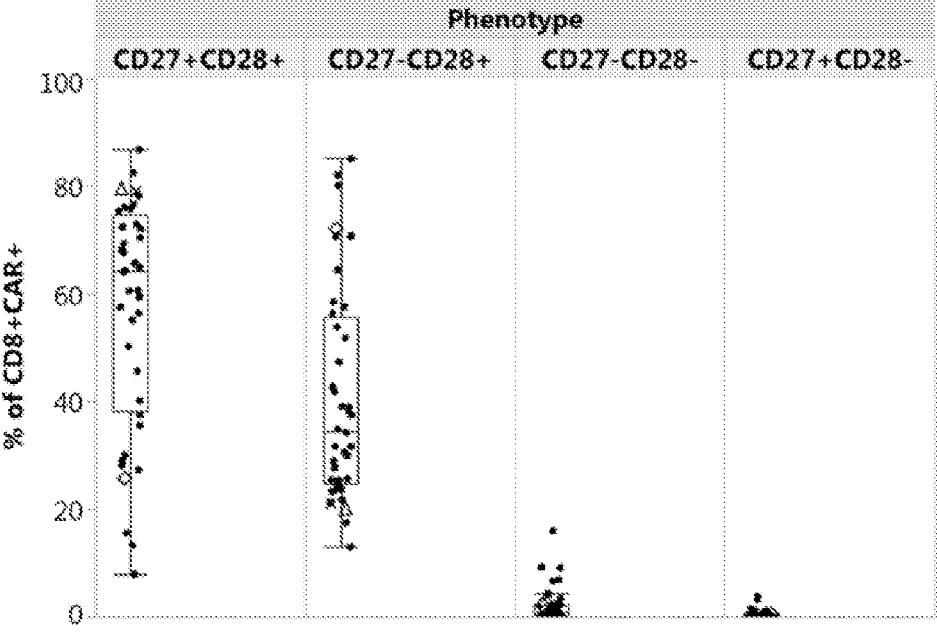

For individual leukapheresis samples obtained from a range of multiple myeloma patients, using this exemplary process to generate engineered cell compositions from such samples, it was observed that the range of duration of the portion of the process from initiation of activation through harvest was between 7 and 10 days, and an average duration among these samples of approximately 7.5 days. It was further determined that the average number of cumulative population doublings over the course of the process among the different samples was approximately 7.5. FIGS. 6A and 6B show median (horizontal lines), interquartile range (box), and 1.5× interquartile range (whiskers) for percentages of cells of the indicated phenotypes (based on CD45RA and CCR7 surface expression), among CD4+ CAR+ cells (FIG. 6A) and among CD8+ CAR+ cells (FIG. 6B) in the engineered cell compositions, respectively. FIGS. 6C and 6D show median (horizontal lines), interquartile range (box), and 1.5× interquartile range (whiskers) for percentages of cells of the indicated phenotypes (based on CD27 and CD28 surface expression), among CD4+ CAR+ cells (FIG. 6C) and among CD8+ CAR+ cells (FIG. 6D)) in the engineered cell compositions, respectively.

Example 2: Assessment of Features of Generated Therapeutic Composition of CD4+ and CD8+ CAR-T Cells A plurality of engineered cell compositions containing CD4+ and CD8+ T cells expressing the anti-BCMA CAR was generated from healthy donors by the exemplary process described in Example 1. Cells were assessed for viability, anti-BCMA CAR expression, and CAR antigen-specific stimulation using a recombinant human BCMA reagent. Engineered cell compositions produced by the exemplary process showed consistently low percentages of caspase positive cells and high cell viability (as measured by acridine orange (AO) and propidium iodide staining). Additionally, the percentage of CAR+ cells was similar in CD4+ and CD8+ cells. Production of cytokines, including IFN-gamma, TNF-alpha, IL2, granzyme B, and perforin, after a 24-hour incubation of the engineered cell compositions with antigen-expressing target cells resulted in production of cytokines at values consistent with an active engineered cell composition, in our experience. These results demonstrated that active CAR-engineered cells can be consistently produced using the process as described in Example 1.

Example 3: Serum-Free Media for Use in a Process for Engineering Cells

The exemplary method described in Example 1 for generating therapeutic T cell compositions included steps in which activation, transduction and cultivation to expand the cells were carried out in a serum-free media that was prepared from: (1) a liquid basal medium containing about 2 mM L-alanyl-L-glutamine (GlutaMax); (2) a first supplement, containing 80 mM glutamine and serum-substituting proteins, that was kept frozen prior to use; and (3) a second supplement provided as a liquid solution, e.g. OpTmizer™ T-Cell Expansion Supplement. The basal medium contained a nutrient mixture and buffers and did not contain phenol red. After thawing the frozen supplement, the components were combined at about 95.0%+/−0.2% (v/v) of the basal media, about 2.5%+/−0.2% (v/v) of the first supplement and about 2.5%+/−0.2% (v/v) of the second supplement, thereby generating an exemplary serum-free cell growth media (designated "SFM-A"). The presence of the L-glutamine in the frozen supplement ensured its stability prior to addition to the basal media to minimize variable glutamine concentration and/or increasing ammonia concentration in the serum-free media formulation that can occur due to instability of L-glutamine. The L-glutamine remained soluble in the first supplement due to the presence of the L-alanyl-L-glutamine. The media additionally was supplemented with cytokines, such as IL-2, IL-7 and/or IL-15.

Seventy-nine individual compositions of engineered T cells were produced from the exemplary process described above. Robust expansion during the cultivation was observed, as determined by the total number of viable cells, from each of the 79 manufacturing runs, including those derived from healthy donors and multiple myeloma patients. All runs were able to produce cell compositions with a cell density above a target threshold of $5.5 \times 10^9$ in total cells within 6 days of the initiation of cultivation. A greater than 27-fold increase in number of viable cells was observed for all manufacturing runs within 6 days of initiating cultivation, with over 85% of the runs achieving such an expansion by day 5. Overall, these data support the robust performance of the serum-free media formulation across the cells derived from healthy donors and patient donors.

Example 4: Assessment of CAR+ T Cells Compositions Produced by a Process Involving Serum-Free Media Genetically engineered human T cells expressing a chimeric antigen receptor (CAR) were produced in the presence of the exemplary SFM-A by the process substantially as described in Examples 1. In this study, to generate CAR-expressing T cells, CD4+ and CD8+ T cells were individually isolated by immunoaffinity-based enrichment from donor leukapheresis samples, mixed at about 1:1, activated in the presence of anti-CD3/anti-CD28 magnetic beads, transduced with a viral vector encoding the anti-BCMA CAR and cultivated by incubation at about 37° C. to expand the cells. Activation, transduction and cultivation to expand the cells were carried out in either 5% (v/v) human serum-containing media or in SFM-A media described in Example 3, each in the presence of cytokines. Exemplary features of the produced engineered T cell compositions were compared among matched cell compositions generated from the same donor either in the presence of SFM-A or serum-containing media.

A. Viability

Viability of the T cells after activation, after activation and transduction, and at each day after initiation (day=0) of cultivation until day 6, was assessed. Early in the process through day 2 after initiation of cultivation, lower cell numbers and viability were observed in cell compositions cultured in the presence of SFM-A compared to serum-containing media. By day 3 of expansion, however, viability was comparable between cells cultured in the presence of SFM-A and the serum-containing formulation. This result is consistent with a delay in T cell expansion in the presence of serum-free media, for example, as the cells adapt to serum-free conditions during the initial stages of the process. In spite of the initial lower cell number, culture of the cells in the presence of SFM-A yielded slightly greater numbers of viable cells by day 5 and 6 and comparable percent viable cells to serum-containing media.

B. CAR-T cell Activity

The functional activity of CAR+ T cells in the T cell compositions post-expansion was assessed by monitoring cytokine accumulation following stimulation with phorbol myristate acetate (PMA)/ionomycin in the presence of Golgi inhibitor. Polyfunctional accumulation of cytokines was assessed by intracellular cytokine staining (ICS) for IL-2, IFN-gamma and TNF-alpha in cells that were also co-stained for surface CD4, CD8 or the anti-BCMA CAR. A comparable percentage of functional CAR+CD4+ T cells or CAR+CD8+ T cells, as determined by polyfunctional accumulation of IL-2, IFN-gamma and TNF-alpha, was observed in cells cultured in the presence of SFM-A as compared to cells cultured with serum-containing media.

Production of cytokines IL-2, IFN-gamma, TNF-alpha and GM-CSF also were measured in supernatant using a Luminex Multiplex Assay following co-culture of the generated anti-BCMA CAR+ T cell compositions with antigen-expressing cells. Secretion of inflammatory cytokines (IL-2, TNF-alpha, GM-CSF and IFN-gamma) was comparable among cultures generated in the presence of SFM-A compared to serum-containing media.

C. Apoptotic Marker

Anti-BCMA CAR+ T cell compositions, which were produced by a process using either serum-containing media or the exemplary SFM-A, and subsequently cryopreserved and thawed prior to analysis, were assessed for surface expression of active caspase 3. Less than 5% of the generated engineered CD3+ CAR+ cell cultured in the presence of SFM-A were positive for active caspase-3. The frequency of CD3+ CAR+ cells that were positive for active caspase-3 was lower in matched T cell compositions produced from an exemplary donor when cultured in the presence of SFM-A compared to serum-containing media.

D. Transduction Frequency

Transduction frequency of the generated T cell compositions was determined by flow cytometry. Surface expression of the anti-BCMA CAR was measured using a CAR specific reagent. In exemplary donor-matched T cell compositions, cells produced by a process involving SFM-A exhibited an increased transduction efficiency compared to cells produced by a process involving serum-containing media. In an exemplary experiment, the transduction efficiency was increased from about 53% to about 68%.

Example 5: Anti-Tumor Effect of CAR-Expressing T Cells Produced by a Serum-Free Media Process An anti-BCMA CAR+ T cell compositions were produced by a process involving the exemplary SFM-A substantially as described in Examples 1 and 3. As a comparison, a T cell composition from a matched donor was produced by a similar process, except using serum-containing media. The anti-tumor effect of the generated CAR+T compositions was assessed by monitoring tumors following adoptive transfer of cells in tumor-bearing animal models, including OPM2 human multiple myeloma disseminated xenograft mouse model.

To generate tumor-bearing mice, six- to eight-week old female NOD.Cg.Prkdc$^{scid}$IL2rg$^{tm1wjl}$/SzJ (NSG) mice were injected with $2 \times 10^6$ OPM2 (multiple myeloma) cells transfected with firefly luciferase (OPM2-ffluc). Tumor size was monitored at day 13 using bioluminescence imaging and at day 14 mice were administered a single intravenous (i.v.) injection of an anti-BCMA CAR+ T cell composition that was produced by a process that included SFM-A or that was produced by a process that included serum-containing media. The assessed anti-BCMA CAR+ T cell compositions were generated from the same human donor. Cells were administered at a dose of $1 \times 10^6$, $5 \times 10^5$, or $2.5 \times 10^5$ CAR-expressing T cells. Cells that did not express a CAR (mock) were used as a negative control. Tumor growth and survival of the mice were monitored over a 100 day time period post administration of cells.

Anti-tumor activity of the adoptively transferred CAR-expressing cells was monitored by bioluminescence imaging on various days post-CAR T cell injection up to day 100. For bioluminescence imaging, mice received intraperitoneal (i.p.) injections of luciferin substrate (CaliperLife Sciences, Hopkinton, Mass.) resuspended in PBS (15 µg/g body weight). Mice were anesthetized and imaged essentially as described in WO2015/095895. The total flux (photon/s) was determined at each time point. For the negative control treated mice, animals were sacrificed between 22 and 26 days after CAR-T transfer, due to high tumor burden. CAR-expressing T cells produced with either SFM-A or serum-containing media slowed tumor growth and prolonged survival, which was generally comparable at all assessed doses.

Example 6: Exemplary Process Conditions

Various parameters related to conditions used in the exemplary processes that were similar to the exemplary process described in Example 1, but in which various aspects of different process steps were varied, were assessed. The aspects varied included aspects of activation density and incubation times, transduction parameters, type and concentration of cytokine(s) used, and perfusion rates Outcomes of cell compositions generated by these different varied processes were assessed.

Each of the processes in this Example 6 included a selection step in which CD4+ T cells and CD8+ T cells were selected from leukapheresis samples from donor subjects, resulting in two separate compositions of CD4+ and CD8+ T cells, respectively, following by mixing viable cells at an approximate 1:1 ratio of viable CD4+ and viable CD8+ cells followed by activation of the mixed cells in the presence of anti-CD3/anti-CD28 magnetic beads and one or more cytokines in serum-free media, transduction with a viral vector encoding an exemplary CAR and cultivation in the presence of anti-CD3/anti-CD28 magnetic beads and one or more cytokines in serum-free media, followed by formulation and cryopreservation with certain specific parameters varied among the different processes.

A. Activation Incubation Times

In one study, the duration of the incubation following selection and prior to transduction (in the presence of anti-CD3/anti-CD28-coated beads, cytokine(s) and serum-free medium) was varied. Specifically, the incubation was carried out for either 24 hours (n=5 cell compositions from 3 individual donors) or 48 hours (n=2 cell compositions from 2 individual donors).

Efficiency of transduction of T cells in the final cell compositions generated by the process was assessed by flow cytometry by staining for surface expression of CD3 (using an anti-CD3 reagent) and the CAR (using a recombinant BCMA-Fc reagent). Engineered cell compositions generated by the process using the 24 hour duration of the incubation prior to transduction initiation were observed to have an approximately 2-fold greater percentage of transduced T (CD3+ CAR+) cells as compared to cell compositions generated by the process using the 48 hour duration of the incubation prior to initiation of transduction.

Additionally, engineered cells produced by the processes with different incubation durations were co-cultured for 4 days with K562-BCMA. To monitor proliferation, the cells were labeled with the proliferation marker dye CELL-TRACE VIOLET (CTV; ThermoFisher Scientific, Waltham Mass.)=. Following co-culture, cells were stained for surface expression of the anti-BCMA CAR, CD4, and CD8, and measured with flow cytometry.

The results are summarized in Table E1. Greater level of CAR surface expression in CAR+ cells, as determined by the mean fluorescence intensity (MFI), and a greater degree of antigen-expressing cell-induced proliferation in this assay (as measured by dilution in CTV dye, indicated by decreased CTV MFI), in both CD4+ and CD8+ T cells, were observed in the engineered cell compositions that were generated with the process using the 24 hour pre-transduction incubation with the anti-CD3/anti-CD28 magnetic beads compared with the process using the 48 hour incubation. These results are consistent with increased CAR transduction efficiency and CAR antigen-specific functionality by an exemplary process that included a post-selection, pre-transduction incubation duration of less than 48 hours, such as a duration of approximately 24 hours.

TABLE E1

CAR and CTV staining following incubation with K562-BCMA target cells

| | Cell type | Median CAR MFI | Median CTV MFI |
|---|---|---|---|
| 24 hour stimulation | CD4+ T cells | 14463 | 4057 |
| | CD8+ T cells | 16187 | 4116 |
| 48 hour stimulation | CD4+ T cells | 5659 | 22932 |
| | CD8+ T cells | 12862 | 8099 |

B. Activation Cell Density

The effect of cell density during the pre-transduction incubation with anti-CD3/anti-CD28 magnetic beads, cytokines and media, also was assessed by comparing features of engineered cell compositions that were generated by a process in which the incubation was initiated with cells at an initial cell density of $1.5\times10^6$ cells/mL, versus those generated by a process in which the incubation was initiated with cells $3\times10^6$ cells/mL, versus those generated by a process in which the incubation step was initiated with cells at an initial density of $5\times10^6$ cells/mL In each case, the incubation duration was approximately 24 hours.

To assess impact of cell density on functional activity of cells generated by such processes, such cells were subjected to a serial stimulation assay in which the generated anti-BCMA CAR-T cells were incubated in co-cultures with irradiated K562-BCMA target cells over multiple rounds of antigen exposure for 7 or more days. On day 4 of the co-culture, cells were harvested, counted, and re-incubated with new target cells under the same culture conditions after resetting the cell number to the initial seeding density. T cells were collected at days 4 and 7 and assessed for proliferation as described above.

In general, processes in which the pre-transduction incubation was initiated at a cell density of $1.5\times10^6$ cells/mL or $3\times10^6$ cells/mL were observed to produce cell compositions across multiple human donors, with consistent antigen-specific functionality and proliferative capacity over multiple rounds of stimulation in this assay, as compared to exemplary engineered cell compositions generated by the process in which the incubation step was initiated at the $5\times10^6$ cells/mL cell density, These results were consistent with a conclusion that an improved consistency in the ability to proliferation and exhibit antigen-specific function over multiple rounds of stimulation in engineered cell compositions generated by a process in which incubation prior to transduction was initiated at a cell density below $5\times10^6$ cells/mL.

C. Transduction Conditions

Impact of transduction conditions were assessed. Cell compositions generated by processes as described above with variations in transduction conditions. Specifically, in the different processes, transduction was carried out with or without spinoculation (e.g. at 1600 g for 60 minutes using a vertical centrifuge), and with or without a transduction adjuvant. Transduction with spinoculation were observed to have significantly greater frequencies of CD3+ CAR+ cells compared to cells in which transduction was carried out without spinoculation. Similar transduction efficiencies were observed in these processes even when a transduction adjuvant was not present during the transduction step.

Example 7: Anti-CD3/Anti-CD28 Bead:Cell Ratio During Expansion

Impacts on features of engineered cells produced by a process similar to those described in Example 1 and Example 6, of varying the anti-CD3/anti-CD28 magnetic beads to cell ratio during post-transduction incubation (expansion) step of processes as described in Example 1, except that serum-containing medium was used in the expansion step, in which either 1:1 or 3:1 beads to cell ratios in serum containing media. During the post-transduction expansion phase of the processes, compositions of cells were assessed daily for expansion, viability, and extracellular pH and lactate levels. In this assay, cells for which this incubation step was carried out using a 3:1 bead:cell ratio displayed a greater degree of expansion at 5 days post-inoculation into rocking motion bioreactors but exhibited a decreasing trend in cell viability 3 days post-inoculation. Extracellular pH and lactate levels were observed to be inversely correlated. For cells incubated at a 1:1 ratio, the extracellular lactate accumulation and pH drop slowed after 3 days even though the cells continued to expand. For cells incubated at a 3:1 ratio, extracellular lactate levels continued to accumulate and pH continued to drop beyond day 3, consistent with decreased cell viability.

Processes for generating engineered cells with different ratios of anti-CD3/anti-CD28 magnetic beads to cells were assessed. Engineered cell compositions were generated by a process that included selection of CD4+ and CD8+ T cells from leukapheresis samples from donor subjects, followed by mixing the cells at an approximate 1:1 ratio prior to activation with anti-CD3/anti-CD28 magnetic beads at a 1:1 or 3:1 bead to cell ratio in serum containing media, transduction with an exemplary anti-BCMA CAR and cultivation to expand the cells.

Cells from the engineered compositions were examined by flow cytometry. Cells were stained for CAR expression using a recombinant BCMA-Fc reagent, and for surface expression of CD3, CD4, CD8 and active caspase 3, an exemplary marker of apoptosis. Approximately 50% of the CD3+ cells that were stimulated at a 3:1 bead to cell ratio were positive for activated caspase 3, approximately half of which were positive for anti-BCMA CAR expression. In contrast, approximately 10% of the CD3+ cells that were stimulated at the 1:1 ratio were positive for active caspase 3, 31% of which expressed the CAR. Similar ratios of CD4+ to CD8+ cells that were positive for active caspase 3 were observed.

These results are consistent with improved viability in engineered cell compositions stimulated at a ratio of 1:1 anti-CD3 and anti-CD28 antibody conjugated beads to cells.

Example 8: Inclusion of Cytokines During the Manufacturing Process for Generating Cell Compositions Containing CAR-T Cells Impacts on features of engineered cells produced by a process similar to those described in Example 1 and Example 6, except with varying the types of cytokines present in the media were assessed. Engineered compositions containing CD4+ and CD8+ T cells expressing an anti-BCMA CAR were generated from isolated T cells in the presence of different combinations of IL-2, IL-7, and IL-15. T cells from six individual donors with multiple myeloma were tested.

CD4+ and CD8+ T cells were isolated from samples derived from patients with multiple myeloma. The cells were stimulated in the presence of anti-CD3/anti-CD28 magnetic beads, transduced with a viral vector encoding an anti-BCMA CAR and cultivated to expand the cells. Each of the steps of stimulation, transduction and expansion was performed in serum free media in the presence of cytokines, either IL-2 only; IL-2, IL-7, and IL-15; IL-2 and IL-15; or IL-2 and IL-7.

Cells from the engineered compositions were assessed by flow cytometry for expression of the anti-BCMA CAR using a recombinant BCMA-Fc reagent, and for surface expression of CD3, CD4, CD8 and active caspase 3.

High frequencies of CD3+ CAR+ cells were observed in all of the engineered cell compositions produced in the presence of different cytokine combinations. The combination of all three cytokines displayed the lowest and most consistent percentages of CD3+ T cells positive for active caspase 3.

Antigen-stimulated activity was assessed with intracellular cytokine staining (ICS). Cells from engineered compositions were co-cultured with irradiated MM.1S cells, a human multiple myeloma cell line that expresses BCMA, in the presence of a Golgi inhibitor. Cells were evaluated for the intracellular cytokine accumulation of IL-2, IFN-gamma, or TNF-alpha, or for polyfunctional staining of all three cytokines. Results indicated that engineered cell compositions produced from each donor contained functional CD4+ CAR+ and CD8+ CAR+ T cells. Antigen stimulated CD4+ and CD8+ cells that were positive for internal IL-2, IFN-gamma, TNF-alpha, and polyfunctional cells positive for all three were observed in engineered cell compositions produced with each combination of cytokines.

Cells of the engineered compositions were assessed for sub-phenotypes by flow cytometry by staining with CD45RA, CCR7, CD27, and CD28. Results of CD45RA and CCR7 staining indicated that the engineered cell compositions generated under each condition were predominantly composed of CD45RA+CCR7+CD4+ and CD8+ T cells. Low levels of CD45RA+CCR7− cells were observed in all of the engineered cell compositions. Results of CD27 and CD28 staining indicated that the engineered cell compositions generated under each condition contained mostly CD27+CD28+CD4+ and CD8+ T cells. Low levels of CD27−CD28−CD4+ and CD8+ T cells were observed in all of the engineered cell compositions.

Example 9: Correlation Between Phenotype of Starting Composition and the Ratio of CD4+ to CD8+ CAR Expressing Cells in a CAR+ T Cell Composition CAR+ T cell compositions containing autologous T cells expressing a chimeric antigen receptor (CAR) were generated from apheresis collected from 11 separate donors with four test samples separately processed from each donor sample. One donor was a patient with myeloma and the remaining donors were healthy subjects. After washing each apheresis sample, each sample was assessed by flow cytometry for cell viability using an apoptotic marker and for surface expression of CD4 and CD8 to determine the ratio of viable CD4+ to CD8+ T cells (CD4/CD8 ratio) in each apheresis sample run.

CD4+ and CD8+ T cells were selected from apheresis samples by immuno-affinity-based selection. CD4+ T cells and CD8+ T cells were combined at a 1:1 ratio of viable CD4+ to CD8+ cells. A sample of the combined cells was assessed by flow cytometry for cell viability using an apoptotic specific marker and for surface expression of markers that included CD4, CD8, CD45RA and CCR7. The ratio of viable CD45RA+/CCR7+CD4+ to viable CD45RA+/CCR7+CD8+(CD45RA+/CCR7+CD4/CD8 ratio) in the mixture of selected CD4 and CD8 cells was determined.

To generate a CAR+ T cell composition, the combined CD4+ and CD8+ T cells were activated by incubation with anti-CD3 and anti-CD28 antibody-coated beads in the presence of cytokines, and then were transduced with a lentiviral vector encoding an anti-BCMA CAR. The CAR contained an scFv antigen-binding domain specific for BCMA, a spacer, a CD28 transmembrane region, a 4-1BB costimulatory signaling region, and a CD3-zeta derived intracellular signaling domain. After transduction, cells were expanded and then frozen by cryopreservation. The cells in the frozen composition were thawed and assessed by flow cytometry for viability, surface expression of CD4 and CD8, and CAR expression using a BCMA-Fc reagent. The ratio of viable CAR+ cells that were CD4+ to viable CAR+ cells that were CD8+ was determined (CAR+CD4/CD8 ratio).

The CD4/CD8 ratio in the apheresis samples, or the CD45RA+/CCR7+CD4/CD8 ratio in the mixture of selected CD4 and CD8 cells, was compared, post facto, to the CAR+CD4/CD8 ratio in the engineered CAR-T cell composition. The degree of correlation of the mean ratios from each subject was assessed by bivariate analysis and the bivariate normal ellipse representing the 0.990 probability region for the plotted data are shown in FIGS. 1A and 1B, respectively. Table E2A and Table E2B display the results of a Pearson correlation analysis carried out with respect to the data plotted in FIG. 1A and FIG. 1B, respectively.

TABLE E2A

| Bivariate Normal Ellipse P = 0.990; CD4/CD8 ratio in apheresis sample | | | | |
| --- | --- | --- | --- | --- |
| Variable | Mean | Std. Dev. | Correlation | Signif. Prob. |
| Starting CD4/CD8 Ratio | 1.57 | 0.42 | −0.11 | 0.75 |
| Final CAR+ CD4/CD8 ratio | 1.35 | 1.00 | | |

TABLE E2B

| Bivariate Normal Ellipse P = 0.990; CD45RA+/CCR7+ CD4/CD8 ratio in mixture of selected CD4 and CD8 cells | | | | |
| --- | --- | --- | --- | --- |
| Variable | Mean | Std. Dev. | Correlation | Signif. Prob. |
| Starting CD45RA+/CCR7+ CD4/CD8 Ratio | 1.52 | 1.09 | 0.99 | <0.0001 |
| Final CAR+ CD4/CD8 ratio | 1.35 | 1.00 | | |

As shown in FIG. 1A and Table E2A, in this experiment the viable CD4/CD8 ratio of CD4+ and CD8+ T cells from the apheresis sample did not correlate with the CAR+CD4/CD8 ratio in the final composition. This result is consistent with observations that mixing of purified CD4 and CD8 T cells at a 1:1 ratio prior to activation based on total viable cells does not necessarily correlate with a 1:1 ratio of CD4+ and CD8+ T cells in an output T cell composition.

As shown in FIG. 1B and Table E2B, in this experiment, the CAR+CD4/CD8 ratio in the final T cell composition positively correlated with the starting naïve-like cell CD4/CD8 T cell ratio, as determined by the ratio of CD45RA+/CCR7+CD4/CD8 ratio in the mixture of CD4 and CD8 cells. In particular, the results in FIG. 1B show that the correlation between the ratio of CD45RA+/CCR7+/CD4+ cells to CD45RA+/CCR7+/CD8+ cells in the starting sample to the CAR+CD4/CD8 ratio in the T cell composition is high based on Pearson correlation coefficient and p value<0.0001. This correlation held despite variations in input composition and between process runs. Based on this model fit from this exemplary sample set, a CD45RA+/CCR7+/CD4+ to CD45RA+/CCR7+/CD8+ ratio of about 1.1:1 was determined to result in a CAR+CD4/CD8 ratio of about 1:1 in the output T cell composition.

These data support the hypothesis that it is possible to control and/or adjust the ratio and/or composition of CD4+ cells and CD8+ cells in an output T cell composition by controlling the ratio of a naïve-like CD4+ subset to a naïve-like CD8+ T cell subject, such as determined by CD45RA+ and CCR7+ surface expression.

Example 10: Correlation Between Phenotypes of the Starting T Cell Population and the Ratio of CAR+CD4+ to CAR+CD8+ T Cells in Engineered CAR+ T Cell Compositions A total of 50 engineered CAR+ T cell compositions were generated from apheresis samples collected from 15 healthy donors and one multiple myeloma patient. To generate the CAR-T compositions, viable selected CD4+ and CD8+ T cells were combined into a starting cell composition at a 1:1 ratio and then activated, transduced, and expanded as described in Example 9. Samples from the starting compositions of combined viable CD4+ and CD8+ T cells were assessed by flow cytometry for viability and for surface expression of markers that included CD4, CD8, CD27, CD45RA, CCR7, and CD62L.

Samples from the engineered CAR+ T cell compositions were assessed for CAR expression and for surface expression of markers that included CD4 and CD8. Averages were calculated for ratios of CD4+ CAR+ T cells to CD8+ CAR+ T cells (CAR+CD4/CD8 ratio) of individual CAR+ T cell compositions of the same donor that were generated using the same exemplary process as described in Example 9, except that certain process parameters were varied. The average CAR+CD4/CD8 ratios were analyzed for correlations with various phenotypes of the starting compositions of combined viable CD4+ to CD8+ cells. Combining the selected CD4+ and CD8+ T-cells at 1:1 ratio prior to the activation did not necessarily correlate with a 1:1 CAR+ CD4/CD8 ratio in the generated output cell compositions.

Figure 2A:
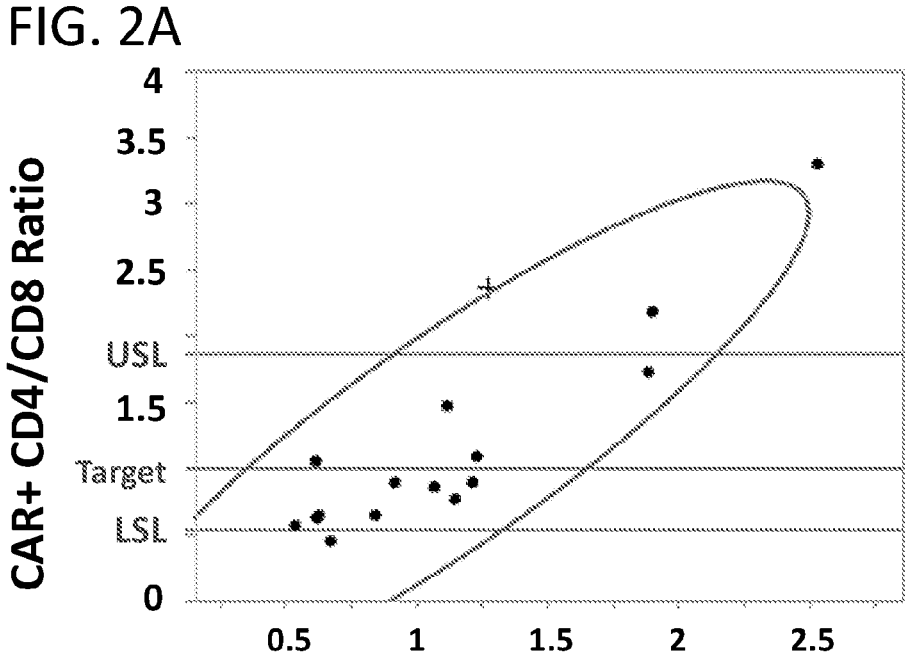
FIGS. 2A-2C show plots of bivariate fit analysis of the ratio of the different phenotypes cells of in a starting mixture of selected CD4 and CD8 cells compared to the CAR+ CD4+/CD8+ ratio in an engineered CAR+ T cell composition.
Figure 2B:
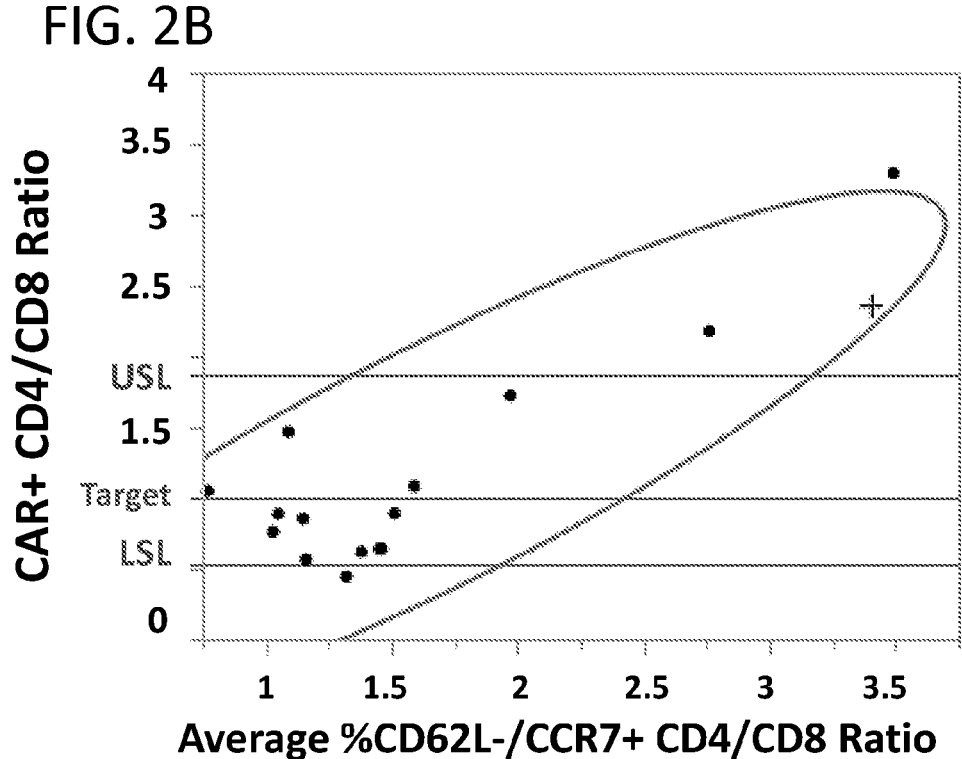
Figure 2C:
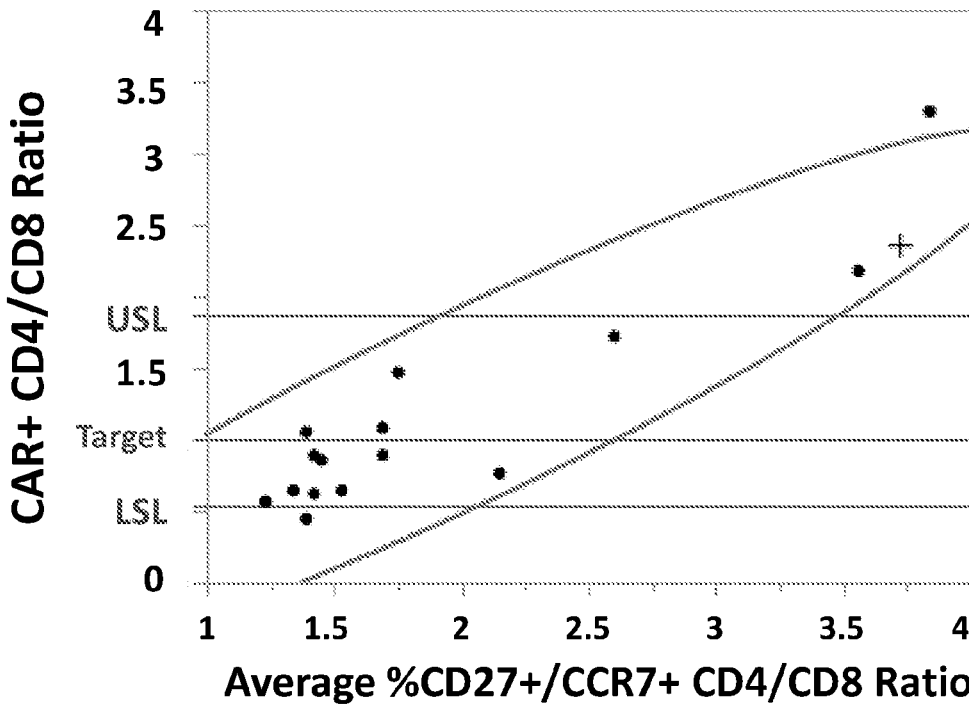

The degree of the correlations between the average CAR+ CD4/CD8 ratios and the phenotypes from each donor were assessed by bivariate analysis. The bivariate normal ellipses representing the 0.950 probability are shown for ratios for CD45RA+/CCR7+/CD4+ T cell to CD45RA+/CCR7+/ CD8+(CD45RA+/CCR7+CD4/CD8 ratio; FIG. 2A); CD62L−/CCR7+/CD4+ to CD62L−/CCR7+/CD8+ (CD62L−/CCR7+CD4/CD8 ratio; FIG. 2B); and CD27+/ CCR7+/CD4+ to CD27+/CCR7+/CD8+ ratio (CD27+/ CCR7+CD4/CD8 ratio; FIG. 2C) Table E3 displays the results of Pearson correlation analysis carried out with respect to the data plotted in FIGS. 2A-2C.

TABLE E3

| Bivariate Normal Ellipse P = 0.950 for Exemplary Phenotypes | | | | | |
|---|---|---|---|---|---|
| Phenotype | Mean | Std. Dev. | Corre- lation | Signif. Prob. | Number |
| CD45RA+/CCR7+ CD4/CD8 Ratio | 1.14 | 0.56 | 0.88 | <0.0001 | 16 |
| % CD62L−/CCR7+ CD4/CD8 Ratio) | 1.66 | 0.83 | 0.88 | <0.0001 | 16 |
| % CD27+/CCR7+ CD4/CD8 Ratio | 2.01 | 0.91 | 0.93 | <0.0001 | 16 |
| Output CAR+ CD4/CD8 ratio | 1.22 | .80 | | | |

The analysis indicated that using the exemplary protocol described in Example 9, the CAR+CD4/CD8 ratio positively correlated with the CD45RA+/CCR7+CD4/CD8 T-cell ratio for healthy donors but, in this experiment, not for the one patient sample. The CAR+CD4/CD8 ratio was shown to correlate positively with CD62L−/CCR7+CD4/CD8 and CD27+/CCR7+CD4/CD8 ratios in both healthy donor and patient sample starting cell compositions. Based on the model fit, it was calculated that a starting CD27+/CCR7+CD4/CD8 ratio of 1.69:1 would be predicted to generate an output cell composition with a CAR+CD4/CD8 ratio of approximately 1:1. These results were consistent with the finding that the CD27+CCR7+CD4/CD8 ratio can be adjusted in the starting cell composition to control and/or predict the resulting CAR+CD4/CD8 ratio of the engineered cell composition.

Example 11: Process to Produce CAR+ T Cell Composition Based on Phenotype of Starting Composition Ten CAR+ T cell compositions containing autologous T cells expressing a CAR were generated from apheresis collected from 3 separate donors, including two healthy donors and one multiple myeloma patient. CD4+ and CD8+ T cells were selected from apheresis samples as described in Example 9. The apheresis samples and the selected CD4+ and CD8+ T cells were assessed by flow cytometry for viability and surface markers including CD27, CCR7, CD4, and CD8. The frequency of CD27+/CCR7+ cells among the selected CD4+ and CD8+ T cells was determined, with each donor exhibiting a different ratio of CD27+/CCR7+CD4+ cells to CD27+/CCR7+CD8+ cells in apheresis samples. For example, the patient sample exhibited a ratio of CD27+/CCR7+CD4+ cells to CD27+/CCR7+CD8+ cells of approximately 12.2:1, whereas the two healthy donor samples exhibited ratios of CD27+/CCR7+CD4+ cells to CD27+/CCR7+CD8+ cells of 3.56:1 and 2.15:1. Input cell compositions were generated by either (1) combining selected CD4+ and CD8+ cells at a 1:1 viable CD4+ to CD8+ ratio (viable CD4/CD8) or (2) combining CD4+ and CD8+ cells at a 1.69:1 ratio of CD27+/CCR7+CD4+ cells and CD27+/CCR7+CD8+ cells (CD27+/CCR7+CD4/CD8) before activation. A total of either 300×10^6 cells or 100×10^6 cells from the input compositions were activated, transduced, and expanded to generate output cell compositions substantially as described in Example 9.

The total number of cells in the activation step was not observed to impact the CAR+CD4/CD8 ratio. The output cell compositions generated from starting compositions containing CD27+/CCR7+CD4/CD8 cells mixed at about a 1.69:1 ratio, including from the patient sample, exhibited CAR+CD4/CD8 ratios that were close to of the desired target ratio of 1:1 (e.g. between approximately 1.86:1 to 1:1.86). Output cell compositions generated from input compositions containing viable CD4/CD8 cells mixed at a 1:1 ratio showed grater variation in CAR+CD4/CAR+CD8 ratios, compared with compositions generated from input compositions containing CD4+ and CD8+ cells at a 1.69:1 ratio of CD27+/CCR7+CD4+ cells and CD27+/CCR7+CD8+ cells. In this experiment, output compositions generated using patient material in an exemplary process exhibited CAR+CD4/CAR+CD8 ratios of approximately 7.6 and 8.6 when 100×10^6 cells or 300×10^6 cells were activated, respectively. When mixed based on the phenotype in a similar process, for example a 1.69:1 ratio of CD27+CCR7+ CD4+: CD27+CCR7+CD8+ T cells, the final CAR+CD4/ CAR+CD8 ratio was 1.6 and 1.3 when 100×10^6 cells or 300×10^6 cells were activated, respectively. These results are consistent with a finding that particular phenotypes, e.g. CD27+/CCR7+ cells, may correlate with the resulting CAR+CD4/CAR+CD8 ratios in output compositions generated from both healthy donor and patient samples.

Example 12: Assessment of Samples from Diseased Subjects of Correlation Between Phenotype of Starting Composition and the Ratio of CD4+ to CD8+ CAR Expressing Cells in a CAR+ T Cell Composition CAR+ T cell compositions containing autologous T cells expressing a chimeric antigen receptor (CAR) were generated from apheresis collected from 7 separate donors with multiple myeloma.

CD4+ and CD8+ T cells were selected from apheresis samples by immuno-affinity-based selection. CD4+ T cells and CD8+ T cells were combined at a 1:1 ratio of viable CD4+ to CD8+ cells. A sample of the combined cells was assessed for surface expression of markers that included CD4, CD8, CD27, CD45RA, CCR7 and CD62L. In the mixture of selected CD4 and CD8 cells, the ratio of the following cell phenotypes were determined (1) CD27+/ CCR7+CD4+ cells to CD27+/CCR7+CD8+ cells (CD27+/ CCR7+CD4/CD8 ratio), (2) CD45RA+/CCR7+CD4+ cells to CD45RA+/CCR7+CD8+ cells (CD45RA+/CCR7+CD4/ CD8 ratio), and (3) CD62L−/CCR7+CD4+ cells to CD62L−/CCR7+CD8+ cells (CD62L−/CCR7+CD4/CD8 ratio).

A CAR+ T cell composition expressing an anti-BCMA CAR was generated using the process substantially as described in Example 9, including activation, transduction, expansion and cryopreservation of generated cells. The cells in the frozen composition were thawed and assessed by flow cytometry for viability, surface expression of CD4 and CD8, and CAR expression using a BCMA-Fc reagent. The ratio of viable CAR+ cells that were CD4+ to viable CAR+ cells that were CD8+ was determined (CAR+CD4/CD8 ratio).

Figure 3A:
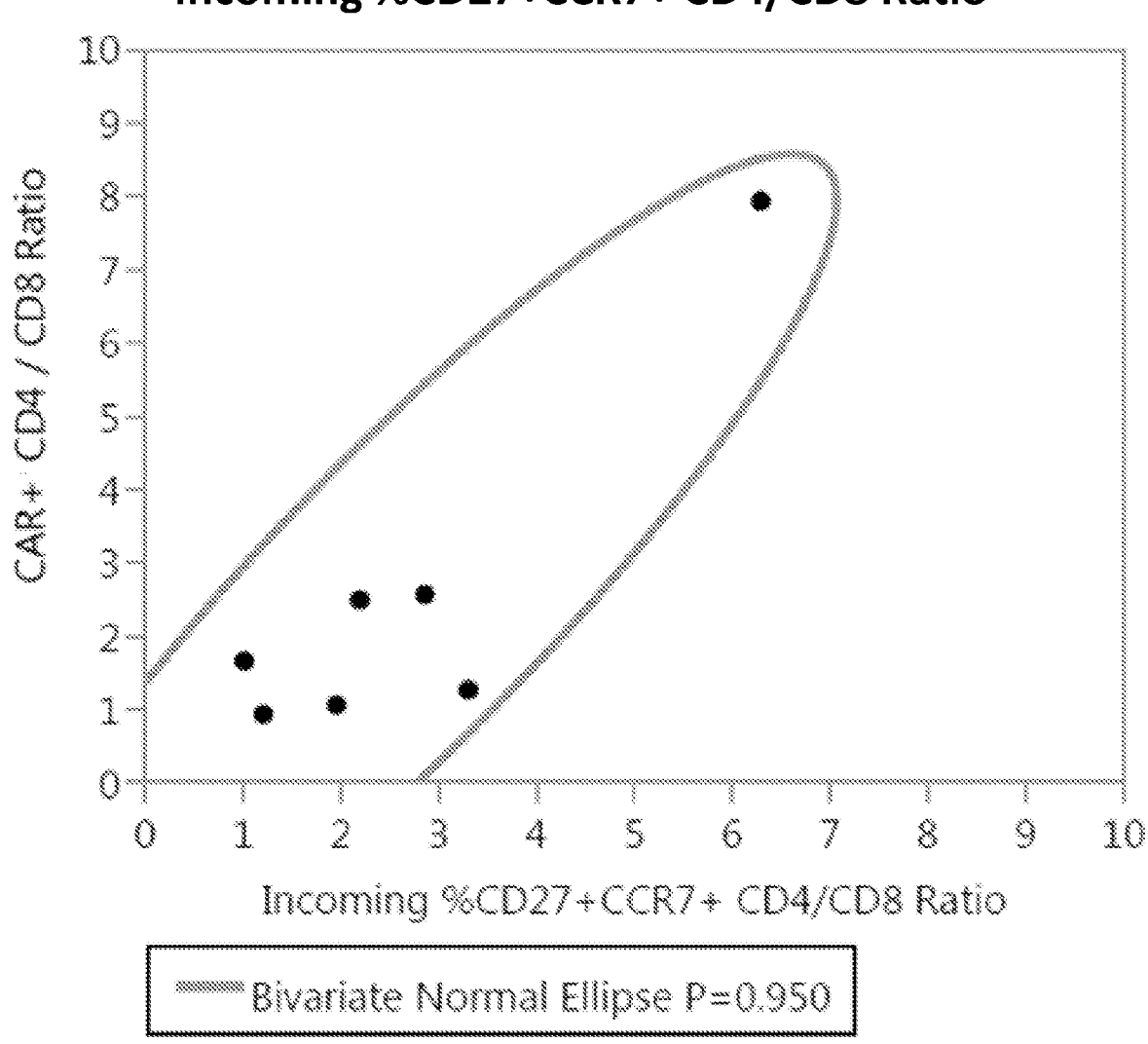
FIGS. 3A-3C show plots of bivariate fit analysis of the ratio of the different phenotypes cells of in a starting mixture of selected CD4 and CD8 cells from seven patients with multiple myeloma compared to the CAR+CD4+/CD8+ ratio in the generated engineered CAR+ T cell composition.
Figure 3B:
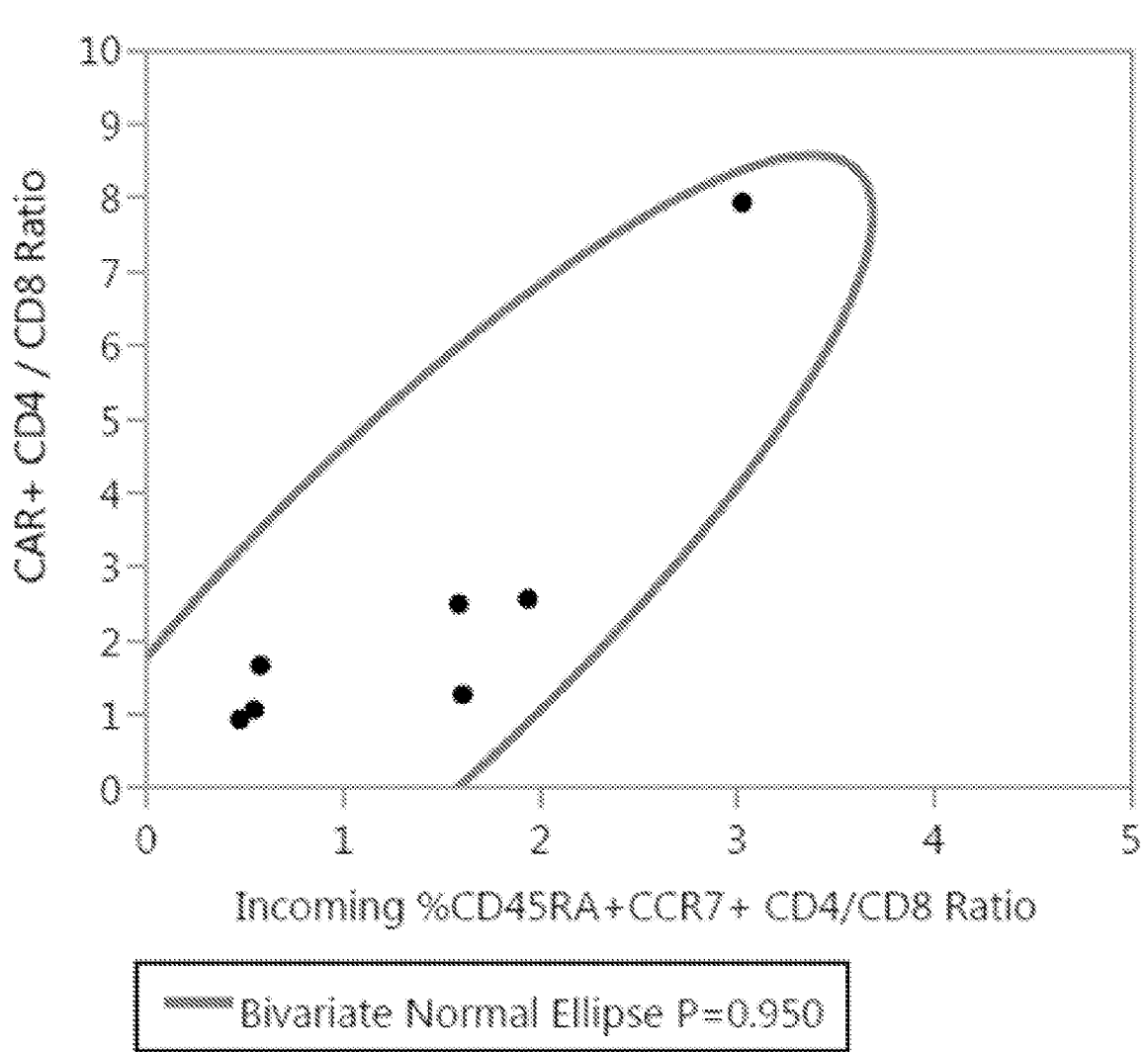
Figure 3C:
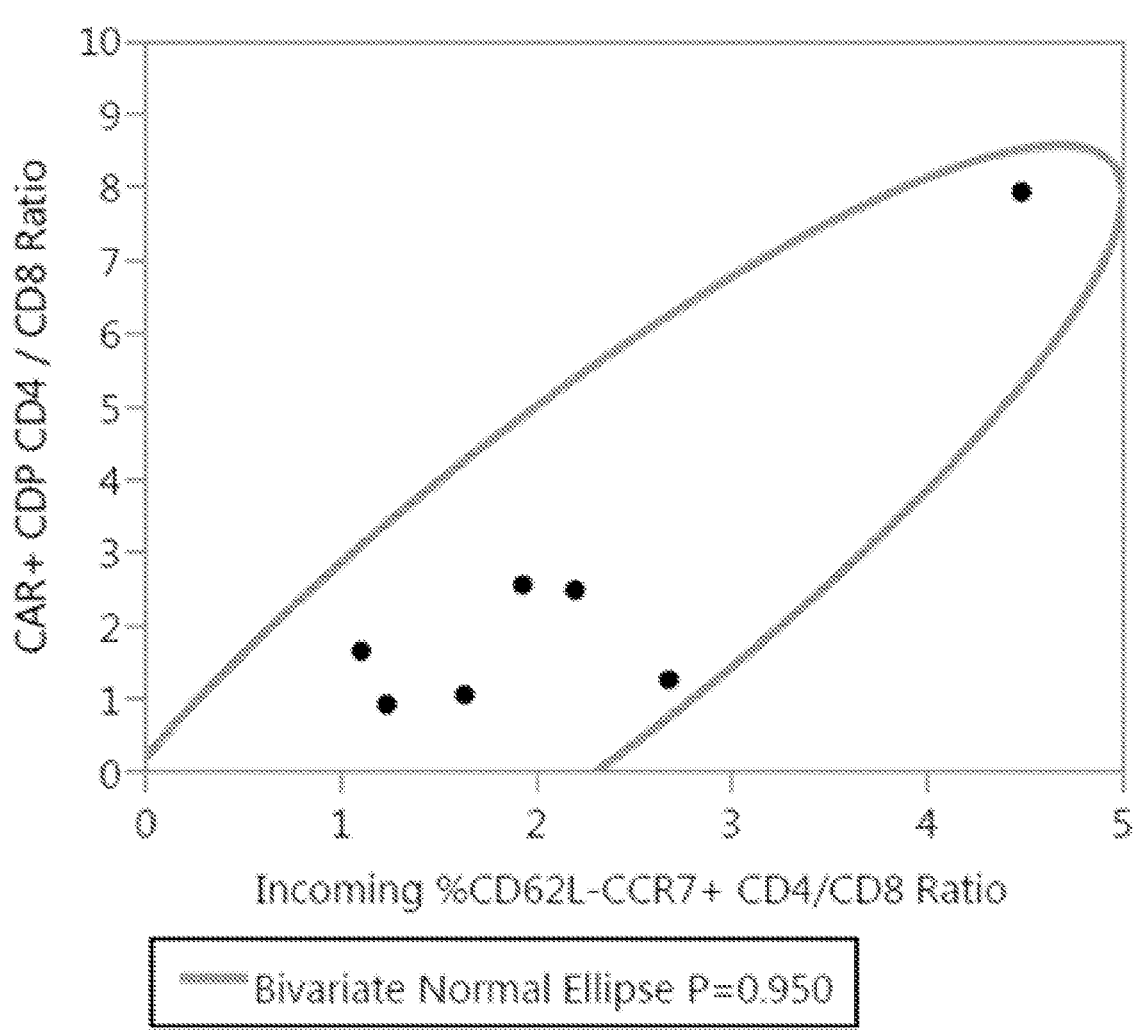

The CD27+/CCR7+CD4/CD8 ratio, CD45RA+/CCR7+ CD4/CD8 ratio, or CD62L−/CCR7+CD4/CD8 ratio in the mixture of selected CD4 and CD8 cells, was compared, post facto, to the CAR+CD4/CD8 ratio in the engineered CAR-T cell composition. The degree of correlation of the mean ratios from each subject was assessed by bivariate normal ellipse representing the 0.950 probability region for the plotted data are shown in FIGS. 3A-3C. As shown, a correlation between the CD27+/CCR7+CD4/CD8 ratio, CD45RA+/CCR7+CD4/CD8 ratio, or CD62L−/CCR7+ CD4/CD8 ratio in the starting sample to the CAR+CD4/CD8 ratio in the T cell composition was significant based on Pearson correlation analysis. Tables E4A-E4C display the results of correlation analysis carried out with respect to the data plotted in FIGS. 3A-3C. Significance <0.05 is noted by *.

TABLE E4A

Bivariate Normal Ellipse P = 0.950; CD4/CD8
ratios in starting sample and output cell composition

| Variable | Mean | Std. Dev. | Correlation | Signif. Prob. |
|---|---|---|---|---|
| Starting % CD27+CCR7+ CD4/CD8 Ratio | 2.689438 | 1.788478 | 0.895786 | 0.0064* |
| CAR+ CD4/CD8 ratio | 2.560108 | 2.459516 | | |

TABLE E4B

Bivariate Normal Ellipse P = 0.950; CD4/CD8
ratios in starting sample and output cell composition

| Variable | Mean | Std. Dev. | Correlation | Signif. Prob. |
|---|---|---|---|---|
| Starting % CD45RA+CCR7+ CD4/CD8 Ratio | 1.394018 | 0.937173 | 0.86723 | 0.0115* |
| CAR+ CD4/CD8 ratio | 2.560108 | 2.459516 | | |

TABLE E4C

Bivariate Normal Ellipse P = 0.950; CD4/CD8
ratios in starting sample and output cell composition

| Variable | Mean | Std. Dev. | Correlation | Signif. Prob. |
|---|---|---|---|---|
| Starting % CD62L-CCR7+ CD4/CD8 Ratio | 2.179702 | 1.153181 | 0.88584 | 0.0079* |
| CAR+ CD4/CD8 ratio | 2.560108 | 2.456516 | | |

Example 13: Continuous in-Line Imaging for Determination of Cell Viability During Cultivation Various optical parameters of T cells in the process of engineering for expression of a recombinant receptor, were obtained using in-line differential digital holography microscopy (DHM). Differential DHM permits label-free imaging of cells, with high-contrast images for object segmentation, and obtaining a plurality of optical or morphological features that quantitatively describe the imaged objects, for example, for determining cell counts and viability.

Primary T cells from a healthy human donor were engineered to express an anti-BCMA chimeric antigen receptor (CAR) using an exemplary engineering process, generally as described in Examples 1 and 6 above. Two experimental runs were performed (Run 1, Run 2). The cells were cultivated for expansion by transfer to a bioreactor (e.g., a rocking motion bioreactor). The cultivation included media replacement with semi-continuous perfusion and continual mixing.

Holographic images and optical parameters of the cells were captured continuously for up to approximately 120 hours of culture using an in-line differential DHM imaging system ("continuous"), for example an Ovizio iLine F (Ovizio Imaging Systems NV/SA, Brussels, Belgium). The in-line differential DHM system contained a disposable tubing system connected to the bioreactor such that a sample can flow from the bioreactor, through the tubing system, where an imaging system captures holographic images and optical parameters of the cells traveling through, and returns the sample to the bioreactor. Cell viability and viable cell count (VCC) were determined from images. Viability of the engineered cells were also compared to results by manual sampling ("manual") and cell counting using an automated cell counter, sampled at various time points for up to approximately 120 hours of culture. The two methods were compared based on time course analysis and linear regression.

Figure 4A:
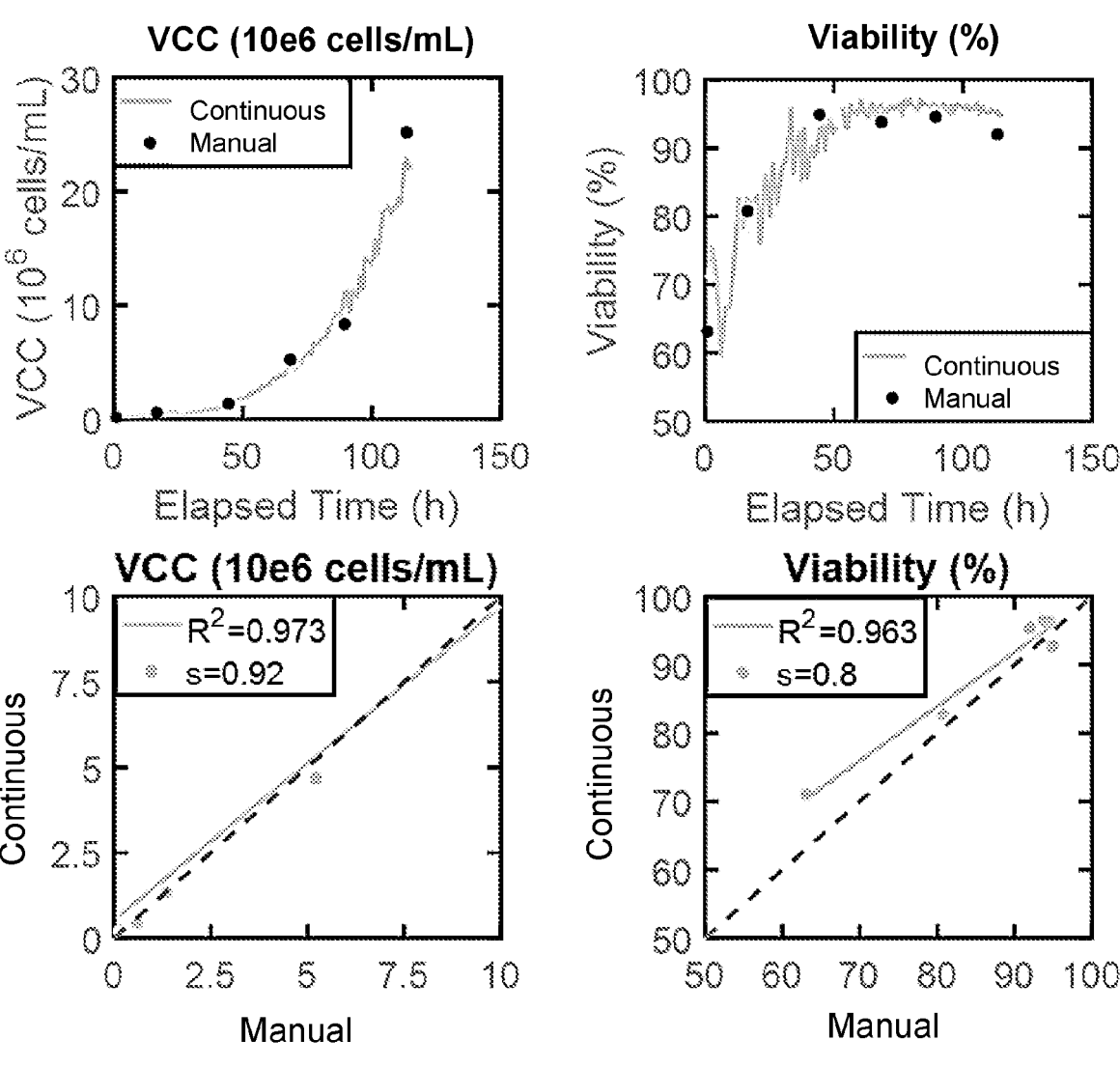
FIGS. 4A and 4B depict viable cell count (VCC; ×10^6 cells/mL) and cell viability (%), assessed using continuous monitoring by differential DHM ("continuous", line) or manual sampling ("manual", dots), in experimental Run 1 (FIG. 4A) and Run 2 (FIG. 4B). Top panels depict the measurements for each, bottom panels depict linear regression analysis and the R^2 and slope (s), for comparing the continuous monitoring and manual sampling.
Figure 4B:
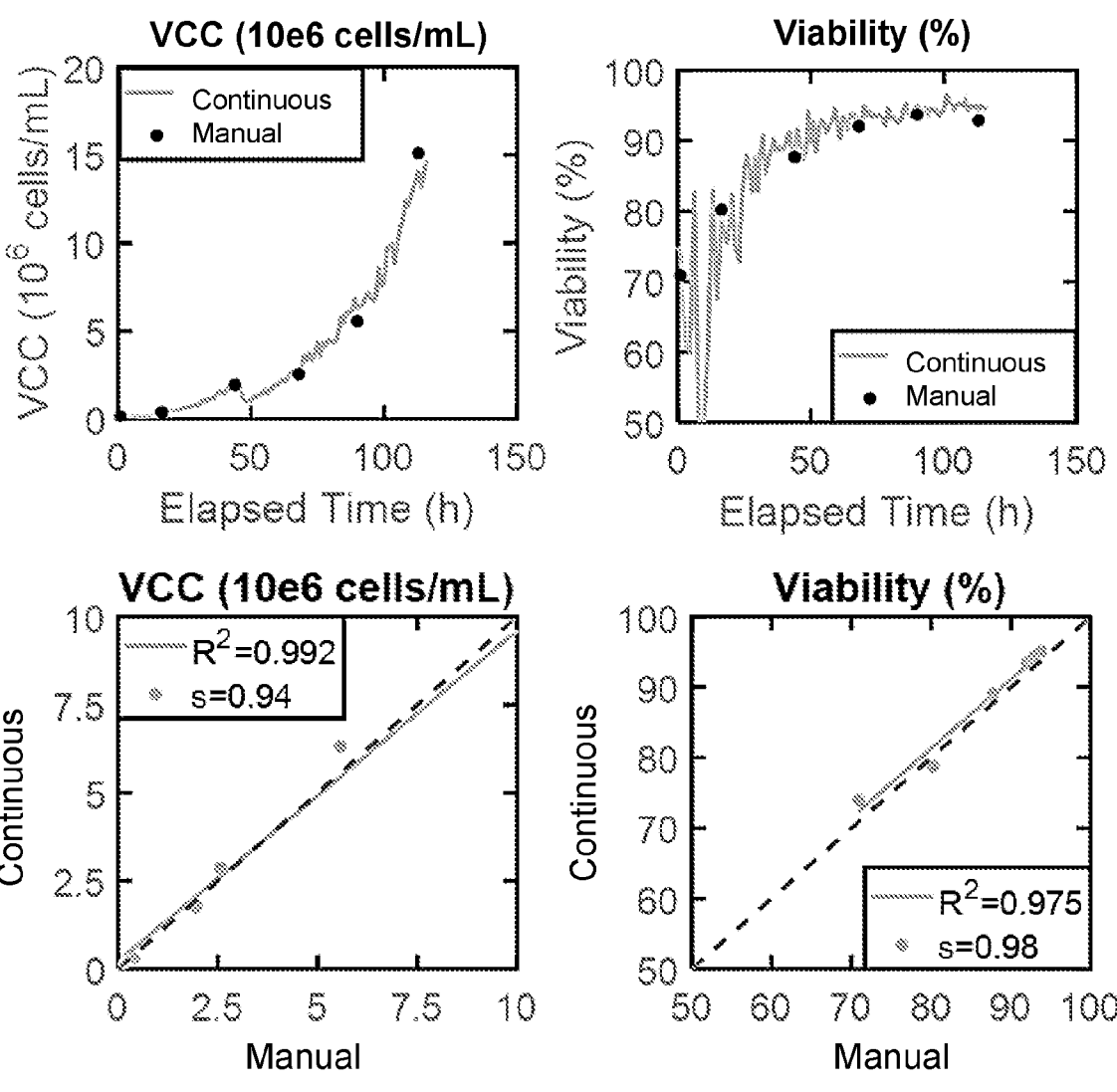

FIGS. 4A and 4B show the comparison of viable cell count (VCC) and viability, assessed using continuous monitoring by differential DHM or manual sampling, in experimental Run 1 (FIG. 4A) and Run 2 (FIG. 4B). The $R^2$ and slope of the comparison is shown in Table E5 below. The difference in VCC as measured using the two methods fell within the expected variance of the manual sampling method.

TABLE E5

$R^2$ and slope of comparison between sampling methods.

| Experiment | $R^2$ | | Slope | |
| | VCC | Viability | VCC | Viability |
|---|---|---|---|---|
| Run 1 | 0.97 | 0.96 | 0.92 | 0.80 |
| Run 2 | 0.99 | 0.98 | 0.94 | 0.98 |

The results showed that the VCC and viability as continuous monitoring and manual sampling were highly correlated. The results were consistent with the utility of the continuous monitoring by differential DHM during cultivation for expansion of the cells in the cell engineering process.

Example 14: Comparison of Manual and Automated Expansion Using Continuous in-Line Imaging A fully automated, operator-free cell expansion method with continuous monitoring of the cells by in-line imaging and automated perfusion, was compared to a manual expansion method.

Primary T cells from a healthy human donor were activated and transduced with a vector to express an exemplary chimeric antigen receptor (CAR), using an exemplary engineering process. After transduction, cells were pooled and inoculated for two different cultures, one automated expansion based on continuous in-line imaging using differential DHM, and one manual expansion method.

In the automated expansion culture, cells were cultivated in a rocking motion bioreactor, with media replacement with semi-continuous perfusion and continual mixing. Cell viability and viable cell count (VCC) were monitored using an automated differential DHM imaging system, generally as described in Example 13 above. The initial VCC at the time of inoculation was similar for both cultures ($0.12 \times 10^6$ cells/mL for automated culture, $0.14 \times 10^6$ cells/mL for manual culture). Perfusion in the automated expansion was based on a four-hour rolling average of VCC calculated by a software algorithm, where a VCC average greater than the target VCC was required for progression of the method. The target VCC was at $0.6 \times 10^6$ cells/mL, $1 \times 10^6$ cells/mL and 4×10⁶ cells/mL for 3 perfusion steps. No additional operator intervention occurred after inoculation. In the manual expansion culture, perfusion was performed generally as described in Example 1 above, with a single daily sampling. Cells were also assessed for cell surface expression of markers by flow cytometry.

Figure 5:
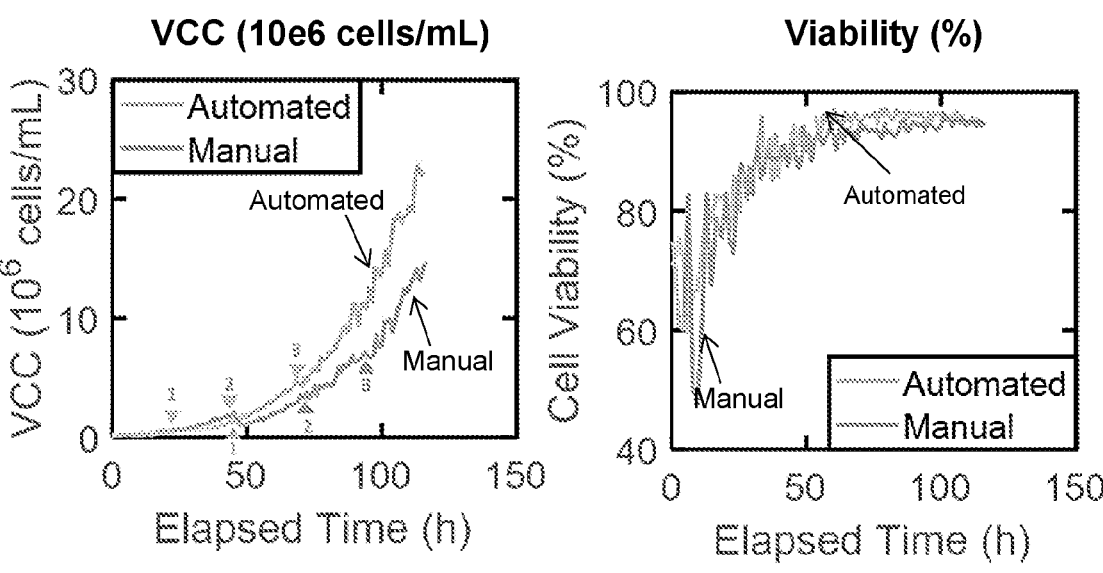
FIG. 5 depicts viable cell count (VCC; ×10^6 cells/mL) and cell viability (%), assessed using continuous monitoring by differential DHM, in an automated expansion process compared to a manual expansion process.

As shown in FIG. 5, higher T cell growth was observed with the automated expansion system. Cell viability as assessed by continuous differential DHM imaging, and cell phenotypes, as assessed by flow cytometry, were similar between the automated vs. manual expansion processes.

The results were consistent with the utility of the continuous DHM imaging and automated expansion process, for cultivation and monitoring of cells during a T cell engineering process, without the need for a human operator. In some aspects, such method can be used to determine the growth kinetics of the primary T cells, and determine the time for harvesting the cells for engineering of administration.

Example 15: Assessment of T Cell Compositions Generated by Exemplary Manufacturing Processes In an exemplary process essentially as described in Example 1, 50 CAR+ T cell compositions containing autologous T cells expressing an anti-BCMA CAR were generated from apheresis collected from 50 separate human subjects (one apheresis from each subject), including 10 healthy donors and 40 multiple myeloma patients. CD4+ and CD8+ T cells were selected from the apheresis samples and separately cryopreserved. The cells were then thawed, and the CD4+ T cells and CD8+ T cells were combined at a 1:1 ratio of viable CD4+ to CD8+ cells. The combined CD4+ and CD8+ T cells were activated, transduced with a vector encoding a CAR, expanded, and frozen by cryopreservation essentially as described in Example 1.

In an exemplary alternative process, therapeutic T cell compositions were generated by a process including immunoaffinity-based selection of T cells from leukapheresis samples from 55 individual human cancer subjects. Bulk T cells were subjected to activation and transduction with a viral vector encoding a CAR, expansion and cryopreservation.

The cells in the frozen compositions were thawed and assessed by flow cytometry for viability, expression of an apoptotic marker such as active caspase 3 (CAS)), surface expression of CD3, CD4, CD8, CD27, CD28, CCR7, and CD45RA, and CAR. The percentage of CD3+ cells, percentage of CAR+ apoptotic marker negative cells in CD3+ CAR+ cells in the compositions, and the percentages of central memory CD4+ CAR+ cells and central memory CD8+ CAR+ cells in the compositions were determined. Cell phenotypes of the cell compositions generated by the manufacturing process were assessed and in some aspects were compared to those of the cell compositions generated by the alternative process.

The manufacturing process of this example resulted in engineered cell compositions meeting certain pre-determined features, including threshold numbers of cells expressing the CAR in a cell composition administration to the patients, in 100% of the human biological samples on which it was carried out. FIGS. 6A and 6B show median (horizontal lines), interquartile range (box), and 1.5× interquartile range (whiskers) for percentages of cells of the indicated phenotypes (based on CD45RA and CCR7 surface expression), among CD4+ CAR+ cells (FIG. 6A) and among CD8+ CAR+ cells (FIG. 6B) in the compositions, respectively, for compositions individually generated from the group of samples from the 40 multiple myeloma subjects. FIGS. 6C and 6D show median (horizontal lines), interquartile range (box), and 1.5× interquartile range (whiskers) for percentages of cells of the indicated phenotypes (based on CD27 and CD28 surface expression), among CD4+ CAR+ cells (FIG. 6C) and among CD8+ CAR+ cells (FIG. 6D)) in the compositions, respectively, for compositions individually generated from the group of samples from the 40 multiple myeloma subjects. For individual leukapheresis samples obtained from a range of multiple myeloma patients, using this exemplary process to generate engineered cell compositions from such samples, it was observed that the range of duration of the portion of the process from initiation of activation through harvest was between 7 and 10 days, and an average duration among these samples of approximately 7.5 days. It was further determined that the average number of cumulative population doublings over the course of the process among the different samples was approximately 7.5.

In this study, engineered T cell populations in the cell compositions produced by the exemplary process included less than 15% cells expressing an apoptotic marker, and were enriched for a central memory phenotype as compared to the starting samples and to cell compositions generated using the exemplary alternative process.

Example 16: Process for Generating Therapeutic Compositions of Engineered T Cells Expressing an Anti-BCMA CAR An exemplary process similar to the process described in Example 1 was carried out to produce engineered compositions containing CD4+ and CD8+ T cells expressing an anti-BCMA chimeric antigen receptor (CAR). Primary CD4+ and CD8+ cells were enriched from biological samples containing PBMCs from a human leukapheresis sample, including from subjects having multiple myeloma (MM). The enriched CD4+ and enriched CD8+ cell compositions were separately cryofrozen and subsequently thawed and mixed at a ratio of 1:1 of viable CD4+ T cells to viable CD8+ T cells, prior to carrying out steps for stimulation, transduction and expansion.

Approximately 300×10⁶ T cells (for example, 150×10⁶ CD4+ and 150×10⁶ CD8+ T cells) from the mixed cell composition, at a density of about 3×10⁶ cells/mL, were incubated for between 18 and 30 hours in the presence of paramagnetic polystyrene-coated beads with attached anti-CD3 and anti-CD28 antibodies, at a 1:1 bead to cell ratio in an exemplary serum-free media (see, e.g., Example 3) containing recombinant IL-2, IL-7, and IL-15.

Following the incubation, at least approximately 100×10⁶ and up to approximately 200×10⁶ viable cells from the incubated cell composition were transduced, in the exemplary serum free media with cytokines, with a lentiviral vector encoding the anti-BCMA CAR by spinoculation for 60 minutes followed by incubation for about 18 to 30 hours at about 37° C. The CAR contained an scFv antigen-binding domain specific for BCMA, a CD28 transmembrane region, a 4-1BB costimulatory signaling region, and a CD3-zeta derived intracellular signaling domain.

The transduced cells were then expanded by cultivation in a bioreactor (e.g. a rocking motion bioreactor) in about 500 mL of the exemplary serum free media containing twice the concentration of IL-2, IL-7, and IL-15 as used during the incubation and transduction steps. The media did not contain poloxamer. After a cell density of greater than at or about $0.6 \times 10^6$ cells/mL was deemed to be achieved, media was added step-wise with shots of fresh media being added periodically, such as between about 2 and about 15 minutes to a volume of 1000 mL and the cells were cultivated under steady rocking conditions (non-perfusion) until a threshold viable cell density of greater than or about $0.6 \times 10^6$ cells/mL was achieved. If the viable cell density was greater than $0.8 \times 10^6$ cells/mL, a combination fill/perfusion step was initiated wherein first media was added in a step-wise manner as indicated above, until a target volume of 1000 mL, then perfusion was initiated as explained below. Media was then replaced by semi-continuous perfusion with continual mixing. The perfusion rate and/or rocking speed were increased at least one time during the expansion phase as cell density increased. The perfusion rate was increased at least one time during the expansion phase as cell density increased. Media was added to the culture in a step-wise manner with total volume per day determined by viable cell density (with higher rates once certain densities were reached), up to a rate, e.g., resulting in approximately 750 mL or 1500 mL of total fresh media added to the culture per day (with higher rates when higher cell concentrations were reached), with shots of fresh media added throughout the day periodically, such as between about every 0.5 and about every 1.5 or 2 hours. The cells were harvested at a time one day after the total number of nucleated cells (TNC) had reached at least or at least approximately $1000 \times 10^6$ and at a point at which the TNC number had reached at least or at least approximately $2400 \times 10^6$ total nucleated cells, with at least 85% viability. Following harvest, the anti-CD3 and anti-CD28 antibody conjugated beads were removed from the cell composition.

The cells were then formulated and aliquots of the composition transferred into containers, e.g., for downstream storage or use. In some embodiments, formulated compositions or portions thereof were transferred freezing bags appropriate for cryopreservation and storage of cell compositions, e.g., for potential administration to subjects (such as CryoStore Freezing Bags) and/or compositions or portions thereof were transferred to vials or other containers, such as for further analysis of the cells. Cells were cryofrozen, such as under conditions appropriate for downstream thawing and use for administration. In some cases, 30 mL volumes of formulated cells were used in individual bags. In some instances, cells were cryopreserved at a variable total cell concentration, for example, to permit a consistent number or concentration of CAR+ T cells in each dose in the context of cells for administration. In some embodiments, the target CAR+CD3+ cell number is at or approximately a desired number (such as at or about $37.5 \times 10^6$) CAR+CD3+ cells per 30 mL or per bag, which in some embodiments involves varying total cell concentrations among compositions generated from different donors or patients.

For individual leukapheresis samples obtained from a range of multiple myeloma patients, it was determined that, using this exemplary process to generate engineered cell compositions from such samples, would result in a range of duration of the portion of the process from initiation of activation through harvest of between 5 and 8 days, and an average duration among these samples of 5.5 days. It was further determined that the average number of cumulative population doublings over the process for this group of samples would be approximately 5.

The exemplary process in this example was used to generate engineered T cell compositions from a number of human multiple myeloma leukapheresis samples. Various parameters, including those reflective of cell phenotype, function and cell engineering were assessed. T cell purity, T cell lineage representation, transduction frequency and functionality were observed to be substantially similar as for compositions generated with these leukapheresis products using a process as described in Example 1. There was observed a reduced number of population doublings and average duration of days between activation initiation and harvest, with production using the exemplary process in this example as compared to the exemplary process in Example 1. In general, similar or increased percentages of central memory-phenotype cells (and similar or decreased percentages of effector memory-phenotype cells) were observed in engineered cell compositions produced by the exemplary process in this example as compared to that in Example 1.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| # | SEQUENCE | ANNOTATION |
|---|---|---|
| 1 | ESKYGPPCPPCP | spacer (IgG4hinge) (aa) |
| 2 | GAATCTAAGTACGGACCGCCCTGCCCCCCTTGCCCT | spacer (IgG4hinge) (nt) |
| 3 | ESKYGPPCPPCPGQPREPQVYTLPPSQEEMTKNQVSLTCLVKGFYPSDIAV EWESNGQPENNYKTTPPVLDSDGSFFLYSRLTVDKSRWQEGNVFSCSVMHE ALHNHYTQKSLSLSLGK | Hinge-$C_H3$ spacer |
| 4 | ESKYGPPCPPCPAPEFLGGPSVFLFPPKPKDTLMISRTPEVTCVVVDVSQE DPEVQFNWYVDGVEVHNAKTKPREEQFNSTYRVVSVLTVLHQDWLNGKEYK CKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGNV FSCSVMHEALHNHYTQKSLSLSLGK | Hinge-$C_H2$-$C_H3$ spacer |
| 5 | RWPESPKAQASSVPTAQPQAEGSLAKATTAPATTRNTGRGGEEKKKEKEKE EQEERETKTPECPSHTQPLGVYLLTPAVQDLWLRDKATFTCFVVGSDLKDA HLTWEVAGKVPTGGVEEGLLERHSNGSQSQHSRLTLPRSLWNAGTSVTCTL NHPSLPPQRLMALREPAAQAPVKLSLNLLASSDPPEAASWLLCEVSGFSPP | IgD-hinge-Fc |

Sequences

| # | SEQUENCE | ANNOTATION |
|---|----------|------------|
|  | NILLMWLEDQREVNTSGFAPARPPPQPGSTTFWAWSVLRVPAPPSPQPATY TCVVSHEDSRTLLNASRSLEVSYVTDH | |
| 6 | LEGGGEGRGSLLTCGDVEENPGPR | T2A |
| 7 | MLLLVTSLLLCELPHPAFLLIPRKVCNGIGIGEFKDSLSINATNIKHFKNC TSISGDLHILPVAFRGDSFTHTPPLDPQELDILKTVKEITGFLLIQAWPEN RTDLHAFENLEIIRGRTKQHGQFSLAVVSLNITSLGLRSLKEISDGDVIIS GNKNLCYANTINWKKLFGTSGQKTKIISNRGENSCKATGQVCHALCSPEGC WGPEPRDCVSCRNVSRGRECVDKCNLLEGEPREFVENSECIQCHPECLPQA MNITCTGRGPDNCIQCAHYIDGPHCVKTCPAGVMGENNTLVWKYADAGHVC HLCHPNCTYGCTGPGLEGCPTNGPKIPSIATGMVGALLLLLVVALGIGLFM | tEGFR |
| 8 | FWVLVVVGGVLACYSLLVTVAFIIFWV | CD28 (amino acids 153-179 of Accession No. P10747) |
| 9 | IEVMYPPPYLDNEKSNGTIIHVKGKHLCPSPLFPGPSKPFWVLVVVGGVLA CYSLLVTVAFIIFWV | CD28 (amino acids 114-179 of Accession No. P10747) |
| 10 | RSKRSRLLHSDYMNMTPRRPGPTRKHYQPYAPPRDFAAYRS | CD28 (amino acids 180-220 of P10747) |
| 11 | RSKRSRGGHSDYMNMTPRRPGPTRKHYQPYAPPRDFAAYRS | CD28 (LL to GG) |
| 12 | KRGRKKLLYIFKQPFMRPVQTTQEEDGCSCRFPEEEEGGCEL | 4-1BB (amino acids 214-255 of Q07011.1) |
| 13 | RVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYD ALHMQALPPR | CD3 zeta |
| 14 | RVKFSRSAEPPAYQQGQNQLYNELNLGRREEYDVLDKRRGRDPEMGGKPRR KNPQEGLYNELQKDKMAEAYSEIGMKGERRRGKGHDGLYQGLSTATKDTYD ALHMQALPPR | CD3 zeta |
| 15 | RVKFSRSADAPAYKQGQNQLYNELNLGRREEYDVLDKRRGRDPEMGGKPRR KNPQEGLYNELQKDKMAEAYSEIGMKGERRRGKGHDGLYQGLSTATKDTYD ALHMQALPPR | CD3 zeta |
| 16 | RKVCNGIGIGEFKDSLSINATNIKHFKNCTSISGDLHILPVAFRGDSFTHT PPLDPQELDILKTVKEITGFLLIQAWPENRTDLHAFENLEIIRGRTKQHGQ FSLAVVSLNITSLGLRSLKEISDGDVIISGNKNLCYANTINWKKLFGTSGQ KTKIISNRGENSCKATGQVCHALCSPEGCWGPEPRDCVSCRNVSRGRECVD KCNLLEGEPREFVENSECIQCHPECLPQAMNITCTGRGPDNCIQCAHYIDG PHCVKTCPAGVMGENNTLVWKYADAGHVCHLCHPNCTYGCTGPGLEGCPTN GPKIPSIATGMVGALLLLLVVALGIGLFM | tEGFR |
| 17 | EGRGSLLTCGDVEENPGP | T2A |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | -PGGG-(SGGGG)5-P- wherein P is proline, G is glycine and S is serine | Linker |
| 23 | GSADDAKKDAAKKDGKS | Linker |
| 24 | atgcttctcctggtgacaagccttctgctctgtgagttaccacacccagca ttcctcctgatccca | GMCSFR alpha chain signal sequence |
| 25 | MLLLVTSLLLCELPHPAFLLIP | GMCSFR alpha chain signal sequence |

-continued

| Sequences | |
|---|---|
| # SEQUENCE | ANNOTATION |

26 MALPVTALLLPLALLLHA

CD8 alpha signal peptide

27 EVQLVQSGAEMKKPGASLKLSCKASGYTFIDYVYVWMRQAPGQGLESMGWI NPNSGGTNYAQKFQGRVTMTRDTSISTAYMELSRLRSDDTAMYYCARSQRD GYMDYWGQGTLVTVSS

Variable heavy $(V_H)$ Anti-BCMA

28 QSALTQPASVSASPGQSIAISCTGTSSDVGWYQQHPGKAPKLMIYEDSKRP SGVSNRFSGSKSGNTASLTISGLQAEDEADYYCSSNTRSSTLVFGGGTKLT VLG

Variable light $(V_H)$ Anti-BCMA

29 ESKYGPPCPPCPAPPVAGPSVFLFPPKPKDTLMISRTPEVTCVVVDVSQED PEVQFNWYVDGVEVHNAKTKPREEQFQSTYRVVSVLTVLHQDWLNGKEYKC KVSNKGLPSSIEKTISKAKGQPREPQVYTLPPSQEEMTKNQVSLTCLVKGF YPSDIAVEWESNGQPENNYKTTPPVLDSDGSFFLYSRLTVDKSRWQEGNVF SCSVMHEALHNHYTQKSLSLSLGK

Hinge-C2-C3 spacer *Homo sapiens*

30 QIQLVQSGPELKKPGETVKISCKASGYTFTDYSINWVKRAPGKGLKWMGWI NTETREPAYAYDFRGRFAFSLETSASTAYLQINNLKYEDTATYFCALDYSY AMDYWGQGTSVTVSS

Variable heavy $(V_H)$ Anti-BCMA

31 DIVLTQSPPSLAMSLGKRATISCRASESVTILGSHLIHWYQQKPGQPPTLL IQLASNVQTGVPARFSGSGSRTDFTLTIDPVEEDDVAVYYCLQSRTIPRTF GGGTKLEIK

Variable light $(V_H)$ Anti-BCMA

32 QIQLVQSGPDLKKPGETVKLSCKASGYTFTNFGMNWVKQAPGKGFKWMAWI NTYTGESYFADDFKGRFAFSVETSATTAYLQINNLKTEDTATYFCARGEIY YGYDGGFAYWGQGTLVTVSA

Variable heavy $(V_H)$ Anti-BCMA

33 DVVMTQSHRFMSTSVGDRVSITCRASQDVNTAVSWYQQKPGQSPKLLIFSA SYRYTGVPDRFTGSGSGADFTLTISSVQAEDLAVYYCQQHYSTPWTFGGGT KLDIK

Variable light $(V_H)$ Anti-BCMA

34 EVQLVQSGAEVKKPGESLKISCKGSGYSFTSYWIGWVRQMPGKGLEWMGII YPGDSDTRYSPSFQGHVTISADKSISTAYLQWSSLKASDTAMYYCARYSGS FDNWGQGTLVTVSS

Variable heavy $(V_H)$ Anti-BCMA

35 SYELTQPPSASGTPGQRVTMSCSGTSSNIGSHSVNWYQQLPGTAPKLLIYT NNQRPSGVPDRFSGSKSGTSASLAISGLQSEDEADYYCAAWDGSLNGLVFG GGTKLTVLG

Variable light $(V_H)$ Anti-BCMA

36 GGGGS

Linker

37 GGGS

Linker

38 GGGGSGGGGSGGGGS

Linker

39 GSTSGSGKPGSGEGSTKG

Linker

40 SRGGGGSGGGGSGGGGSLEMA

Linker

41 EVQLVQSGAEVKKPGSSVKVSCKASGGTFSSYAISWVRQAPGQGLEWMGRI IPILGIANYAQKFQGRVTMTEDTSTDTAYMELSSLRSEDTAVYYCARSGYS KSIVSYMDYWGQGTLVTVSS

Variable heavy $(V_H)$ Anti-BCMA

42 LPVLTQPPSTSGTPGQRVTVSCSGSSSNIGSNVVFWYQQLPGTAPKLVIYR NNQRPSGVPDRFSVSKSGTSASLAISGLRSEDEADYYCAAWDDSLSGYVFG TGTKVTVLG

Variable light $(V_H)$ Anti-BCMA

43 QVQLVQSGAEVKKPGSSVKVSCKASGGTFSSYAISWVRQAPGQGLEWMGRI IPILGTANYAQKFQGRVTITADESTSTAYMELSSLRSEDTAVYYCARSGYG SYRWEDSWGQGTLVTVSS

Variable heavy $(V_H)$ Anti-BCMA

44 QAVLTQPPSASGTPGQRVTISCSGSSSNIGSNYVFWYQQLPGTAPKLLIYS NNQRPSGVPDRFSGSKSGTSASLAISGLRSEDEADYYCAAWDDSLSASYVF GTGTKVTVLG

Variable light $(V_H)$ Anti-BCMA

45 QVQLVQSGAEVKKPGASVKVSCKASGYTFTDYYMHWVRQAPGQRLEWMGWI NPNSGGTNYAQKFQDRITVTRDTSSNTGYMELTRLRSDDTAVYYCARSPYS GVLDKWGQGTLVTVSS

Variable heavy $(V_H)$ Anti-BCMA

46 QSVLTQPPSVSGAPGQRVTISCTGSSSNIGAGFDVHWYQQLPGTAPKLLIY GNSNRPSGVPDRFSGSKSGTSASLAITGLQAEDEADYYCQSYDSSLSGYVF GTGTKVTVLG

Variable light $(V_H)$ Anti-BCMA

-continued

| Sequences | |
|---|---|
| # SEQUENCE | ANNOTATION |

47 RASQDISKYLN — CDR L1

48 SRLHSGV — CDR L2

49 GNTLPYTFG — CDR L3

50 DYGVS — CDR H1

51 VIWGSETTYYNSALKS — CDR H2

52 YAMDYWG — CDR H3

53 EVKLQESGPGLVAPSQSLSVTCTVSGVSLPDYGVSWIRQPPRKGLEWLGVI — V$_H$
   WGSETTYYNSALKSRLTIIKDNSKSQVFLKMNSLQTDDTAIYYCAKHYYYG
   GSYAMDYWGQGTSVTVSS

54 DIQMTQTTSSLSASLGDRVTISCRASQDISKYLNWYQQKPDGTVKLLIYHT — V$_L$
   SRLHSGVPSRFSGSGSGTDYSLTISNLEQEDIATYFCQQGNTLPYTFGGGT
   KLEIT

55 DIQMTQTTSSLSASLGDRVTISCRASQDISKYLNWYQQKPDGTVKLLIYHT — scFv
   SRLHSGVPSRFSGSGSGTDYSLTISNLEQEDIATYFCQQGNTLPYTFGGGT
   KLEITGSTSGSGKPGSGEGSTKGEVKLQESGPGLVAPSQSLSVTCTVSGVS
   LPDYGVSWIRQPPRKGLEWLGVIWGSETTYYNSALKSRLTIIKDNSKSQVF
   LKMNSLQTDDTAIYYCAKHYYYGGSYAMDYWGQGTSVTVSS

56 KASQNVGTNVA — CDR L1

57 SATYRNS — CDR L2

58 QQYNRYPYT — CDR L3

59 SYWMN — CDR H1

60 QIYPGDGDTNYNGKFKG — CDR H2

61 KTISSVVDFYFDY — CDR H3

62 EVKLQQSGAELVRPGSSVKISCKASGYAFSSYWMNWVKQRPGQGLEWIGQI — V$_H$
   YPGDGDTNYNGKFKGQATLTADKSSSTAYMQLSGLTSEDSAVYFCARKTIS
   SVVDFYFDYWGQGTTVTVSS

63 DIELTQSPKFMSTSVGDRVSVTCKASQNVGTNVAWYQQKPGQSPKPLIYSA — V$_L$
   TYRNSGVPDRFTGSGSGTDFTLTITNVQSKDLADYFCQQYNRYPYTSGGGT
   KLEIKR

64 GGGGSGGGGSGGGGS — Linker

65 EVKLQQSGAELVRPGSSVKISCKASGYAFSSYWMNWVKQRPGQGLEWIGQI — scFv
   YPGDGDTNYNGKFKGQATLTADKSSSTAYMQLSGLTSEDSAVYFCARKTIS
   SVVDFYFDYWGQGTTVTVSSGGGGSGGGGSGGGGSDIELTQSPKFMSTSVG
   DRVSVTCKASQNVGTNVAWYQQKPGQSPKPLIYSATYRNSGVPDRFTGSGS
   GTDFTLTITNVQSKDLADYFCQQYNRYPYTSGGGTKLEIKR

66 HYYYGGSYAMDY — HC-CDR3

67 HTSRLHS — LC-CDR2

68 QQGNTLPYT — LC-CDR3

69 gacatccagatgacccagaccacctccagcctgagcgccagcctgggcgac — Sequence encoding
   cgggtgaccatcagctgccgggccagccaggacatcagcaagtacctgaac — scFv
   tggtatcagcagaagcccgacggcaccgtcaagctgctgatctaccacacc
   agccggctgcacagcggcgtgcccagccggtttagcggcagcggctccggc
   accgactacagcctgaccatctccaacctggaacaggaagatatcgccacc
   tactttttgccagcagggcaacacactgccctacacctttggcggcggaaca
   aagctggaaatcaccggcagcacctccggcagcggcaagcctggcagcggc
   gagggcagcaccaagggcgaggtgaagctgcaggaaagcggccctggcctg
   gtggccccagccagagcctgagcgtgacctgcaccgtgagcggcgtgagc
   ctgcccgactacggcgtgagctggatccggcagcccccaggaagggcctg
   gaatggctgggcgtgatctggggcagcgagaccacctactacaacagcgcc
   ctgaagagccggctgaccatcatcaaggacaacagcaagagccaggtgttc -continued

| Sequences | |
|---|---|
| # SEQUENCE | ANNOTATION |

| # | SEQUENCE | ANNOTATION |
|---|---|---|
| | ctgaagatgaacagcctgcagaccgacgacaccgccatctactactgcgcc aagcactactactacggcggcagctacgccatggactactggggccagggc accagcgtgaccgtgagcagc | |
| 70 | X1PPX2P<br>X1 is glycine, cysteine or arginine<br>X2 is cysteine or threonine | Hinge |
| 71 | GSTSGSGKPGSGEGSTKG | Linker |
| 72 | DPSKDSKAQVSAAEAGITGTWYNQLGSTFIVTAGADGALTGTYESAVGNAE SRYVLTGRYDSAPATDGSGTALGWTVAWKNNYRNAHSATTWSGQYVGGAEA RINTQWLLTSGTTEANAWKSTLVGHDTFTKVKPSAASIDAAKKAGVNNGNP LDAVQQ | Streptavidin Species: *Streptomyces avidinii* UniProt No. P22629 |
| 73 | EAGITGTWYNQLGSTFIVTAGADGALTGTYESAVGNAESRYVLTGRYDSAP ATDGSGTALGWTVAWKNNYRNAHSATTWSGQYVGGAEARINTQWLLTSGTT EANAWKSTLVGHDTFTKVKPSAAS | Minimal streptavidin Species: *Streptomyces avidinii* |
| 74 | EAGITGTWYNQLGSTFIVTAGADGALTGTYIGARGNAESRYVLTGRYDSAP ATDGSGTALGWTVAWKNNYRNAHSATTWSGQYVGGAEARINTQWLLTSGTT EANAWKSTLVGHDTFTKVKPSAAS | Mutein Streptavidin Ile44-Gly45-Ala-46-Arg47 Species: *Streptomyces avidinii* |
| 75 | WSHPQFEK | Strep-tag ® II |
| 76 | WSHPQFEKGGGSGGGSGGGSWSHPQFEK | Twin-Strep-tag |
| 77 | WSHPQFEKGGGSGGGSWSHPQFEK | Twin-Strep-tag |
| 78 | WSHPQFEKGGGSGGGSGGGSAWSHPQFEK | Twin-Strep-tag |
| 79 | MEAGITGTWYNQLGSTFIVTAGADGALTGTYIGARGNAESRYVLTGRYDSA PATDGSGTALGWTVAWKNNYRNAHSATTWSGQYVGGAEARINTQWLLTSGT TEANAWKSTLVGHDTFTKVKPSAAS | Mutein Streptavidin Ile44-Gly45-Ala-46-Arg47 Species: *Streptomyces avidinii* |
| 80 | -Trp-Xaa-His-Pro-Gln-Phe-Yaa-Zaa- | Streptavidin-binding peptide Xaa is any amino acid; Yaa is Gly or Glu Zaa is Gly, Lys or Arg |
| 81 | Trp-Arg-His-Pro-Gln-Phe-Gly-Gly | Streptavidin binding peptide, Strep-tag ® |
| 82 | Trp-Ser-His-Pro-Gln-Phe-Glu-Lys-(Xaa)n-Trp-Ser-His-Pro-Gln-Phe-Glu-Lys- | Sequential modules of streptavidin-binding peptide Xaa is any amino acid; n is either 8 or 12 |
| 83 | Trp-Ser-His-Pro-Gln-Phe-Glu-Lys-(GlyGlyGlySer)n-Trp-Ser-His-Pro-Gln-Phe-Glu-Lys | Sequential modules of streptavidin-binding peptide n is 2 or 3 |
| 84 | SAWSHPQFEKGGGSGGGSGGGSWSHPQFEK | Twin-Strep-tag |
| 85 | SAWSHPQFEKGGGSGGGSGGGSAWSHPQFEK | Twin-Strep-tag |

-continued

| Sequences | |
|---|---|
| # SEQUENCE | ANNOTATION |
| 86 DPSKDSKAQVSAAEAGITGTWYNQLGSTFIVTAGADGALTGTYVTARGNAE SRYVLTGRYDSAPATDGSGTALGWTVAWKNNYRNAHSATTWSGQYVGGAEA RINTQWLLTSGTTEANAWKSTLVGHDTFTKVKPSAASIDAAKKAGVNNGNP LDAVQQ | Mutein Streptavidin Val44- Thr45-Ala46- Arg47 Species: *Streptomyces avidinii* |
| 87 EAGITGTWYNQLGSTFIVTAGADGALTGTYVTARGNAESRYVLTGRYDSAP ATDGSGTALGWTVAWKNNYRNAHSATTWSGQYVGGAEARINTQWLLTSGTT EANAWKSTLVGHDTFTKVKPSAAS | Mutein Streptavidin Val44- Thr45-Ala46- Arg47 Species: *Streptomyces avidinii* |
| 88 MEAGITGTWYNQLGSTFIVTAGADGALTGTYVTARGNAESRYVLTGRYDSA PATDGSGTALGWTVAWKNNYRNAHSATTWSGQYVGGAEARINTQWLLTSGT TEANAWKSTLVGHDTFTKVKPSAAS | Mutein Streptavidin Val44- Thr45-Ala46- Arg47 Species: *Streptomyces avidinii* |
| 89 His-Pro-Gln-Phe | Streptavidin- binding peptide |
| 90 Oaa-Xaa-His-Pro-Gln-Phe-Yaa-Zaa | Streptavidin- binding peptide Oaa is Trp, Lys or Arg; Xaa is any amino acid; Yaa is Gly or Glu; Zaa is Gly, Lys or Arg |
| 91 DPSKDSKAQVSAAEAGITGTWYNQLGSTFIVTAGADGALTGTYIGARGNAE SRYVLTGRYDSAPATDGSGTALGWTVAWKNNYRNAHSATTWSGQYVGGAEA RINTQWLLTSGTTEANAWKSTLVGHDTFTKVKPSAASIDAAKKAGVNNGNP LDAVQQ | Mutein Streptavidin Ile44- Gly45-Ala-46- Arg47 Species: *Streptomyces avidinii* |
| 92 EAGITGTWYNQLGSTFIVTAGADGALTGTYVTARGNAESRYVLTGRYDSAP ATDGSGTALGWTVAWKNNYRNAHSATTWSGQYVGGAEARINTQWLLTSGTT EENAGYSTLVGHDTFTKVKPSAAS | Mutein Streptavidin Val44- Thr45-Ala46- Arg47 and Glu117, Gly120, Try121 (mutein m1-9) Species: *Streptomyces avidinii* |
| 93 DPSKDSKAQVSAAEAGITGTWYNQLGSTFIVTAGADGALTGTYVTARGNAE SRYVLTGRYDSAPATDGSGTALGWTVAWKNNYRNAHSATTWSGQYVGGAEA RINTQWLLTSGTTEENAGYSTLVGHDTFTKVKPSAAS | Mutein Streptavidin Val44- Thr45-A1a46- Arg47 and Glu117, Gly120, Try121 (mutein m1-9) Species: *Streptomyces avidinii* |
| 94 MEAGITGTWYNQLGSTFIVTAGADGALTGTYESAVGNAESRYVLTGRYDSA PATDGSGTALGWTVAWKNNYRNAHSATTWSGQYVGGAEARINTQWLLTSGT TEANAWKSTLVGHDTFTKVKPSAAS | Minimal streptavidin Species: *Streptomyces avidinii* |

The invention claimed is:

1. A method for producing a composition of engineered cells, the method comprising:
(a) incubating an input composition under stimulating conditions, thereby generating a stimulated composition, wherein:
the input composition comprises between $100 \times 10^6$ and $500 \times 10^6$ total CD4+ and CD8+ T cells at a concentration of between $1 \times 10^6$ cells/mL and $5 \times 10^6$ cells/mL and a ratio of between 3:1 and 1:3 CD4+to CD8+ T cells, wherein the T cells of the input composition are primary T cells obtained from a human subject having a cancer; and
the stimulating conditions comprise the presence of a stimulatory reagent comprising a primary agent that specifically binds to CD3 and a secondary agent that specifically binds to CD28;
(b) introducing a chimeric antigen receptor (CAR) into T cells from the stimulated composition, thereby generating an engineered cell composition, wherein:
the incubation and introducing are each performed in a first serum-free medium comprising 0.5 mM to 5 mM L-glutamine, 0.5 mM to 5 mM L-alanyl-L-glutamine, between 50 IU/mL and 500 IU/mL recombinant IL-2, between 100 IU/mL and 2,000 IU/mL recombinant IL-7, and between 50 IU/mL and 500 IU/mL recombinant IL-15;
the introducing is initiated within 2 days after the initiation of the incubation under stimulating conditions;
the introducing comprises contacting between $50 \times 10^6$ T cells and $200 \times 10^6$ T cells from the stimulated composition with an agent comprising a polynucleotide encoding the CAR; and
during the introducing, the T cells from the stimulated composition are cultured at a concentration of between $0.5 \times 10^6$ cells/mL and $2 \times 10^6$ cells/mL; and
(c) cultivating the engineered composition under conditions to promote expansion of the engineered T cells, thereby producing an output composition comprising engineered T cells, wherein:
the cultivating is performed in a second serum-free medium comprising 0.5 mM to 5 mM L-glutamine, 0.5 mM to 5 mM L-alanyl-L-glutamine, between 50 IU/mL and 500 IU/mL recombinant IL-2, between 100 IU/mL and 2,000 IU/mL recombinant IL-7, and between 50 IU/mL and 500 IU/mL recombinant IL-15;
the cultivating is initiated within 3 days after the initiation of the of the incubation under stimulating conditions;
the cultivating is performed under steady rocking conditions;
at least a portion of the cultivating is performed with perfusion using the second serum-free medium; and
the cultivating is performed at least until the engineered composition comprises a threshold number of viable T cells that is at least $2,000 \times 10^6$ viable T cells, wherein the threshold number of viable T cells is achieved within 9 days of the initiation of the incubation.

2. The method of claim 1, wherein the input composition comprises at or about $300 \times 10^6$ total CD4+ and CD8+ T cells.

3. The method of claim 1, wherein the input composition comprises a concentration of between $3 \times 10^6$ cells/mL and $5 \times 10^6$ cells/mL.

4. The method of claim 1, wherein the input composition comprises a concentration of or of about $3 \times 10^6$ cells/mL.

5. The method of claim 1, wherein the input composition comprises a ratio of between 2:1 and 1:2 CD4+to CD8+ cells.

6. The method of claim 1, wherein the input composition comprises a ratio of or of about 1:1 CD4+to CD8+cells.

7. The method of claim 1, wherein the contacting is by transduction with a viral vector.

8. The method of claim 7, wherein the viral vector is a retroviral vector.

9. The method of claim 1, wherein at least about $100 \times 10^6$ T cells and up to about $200 \times 10^6$ T cells of the stimulated composition are contacted with the agent comprising the polynucleotide.

10. The method of claim 1, wherein during the introducing, the T cells from the stimulated composition are cultured at a concentration of or of about $1 \times 10^6$ cells/mL.

11. The method of claim 1, wherein the primary agent comprises an anti-CD3 antibody or an antigen-binding fragment thereof, and the secondary agent comprises an anti-CD28 antibody or an antigen-binding fragment thereof.

12. The method of claim 11, wherein the primary agent and secondary agent are present on the surface of a solid support.

13. The method of claim 12, wherein the solid support is a bead.

14. The method of claim 13, wherein the ratio of beads to cells is from or from about 2:1 to 0.5:1.

15. The method of claim 13, wherein the ratio of beads to cells is or is about 1:1.

16. The method of claim 1, wherein the input composition is incubated under stimulating conditions for between 12 hours and 36 hours, inclusive.

17. The method of claim 1, wherein the contacting is carried out for between 12 hours and 36 hours, inclusive.

18. The method of claim 1, wherein at least a portion of the cultivating is performed with perfusion at a rate of at least 500 mL/day.

19. The method of claim 1, wherein at least a first portion of the cultivating is performed with a perfusion rate of or of about 750 mL/day, and at least a second portion of the cultivating is performed with a perfusion rate of or of about 1,500 mL/day.

20. The method of claim 1, wherein:
the perfusion is initiated at a rate of or of about 750 mL/day when the cells reach a density of or of about $0.6 \times 10^6$ cells/mL; and the perfusion is increased to a rate of or of about 1500 mL/day when the cells reach a density of or of about $2.0 \times 10^6$ cells/mL.

21. The method of claim 1, wherein the threshold number of viable T cells is achieved between about 5 days and about 9 days from the initiation of the incubation.

22. The method of claim 1, further comprising formulating cells of the output composition for cryopreservation or administration to a subject.

23. The method of claim 1, further comprising isolating the CD4+ and the CD8+ T cells from a biological sample from the subject prior to the incubation.

24. The method of claim 1, wherein the CAR is capable of binding to a target antigen that is associated with, specific to, or expressed on a cell or tissue of a disease, disorder or condition.

25. The method of claim 1, wherein the recombinant receptor is an anti-B cell maturation antigen (BCMA) CAR.

26. The method of claim 1, wherein during at least a portion of the cultivating, the cells are monitored for cell viability, concentration, density, number, or a combination thereof, wherein the monitoring is carried out by differential digital holography microscopy (DDHM).

27. The method of claim 1, wherein the input composition comprises at least 80% cells that are CD4+ T cells and CD8+ T cells.

28. The method of claim 1, wherein the input composition comprises at least 90% cells that are CD4+ T cells and CD8+ T cells.

29. The method of claim 1, wherein the threshold number of viable T cells is achieved within 8 days of the initiation of the incubation.

30. The method of claim 1, wherein the threshold number of viable T cells is achieved between about 5 days and about 8 days from the initiation of the incubation.

31. The method of claim 1, wherein the cancer is a multiple myeloma.

32. The method of claim 1, wherein at least 30% of the cells in the output composition are CCR7+/CD45RA− or CCR7+/CD45RO+.

33. The method of claim 1, wherein for a plurality of output compositions produced by the method for a plurality of different human subjects having the cancer, the mean percentage of cells that are CCR7+/CD45RA− or CCR7+/CD45RO+in the plurality of the output compositions is between about 40% and about 65%.

34. The method of claim 1, wherein the contacting is effected by spinoculation.

35. The method of claim 1, wherein each of the first serum-free medium and the second serum-free medium do not comprise phenol red.

36. The method of claim 1, wherein each of the first serum-free medium and the second serum-free medium comprise a serum-substitute protein.

37. The method of claim 1, wherein the concentration of at least one of the cytokines in the first serum-free medium and second serum-free medium is different.

38. The method of claim 1, wherein the concentrations of recombinant IL-2, IL-7, and IL-15 in the second serum-free medium are twice the concentrations of recombinant IL-2, IL-7, and IL-15 in the first serum-free medium.

39. The method of claim 1, wherein:
the first serum-free medium comprises between at or about 100 IU/mL and at or about 300 IU/mL recombinant IL-2, between at or about 500 IU/mL and at or about 1,500 IU/mL recombinant IL-7, and between at or about 100 IU/mL and at or about 300 IU/mL recombinant IL-15; and/or
the second serum-free medium comprises between at or about 100 IU/mL and at or about 300 IU/mL recombinant IL-2, between at or about 500 IU/mL and at or about 1,500 IU/mL recombinant IL-7, and between at or about 100 IU/mL and at or about 300 IU/mL recombinant IL-15.

40. The method of claim 1, wherein the first and/or second serum-free medium comprises between at or about 50 IU/mL and at or about 150 IU/mL recombinant IL-2, between at or about 500 IU/mL and at or about 1,000 IU/mL recombinant IL-7, and between at or about 50 IU/mL and at or about 150 IU/mL recombinant IL-15.

41. The method of claim 1, wherein the first serum-free medium comprises between at or about 50 IU/mL and at or about 150 IU/mL recombinant IL-2, between at or about 500 IU/mL and at or about 1,000 IU/mL recombinant IL-7, and between at or about 50 IU/mL and at or about 150 IU/mL recombinant IL-15.

42. The method of claim 41, wherein the second serum-free medium comprises between at or about 150 IU/mL and at or about 250 IU/mL recombinant IL-2, between at or about 1000 IU/mL and at or about 1,500 IU/mL recombinant IL-7, and between at or about 150 IU/mL and at or about 250 IU/mL recombinant IL-15.

43. The method of claim 1, wherein the second serum-free medium comprises between at or about 150 IU/mL and at or about 250 IU/mL recombinant IL-2, between at or about 1000 IU/mL and at or about 1,500 IU/mL recombinant IL-7, and between at or about 150 IU/mL and at or about 250 IU/mL recombinant IL-15.

44. The method of claim 1, wherein at least a portion of the cultivating is performed with perfusion using the second serum-free medium at a rate of between 500 mL/day and 800 mL/day.

45. The method of claim 1, wherein at least a portion of the cultivating is performed with perfusion using the second serum-free medium at a rate of between 900 mL/day and 1,500 mL/day.

46. The method of claim 1, wherein:
at least a first portion of the cultivating is performed with perfusion using the second serum-free medium at a rate of between 500 mL/day and 800 mL/day; and
at least a second portion of the cultivating is performed with perfusion using the second serum-free medium at a rate of between 900 mL/day and 1,500 mL/day.

47. The method of claim 1, wherein the perfusion using the second serum-free medium is performed at a rate of between 500 mL/day and 800 mL/day when the cells reach a density of between or between about $0.4 \times 10^6$ cells/mL and $0.8 \times 10^6$ cells/mL.

48. The method of claim 1, wherein the perfusion using the second serum-free medium is performed at a rate of between 900 mL/day and 1,500 mL/day when the cells reach a density of between or between about $1.0 \times 10^6$ cells/mL and $1.4 \times 10^6$ cells/mL.

49. The method of claim 1, wherein:
the perfusion using the second serum-free medium is performed at a rate of between 500 mL/day and 800 mL/day when the cells reach a density of between or between about $0.4 \times 10^6$ cells/mL and $0.8 \times 10^6$ cells/mL; and
the perfusion using the second serum-free medium is performed at a rate of between 900 mL/day and 1,500 mL/day when the cells reach a density of between or between about $1.0 \times 10^6$ cells/mL and $1.4 \times 10^6$ cells/mL.

50. The method of claim 1, wherein the threshold number of viable T cells that is at least $2400 \times 10^6$ viable T cells.

51. The method of claim 1, wherein the second serum-free medium comprises between 600 IU/mL and 2,000 IU/mL recombinant IL-7.

52. A method for producing a composition of engineered cells, the method comprising:

(a) combining a composition of CD4+ T cells and a composition of CD8+ T cells at a ratio of between 2:1 and 1:2 CD4+to CD8+ T cells, thereby generating an input composition, wherein:

the input composition comprises between $100 \times 10^6$ and $500 \times 10^6$ total CD4+ and CD8+ T cells at a concentration of between $1 \times 10^6$ cells/mL and $5 \times 10^6$ cells/mL; and the T cells of the input composition are primary T cells obtained from a human subject having a cancer;

(b) incubating the input composition under stimulating conditions, thereby generating a stimulated composition, wherein the stimulating conditions comprise a primary agent that specifically binds to CD3 and a secondary agent that specifically binds to CD28;

(c) introducing a chimeric antigen receptor (CAR) into T cells from the stimulated composition, thereby generating an engineered cell composition, wherein:

the incubation and introducing are each performed in a first serum-free medium comprising 0.5 mM to 5 mM L-glutamine, 0.5 mM to 5 mM L-alanyl-L-glutamine, between 50 IU/mL and 500 IU/mL recombinant IL-2, between 100 IU/mL and 2,000 IU/mL recombinant IL-7, and between 50 IU/mL and 500 IU/mL recombinant IL-15;

the introducing is initiated within 2 days after the initiation of the incubation under stimulating conditions;

the introducing comprises contacting between $50 \times 10^6$ T cells and $200 \times 10^6$ T cells from the stimulated composition with an agent comprising a polynucleotide encoding the CAR; and during the introducing, the T cells from the stimulated composition are cultured at a concentration of between $0.5 \times 10^6$ cells/mL and $2 \times 10^6$ cells/mL; and (c) cultivating the engineered composition under conditions to promote expansion of the engineered T cells, thereby producing an output composition comprising engineered T cells, wherein:

the cultivating is performed in a second serum-free medium comprising 0.5 mM to 5 mM L-glutamine, 0.5 mM to 5 mM L-alanyl-L-glutamine, between 50 IU/mL and 500 IU/mL recombinant IL-2, between 100 IU/mL and 2,000 IU/mL recombinant IL-7, and between 50 IU/mL and 500 IU/mL recombinant IL-15;

the cultivating is initiated within 3 days after the initiation of the incubation under stimulating conditions;

the cultivating is performed under steady rocking conditions;

at least a portion of the cultivating is performed with perfusion using the second serum-free medium; and the cultivating is performed at least until the engineered composition comprises a threshold number of viable T cells that is at least $2,000 \times 10^6$ viable T cells, wherein the threshold number of viable T cells is achieved within 9 days of the initiation of the incubation.

53. A method for producing a composition of engineered cells, the method comprising:

(a) incubating an input composition under stimulating conditions, thereby generating a stimulated composition, wherein:

the input composition comprises between $100 \times 10^6$ and $500 \times 10^6$ total CD4+ and CD8+ T cells at a concentration of between $1 \times 10^6$ cells/mL and $5 \times 10^6$ cells/mL and a ratio of between 3:1 and 1:3 CD4+to CD8+ T cells, wherein the T cells of the input composition are primary T cells obtained from a human subject having a cancer; and the stimulating conditions comprise the presence of a stimulatory reagent comprising a primary agent that specifically binds to CD3 and a secondary agent that specifically binds to CD28;

(b) introducing a chimeric antigen receptor (CAR) into T cells from the stimulated composition, thereby generating an engineered cell composition, wherein:

the incubation and introducing are each performed in a first serum-free medium comprising 0.5 mM to 5 mM L-glutamine, 0.5 mM to 5 mM L-alanyl-L-glutamine, between 50 IU/mL and 500 IU/mL recombinant IL-2, between 100 IU/mL and 2,000 IU/mL recombinant IL-7, and between 50 IU/mL and 500 IU/mL recombinant IL-15;

the introducing is initiated within 2 days after the initiation of the incubation under stimulating conditions;

the introducing comprises contacting between $50 \times 10^6$ T cells and $200 \times 10^6$ T cells from the stimulated composition with an agent comprising a polynucleotide encoding the CAR; and during the introducing, the T cells from the stimulated composition are cultured at a concentration of between $0.5 \times 10^6$ cells/mL and $2 \times 10^6$ cells/mL; and (c) cultivating the engineered composition under conditions to promote expansion of the engineered T cells, thereby producing an output composition comprising engineered T cells, wherein:

the cultivating is performed in a second serum-free medium comprising 0.5 mM to 5 mM L-glutamine, 0.5 mM to 5 mM L-alanyl-L-glutamine, between 50 IU/mL and 500 IU/mL recombinant IL-2, between 100 IU/mL and 2,000 IU/mL recombinant IL-7, and between 50 IU/mL and 500 IU/mL recombinant IL-15;

the cultivating is initiated within 3 days after the initiation of the incubation under stimulating conditions;

the cultivating is performed under steady rocking conditions;

at least a portion of the cultivating is performed with perfusion using the second serum-free medium; and the cultivating is performed at least until the engineered composition comprises a threshold number of viable T cells that is at least $2,400 \times 10^6$ viable T cells, wherein the threshold number of viable T cells is achieved between 5 days and 9 days from the initiation of the incubation.

\* \* \* \* \*